United States Patent
Halbert et al.

(10) Patent No.: US 10,942,184 B2
(45) Date of Patent: *Mar. 9, 2021

(54) APTAMERS AND USES THEREOF

(71) Applicant: Caris Science, Inc., Irving, TX (US)

(72) Inventors: David D. Halbert, Colleyville, TX (US); Valeriy Domenyuk, Tempe, AZ (US); David Spetzler, Paradise Valley, AZ (US); Tassilo Hornung, Tempe, AZ (US); Frank Schafer, Dusseldorf (DE); Nianqing Xiao, Rockville, MD (US)

(73) Assignee: Caris Science, Inc., Irving, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/913,772

(22) Filed: Mar. 6, 2018

(65) Prior Publication Data

US 2019/0317099 A1    Oct. 17, 2019

Related U.S. Application Data

(63) Continuation of application No. 14/438,172, filed as application No. PCT/IB2013/003092 on Oct. 23, 2013, now Pat. No. 9,958,448.

(60) Provisional application No. 61/717,566, filed on Oct. 23, 2012.

(51) Int. Cl.
*C12N 15/115* (2010.01)
*G01N 33/574* (2006.01)

(52) U.S. Cl.
CPC ..... *G01N 33/57492* (2013.01); *C12N 15/115* (2013.01); *C12N 2310/16* (2013.01); *C12N 2310/344* (2013.01); *C12N 2320/13* (2013.01); *G01N 2800/50* (2013.01)

(58) Field of Classification Search
None
See application file for complete search history.

(56) References Cited

U.S. PATENT DOCUMENTS

| | | |
|---|---|---|
| 4,275,149 A | 6/1981 | Litman |
| 4,551,435 A | 11/1985 | Liberti |
| 4,666,828 A | 5/1987 | Gusella |
| 4,683,202 A | 7/1987 | Mullis |
| 4,737,456 A | 4/1988 | Weng |
| 4,795,698 A | 1/1989 | Owen |
| 4,801,531 A | 1/1989 | Frossard |
| 4,925,788 A | 5/1990 | Liberti |
| 5,108,933 A | 4/1992 | Liberti |
| 5,158,871 A | 10/1992 | Rossomando |
| 5,186,827 A | 2/1993 | Liberti |
| 5,192,659 A | 3/1993 | Simons |
| 5,200,084 A | 4/1993 | Liberti |
| 5,270,163 A | 12/1993 | Gold |
| 5,272,057 A | 12/1993 | Smulson |
| 5,376,252 A | 12/1994 | Ekstrom |
| 5,434,064 A | 7/1995 | Schlessinger |
| 5,475,096 A | 12/1995 | Gold |
| 5,496,938 A | 3/1996 | Gold |
| 5,541,061 A | 7/1996 | Fodor et al. |
| 5,567,588 A | 10/1996 | Gold |
| 5,580,737 A | 12/1996 | Polisky |
| 5,637,459 A | 6/1997 | Burke |
| 5,648,214 A | 7/1997 | Nieuwlandt |
| 5,650,275 A | 7/1997 | Pitner |
| 5,660,985 A | 8/1997 | Pieken |
| 5,672,695 A | 9/1997 | Eckstein |
| 5,683,867 A | 11/1997 | Biesecker |
| 5,698,687 A | 12/1997 | Eckstein |
| 5,705,337 A | 1/1998 | Gold |
| 5,707,796 A | 1/1998 | Gold |
| 5,712,375 A | 1/1998 | Jensen |
| 5,736,330 A | 4/1998 | Fulton |
| 5,756,287 A | 5/1998 | Allen |
| 5,763,177 A | 6/1998 | Gold |
| 5,763,566 A | 6/1998 | Jensen |
| 5,789,157 A | 8/1998 | Jensen |
| 5,789,163 A | 8/1998 | Drolet |
| 5,800,992 A | 9/1998 | Fodor et al. |
| 5,817,635 A | 10/1998 | Eckstein |

(Continued)

FOREIGN PATENT DOCUMENTS

| | | |
|---|---|---|
| CN | 101755208 | 6/2010 |
| CN | 101896605 | 11/2010 |

(Continued)

OTHER PUBLICATIONS

Altschul S F, et al, Basic local alignment search tool. J Mol. Biol. 1990; 215(3):403-10.
Altschul S F, et al, Gapped BLAST and PSI-BLAST: a new generation of protein database search programs. Nucleic Acids Res. 1997; 25(17):3389-402.
Arnold, S, et al. One round of SELEX for the generation of DNA aptamers directed against KLK6. Biol Chem. Apr. 1, 2012;393(5):343-53.
Bennet, Current Drug Discovery; Feb. 2004; pp. 15-19.
BioIT-World. Solexa History. 2010. Available at http://www.bio-itworld.com/2010/issues/sept-oct/solexa.html.
Blank M et al., Systematic evolution of a DNA aptamer binding to rat brain tumor microvessels. Selective targeting of endothelial regulatory protein pigpen. J Biol Chem. May 11, 2001;276(19):16464-8. Epub Feb. 13, 2001.

(Continued)

Primary Examiner — James Martinell
(74) Attorney, Agent, or Firm — Fish & Richardson P.C.

(57) ABSTRACT

Methods and compositions are provided for specific aptamers and aptamer pools that bind biomarkers of interest such as microvesicle surface antigens or functional fragments of microvesicle surface antigens. In various embodiments, aptamers of the invention are used in diagnostic, prognostic, or theranostic processes to screen a biological sample for the presence or levels of biomarkers such as microvesicles that are determined to provide a diagnostic, prognostic, or theranostic readout. The diagnosis, prognosis, or theranosis may be related to cancer or other diseases and disorders. The invention also provides methods and composition to facilitate aptamer library screening and aptamer detection methods.

18 Claims, 78 Drawing Sheets

Specification includes a Sequence Listing.

(56) References Cited

U.S. PATENT DOCUMENTS

| | | |
|---|---|---|
| 5,853,984 A | 12/1998 | Davis |
| 5,861,254 A | 1/1999 | Schneider |
| 5,864,026 A | 1/1999 | Jensen |
| 5,958,691 A | 9/1999 | Pieken |
| 6,011,020 A | 1/2000 | Gold |
| 6,013,443 A | 1/2000 | Heilig |
| 6,051,698 A | 4/2000 | Janjic |
| 6,057,107 A | 5/2000 | Fulton |
| 6,114,120 A | 9/2000 | Jensen |
| 6,180,348 B1 | 1/2001 | Li |
| 6,269,957 B1 | 8/2001 | Bowers |
| 6,287,765 B1 | 9/2001 | Cubicciotti |
| 6,309,822 B1 | 10/2001 | Fodor |
| 6,329,145 B1 | 12/2001 | Janjic |
| 6,329,209 B1 | 12/2001 | Wagner |
| 6,357,601 B1 | 3/2002 | Bowers |
| 6,365,418 B1 | 4/2002 | Wagner |
| 6,376,190 B1 | 4/2002 | Gold |
| 6,376,474 B1 | 4/2002 | Heilig |
| 6,379,698 B1 | 4/2002 | Leamon |
| 6,387,620 B1 | 5/2002 | Smith |
| 6,406,921 B1 | 6/2002 | Wagner |
| 6,408,878 B2 | 6/2002 | Unger |
| 6,423,493 B1 | 7/2002 | Gorenstein |
| 6,475,808 B1 | 11/2002 | Wagner |
| 6,475,809 B1 | 11/2002 | Wagner |
| 6,506,887 B1 | 1/2003 | Smith |
| 6,544,776 B1 | 4/2003 | Gold |
| 6,569,620 B1 | 5/2003 | Gold |
| 6,599,331 B2 | 7/2003 | Chandler |
| 6,613,526 B2 | 9/2003 | Heilig |
| 6,623,526 B1 | 9/2003 | Lloyd |
| 6,645,432 B1 | 11/2003 | Anderson |
| 6,706,481 B2 | 3/2004 | Rajendran |
| 6,716,580 B2 | 4/2004 | Gold |
| 6,719,868 B1 | 4/2004 | Schueller |
| 6,762,025 B2 | 7/2004 | Cubicciotti |
| 6,773,812 B2 | 8/2004 | Chandler |
| 6,787,308 B2 | 9/2004 | Balasubramanian |
| 6,793,753 B2 | 9/2004 | Unger |
| 6,812,023 B1 | 11/2004 | Lamparski |
| 6,864,048 B2 | 3/2005 | Fodor |
| 6,867,289 B1 | 3/2005 | Gorenstein |
| 6,899,137 B2 | 5/2005 | Unger |
| 6,899,863 B1 | 5/2005 | Dhelin |
| 6,929,030 B2 | 8/2005 | Unger |
| 6,962,784 B2 | 11/2005 | Janjic |
| 6,986,902 B1 | 1/2006 | Chen |
| 7,040,338 B2 | 5/2006 | Unger |
| 7,074,586 B1 | 7/2006 | Cheronis |
| 7,083,958 B2 | 8/2006 | Sligar |
| 7,118,661 B2 | 10/2006 | Surh |
| 7,118,910 B2 | 10/2006 | Unger |
| 7,125,711 B2 | 10/2006 | Pugia |
| 7,135,147 B2 | 11/2006 | Cox |
| 7,138,062 B2 | 11/2006 | Yin |
| 7,141,978 B2 | 11/2006 | Peck |
| 7,144,616 B1 | 12/2006 | Unger |
| 7,160,856 B2 | 1/2007 | Danishefsky |
| 7,189,368 B2 | 3/2007 | Andersson |
| 7,189,580 B2 | 3/2007 | Beebe |
| 7,189,581 B2 | 3/2007 | Beebe |
| 7,195,986 B1 | 3/2007 | Bousse |
| 7,198,923 B1 | 4/2007 | Abrignani |
| 7,201,881 B2 | 4/2007 | Cox |
| 7,216,671 B2 | 5/2007 | Unger |
| 7,229,538 B2 | 6/2007 | Tseng |
| 7,233,865 B2 | 6/2007 | Chien |
| 7,238,255 B2 | 7/2007 | Derand |
| 7,238,324 B2 | 7/2007 | Ko |
| 7,250,128 B2 | 7/2007 | Unger |
| 7,253,003 B2 | 8/2007 | Beebe |
| 7,258,837 B2 | 8/2007 | Yager |
| 7,261,824 B2 | 8/2007 | Schlautmann |
| 7,274,316 B2 | 9/2007 | Moore |
| 7,288,368 B2 | 10/2007 | Zweig |
| 7,323,140 B2 | 1/2008 | Handique |
| 7,329,391 B2 | 2/2008 | Cox |
| 7,338,637 B2 | 3/2008 | Pease |
| 7,338,762 B2 | 3/2008 | Gorenstein |
| 7,348,184 B2 | 3/2008 | Rich |
| 7,351,380 B2 | 4/2008 | Simmons |
| 7,351,592 B2 | 4/2008 | Storek |
| 7,357,864 B2 | 4/2008 | Takada |
| 7,371,404 B2 | 5/2008 | Panzner |
| 7,381,471 B2 | 6/2008 | Augustine |
| 7,390,463 B2 | 6/2008 | He |
| 7,399,600 B2 | 7/2008 | Carr |
| 7,399,632 B2 | 7/2008 | Simmons |
| 7,402,229 B2 | 7/2008 | Sibbett |
| 7,407,947 B2 | 8/2008 | Panzner |
| 7,411,184 B2 | 8/2008 | Sarrut |
| 7,413,709 B2 | 8/2008 | Roitman |
| 7,419,639 B2 | 9/2008 | Osterfeld |
| 7,419,822 B2 | 9/2008 | Jeon |
| 7,422,669 B2 | 9/2008 | Jacobson |
| 7,422,725 B2 | 9/2008 | Kimizuka |
| 7,431,887 B2 | 10/2008 | Storek |
| 7,445,844 B2 | 11/2008 | Chandler |
| 7,449,096 B2 | 11/2008 | Berndt |
| 7,452,509 B2 | 11/2008 | Cox |
| 7,452,713 B2 | 11/2008 | Barlocchi |
| 7,467,928 B2 | 12/2008 | Fakunle |
| 7,485,214 B2 | 2/2009 | Palmieri |
| 7,488,596 B2 | 2/2009 | Lee |
| 7,494,555 B2 | 2/2009 | Unger |
| 7,501,245 B2 | 3/2009 | Quake |
| 7,514,400 B2 | 4/2009 | Peterson |
| 7,518,726 B2 | 4/2009 | Rulison |
| 7,541,578 B2 | 6/2009 | Weng |
| 7,544,506 B2 | 6/2009 | Breidford |
| 7,552,741 B2 | 6/2009 | Yamada |
| 7,568,399 B2 | 8/2009 | Sparks |
| 7,575,722 B2 | 8/2009 | Arnold |
| 7,579,136 B2 | 8/2009 | Shim |
| 7,581,429 B2 | 9/2009 | Sparks |
| 7,591,936 B2 | 9/2009 | Sarrut |
| 7,601,270 B1 | 10/2009 | Unger |
| 7,611,863 B2 | 11/2009 | Fromherz |
| 7,640,947 B2 | 1/2010 | Fernandes |
| 7,666,361 B2 | 2/2010 | McBride |
| 7,678,574 B2 | 3/2010 | Blake |
| 7,691,333 B2 | 4/2010 | McBride |
| 7,704,735 B2 | 4/2010 | Facer |
| 7,751,053 B2 | 7/2010 | Carr |
| 7,754,010 B2 | 7/2010 | Unger |
| 7,819,796 B2 | 10/2010 | Blake |
| 7,837,946 B2 | 11/2010 | McBride et al. |
| 7,855,054 B2 | 12/2010 | Schneider |
| 7,858,117 B2 | 12/2010 | Panzner |
| 7,867,763 B2 | 1/2011 | Facer |
| 7,888,035 B2 | 2/2011 | Klass |
| 7,897,356 B2 | 3/2011 | Klass |
| 7,947,447 B2 | 5/2011 | Zichi |
| 7,947,647 B2 | 5/2011 | Peterson |
| 7,955,802 B2 | 6/2011 | Whitman |
| 8,008,019 B2 | 8/2011 | Merante |
| 8,013,131 B2 | 9/2011 | Bovin |
| 8,048,448 B2 | 11/2011 | Ludwig |
| 8,071,288 B2 | 12/2011 | Gold |
| 8,088,601 B2 | 1/2012 | Fox |
| 8,124,015 B2 | 2/2012 | Diercks |
| 8,143,004 B2 | 3/2012 | Ikebukuro |
| 8,198,230 B2 | 6/2012 | Peterson |
| 8,216,784 B2 | 7/2012 | Taylor |
| 8,288,356 B2 | 10/2012 | Obad |
| 8,329,404 B2 | 12/2012 | McKernan |
| 8,367,627 B2 | 2/2013 | Sullenger |
| 8,409,795 B2 | 4/2013 | Schneider |
| 8,455,199 B2 | 6/2013 | Marsh |
| 8,492,082 B2 | 7/2013 | Franciscis |
| 8,587,214 B2 | 11/2013 | Niedermeier |
| 8,598,139 B2 | 12/2013 | Fitzgerald |
| 8,768,629 B2 | 7/2014 | Von Hoff |

(56) References Cited

U.S. PATENT DOCUMENTS

| | | |
|---|---|---|
| 8,841,095 B2 | 9/2014 | Shuber |
| 8,945,830 B2 | 2/2015 | Heil |
| 8,975,026 B2 | 3/2015 | Zichi |
| 8,975,215 B2 | 3/2015 | Park |
| 9,012,498 B2 | 4/2015 | Manoharan |
| 9,128,101 B2 | 9/2015 | Halbert |
| 9,939,443 B2 | 4/2016 | Spetzler |
| 9,469,876 B2 | 10/2016 | Kuslich |
| 9,758,811 B2 | 9/2017 | Brown |
| 9,803,028 B2 | 10/2017 | Pettersson et al. |
| 9,958,448 B2 | 5/2018 | Halbert |
| 2001/0053519 A1 | 12/2001 | Fodor et al. |
| 2003/0061687 A1 | 4/2003 | Hansen |
| 2003/0087239 A1 | 5/2003 | Stanton |
| 2003/0143580 A1 | 7/2003 | Straus |
| 2003/0191084 A1 | 10/2003 | Biesecker et al. |
| 2003/0219801 A1 | 11/2003 | Lipshultz |
| 2004/0197804 A1 | 10/2004 | Keefe |
| 2004/0214184 A1 | 10/2004 | Skubitz et al. |
| 2005/0037394 A1 | 2/2005 | Keefe |
| 2005/0084421 A1 | 4/2005 | Unger |
| 2005/0112882 A1 | 5/2005 | Unger et al. |
| 2005/0123939 A1 | 6/2005 | Gorenstein |
| 2005/0129581 A1 | 6/2005 | McBride et al. |
| 2005/0142582 A1 | 6/2005 | Doyle |
| 2005/0145496 A1 | 7/2005 | Goodsaid |
| 2005/0153317 A1 | 7/2005 | DeNise et al. |
| 2005/0158708 A1 | 7/2005 | Alroy |
| 2005/0201901 A1 | 9/2005 | Grossman |
| 2005/0214173 A1 | 9/2005 | Facer et al. |
| 2005/0252773 A1 | 11/2005 | McBride |
| 2006/0006067 A1 | 1/2006 | Unger |
| 2006/0068388 A1 | 3/2006 | Barberis |
| 2006/0211044 A1 | 9/2006 | Green |
| 2006/0222637 A1 | 10/2006 | Bamdad |
| 2007/0166741 A1 | 7/2007 | Heil |
| 2007/0172873 A1 | 7/2007 | Brenner |
| 2008/0014146 A1 | 1/2008 | Von Hoff et al. |
| 2008/0241126 A1 | 10/2008 | Better et al. |
| 2008/0254446 A1 | 10/2008 | Sode |
| 2008/0261204 A1 | 10/2008 | Lexow |
| 2009/0062129 A1 | 3/2009 | McKernan |
| 2009/0143326 A1 | 6/2009 | Obad et al. |
| 2009/0258379 A1 | 10/2009 | Klein et al. |
| 2009/0264508 A1 | 10/2009 | Sullenger |
| 2009/0304677 A1 | 12/2009 | Ichim |
| 2009/0305237 A1 | 12/2009 | Cantor |
| 2009/0305254 A1 | 12/2009 | Sode |
| 2009/0325153 A1 | 12/2009 | Shuber |
| 2010/0060820 A1 | 3/2010 | Kleppinger et al. |
| 2010/0070191 A1 | 3/2010 | Gold |
| 2010/0086948 A1 | 4/2010 | Gold |
| 2010/0111768 A1 | 5/2010 | Banerjee |
| 2010/0184046 A1 | 7/2010 | Klass et al. |
| 2010/0196426 A1 | 8/2010 | Skog |
| 2010/0221752 A2 | 9/2010 | Gold |
| 2010/0254901 A1 | 10/2010 | Smith |
| 2010/0298151 A1 | 11/2010 | Douglas |
| 2011/0003704 A1 | 1/2011 | Skog et al. |
| 2011/0053157 A1 | 3/2011 | Skog |
| 2011/0059867 A1 | 3/2011 | Kim |
| 2011/0104823 A1 | 5/2011 | Owen |
| 2011/0141975 A1 | 6/2011 | Herzog et al. |
| 2011/0263459 A1 | 10/2011 | Borer |
| 2011/0275794 A1 | 11/2011 | Rohloff |
| 2012/0077263 A1 | 3/2012 | Ward et al. |
| 2012/0077695 A1 | 3/2012 | Ostroff |
| 2012/0101002 A1 | 4/2012 | Riel-Mehan |
| 2012/0101148 A1 | 4/2012 | Akinc |
| 2012/0164628 A1 | 6/2012 | Duffin et al. |
| 2012/0178917 A1 | 7/2012 | Sullenger |
| 2012/0258870 A1 | 10/2012 | Schwartz |
| 2012/0264810 A1 | 10/2012 | Lin |
| 2012/0289411 A1 | 11/2012 | Hatakeyama |
| 2013/0017837 A1 | 1/2013 | Hakola et al. |
| 2013/0029339 A1 | 1/2013 | Skog |
| 2013/0115631 A1 | 5/2013 | Nayak |
| 2013/0116129 A1 | 5/2013 | Miyagishi |
| 2013/0178372 A1 | 7/2013 | Geiss |
| 2013/0202559 A1 | 8/2013 | Skog et al. |
| 2013/0203061 A1 | 8/2013 | Kuslich |
| 2013/0217582 A1 | 8/2013 | Borer |
| 2014/0057986 A1 | 2/2014 | Von Hoff et al. |
| 2014/0141986 A1 | 5/2014 | Spetzler |
| 2014/0148348 A1 | 5/2014 | Kuslich |
| 2014/0148350 A1 | 5/2014 | Spetzler |
| 2014/0220580 A1 | 8/2014 | Brown |
| 2014/0222443 A1 | 8/2014 | Danenberg et al. |
| 2014/0228233 A1 | 8/2014 | Pawlowski |
| 2014/0371088 A1 | 12/2014 | Webster |
| 2015/0024952 A1 | 1/2015 | Alarcon |
| 2015/0152474 A1 | 6/2015 | Pawlowski |
| 2015/0301058 A1 | 10/2015 | Schettini |
| 2015/0377947 A1 | 10/2015 | Basu et al. |
| 2016/0003835 A1 | 1/2016 | Halbert |
| 2016/0186266 A1 | 6/2016 | Alarcon |
| 2016/0319361 A1 | 11/2016 | Spetzler |
| 2017/0356903 A1 | 12/2017 | Domenyuk et al. |
| 2018/0045727 A1 | 2/2018 | Spetzler et al. |

FOREIGN PATENT DOCUMENTS

| | | |
|---|---|---|
| EP | 2209893 | 11/2013 |
| JP | 2007-014292 A | 1/2007 |
| JP | 2012-507300 | 3/2012 |
| JP | 2013-521502 | 6/2013 |
| JP | 5766948 | 8/2015 |
| WO | WO 98/018480 | 5/1998 |
| WO | WO/1999/005255 | 3/1999 |
| WO | WO 00/06770 | 2/2000 |
| WO | WO 0194638 | 12/2001 |
| WO | WO 2005/003291 | 1/2005 |
| WO | WO 2005/049826 | 6/2005 |
| WO | WO 2005/071110 | 8/2005 |
| WO | WO 2006/128010 | 11/2006 |
| WO | WO/2007/032359 | 3/2007 |
| WO | WO 2007/044071 | 4/2007 |
| WO | WO 2007/086403 | 8/2007 |
| WO | WO 2007/123744 | 11/2007 |
| WO | WO 2009/047526 | 4/2009 |
| WO | WO/2010/072410 | 7/2010 |
| WO | WO 2011/115885 | 8/2012 |
| WO | WO 2012/115885 | 8/2012 |
| WO | WO 2013/022995 | 2/2013 |
| WO | WO 2014/111550 | 7/2014 |
| WO | WO 2014/193999 | 12/2014 |

OTHER PUBLICATIONS

Branton et al., the potential and challenges of nanopore sequencing, 26:1146-1153 (2008). Published online Oct. 9, 2008; doi:10.1038/nbt.1495.

Brenner et al., Gene expression analysis by massively parallel signature sequencing (MPSS) on micro bead arrays, Nat Biotechnol. Jun. 2000;18(6):630-4.

Brody and Gold, Aptamers as therapeutic and diagnostic agents. Rev. Mol. Biotech. 2000, 74:5-13.

Brody et al., Life's Simple Measures: Unlocking the Proteome, J. Mol. Biol. (2012) 422, 595-606.

Bruno et al. Development of DNA aptamers for cytochemical detection of acetylcholine. In Vitro Cell Dev Biol Anim. Mar.-Apr. 2008;44(3-4):63-72.

Caras et al., Signal peptide for protein secretion directing glycophospholipid membrane anchor attachment, Science, vol. 243:1196-1198 (1989).

Cerchia et al., Minireview: Nucleic acid aptamers in cancer medicine, FEBS Letters 528 (2002) pp. 12-16.

Cerchia, L., and V. de Franciscis. Nucleic Acid Aptamers Against Protein Kinases. Current medicinal chemistry 18.27 (2011): 4152-4158.

(56) References Cited

OTHER PUBLICATIONS

Chang YM et al., Using aptamers for cancer biomarker discovery. J Nucleic Acids. 2013;2013:817350. doi: 10.1155/2013/817350. Epub Jan. 15, 2013.

Charras and Palluch, Blebs lead the way: how to migrate without lamellipodia. Nature Reviews Molecular and Cell Biology, vol. 9, No. 11, p. 730-736 (2008).

Chaudry MA, et al. (Apr. 2007). EpCAM an immunotherapeutic target for gastrointestinal malignancy: current experience and future challenges. Br J Cancer. Apr. 10, 2007;96(7):1013-9.

Chen et al., Aptamer-mediated nanoparticle-based protein labeling platform for intracellular imaging and tracking endocytosis dynamics. Anal Chem. Apr. 3, 2012;84(7):3099-110.

Chen et al., Microfluidic isolation and transcriptome analysis of serum vesicles, Lab Chip. Feb. 21, 2010;10(4):505-11. doi: 10.1039/b916199f. Epub Dec. 8, 2009.

Cho et al., Optimization of aptamer microarray technology for multiple protein targets, Analytica Chimica Acta 564 (2006) 82-90.

Colcher, et al. (1999) Effects of genetic engineering on the pharmacokinetics of antibodies, Q. J. Nucl. Med., 43: 132-139.

Cotten, et al., 2'-O-methyl, 2'-O-ethyl oligoribonucleotides and phosphorothioate oligodeoxyribonucleotides as inhibitors of the in vitro U7 snRNP-dependent mRNA processing event. Nucl. Acid Res. 19:2629-2635 (1991).

Cutillas et al. Proteomic analysis of plasma membrane vesicles isolated from the rat renal cortex. Proteomics, 2005;5:101-112.

Cutillas et al., Quantification of gel-separated proteins and their phosphorylation sites by LC-MS using unlabeled internal standards: analysis of phosphoprotein dynamics in a B cell lymphoma cell line. Mol Cell Proteomics 2005;4:1038-1051.

Dear, One by one: Single molecule tools for genomics. Brief Funct Genomic Proteomic 2003; 1: 397-416.

Dua P, et al. Patents on SELEX and therapeutic aptamers. Recent Pat DNA Gene Seq. 2008;2(3):172-86.

Dua P, et al., Nucleic acid aptamers targeting cell-surface proteins, Methods 54 (2011) 215-225.

Ellington & Szostak, In vitro selection of RNA molecules that bind specific ligands, Nature 346:818-822, (1990).

Elrick et al., Proteomics: Recent Applications and New Technologies, Basic & Clinical Pharmacology & Toxicology 2006, 98, 432-441.

Erlandsen, et al. High resolution backscatter electron (bse) imaging of immunogold with in-lens and below-the-lens field emission scanning electron microscopes. Scanning Microscopy 13:43-54 (1999).

ExoQuick™ Exosome Precipitation Solution User Manual, System Biosciences (SBI), Palo Alto CA, Version 10 Jan. 30, 2017.

Fan et al., Highly Parallel Genomic Assays, Nature Reviews, Genetics, 7:632-644 (2006).

Ferreira CS et al, DNA aptamers against the MUC1 tumour marker: design of aptamer-antibody sandwich ELISA for the early diagnosis of epithelial tumours, Anal Bioanal Chem. Feb. 2008;390(4):1039-50.

Ferreim CS et al, DNA Aptamers That Bind to MUC1 Tumour Marker: Design and Characterization of MUC1-Binding Single-Stranded DNA Aptamers, Tumour Biol. 2006;27(6):289-301.

Froehler et al., Synthesis of DNA via deoxynucleoside H-phosphonate intermediates. Nucleic Acids Res. Jul. 11, 1986;14(13):5399-407.

Froehler, Deoxynucleoside H-Phosphonate diester intermediates in the synthesis of internucleotide phosphate analogues. Tetrahedron Lett. 27:5575-5578 (1986).

Graham JC and Zarbl H (2012) Use of Cell-SELEX to Generate DNA Aptamers as Molecular Probes of HPV-Associated Cervical Cancer Cells. PLoS ONE 7(4).

Haimovich, Methods, challenges, and promise of next-generation sequencing in cancer biology. Yale J Biol Med. Dec. 2011;84(4):439-46.

Hamedani, N. et al. Selection of high affinity DNA-aptamer for activated protein C using capillary electrophoresis. Research in Pharmaceutical Sciences 7.5 (2012): S987.

Harris TD et al. Single-molecule DNA sequencing of a viral genome. 2008 Science, 320, 106-109.

Hicke, B. J., Stephens, A. W., Escort aptamers: a delivery service for diagnosis and therapy, J. Clin. Invest., 106:923-928 (2000).

Hirose et al., Rapid synthesis of trideoxyribonucleotide blocks. Tetrahedron Lett. 1978; 19(28): 2449-2452.

Hobbs, et al., Polynucleotides containing 2'-amino-2'-deoxyribose and 2'-azido-2'-deoxyribose. Biochemistry 12:5138-5145 (1973).

Hofacker et al., Fast folding and comparison of RNA secondary structures. Monatshefte für Chemie. 125: 167-188 (1994).

Hofacker, I. L. Vienna RNA secondary structure server. Nucleic Acids Res. 31, 3429-3431 (2003).

Huang et al. Integrated microfluidic system for rapid screening of CRP aptamers utilizing systematic evolution of ligands by exponential enrichment (SELEX). Biosens Bioelectron. 2010, vol. 25(7), p. 1761-6.

Hussey, Stephen L., et al., A Synthetic Membrane-Anchored Antigen Efficiently Promotes Uptake of Antifluorescein Antibodies and Associated Protein a by Mammalian Cells, J. Am. Chem. Soc., 2001, vol. 123, pp. 12712-12713.

International Preliminary Report on Patentability for PCT/GB2008/003447, dated Apr. 13, 2010.

International Search Report for PCT/IB13/03092, dated Sep. 1, 2014.

International Search Report for PCT/US13/76611, dated Mar. 31, 2014.

International Search Report for PCT/US14/53306, dated Mar. 24, 2015.

Jain KK: Integrative Omics, Pharmacoproteomics, and Human Body Fluids. In: Thongboonkerd V, ed., ed. Proteomics of Human Body Fluids: Principles, Methods and Applications. vol. 1: Totowa, N.J.: Humana Press, 2007, pp. 175-192.

Janas and Janas, The selection of aptamers specific for membrane molecular targets. Cell Mol Biol Lett. Mar. 2011;16(1):25-39.

Jayasena SD, Aptamers: an emerging class of molecules that rival antibodies in diagnostics. Clin Chem. Sep. 1999;45(9):1628-50.

Kanwar JR et al., Chimeric aptamers in cancer cell-targeted drug delivery, Crit Rev Biochem Mol Biol. Dec. 2011;46(6):459-77.

Kartalov EP et al., High-throughput multi-antigen microfluidic fluorescence immunoassays. Biotechniques 2006; 40(1):85-90.

Kasschau et al., Genome-wide profiling and analysis of Arabidopsis siRNAs, PLoS Biol (2007) 5(3):e57.

Kaur H, Yung L-YL (2012) Probing High Affinity Sequences of DNA Aptamer against VEGF165. PLoS ONE 7(2): e31196. doi:10.1371/journal.pone.0031196.

Kellar, K.L. and J.P. Douglass, 2003, Multiplexed microsphere-based flow cytometric immunoassays for human cytokines. Journal of Immunological Methods, 279: 277-285.

Kellar, K.L. and M.A. Iannone, 2002, Multiplexed microsphere-based flow cytometric assays. Experimental Hematology, 30: 1227-1237.

Kellar, K.L., 2003, Applications of multiplexed fluorescent microsphere-based assays to studies of infectious disease. Journal of Clinical Ligand Assay, 26:76-86.

Kellar, K.L., et al, 2001, Multiplexed fluorescent bead-based immunoassays for quantitation of human cytokines in serum and culture supernatants. Cytometry, 45: 27-36.

Keller et al., Exosomes: From biogenesis and secretion to biological function, Immunol. Lett. 107 (2): 102-8 (2006).

Kim, JW et al., Identification of DNA Aptamers toward Epithelial Cell Adhesion Molecule via Cell-SELEX, Mol. Cells 2014; 37(10): 742-746.

Klug and Famulok. All you wanted to know about SELEX. Mol Biol Rep. 1994, vol. 20(2), p. 97-107.

Kulbachinskiy, Methods for Selection of Aptamers to Protein Targets, Biochemistry (Moscow), 73:1505-1518 (2007).

Lee et al., Biomarker Assay Translation from Discovery to Clinical Studies in Cancer Drug Development: Quantification of Emerging Protein Biomarkers, Adv Cancer Res. (2007) 96:269-98.

Li et al., The Oral Fluid MEMS/NEMS Chip (OFMNC): diagnostic and translational applications. Adv Dent Res 18(1): 3-5 (2005).

Lin et al., Expression of T Cell Antigen Receptor Heterodimers in a Lipid-Linked Form, Science Reports, 1990; 249:677-679.

(56) References Cited

OTHER PUBLICATIONS

Liu et al. (2008) TiGER: a database for tissue-specific gene expression and regulation. BMC Bioinformatics. 9:271.
Lu et al., Elucidation of the Small RNA Component of the Transcriptome, Science. Sep. 2, 2005;309(5740):1567-9.
Margulies, M. et al. Genome Sequencing in Open Microfabricated High Density Picoliter Reactors. 2005 Nature 437, (376-380).
Martins, T.B, 2002, Development of internal controls for the Luminex instrument as part of a multiple seven-analyte viral respiratory antibody profile. Clin Diagn Lab Immunol, 9: 41-45.
Martins, T.B., et al., 2004, Heterophile antibody interference in a multiplexed fluorescent microsphere immunoassay for quantitation of cytokines in human serum. Clin Diagn Lab Immunol. Mar. 2004;11(2):325-9.
Mathews, D., et al. Expanded sequence dependence of thermodynamic parameters improves prediction of RNA secondary structure. J. Mol. Biol. 288, 911-940 (1999).
Mayer et al. Fluorescence-activated cell sorting for aptamer SELEX with cell mixtures. Nat Protoc. 2010, vol. 5(12), p. 1993-2004.
Mehan et al., Highly Multiplexed Proteomic Platform for Biomarker Discovery, Diagnostics, and Therapeutics, Adv Exp Med Biol. (2013) 734:283-300.
Mei et al., Functional-Group Specific Aptamers Indirectly Recognizing Compounds with Alkyl Amino Group, Anal. Chem. 2012, 84, 7323-7329.
Mere L, et al.,Miniaturized FRET assays and microfluidics: key components for ultra-high-throughput screening, Drug Discovery Today 4(8):363-369 (1999).
Metzker, Sequencing technologies—the next generation. Nat Rev Genet. Jan. 2010;11(1):31-46.
Mitkevich, Olga V., et al. DNA aptamers detecting generic amyloid epitopes. Prion 6.4 (2012): 400-406.
Morris KN et al., High affinity ligands from in vitro selection: complex targets. Proc. Natl Acad Sci U S A. Mar. 17, 1998;95(6):2902-7.
Nagarkatti et al., Development of an aptamer-based concentration method for the detection of Trypanosoma cruzi in blood. PLoS One. 2012;7(8):e43533.
Nida et al., Fluorescent nanocrystals for use in early cervical cancer detection. Gynecologic Oncology 2005;4 S89-S94.
Nizard et al., Anchoring Antibodies to Membranes Using a Diphtheria Toxin T Domain-ZZ Fusion Protein as a pH Sensitive Membrane Anchor, FEBs Letters 433:83-88, 1998.
Nizard et al., Prolonged Display or Rapid Internalization of the IgG-Binding Protein ZZ Anchored to the Surface of Cells Using the Diphtheria Toxin T Domain, Protein Engineering 14(6):439-446, 2001.
Non-final Office Action for U.S. Appl. No. 14/652,728 dated Jun. 28, 2017.
Ohuchi S., Cell-SELEX Technology, Biores Open Access. Dec. 2012;1(6):265-72.
Pan and Clawson, Primer-free aptamer selection using a random DNA library. Methods Mol Biol. 2010;629:367-83.
Parameswaran et al., A pyrosequencing-tailored nucleotide barcode design unveils opportunities for large-scale sample multiplexing, Nucleic Acids Res. 2007;35(19):e130. Epub Oct. 11, 2007.
Pipper et al., Clockwork PCR including sample preparation. Angewandte Chemie, 47(21), p. 3900-3904 (2008).
Pohl and Shih. Principle and applications of digital PCR. Expert Rev Mol Diagn. Jan. 2004;4(1):41-7.
Reff and Heard, A review of modifications to recombinant antibodies: attempt to increase efficacy in oncology applications. Critical Reviews in Oncology/Hematology, 40 (2001):25-35.
Reinartz et al., Massively parallel signature sequencing (MPSS) as a tool for in-depth quantitative gene expression profiling in all organisms, Brief Funct Genomic Proteomic. Feb. 2002;1(1):95-104.
Rieu S et al., Exosomes released during reticulocyte maturation bind to fibronectin via integrin alpha4betal. Eur J Biochem. Jan. 2000;267(2):583-90.

Robinson and Smyth, Moderated statistical tests for assessing differences in tag abundance, Bioinformatics. Nov. 1, 2007;23(21):2881-7. Epub Sep. 19, 2007.
Rokhlin et al., 5E10: a prostate-specific surface-reactive monoclonal antibody. Cancer. Lett. 1998 131:129-36).
Ruby et al., Large-scale sequencing reveals 21U-RNAs and additional microRNAs and endogenous siRNAs in C. elegans, Cell (2006) 127:1193-1207.
Ruff, et al, Real-Time PCR-Coupled CE-SELEX for DNA Aptamer Selection. ISRN Mol Biol. Aug. 8, 2012;2012:939083. doi: 10.5402/2012/939083. eCollection 2012.
Schorey and Bhatnagar. Exosome function: from tumor immunology to pathogen biology. Traffic. Jun. 2008;9(6):871-81.
Schuster, Next-generation sequencing transforms today's biology, Nature Methods 5:16-18 (2008).
Sefah et al., Development of DNA aptamers using Cell-SELEX. Nat Protoc. Jun. 2010;5(6):1169-85.
Shendure et al., Advanced sequencing technologies: methods and goals. Nat Rev Genet. May 2004;5(5):335-44.
Shigdar S et al. RNA aptamer against a cancer stem cell marker epithelial cell adhesion molecule. Cancer Sci. May 2011;102(5):991-8.
Soni G V and Meller A. Progress toward ultrafast DNA sequencing using solid-state nanopores. 2007 Clin Chem 53: 1996-2001.
Sood and Narang, A rapid and convenient synthesis of polythymidylic acid by the modified triester approach Nucleic Acids Res. Aug. 1977;4(8):2757-65.
Sproat, et al., New synthetic routes to synthons suitable for 2'-O-allyloligoribonucleotide assembly. Nucl. Acid Res. 19:733-738 (1991).
Srinivas et al. Aptamer functionalized Microgel Particles for Protein Detection, Anal. Chem. Dec. 1, 2011;83(23):9138-45.
Subramanian et al., Target-specific delivery of doxorubicin to retinoblastoma using epithelial cell adhesion molecule aptamer, Molecular Vision 2012; 18:2783-2795.
Suchanek, M., et al. (2005). Photo-leucine and photo-methionine allow identification of protein-protein interactions. Nat. Methods 2:261-267.
Thery et al., Membrane vesicles as conveyers of immune responses. Nat Rev Immunol. Aug. 2009;9(8):581-93.
Thiel WH et al., Nucleotide bias observed with a short SELEX RNA aptamer library. Nucleic Acid Ther. Aug. 2011;21(4):253-63.
Tombelli et al., Analytical applications of aptamers. Biosens Bioelectron. Jun. 15, 2005;20(12):2424-34.
Traverso et al., Detection of proximal colorectal cancers through analysis of faecal DNA, Lancet 2002; 359:403-404.
Troy et al., Understanding barriers to Borrelia burgdorferi dissemination during infection using massively parallel sequencing. Infect Immun. Jul. 2013;81(7):2347-57.
Tucker et al., Detection and plasma pharmacokinetics of an anti-vascular endothelial growth factor oligonucleotide-aptamer (NX1838) in rhesus monkeys. .J Chromatogr B Biomed Sci Appl. Sep. 10, 1999;732(1):203-12.
Tuerk & Gold, Systematic Evolution of Ligands by Exponential Enrichment: RNA Ligands to Bacteriophage T4 DNA Polymerase, Science 249:505-510, 1990.
Turner et al., Toward Clinical Proteomics on a Next-Generation Sequencing Platform, Anal. Chem. 2011, 83, 666-670.
Ulrich and Wrenger, Disease-specific biomarker discovery by aptamers. Cytometry A. Sep. 2009;75(9):727-33.
Ulrich H et al, DNA and RNA Aptamers: From Tools for Basic Research Towards Therapeutic Applications, Comb Chem High Throughput Screen. Sep. 2006;9(8):619-32.
Ulrich, H et al., In vitro selection of RNA molecules that displace cocaine from the membrane-bound nicotinic acetylcholine receptor, Proc. Natl. Acad. Sci. USA, vol. 95, pp. 14051-14056, Nov. 1998.
Unger M et al., Single-molecule fluorescence observed with mercury lamp illumination. Biotechniques 1999; 27(5):1008-14.
Velculescu et al., Gene Expression Analysis Goes Digital, Nature Biotechnology, 25(8):878-880 (2007).
Voelkerding et al., Next Generation Sequencing for Clinical Diagnostics—Principles and Application to Targeted Resequencing for Hypertrophic Cardiomyopathy, Journal of Molecular Diagnostics, 12(5):539 (2010).

(56) References Cited

OTHER PUBLICATIONS

Wang S et al., Delivery of antisense oligodeoxyribonucleotides against the human epidermal growth factor receptor into cultured KB cells with liposomes conjugated to folate via polyethylene glycol, Proc Natl Acad Sci U S A. Apr. 11, 1995;92(8):3318-22.
Wilbur and Lipman, Rapid similarity searches of nucleic acid and protein data banks. Proc Natl Acad Sci USA 80: 726-30 (1983).
Wu, Jie, et al. Identification, Characterization and Application of a G-Quadruplex Structured DNA Aptamer against Cancer Biomarker Protein Anterior Gradient Homolog 2. PloS ONE 7.9 (2012): e46393.
Ye et al., Generating aptamers by cell-SELEX for applications in molecular medicine. Int J Mol Sci. 2012;13(3):3341-53.
Zhang et al., Ultrasensitive Detection of Proteins by Amplification of Affinity Aptamers, Angew Chem Int Ed Engl. Feb. 27, 2006;45(10):1576-80.
Zhang Y et al., Aptamers selected by cell-SELEX for application in cancer studies. Bioanalysis. May 2010;2(5):907-18.
Ann-Charlotte, "Inflammatory mechanisms in preeclampsia," Pregnancy Hypertens. Apr. 2013;3(2):58.
Antonio Vizcaino et al., "The Proteomics Identifications (PRIDE) database and associated tools: status in 2013," Nucleic Acids Research, 2013, 41: D1063-D1069.
Audo et al., "Development and application of a next-generation sequencing (NGS) approach to detect known and novel gene defects underlying retinal diseases," Orphanet Journal of Rare Diseases, 2012, 7:8.
Avci-Adali et al., "Upgrading SELEX Technology by Using Lambda Exonuclease Digestion for Single-Stranded DNA Generation," Molecules, 2010, 15: 1-11.
Bastos-Amador et al., "Proteomic analysis of microvesicles from plasma of healthy donors reveals high individual variability," Journal of Proteomics, Apr. 2012, 75: 3574-3584.
Benner et al., "Evolution, language and analogy in functional genomics," Trends in Genetics, 2001, 17: 414-418.
Boyd et al., "Discovery of cyanovirin-N, a novel human immunodeficiency virus-inactivating protein that binds viral surface envelope glycoprotein gp120: potential applications to microbicide development," Antimicrob Agents Chemother, 1997, 41(7): 1521 1530.
Budayeva and Cristea, "A mass spectrometry view of stable and transient protein interactions," Adv Exp Med Biol, 2014, 806:263-82.
Cao et al., "Combining use of a panel of ssDNA aptamers in the detection of *Staphylococcus aureus*," Nucleic Acids Research, Jun. 2009, 37: 4621-4628.
Chen et al., "Aptamer-mediated nanoparticle-based protein labeling platform for intracellular imaging and tracking endocytosis dynamics," Anal Chem, Apr. 2012, 84(7):3099-110.
Chervenak et al., "Calorimetric Analysis of the Binding of Lectins with Overlapping Carbohydrate-Binding Ligand Specificities," Biochemistry, 1995, 34(16): 5685 5695.
Chromy et al., "Proteomic analysis of human serum by two-dimensional differential gel electrophoresis after depletion of high-abundant proteins," J Proteome Res, 2004, 3:1120-1127.
Cocucci and Meldolesi, "Ectosomes," Current Biology, 2011, 21: R940-R941.
Datta et al., "Discovery of Prognostic Biomarker Candidates of Lacunar Infarction by Quantitative Proteomics of Microvesicles Enriched Plasma," PLOS ONE, Apr. 2014, 9: e94663.
Espelund et al., "A simple method for generating single-stranded DNA probes labeled to high activities," Nucleic Acids Res, 1990, 18: 6157-6158.
Extended European Search Report in Application No. 15861137.6, dated Oct. 19, 2018, 20 pages.
Extended European Search Report in Application No. 16762466.7, dated Sep. 13, 2018, 9 pages.
Faoro and Ataide, "Ribonomic approaches to study the RNA-binding proteome," FEBS Lett, 2014, 588(20):3649-64.

Ferreira et al, "DNA aptamers against the MUC1 tumour marker: design of aptamer-antibody sandwich ELISA for the early diagnosis of epithelial tumours," Anal Bioanal Chem, Feb. 2008, 390(4):1039-50.
Final Rejection for U.S. Appl. No. 14/438,172 dated Sep. 28, 2017.
Gasser et al., "Characterisation and properties of ectosomes released by human polymorphonuclear neutrophils," Experimental cell Research, May 2003, 285: 243-257.
GenBank Accession No. LK799386.1. "Dicrocoelium dendriticum genome assembly D_dendriticum_Leon_v1_0_4, scaffold DDEL_scaffold0362290," Sep. 22, 2014 [Retrieved from the Internet Feb. 23, 2019] <https://www.ncbi.nlm.nih.gov/nuccore/LK799386.1. 1 page.
Grant et al., "A filtration-based protocol to isolate human Plasma Membrane-derived Vesicles and exosomes from blood plasma," J Immunol Methods, 2011, 371:143-51.
Gyllensten and Erlich, "Generation of single-stranded DNA by the polymerase chain reaction and its application to direct sequencing of the HLA-DQA locus," PNAS, 1988, 85: 7652-7656.
Halmer et al., "Matrix-assisted laser desorption/ionization mass spectrometry of DNA using photocleavable biotin," Biomol Eng, 1999, 16: 127-133.
Hammar et al., "Lectin effects on HIV-1 infectivity," Ann N Y Acad Sci, 1994, 724: 166-169.
Higuchi and Ochman, "Production of single-stranded DNA templates by exonuclease digestion following the polymerase chain reaction," Nucleic Acids Res, 1989, 17: 5865.
Illumina—Specification Sheet: Illumina® Sequencing Genome Analyzer System. 2007. Available at web.archive.org/web/20071011095455/http://www.illumina.com/downloads/GenomeAnalyzerSpecSheet.pdf. 4 pages.
Illumina Solexa presentation filed with the U.S. Securities and Exchange Commission. 2006. Available at www.sec.gov/Archives/edgar/data/913275/000095012306014236/0000950123-06-014236-index.htm. 47 pages.
Illumina® Systems & Software—Technology Spotlight; "DNA Sequencing with Solexa Technology" 2007. Available at: web.archive.org/web/20071011095600/http://www.illumina.com/downloads/SS_DNAsequencing.pdf. 4 pages.
Jones et al., "High-affinity aptamers to subtype 3a hepatitis C virus polymerase display genotypic specificity," Antimicrob. Agents Chemother, 2006, 50: 3019-3027.
Kaku et al., "Carbohydrate-binding specificity of the daffodil (*Narcissus pseudonarcissus*) and amaryllis (*Hippeastrum* hybr.) bulb lectins," Arch Biochem Biophys, 1990, 279(2): 298 304.
Kennel et al, "Serum exosomal protein profiling for the non-invasive detection of cardiac allograft rejection," J Heart Lung Transplant, 2018, 37: 409-417.
Kennel et al., "Serum Exosomal Protein Profiling for the Non-invasive Detection of Cardiac Allograft Rejection," Scientific Sessions and Resuscitation Science Symposium of the American-Heart-Association, Orlando, FL, Nov. 2015, Abstract 16438, 2 pages.
Kim et al., "Proteomic Analysis of Microvesicles Derived from Human Mesenchymal Stem Cells," Journal of Proteome Research, Dec. 2011, 11:839-849.
King et al., Meeting report: The Fourth International Symposium on the Intraductal Approach to Breast Cancer, Santa Barbara, California, Breast Cancer Res, Mar. 2005, 7(5): 198-204.
Lakhin et al., "Aptamers: Problems, Solutions and Prospects," Acta Naturae, 2013, 5: 34-43.
Li et al., "Detection of Protein Biomarkers using RNA Aptamer Microarrays and Enzymatically Amplified SPR Imaging", NIH Public Access, Author Manuscript, Anal Chem, 2007, 79(3): 1082-1088.
Liang et al., "Comparison of the methods for generating single-stranded DNA in SELEX," The Royal Society of Chemistry Journal, Jan. 2013, 1-3.
lllumina Corporation webpage: illumina and solexa-finding the answers together. 2007. Available at web .archive.org/web/20070603161104/http://www.illumina.com/pagesnm.ilmn?ID=222. 1 page.

(56) References Cited

OTHER PUBLICATIONS

Lutzelberger and Kjems, "Strategies to Identify Potential Therapeutic Target Sites in RNA," RNA Towards Medicine, Jan. 2006, 173: 243-259.
Martinez and Tuschl, "RISC is a 5' phosphomonoester-producing RNA endonuclease," Genes Dev, May 2004, 18(9):975-80.
May et al., "How Many Species are There on Earth?," Science, 1988, 241: 1441-1449.
Miguet et al., "Proteomic analysis of malignant lymphocyte membrane microparticles using double ionization coverage optimization," Proteomics, Jan. 2006, 6: 153-171.
Ng et al., "Multiplex Sequencing of Paired-End Ditags (MS-PECT): A Strategy for the Ultra-High-Throughput Analysis of Transcriptomes and Genomes," Nucleic Acids Research, Jul. 2006, 34(12): 1-10.
Non-final Office Action for U.S. Appl. No. 14/438,172 dated May 13, 2016.
Office Action in Australian Application No. 2013340414, dated Jul. 24, 2018, 4 pages.
Office Action in Korean Application No. 10-2015-7013515, dated Nov. 8, 2018, 9 pages (check with attorney on translation).
Office Action in U.S. Appl. No. 14/915,249, dated May 3, 2019, 28 pages.
Office Action in U.S. Appl. No. 15/528,417, dated Mar. 5, 2019, 16 pages.
Office Action in U.S. Appl. No. 15/557,010, dated May 24, 2019, 37 pages.
Ogawa, "Aptamer selection for the inhibition of cell adhesion with fibronectin as target," Bioorganic & Medicinal Chemistry Letters, 2004, 14: 4001-4004.
Oh et al., "Rapid, Efficient Aptamer Generation: Kinetic-Challenge Microfluidic SELEX," presented in the 12th Annual UC Systemwide Bioengineering Symposium, Jun. 13~15, 2011, Santa Barbara, U.S.A.
Olejnik et al., "Photocleavable affinity tags for isolation and detection of biomolecules," Methods Enzymol, 1998, 291: 135-154.
Olejnik et al., "Photocleavable biotin derivatives: a versatile approach for the isolation of biomolecules," PNAS, 1995, 16, 7590-7594.
Olejnik et al., "Photocleavable biotin phosphoramidite for 5'-end-labeling, affinity purification and phosphorylation of synthetic oligonucleotides," Nucleic Acids Res. 1996, 2, 361-366.
Paul et al., "Streptavidin-coated magnetic beads for DNA strand separation implicate a multitude of problems during cell-SELEX," Oligonucleotides, 2009, 19: 243-254.
Pisitkun et al., "Identification and proteomic profiling of exosomes in human urine," PNAS, 2004, 101:13368-13373.
Redman et al., "Review: Does size matter? Placental debris and the pathophysiology of pre-eclampsia," Placenta, 2012, 26: s48-s54.
Rood et al., "Comparison of three methods for isolation of urinary microvesicles to identify biomarkers of nephrotic syndrome," Kidney International, Aug. 2010, 78: 810-816.
Sadallah et al., "Erythrocyte-derived ectosomes have immunosuppressive properties," Journal of Leukocyte Biology, Nov. 2008, 84: 1316-1325.
Sadallah et al., "Microparticles (Ectosomes) Shed by Stored Human Platelets Downregulate Macrophages and Modify the Development of Dendritic Cells," The Journal of Immunology, Apr. 2011, 186: 6543-6552.
Shao et al., "Protein typing of circulating microvesicles allows real-time monitoring of glioblastoma therapy," Nat Med, 2012, 18: 1835-1840.
Svobodova et al., "Comparison of different methods for generation of single-stranded DNA for SELEX processes," Anal. Bioanal. Chem, 2012, 404: 835-842.
Tacheny et al., "Mass spectrometry-based identification of proteins interacting with nucleic acids," Journal of Proteomics, 2013, 94; 89-109.
Tang et al., "Chip-based genotyping by mass spectrometry," PNAS, 1999, 96: 10016-10020.

Tannetta et al., "OS045. Multi-dimensional protein identification technology analysis of syncytiotrophoblast vesicles released from perfused preeclampsia placentas," Cardiovascular Health, Jul. 2012, 2: 200-201.
Taylor, "Exosomes/microvesicles: mediators of cancer-associated immunosuppressive microenvironments," Semin lmmunopathol, 2011, 33: 441-454.
Vickenborg et al., "Aptamer based affinity labeling of proteins," Angew Chem Int, 2012, 51(36):9176-80.
Webster's Third New International Dictionary. 1993. Gove, eds. p. 344; definition of "carry out". 4 pages.
Wee et al., Argonaute Divides Its RNA Guide into Domains with Distinct Functions and RNA-Binding Properties,: Cell, 2012, 151(5):1055-1067
Williams and Bartel, "PCR product with strands of unequal length," Nucleic Acids Research, 1995, 23(20): 4220-4221.
Wu and Curran, "An allosteric synthetic DNA," Nucleic Acids Res, 1999, 27: 1512-1516.
Xiao et al., "Proteomic analysis of microvesicles in human saliva by gel electrophoresis with liquid chromatography-mass spectrometry," Analytica Chima Acta, Feb. 2012, 723: 61-67.
Zhang et al, "High throughput quantitative analysis of serum proteins using glycopeptide capture and liquid chromatography mass spectrometry," Mol Cell Proteomics, 2005, 4:144-155.
Office Action in Israeli Application No. 244236, dated Jan. 27, 2019, 8 pages (with English translation).
Office Action in Korean Application No. 10-2015-7013515, dated Jul. 22, 2019, 4 pages (with English translation).
BR Office Action in Brazilian Appln. No. BR112016004153-4, dated Dec. 26, 2019, 5 pages (with English translation).
CN Office Action for Chinese Application No. 200880120684.1, received Feb. 28, 2012, 17 pages (with English translation).
CN Office Action in Chinese Application No. 201380067130.0, dated Feb. 3, 2020, 17 pages (with English translation).
CN Patent application No. 200880120684.1, Notification of Reexamination, dated Feb. 14, 2016, 6 pages (English Translation).
CN Patent application No. 201310045505.5 (divisional of CN200880120684.1 ), First Office Action, dated Jun. 18, 2014, 11 pages (English Translation).
CN Patent application No. 201310045505.5, Second Office Action, dated Dec. 24, 2014, 9 pages (English Translation).
CN Patent application No. 201310045505.5, Third Office Action, dated Nov. 2, 2015, 10 pages.
Da Cunhua et al., "Bioinfotmatics construction of the human cell sutfaceome," Proceedings of the National Academy of Sciences of the United States of America, Sep. 2009, 106:16752-16757.
EP Patent application No. 08837175.2, Decision to Grant (European Patent No. 2209893) dated Oct. 24, 2013, 4 pages.
EP Patent application No. 08837175.2, Intention to Grant dated Feb. 15, 2013, 6 pages.
EP Patent application No. 08837175.2, Search Report dated Aug. 22, 2012, 6 pages.
EP Patent No. 2209893, Notice of Opposition to a European Patent dated Aug. 20, 2014, 71 pages.
EP Patent No. 2209893, Opposition Result (opposition rejected I patent upheld) dated Jun. 7, 2016, 1 page.
EP Patent No. 2209893, Summons to Attend Oral Proceedings re Opposition dated Jul. 16, 2015, 8 pages.
EP Patent No. 2209893, Supplemental Submission Re Opposition dated May 4, 2016, 11 pages.
Fan et al., "Illumina universal bead arrays," Methods Enzymol, 2006 410:57-73.
GenBank Accession No. AED05156 "Mouse IL-23 binding aptamer, SEQ ID No. 126," Dec. 1, 2017, 2 pages.
Henderson et al., "The Genomic and Proteomic Content of Cancer Cell-Derived. Exosomes," Frontiers in Oncology, Apr. 2012, 2(17):38, 9 pages.
Hoorn et al., "Prospects for urinary proteomics: Exosomes as a source of urinary biomarkers," Nephrology. Jun. 2005. 10(3):283-290.
IL Office Action in Israeli Appln. No, 269045, dated Sep. 1, 2020, 8 pages (with English translation).

(56) References Cited

OTHER PUBLICATIONS

IN Office Action in India Appln. No. 3376/DELNP/2015, dated Oct. 6, 2016, 11 pages (with English translation).
International Preliminary Report on Patentability in International Application No. PCT/US2015/062184, dated May 23, 2017, 8 pages.
International Preliminary Report on Patentability in International Application No. PCT/US2016/21632, dated Sep. 12, 2017, 7 pages.
International Search Report and Written Opinion in International Application No. PCT/US2016/21632, dated Aug. 22, 2016, 11 pages.
International Search Report for PCT/US11/26750, dated May 17, 2011, 3 pages.
JP Office Action in Japanese Appln. No. 2018-171131, dated Aug. 14, 2019, 12 pages (with English translation).
JP Patent application No. 2010-528482, Decision to Grant dated May 19, 2015.
JP Patent application No. 2010-528482, Notification of Reason(s) for Refusal dated Sep. 30, 2014,English translation at pp. 6-10.
Khambata-Ford et al. "Expression of Epiregulin and Amphiregulin and K-ras Mutation Status Predict Disease Control in Metastatic Colorectal Cancer Patients Treated With Cetuximab," Journal of Clinical Oncology, Aug. 2007, (25)22:3230-3237.
Kuypers et al., "On-line melting of double-stranded DNA for analysis of single-stranded DNA using capillary electrophoresis," J. Chromatogr. B Biomed. Appl. 1996, 675: 205-211.
Muralidharan-Chair et al., "Microvesicles: mediators of extracellular communication during cancer progression," Journal of Cell science, 2010, 123:1603-1611.
Solexa webpage "Advancing genetic analysis." 2005. Available at web.archive.org/web/20051224140319/http://www.solexa.com/wt/page/index, 1 page.
Tang et al,, "Selection of Aptamers for Molecular Recognition and Characterization of Cancer Cells," Anal. Chem., Jul. 2007, 79(13):4900-4907.
Taylor et al., "MicroRNA signatures of tumor-derived exosomes as diagnositic biomarkers of ovarian cancer," Gynecologic Oncology, Mar. 2008, 110:13-21.
Ulrich & Wrenger., "Disease-Specific Biomarker Discovery by Aptamers," Cytometry Part A, 2009, 75(9):727-733.
EP Office Action in European Appln. No. 13840121.1, dated Aug. 6, 2020, 4 pages.

Screening Scheme

| 5 | x | 20 | = | 100 |
|---|---|---|---|---|
| Detection Agents | | Capture Agents | | Combinations Screened |

Detection Agents:
- CD63
- CD9
- CD81
- B7H3
- EpCam

Capture Agents:
- CD9
- PSCA
- TNFR
- CD63 2X
- B7H3
- Rab IgG
- MFG-E8
- EpCam 2X
- CD63
- Rab
- IgG
- CD81
- STEAP
- PCSA
- PSMA
- 5T4
- CD24
- TMEM211

General vesicle biomarkers: CD9, CD63, CD81
Cell of Origin biomarkers: PSCA, MFG-E8, Rab, STEAP, PCSA, PSMA, 5T4, TMEM211
Cancer biomarkers: EpCam, B7H3, CD24
Control biomarkers: Rab IgG, IgG

FIG. 1C

SEQ ID NO. 3840

SEQ ID NO. 1

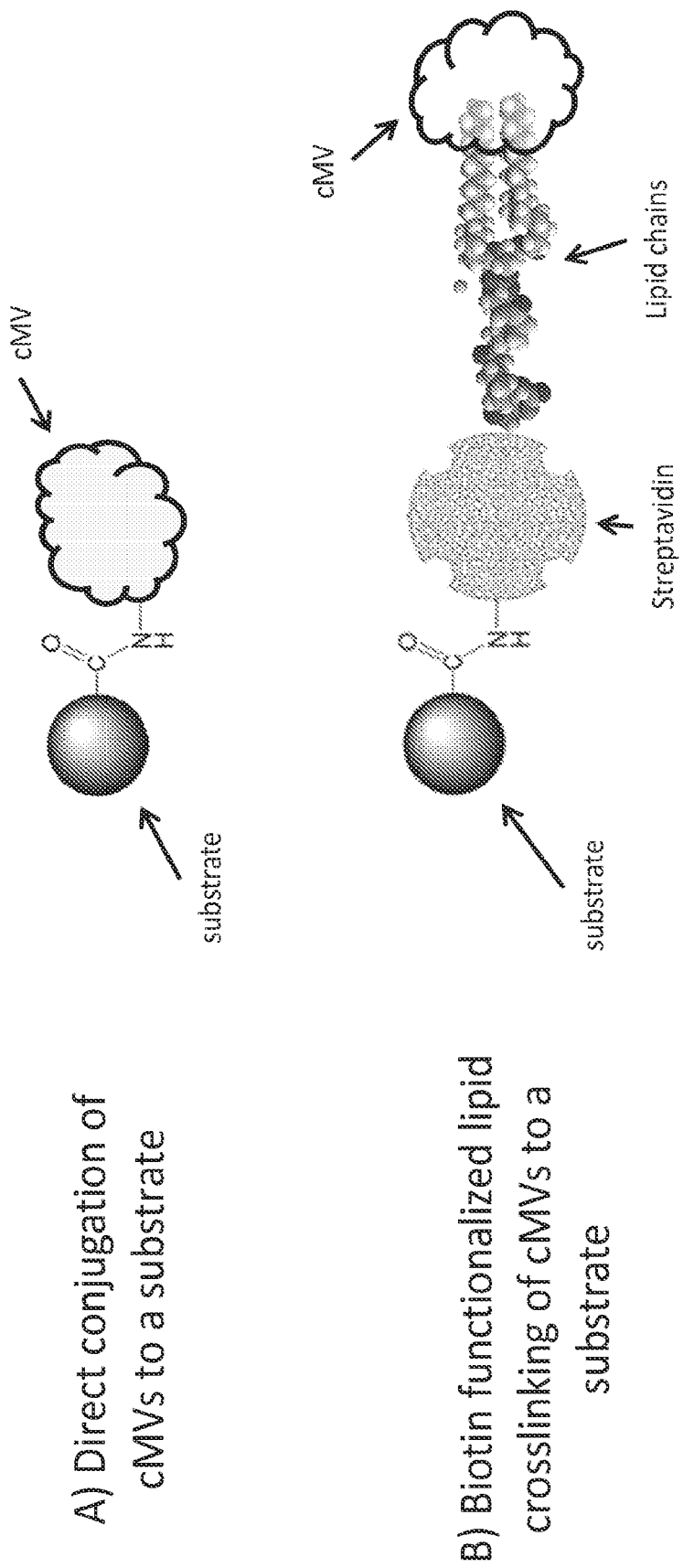
FIGS. 7A-B

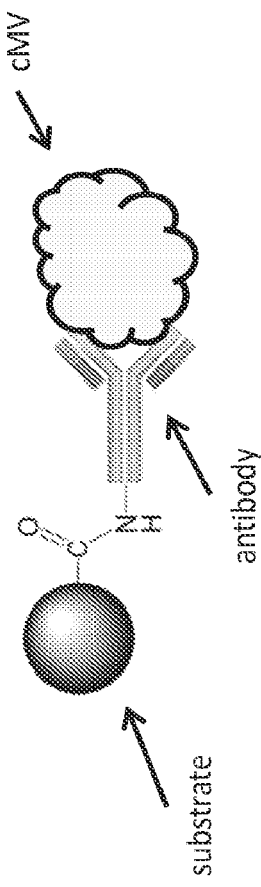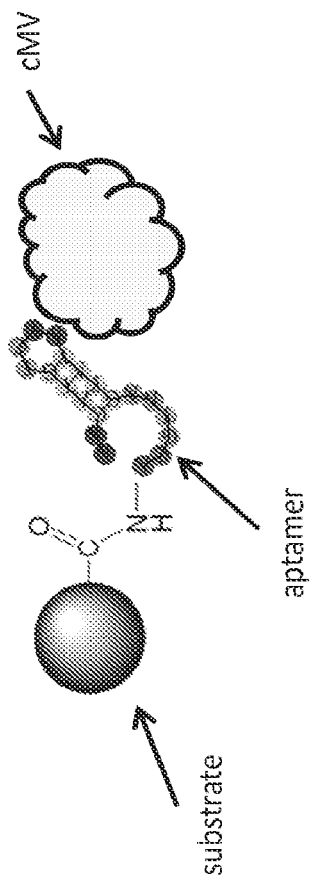
C) Immuno-precipitation of cMVs with cMV specific antibodies immobilized to a substrate
D) Immuno-precipitation of cMVs with cMV specific aptamer immobilized to a substrate
FIGs. 7C-D

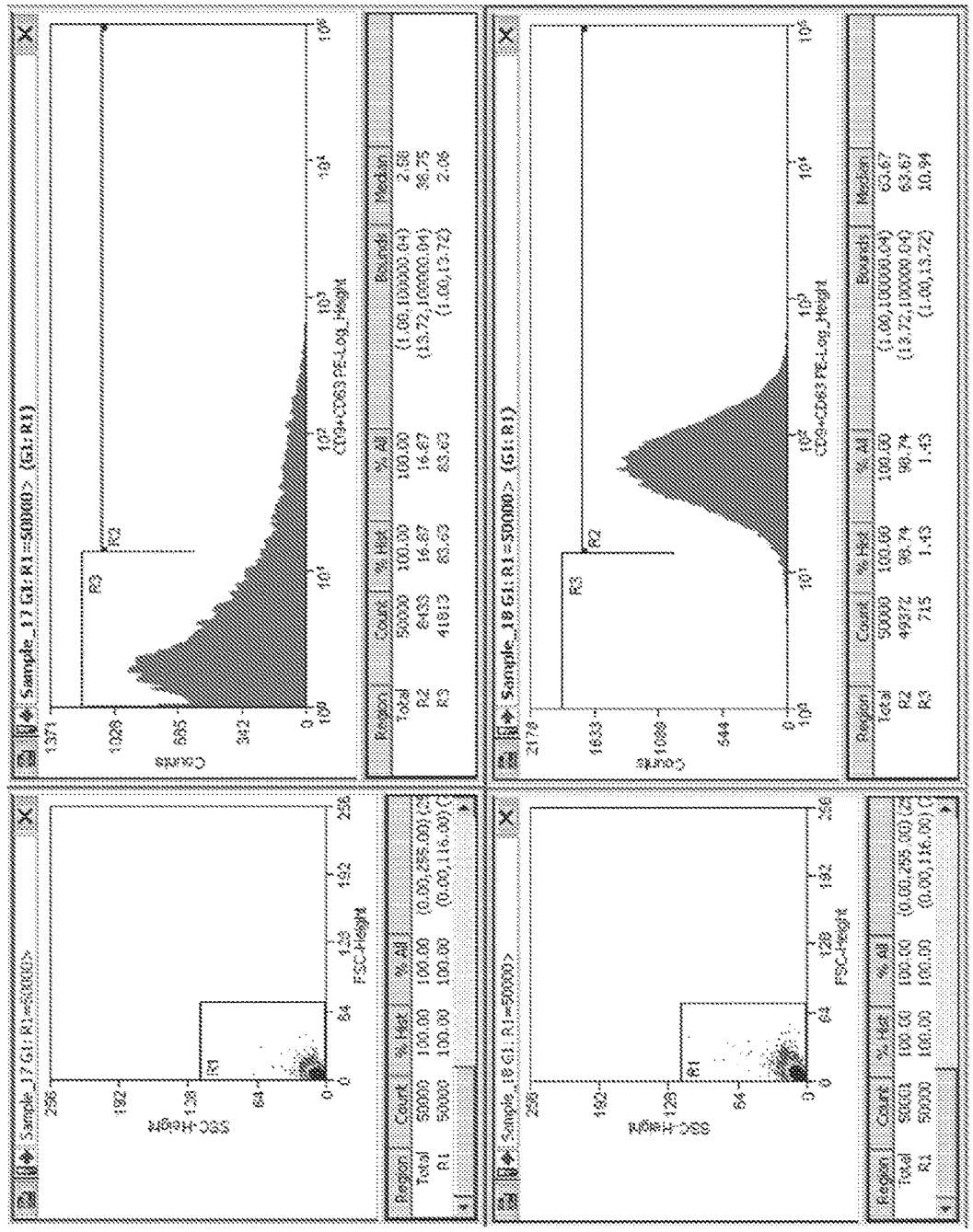
FIGs. 10C-D

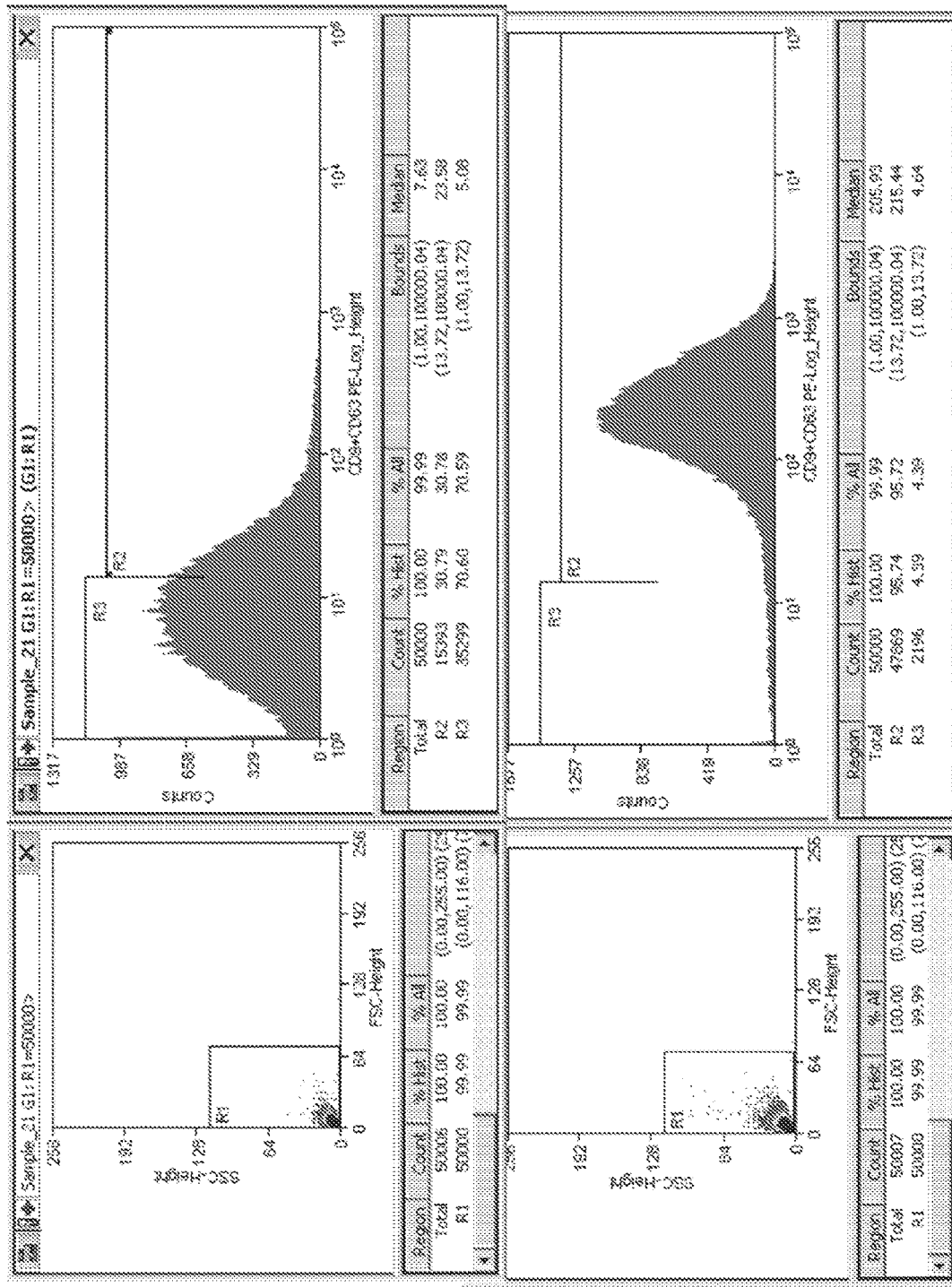
FIGS. 10E-F

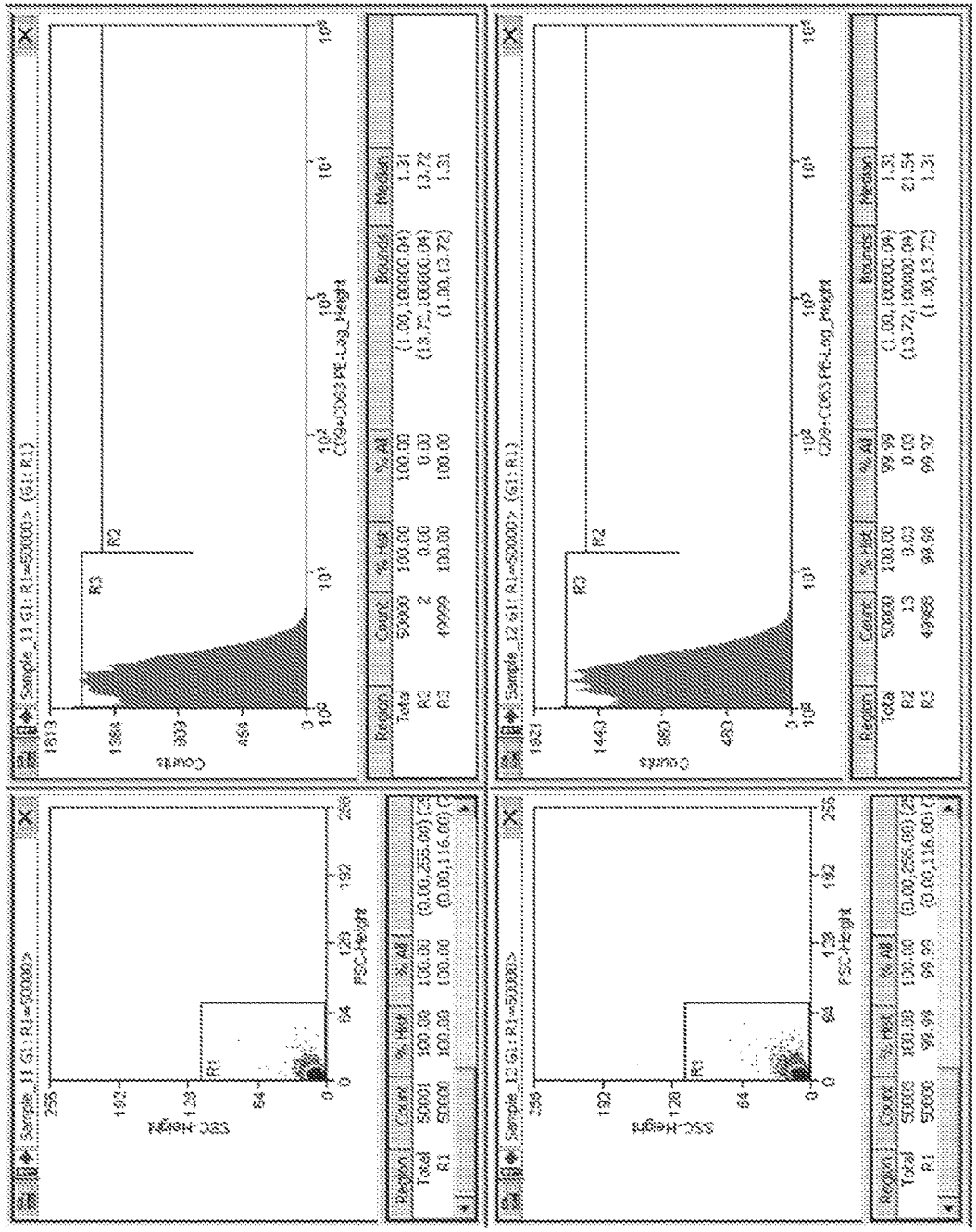
FIGS. 10K-L

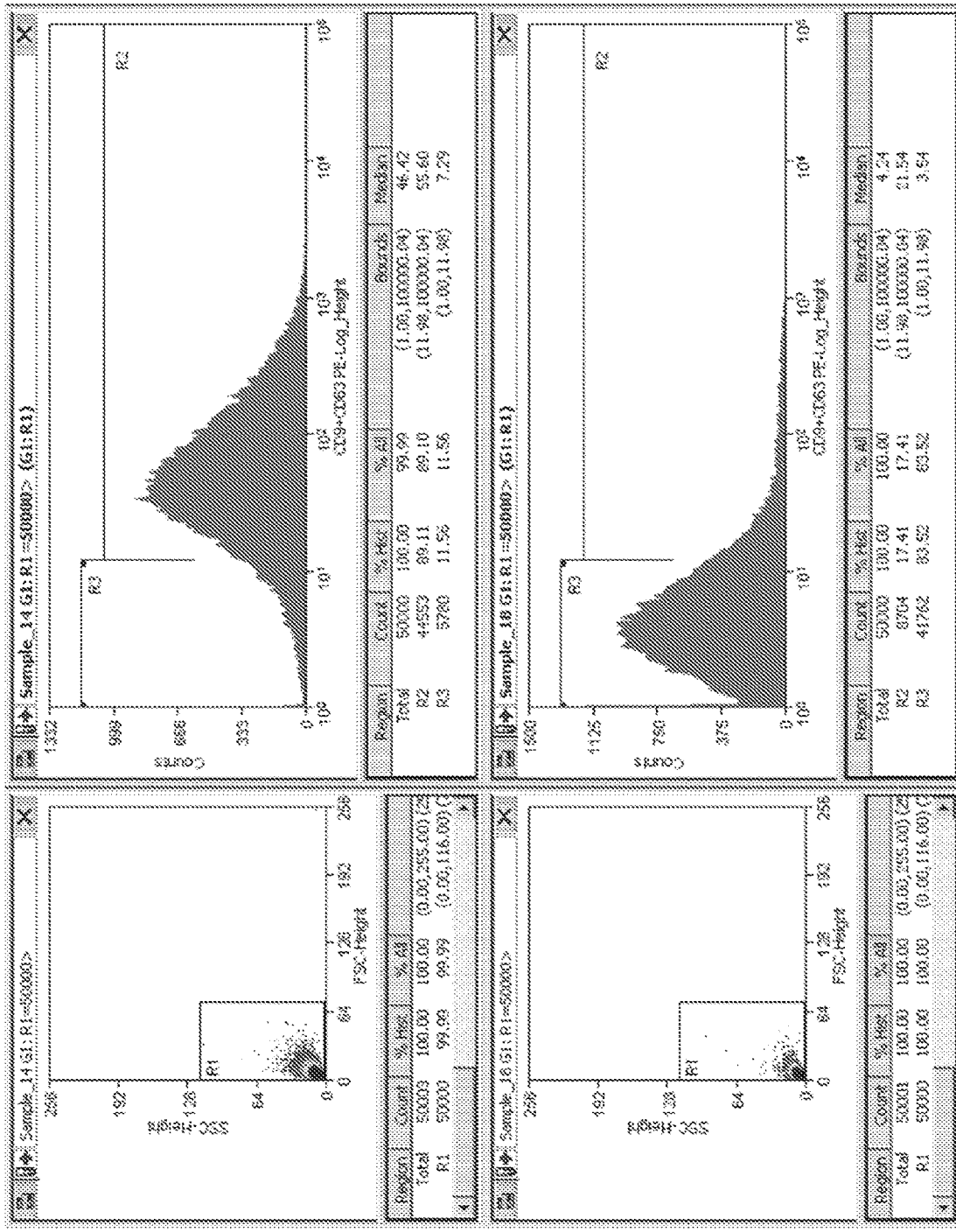
FIGs. 10M-N

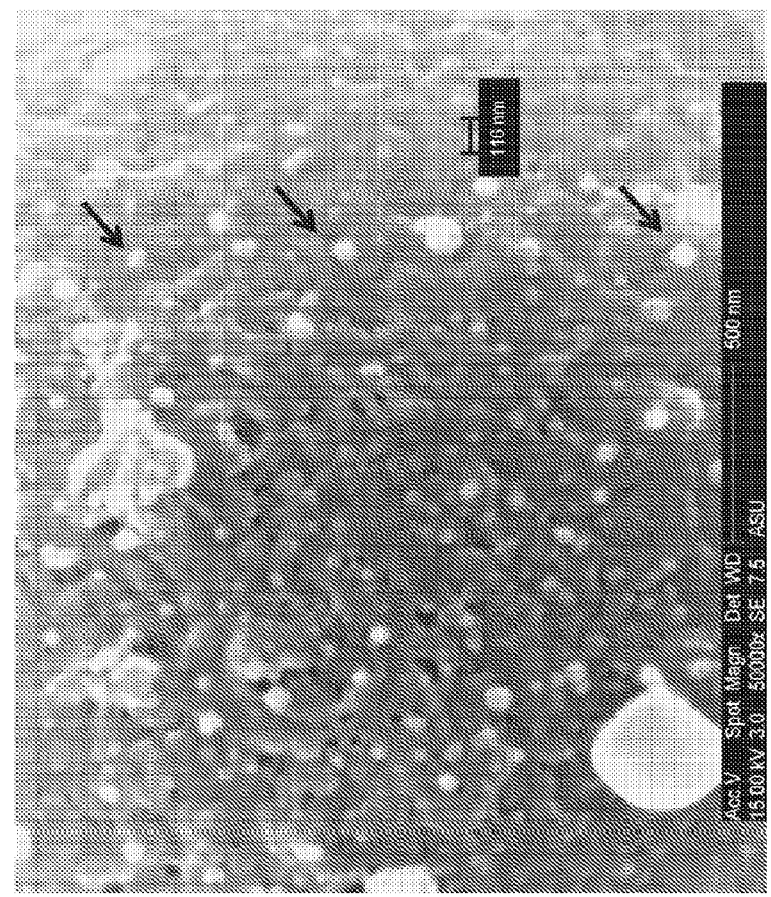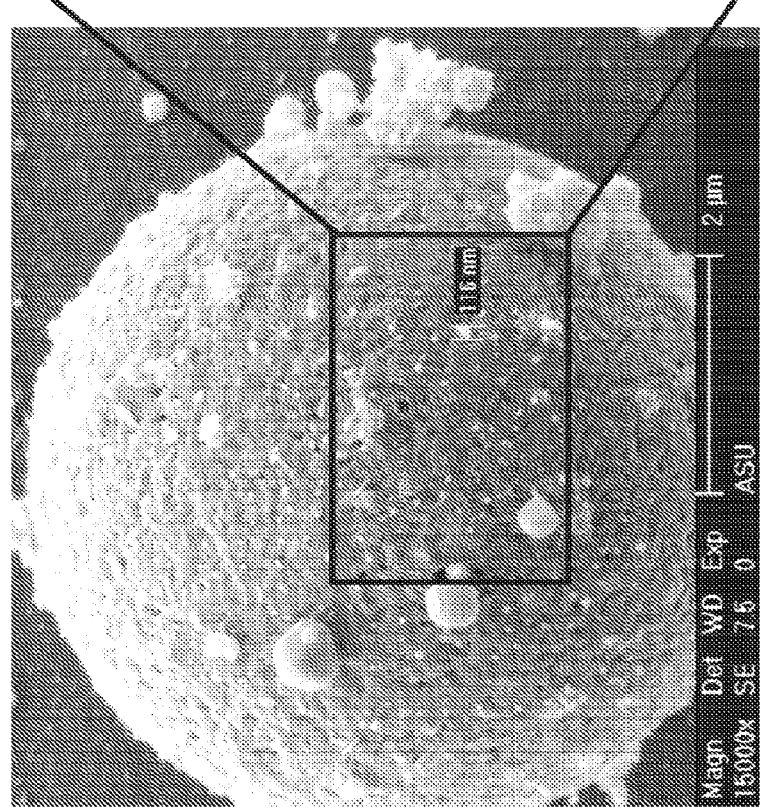
FIGs. 11B-C

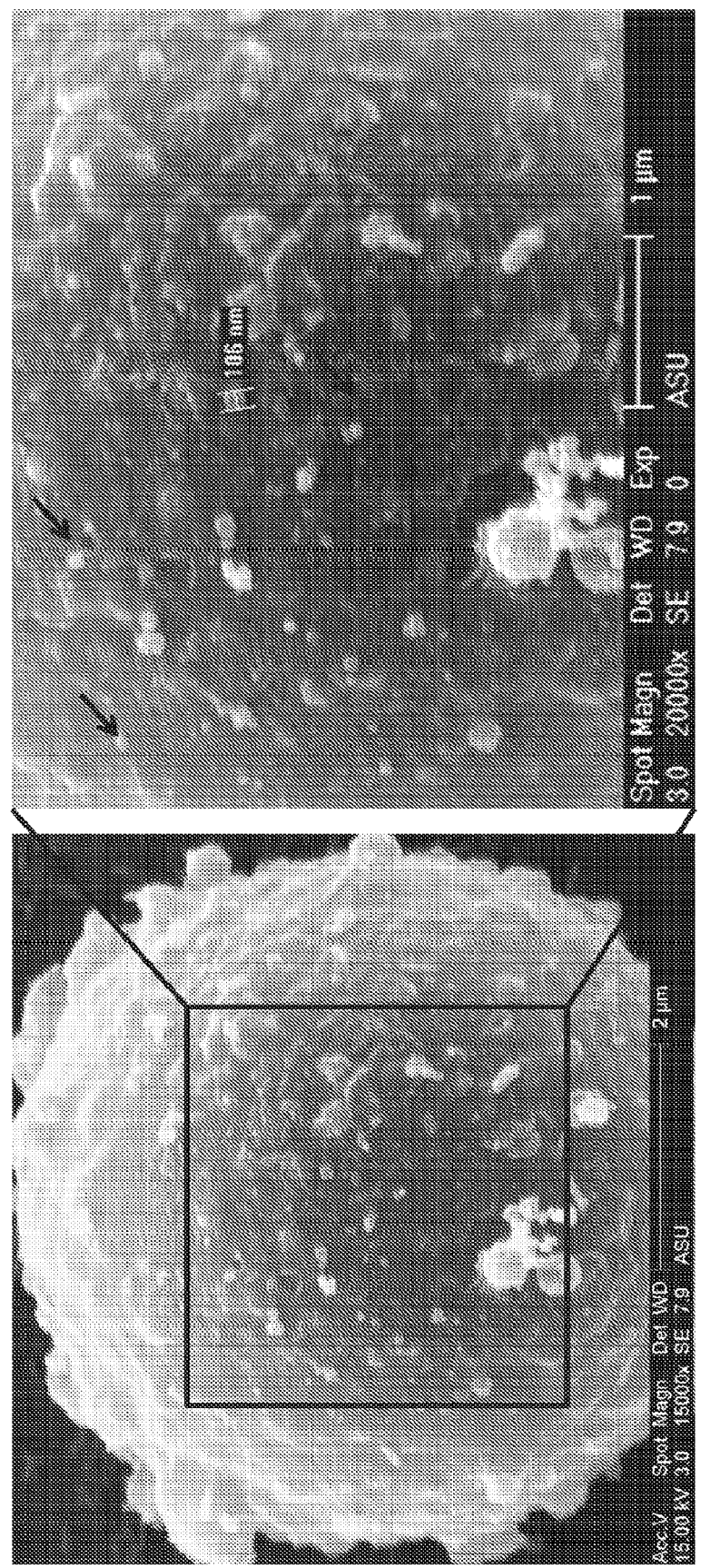
FIGS. 11D-E

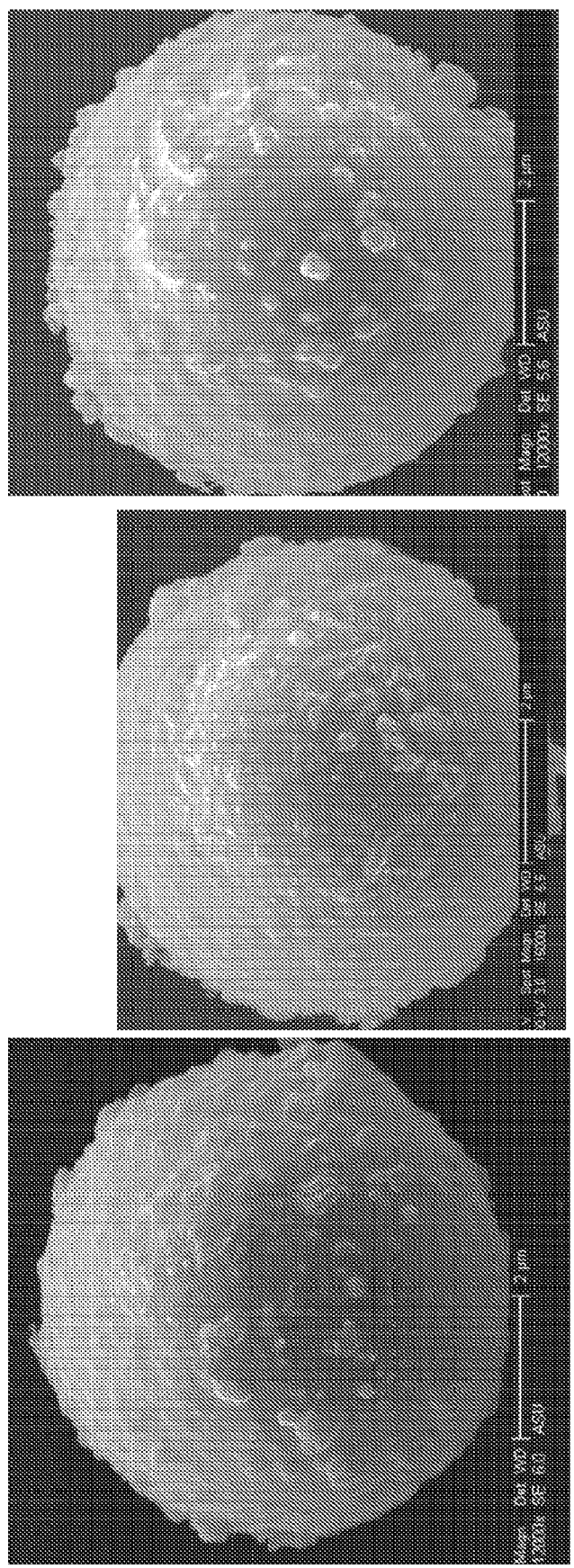
FIGs. 11F-H

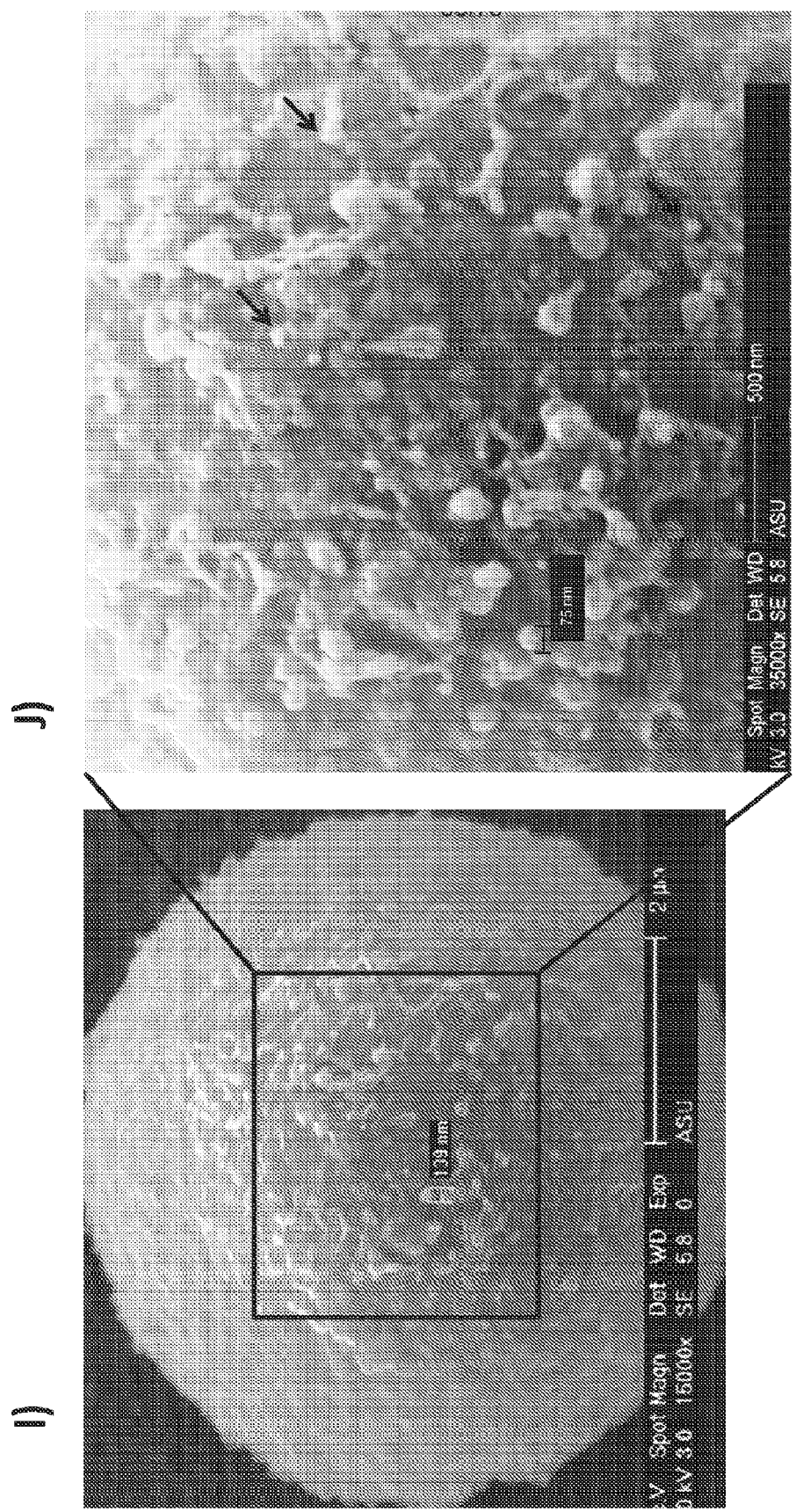
FIGs. 11I-J

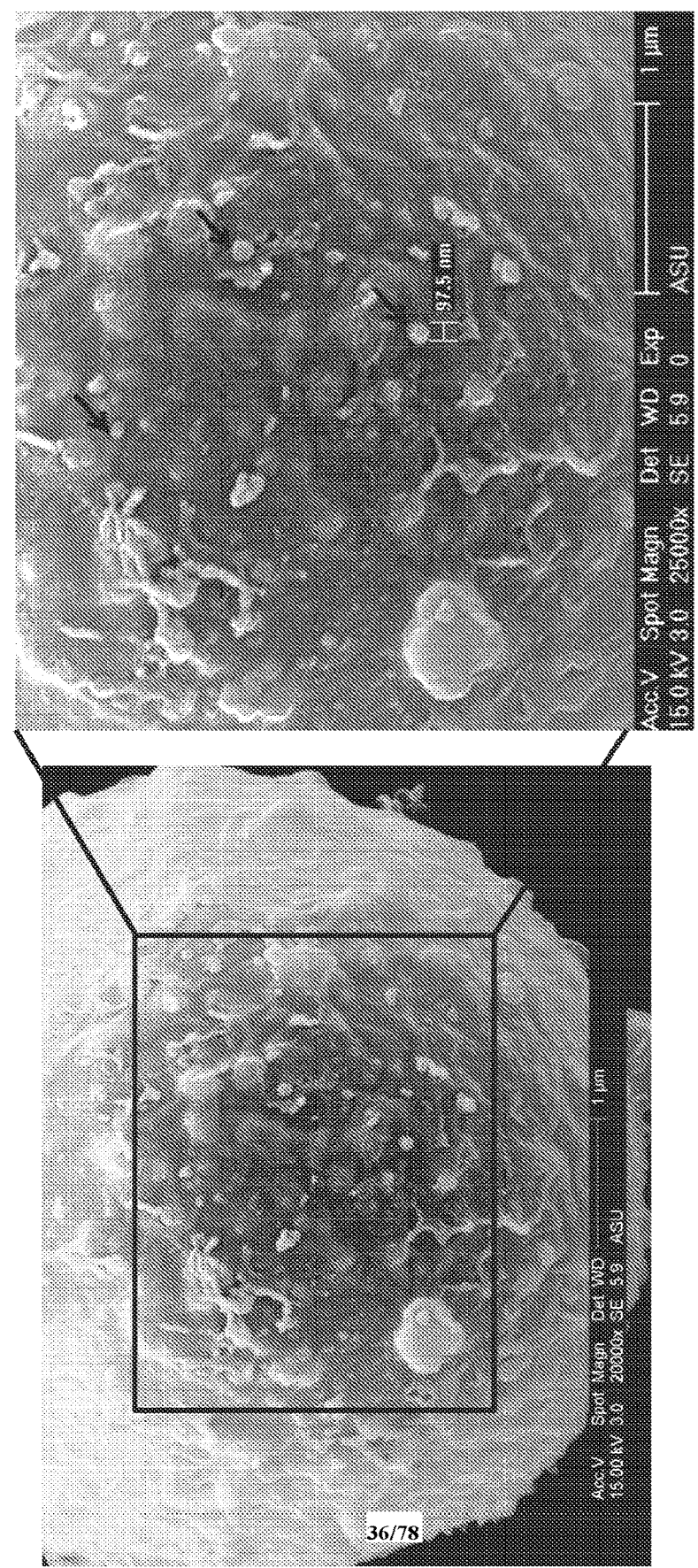
FIGS. 11K-L

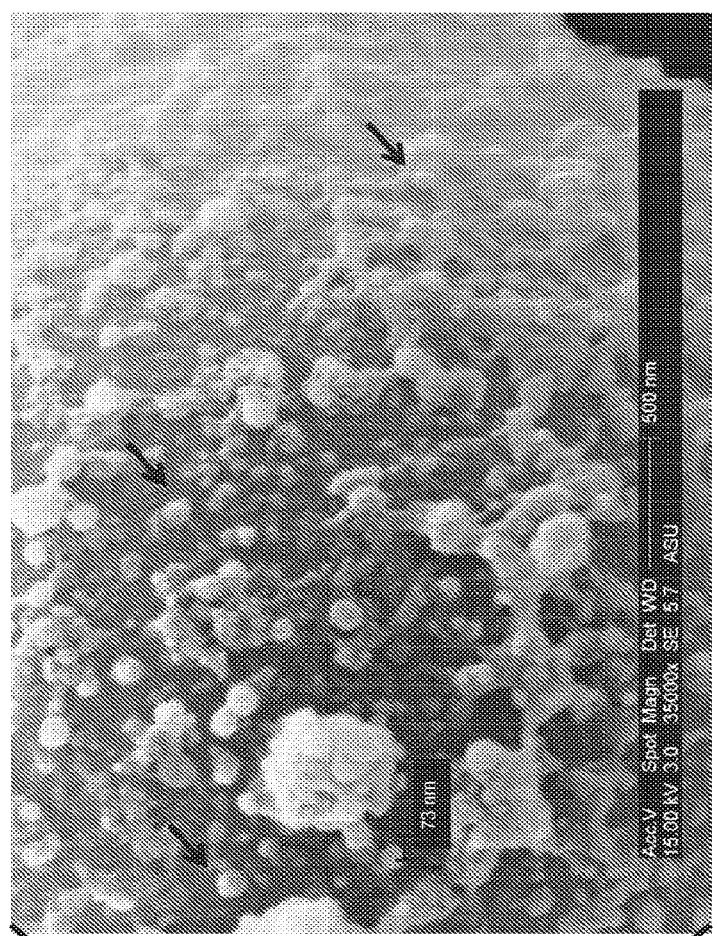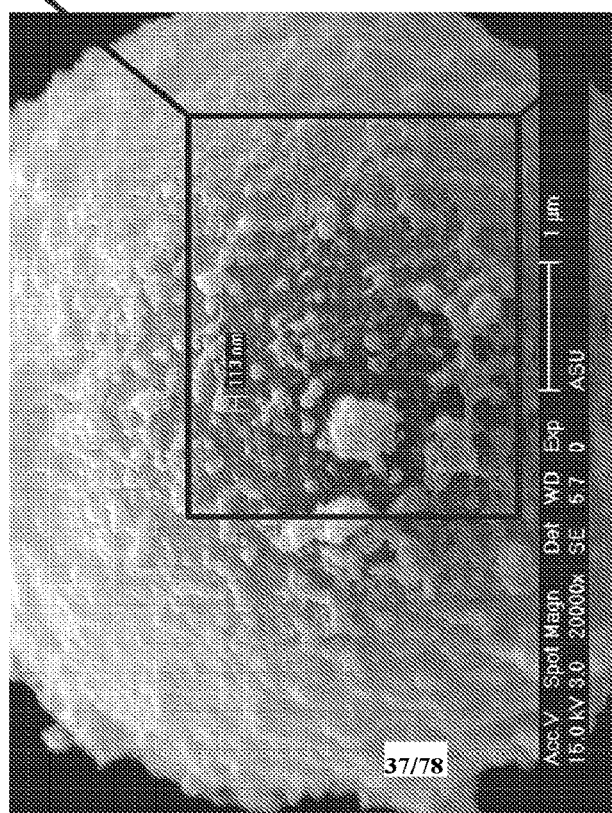
FIGS. 11M-N

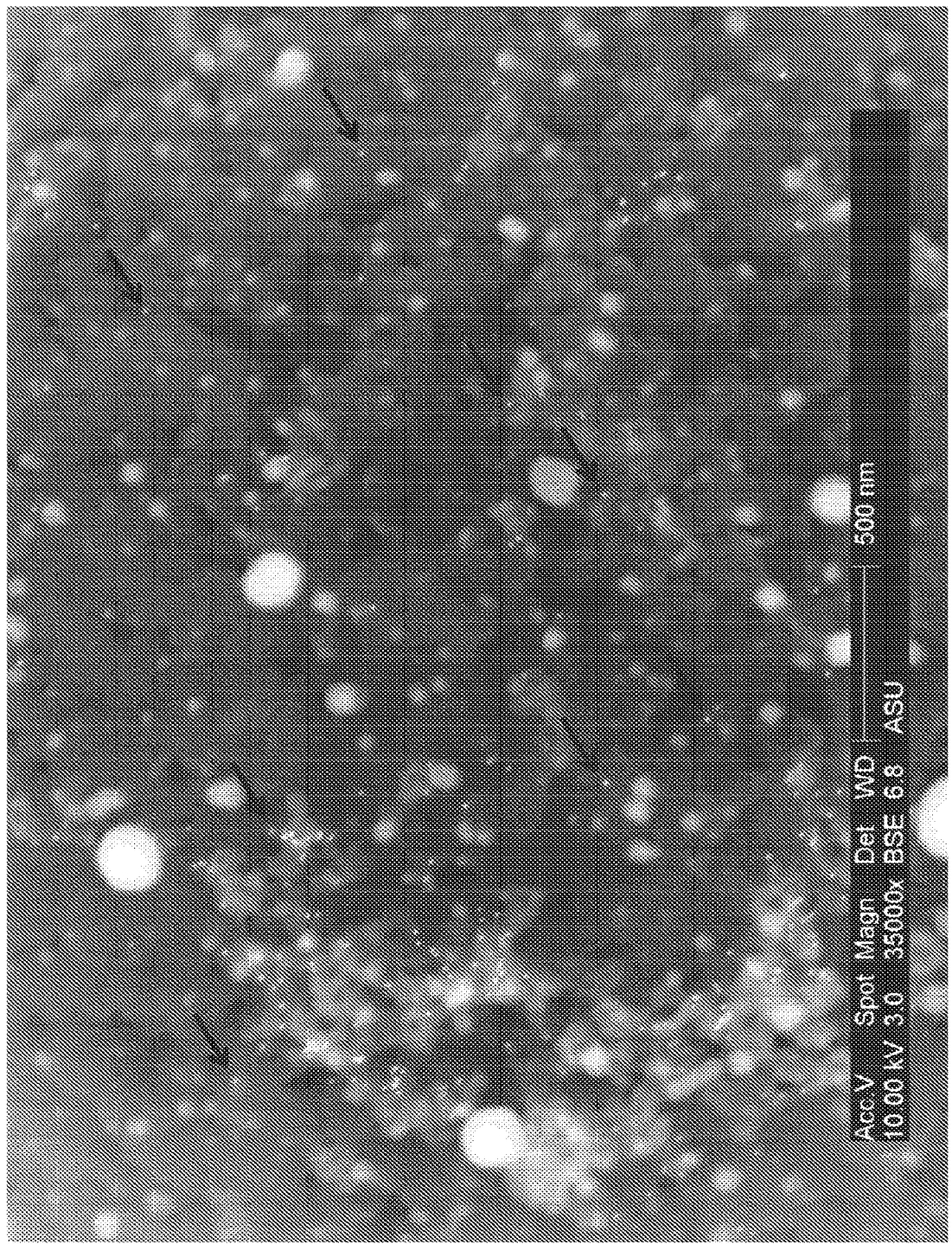

| | |
|---|---|
| Selection 1 | Ca1 > nCa1 > Ca2 > nCa2 > Ca3 > nCa3 > Ca4 > nCa4 > Ca5 > nCa5 > Ca6 > nCa6 > Ca7 > nCa7 > Ca8 |
| Selection 2 | Ca8 > nCa1 > Ca7 > nCa2 > Ca6 > nCa3 > Ca5 > nCa4 > Ca4 > nCa5 > Ca3 > nCa6 > Ca2 > nCa7 > Ca1 |
| Selection 3 | Ca8 > nCa7 > Ca7 > nCa6 > Ca6 > nCa5 > Ca5 > nCa4 > Ca4 > nCa3 > Ca3 > nCa2 > Ca2 > nCa1 > Ca1 |
| Selection 4 | Ca2 > nCa7 > Ca3 > nCa6 > Ca4 > nCa5 > Ca5 > nCa4 > Ca6 > nCa3 > Ca7 > nCa2 > Ca1 > nCa1 |
| Selection 5 | Ca7 > nCa2 > Ca5 > nCa4 > Ca3 > nCa6 > Ca1 > nCa1 > Ca8 > nCa3 > Ca6 > nCa5 > Ca4 > nCa7 > Ca2 |
| Selection 6 | Ca4 > nCa3 > Ca5 > nCa2 > Ca6 > nCa1 > Ca7 > nCa8 > Ca8 > nCa6 > Ca1 > nCa5 > Ca2 > nCa4 > Ca3 |
| Selection 7 | Ca5 > nCa1 > Ca3 > nCa3 > Ca1 > nCa2 > Ca2 > nCa8 > Ca6 > nCa4 > Ca4 > nCa5 > Ca2 > nCa7 > Ca7 |

FIG. 13B

A) CAR016 (SEQ ID NO. 230840)   B) CAR016_M13 (SEQ ID NO. 230883)

C) CAR016_M14 (SEQ ID NO. 230884)

D) CAR016_M23 (SEQ ID NO. 230893)

E) CAR016_M24 (SEQ ID NO. 230894)   F) CAR016_M25 (SEQ ID NO. 230895)

H) CAR016_M27 (SEQ ID NO. 230897)

G) CAR016_M26 (SEQ ID NO. 230896)

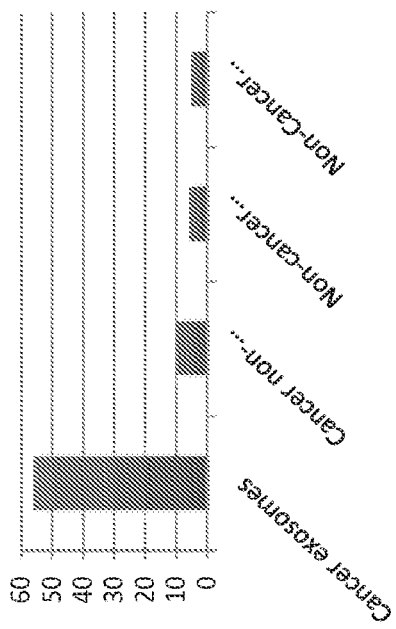
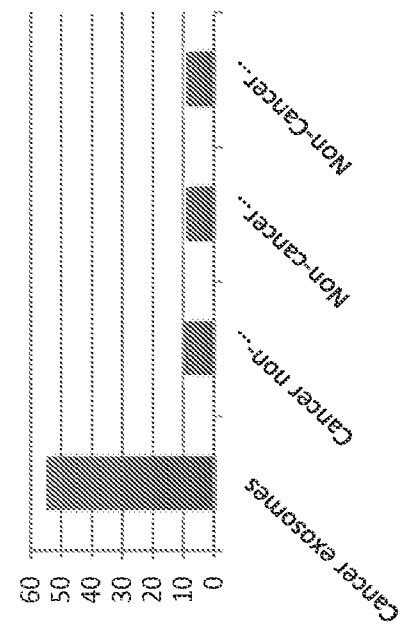
FIG. 23C

APTAMERS AND USES THEREOF

CROSS REFERENCE

This application is a continuation of U.S. application Ser. No. 14/438,172, filed Apr. 23, 2015, which is a U.S. national phase application under 35 U.S.C. § 371 of International Patent Application No. PCT/IB2013/003092, filed Oct. 23, 2013, which claims the benefit of U.S. Provisional Patent Application Nos. 61/717,566, filed Oct. 23, 2012; 61/731,419, filed Nov. 29, 2012; 61/735,915, filed Dec. 11, 2012; 61/748,437, filed Jan. 2, 2013; 61/749,773, filed Jan. 7, 2013; 61/750,331, filed Jan. 8, 2013; 61/754,471, filed Jan. 18, 2013; 61/767,131, filed Feb. 20, 2013; 61/769,064, filed Feb. 25, 2013; 61/805,365, filed Mar. 26, 2013; 61/808,144, filed Apr. 3, 2013; 61/820,419, filed May 7, 2013; 61/826,957, filed May 23, 2013; 61/838,762, filed Jun. 24, 2013; 61/843,256, filed Jul. 5, 2013; 61/862,809, filed Aug. 6, 2013; 61/863,828, filed Aug. 8, 2013; 61/866,014, filed Aug. 14, 2013; 61/867,978, filed Aug. 20, 2013; 61/871,107, filed Aug. 28, 2013; and 61/874,621, filed Sep. 6, 2013; all of which applications are incorporated herein by reference in their entirety.

SEQUENCE LISTING SUBMITTED VIA EFS-WEB

The entire content of the following electronic submission of the sequence listing via the USPTO EFS-WEB server, as authorized and set forth in MPEP § 1730 II.B.2(a), is incorporated herein by reference in its entirety for all purposes. The sequence listing is within the electronically filed text file that is identified as follows:

File Name: seq_listing_14438172.txt
Date of Creation: Aug. 18, 2015
Size (bytes): 95,427,070 bytes

BACKGROUND OF THE INVENTION

The invention relates generally to the field of aptamers capable of binding to microvesicle surface antigens, which are useful as therapeutics in and diagnostics of cancer and/or other diseases or disorders in which microvesicles implicated. The invention further relates to materials and methods for the administration of aptamers capable of binding to microvesicles. The microvesicles may be derived from cells indicative of cancer.

Aptamers are nucleic acid molecules having specific binding affinity to molecules through interactions other than classic Watson-Crick base pairing.

Aptamers, like peptides generated by phage display or monoclonal antibodies ("mAbs"), are capable of specifically binding to selected targets and modulating the target's activity, e.g., through binding aptamers may block their target's ability to function. Created by an in vitro selection process from pools of random sequence oligonucleotides, aptamers have been generated for over 100 proteins including growth factors, transcription factors, enzymes, immunoglobulins, and receptors. A typical aptamer is 10-15 kDa in size (30-45 nucleotides), binds its target with sub-nanomolar affinity, and discriminates against closely related targets (e.g., aptamers will typically not bind other proteins from the same gene family) A series of structural studies have shown that aptamers are capable of using the same types of binding interactions (e.g., hydrogen bonding, electrostatic complementarity, hydrophobic contacts, steric exclusion) that drive affinity and specificity in antibody-antigen complexes.

Aptamers have a number of desirable characteristics for use as therapeutics and diagnostics including high specificity and affinity, biological efficacy, and excellent pharmacokinetic properties. In addition, they offer specific competitive advantages over antibodies and other protein biologics, for example:

Speed and control. Aptamers are produced by an entirely in vitro process, allowing for the rapid generation of initial leads, including therapeutic leads. In vitro selection allows the specificity and affinity of the aptamer to be tightly controlled and allows the generation of leads, including leads against both toxic and non-immunogenic targets.

Toxicity and Immunogenicity. Aptamers as a class have demonstrated little or no toxicity or immunogenicity. In chronic dosing of rats or woodchucks with high levels of aptamer (10 mg/kg daily for 90 days), no toxicity is observed by any clinical, cellular, or biochemical measure. Whereas the efficacy of many monoclonal antibodies can be severely limited by immune response to antibodies themselves, it is extremely difficult to elicit antibodies to aptamers most likely because aptamers cannot be presented by T-cells via the MHC and the immune response is generally trained not to recognize nucleic acid fragments.

Administration. Whereas most currently approved antibody therapeutics are administered by intravenous infusion (typically over 2-4 hours), aptamers can be administered by subcutaneous injection (aptamer bioavailability via subcutaneous administration is >80% in monkey studies (Tucker et al., J. Chromatography B. 732: 203-212, 1999)). This difference is primarily due to the comparatively low solubility and thus large volumes necessary for most therapeutic mAbs. With good solubility (>150 mg/mL) and comparatively low molecular weight (aptamer: 10-50 kDa; antibody: 150 kDa), a weekly dose of aptamer may be delivered by injection in a volume of less than 0.5 mL. In addition, the small size of aptamers allows them to penetrate into areas of conformational constrictions that do not allow for antibodies or antibody fragments to penetrate, presenting yet another advantage of aptamer-based therapeutics or prophylaxis.

Scalability and cost. Aptamers are chemically synthesized and are readily scaled as needed to meet production demand for diagnostic or therapeutic applications. Whereas difficulties in scaling production are currently limiting the availability of some biologics and the capital cost of a large-scale protein production plant is enormous, a single large-scale oligonucleotide synthesizer can produce upwards of 100 kg/year and requires a relatively modest initial investment. The current cost of goods for aptamer synthesis at the kilogram scale is estimated at $100/g, comparable to that for highly optimized antibodies.

Stability. Aptamers are chemically robust. They are intrinsically adapted to regain activity following exposure to factors such as heat and denaturants and can be stored for extended periods (>1 yr) at room temperature as lyophilized powders.

INCORPORATION BY REFERENCE

All publications, patents and patent applications mentioned in this specification are herein incorporated by reference to the same extent as if each individual publication,

SUMMARY OF THE INVENTION

Compositions and methods of the invention provide aptamers that bind biomarkers of interest such as microvesicle surface antigens or functional fragments of microvesicle surface antigens. In various embodiments, aptamers of the invention are used in diagnostic, prognostic, or theranostic processes to screen a biological sample for the presence or levels of microvesicle surface antigens determined to provide a diagnostic, prognostic, or theranostic readout. The diagnosis, prognosis, or theranosis may be related to cancer. The invention also provides methods and composition to facilitate aptamer library screening and aptamer detection methods.

In an aspect, the invention provides an aptamer that binds to a microvesicle, comprising a nucleic acid sequence that is at least 50, 55, 60, 65, 70, 75, 80, 85, 90, 95, 96, 97, 98, 99 or 100 percent homologous of any of: a) SEQ ID NOs. 230900-230903, 230908, 230913-230927 or a variable sequence of any preceding sequence as described in Table 18; orb) a functional fragment of any preceding sequence. The aptamer may comprise any of SEQ ID NOs. 230900-230903, 230908, 230913-230927, or a functional fragment thereof. The functional fragment may comprise any fragment that retains ability to bind the aptamer target, including without limitation a "Variable Sequence" region as indicated in Table 18. In some embodiments, the microvesicle is shed from a prostate-cancer cell.

In another aspect, the invention provides an aptamer that binds to a microvesicle, comprising a nucleic acid sequence that is at least 50, 55, 60, 65, 70, 75, 80, 85, 90, 95, 96, 97, 98, 99 or 100 percent homologous of any of: a) SEQ ID NOs. 231018-231031 or a variable sequence thereof as described in Table 23; b) SEQ ID NOs. 231032-231051 or a variable sequence thereof as described in Table 24; c) SEQ ID NOs. 231032-241535; or d) a functional fragment of any preceding sequence. The aptamer may comprise any of SEQ ID NOs. 231018-231031, or a functional fragment thereof. The aptamer may also comprise any of SEQ ID NOs. 231032-231051, or a functional fragment thereof. The functional fragment may comprise any fragment that retains ability to bind the aptamer target, including without limitation a "Variable Sequence" region as indicated in any of Tables 23-24. In some embodiments, the microvesicle is shed from a breast-cancer cell.

In still another aspect, the invention provides an aptamer that binds to an epithelial cell adhesion molecule (EpCAM) protein, comprising a nucleic acid sequence that is at least 50, 55, 60, 65, 70, 75, 80, 85, 90, 95, 96, 97, 98, 99 or 100 percent homologous of any of: a) SEQ ID NOs. 1-230810; b) SEQ ID NOs. 230822-230899, 230904-230907, 230909-230911 or a variable sequence of any thereof as described in Tables 11, 12, 13, 15; or c) a functional fragment of any preceding sequence. The aptamer may comprise any of Aptamer4 (SEQ ID NO. 1), Oligo6 (SEQ ID NO. 230810), Oligo4B (SEQ ID NO. 183132), CAR003 (SEQ ID NO. 230822 or SEQ ID NO. 230823), CAR016 (SEQ ID NO. 230840), or a functional fragment thereof. The aptamer can be from any of Tables 5, 6, 7, 8, 11, 12, 13, 15, 16, or a functional fragment thereof. The functional fragment may comprise any fragment that retains ability to bind the aptamer target, including without limitation a "Variable Sequence" region as indicated in any of Tables 11, 12, 13, 15, or a functional fragment thereof. In some embodiments, the aptamer has the ability to modulate EpCAM signal transduction in vitro. Further, the aptamer may have the ability to modulate EpCAM signal transduction in vivo.

In yet another aspect, the invention provides an aptamer that binds to a prostate specific membrane antigen (PSMA) protein, comprising a nucleic acid sequence that is at least 50, 55, 60, 65, 70, 75, 80, 85, 90, 95, 96, 97, 98, 99 or 100 percent homologous of any of: a) SEQ ID NOs. 230932-230935 or a variable sequence thereof as described in Table 20; orb) a functional fragment of any preceding sequence.

The aptamers of the invention may be identified herein in the form of DNA or RNA. Unless otherwise specified, one of skill in the art will appreciate that an aptamer may generally be synthesized in various forms of nucleic acid. The aptamers may also carry various chemical modifications and remain within the scope of the invention.

In some embodiments, an aptamer of the invention is modified to comprise at least one chemical modification. The modification may include without limitation a chemical substitution at a sugar position; a chemical substitution at a phosphate position; and a chemical substitution at a base position of the nucleic acid. In some embodiments, the modification is selected from the group consisting of: biotinylation, incorporation of a fluorescent label, incorporation of a modified nucleotide, a 2'-modified pyrimidine, 3' capping, conjugation to an amine linker, conjugation to a high molecular weight, non-immunogenic compound, conjugation to a lipophilic compound, conjugation to a drug, conjugation to a cytotoxic moiety, and labeling with a radioisotope, or other modification as disclosed herein. The position of the modification can be varied as desired. For example, the biotinylation, fluorescent label, or cytotoxic moiety can be conjugated to the 5' end of the aptamer. The biotinylation, fluorescent label, or cytotoxic moiety can also be conjugated to the 3' end of the aptamer.

In some embodiments, the cytotoxic moiety is encapsulated in a nanoparticle. The nanoparticle can be selected from the group consisting of: liposomes, dendrimers, and comb polymers. In other embodiments, the cytotoxic moiety comprises a small molecule cytotoxic moiety. The small molecule cytotoxic moiety can include without limtation vinblastine hydrazide, calicheamicin, vinca alkaloid, a ciyptophycin, a tubulysin, dolastatin-10, dolastatin-15, auristatin E, rhizoxin, epothilone B, epithilone D, taxoids, maytansinoids and any variants and derivatives thereof. In still other embodiments, the cytotoxic moiety comprises a protein toxin. For example, the protein toxin can be selected from the group consisting of diphtheria toxin, ricin, abrin, gelonin, and *Pseudomonas* exotoxin A. Non-immunogenic, high molecular weight compounds for use with the invention include polyalkylene glycols, e.g., polyethylene glycol. Appropriate radioisotopes include yttrium-90, indium-111, iodine-131, lutetium-177, copper-67, rhenium-186, rhenium-188, bismuth-212, bismuth-213, astatine-211, and actinium-225. The aptamer may be labeled with a gamma-emitting radioisotope.

In some embodiments of the invention, an active agent is conjugated to the aptamer. For example, the active agent may be a therapeutic agent or a diagnostic agent. The therapeutic agent may be selected from the group consisting of tyrosine kinase inhibitors, kinase inhibitors, biologically active agents, biological molecules, radionuclides, adriamycin, ansamycin antibiotics, asparaginase, bleomycin, busulphan, cisplatin, carboplatin, carmustine, capecotabine, chlorambucil, cytarabine, cyclophosphamide, camptothecin, dacarbazine, dactinomycin, daunorubicin, dexrazoxane, docetaxel, doxorubicin, etoposide, epothilones, floxuridine, fludarabine, fluorouracil, gemcitabine, hydroxyurea, idarubicin, ifosfamide, irinotecan, lomustine, mechlorethamine, mercaptopurine, melphalan, methotrexate, rapamycin (sirolimus), mitomycin, mitotane, mitoxantrone, nitrosurea, paclitaxel, pamidronate, pentostatin, plicamycin, procarbazine, rituximab, streptozocin, teniposide, thioguanine, thiotepa, taxanes, vinblastine, vincristine, vinorelbine, taxol, combretastatins, discodermolides, transplatinum, anti-vascular endothelial growth factor compounds ("anti-VEGFs"), anti-epidermal growth factor receptor compounds ("anti-EGFRs"), 5-fluorouracil and derivatives, radionuclides, polypeptide toxins, apoptosis inducers, therapy sensitizers, enzyme or active fragment thereof, and combinations thereof.

The invention further provides a pharmaceutical composition comprising a therapeutically effective amount of the aptamer described above or a salt thereof, and a pharmaceutically acceptable carrier or diluent. The invention also provides a pharmaceutical composition comprising a therapeutically effective amount of the aptamer or a salt thereof, and a pharmaceutically acceptable carrier or diluent. Relatedly, the invention provides a method of treating or ameliorating a disease or disorder, comprising administering the pharmaceutical composition to a subject in need thereof. Administering a therapeutically effective amount of the composition to the subject may result in: (a) an enhancement of the delivery of the active agent to a disease site relative to delivery of the active agent alone; or (b) an enhancement of microvesicles clearance resulting in a decrease of at least 10%, 20%, 30%, 40%, 50%, 60%, 70%, 80%, or 90% in a blood level of microvesicles targeted by the aptamer; or (c) an decrease in biological activity of microvesicles targeted by the aptamer of at least 10%, 20%, 30%, 40%, 50%, 60%, 70%, 80%, or 90%. In an embodiment, the biological activity of microvesicles comprises immune suppression or transfer of genetic information. The disease or disorder can include without limitation those disclosed herein. For example, the disease or disorder may comprise a neoplastic, proliferative, or inflammatory, metabolic, cardiovascular, or neurological disease or disorder. See section "Phenotypes."

The invention further provides a kit comprising an aptamer disclosed herein, or a pharmaceutical composition thereof.

In an aspect, the invention provides a method comprising contacting the aptamer as described above with a biological sample and detecting the presence or absence of binding of the aptamer to a microvesicle in the biological sample. As disclosed herein, the biological sample can be a tissue, fluid or cell culture sample. For example, the biological sample may comprise blood or a blood component. In some embodiments, the aptamer is conjugated to a substrate prior to the contacting with the biological sample. For example, the substrate may comprise a bead or a plate well. The aptamer may also be conjugated to a detectable label. Various configurations of the method are provided herein. See, e.g., FIGS. 1A-1B.

In a related aspect, the invention provides a method of detecting a presence or level of a microvesicle population in a biological sample suspected of containing the microvesicle population, comprising contacting the biological sample with one or more binding agent specific to the microvesicle population and one or more aptamer as described above, and detecting microvesicles that are recognized by both the one or more binding agent and the one or more aptamer, thereby detecting the presence or level of the microvesicle population in the biological sample.

The biological sample can be a tissue sample, a cell culture, or a bodily fluid. The bodily fluid can be any useful fluid, including without limitation one or more of peripheral blood, sera, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, female ejaculate, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, and umbilical cord blood. In some embodiments, the bodily fluid comprises blood, serum or plasma.

Any useful binding agent can be used in the subject methods. In some embodiments, the one or more binding agent comprises an antibody or aptamer to a microvesicle surface antigen selected from Table 3, Table 4, and a combination thereof. The one or more binding agent can also be an antibody or aptamer to a microvesicle surface antigen selected from a target in Table 26. For example, the one or more binding agent may be an antibody or aptamer to a microvesicle surface antigen selected from the group consisting of EpCam, CD9, PCSA, CD63, CD81, PSMA, B7H3, PSCA, ICAM, STEAP, KLK2, SSX2, SSX4, PBP, SPDEF, EGFR, and a combination thereof. The one or more binding agent can also comprise an antibody or aptamer to a microvesicle surface antigen selected from the group consisting of EGFR, PBP, EpCAM, KLK2, and a combination thereof.

The invention contemplates various configurations. For example, a "sandwich" format can be used. See, e.g., FIGS. 1A-1B. In some embodiments of the method, the one or more binding agent is conjugated to a substrate prior to the contacting with the biological sample. In this configuration, the one or more aptamer may be conjugated to a detectable label to serve as a detector agent. In other embodiments, the one or more binding agent is conjugated to a detectable label. In this configuration, the one or more aptamer may be conjugated to a substrate prior to the contacting with the biological sample to serve as a capture agent. Furthermore, the one or more aptamer can be conjugated to a substrate prior to the contacting with the biological sample, and/or the one or more aptamer is conjugated to a detectable label. In such cases, the one or more aptamer can act as either or both of a capture agent and a detection agent.

The method of detecting a presence or level of a microvesicle population in a biological sample can be used to provide a diagnosis, prognosis or theranosis of a disease or disorder. The disease or disorder can include without limitation those disclosed herein. For example, the disease or disorder may comprise a neoplastic, proliferative, or inflammatory, metabolic, cardiovascular, or neurological disease or disorder. See section "Phenotypes." In an embodiment, the disease comprises a cancer. For example, the disease can be an acute lymphoblastic leukemia; acute myeloid leukemia; adrenocortical carcinoma; AIDS-related cancers; AIDS-related lymphoma; anal cancer; appendix cancer; astrocytomas; atypical teratoid/rhabdoid tumor; basal cell carcinoma; bladder cancer; brain stem glioma; brain tumor (including brain stem glioma, central nervous system atypical teratoid/rhabdoid tumor, central nervous system embryonal tumors, astrocytomas, craniopharyngioma, ependymoblastoma, ependymoma, medulloblastoma, medulloepithelioma, pineal parenchymal tumors of intermediate differentiation, supratentorial primitive neuroectodermal tumors and pineoblastoma); breast cancer; bronchial tumors; Burkitt lymphoma; cancer of unknown primary site; carcinoid tumor; carcinoma of unknown primary site; central nervous system atypical teratoid/rhabdoid tumor; central nervous system embryonal tumors; cervical cancer; childhood cancers; chordoma; chronic lymphocytic leukemia; chronic myelogenous leukemia; chronic myeloproliferative disorders; colon cancer; colorectal cancer; craniopharyngioma; cutaneous T-cell lymphoma; endocrine pancreas islet cell tumors; endometrial cancer; ependymoblastoma; ependymoma; esophageal cancer; esthesioneuroblastoma; Ewing sarcoma; extracranial germ cell tumor; extragonadal germ cell tumor; extrahepatic bile duct cancer; gallbladder cancer; gastric (stomach) cancer; gastrointestinal carcinoid tumor; gastrointestinal stromal cell tumor; gastrointestinal stromal tumor (GIST); gestational trophoblastic tumor; glioma; hairy cell leukemia; head and neck cancer; heart cancer; Hodgkin lymphoma; hypopharyngeal cancer; intraocular melanoma; islet cell tumors; Kaposi sarcoma; kidney cancer; Langerhans cell histiocytosis; laryngeal cancer; lip cancer; liver cancer; lung cancer; malignant fibrous histiocytoma bone cancer; medulloblastoma; medulloepithelioma; melanoma; Merkel cell carcinoma; Merkel cell skin carcinoma; mesothelioma; metastatic squamous neck cancer with occult primary; mouth cancer; multiple endocrine neoplasia syndromes; multiple myeloma; multiple myeloma/plasma cell neoplasm; mycosis fungoides; myelodysplastic syndromes; myeloproliferative neoplasms; nasal cavity cancer; nasopharyngeal cancer; neuroblastoma; Non-Hodgkin lymphoma; nonmelanoma skin cancer; non-small cell lung cancer; oral cancer; oral cavity cancer; oropharyngeal cancer; osteosarcoma; other brain and spinal cord tumors; ovarian cancer; ovarian epithelial cancer; ovarian germ cell tumor; ovarian low malignant potential tumor; pancreatic cancer; papillomatosis; paranasal sinus cancer; parathyroid cancer; pelvic cancer; penile cancer; pharyngeal cancer; pineal parenchymal tumors of intermediate differentiation; pineoblastoma; pituitary tumor; plasma cell neoplasm/multiple myeloma; pleuropulmonary blastoma; primary central nervous system (CNS) lymphoma; primary hepatocellular liver cancer; prostate cancer; rectal cancer; renal cancer; renal cell (kidney) cancer; renal cell cancer; respiratory tract cancer; retinoblastoma; rhabdomyosarcoma; salivary gland cancer; Sézary syndrome; small cell lung cancer; small intestine cancer; soft tissue sarcoma; squamous cell carcinoma; squamous neck cancer; stomach (gastric) cancer; supratentorial primitive neuroectodermal tumors; T-cell lymphoma; testicular cancer; throat cancer; thymic carcinoma; thymoma; thyroid cancer; transitional cell cancer; transitional cell cancer of the renal pelvis and ureter; trophoblastic tumor; ureter cancer; urethral cancer; uterine cancer; uterine sarcoma; vaginal cancer; vulvar cancer; Waldenström macroglobulinemia; or Wilm's tumor. The cancer can be a prostate cancer. The cancer can be a breast cancer.

In another related aspect, the invention provides a method of characterizing a disease or disorder, comprising: (a) contacting a biological test sample with one or more aptamer as provided herein; (b) detecting a presence or level of a complex between the one or more aptamer and the target bound by the one or more aptamer in the biological test sample formed in step (a); and (c) comparing the presence or level detected in step (b) to a reference level from a biological control sample, thereby characterizing the disease or disorder. The reference level may be derived from a level of the target in a healthy sample individual, e.g., one that does not have or is not known to have the disease or disorder. The reference level may also be derived from an individual or sample having a treated, controlled, or alternate disease.

The biological test sample and biological control sample may each comprise a tissue sample, a cell culture, or a biological fluid. In some embodiments, the biological fluid comprises a bodily fluid. The bodily fluid can be any useful fluid, including without limitation one or more of peripheral blood, sera, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, female ejaculate, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, or umbilical cord blood. In some embodiments, the bodily fluid comprises blood, serum or plasma. The biological fluid may comprise or be suspected to comprise microvesicles.

The one or more aptamer may bind a polypeptide or fragment thereof. The binding may be promiscuous or selective as desired. The polypeptide or fragment thereof can be soluble or membrane bound, e.g., in the membrane of a microvesicle or cell fragment. The polypeptide or fragment thereof comprises a biomarker in Table 3, Table 4, or Table 26. The one or more aptamer can bind a microvesicle surface antigen in the biological sample.

The method herein of characterizing a disease or disorder may include providing a diagnosis, prognosis or theranosis of the disease or disorder. The disease or disorder can include without limitation those disclosed herein. For example, the disease or disorder may comprise a cancer, a premalignant condition, an inflammatory disease, an immune disease, an autoimmune disease or disorder, a cardiovascular disease or disorder, a neurological disease or disorder, an infectious disease, and/or pain. See section "Phenotypes" herein. In some embodiments, the disease or disorder comprises a cancer. The cancer comprises an acute lymphoblastic leukemia; acute myeloid leukemia; adrenocortical carcinoma; AIDS-related cancers; AIDS-related lymphoma; anal cancer; appendix cancer; astrocytomas; atypical teratoid/rhabdoid tumor; basal cell carcinoma; bladder cancer; brain stem glioma; brain tumor (including brain stem glioma, central nervous system atypical teratoid/rhabdoid tumor, central nervous system embryonal tumors, astrocytomas, craniopharyngioma, ependymoblastoma, ependymoma, medulloblastoma, medulloepithelioma, pineal parenchymal tumors of intermediate differentiation, supratentorial primitive neuroectodermal tumors and pineoblastoma); breast cancer; bronchial tumors; Burkitt lymphoma; cancer of unknown primary site; carcinoid tumor; carcinoma of unknown primary site; central nervous system atypical teratoid/rhabdoid tumor; central nervous system embryonal tumors; cervical cancer; childhood cancers; chordoma; chronic lymphocytic leukemia; chronic myelogenous leukemia; chronic myeloproliferative disorders; colon cancer; colorectal cancer; craniopharyngioma; cutaneous T-cell lymphoma; endocrine pancreas islet cell tumors; endometrial cancer; ependymoblastoma; ependymoma; esophageal cancer; esthesioneuroblastoma; Ewing sarcoma; extracranial germ cell tumor; extragonadal germ cell tumor; extrahepatic bile duct cancer; gallbladder cancer; gastric (stomach) cancer; gastrointestinal carcinoid tumor; gastrointestinal stromal cell tumor; gastrointestinal stromal tumor (GIST); gestational trophoblastic tumor; glioma; hairy cell leukemia; head and neck cancer; heart cancer;

Hodgkin lymphoma; hypopharyngeal cancer; intraocular melanoma; islet cell tumors; Kaposi sarcoma; kidney cancer; Langerhans cell histiocytosis; laryngeal cancer; lip cancer; liver cancer; lung cancer; malignant fibrous histiocytoma bone cancer; medulloblastoma; medulloepithelioma; melanoma; Merkel cell carcinoma; Merkel cell skin carcinoma; mesothelioma; metastatic squamous neck cancer with occult primary; mouth cancer; multiple endocrine neoplasia syndromes; multiple myeloma; multiple myeloma/plasma cell neoplasm; mycosis fungoides; myelodysplastic syndromes; myeloproliferative neoplasms; nasal cavity cancer; nasopharyngeal cancer; neuroblastoma; Non-Hodgkin lymphoma; nonmelanoma skin cancer; non-small cell lung cancer; oral cancer; oral cavity cancer; oropharyngeal cancer; osteosarcoma; other brain and spinal cord tumors; ovarian cancer; ovarian epithelial cancer; ovarian germ cell tumor; ovarian low malignant potential tumor; pancreatic cancer; papillomatosis; paranasal sinus cancer; parathyroid cancer; pelvic cancer; penile cancer; pharyngeal cancer; pineal parenchymal tumors of intermediate differentiation; pineoblastoma; pituitary tumor; plasma cell neoplasm/multiple myeloma; pleuropulmonary blastoma; primary central nervous system (CNS) lymphoma; primary hepatocellular liver cancer; prostate cancer; rectal cancer; renal cancer; renal cell (kidney) cancer; renal cell cancer; respiratory tract cancer; retinoblastoma; rhabdomyosarcoma; salivary gland cancer; Sézary syndrome; small cell lung cancer; small intestine cancer; soft tissue sarcoma; squamous cell carcinoma; squamous neck cancer; stomach (gastric) cancer; supratentorial primitive neuroectodermal tumors; T-cell lymphoma; testicular cancer; throat cancer; thymic carcinoma; thymoma; thyroid cancer; transitional cell cancer; transitional cell cancer of the renal pelvis and ureter; trophoblastic tumor; ureter cancer; urethral cancer; uterine cancer; uterine sarcoma; vaginal cancer; vulvar cancer; Waldenström macroglobulinemia; or Wilm's tumor. The cancer can be a prostate cancer. The cancer can be a breast cancer.

The invention further provides a kit comprising a reagent for carrying out the methods herein and also use of the reagent for carrying out the methods. The reagent may comprise an aptamer disclosed herein and/or other components as disclosed herein.

The invention provides compositions and methods for use of an aptamer pool comprising a plurality of oligonucleotides for detecting biomarkers of interest. Such compositions and methods may facilitate characterization of a phenotype in a biological sample. In one aspect, the invention provides a composition of matter comprising a plurality of oligonucleotides selected from SEQ ID NOs. 1-230810, 230811-230899, 230900-230927 or 231018-241535, which oligonucleotides are capable of binding to a plurality of targets present in a biological sample. The composition of matter may also comprise an oligonucleotide selected from SEQ ID NOs. 1-230810, 230811-230899, 230900-230927 or 231018-241535. In an embodiment, the compositions comprise at least 2, 3, 4, 5, 6, 7, 8, 9, 10, 11, 12, 13, 14, 15, 16, 17, 18, 19, 20, 25, 30, 40, 50, 60, 70, 80, 90, 100, 200, 300, 400, 500, 600, 700, 800, 900, 1000, 2000, 3000, 4000, 5000, 6000, 7000, 8000, 9000, 10000 or all oligonucleotides listed in SEQ ID NOs. 231018-241535. In another embodiment, the compositions comprise at least 2, 3, 4, 5, 6, 7, 8, 9, 10, 11, 12, 13, 14, 15, 16, 17, 18, 19, 20, 25, 30, 40, 50, 60, 70, 80, 90, 100, 200, 300, 400, 500, 600, 700, 800, 900, 1000, 2000, 3000, 4000, 5000, 6000, 7000, 8000, 9000, 10000 or all oligonucleotides listed in SEQ ID NOs. 1-230810. The invention also provides a composition of matter comprising one or more oligonucleotides set forth in any of Tables 23-24 capable of binding to a plurality of targets present in a biological sample. The composition of matter may comprise one or more oligonucleotide listed in any of Tables 23-24. In some embodiments, the composition comprises 1, 2, 3, 4, 5, 6, 7, 8, 9, 10, 11, 12, 13, 14, 15, 16, 17, 18, 19 or 20 oligonucleotides listed in Table 23 or Table 24.

In a related aspect, the invention provides a method for characterizing a condition for a test sample comprising: contacting a microvesicle sample with a plurality of oligonucleotides capable of binding one or more target(s) present in said microvesicle sample, identifying a set of oligonucleotides that form a complex with the sample wherein the set is predetermined to characterize a condition for the sample, thereby characterizing a condition for a sample. Identifying oligonucleotides may comprise performing sequencing of all or some of the oligonucleotides. Identifying can also comprise performing amplification of all or some of the oligonucleotides, e.g. via PCR methodology and variants thereof (RT-PCR, qPCR, etc). Identifying can also comprise performing hybridization of all or some of the oligonucleotides to an array. The condition can be a disease or disorder. For example, the condition can be a cancer, a premalignant condition, an inflammatory disease, an immune disease, an autoimmune disease or disorder, a cardiovascular disease or disorder, a neurological disease or disorder, an infectious disease, and/or pain. See section "Phenotypes" herein.

In another related aspect, the invention provides a method for identifying a set of oligonucleotides associated with a test sample, comprising: (a) contacting a microvesicle sample with a plurality of oligonucleotides, isolating a set of oligonucleotides that form a complex with the microvesicle sample, (b) determining a sequence and/or a copy number for each of the oligonucleotides that formed a complex with the microvesicle sample in (a), thereby identifying a set of oligonucleotides associated with the test sample. Step (b) can include performing high-throughput sequencing. Step (b) can also include performing hybridization to an array or amplification. In an embodiment, the sample is from a subject suspected of having or being predisposed to having a cancer. In some embodiments, the plurality of oligonucleotides is capable of preferentially binding a microvesicle that is shed from diseased cells versus normal cells. The diseased cells can be associated with a cancer, a premalignant condition, an inflammatory disease, an immune disease, an autoimmune disease or disorder, a cardiovascular disease or disorder, neurological disease or disorder, infectious disease or pain.

In still another related aspect, the invention provides a method of diagnosing a sample as cancerous or predisposed to be cancerous, comprising contacting a microvesicle sample with a plurality of oligonucleotides that are predetermined to preferentially form a complex with microvesicles from a cancer sample as compared to microvesicles from a non-cancer sample.

In some embodiments, the plurality of oligonucleotides are pre-selected through a one or more steps of positive or negative selection, wherein positive selection comprises selection of oligonucleotides against a sample having substantially similar characteristics compared to the test sample, and wherein negative selection comprises selection of oligonucleotides against a sample having substantially different characteristics compared to the test sample.

In yet another related aspect, the invention provides a method of characterizing a disease or disorder, comprising: (a) contacting a biological test sample with an aptamer pool;

(b) detecting a presence or level of a complex formed in step (a) between the members of the aptamer pool and biological test sample; and (c) comparing the presence or level detected in step (b) to a reference level, thereby characterizing the disease or disorder. The reference level may be derived from a level of the target in a healthy sample individual, e.g., one that does not have or is not known to have the disease or disorder. The reference level may also be derived from an individual or sample having a treated, controlled, or alternate disease. The biological test sample may comprise a tissue sample, a cell culture, or a biological fluid. In some embodiments, the biological fluid comprises a bodily fluid. The bodily fluid can be any useful fluid, including without limitation one or more of peripheral blood, sera, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, female ejaculate, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, or umbilical cord blood. In some embodiments, the bodily fluid comprises blood, serum or plasma. The biological fluid may comprise or be suspected to comprise microvesicles. In such cases, the aptamer pool can be chosen to bind to microvesicles. The microvesicles can be isolated before contact with the aptamer pool, or the test sample can be directly contacted with the aptamer pool before isolating microvesicles.

As noted, the compositions and methods for use of an aptamer pool comprising a plurality of oligonucleotides can be used to detect, diagnose, prognose or theranose various diseases and disorders, including without limitation a cancer, a premalignant condition, an inflammatory disease, an immune disease, an autoimmune disease or disorder, a cardiovascular disease or disorder, neurological disease or disorder, infectious disease or pain. In embodiments, the cancer comprises an acute lymphoblastic leukemia; acute myeloid leukemia; adrenocortical carcinoma; AIDS-related cancers; AIDS-related lymphoma; anal cancer; appendix cancer; astrocytomas; atypical teratoid/rhabdoid tumor; basal cell carcinoma; bladder cancer; brain stem glioma; brain tumor (including brain stem glioma, central nervous system atypical teratoid/rhabdoid tumor, central nervous system embryonal tumors, astrocytomas, craniopharyngioma, ependymoblastoma, ependymoma, medulloblastoma, medulloepithelioma, pineal parenchymal tumors of intermediate differentiation, supratentorial primitive neuroectodermal tumors and pineoblastoma); breast cancer; bronchial tumors; Burkitt lymphoma; cancer of unknown primary site; carcinoid tumor; carcinoma of unknown primary site; central nervous system atypical teratoid/rhabdoid tumor; central nervous system embryonal tumors; cervical cancer; childhood cancers; chordoma; chronic lymphocytic leukemia; chronic myelogenous leukemia; chronic myeloproliferative disorders; colon cancer; colorectal cancer; craniopharyngioma; cutaneous T-cell lymphoma; endocrine pancreas islet cell tumors; endometrial cancer; ependymoblastoma; ependymoma; esophageal cancer; esthesioneuroblastoma; Ewing sarcoma; extracranial germ cell tumor; extragonadal germ cell tumor; extrahepatic bile duct cancer; gallbladder cancer; gastric (stomach) cancer; gastrointestinal carcinoid tumor; gastrointestinal stromal cell tumor; gastrointestinal stromal tumor (GIST); gestational trophoblastic tumor; glioma; hairy cell leukemia; head and neck cancer; heart cancer; Hodgkin lymphoma; hypopharyngeal cancer; intraocular melanoma; islet cell tumors; Kaposi sarcoma; kidney cancer; Langerhans cell histiocytosis; laryngeal cancer; lip cancer; liver cancer; lung cancer; malignant fibrous histiocytoma bone cancer; medulloblastoma; medulloepithelioma; melanoma; Merkel cell carcinoma; Merkel cell skin carcinoma; mesothelioma; metastatic squamous neck cancer with occult primary; mouth cancer; multiple endocrine neoplasia syndromes; multiple myeloma; multiple myeloma/plasma cell neoplasm; mycosis fungoides; myelodysplastic syndromes; myeloproliferative neoplasms; nasal cavity cancer; nasopharyngeal cancer; neuroblastoma; Non-Hodgkin lymphoma; nonmelanoma skin cancer; non-small cell lung cancer; oral cancer; oral cavity cancer; oropharyngeal cancer; osteosarcoma; other brain and spinal cord tumors; ovarian cancer; ovarian epithelial cancer; ovarian germ cell tumor; ovarian low malignant potential tumor; pancreatic cancer; papillomatosis; paranasal sinus cancer; parathyroid cancer; pelvic cancer; penile cancer; pharyngeal cancer; pineal parenchymal tumors of intermediate differentiation; pineoblastoma; pituitary tumor; plasma cell neoplasm/multiple myeloma; pleuropulmonary blastoma; primary central nervous system (CNS) lymphoma; primary hepatocellular liver cancer; prostate cancer; rectal cancer; renal cancer; renal cell (kidney) cancer; renal cell cancer; respiratory tract cancer; retinoblastoma; rhabdomyosarcoma; salivary gland cancer; Sézary syndrome; small cell lung cancer; small intestine cancer; soft tissue sarcoma; squamous cell carcinoma; squamous neck cancer; stomach (gastric) cancer; supratentorial primitive neuroectodermal tumors; T-cell lymphoma; testicular cancer; throat cancer; thymic carcinoma; thymoma; thyroid cancer; transitional cell cancer; transitional cell cancer of the renal pelvis and ureter; trophoblastic tumor; ureter cancer; urethral cancer; uterine cancer; uterine sarcoma; vaginal cancer; vulvar cancer; Waldenström macroglobulinemia; or Wilm's tumor. The premalignant condition may be Barrett's Esophagus. In some embodiments, the autoimmune disease comprises inflammatory bowel disease (IBD), Crohn's disease (CD), ulcerative colitis (UC), pelvic inflammation, vasculitis, psoriasis, diabetes, autoimmune hepatitis, multiple sclerosis, myasthenia gravis, Type I diabetes, rheumatoid arthritis, psoriasis, systemic lupus erythematosus (SLE), Hashimoto's Thyroiditis, Grave's disease, Ankylosing Spondylitis Sjogrens Disease, CREST syndrome, Scleroderma, Rheumatic Disease, organ rejection, Primary Sclerosing Cholangitis, or sepsis. In other embodiments, the cardiovascular disease comprises atherosclerosis, congestive heart failure, vulnerable plaque, stroke, ischemia, high blood pressure, stenosis, vessel occlusion or a thrombotic event. The neurological disease may include without limitation Multiple Sclerosis (MS), Parkinson's Disease (PD), Alzheimer's Disease (AD), schizophrenia, bipolar disorder, depression, autism, Prion Disease, Pick's disease, dementia, Huntington disease (HD), Down's syndrome, cerebrovascular disease, Rasmussen's encephalitis, viral meningitis, neurospsychiatric systemic lupus erythematosus (NPSLE), amyotrophic lateral sclerosis, Creutzfeldt-Jacob disease, Gerstmann-Straussler-Scheinker disease, transmissible spongiform encephalopathy, ischemic reperfusion damage (e.g. stroke), brain trauma, microbial infection, or chronic fatigue syndrome. The pain may include fibromyalgia, chronic neuropathic pain, or peripheral neuropathic pain. In embodiments, the infectious disease comprises a bacterial infection, viral infection, yeast infection, Whipple's Disease, Prion Disease, cirrhosis, methicillin-resistant

*Staphylococcus aureus*, HIV, HCV, hepatitis, syphilis, meningitis, malaria, tuberculosis, influenza.

In the methods for use of an aptamer pool comprising a plurality of oligonucleotides, the plurality of oliognucleotides can be a composition as provided herein.

In another related aspect, the invention provides a method of performing high-throughput sequencing comprising: (a) performing at least one (i) negative selection or (ii) one positive selection of a plurality of oligonucleotides with a microvesicle sample; (b) obtaining a set of oliognucleotides to provide a negative binder subset or positive binder subset of the plurality of oligonucleotides, wherein the negative binder subset of the plurality of oligonucleotides does not bind the microvesicle sample and wherein the positive binder subset of the plurality of oligonucleotides does bind the microvesicle sample; (c) contacting the negative binder subset or positive binder subset with a test sample; (d) eluting oligonucleotides that bound to the test sample to provide a plurality of eluate oligonucleotides; and (e) performing high-throughput sequencing of the plurality of eluate oligonucleotides to identify sequence and/or copy number of the members of the plurality of eluate oligonucleotides.

In another related aspect, the invention provides a method for identifying oligonucleotides specific for a test sample comprising: (a) enriching a plurality of oligonucleotides for a sample to provide a set of oligonucleotides predetermined to form a complex with a target sample; (b) contacting the plurality in (a) with a test sample to allow formation of complexes of oligonucleotides with test sample; (c) recovering oligonucleotides that formed complexes in (b) to provide a recovered subset of oligonucleotides; and (d) profiling the recovered subset of oligonucleotides by high-throughput sequencing, amplification or hybridization, thereby identifying oligonucleotides specific for a test sample. The test sample can include a plurality of microvesicles. The oligonucleotides can be RNA, DNA or both. The method may further comprise performing informatics analysis to identify a subset of oligonucleotides comprising sequence identity of at least 90%.

The invention further provides a kit comprising a reagent for carrying out the methods of use of an aptamer pool and also use of the reagent for carrying out such methods. The reagent may comprise a related aptamer or composition disclosed herein and/or other components as disclosed herein.

The invention also provides methods of identifying the pool of aptamers. In one aspect, such a method of identifying a target-specific aptamer profile for a biological sample comprises contacting a biological test sample with a pool of aptamer molecules, contacting the pool to a control or reference biological sample, identifying one or more aptamers that bind to a component in said test sample but not to the control or reference sample, thereby identifying an aptamer profile for said biological test sample.

In another related aspect, the invention provides a method of selecting a pool of aptamers, comprising: (a) contacting a biological control sample with a pool of oligonucleotides; (b) isolating a first subset of the pool of oligonucleotides that do not bind the biological control sample; (c) contacting the biological test sample with the first subset of the pool of oligonucleotides; and (d) isolating a second subset of the pool of oligonucleotides that bind the biological test sample, thereby selecting the pool of aptamers. The starting pool of oligonucleotides may comprise a large number of sequences, e.g., at least $10^7$, $10^8$, $10^9$, $10^{10}$, $10^{11}$, $10^{12}$, $10^{13}$, $10^{14}$, $10^{15}$, $10^{16}$, $10^{17}$, or at least $10^{18}$ oligonucleotides.

Steps (a)-(d) can be repeated at least 1, 2, 3, 4, 5, 6, 7, 8, 9, 10, 11, 12, 13, 14, 15, 16, 17, 18, 19 or at least 20 times, wherein the pool of aptamers selected in step (d) is used as the pool of oligonucleotides in step (a) in each iteration.

In some embodiments, the biological test sample and biological control sample comprise microvesicles. The biological test sample and optionally biological control sample can be any useful biological sample as disclosed herein. For example, they may comprise a bodily fluid. The bodily fluid may include without limitation peripheral blood, sera, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, Cowper's fluid, pre-ejaculatory fluid, female ejaculate, sweat, fecal matter, hair, tears, cyst fluid, pleural fluid, peritoneal fluid, malignant fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates or other lavage fluids. The biological test sample and optionally biological control sample may also comprise a tissue sample or cell culture. The biological test sample can be a diseased sample and the biological control sample can be a non-diseased sample. Such configuration can allow identification of pools of aptamers that preferentially recognize a diseased sample, or preferentially recognize a non-diseased sample.

In still another related aspect, the invention provides a method of selecting a group of aptamers, comprising: (a) contacting a pool of aptamers to a population of microvesicles from a first sample; (b) enriching a subpool of aptamers that show affinity to the population of microvesicles from the first sample; (c) contacting the subpool to a second population of microvesicles from a second sample; and (d) depleting a second subpool of aptamers that show affinity to the second population of microvesicles from the second sample, thereby selecting the group of aptamers that have preferential affinity for the population of microvesicles from the first sample.

The first sample and/or second sample can be any useful can be any useful biological sample as disclosed herein. For example, they may comprise a bodily fluid. The bodily fluid may include without limitation peripheral blood, sera, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, Cowper's fluid, pre-ejaculatory fluid, female ejaculate, sweat, fecal matter, hair, tears, cyst fluid, pleural fluid, peritoneal fluid, malignant fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates or other lavage fluids. The first sample and/or and the second sample may each comprise a pooled sample, i.e., a sample pooled together from various sources such as different individuals. The first sample may be a diseased sample while the second sample comprises a control sample, optionally wherein the control sample is a non-disease sample. Alternately, the first sample may be a control sample while the second sample comprises a disease sample, optionally wherein the control sample is a non-disease sample.

Steps (a)-(d) may be repeated at least 1, 2, 3, 4, 5, 6, 7, 8, 9, 10, 11, 12, 13, 14, 15, 16, 17, 18, 19 or 20 times, wherein the group of aptamers selected in step (d) is used as the pool of aptamers in step (a) in each iteration. In embodiments, the first sample and/or second sample are replaced with a different sample before repeating steps (a)-(d). For example, the first sample and/or second sample can be from a different individual or comprise a different sample pool.

The method may further comprise identifying the members of the selected group of aptamers, optionally wherein the identifying is performed by high-throughput sequencing, amplification or hybridization.

In an aspect, the invention provides a method of selecting a group of aptamers, comprising: (a) contacting a pool of aptamer candidates to a sample comprising a target molecule; (b) removing unbound aptamer candidates; (c) contacting the sample with a ligand to the target molecule; and (d) isolating aptamer candidates that are disassociated from the target molecule by competition with the ligand, thereby selecting the group of aptamers that bind the same target as the ligand. The target molecule can be a protein, including without limitation a microvesicle surface antigen. The target molecule is tethered to a substrate. In some embodiments, the target molecule is a surface antigen of a microvesicle and the microvesicle is tethered to a substrate. The ligand can be a small molecule or protein, e.g., the ligand can be an antibody. Steps (a)-(d) can be repeated at least 1, 2, 3, 4, 5, 6, 7, 8, 9, 10, 11, 12, 13, 14, 15, 16, 17, 18, 19 or 20 times, wherein the aptamer candidates isolated in the step (d) are used the pool of aptamer candidates input into step (a) in each iteration. The method may further comprise identifying the members of the selected group of aptamers, optionally wherein the identifying is performed by high throughput sequencing, amplification or hybridization. The first sample may be a diseased sample while the second sample comprises a control sample, optionally wherein the control sample is a non-disease sample. Alternately, the first sample may be a control sample while the second sample comprises a disease sample, optionally wherein the control sample is a non-disease sample.

In a related aspect, the invention provides a method of selecting one or more aptamer that bind a target of interest, comprising: (a) separating the target from a first biological sample to form a target depleted biological sample; (b) tethering the separated target to a substrate; (c) mixing the tethered target with an interfering biological sample; (d) contacting the mixture from (c) with a starting aptamer library; and (e) recovering members of the aptamer library that preferentially bind the tethered target, thereby selecting the one or more aptamer that bind the target. The substrate can be a bead or planar surface. The interfering biological sample may comprise the target depleted biological sample from (a). The target can be a microvesicle. In some embodiments, the target comprises a microvesicle of interest and the interfering biological sample comprises a non-target microvesicle. The non-target microvesicle can be tethered to a different substrate than the target microvesicle prior to step (c). In some embodiments, the substrate comprises a magnetic bead and the different substrate comprises a non-magnetic bead, or the substrate comprises a non-magnetic bead and the different substrate comprises a magnetic bead.

The first biological sample and/or interfering biological sample can be any useful can be any useful biological sample as disclosed herein. For example, they may comprise a bodily fluid. The bodily fluid may include without limitation peripheral blood, sera, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, Cowper's fluid, pre-ejaculatory fluid, female ejaculate, sweat, fecal matter, hair, tears, cyst fluid, pleural fluid, peritoneal fluid, malignant fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates or other lavage fluids. In an embodiment, the first biological sample comprises a diseased sample and the interfering biological sample comprises a non-disease sample. Alternately, the first biological sample may comprise a non-disease sample while the interfering biological sample comprises a disease sample.

The invention provides methods of screening a library of binding agents such as aptamers to identify binding agents to a target of interest. In an aspect, the invention provides a method for identifying a plurality of target ligands comprising: (a) contacting a reference microvesicle population with a plurality of ligands that are capable of binding one or more microvesicle surface markers; (b) isolating a plurality of reference ligands, wherein the plurality of reference ligands comprise a subset of the plurality of ligands that do not have an affinity for the reference microvesicle population; (c) contacting one or more test microvesicle with the plurality of reference ligands; and (d) identifying a subset of ligands from the plurality of reference ligands that form complexes with a surface marker on the one or more test microvesicle, thereby identifying the plurality of target ligands. The method may further comprise identifying the surface marker of the target microvesicle. The plurality of ligands can be aptamers and/or antibodies.

In a related aspect, the invention provides a method of identifying an aptamer specific to a target of interest, comprising: (a) contacting a pool of candidate aptamers with one or more assay components, wherein the assay components do not comprise the target of interest; (b) recovering the members of the pool of candidate aptamers that do not bind to the one or more assay components in (a); (c) contacting the members of the pool of candidate aptamers recovered in (b) with the target of interest in the presence of one or more confounding target; and (d) recovering a candidate aptamer that binds to the target of interest in step (c), thereby identifying the aptamer specific to the target of interest. The method can remove candidate aptamers that bind non-target molecules. Steps (a)-(b) can be repeated at least 1, 2, 3, 4, 5, 6, 7, 8, 9, 10, 11, 12, 13, 14, 15, 16, 17, 18, 19 or at least 20 times before step (c) is performed. In addition, steps (c)-(d) can be repeated at least 1, 2, 3, 4, 5, 6, 7, 8, 9, 10, 11, 12, 13, 14, 15, 16, 17, 18, 19 or at least 20 times before identifying the aptamer specific to the target of interest. The starting pool of candidate aptamers can include at least $10^6$, $10^7$, $10^8$, $10^9$, $10^{10}$, $10^{11}$, $10^{12}$, $10^{13}$, $10^{14}$, $10^{15}$, $10^{16}$, $10^{17}$, or at least $10^{18}$ nucleic acid sequences. The one or more assay components can include without limitation one or more of a substrate, a bead, a planar array, a column, a tube, a well, or a filter.

In an embodiment, the target of interest and the one or more confounding target comprise proteins. The target of interest and the one or more confounding target may also comprise a microvesicle. In some embodiments, the target of interest and the one or more confounding target comprise one or more microvesicle surface antigen. The microvesicle surface antigen can be selected from Tables 3, 4 and/or 26. By way of non-limiting example, the target of interest can be a protein selected from the group consisting of SSX4, SSX2, PBP, KLK2, SPDEF, while the one or more confounding target comprises the other members of the group.

The one or more microvesicle surface antigen can be a biomarker of a disease or disorder, including without limitation those disclosed herein. In some embodiments, the disease comprises a cancer, a premalignant condition, an inflammatory disease, an immune disease, an autoimmune disease or disorder, a cardiovascular disease or disorder, neurological disease or disorder, infectious disease or pain. The cancer can be an acute lymphoblastic leukemia; acute myeloid leukemia; adrenocortical carcinoma; AIDS-related cancers; AIDS-related lymphoma; anal cancer; appendix cancer; astrocytomas; atypical teratoid/rhabdoid tumor; basal cell carcinoma; bladder cancer; brain stem glioma; brain tumor (including brain stem glioma, central nervous system atypical teratoid/rhabdoid tumor, central nervous system embryonal tumors, astrocytomas, craniopharyngioma, ependymoblastoma, ependymoma, medulloblastoma, medulloepithelioma, pineal parenchymal tumors of intermediate differentiation, supratentorial primitive neuroectodermal tumors and pineoblastoma); breast cancer; bronchial tumors; Burkitt lymphoma; cancer of unknown primary site; carcinoid tumor; carcinoma of unknown primary site; central nervous system atypical teratoid/rhabdoid tumor; central nervous system embryonal tumors; cervical cancer; childhood cancers; chordoma; chronic lymphocytic leukemia; chronic myelogenous leukemia; chronic myeloproliferative disorders; colon cancer; colorectal cancer; craniopharyngioma; cutaneous T-cell lymphoma; endocrine pancreas islet cell tumors; endometrial cancer; ependymoblastoma; ependymoma; esophageal cancer; esthesioneuroblastoma; Ewing sarcoma; extracranial germ cell tumor; extragonadal germ cell tumor; extrahepatic bile duct cancer; gallbladder cancer; gastric (stomach) cancer; gastrointestinal carcinoid tumor; gastrointestinal stromal cell tumor; gastrointestinal stromal tumor (GIST); gestational trophoblastic tumor; glioma; hairy cell leukemia; head and neck cancer; heart cancer; Hodgkin lymphoma; hypopharyngeal cancer; intraocular melanoma; islet cell tumors; Kaposi sarcoma; kidney cancer; Langerhans cell histiocytosis; laryngeal cancer; lip cancer; liver cancer; lung cancer; malignant fibrous histiocytoma bone cancer; medulloblastoma; medulloepithelioma; melanoma; Merkel cell carcinoma; Merkel cell skin carcinoma; mesothelioma; metastatic squamous neck cancer with occult primary; mouth cancer; multiple endocrine neoplasia syndromes; multiple myeloma; multiple myeloma/plasma cell neoplasm; mycosis fungoides; myelodysplastic syndromes; myeloproliferative neoplasms; nasal cavity cancer; nasopharyngeal cancer; neuroblastoma; Non-Hodgkin lymphoma; nonmelanoma skin cancer; non-small cell lung cancer; oral cancer; oral cavity cancer; oropharyngeal cancer; osteosarcoma; other brain and spinal cord tumors; ovarian cancer; ovarian epithelial cancer; ovarian germ cell tumor; ovarian low malignant potential tumor; pancreatic cancer; papillomatosis; paranasal sinus cancer; parathyroid cancer; pelvic cancer; penile cancer; pharyngeal cancer; pineal parenchymal tumors of intermediate differentiation; pineoblastoma; pituitary tumor; plasma cell neoplasm/multiple myeloma; pleuropulmonary blastoma; primary central nervous system (CNS) lymphoma; primary hepatocellular liver cancer; prostate cancer; rectal cancer; renal cancer; renal cell (kidney) cancer; renal cell cancer; respiratory tract cancer; retinoblastoma; rhabdomyosarcoma; salivary gland cancer; Sézary syndrome; small cell lung cancer; small intestine cancer; soft tissue sarcoma; squamous cell carcinoma; squamous neck cancer; stomach (gastric) cancer; supratentorial primitive neuroectodermal tumors; T-cell lymphoma; testicular cancer; throat cancer; thymic carcinoma; thymoma; thyroid cancer; transitional cell cancer; transitional cell cancer of the renal pelvis and ureter; trophoblastic tumor; ureter cancer; urethral cancer; uterine cancer; uterine sarcoma; vaginal cancer; vulvar cancer; Waldenström macroglobulinemia; or Wilm's tumor. The premalignant condition may be Barrett's Esophagus. In some embodiments, the autoimmune disease comprises inflammatory bowel disease (IBD), Crohn's disease (CD), ulcerative colitis (UC), pelvic inflammation, vasculitis, psoriasis, diabetes, autoimmune hepatitis, multiple sclerosis, myasthenia gravis, Type I diabetes, rheumatoid arthritis, psoriasis, systemic lupus erythematosis (SLE), Hashimoto's Thyroiditis, Grave's disease, Ankylosing Spondylitis Sjogrens Disease, CREST syndrome, Scleroderma, Rheumatic Disease, organ rejection, Primary Sclerosing Cholangitis, or sepsis. In other embodiments, the cardiovascular disease comprises atherosclerosis, congestive heart failure, vulnerable plaque, stroke, ischemia, high blood pressure, stenosis, vessel occlusion or a thrombotic event. The neurological disease may include without limitation Multiple Sclerosis (MS), Parkinson's Disease (PD), Alzheimer's Disease (AD), schizophrenia, bipolar disorder, depression, autism, Prion Disease, Pick's disease, dementia, Huntington disease (HD), Down's syndrome, cerebrovascular disease, Rasmussen's encephalitis, viral meningitis, neurospsychiatric systemic lupus erythematosus (NPSLE), amyotrophic lateral sclerosis, Creutzfeldt-Jacob disease, Gerstmann-Straussler-Scheinker disease, transmissible spongiform encephalopathy, ischemic reperfusion damage (e.g. stroke), brain trauma, microbial infection, or chronic fatigue syndrome. The pain may include fibromyalgia, chronic neuropathic pain, or peripheral neuropathic pain. In embodiments, the infectious disease comprises a bacterial infection, viral infection, yeast infection, Whipple's Disease, Prion Disease, cirrhosis, methicillin-resistant *Staphylococcus aureus*, HIV, HCV, hepatitis, syphilis, meningitis, malaria, tuberculosis, influenza.

The invention provides methods for identifying binding agents comprising contacting a plurality of extracellular microvesicles with a randomly generated library of binding agents, and identifying a subset of the library of binding agents that have an affinity to one or more components of the extracellular microvesicles. The binding agents can be aptamers and/or antibodies.

The ligands including oligonucleotide aptamers identified by the methods of the invention can be used in assays to characterize a phenotype of a sample, e.g., to provide a diagnosis, prognosis and/or theranosis of a disease or disorder. Such method of characterizing a phenotype may comprise contacting a test biological sample with the one or more ligand or aptamer aptamer that bind a target of interest. The phenotype may include detecting a disease or disorder as disclosed herein.

The invention further provides a kit comprising a reagent for carrying out the methods of screening ligand and aptamer libraries against one or more target of interest. The invention also provides for use of the reagent for carrying out the methods of screening ligand and aptamer libraries against one or more target of interest. The reagent may comprise an aptamer library or composition disclosed herein and/or other components as disclosed herein.

The methods of screening ligand and aptamer libraries against one or more target of interest can further include identifying one or more target of the selected ligands/aptamers. Such methods are disclosed herein and/or known in the art. See, e.g., FIG. 14. In such an aspect, the invention provides a method of identifying a target of a binding agent comprising: (a) contacting the binding agent with the target to bind the target with the binding agent, wherein the target comprises a surface antigen of a microvesicle; (b) disrupting the microvesicle under conditions which do not disrupt the binding of the target with the binding agent; (c) isolating the complex between the target and the binding agent; and (d) identifying the target bound by the binding agent. The binding agent may be a ligand or an aptamer identified by the screening methods above or elsewhere herein. See, e.g., FIGS. 13A-13B. The target of the binding agent can be any appropriate biomarker, including a protein, nucleic acid, lipid, carbohydrate, or microvesicle.

In some embodiments, the target is cross-linked to the binding agent prior to step (b). The cross-linking may comprise photocrosslinking, an imidoester crosslinker, dimethyl suberimidate, an N-Hydroxysuccinimide-ester crosslinker, bissulfosuccinimidyl suberate (BS3), an aldehyde, acrolein, crotonaldehyde, formaldehyde, a carbodiimide crosslinker, N,N'-dicyclohexylcarbodiimide (DDC), N,N'-diisopropylcarbodiimide (DIC), 1-Ethyl-3-[3-dimethylaminopropyl]carbodiimide hydrochloride (EDC or EDAC), Succinimidyl-4-(N-maleimidomethyl)cyclohexane-1-carboxylate (SMCC), and Sulfosuccinimidyl-4-(N-maleimidomethyl)cyclohexane-1-carboxylate (Sulfo-SMCC), a Sulfo-N-hydroxysuccinimidyl-2-(6-[biotinamido]-2-(p-azido benzamido)-hexanoamido)ethyl-1,3'-dithioproprionate (Sulfo-SBED), 2-[N2-(4-Azido-2,3,5,6-tetrafluorobenzoyl)-N6-(6-biotin-amidocaproyl)-L-lysinyl]ethyl methanethiosulfonate (Mts-Atf-Biotin), 2-{N2-[N6-(4-Azido-2,3,5,6-tetrafluorobenzoyl-6-amino-caproyl)-N6-(6-biotinamidocaproyl)-L-lysinylamido]}ethyl methanethiosultonate (Mts-Atf-LC-Biotin), a photoreactive amino acid, L-Photo-Leucine, L-Photo-Methionine, an N-Hydroxysuccinimide (NHS) crosslinker, an NHS-Azide reagent, NHS-Azide, NHS-PEG4-Azide, NHS-PEG12-Azide, an NHS-Phosphine reagent, NHS-Phosphine, Sulfo-NHS-Phosphine, or any combination or modification thereof. Disrupting the microvesicle in step (b) can include use of one or more of a detergent, a surfactant, a solvent, an enzyme, mechanical shear, bead milling, homogenation, microfluidization, sonication, French Press, impingement, a colloid mill, decompression, osmotic shock, thermolysis, freeze-thaw, and desiccation. The enzyme can be one or more of lysozyme, lysostaphin, zymolase, cellulase, mutanolysin, a glycanase, a protease, and mannase Useful detergents include one or more of a octylthioglucoside (OTG), octyl beta-glucoside (OG), a nonionic detergent, Triton X, Tween 20, a fatty alcohol, a cetyl alcohol, a stearyl alcohol, cetostearyl alcohol, an oleyl alcohol, a polyoxyethylene glycol alkyl ether (Brij), octaethylene glycol monododecyl ether, pentaethylene glycol monododecyl ether, a polyoxypropylene glycol alkyl ether, a glucoside alkyl ether, decyl glucoside, lauryl glucoside, octyl glucoside, a polyoxyethylene glycol octylphenol ethers, a polyoxyethylene glycol alkylphenol ether, nonoxynol-9, a glycerol alkyl ester, glyceryl laurate, a polyoxyethylene glycol sorbitan alkyl esters, polysorbate, a sorbitan alkyl ester, cocamide MEA, cocamide DEA, dodecyldimethylamine oxide, a block copolymers of polyethylene glycol and polypropylene glycol, poloxamers, polyethoxylated tallow amine (POEA), a zwitterionic detergent, 3-[(3-cholamidopropyl)dimethylammonio]-1-propanesulfonate (CHAPS), a linear alkylbenzene sulfonate (LAS), a alkyl phenol ethoxylate (APE), cocamidopropyl hydroxysultaine, a betaine, cocamidopropyl betaine, lecithin, an ionic detergent, sodium dodecyl sulfate (SDS), cetrimonium bromide (CTAB), cetyl trimethylammonium chloride (CTAC), octenidine dihydrochloride, cetylpyridinium chloride (CPC), benzalkonium chloride (BAC), benzethonium chloride (BZT), 5-Bromo-5-nitro-1,3-dioxane, dimethyldioctadecylammonium chloride, dioctadecyldimethylammonium bromide (DODAB), sodium deoxycholate, nonyl phenoxypolyethoxylethanol (Tergitol-type NP-40; NP-40), ammonium lauryl sulfate, sodium laureth sulfate (sodium lauryl ether sulfate (SLES)), sodium myreth sulfate, an alkyl carboxylate, sodium stearate, sodium lauroyl sarcosinate, a carboxylate-based fluorosurfactant, perfluorononanoate, perfluorooctanoate (PFOA or PFO), and a biosurfactant.

In an embodiment, the binding agent is tethered to a substrate. See, e.g., FIG. 14. The substrate can be a microsphere or a planar substrate. The binding agent can be labeled. In some embodiments, isolating the complex between the target and the binding agent comprises capturing the binding agent via the label. The label can be a biotin label.

In embodiments wherein the target comprises a protein, identifying the target may comprise use of mass spectrometry (MS), peptide mass fingerprinting (PMF; protein fingerprinting), sequencing, N-terminal amino acid analysis, C-terminal amino acid analysis, Edman degradation, chromatography, electrophoresis, two-dimensional gel electrophoresis (2D gel), antibody array, and immunoassay.

The invention further provides a kit comprising a reagent for carrying out the methods of target identification. The invention also provides for use of the reagent for carrying out the methods of target identification. The reagent may comprise various substrates, linkers, detergents, and/or other components as disclosed herein.

The invention provides compositions and methods to facilitate aptamer library screening and aptamer-based assays. These include without limitation negative control and blocking aptamers. In such an aspect, the invention provides a nucleic acid comprising a sequence at least 50, 60, 70, 75, 80, 85, 90, 91, 92, 93, 94, 95, 96, 97, 98, 99, or 100% homologous to a sequence selected from the group consisting of any of SEQ ID NOs. 230938-231008. The invention also provides a nucleic acid comprising a sequence selected from the group consisting of any of SEQ ID NOs. 230938-231008. The invention further provides an isolated nucleic acid comprising a sequence at least 50, 60, 70, 75, 80, 85, 90, 91, 92, 93, 94, 95, 96, 97, 98, 99, or 100% homologous to a sequence selected from the group consisting of any of SEQ ID NOs. 230938-231008. The invention provides an isolated nucleic acid comprising a sequence selected from the group consisting of any of SEQ ID NOs. 230938-231008. The nucleic acids can be further modified to comprise at least one chemical modification. The modification may include without limitation a chemical substitution at a sugar position; a chemical substitution at a phosphate position; and a chemical substitution at a base position of the nucleic acid. The modification can be selected from the group consisting of: incorporation of a modified nucleotide, 3' capping, a 2'-modified pyrimidine, biotinylation, conjugation to an amine linker, conjugation to a high molecular weight, non-immunogenic compound, conjugation to a lipophilic compound. In embodiments, the non-immunogenic, high molecular weight compound is a polyalkylene glycol, e.g, polyethylene glycol.

The invention provides a composition comprising a nucleic acid above, and also a kit comprising a nucleic acid above or the composition. The invention further provides a negative control composition comprising a non-target binding nucleic acid bound to a substrate. The non-target binding nucleic acid may be covalently bound to a substrate. Alternately, the non-target binding nucleic acid may be non-covalently bound to a substrate. The non-target binding nucleic acid can be a nucleic acid above (e.g., as relates to any of SEQ ID NOs. 230938-231008). The non-target binding nucleic acid may comprise a scrambled sequence of any of SEQ ID NOs. 1-241535 or a functional fragment thereof. A scrambled sequence includes a sequence that is randomly rearranged in whole or in part.

In a related aspect, the invention provides a method of detecting a presence or level of a biological entity in a biological sample suspected of containing the biological entity, comprising: (a) providing a composition comprising a substrate and a negative control composition as described above, wherein the substrate comprises one or more binding agent to the biological entity; (b) contacting the biological sample with the composition provided in step (a); (c) detecting a target signal corresponding to the amount of biological entity recognized by the one or more binding agent in step (b); and (d) normalizing the target signal detected in step (c) to a control signal corresponding to the amount of signal produced by the negative control composition, thereby detecting the presence or level of the biological entity in the biological sample. Normalizing the target signal may comprise subtracting the control signal from the target signal.

In an embodiment, the one or more binding agent comprises an antibody or aptamer. The biological entity can be a protein. The biological entity can also be a microvesicle. In some embodiments, the one or more binding agent is specific to a microvesicle surface antigen, including without limitation a microvesicle surface antigen selected from any of Tables 3-4, or 26. The biological entity, e.g., a protein, microvesicle or microvesicle surface antigen, can be chosen as a biomarker of a disease or disorder. In such cases, the method may provide a diagnosis, prognosis or theranosis of the disease or disorder as further described herein.

The invention further provides a kit comprising a reagent for carrying out the method. The invention also provides for use of the reagent for carrying out the methods. The reagent may comprise the negative control composition.

In another related aspect, the invention provides a blocking composition comprising a non-target binding nucleic acid. The non-target binding nucleic acid may comprise a nucleic acid disclosed above, e.g., as relates to any of SEQ ID NOs. 230938-231008. The blocking composition can further include one or more component selection from the group consisting of bovine serum albumin (BSA), casein, pepticase, a non-ionic surfactants, Tween® 20, Triton® X-100), a non-reacting antibody or fragment thereof, FSG (fish skin gelatin), pure gelatin, a gelatin hydrolase, polyethylene glycol (PEG), non-reacting sera, and a non-reacting protein.

In still another related aspect, the invention provides method of detecting a presence or level of a biological entity in a biological sample suspected of containing the biological entity, comprising: (a) contacting a substrate with the blocking composition described above, wherein the substrate comprises one or more binding agent to the biological entity; (b) contacting the biological sample with the blocked substrate provided in step (a); and (c) detecting whether the biological entity is recognized by the one or more binding agent in step (b), thereby detecting the presence or level of the biological entity in the biological sample.

In an embodiment, the one or more binding agent comprises an antibody or aptamer. The biological entity can be a protein. The biological entity can also be a microvesicle. In some embodiments, the one or more binding agent is specific to a microvesicle surface antigen, including without limitation a microvesicle surface antigen selected from any of Tables 3-4, or 26. The biological entity, e.g., a protein, microvesicle or microvesicle surface antigen, can be chosen as a biomarker of a disease or disorder. In such cases, the method may provide a diagnosis, prognosis or theranosis of the disease or disorder as further described herein.

The invention further provides a kit comprising a reagent for carrying out the method. The invention also provides for use of the reagent for carrying out the methods. The reagent may comprise the negative control composition.

In an aspect, the invention provides an aptamer that specifically binds to a functional group. The functional group binding aptamer may comprise a nucleic acid disclosed above, e.g., as relates to any of SEQ ID NOs. 230938-231008. In some embodiments, the functional group binding aptamer serves as a blocking agent by blocking various functional groups and may therefore be used to enhance an assay's performance.

The functional group can be selected from the group consisting of a hydrocarbon, a halogen, a group containing oxygen (i.e., C—O bonds), a group containing nitrogen, a group containing sulfur, a group containing phosphorus, or a group containing boron. In some embodiments, the hydrocarbon is selected from the group consisting of alkanes, alkenes, alkynes, benzene derivatives, toluene derivatives, branched or ring alkanes, carbocations and carboanions. In other embodiments, the halogen is selected from the group consisting of haloalkanes, fluoroalkanes, chloroalkanes, bromoalkanes and iodoalkanes. In still other embodiments, the group containing oxygen is selected from the group consisting of alcohols, ketones, aldehydes, acyl halides, carbonates, carboxylates, carboxylic acids, esters, hydroperoxides, ethers, hemiacetals, hemiketals, acetals, ketals, orthoesters, and orthocarbonates. The group containing nitrogen can be selected from the group consisting of amides, amines, imines, imides, azides, azo compounds, cyanates, nitrates, nitriles, nitrites, nitro compounds, nitroso compounds, and pyridine derivatives. The group containing sulfur can be selected from the group consisting of thiols, sulfides, disulfides, sulfoxides, sulfones, sulfunic acids, sulfonic acids, thiocyantes, isothyanates, thiones, and thials. In an embodiment, the group containing phosphorus is selected from the group consisting of phosphines, phosphanes, phophonic acids, phosphates, and phosphodiesters. The group containing boron may be selected from the group consisting of boronic acids, boronic esters, borinic acids and borinic esters.

The functional group can be selected from the group consisting of acetals, acyl groups, acyl halides, alkenyl groups, alkoxides, alkoxy groups, alkynyl groups, amides, amine oxides, amines, carbodiimides, carboximidates, carboxylic acids, cyanamides, cyanates, dithiocarbamates, enols, esters, ethers, hydrazines, hydrazones, hydroxamic acids, imides, isocyanates, isocyanides, isothiocyanates, ketals, ketenes, ketones, leaving groups, nitriles, organohalides, organophosphorus, orthoesters, oximes, phosphonofluoridates, phosphonothioates, phosphoramidothioates, phosphorodithioates, phosphorofluoridates, phosphorothioates, protecting groups, pyrophosphates, semicarbazides, semicarbazones, sulfamates, sulfonate esters, sulfones, sulfonic acids, sulfonyl groups, sulfoximines, sulfuryl compounds, thioamides, thiocyanates, thioesters, thiolates, thiones, thiophosphoryl compounds, and thiosulfinates. The functional group can also be selected from the group consisting of acetal, acetoxy group, acetylide, acid anhydride, activating group, acyl chloride, acyl halide, acylal, acyloin, acylsilane, alcohol, aldehyde, aldimine, alkane, alkene, alkoxide, alkyl cycloalkane, alkyl nitrites, alkyne, allene, amide, amidine, aminal, amine oxide, azide, azine, aziridine, azoxy, bifunctional, bisthiosemicarbazone, biuret, boronic acid, carbamate, calbamino, carbazide, carbene, carbinol, carbonate ester, carbonyl, carboxamide, carboximidate, carboxylic acid, chloroformate, cumulene, cyanate ester, cyanimide, cyanohydrin, deactivating groups, depside, diazo, diol, dithiocarbamate, enamine, enediyne, enol, enol ether, enone, enyne, episulfide, epoxide, ester, ether, fluorosulfonate, halohydrin, haloketone, hemiacetal, hemiaminal, hemithioacetal, hydrazide, hydrazone, hydroxamic acid, hydroxyl, hydroxylamine, imine, iminium, isothiouronium, ketene, ketenimine, ketone, ketyl, lactam, lactol, lactone, methine, methyl group, nitrate, nitrile ylide, nitrilimine, nitro compound, nitroamine, nitronate, nitrone, nitronium ion, nitrosamine, nitroso, orthoester, osazone, oxaziridine, oxime, n-oxoammonium salt, peroxide, peroxy acid, persistent carbene, phenols, phosphaalkene, phosphaalkyne, phosphate, phosphinate, phosphine, phosphine oxide, phosphinite, phosphonate, phosphonite, phosphonium, phosphorane, s-nitrosothiol, schiff base, selenol, selenonic acid, selone, semicarbazide, semicarbazone, silyl enol ether, silyl ether, sulfenamide, sulfenic acid, sulfenyl chloride, sulfide, sulfilimine, sulfinamide, sulfinic acid, sulfite ester, sulfonamide, sulfonanilide, sulfonate, sulfonyl, sulfonyl halide, sulfoxide, sulfuryl, sultone, tellurol, thial, thioacetal, thioamide, thiocarbamate, thiocarboxy, thiocyanate, thioester, thioether, thioketal, thioketone, thiol, thiolactone, thiourea, tosylhydrazone, triazene, triol, urea, vanillyl, xanthate, ylide, and ynolate. In some embodiments, the functional group comprises a carboxyl group, an amino group, a hydroxyl group, a hydrazide group and/or a chloromethyl group. For example, the functional group can be a carboxyl group.

The invention further provides a composition comprising the functional group binding aptamer and a substrate. The substrate can be any useful substrate, e.g., a planar substrate or a microsphere. See, e.g., FIGS. 16A-16B. The substrate can be modified, e.g., with one or more modification selected from the group consisting of carboxyl-modified, amino-modified, hydroxyl-modified, hydrazide-modified, chloromethyl-modified, and a combination thereof. In an embodiment, the substrate comprises a carboxyl group. The aptamer may be bound to the carboxyl group. The substrate can also comprise a binding agent, including without limitation an antibody or aptamer. In some embodiments, the composition further comprises a microvesicle.

The invention further provides a kit comprising a reagent and use of the reagent, wherein the reagent may comprise a functional group binding aptamer and/or the composition described above.

In a related aspect, the invention provides a method comprising contacting a functional group binding aptamer as described above with a substrate, e.g., a planar substrate or a microsphere. As described above, the substrate can be modified, e.g., with one or more modification selected from the group consisting of carboxyl-modified, amino-modified, hydroxyl-modified, hydrazide-modified, chloromethyl-modified, and a combination thereof. In an embodiment, the substrate comprises a carboxyl group. The aptamer may be bound to the carboxyl group. The substrate can also comprise a binding agent, including without limitation an antibody or aptamer. In some embodiments, the composition further comprises. The method can further comprise contacting the substrate with a target of the binding agent, e.g., a protein or a microvesicle.

The invention further provides a kit comprising a reagent for carrying out the method. The invention also provides for use of the reagent for carrying out the methods. The reagent may comprise a functional group binding aptamer and/or the composition described above.

In another related aspect, the invention provides a method of detecting a presence or level of a biological entity in a biological sample suspected of containing the biological entity, comprising: (a) providing a composition comprising one or more binding agent specific to the biological entity attached to a carboxylated substrate, wherein the carboxylated substrate is bound to a functional group binding aptamer; (b) contacting the biological sample with the composition provided in step (a); and (c) detecting whether the biological entity is recognized by the one or more binding agent in step (b), thereby detecting the presence or level of the biological entity in the biological sample. The functional group binding aptamer can be a functional group binding aptamer described above.

In an embodiment, the one or more binding agent comprises an antibody or aptamer. The biological entity can be a protein. The biological entity can also be a microvesicle. In some embodiments, the one or more binding agent is specific to a microvesicle surface antigen, including without limitation a microvesicle surface antigen selected from any of Tables 3-4, or 26. The biological entity, e.g., a protein, microvesicle or microvesicle surface antigen, can be chosen as a biomarker of a disease or disorder. In such cases, the method may provide a diagnosis, prognosis or theranosis of the disease or disorder as further described herein.

The invention further provides a kit comprising a reagent for carrying out the method. The invention also provides for use of the reagent for carrying out the methods. The reagent may comprise one or more of the functional group binding aptamer and the substrate.

In another related aspect, the invention provides a method for enhancing binding comprising: (a) contacting a substrate with an aptamer capable of binding a carboxyl group, wherein the substrate also comprises one or more selected nucleic acid or polypeptide molecules; and (b) contacting the substrate with a binding agent capable of binding the nucleic acid or polypeptide molecule, whereby the aptamer binding to the carboxyl group enhances the binding of the binding agent to the nucleic acid or polypeptide molecule. The functional group binding aptamer can be a functional group binding aptamer described above. The substrate can be any useful substrate, e.g., a planar substrate or a microsphere. The nucleic acid or polypeptide can be covalently bound to a carboxyl group via an amide linkage. In some embodiments, the substrate comprises the binding agent.

The invention further provides a kit comprising a reagent for carrying out the method. The invention also provides for use of the reagent for carrying out the methods. The reagent may comprise one or more of the functional group binding aptamer and the substrate.

The invention provides compositions comprising a complex between a substrate and a sample, and methods of use thereof. In such an aspect, the invention provides a method of selecting one or more binding agent comprising: (a) contacting a substrate with a biological sample to allow formation of a substrate biological sample complex; (b) contacting the substrate-biological sample complex with a plurality of candidate binding agents; and (c) identifying one or more member of the plurality of candidate binding agents that associates with the substrate-biological sample complex, thereby selecting the one or more binding agent. The one or more binding agent can be a nucleic acid, DNA molecule, RNA molecule, antibody, antibody conjugate, antibody fragment, aptamer, peptoid, zDNA, peptide nucleic acid (PNA), locked nucleic acid (LNA), lectin, polypeptide, peptide, dendrimer, membrane protein labeling agent, chemical compound, or a combination thereof. In some embodiments, the one or more binding agent comprises an aptamer.

The biological sample can be any useful sample, e.g., a tissue sample, a cell culture sample, or a biological fluid. In some embodiments, the biological sample comprises a bodily fluid, optionally wherein the bodily fluid comprises peripheral blood, sera, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, female ejaculate, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, umbilical cord blood, or a derivative of any thereof. The biological sample can include a heterogeneous microvesicle population or a homogeneous microvesicle population.

In some embodiments, the biological sample is a concentrated plasma sample, a serum sample, a clarified serum sample, or a clarified plasma sample. The clarified serum or clarified plasma sample may have reduced levels of one or more abundant protein as compared to an unclarified control sample. The one or more abundant protein can be a blood protein. Such abundant blood proteins include without limitation albumin, IgG, transferrin, fibrinogen, fibrin, IgA, α2-Macroglobulin, IgM, α1-Antitrypsin, complement C3, haptoglobulin, apolipoprotein A1, A3 and B; α1-Acid Glycoprotein, ceruloplasmin, complement C4, C1q, IgD, prealbumin (transthyretin), plasminogen, a derivative of any thereof, and a combination thereof. The one or more abundant protein may comprise one or more of Albumin, Immunoglobulins, Fibrinogen, Prealbumin, Alpha 1 antitrypsin, Alpha 1 acid glycoprotein, Alpha 1 fetoprotein, Haptoglobin, Alpha 2 macroglobulin, Ceruloplasmin, Transferrin, complement proteins C3 and C4, Beta 2 microglobulin, Beta lipoprotein, Gamma globulin proteins, C-reactive protein (CRP), Lipoproteins (chylomicrons, VLDL, LDL, HDL), other globulins (types alpha, beta and gamma), Prothrombin, Mannose-binding lectin (MBL), a derivative of any thereof, and a combination thereof.

In some embodiments, the one or more abundant protein is separated from the clarified serum or clarified plasma sample in whole or in part by chromatography, size exclusion chromatography, ion exchange chromatography, affinity chromatography, immunoaffinity, precipitation, or a combination thereof. The one or more abundant protein can also be separated from the clarified serum or clarified plasma sample after contacting the biological sample with thromboplastin. In some embodiments, at least 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% or 100% of the one or more abundant protein is separated from the clarified serum or clarified plasma sample as compared to the unclarified control sample.

The substrate-biological sample complex may comprise a cross-link between the substrate and a component of the biological sample, optionally wherein the cross-link comprises a photocrosslink, an imidoester crosslinker, dimethyl suberimidate, a lipid crosslinker, an N-Hydroxysuccinimide-ester crosslinker, bissulfosuccinimidyl suberate (BS3), an aldehyde, acrolein, crotonaldehyde, formaldehyde, a carbodiimide crosslinker, N,N'-dicyclohexylcarbodiimide (DDC), N,N'-diisopropylcarbodiimide (DIC), 1-Ethyl-3-[3-dimethylaminopropyl]carbodiimide hydrochloride (EDC or EDAC), Succinimidyl-4-(N-maleimidomethyl)cyclohexane-1-carboxylate (SMCC), a Sulfosuccinimidyl-4-(N-maleimidomethyl)cyclohexane-1-carboxylate (Sulfo-SMCC), a Sulfo-N-hydroxysuccinimidyl-2-(6-[biotinamido]-2-(p-azido benzamido)-hexanoamido)ethyl-1,3'-dithioproprionate (Sulfo-SBED), 2-[N2-(4-Azido-2,3,5,6-tetrafluorobenzoyl)-N6-(6-biotin-amidocaproyl)-L-lysinyl]ethyl methanethiosulfonate (Mts-Atf-Biotin), 2-{N2-[N6-(4-Azido-2,3,5,6-tetrafluorobenzoyl-6-amino-caproyl)-N6-(6-biotinamidocaproyl)-L-lysinylamido]}ethyl methanethiosultonate (Mts-Atf-LC-Biotin), a photoreactive amino acid, L-Photo-Leucine, L-Photo-Methionine, an N-Hydroxysuccinimide (NHS) crosslinker, an NHS-Azide reagent, NHS-Azide, NHS-PEG4-Azide, NHS-PEG12-Azide, an NHS-Phosphine reagent, NHS-Phosphine, Sulfo-NHS-Phosphine, or any combination or modification thereof. The substrate can be directly crosslinked to the component of the biological sample, or the substrate can be crosslinked to the component of the biological sample via a linker.

In some embodiments of the method, the component of the biological sample comprises a microvesicle. When a linker is used, the linker may be embedded within the microvesicle membrane. See, e.g., FIGS. 10A-10B. Such linker may include without limitation a functionalized lipid, optionally wherein the functionalized lipid comprises 16:0 Biotinyl PE 1,2-dipalmitoyl-sn-glycero-3-phosphoethanolamine-N-(biotinyl) (sodium salt), 18:1 Biotinyl PE 1,2-dioleoyl-sn-glycero-3-phosphoethanolamine-N-(biotinyl) (sodium salt), 16:0 Biotinyl Cap PE 1,2-dipalmitoyl-sn-glycero-3-phosphoethanolamine-N-(cap biotinyl) (sodium salt), 18:1 Biotinyl Cap PE 1,2-dioleoyl-sn-glycero-3-phosphoethanolamine-N-(cap biotinyl) (sodium salt), or a combination thereof.

The linker can also comprise a diacyl glycerol, diacyl phosphoglycerol (phospholipid) or sterol, dialkyl glycerol, dialkyl- or diacyl-1-amino-2,3-dihydroxypropane, long-chain alkyl or acyl, sphingolipid, ceramide, phospholipid, glycosyl phosphatidylinositol (GPI) membrane anchor sequence, glycophospholipid membrane anchor, membrane receptor fragment, protein-binding receptor, metal-chelating receptor, immunoglobulin Fc-binding receptor, cytokine or growth factor-binding receptor, drug-binding receptor, lipid mimicking receptor, transmembrane receptor, synthetic protein-binding receptor, synthetic metal-chelating receptor, synthetic immunoglobulin Fc-binding receptor, synthetic cytokine or growth factor-binding receptor, synthetic drug-binding receptor, synthetic lipid mimicking receptor, synthetic transmembrane receptor, protein, peptide, peptidomimetic, sphingolipid, steroid, cholesterol, dihydrocholesterol, ergosterol, brassicasterol, cholesterylamine, dihydrocholesterylamine, ergosterylamine, brassicasteiylamine, 3-cholesterylamine, 3-dihydrocholesterylamine, 3-ergosterylamine, 3-brassicasterylamine 3β-cholesterylamine, 3β-dihydrocholesterylamine, 3β-ergosterylamine, 3β-brassicasterylamine, or a functional fragment or derivative of any thereof.

In some embodiments of the method, the substrate is conjugated to a binding agent to the component of the biological sample. The binding agent may be an antibody, an aptamer, or a lectin, optionally wherein the lectin comprises concanavalin A (ConA). The component of the biological sample can be a microvesicle, optionally wherein the binding agent comprises a binding agent to a microvesicle surface antigen. See, e.g., FIGS. 7A-7D.

The method may further comprise identifying the one or more binding agent, e.g., using methods disclosed herein.

In a related aspect, the invention provides a composition of matter comprising a substrate-microvesicle complex, wherein the substrate comprises a synthetic substrate. Such substrate may be a bead, a well, or a planar substrate, optionally wherein the bead comprises a magnetic bead, or a polystyrene bead.

The invention further provides a kit comprising a reagent for carrying out the method. The invention also provides for use of the reagent for carrying out the methods. The reagent may comprise one or more of a substrate-microvesicle complex and a linker agent. The reagent may comprise the composition above.

In another related aspect, the invention provides method of producing a stable substrate-microvesicle complex comprising contacting a substrate with a microvesicle, wherein the substrate is functionalized with a chemical group capable of binding directly to at least one component present on the surface of the microvesicle. The substrate can be a bead, a well, a matrix or a planar substrate. The at least one component may be a useful biomarker, including without limitation a peptide, polypeptide, protein, lipid, carbohydrate, a derivative thereof, or a combination thereof. The chemical group can be a peptoid, zDNA, peptide nucleic acid (PNA), locked nucleic acid (LNA), lectin, peptide/polypeptide, dendrimer, membrane protein labeling agent, chemical compound, a photocrosslink, an imidoester crosslinker, dimethyl suberimidate, a lipid crosslinker, an N-Hydroxysuccinimide-ester crosslinker, bissulfosuccinimidyl suberate (BS3), an aldehyde, acrolein, crotonaldehyde, formaldehyde, a carbodiimide crosslinker, N,N'-dicyclohexylcarbodiimide (DDC), N,N'-diisopropylcarbodiimide (DIC), 1-Ethyl-3-[3-dimethylaminopropyl]carbodiimide hydrochloride (EDC or EDAC), Succinimidyl-4-(N-maleimidomethyl)cyclohexane-1-carboxylate (SMCC), a Sulfosuccinimidyl-4-(N-maleimidomethyl)cyclohexane-1-carboxylate (Sulfo-SMCC), a Sulfo-N-hydroxysuccinimidyl-2-(6-[biotinamido]-2-(p-azido benzamido)-hexanoamido) ethyl-1,3'-dithioproprionate (Sulfo-SBED), 2-[N2-(4-Azido-2,3,5,6-tetrafluorobenzoyl)-N6-(6-biotin-amidocaproyl)-L-lysinyl]ethyl methanethiosulfonate (Mts-Atf-Biotin), 2-{N2-[N6-(4-Azido-2,3,5,6-tetrafluorobenzoyl-6-amino-caproyl)-N6-(6-biotinamidocaproyl)-L-lysinylamido]}ethyl methanethiosultonate (Mts-Atf-LC-Biotin), a photoreactive amino acid, L-Photo-Leucine, L-Photo-Methionine, an N-Hydroxysuccinimide (NHS) crosslinker, an NHS-Azide reagent, NHS-Azide, NHS-PEG4-Azide, NHS-PEG12-Azide, an NHS-Phosphine reagent, NHS-Phosphine, Sulfo-NHS-Phosphine, or a combination thereof. In an embodiment, the chemical group comprises a hydrocarbon, a halogen, a group containing oxygen (i.e., C—O bonds), a group containing nitrogen, a group containing sulfur, a group containing phosphorus, a group containing boron, or a combination thereof. In another embodiment, the hydrocarbon is selected from the group consisting of alkanes, alkenes, alkynes, benzene derivatives, toluene derivatives, branched or ring alkanes, carbocation and carboanions. In still another embodiment, the halogen is selected from the group consisting of haloalkanes, fluoroalkanes, chloroalkanes, bromoalkanes and iodoalkanes. The group containing oxygen can be selected from the group consisting of alcohols, ketones, aldehydes, acyl halides, carbonates, carboxylates, carboxylic acids, esters, hydroperoxides, ethers, hemiacetals, hemiketals, acetals, ketals, orthoesters, and orthocarbonates. The group containing nitrogen can be selected from the group consisting of amides, amines, imines, imides, azides, azo compounds, cyanates, nitrates, nitriles, nitrites, nitro compounds, nitroso compounds, and pyridine derivatives. In some embodiments, the group containing sulfur is selected from the group consisting of thiols, sulfides, disulfides, sulfoxides, sulfones, sulfunic acids, sulfonic acids, thiocyantes, isothyanates, thiones, and thials. The group containing phosphorus can be selected from the group consisting of phosphines, phosphanes, phophonic acids, phosphates, and phosphodiesters. In embodiments, the group containing boron is selected from the group consisting of boronic acids, boronic esters, borinic acids and borinic esters.

The chemical group may comprise an acetal, acyl group, acyl halide, alkenyl group, alkoxide, alkoxy group, alkynyl group, amide, amine oxide, amine, carbodiimide, carboximidate, carboxylic acid, cyanamide, cyanate, dithiocarbamate, enol, ester, ether, hydrazine, hydrazone, hydroxamic acid, imide, isocyanate, isocyanide, isothiocyanate, ketal, ketene, ketone, leaving group, nitrile, organohalide, organophosphorus, orthoester, oxime, phosphonofluoridate, phosphonothioate, phosphoramidothioate, phosphorodithioate, phosphorofluoridate, phosphorothioate, protecting group, pyrophosphate, semicarbazide, semicarbazone, sulfamate, sulfonate ester, sulfone, sulfonic acid, sulfonyl group, sulfoximine, sulfuryl compound, thioamide, thiocyanate, thioester, thiolate, thione, thiophosphoryl compound, and/or thiosulfinates. The chemical group may be selected from the group consisting of acetal, acetoxy group, acetylide, acid anhydride, activating group, acyl chloride, acyl halide, acylal, acyloin, acylsilane, alcohol, aldehyde, aldimine, alkane, alkene, alkoxide, alkyl cycloalkane, alkyl nitrites, alkyne, allene, amide, amidine, aminal, amine oxide, azide, azine, aziridine, azoxy, bifunctional, bisthiosemicarbazone, biuret, boronic acid, carbamate, carbamino, carbazide, carbene, carbinol, carbonate ester, carbonyl, carboxamide, carboximidate, carboxylic acid, chloroformate, cumulene, cyanate ester, cyanimide, cyanohydrin, deactivating groups, depside, diazo, diol, dithiocarbamate, enamine, enediyne, enol, enol ether, enone, enyne, episulfide, epoxide, ester, ether, fluorosulfonate, halohydrin, haloketone, hemiacetal, hemiaminal, hemithioacetal, hydrazide, hydrazone, hydroxamic acid, hydroxyl, hydroxylamine, imine, iminium, isothiouronium, ketene, ketenimine, ketone, ketyl, lactam, lactol, lactone, methine, methyl group, nitrate, nitrile ylide, nitrilimine, nitro compound, nitroamine, nitronate, nitrone, nitronium ion, nitrosamine, nitroso, orthoester, osazone, oxaziridine, oxime, n-oxoammonium salt, peroxide, peroxy acid, persistent carbene, phenols, phosphaalkene, phosphaalkyne, phosphate, phosphinate, phosphine, phosphine oxide, phosphinite, phosphonate, phosphonite, phosphonium, phosphorane, s-nitrosothiol, schiff base, selenol, selenonic acid, selone, semicarbazide, semicarbazone, silyl enol ether, silyl ether, sulfenamide, sulfenic acid, sulfenyl chloride, sulfide, sulfilimine, sulfinamide, sulfinic acid, sulfite ester, sulfonamide, sulfonanilide, sulfonate, sulfonyl, sulfonyl halide, sulfoxide, sulfuryl, sultone, tellurol, thial, thioacetal, thioamide, thiocarbamate, thiocarboxy, thiocyanate, thioester, thioether, thioketal, thioketone, thiol, thiolactone, thiourea, tosylhydrazone, triazene, triol, urea, vanillyl, xanthate, ylide, and ynolate. In embodiments, the chemical group comprises a carboxyl group, an amino group, a hydroxyl group, a hydrazide group and/or a chloromethyl group. For example, the chemical group can be a carboxyl group.

In a related aspect, the invention provides a composition of matter comprising a substrate-microvesicle complex, wherein the substrate comprises a synthetic substrate as described above. The invention further provides a stabilized microvesicle composition comprising a microvesicle directly conjugated to an inert substrate. The substrate can be a bead, a well, a matrix, or a planar substrate, optionally wherein the bead comprises a magnetic bead, or a polystyrene bead. See, e.g., any of FIGS. 7A-7D, FIGS. 10A-12E.

The invention also provides a kit comprising one or more reagent for carrying out the method above, optionally wherein the one or more reagent comprises one or more of a substrate-microvesicle complex and a linker agent. The invention further provides use of the one or more reagent for carrying out the method.

In an aspect, the invention provides a method of visualizing a microvesicle. See, e.g., FIGS. 11A-12E. The method comprises: (a) contacting the microvesicle with a binding agent to a microvesicle antigen, wherein the binding agent comprises a label; (b) fixing the contacted microvesicle to a scanning electron microscopy (SEM) substrate; (c) sputter coating the fixed microvesicle; and (d) using SEM to visualize the microvesicle and the label. The microvesicle can be attached to a substrate prior to step (a). The microvesicle may be attached to the substrate via covalent linkage. The microvesicle may also be attached to the substrate via immunoaffinity linkage. See, e.g., FIGS. 7A-7E; FIG. 10B.

The binding agent can be directly labeled or the binding agent can be indirectly labeled. The indirect label may comprise a labeled binding agent that forms a complex with the binding agent to the microvesicle antigen. Any useful binding agent can be used in the method, e.g., an antibody, a functional antibody fragment, or an aptamer.

The microvesicle antigen can be chosen to visualize a microvesicle of interest. In some embodiments, the antigen is selected from Table 3, Table 4, or Table 26. For example, the microvesicle antigen can be to a general vesicle marker, including without limitation a tetraspanin, CD9, CD63, CD81, or any combination thereof.

The sputter coating may comprise gold and/or palladium coating. The sputter coating may comprise carbon coating. In some embodiments, the SEM comprises secondary electrons (SE) mode to visualize the microvesicles and/or back scattered electrons (BSE) mode to visualize the label. The label can comprise gold.

In embodiments of the invention, the (i) the microvesicle is attached to a substrate prior to step (a) via covalent linkage; (ii) the binding agent to the microvesicle antigen is an indirectly labeled antibody, wherein the indirect label comprises a gold labeled antibody that forms a complex with the antibody to the microvesicle antigen; (iii) the microvesicle antigen is CD9; (iv) the sputter coating comprises carbon coating; and (v) the SEM comprises secondary electrons (SE) mode to visualize the microvesicles and/or back scattered electrons (BSE) mode to visualize the label.

The invention further provides kits and uses of one or more reagent for carrying out the methods of the invention. The one or more reagent may comprise any useful reagents for carrying out the subject methods, including without limitation aptamer libraries, substrates such as microbeads or planar arrays or wells, reagents for biomarker and/or microvesicle isolation, aptamers directed to specific targets, aptamer pools that facilitate detection of a biomarker/microvesicle population, reagents such as primers for nucleic acid sequencing or amplification, arrays for nucleic acid hybridization, detectable labels, solvents or buffers and the like, various linkers, various assay components, blockers, and the like. The one or more reagent may also comprise various compositions provided by the invention.

BRIEF DESCRIPTION OF THE DRAWINGS

FIGS. 1A-1F illustrate methods of assessing biomarkers such as microvesicle surface antigens. FIG. 1A is a schematic of a planar substrate coated with a capture agent, such as an aptamer or antibody, which captures vesicles expressing the target antigen of the capture agent. The capture agent may bind a protein expressed on the surface of vesicles shed from diseased cells ("disease vesicle"). The detection agent, which may also be an aptamer or antibody, carries a detectable label, here a fluorescent signal. The detection agent binds to the captured vesicle and provides a detectable signal via its fluorescent label. The detection agent can detect an antigen that is generally associated with vesicles, or is associated with a cell-of-origin or a disease, e.g., a cancer. FIG. 1B is a schematic of a particle bead conjugated with a capture agent, which captures vesicles expressing the target antigen of the capture agent. The capture agent may bind a protein expressed on the surface of vesicles shed from diseased cells ("disease vesicle"). The detection agent, which may also be an aptamer or antibody, carries a detectable label, here a fluorescent signal. The detection agent binds to the captured vesicle and provides a detectable signal via its fluorescent label. The detection agent can detect an antigen that is generally associated with vesicles, or is associated with a cell-of-origin or a disease, e.g., a cancer. FIG. 1C is an example of a screening scheme that can be performed by using different combinations of capture and detection agents to the indicated biomarkers. The biomarker combinations can be detected using assays as shown in FIGS. 1A-1B. FIGS. 1D-1E present illustrative schemes for capturing and detecting vesicles to characterize a phenotype. FIG. 1F presents illustrative schemes for assessing vesicle payload to characterize a phenotype.

FIG. 2A illustrates aptamer candidate 201 bound to target 202. In step i), a competing antibody 203 is then added to the reaction. FIG. 2B illustrates candidate antibody 203 competing with aptamer candidate 201 at the epitope of the antibody. Aptamer candidate 201 is displaced by the antibody and then collected.

FIG. 5A illustrates a secondary structure of a 32-mer oligonucleotide, Aptamer 4, with sequence 5'-CCCCCCGAATCACATGACTTGGGCGGGGGTCG (SEQ ID NO. 1). In the figure, the sequence is shown with 6 thymine nucleotides added to the end, which can act as a spacer to attach a biotin molecule. This particular oligo has a high binding affinity to the target, EpCAM (see Table 5). Additional candidate EpCAM binders are identified by modeling the entire database of sequenced oligos to the secondary structure of this oligo. FIG. 5B illustrates another 32-mer oligo with sequence 5'-ACCGGATAGCGGTTGGAGGCGTGCTC-CACTCG (SEQ ID NO. 3840) that has a different secondary structure than the aptamer in FIG. 5A. This aptamer is also shown with a 6-thymine tail.

FIGS. 7A-7D illustrate methods to attach microvesicles to a substrate. FIG. 7A illustrates direct conjugation of a carboxylated microsphere to a vesicle surface antigen. FIG. 7B illustrates anchoring of a microvesicle to a microsphere via a biotin functionalized lipid anchor. FIG. 7C illustrates antibody binding to a vesicle surface antigen, wherein the antibody is conjugated to a carboxylated microsphere. FIG. 7D illustrates aptamer binding to a vesicle surface antigen, wherein the aptamer is conjugated to a carboxylated microsphere.

FIG. 9A shows Vcap derived microvesicle titers against Ab conjugated beads. MagPlex beads were conjugated with antibodies to EpCAM, CD63 or CD81 according to manufacturer's protocol (Luminex Corp., Austin Tex.). The microvesicles were detected with phycoerythrin (PE) labeled antibodies to CD9, a common microvesicle surface protein. The Y-axis in the figures shows median fluorescent intensity (MFI) of the detected microvesicles. The X-axis indicates the amount of VCap vesicle input. FIG. 9B shows capture of microvesicles from plasma using bead conjugated anti-CD63 antibodies for capture and PE-labeled anti-CD9 antibodies for detection. The plot shows detection of various numbers of microspheres as indicated for microvesicles isolated under various conditions: microvesicles after ultracentrifugation with sucrose gradient without or with 0.1% Tween 20 ("UC-PBS" and "UC-PBST", respectively), concentrated microvesicles from plasma subjected to ultrafiltration ("N3-Conc"), and microvesicles purified using ExoQuick methodology ("N3-Exo"). "Control (PBS)" samples do not have microvesicles. FIG. 9C shows titration of microvesicles captured with antibody-conjugated microspheres with input comprising plasma-derived microvesicles from two patients. In all samples, 5000 microspheres were detected. Microvesicles (cMVs) were captured using bead conjugated anti-CD63 antibodies or anti-CD81 antibodies, as indicated, and PE-labeled anti-CD9 antibodies for detection. The X-axis in the plots indicates the number of vesicles in the sample. FIG. 9D shows the stability of the antibody-captured microvesicle-microsphere complexes. Microvesicles (cMVs) from three patients were purified using the ExoQuick technology then captured using bead conjugated anti-CD81 antibodies and PE-labeled anti-CD9 antibodies for detection. Approximately 8.96E+07 microvesicles per 5000 beads were detected before and after incubation of the bead—captured microvesicles for 1 h at 800 rpm at room temperature.

FIGS. 10A-10P illustrate anchoring of microvesicles to microspheres using a heterobifunctional linker with a lipid functional group. FIG. 10A illustrates an illustrative lipid anchor: 1,2-dipalmitoyl-sn-glycero-3-phosphoethanolamine-N-(cap biotinyl) (sodium salt) ("16:0 Biotinyl Cap PE"). Molecular weight is 1053.394. FIG. 10A shows the chemical structure above and 3D structure below. The crosslinker is available from Avanti Polar Lipids, Inc., Alabaster, Ala. FIGS. 10C-10E illustrate flow cytometry of VCAP microvesicles anchored to microspheres using the lipid anchor in FIGS. 10A-10B. The microvesicles were detected using PE labeled anti-CD9 and anti-CD63 antibodies. In FIG. 10C, no lipid anchor was used. FIG. 10D is identical to FIG. 10C with the addition of the lipid anchor. These data illustrate enriched microvesicles conjugated to microspheres via the lipid anchor. FIG. 10E and FIG. 10F illustrate independent replication of the experiments in FIG. 10C and FIG. 10D, respectively. FIGS. 10K-10L illustrate detection of vesicles isolated from plasma samples using ultracentrifugation. Otherwise, experimental conditions are as in FIG. 10C and FIG. 10D, respectively. FIG. 10M and FIG. 10N illustrate detection of VCAP microvesicles anchored to microspheres using the lipid anchor in FIGS. 10A-10B. The microvesicles were detected using PE labeled anti-CD9 and anti-CD63 antibodies. In FIG. 10M, conditions are similar to FIG. 10D and FIG. 10F. However, in the experiment shown in FIG. 10N, 30 mg/ml human serum albumin (HSA) was added to the samples prior to detection. FIGS. 10O-10P shows the MFI values of microsphere-conjugated microvesicles before (Day 0; FIG. 10O) and after (Day 12; FIG. 10P) 12 days of storage at −80° C. Vesicles isolated using different methods were tested as indicated by conditions along the X-axis: 1) ExoQuick™ Kit (System Biosciences, Inc., Mountain View, Calif.) followed by ultrafiltration; 2) ultracentrifugation; 3) ultracentrifugation followed by Exoquick; 4) ExoQuick to ExoMir™ Kit (Bioo Scientific Corp., Austin Tex.); 5) ultra-filtered VCAP vesicle prep #1; 6) ultrafiltered VCAP vesicle prep #2; and 7) ultrafiltration followed by ultracentrifugation.

FIGS. 11A-11M illustrate field emission scanning electron microscopy (FE-SEM) imaging used for evaluation of alternative protocols for tethering microvesicles isolated from plasma to the surface of microspheres. FIG. 11A shows a microsphere that has not been functionalized or conjugated. FIG. 11B shows direct conjugation of plasma microvesicles isolated using ultracentrifugation to non-magnetic beads. FIG. 11C shows a blow up of the indicated region of FIG. 11B. The arrows point to various microvesicles. FIG. 11D and FIG. 11E correspond to FIG. 11B and FIG. 11C, respectively, except that the beads are magnetic. FIGS. 11F-H show functionalized magnetic beads. FIG. 11F shows avidin conjugated beads functionalized with biotinylated concanavalin A (ConA), which is a lectin (i.e., a carbohydrate binding protein) that binds specifically to certain structures found in various sugars, glycoproteins, and glycolipids, mainly internal and nonreducing terminal α-D-mannosyl and α-D-glucosyl groups. FIG. 11G shows avidin conjugated beads functionalized with a biotinylated lipid anchor. FIG. 11H shows beads directly conjugated with anti-CD9 antibodies. FIG. 11I shows bead capture of plasma microvesicles isolated using ultracentrifugation to ConA functionalized beads. FIG. 11J shows a blow up of the indicated region of FIG. 11I. The arrows point to various microvesicles. FIG. 11K shows bead capture of plasma microvesicles isolated using ultracentrifugation to lipid anchor functionalized beads. FIG. 11L shows a blow up of the indicated region of FIG. 11K. The arrows point to various microvesicles. FIG. 11M shows bead capture of plasma microvesicles isolated using ultracentrifugation to lipid anchor functionalized beads. FIG. 11N shows a blow up of the indicated region of FIG. 11M. The arrows point to various microvesicles.

FIGS. 12A-12E illustrate FE-SEM-ImmunoGold protocol for imaging microvesicles conjugated to microbeads. The images shows secondary electron imaging (SE) and Back Scattered Electrons (BSE) images of carboxylated beads conjugated with microvesicles. FIGS. 12A-12B image microvesicles stained with 10 µg/ml anti CD9 primary antibody labeled in suspension. FIG. 12A shows SE imaging and FIG. 12B shows BSE imaging. In FIG. 12B, the gold nanoparticles are white bright spots pointed with arrows. Larger features are may be either inorganic matters (buffer crystals) or lipid plaques since they are more dense and seen at BSE. FIGS. 12C-12D image microvesicles stained with 10 µg/ml anti CD9 primary antibody labeled on glass slides. FIG. 12C shows SE imaging and FIG. 12D shows BSE imaging. In FIG. 12D, the gold nanoparticles are white bright spots pointed with arrows. FIG. 12E shows a BSE image (ImmunoGold) overlaid on top of SE images (microvesicles). Gold nanoparticles (10 nm) are depicted with arrows. Larger features are may be either inorganic matters (buffer crystals) or lipid plaques since they are more dense and seen at BSE.

FIGS. 13A-13B illustrate schemes for screening an aptamer library to identify one or more candidate aptamer. FIG. 13A illustrates a scheme 1300 for positive and optionally negative rounds of screening an oligonucleotide library against a target of interest. A library of oligo candidates is provided 1301. To perform positive selection, the oligos are contacted with the target of interest 1302. The mixture is washed to remove unbound oligos and then oligos are disassociated from the washed mixture and collected 1303. The collected oligos can be used as input to a new round of target binding, which can be repeated any number of times (indicated as 1 . . . n). Between rounds of positive selection, negative selection is optionally performed wherein oligos are contacted with one or more non-target entity 1304. During negative selection, oligos that do not bind the one or more non-target entity are retained and used as input to a new round of positive selection 1302. The oligos collected after the desired numbers of rounds of positive selection 1303 or negative selection 1304 are collected as candidate aptamers which are indicated to bind the target of interest 1305. FIG. 13B illustrates a scheme for selection of aptamers against cancer samples versus non-cancer control samples. The scheme shows 8 cancer samples (Ca1-Ca8) and 7 control samples (nCa1-nCa7) each consisting of individual samples or pooled samples. Seven different selections (Selection 1-Selection 7) are run in parallel. In each Selection, an input pool of candidate aptamers is enriched for aptamers against one of the cancer samples ("positive selection"), and then the pool is depleted of aptamers against one of the control samples ("negative selection"). This process is repeated as indicated. The ordering of the samples is altered in each Selection to avoid selection bias. The aptamers remaining after the last round of positive selection comprise the selected aptamers, which can then be further developed, e.g., as part of an assay to differentiate cancer from non-cancer samples. The aptamer pools can be sequenced after each round to track enrichment, depletion, potential issues, etc.

FIG. 15A is a schematic 1500 showing an assay configuration that can be used to detect and/or quantify a target of interest. In the figure, capture aptamer 1502 is attached to substrate 1501. Target of interest 1503 is bound by capture aptamer 1502. Detection aptamer 1504 is also bound to target of interest 1503. Detection aptamer 1504 carries label 1505 which can be detected to identify target captured to substrate 1501 via capture aptamer 1502. FIG. 15B is a schematic 1510 showing use of an aptamer pool to characterize a phenotype. A pool of aptamers to a target of interest is provided 1511. The pool is contacted with a test sample to be characterized 1512. The mixture is washed to remove unbound aptamers. The remaining aptamers are disassociated and collected 1513. The collected aptamers are identified and the identity of the retained aptamers is used to characterize the phenotype 1514.

In FIG. 17A, a binding agent 1704 is also attached to the substrate 1703. The binding agent has specificity for target 1705, which may be a biological entity such as a protein, nucleic acid, microvesicle, cell, or a portion of any thereof. In FIG. 17B, target 1705, which may be a biological entity such as a protein, nucleic acid, microvesicle, cell, or a portion of any thereof, is also attached to the substrate 1703. Target 1705 is bound by binding agent 1704.

FIG. 18A) EGFR; FIG. 18B) PBP; FIG. 18C) EpCAM; and FIG. 18D) KLK2. Fluorescently labeled Aptamer 4 was used as a detector in the microbead assay. The figures show average median fluorescence values (MFI values) for three cancer (C1-C3) and three normal samples (N1-N3) in each plot. In each plot, the samples from left to right are ordered as: C1, C2, C3, N1, N2, N3.

FIGS. 19A-19C illustrate aptamers recovered from each starting library after one (FIG. 19A), two (FIG. 19B), and three rounds (FIG. 19C) of positive selection. FIGS. 19D-19E illustrate screening 25 aptamer libraries after the 13th round of positive selection against specific antigen (5 libraries per each of SSX2, SSX4, PBP, KLK2 and SPDEF antigens). The aptamer selection after this round was modified with the inclusion of confounding antigens as described in Example 9 (section entitled "*Round 14 of positive selection was modified as follows*"). DNA aptamers bound to magnetic beads conjugated to the aptamers of interest were extracted from beads and re-amplified. The recovered libraries are shown in FIG. 19D. FIG. 19E shows the libraries after an addition round of selection and stringent wash.

FIGS. 23A-C illustrate binding of selected aptamers against microbeads conjugated to various input samples. The aptamers were selected from an aptamer library as binding to microbeads conjugated to breast cancer-derived microvesicles. Experimental details are in Example 20. Each plot shows results obtained with the aptamer indicated above the plot. The Y-axis indicates level of binding. In each group of samples, binding of 9 purified aptamer candidates is shown. The input sample is indicated on the X axis from left to right as follows: 1) Cancer Exosome: aptamer binding to microbeads conjugated to microvesicles isolated from plasma samples from breast cancer patients; 2) Cancer Non-exosome: aptamer binding to microbeads conjugated to plasma samples from breast cancer patients after removal of microvesicles by ultracentrifugation; 3) Non-Cancer Exosome: aptamer binding to microbeads conjugated to microvesicles isolated from plasma samples from normal (i.e., non breast cancer) patients; 4) Non-Cancer Non-Exosome: aptamer binding to microbeads conjugated to plasma samples from breast cancer patients after removal of microvesicles by ultracentrifugation.

FIGS. 24A-24B illustrate results for two non-antigen binding aptamers, which each serve as negative controls. The two non-antigen binding aptamers are: Neg 5 (FIG. 24A): 5' TGCAAGCTGC TAATCAGCGA TGCTCTTTGG AGTTTTTT (Biotin) 3' (SEQ ID NO. 230936); Neg 9 (FIG. 24B): 5' TTTCAAGGCA CTCGTGTTCC CGACATGAGT GTTTTTT (Biotin) 3' (SEQ ID NO. 230937).

DETAILED DESCRIPTION OF THE INVENTION

Figure 1A:
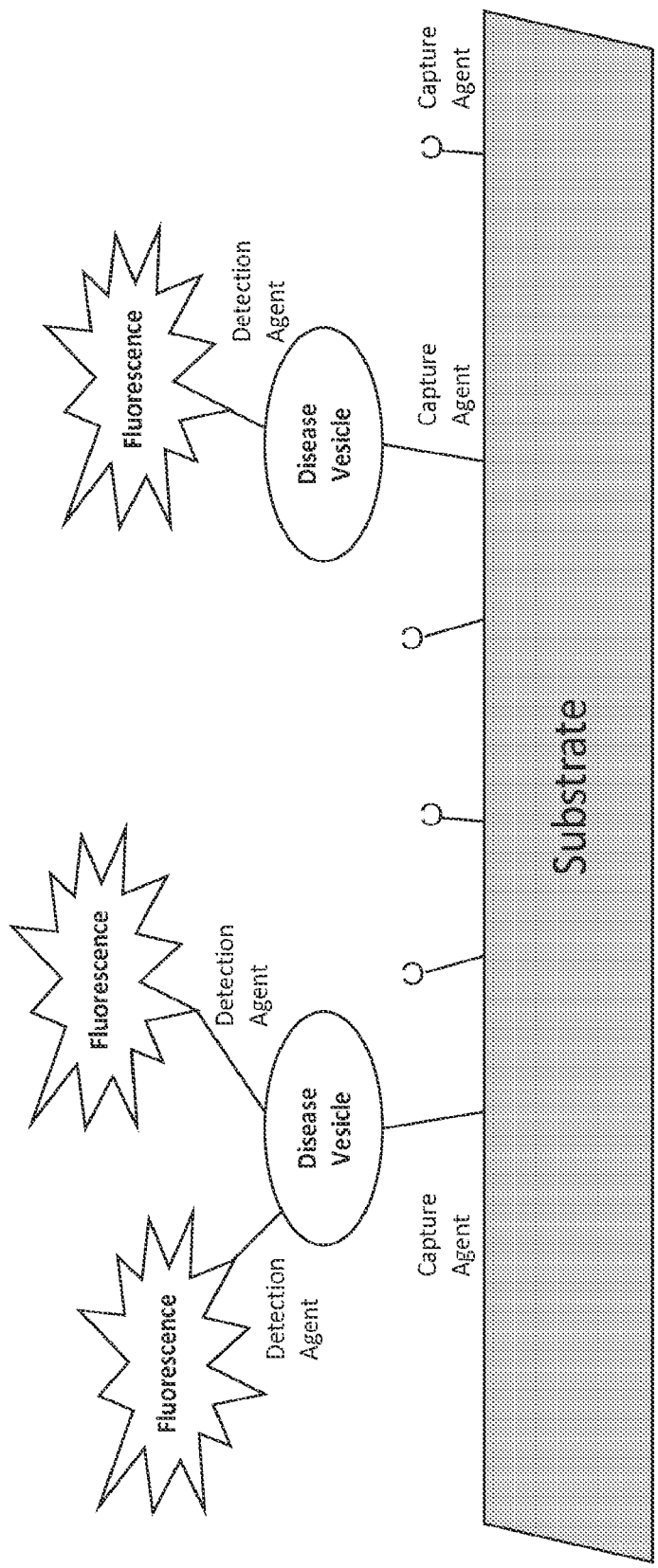

The details of one or more embodiments of the invention are set forth in the accompanying description below. Although any methods and materials similar or equivalent to those described herein can be used in the practice or testing of the present invention, the preferred methods and materials are now described. Other features, objects, and advantages of the invention will be apparent from the description. In the specification, the singular forms also include the plural unless the context clearly dictates otherwise. Unless defined otherwise, all technical and scientific terms used herein have the same meaning as commonly understood by one of ordinary skill in the art to which this invention belongs. In the case of conflict, the present Specification will control.

Disclosed herein are compositions and methods that can be used to assess a biomarker profile, which can include a presence or level of one or more biomarkers. The compositions and methods of the invention comprise the use of aptamers that bind microvesicle surface antigens or a functional fragment thereof. The antigens typically comprise proteins or polypeptides but can be any component displayed on a microvesicle surface including lipids and/or carbohydrates. In general, aptamers disclosed are nucleic acid molecules, including DNA and RNA, and variations thereof. The methods disclosed comprise diagnostic processes and techniques using one or more aptamer of the invention, to determine level or presence of relevant microvesicle surface antigens or a functional fragment thereof. Alternatively, an aptamer of the invention can also be used as a binding agent to capture, isolate, or enrich, a cell, cell fragment, vesicle or any other fragment or complex that comprises the surface antigens or functional fragments thereof.

The compositions and methods of the invention comprise individual aptamers that are identified for use in assessing a biomarker profile. The invention further discloses compositions and methods of aptamer pools that can be used to detect a biomarker profile in a given sample.

Aptamers and aptamer sequences disclosed in the compositions and methods of the invention may be identified herein in the form of DNA or RNA. Unless otherwise specified, one of skill in the art will appreciate that an aptamer may generally be synthesized as either form of nucleic acid and carry various chemical modifications and remain within the scope of the invention.

In addition, an aptamer of the invention can also be used to provide in vitro or in vivo detection or imaging, to provide any diagnostic readout (e.g., diagnostic, prognostic or theranostic).

Separately, an aptamer of the invention can also be used in for treatment or as a therapeutic to specifically target a cell, tissue or organ.

Aptamers

SELEX

A suitable method for generating an aptamer is with the process entitled "Systematic Evolution of Ligands by Exponential Enrichment" ("SELEX") generally described in, e.g., U.S. patent application Ser. No. 07/536,428, filed Jun. 11, 1990, now abandoned, U.S. Pat. No. 5,475,096 entitled "Nucleic Acid Ligands", and U.S. Pat. No. 5,270,163 (see also WO 91/19813) entitled "Nucleic Acid Ligands". Each SELEX-identified nucleic acid ligand, i.e., each aptamer, is a specific ligand of a given target compound or molecule. The SELEX process is based on the unique insight that nucleic acids have sufficient capacity for forming a variety of two- and three-dimensional structures and sufficient chemical versatility available within their monomers to act as ligands (i.e., form specific binding pairs) with virtually any chemical compound, whether monomeric or polymeric. Molecules of any size or composition can serve as targets.

SELEX relies as a starting point upon a large library or pool of single stranded oligonucleotides comprising randomized sequences. The oligonucleotides can be modified or unmodified DNA, RNA, or DNA/RNA hybrids. In some examples, the pool comprises 100% random or partially random oligonucleotides. In other examples, the pool comprises random or partially random oligonucleotides containing at least one fixed and/or conserved sequence incorporated within randomized sequence. In other examples, the pool comprises random or partially random oligonucleotides containing at least one fixed and/or conserved sequence at its 5' and/or 3' end which may comprise a sequence shared by all the molecules of the oligonucleotide pool. Fixed sequences are sequences such as hybridization sites for PCR primers, promoter sequences for RNA polymerases (e.g., T3, T4, T7, and SP6), restriction sites, or homopolymeric sequences, such as poly A or poly T tracts, catalytic cores, sites for selective binding to affinity columns, and other sequences to facilitate cloning and/or sequencing of an oligonucleotide of interest. Conserved sequences are sequences, other than the previously described fixed sequences, shared by a number of aptamers that bind to the same target.

The oligonucleotides of the pool preferably include a randomized sequence portion as well as fixed sequences necessary for efficient amplification. Typically the oligonucleotides of the starting pool contain fixed 5' and 3' terminal sequences which flank an internal region of 30-50 random nucleotides. The randomized nucleotides can be produced in a number of ways including chemical synthesis and size selection from randomly cleaved cellular nucleic acids. Sequence variation in test nucleic acids can also be introduced or increased by mutagenesis before or during the selection/amplification iterations.

The random sequence portion of the oligonucleotide can be of any length and can comprise ribonucleotides and/or deoxyribonucleotides and can include modified or non-natural nucleotides or nucleotide analogs. See, e.g. U.S. Pat. Nos. 5,958,691; 5,660,985; 5,958,691; 5,698,687; 5,817, 635; 5,672,695, and PCT Publication WO 92/07065. Random oligonucleotides can be synthesized from phosphodi-ester-linked nucleotides using solid phase oligonucleotide synthesis techniques well known in the art. See, e.g., Froehler et al., Nucl. Acid Res. 14:5399-5467 (1986) and Froehler et al., Tet. Lett. 27:5575-5578 (1986). Random oligonucleotides can also be synthesized using solution phase methods such as triester synthesis methods. See, e.g., Sood et al., Nucl. Acid Res. 4:2557 (1977) and Hirose et al., Tet. Lett., 28:2449 (1978). Typical syntheses carried out on automated DNA synthesis equipment yield $10^{14}$-$10^{16}$ individual molecules, a number sufficient for most SELEX experiments. Sufficiently large regions of random sequence in the sequence design increases the likelihood that each synthesized molecule is likely to represent a unique sequence.

The starting library of oligonucleotides may be generated by automated chemical synthesis on a DNA synthesizer. To synthesize randomized sequences, mixtures of all four nucleotides are added at each nucleotide addition step during the synthesis process, allowing for random incorporation of nucleotides. As stated above, in one embodiment, random oligonucleotides comprise entirely random sequences; however, in other embodiments, random oligonucleotides can comprise stretches of nonrandom or partially random sequences. Partially random sequences can be created by adding the four nucleotides in different molar ratios at each addition step.

The starting library of oligonucleotides may be for example, RNA, DNA, or RNA/DNA hybrid. In those instances where an RNA library is to be used as the starting library it is typically generated by transcribing a DNA library in vitro using T7 RNA polymerase or modified T7 RNA polymerases and purified. The library is then mixed with the target under conditions favorable for binding and subjected to step-wise iterations of binding, partitioning and amplification, using the same general selection scheme, to achieve virtually any desired criterion of binding affinity and selectivity. More specifically, starting with a mixture containing the starting pool of nucleic acids, the SELEX method includes steps of: (a) contacting the mixture with the target under conditions favorable for binding; (b) partitioning unbound nucleic acids from those nucleic acids which have bound specifically to target molecules; (c) dissociating the nucleic acid-target complexes; (d) amplifying the nucleic acids dissociated from the nucleic acid-target complexes to yield a ligand-enriched mixture of nucleic acids; and (e) reiterating the steps of binding, partitioning, dissociating and amplifying through as many cycles as desired to yield highly specific, high affinity nucleic acid ligands to the target molecule. In those instances where RNA aptamers are being selected, the SELEX method further comprises the steps of: (i) reverse transcribing the nucleic acids dissociated from the nucleic acid-target complexes before amplification in step (d); and (ii) transcribing the amplified nucleic acids from step (d) before restarting the process.

Within a nucleic acid mixture containing a large number of possible sequences and structures, there is a wide range of binding affinities for a given target. A nucleic acid mixture comprising, for example, a 20 nucleotide randomized segment can have $4^{20}$ candidate possibilities. Those which have the higher affinity constants for the target are most likely to bind to the target. After partitioning, dissociation and amplification, a second nucleic acid mixture is generated, enriched for the higher binding affinity candidates. Additional rounds of selection progressively favor better ligands until the resulting nucleic acid mixture is predominantly composed of only one or a few sequences. These can then be cloned, sequenced and individually tested for binding affinity as pure ligands or aptamers.

Cycles of selection and amplification are repeated until a desired goal is achieved. In the most general case, selection/amplification is continued until no significant improvement in binding strength is achieved on repetition of the cycle. The method is typically used to sample approximately $10^n$ different nucleic acid species but may be used to sample as many as about $10^{18}$ different nucleic acid species. Generally, nucleic acid aptamer molecules are selected in a 5 to 20 cycle procedure. In one embodiment, heterogeneity is introduced only in the initial selection stages and does not occur throughout the replicating process.

In one embodiment of SELEX, the selection process is so efficient at isolating those nucleic acid ligands that bind most strongly to the selected target, that only one cycle of selection and amplification is required. Such an efficient selection may occur, for example, in a chromatographic-type process wherein the ability of nucleic acids to associate with targets bound on a column operates in such a manner that the column is sufficiently able to allow separation and isolation of the highest affinity nucleic acid ligands.

In many cases, it is not necessarily desirable to perform the iterative steps of SELEX until a single nucleic acid ligand is identified. The target-specific nucleic acid ligand solution may include a family of nucleic acid structures or motifs that have a number of conserved sequences and a number of sequences which can be substituted or added without significantly affecting the affinity of the nucleic acid ligands to the target. By terminating the SELEX process prior to completion, it is possible to determine the sequence of a number of members of the nucleic acid ligand solution family. The invention provides for the identification of aptamer pools and uses thereof that jointly can be used to characterize a test sample. For example, the aptamer pools can be identified through rounds of positive and negative selection to identify microvesicle indicative of a disease or condition. The invention further provides use of such aptamer pools to detect and/or quantify such microvesicles in a sample, thereby allowing a diagnosis, prognosis or theranosis to be provided.

A variety of nucleic acid primary, secondary and tertiary structures are known to exist. The structures or motifs that have been shown most commonly to be involved in non-Watson-Crick type interactions are referred to as hairpin loops, symmetric and asymmetric bulges, pseudoknots and myriad combinations of the same. Almost all known cases of such motifs suggest that they can be formed in a nucleic acid sequence of no more than 30 nucleotides. For this reason, it is often preferred that SELEX procedures with contiguous randomized segments be initiated with nucleic acid sequences containing a randomized segment of between about 20 to about 50 nucleotides and in some embodiments, about 30 to about 40 nucleotides. In one example, the 5'-fixed:random:3'-fixed sequence comprises a random sequence of about 30 to about 50 nucleotides.

The core SELEX method has been modified to achieve a number of specific objectives. For example, U.S. Pat. No. 5,707,796 describes the use of SELEX in conjunction with gel electrophoresis to select nucleic acid molecules with specific structural characteristics, such as bent DNA. U.S. Pat. No. 5,763,177 describes SELEX based methods for selecting nucleic acid ligands containing photoreactive groups capable of binding and/or photocrosslinking to and/or photoinactivating a target molecule. U.S. Pat. Nos. 5,567,588 and 5,861,254 describe SELEX based methods which achieve highly efficient partitioning between oligonucleotides having high and low affinity for a target molecule. U.S. Pat. No. 5,496,938 describes methods for obtaining improved nucleic acid ligands after the SELEX process has been performed. U.S. Pat. No. 5,705,337 describes methods for covalently linking a ligand to its target.

SELEX can also be used to obtain nucleic acid ligands that bind to more than one site on the target molecule, and to obtain nucleic acid ligands that include non-nucleic acid species that bind to specific sites on the target. SELEX provides means for isolating and identifying nucleic acid ligands which bind to any envisionable target, including large and small biomolecules such as nucleic acid-binding proteins and proteins not known to bind nucleic acids as part of their biological function as well as cofactors and other small molecules. For example, U.S. Pat. No. 5,580,737 discloses nucleic acid sequences identified through SELEX which are capable of binding with high affinity to caffeine and the closely related analog, theophylline.

Counter-SELEX is a method for improving the specificity of nucleic acid ligands to a target molecule by eliminating nucleic acid ligand sequences with cross-reactivity to one or more non-target molecules. Counter-SELEX is comprised of the steps of: (a) preparing a candidate mixture of nucleic acids; (b) contacting the candidate mixture with the target, wherein nucleic acids having an increased affinity to the target relative to the candidate mixture may be partitioned from the remainder of the candidate mixture; (c) partitioning the increased affinity nucleic acids from the remainder of the candidate mixture; (d) dissociating the increased affinity nucleic acids from the target; e) contacting the increased affinity nucleic acids with one or more non-target molecules such that nucleic acid ligands with specific affinity for the non-target molecule(s) are removed; and (f) amplifying the nucleic acids with specific affinity only to the target molecule to yield a mixture of nucleic acids enriched for nucleic acid sequences with a relatively higher affinity and specificity for binding to the target molecule. As described above for SELEX, cycles of selection and amplification are repeated as necessary until a desired goal is achieved.

One potential problem encountered in the use of nucleic acids as therapeutics and vaccines is that oligonucleotides in their phosphodiester form may be quickly degraded in body fluids by intracellular and extracellular enzymes such as endonucleases and exonucleases before the desired effect is manifest. The SELEX method thus encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX identified nucleic acid ligands containing modified nucleotides are described, e.g., in U.S. Pat. No. 5,660,985, which describes oligonucleotides containing nucleotide derivatives chemically modified at the 2' position of ribose, 5 position of pyrimidines, and 8 position of purines, U.S. Pat. No. 5,756,703 which describes oligonucleotides containing various 2'-modified pyrimidines, and U.S. Pat. No. 5,580,737 which describes highly specific nucleic acid ligands containing one or more nucleotides modified with 2'-amino (2'-$NH_2$), 2'-fluoro (2'-F), and/or 2'-O-methyl (2'-OMe) substituents.

Modifications of the nucleic acid ligands contemplated in this invention include, but are not limited to, those which provide other chemical groups that incorporate additional charge, polarizability, hydrophobicity, hydrogen bonding, electrostatic interaction, and fluxionality to the nucleic acid ligand bases or to the nucleic acid ligand as a whole. Modifications to generate oligonucleotide populations which are resistant to nucleases can also include one or more substitute internucleotide linkages, altered sugars, altered bases, or combinations thereof. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, phosphorothioate or allyl phosphate modifications, methylations, and unusual base-pairing combinations such as the isobases isocytidine and isoguanosine. Modifications can also include 3' and 5' modifications such as capping.

In one embodiment, oligonucleotides are provided in which the P(O)O group is replaced by P(O)S ("thioate"), P(S)S ("dithioate"), P(O)$NR_2$ ("amidate"), P(O)R, P(O)OR', CO or $CH_2$ ("formacetal") or 3'-amine (—NH—$CH_2$—$CH_2$—), wherein each R or R' is independently H or substituted or unsubstituted alkyl. Linkage groups can be attached to adjacent nucleotides through an —O—, —N—, or —S— linkage. Not all linkages in the oligonucleotide are required to be identical. As used herein, the term phosphorothioate encompasses one or more non-bridging oxygen atoms in a phosphodiester bond replaced by one or more sulfur atoms.

In further embodiments, the oligonucleotides comprise modified sugar groups, for example, one or more of the hydroxyl groups is replaced with halogen, aliphatic groups, or functionalized as ethers or amines. In one embodiment, the 2'-position of the furanose residue is substituted by any of an O-methyl, O-alkyl, 0-allyl, S-alkyl, S-allyl, or halo group. Methods of synthesis of 2'-modified sugars are described, e.g., in Sproat, et al., Nucl. Acid Res. 19:733-738 (1991); Cotten, et al., Nucl. Acid Res. 19:2629-2635 (1991); and Hobbs, et al., Biochemistry 12:5138-5145 (1973). Other modifications are known to one of ordinary skill in the art. Such modifications may be pre-SELEX process modifications or post-SELEX process modifications (modification of previously identified unmodified ligands) or may be made by incorporation into the SELEX process.

Pre-SELEX process modifications or those made by incorporation into the SELEX process yield nucleic acid ligands with both specificity for their SELEX target and improved stability, e.g., in vivo stability. Post-SELEX process modifications made to nucleic acid ligands may result in improved stability, e.g., in vivo stability without adversely affecting the binding capacity of the nucleic acid ligand.

The SELEX method encompasses combining selected oligonucleotides with other selected oligonucleotides and non-oligonucleotide functional units as described in U.S. Pat. Nos. 5,637,459 and 5,683,867. The SELEX method further encompasses combining selected nucleic acid ligands with lipophilic or non-immunogenic high molecular weight compounds in a diagnostic or therapeutic complex, as described, e.g., in U.S. Pat. Nos. 6,011,020, 6,051,698, and PCT Publication No. WO 98/18480. These patents and applications teach the combination of a broad array of shapes and other properties, with the efficient amplification and replication properties of oligonucleotides, and with the desirable properties of other molecules.

The identification of nucleic acid ligands to small, flexible peptides via the SELEX method has also been explored. Small peptides have flexible structures and usually exist in solution in an equilibrium of multiple conformers, and thus it was initially thought that binding affinities may be limited by the conformational entropy lost upon binding a flexible peptide. However, the feasibility of identifying nucleic acid ligands to small peptides in solution was demonstrated in U.S. Pat. No. 5,648,214. In this patent, high affinity RNA nucleic acid ligands to substance P, an 11 amino acid peptide, were identified.

The aptamers with specificity and binding affinity to the target(s) of the present invention can be selected by the SELEX N process as described herein. As part of the SELEX process, the sequences selected to bind to the target are then optionally minimized to determine the minimal sequence having the desired binding affinity. The selected sequences and/or the minimized sequences are optionally optimized by performing random or directed mutagenesis of the sequence to increase binding affinity or alternatively to determine which positions in the sequence are essential for binding activity. Additionally, selections can be performed with sequences incorporating modified nucleotides to stabilize the aptamer molecules against degradation in vivo.

2' Modified SELEX

In order for an aptamer to be suitable for use as a therapeutic, it is preferably inexpensive to synthesize, safe and stable in vivo. Wild-type RNA and DNA aptamers are typically not stable is vivo because of their susceptibility to degradation by nucleases. Resistance to nuclease degradation can be greatly increased by the incorporation of modifying groups at the 2'-position.

Fluoro and amino groups have been successfully incorporated into oligonucleotide pools from which aptamers have been subsequently selected. However, these modifications greatly increase the cost of synthesis of the resultant aptamer, and may introduce safety concerns in some cases because of the possibility that the modified nucleotides could be recycled into host DNA by degradation of the modified oligonucleotides and subsequent use of the nucleotides as substrates for DNA synthesis.

Aptamers that contain 2'-O-methyl ("2'-OMe") nucleotides, as provided herein, may overcome many of these drawbacks. Oligonucleotides containing 2'-OMe nucleotides are nuclease-resistant and inexpensive to synthesize. Although 2'-OMe nucleotides are ubiquitous in biological systems, natural polymerases do not accept 2'-OMe NTPs as substrates under physiological conditions, thus there are no safety concerns over the recycling of 2'-OMe nucleotides into host DNA. The SELEX method used to generate 2'-modified aptamers is described, e.g., in U.S. Provisional Patent Application Ser. No. 60/430,761, filed Dec. 3, 2002, U.S. Provisional Patent Application Ser. No. 60/487,474, filed Jul. 15, 2003, U.S. Provisional Patent Application Ser. No. 60/517,039, filed Nov. 4, 2003, U.S. patent application Ser. No. 10/729,581, filed Dec. 3, 2003, and U.S. patent application Ser. No. 10/873,856, filed Jun. 21, 2004, entitled "Method for in vitro Selection of 2'-O-methyl substituted Nucleic Acids", each of which is herein incorporated by reference in its entirety.

Methods

Biomarker Detection and Diagnostics

The aptamers of the invention can be used in various methods to assess presence or level of biomarkers in a biological sample, e.g., biological entities of interest such as proteins, nucleic acids, or microvesicles. The aptamer functions as a binding agent to assess presence or level of the cognate target molecule. Therefore, in various embodiments of the invention directed to diagnostics, prognostics or theranostics, one or more aptamers of the invention are configured in a ligand-target based assay, where one or more aptamer of the invention is contacted with a selected biological sample, where the or more aptamer associates with or binds to its target molecules. Aptamers of the invention are used to identify candidate biosignatures based on the biological samples assessed and biomarkers detected. In further embodiments, aptamers may themselves provide a biosignature for a particular condition or disease. A biosignature refers to a biomarker profile of a biological sample comprising a presence, level or other characteristic that can be assessed (including without limitation a sequence, mutation, rearrangement, translocation, deletion, epigenetic modification, methylation, post-translational modification, allele, activity, complex partners, stability, half life, and the like) of one or more biomarker of interest. Biosignatures can be used to evaluate diagnostic and/or prognostic criteria such as presence of disease, disease staging, disease monitoring, disease stratification, or surveillance for detection, metastasis or recurrence or progression of disease. For example, methods of the invention using aptamers against microvesicle surface antigen are useful for correlating a biosignature comprising microvesicle antigens to a selected condition or disease. A biosignature can also be used clinically in making decisions concerning treatment modalities including therapeutic intervention. A biosignature can further be used clinically to make treatment decisions, including whether to perform surgery or what treatment standards should be used along with surgery (e.g., either pre-surgery or post-surgery). As an illustrative example, a biosignature of circulating biomarkers that indicates an aggressive form of cancer may call for a more aggressive surgical procedure and/or more aggressive therapeutic regimen to treat the patient.

A biosignature can be used in any methods disclosed herein, e.g., to assess whether a subject is afflicted with disease, is at risk for developing disease or to assess the stage or progression of the disease. For example, a biosignature can be used to assess whether a subject has prostate cancer, colon cancer, or other cancer as described herein. Furthermore, a biosignature can be used to determine a stage of a disease or condition, such as colon cancer. The biosignature/biomarker profile comprising a microvesicle can include assessment of payload within the microvesicle. For example, one or more aptamer of the invention can be used to capture a microvesicle population, thereby providing readout of microvesicle antigens, and then the payload content within the captured microvesicles can be assessed, thereby providing further biomarker readout of the payload content.

A biosignature for characterizing a phenotype may comprise any number of useful criteria. As described further below, the term "phenotype" as used herein can mean any trait or characteristic that is attributed to a biosignature/biomarker profile. A phenotype can be detected or identified in part or in whole using the compositions and/or methods of the invention. In some embodiments, at least one criterion is used for each biomarker. In some embodiments, at least 1, 2, 3, 4, 5, 6, 7, 8, 9, 10, 15, 20, 30, 40, 50, 60, 70, 80, 90 or at least 100 criteria are used. For example, for the characterizing of a cancer, a number of different criteria can be used when the subject is diagnosed with a cancer: 1) if the amount of microRNA in a sample from a subject is higher than a reference value; 2) if the amount of a microRNA within cell type specific vesicles (i.e. vesicles derived from a specific tissue or organ) is higher than a reference value; or 3) if the amount of microRNA within vesicles with one or more cancer specific biomarkers is higher than a reference value Similar rules can apply if the amount of microRNA is less than or the same as the reference. The method can further include a quality control measure, such that the results are provided for the subject if the samples meet the quality control measure. In some embodiments, if the criteria are met but the quality control is questionable, the subject is reassessed.

Theranostics

A biosignature can be used in therapy related diagnostics to provide tests useful to diagnose a disease or choose the correct treatment regimen, such as provide a theranosis. Theranostics includes diagnostic testing that provides the ability to affect therapy or treatment of a diseased state. Theranostics testing provides a theranosis in a similar manner that diagnostics or prognostic testing provides a diagnosis or prognosis, respectively. As used herein, theranostics encompasses any desired form of therapy related testing, including predictive medicine, personalized medicine, integrated medicine, pharmacodiagnostics and Dx/Rx partnering. Therapy related tests can be used to predict and assess drug response in individual subjects, i.e., to provide personalized medicine. Predicting a drug response can be determining whether a subject is a likely responder or a likely non-responder to a candidate therapeutic agent, e.g., before the subject has been exposed or otherwise treated with the treatment. Assessing a drug response can be monitoring a response to a drug, e.g., monitoring the subject's improvement or lack thereof over a time course after initiating the treatment. Therapy related tests are useful to select a subject for treatment who is particularly likely to benefit from the treatment or to provide an early and objective indication of treatment efficacy in an individual subject. Thus, a biosignature as disclosed herein may indicate that treatment should be altered to select a more promising treatment, thereby avoiding the great expense of delaying beneficial treatment and avoiding the financial and morbidity costs of administering an ineffective drug(s).

The compositions and methods of the invention can be used to identify or detect a biosignature that associated with selected diseases and disorders, which include, but are not limited to cardiovascular disease, cancer, infectious diseases, sepsis, neurological diseases, central nervous system related diseases, endovascular related diseases, and autoimmune related diseases. Therapy related diagnostics also aid in the prediction of drug toxicity, drug resistance or drug response. Therapy related tests may be developed in any suitable diagnostic testing format, which include, but are not limited to, e.g., immunohistochemical tests, clinical chemistry, immunoassay, cell-based technologies, nucleic acid tests or body imaging methods. Therapy related tests can further include but are not limited to, testing that aids in the determination of therapy, testing that monitors for therapeutic toxicity, or response to therapy testing. Thus, a biosignature can be used to predict or monitor a subject's response to a treatment. A biosignature can be determined at different time points for a subject after initiating, removing, or altering a particular treatment.

In some embodiments, the compositions and methods of the invention provide for a determination or prediction as to whether a subject is responding to a treatment is made based on a change in the amount of one or more components of a biosignature (i.e., the microRNA, vesicles and/or biomarkers of interest), an amount of one or more components of a particular biosignature, or the biosignature detected for the components. In another embodiment, a subject's condition is monitored by determining a biosignature at different time points. The progression, regression, or recurrence of a condition is determined. Response to therapy can also be measured over a time course. Thus, the invention provides a method of monitoring a status of a disease or other medical condition in a subject, comprising isolating or detecting a biosignature from a biological sample from the subject, detecting the overall amount of the components of a particular biosignature, or detecting the biosignature of one or more components (such as the presence, absence, or expression level of a biomarker). The biosignatures are used to monitor the status of the disease or condition.

One or more novel biosignatures of a vesicle can also be identified. For example, one or more vesicles can be isolated from a subject that responds to a drug treatment or treatment regimen and compared to a reference, such as another subject that does not respond to the drug treatment or treatment regimen. Differences between the biosignatures can be determined and used to identify other subjects as responders or non-responders to a particular drug or treatment regimen.

In some embodiments, a biosignature is used to determine whether a particular disease or condition is resistant to a drug, in which case a physician need not waste valuable time with such drug treatment. To obtain early validation of a drug choice or treatment regimen, a biosignature is determined for a sample obtained from a subject. The biosignature is used to assess whether the particular subject's disease has the biomarker associated with drug resistance. Such a determination enables doctors to devote critical time as well as the patient's financial resources to effective treatments.

Biosignatures can be used in the theranosis of a cancer, such as identifying whether a subject suffering from cancer is a likely responder or non-responder to a particular cancer treatment. The subject methods can be used to theranose cancers including those listed herein, e.g., in the "Phenotype" section above. These include without limitation lung cancer, non-small cell lung cancer small cell lung cancer (including small cell carcinoma (oat cell cancer), mixed small cell/large cell carcinoma, and combined small cell carcinoma), colon cancer, breast cancer, prostate cancer, liver cancer, pancreatic cancer, brain cancer, kidney cancer, ovarian cancer, stomach cancer, melanoma, bone cancer, gastric cancer, breast cancer, glioma, glioblastoma, hepatocellular carcinoma, papillary renal carcinoma, head and neck squamous cell carcinoma, leukemia, lymphoma, myeloma, or other solid tumors.

A biosignature of circulating biomarkers, including markers associated with a component present in a biological sample (e.g., cell, cell-fragment, cell-derived extracellular vesicle), in a sample from a subject suffering from a cancer can be used select a candidate treatment for the subject. The biosignature can be determined according to the methods of the invention presented herein. In some embodiments, the candidate treatment comprises a standard of care for the cancer. The treatment can be a cancer treatment such as radiation, surgery, chemotherapy or a combination thereof. The cancer treatment can be a therapeutic such as anticancer agents and chemotherapeutic regimens. Further drug associations and rules that are used in embodiments of the invention are found in U.S. patent application Ser. No. 12/658,770, filed Feb. 12, 2010; International PCT Patent Application PCT/US2010/000407, filed Feb. 11, 2010; International PCT Patent Application PCT/US2010/54366, filed Oct. 27, 2010; and U.S. Provisional Patent Application 61/427,788, filed Dec. 28, 2010; all of which applications are incorporated by reference herein in their entirety. See, e.g., "Table 4: Rules Summary for Treatment Selection" of PCT/US2010/54366.

Biomarker Detection

The compositions and methods of the invention can be used to assess any useful biomarkers in a biological sample for charactering a phenotype associated with the sample.

Such biomarkers include all sorts of biological entities such as proteins, nucleic acids, lipids, carbohydrates, complexes of any thereof, and microvesicles. Various molecules associated with a microvesicle surface or enclosed within the microvesicle (referred to herein as "payload") can serve as biomarkers. The microvesicles themselves can also be used as biomarkers.

The aptamers of the invention can be used to assess levels or presence of a microvesicle population. See, e.g., FIGS. 15B-15C. The aptamers of the invention can also be used to assess levels or presence of their specific target molecule. See, e.g., FIG. 15A. In addition, aptamers of the invention are used to capture or isolated a component present in a biological sample that has the aptamer's target molecule present. For example, if a given microvesicle surface antigen is present on a cell, cell fragment or cell-derived extracellular vesicle. A binding agent to the biomarker, including without limitation an aptamer provided by the invention, may be used to capture or isolate the cell, cell fragment or cell-derived extracellular vesicles. See, e.g., FIGS. 1A-1B, 1D-1E. Such captured or isolated entities may be further characterized to assess additional surface antigens or internal "payload" molecules present (i.e., nucleic acid molecules, lipids, sugars, polypeptides or functional fragments thereof, or anything else present in the cellular milieu that may be used as a biomarker), where one or more biomarkers provide a biosignature to assess a desired phenotype, such as disease or condition. See, e.g., FIG. 1F. Therefore, aptamers of the invention are used not only to assess one or more microvesicle surface antigen of interest but are also used to separate a component present in a biological sample, where the components themselves can be further assessed to identify a candidate biosignature.

The methods of the invention can comprise multiplex analysis of at least 2, 3, 4, 5, 6, 7, 8, 9, 10, 11, 12, 13, 14, 15, 16, 17, 18, 19, 20, 25, 50, 75 or 100 different biomarkers. For example, an assay of a heterogeneous population of vesicles can be performed with a plurality of particles that are differentially labeled. There can be at least 2, 3, 4, 5, 6, 7, 8, 9, 10, 11, 12, 13, 14, 15, 16, 17, 18, 19, 20, 25, 50, 75 or 100 differentially labeled particles. The particles may be externally labeled, such as with a tag, or they may be intrinsically labeled. Each differentially labeled particle can be coupled to a capture agent, such as a binding agent, for a vesicle, resulting in capture of a vesicle. The multiple capture agents can be selected to characterize a phenotype of interest, including capture agents against general vesicle biomarkers, cell-of-origin specific biomarkers, and disease biomarkers. One or more biomarkers of the captured vesicle can then be detected by a plurality of binding agents. The binding agent can be directly labeled to facilitate detection. Alternatively, the binding agent is labeled by a secondary agent. For example, the binding agent may be an antibody for a biomarker on the vesicle, wherein the binding agent is linked to biotin. A secondary agent comprises streptavidin linked to a reporter and can be added to detect the biomarker. In some embodiments, the captured vesicle is assayed for at least 2, 3, 4, 5, 6, 7, 8, 9, 10, 11, 12, 13, 14, 15, 16, 17, 18, 19, 20, 25, 50, 75 or 100 different biomarkers. For example, multiple detectors, i.e., detection of multiple biomarkers of a captured vesicle or population of vesicles, can increase the signal obtained, permitted increased sensitivity, specificity, or both, and the use of smaller amounts of samples. Detection can be with more than one biomarker, including without limitation more than one general vesicle marker such as in Table 3.

Figure 1B:
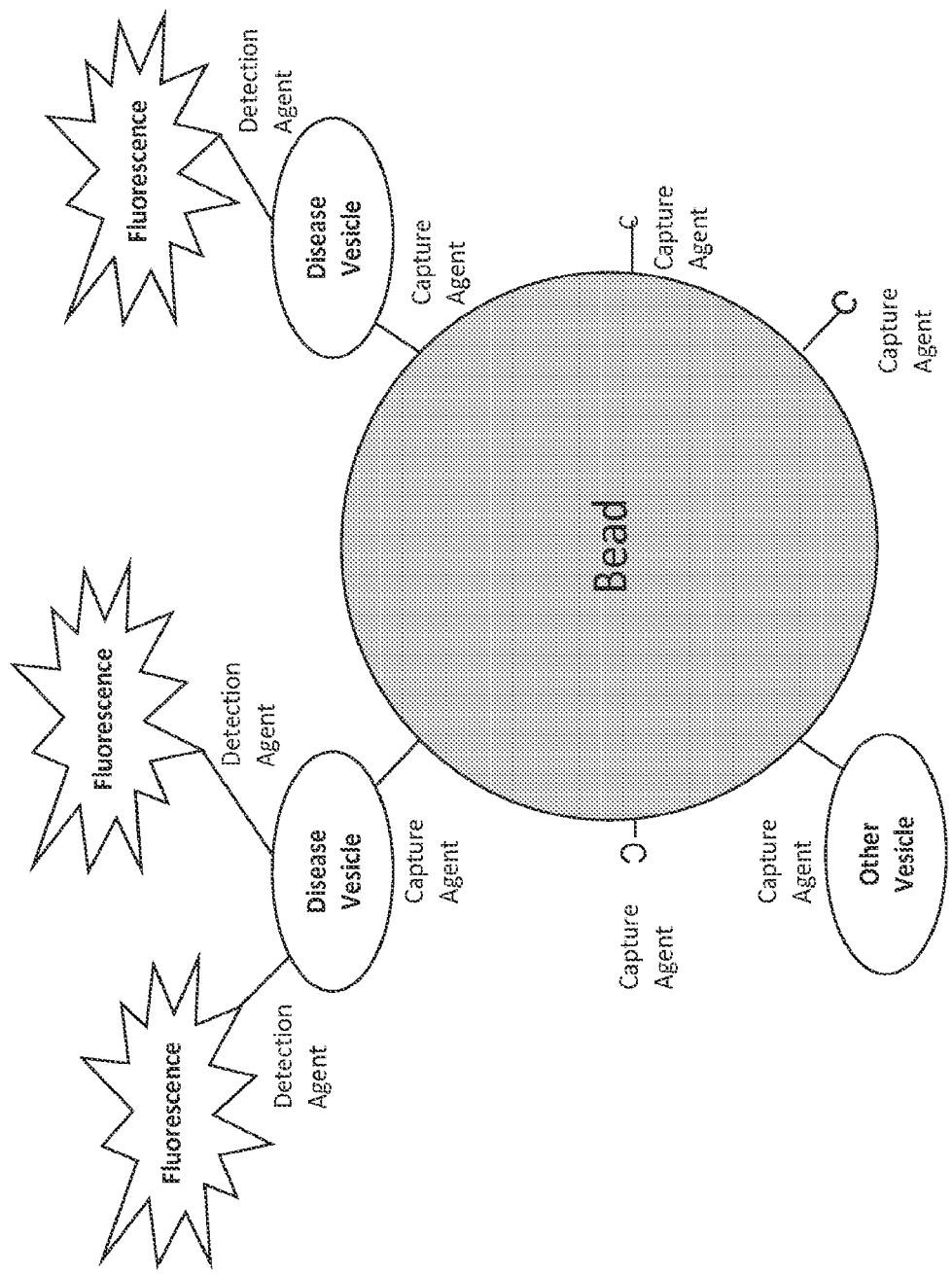

An immunoassay based method (e.g., sandwich assay) can be used to detect a biomarker of a vesicle. An example includes ELISA. A binding agent can be bound to a well. For example, a binding agent such as an aptamer or antibody to an antigen of a vesicle can be attached to a well. A biomarker on the captured vesicle can be detected based on the methods described herein. FIG. 1A shows an illustrative schematic for a sandwich-type of immunoassay. The capture agent can be against a vesicle antigen of interest, e.g., a general vesicle biomarker, a cell-of-origin marker, or a disease marker. In the figure, the captured vesicles are detected using fluorescently labeled binding agent (detection agent) against vesicle antigens of interest. Multiple capture binding agents can be used, e.g., in distinguishable addresses on an array or different wells of an immunoassay plate. The detection binding agents can be against the same antigen as the capture binding agent, or can be directed against other markers. The capture binding agent can be any useful binding agent, e.g., tethered aptamers, antibodies or lectins, and/or the detector antibodies can be similarly substituted, e.g., with detectable (e.g., labeled) aptamers, antibodies, lectins or other binding proteins or entities. In an embodiment, one or more capture agents to a general vesicle biomarker, a cell-of-origin marker, and/or a disease marker are used along with detection agents against general vesicle biomarker, such as tetraspanin molecules including without limitation one or more of CD9, CD63 and CD81, or other markers in Table 3 herein. Examples of microvesicle surface antigens are disclosed herein, e.g. in Tables 3 or 4, or are known in the art, and examples useful in methods and compositions of the invention are disclosed of International Patent Application Serial No. PCT/US2011/031479, entitled "Circulating Biomarkers for Disease" and filed Apr. 6, 2011.

Figure 1D:
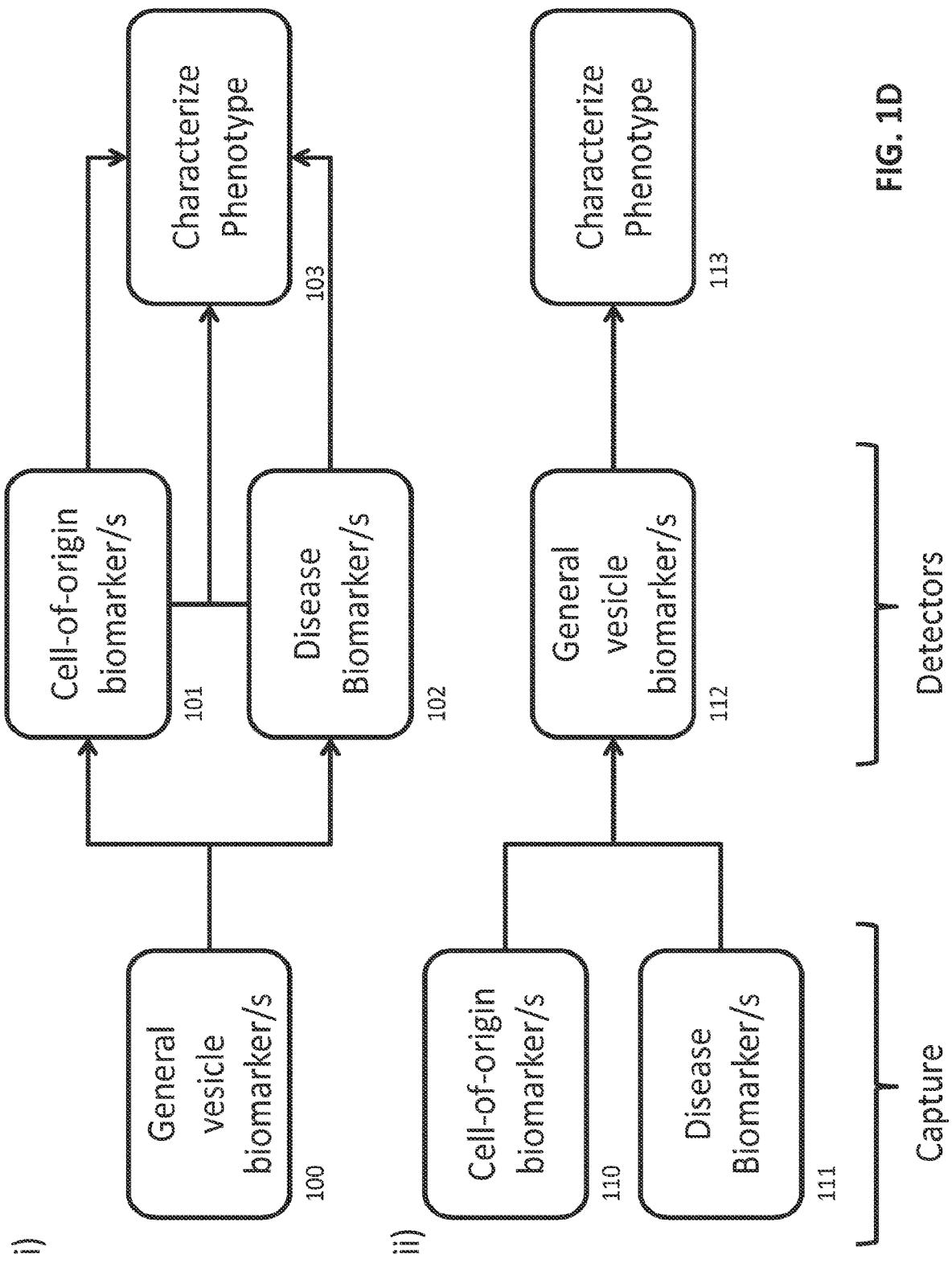

FIG. 1D presents an illustrative schematic for analyzing vesicles according to the methods of the invention. Capture agents are used to capture vesicles, detectors are used to detect the captured vesicles, and the level or presence of the captured and detected microvesicles is used to characterize a phenotype. Capture agents, detectors and characterizing phenotypes can be any of those described herein. For example, capture agents include antibodies or aptamers tethered to a substrate that recognize a vesicle antigen of interest, detectors include labeled antibodies or aptamers to a vesicle antigen of interest, and characterizing a phenotype includes a diagnosis, prognosis, or theranosis of a disease. In the scheme shown in FIG. 1D i), a population of vesicles is captured with one or more capture agents against general vesicle biomarkers (100). The captured vesicles are then labeled with detectors against cell-of-origin biomarkers (101) and/or disease specific biomarkers (102). If only cell-of-origin detectors are used (101), the biosignature used to characterize the phenotype (103) can include the general vesicle markers (100) and the cell-of-origin biomarkers (101). If only disease detectors are used (102), the biosignature used to characterize the phenotype (103) can include the general vesicle markers (100) and the disease biomarkers (102). Alternately, detectors are used to detect both cell-of-origin biomarkers (101) and disease specific biomarkers (102). In this case, the biosignature used to characterize the phenotype (103) can include the general vesicle markers (100), the cell-of-origin biomarkers (101) and the disease biomarkers (102). The biomarkers combinations are selected to characterize the phenotype of interest and can be selected from the biomarkers and phenotypes described herein, e.g., in Tables 3 or 4.

In the scheme shown in FIG. 1D ii), a population of vesicles is captured with one or more capture agents against cell-of-origin biomarkers (110) and/or disease biomarkers (111). The captured vesicles are then detected using detectors against general vesicle biomarkers (112). If only cell-of-origin capture agents are used (110), the biosignature used to characterize the phenotype (113) can include the cell-of-origin biomarkers (110) and the general vesicle markers (112). If only disease biomarker capture agents are used (111), the biosignature used to characterize the phenotype (113) can include the disease biomarkers (111) and the general vesicle biomarkers (112). Alternately, capture agents to one or more cell-of-origin biomarkers (110) and one or more disease specific biomarkers (111) are used to capture vesicles. In this case, the biosignature used to characterize the phenotype (113) can include the cell-of-origin biomarkers (110), the disease biomarkers (111), and the general vesicle markers (113). The biomarkers combinations are selected to characterize the phenotype of interest and can be selected from the biomarkers and phenotypes described herein.

Figure 1E:
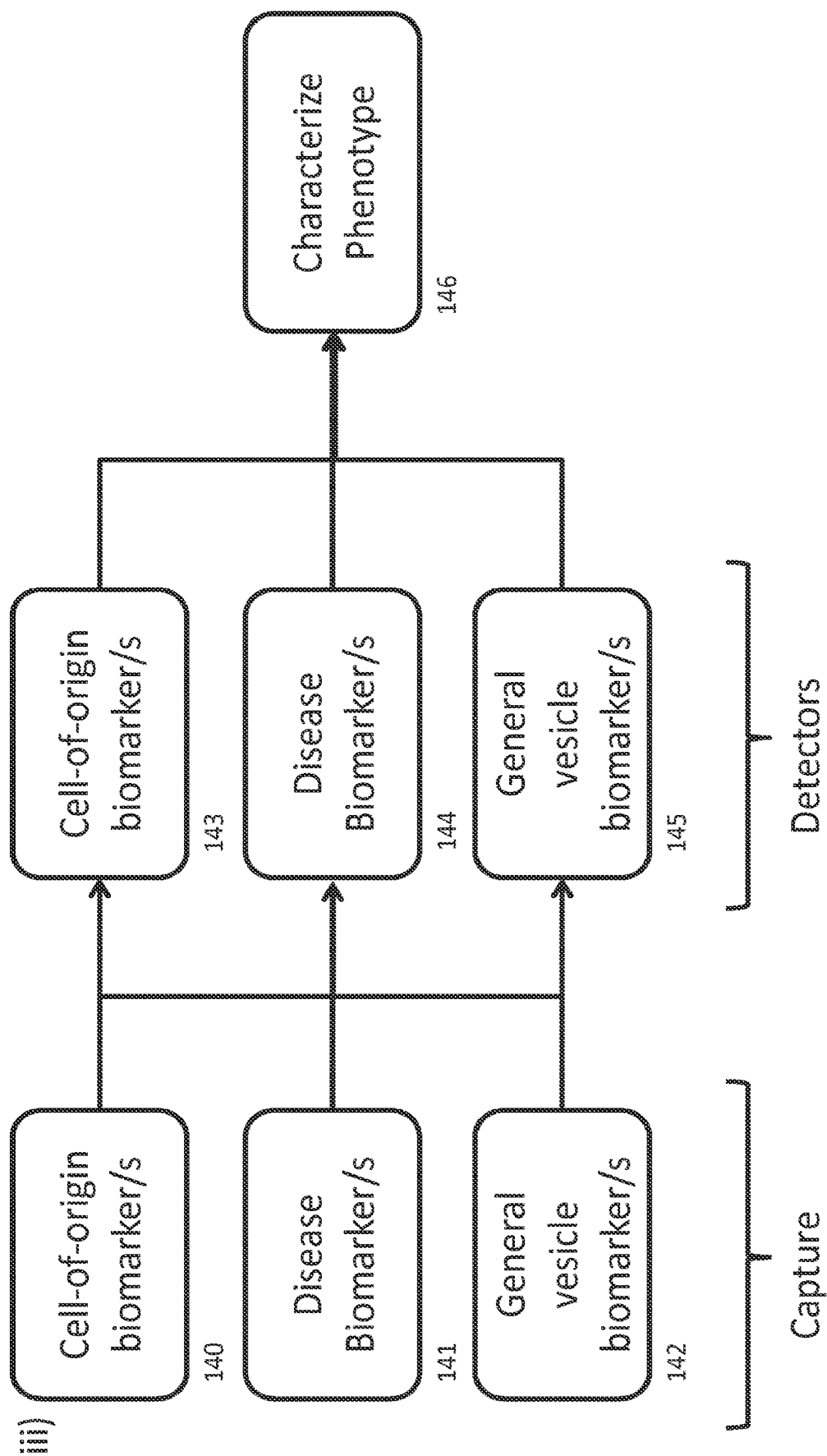
Figure 1F:
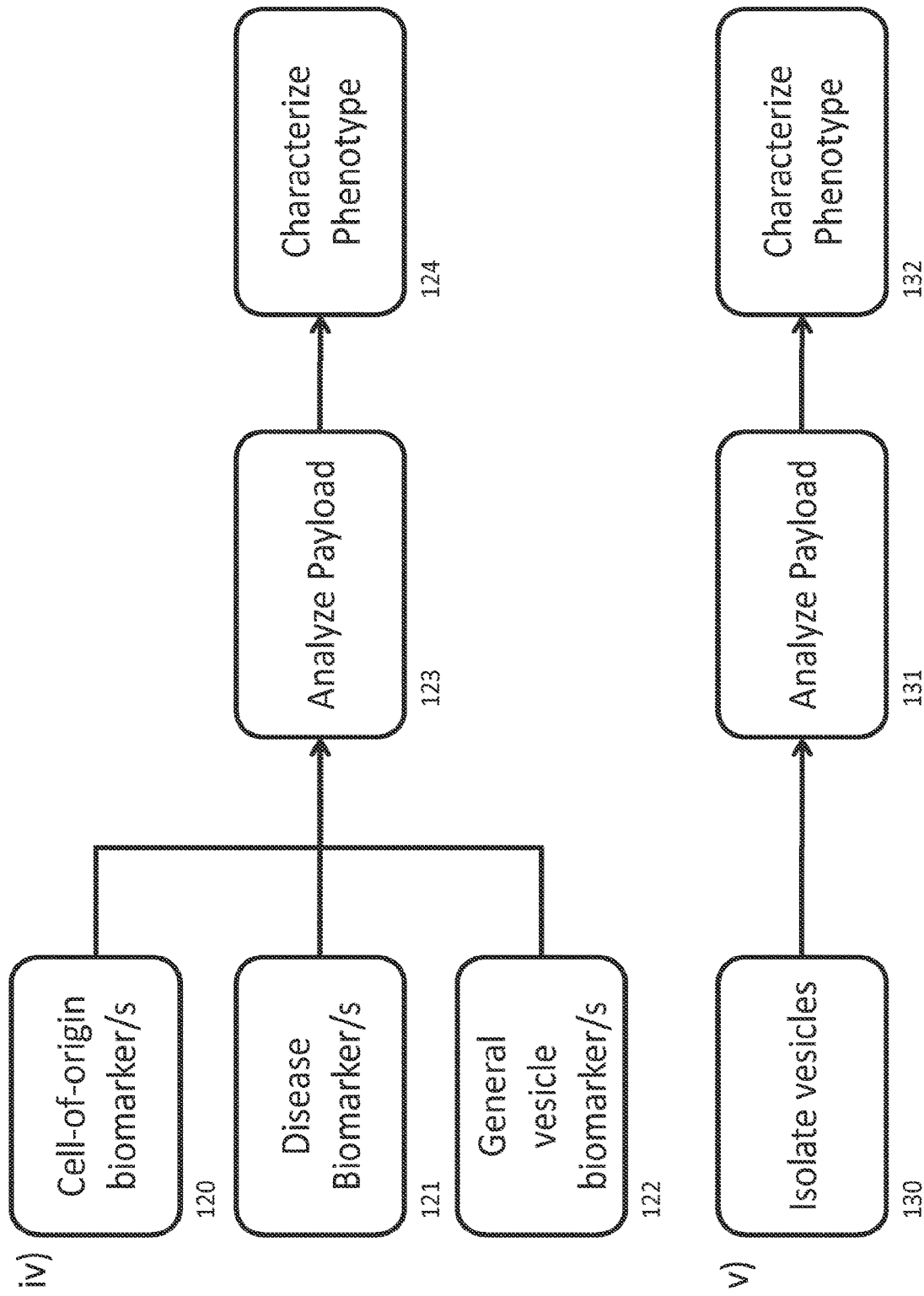

The methods of the invention comprise capture and detection of microvesicles of interest using any combination of useful biomarkers. For example, a microvesicle population can be captured using one or more binding agent to any desired combination of cell of origin, disease specific, or general vesicle markers. The captured microvesicles can then be detected using one or more binding agent to any desired combination of cell of origin, disease specific, or general vesicle markers. FIG. 1E represents a flow diagram of such configurations. Any one or more of a cell-of-origin biomarker (140), disease biomarkers (141), and general vesicle biomarker (142) is used to capture a microvesicle population. Thereafter, any one or more of a cell-of-origin biomarker (143), disease biomarkers (144), and general vesicle biomarker (145) is used to detect the captured microvesicle population. The biosignature of captured and detected microvesicles is then used to characterize a phenotype (146). The biomarkers combinations are selected to characterize the phenotype of interest and can be selected from the biomarkers and phenotypes described herein.

A microvesicle payload molecule can be assessed as a member of a biosignature panel. A payload molecule comprises any of the biological entities contained within a cell, cell fragment or vesicle membrane. These entities include without limitation nucleic acids, e.g., mRNA, microRNA, or DNA fragments; protein, e.g., soluble and membrane associated proteins; carbohydrates; lipids; metabolites; and various small molecules, e.g., hormones. The payload can be part of the cellular milieu that is encapsulated as a vesicle is formed in the cellular environment. In some embodiments of the invention, the payload is analyzed in addition to detecting vesicle surface antigens. Specific populations of vesicles can be captured as described above then the payload in the captured vesicles can be used to characterize a phenotype. For example, vesicles captured on a substrate can be further isolated to assess the payload therein. Alternately, the vesicles in a sample are detected and sorted without capture. The vesicles so detected can be further isolated to assess the payload therein. In an embodiment, vesicle populations are sorted by flow cytometry and the payload in the sorted vesicles is analyzed. In the scheme shown in FIG. 1F iii), a population of vesicles is captured and/or detected (120) using one or more of cell-of-origin biomarkers (120), disease biomarkers (121), and/or general vesicle markers (122). The payload of the isolated vesicles is assessed (123). A biosignature detected within the payload can be used to characterize a phenotype (124). In a non-limiting example, a vesicle population can be analyzed in a plasma sample from a patient using antibodies against one or more vesicle antigens of interest. The antibodies can be capture antibodies which are tethered to a substrate to isolate a desired vesicle population. Alternately, the antibodies can be directly labeled and the labeled vesicles isolated by sorting with flow cytometry. The presence or level of microRNA or mRNA extracted from the isolated vesicle population can be used to detect a biosignature. The biosignature is then used to diagnose, prognose or theranose the patient.

In other embodiments, vesicle or cellular payload is analyzed in a population (e.g., cells or vesicles) without first capturing or detected subpopulations of vesicles. For example, a cellular or extracellular vesicle population can be generally isolated from a sample using centrifugation, filtration, chromatography, or other techniques as described herein and known in the art. The payload of such sample components can be analyzed thereafter to detect a biosignature and characterize a phenotype. In the scheme shown in FIG. 1F v), a population of vesicles is isolated (130) and the payload of the isolated vesicles is assessed (131). A biosignature detected within the payload can be used to characterize a phenotype (132). In a non-limiting example, a vesicle population is isolated from a plasma sample from a patient using size exclusion and membrane filtration. The presence or level of microRNA or mRNA extracted from the vesicle population is used to detect a biosignature. The biosignature is then used to diagnose, prognose or theranose the patient.

The biomarkers used to detect a vesicle population can be selected to detect a microvesicle population of interest, e.g., a population of vesicles that provides a diagnosis, prognosis or theranosis of a selected condition or disease, including but not limited to a cancer, a premalignant condition, an inflammatory disease, an immune disease, an autoimmune disease or disorder, a cardiovascular disease or disorder, neurological disease or disorder, infectious disease or pain. See Section "Phenotypes" herein for more detail. In an embodiment, the biomarkers are selected from the group consisting of EpCam (epithelial cell adhesion molecule), CD9 (tetraspanin CD9 molecule), PCSA (prostate cell specific antigen, see Rokhlin et al., 5E10: a prostate-specific surface-reactive monoclonal antibody. Cancer Lett. 1998 131:129-36), CD63 (tetraspanin CD63 molecule), CD81 (tetraspanin CD81 molecule), PSMA (FOLH1, folate hydrolase (prostate-specific membrane antigen) 1), B7H3 (CD276 molecule), PSCA (prostate stem cell antigen), ICAM (intercellular adhesion molecule), STEAP (STEAP1, six transmembrane epithelial antigen of the prostate 1), KLK2 (kallikrein-related peptidase 2), SSX2 (synovial sarcoma, X breakpoint 2), SSX4 (synovial sarcoma, X breakpoint 4), PBP (prostatic binding protein), SPDEF (SAM pointed domain containing ets transcription factor), EGFR (epidermal growth factor receptor), and a combination thereof. One or more of these markers can provide a biosignature for a specific condition, such as to detect a cancer, including without limitation a carcinoma, a prostate cancer, a breast cancer, a lung cancer, a colorectal cancer, an ovarian cancer, melanoma, a brain cancer, or other type of cancer as disclosed herein. In an embodiment, a binding agent to one or more of these markers is used to capture a microvesicle population, and an aptamer of the invention is used to assist in detection of the capture vesicles as described herein. In other embodiments, an aptamer of the invention is used to capture a microvesicle population, and a binding agent to one or more of these markers is used to assist in detection of the capture vesicles as described herein. The binding agents can be any useful binding agent as disclosed herein or known in the art, e.g., antibodies or aptamers.

The methods of characterizing a phenotype can employ a combination of techniques to assess a component or population of components present in a biological sample of interest. For example, an aptamer of the invention can be used to assess a single cell, or a single extracellular vesicle or a population of cells or population of vesicles. A sample may be split into various aliquots, where each is analyzed separately. For example, protein content of one or more aliquot is determined and microRNA content of one or more other aliquot is determined. The protein content and microRNA content can be combined to characterize a phenotype. In another embodiment, a component present in a biological sample of interest is isolated and the payload therein is assessed (e.g., capture a population of subpopulation of vesicles using an aptamer of the invention and further assess nucleic acid or proteins present in the isolated vesicles).

In one embodiment, a population of vesicles with a given surface marker can be isolated by using a binding agent to a microvesicle surface marker. See, e.g., FIGS. 1A, 1B, 15A. The binding agent can be an aptamer that was identified to target the microvesicle surface marker using to the methods of the invention. The isolated vesicles is assessed for additional biomarkers such as surface content or payload, which can be contemporaneous to detection of the aptamer-specific target or the assessment of additional biomarkers can be before or subsequent to aptamer-specific target detection.

A biosignature can be detected qualitatively or quantitatively by detecting a presence, level or concentration of a circulating biomarker, e.g., a microRNA, protein, vesicle or other biomarker, as disclosed herein. These biosignature components can be detected using a number of techniques known to those of skill in the art. For example, a biomarker can be detected by microarray analysis, polymerase chain reaction (PCR) (including PCR-based methods such as real time polymerase chain reaction (RT-PCR), quantitative real time polymerase chain reaction (Q-PCR/qPCR) and the like), hybridization with allele-specific probes, enzymatic mutation detection, ligation chain reaction (LCR), oligonucleotide ligation assay (OLA), flow-cytometric heteroduplex analysis, chemical cleavage of mismatches, mass spectrometry, nucleic acid sequencing, single strand conformation polymorphism (SSCP), denaturing gradient gel electrophoresis (DGGE), temperature gradient gel electrophoresis (TGGE), restriction fragment polymorphisms, serial analysis of gene expression (SAGE), or combinations thereof. A biomarker, such as a nucleic acid, can be amplified prior to detection. A biomarker can also be detected by immunoassay, immunoblot, immunoprecipitation, enzyme-linked immunosorbent assay (ELISA; EIA), radioimmunoassay (RIA), flow cytometry, or electron microscopy (EM).

Biosignatures can be detected using aptamers of the invention that function as either as capture agents and detection agents, as described herein. A capture agent can comprise an antibody, aptamer or other entity which recognizes a biomarker and can be used for capturing the biomarker. Biomarkers that can be captured include circulating biomarkers, e.g., a protein, nucleic acid, lipid or biological complex in solution in a bodily fluid. Similarly, the capture agent can be used for capturing a vesicle. A detection agent can comprise an antibody or other entity which recognizes a biomarker and can be used for detecting the biomarker vesicle, or which recognizes a vesicle and is useful for detecting a vesicle. In some embodiments, the detection agent is labeled and the label is detected, thereby detecting the biomarker or vesicle. The detection agent can be a binding agent, e.g., an antibody or aptamer. In other embodiments, the detection agent comprises a small molecule such as a membrane protein labeling agent. See, e.g., the membrane protein labeling agents disclosed in Alroy et al., US Patent Publication US 2005/0158708. In an embodiment, vesicles are isolated or captured as described herein, and one or more membrane protein labeling agent is used to detect the vesicles. In many cases, the antigen or other vesicle-moiety that is recognized by the capture and detection agents are interchangeable.

In a non-limiting embodiment, a vesicle having a cell-of-origin specific antigen on its surface and a cancer-specific antigen on its surface, is captured using a binding agent that is specific to a cells-specific antigen, e.g., by tethering the capture antibody or aptamer to a substrate, and then the vesicle is detected using a binding agent to a disease-specific antigen, e.g., by labeling the binding agent used for detection with a fluorescent dye and detecting the fluorescent radiation emitted by the dye.

It will be apparent to one of skill in the art that where the target molecule for a binding agent (such as an aptamer of the invention) is informative as to assessing a condition or disease, the same binding agent can be used to both capture a component comprising the target molecule (e.g., microvesicle surface antigen of interest) and also be modified to comprise a detectable label so as to detect the target molecule, e.g., binding agent$_1$-antigen-binding agent$_2$*, wherein the * signifies a detectable label; binding agent$_1$ and binding agent$_2$ may be the same binding agent or a different binding agent (e.g., same aptamer or different aptamer). In addition, binding agent$_1$ and binding agent$_2$ can be selected from wholly different categories of binding agents (e.g., antibody, aptamer, synthetic antibody, peptide-nucleic acid molecule, or any molecule that is configured to specifically bind to or associate with its target molecule). Such binding molecules can be selected solely based on their binding specificity for a target molecule.

Techniques of detecting biomarkers or capturing sample components using an aptamer of the invention include the use of a planar substrate such as an array (e.g., biochip or microarray), with molecules immobilized to the substrate as capture agents that facilitate the detection of a particular bio signature. The array can be provided as part of a kit for assaying one or more biomarkers. Additional examples of binding agents described above and useful in the compositions and methods of the invention are disclosed in International Patent Application Serial No. PCT/US2011/031479, entitled "Circulating Biomarkers for Disease" and filed Apr. 6, 2011, which application is incorporated by reference in its entirety herein. Aptamers of the invention can be included in an array for detection and diagnosis of diseases including presymptomatic diseases. In some embodiments, an array comprises a custom array comprising biomolecules selected to specifically identify biomarkers of interest. Customized arrays can be modified to detect biomarkers that increase statistical performance, e.g., additional biomolecules that identifies a biosignature which lead to improved cross-validated error rates in multivariate prediction models (e.g., logistic regression, discriminant analysis, or regression tree models). In some embodiments, customized array(s) are constructed to study the biology of a disease, condition or syndrome and profile biosignatures in defined physiological states. Markers for inclusion on the customized array be chosen based upon statistical criteria, e.g., having a desired level of statistical significance in differentiating between phenotypes or physiological states.

In some embodiments, standard significance of p-value=0.05 is chosen to exclude or include biomolecules on the microarray. The p-values can be corrected for multiple comparisons. As an illustrative example, nucleic acids extracted from samples from a subject with or without a disease can be hybridized to a high density microarray that binds to thousands of gene sequences. Nucleic acids whose levels are significantly different between the samples with or without the disease can be selected as biomarkers to distinguish samples as having the disease or not. A customized array can be constructed to detect the selected biomarkers. In some embodiments, customized arrays comprise low density microarrays, which refer to arrays with lower number of addressable binding agents, e.g., tens or hundreds instead of thousands. Low density arrays can be formed on a substrate. In some embodiments, customizable low density arrays use PCR amplification in plate wells, e.g., TaqMan® Gene Expression Assays (Applied Biosystems by Life Technologies Corporation, Carlsbad, Calif.).

An aptamer of the invention or other useful binding agent may be linked directly or indirectly to a solid surface or substrate. See, e.g., FIGS. 1A-1B, 14, 15A. A solid surface or substrate can be any physically separable solid to which a binding agent can be directly or indirectly attached including, but not limited to, surfaces provided by microarrays and wells, particles such as beads, columns, optical fibers, wipes, glass and modified or functionalized glass, quartz, mica, diazotized membranes (paper or nylon), polyformaldehyde, cellulose, cellulose acetate, paper, ceramics, metals, metalloids, semiconductive materials, quantum dots, coated beads or particles, other chromatographic materials, magnetic particles; plastics (including acrylics, polystyrene, copolymers of styrene or other materials, polypropylene, polyethylene, polybutylene, polyurethanes, Teflon material, etc.), polysaccharides, nylon or nitrocellulose, resins, silica or silica-based materials including silicon and modified silicon, carbon, metals, inorganic glasses, plastics, ceramics, conducting polymers (including polymers such as polypyrrole and polyindole); micro or nano structured surfaces such as nucleic acid tiling arrays, nanotube, nanowire, or nanoparticulate decorated surfaces; or porous surfaces or gels such as methacrylates, acrylamides, sugar polymers, cellulose, silicates, or other fibrous or stranded polymers. In addition, as is known the art, the substrate may be coated using passive or chemically-derivatized coatings with any number of materials, including polymers, such as dextrans, acrylamides, gelatins or agarose. Such coatings can facilitate the use of the array with a biological sample.

As provided in the examples, below, an aptamer or other useful binding agent can be conjugated to a detectable entity or label. Appropriate labels include without limitation a magnetic label, a fluorescent moiety, an enzyme, a chemiluminescent probe, a metal particle, a non-metal colloidal particle, a polymeric dye particle, a pigment molecule, a pigment particle, an electrochemically active species, semiconductor nanocrystal or other nanoparticles including quantum dots or gold particles, fluorophores, quantum dots, or radioactive labels. Protein labels include green fluorescent protein (GFP) and variants thereof (e.g., cyan fluorescent protein and yellow fluorescent protein); and luminescent proteins such as luciferase, as described below. Radioactive labels include without limitation radioisotopes (radionuclides), such as $^3$H, $^{11}$C, $^{14}$C, $^{18}$F, $^{32}$P, $^{35}$S, $^{64}$Cu, $^{68}$Ga, $^{86}$Y, $^{99}$Tc, $^{111}$In, $^{123}$I, $^{124}$I, $^{125}$I, $^{131}$I, $^{133}$Xe, $^{177}$Lu, $^{211}$At, or $^{213}$Bi. Fluorescent labels include without limitation a rare earth chelate (e.g., europium chelate); fluorescein types including without limitation FITC, 5-carboxyfluorescein, 6-carboxy fluorescein; a rhodamine type including without limitation TAMRA; dansyl; Lissamine; cyanines; phycoerythrins; Texas Red; Cy3, Cy5, dapoxyl, NBD, Cascade Yellow, dansyl, PyMPO, pyrene, 7-diethylaminocoumarin-3-carboxylic acid and other coumarin derivatives, Marina Blue™, Pacific Blue™, Cascade Blue™, 2-anthracenesulfonyl, PyMPO, 3,4,9,10-perylenetetracarboxylic acid, 2,7-difluorofluorescein (Oregon Green™ 488-X), 5-carboxyfluorescein, Texas Red™-X, Alexa Fluor 430, 5-carboxytetramethylrhodamine (5-TAMRA), 6-carboxytetramethylrhodamine (6-TAMRA), BODIPY FL, bimane, and Alexa Fluor 350, 405, 488, 500, 514, 532, 546, 555, 568, 594, 610, 633, 647, 660, 680, 700, and 750, and derivatives thereof, among many others. See, e.g., "The Handbook—A Guide to Fluorescent Probes and Labeling Technologies," Tenth Edition, available on the internet at probes (dot) invitrogen (dot) com/handbook. The fluorescent label can be one or more of FAM, dRHO, 5-FAM, 6FAM, dR6G, JOE, HEX, VIC, TET, dTAMRA, TAMRA, NED, dROX, PET, BHQ, Gold540 and LIZ.

Using conventional techniques, an aptamer can be directly or indirectly labeled, e.g., the label is attached to the aptamer through biotin-streptavidin (e.g., synthesize a biotinylated aptamer, which is then capable of binding a streptavidin molecule that is itself conjugated to a detectable label; non-limiting example is streptavidin, phycoerythrin conjugated (SAPE)). Methods for chemical coupling using multiple step procedures include biotinylation, coupling of trinitrophenol (TNP) or digoxigenin using for example succinimide esters of these compounds. Biotinylation can be accomplished by, for example, the use of D-biotinyl-N-hydroxysuccinimide. Succinimide groups react effectively with amino groups at pH values above 7, and preferentially between about pH 8.0 and about pH 8.5. Alternatively, an aptamer is not labeled, but is later contacted with a second antibody that is labeled after the first antibody is bound to an antigen of interest.

Various enzyme-substrate labels may also be used in conjunction with a composition or method of the invention. Such enzyme-substrate labels are available commercially (e.g., U.S. Pat. No. 4,275,149). The enzyme generally catalyzes a chemical alteration of a chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRP), alkaline phosphatase (AP), β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Examples of enzyme-substrate combinations include, but are not limited to, horseradish peroxidase (HRP) with hydrogen peroxidase as a substrate, wherein the hydrogen peroxidase oxidizes a dye precursor (e.g., orthophenylene diamine (OPD) or 3,3',5,5'-tetramethylbenzidine hydrochloride (TMB)); alkaline phosphatase (AP) with para-nitrophenyl phosphate as chromogenic substrate; and β-D-galactosidase (β-D-Gal) with a chromogenic substrate (e.g., p-nitrophenyl-β-D-galactosidase) or fluorogenic substrate 4-methylumbelliferyl-β-D-galactosidase.

Aptamer(s) can be linked to a substrate such as a planar substrate. A planar array generally contains addressable locations (e.g., pads, addresses, or micro-locations) of biomolecules in an array format. The size of the array will depend on the composition and end use of the array. Arrays can be made containing from 2 different molecules to many thousands. Generally, the array comprises from two to as many as 100,000 or more molecules, depending on the end use of the array and the method of manufacture. A microarray for use with the invention comprises at least one biomolecule that identifies or captures a biomarker present in a biosignature of interest, e.g., a microRNA or other biomolecule or vesicle that makes up the biosignature. In some arrays, multiple substrates are used, either of different or identical compositions. Accordingly, planar arrays may comprise a plurality of smaller substrates.

The present invention can make use of many types of arrays for detecting a biomarker, e.g., a biomarker associated with a biosignature of interest. Useful arrays or microarrays include without limitation DNA microarrays, such as cDNA microarrays, oligonucleotide microarrays and SNP microarrays, microRNA arrays, protein microarrays, antibody microarrays, tissue microarrays, cellular microarrays (also called transfection microarrays), chemical compound microarrays, and carbohydrate arrays (glycoarrays). These arrays are described in more detail above. In some embodiments, microarrays comprise biochips that provide high-density immobilized arrays of recognition molecules (e.g., aptamers or antibodies), where biomarker binding is monitored indirectly (e.g., via fluorescence).

An array or microarray that can be used to detect one or more biomarkers of a biosignature and comprising one or more aptamers can be made according to the methods described in U.S. Pat. Nos. 6,329,209; 6,365,418; 6,406, 921; 6,475,808; and 6,475,809, and U.S. patent application Ser. No. 10/884,269, each of which is herein incorporated by reference in its entirety. Custom arrays to detect specific selections of sets of biomarkers described herein can be made using the methods described in these patents. Commercially available microarrays can also be used to carry out the methods of the invention, including without limitation those from Affymetrix (Santa Clara, Calif.), Illumina (San Diego, Calif.), Agilent (Santa Clara, Calif.), Exiqon (Denmark), or Invitrogen (Carlsbad, Calif.). Custom and/or commercial arrays include arrays for detection proteins, nucleic acids, and other biological molecules and entities (e.g., cells, vesicles, virii) as described herein.

In some embodiments, multiple capture molecules are disposed on an array, e.g., proteins, peptides or additional nucleic acid molecules. In certain embodiments, the proteins are immobilized using methods and materials that minimize the denaturing of the proteins, that minimize alterations in the activity of the proteins, or that minimize interactions between the protein and the surface on which they are immobilized. The capture molecules can comprise one or more aptamer of the invention. In one embodiment, an array is constructed for the hybridization of a pool of aptamers. The array can then be used to identify pool members that bind a sample, thereby facilitating characterization of a phenotype. See FIGS. 15B-15C and related disclosure for further details.

Array surfaces useful may be of any desired shape, form, or size. Non-limiting examples of surfaces include chips, continuous surfaces, curved surfaces, flexible surfaces, films, plates, sheets, or tubes. Surfaces can have areas ranging from approximately a square micron to approximately 500 cm$^2$. The area, length, and width of surfaces may be varied according to the requirements of the assay to be performed. Considerations may include, for example, ease of handling, limitations of the material(s) of which the surface is formed, requirements of detection systems, requirements of deposition systems (e.g., arrayers), or the like.

In certain embodiments, it is desirable to employ a physical means for separating groups or arrays of binding islands or immobilized biomolecules: such physical separation facilitates exposure of different groups or arrays to different solutions of interest. Therefore, in certain embodiments, arrays are situated within microwell plates having any number of wells. In such embodiments, the bottoms of the wells may serve as surfaces for the formation of arrays, or arrays may be formed on other surfaces and then placed into wells. In certain embodiments, such as where a surface without wells is used, binding islands may be formed or molecules may be immobilized on a surface and a gasket having holes spatially arranged so that they correspond to the islands or biomolecules may be placed on the surface. Such a gasket is preferably liquid tight. A gasket may be placed on a surface at any time during the process of making the array and may be removed if separation of groups or arrays is no longer necessary.

In some embodiments, the immobilized molecules can bind to one or more biomarkers or vesicles present in a biological sample contacting the immobilized molecules. In some embodiments, the immobilized molecules modify or are modified by molecules present in the one or more vesicles contacting the immobilized molecules. Contacting the sample typically comprises overlaying the sample upon the array.

Modifications or binding of molecules in solution or immobilized on an array can be detected using detection techniques known in the art. Examples of such techniques include immunological techniques such as competitive binding assays and sandwich assays; fluorescence detection using instruments such as confocal scanners, confocal microscopes, or CCD-based systems and techniques such as fluorescence, fluorescence polarization (FP), fluorescence resonant energy transfer (FRET), total internal reflection fluorescence (TIRF), fluorescence correlation spectroscopy (FCS); colorimetric/spectrometric techniques; surface plasmon resonance, by which changes in mass of materials adsorbed at surfaces are measured; techniques using radioisotopes, including conventional radioisotope binding and scintillation proximity assays (SPA); mass spectroscopy, such as matrix-assisted laser desorption/ionization mass spectroscopy (MALDI) and MALDI-time of flight (TOF) mass spectroscopy; ellipsometry, which is an optical method of measuring thickness of protein films; quartz crystal microbalance (QCM), a very sensitive method for measuring mass of materials adsorbing to surfaces; scanning probe microscopies, such as atomic force microscopy (AFM), scanning force microscopy (SFM) or scanning electron microscopy (SEM); and techniques such as electrochemical, impedance, acoustic, microwave, and IR/Raman detection. See, e.g., Mere L, et al., "*Miniaturized FRET assays and microfluidics: key components for ultra-high-throughput screening,*" Drug Discovery Today 4(8):363-369 (1999), and references cited therein; Lakowicz J R, *Principles of Fluorescence Spectroscopy*, 2nd Edition, Plenum Press (1999), or Jain K K: *Integrative Omics, Pharmacoproteomics, and Human Body Fluids*. In: Thongboonkerd V, ed., ed. *Proteomics of Human Body Fluids: Principles, Methods and Applications. Volume* 1: Totowa, N.J.: Humana Press, 2007, each of which is herein incorporated by reference in its entirety.

Microarray technology can be combined with mass spectroscopy (MS) analysis and other tools. Electrospray interface to a mass spectrometer can be integrated with a capillary in a microfluidics device. For example, one commercially available system contains eTag reporters that are fluorescent labels with unique and well-defined electrophoretic mobilities; each label is coupled to biological or chemical probes via cleavable linkages. The distinct mobility address of each eTag reporter allows mixtures of these tags to be rapidly deconvoluted and quantitated by capillary electrophoresis. This system allows concurrent gene expression, protein expression, and protein function analyses from the same sample Jain K K: *Integrative Omics, Pharmacoproteomics, and Human Body Fluids. In: Thongboonkerd V, ed., ed. Proteomics of Human Body Fluids: Principles, Methods and Applications. Volume* 1: Totowa, N.J.: Humana Press, 2007, which is herein incorporated by reference in its entirety.

A biochip can include components for a microfluidic or nanofluidic assay. A microfluidic device can be used for isolating or analyzing biomarkers, such as determining a biosignature. Microfluidic systems allow for the miniaturization and compartmentalization of one or more processes for isolating, capturing or detecting a vesicle, detecting a microRNA, detecting a circulating biomarker, detecting a biosignature, and other processes. The microfluidic devices can use one or more detection reagents in at least one aspect of the system, and such a detection reagent can be used to detect one or more biomarkers. In one embodiment, the device detects a biomarker on an isolated or bound vesicle. Various probes, antibodies, proteins, or other binding agents can be used to detect a biomarker within the microfluidic system. The detection agents may be immobilized in different compartments of the microfluidic device or be entered into a hybridization or detection reaction through various channels of the device.

A vesicle in a microfluidic device can be lysed and its contents detected within the microfluidic device, such as proteins or nucleic acids, e.g., DNA or RNA such as miRNA or mRNA. The nucleic acid may be amplified prior to detection, or directly detected, within the microfluidic device. Thus microfluidic system can also be used for multiplexing detection of various biomarkers. In an embodiment, vesicles are captured within the microfluidic device, the captured vesicles are lysed, and a biosignature of microRNA from the vesicle payload is determined. The biosignature can further comprise the capture agent used to capture the vesicle.

Novel nanofabrication techniques are opening up the possibilities for biosensing applications that rely on fabrication of high-density, precision arrays, e.g., nucleotide-based chips and protein arrays otherwise known as heterogeneous nanoarrays. Nanofluidics allows a further reduction in the quantity of fluid analyte in a microchip to nanoliter levels, and the chips used here are referred to as nanochips. See, e.g., Unger M et al., *Biotechniques* 1999; 27(5):1008-14, Kartalov E P et al., *Biotechniques* 2006; 40(1):85-90, each of which are herein incorporated by reference in their entireties. Commercially available nanochips currently provide simple one step assays such as total cholesterol, total protein or glucose assays that can be run by combining sample and reagents, mixing and monitoring of the reaction. Gel-free analytical approaches based on liquid chromatography (LC) and nanoLC separations (Cutillas et al. *Proteomics*, 2005; 5:101-112 and Cutillas et al., *Mol Cell Proteomics* 2005; 4: 1038-1051, each of which is herein incorporated by reference in its entirety) can be used in combination with the nanochips.

An array suitable for identifying a disease, condition, syndrome or physiological status can be included in a kit. A kit can include, an aptamer of the invention, including as non-limiting examples, one or more reagents useful for preparing molecules for immobilization onto binding islands or areas of an array, reagents useful for detecting binding of a vesicle to immobilized molecules, and instructions for use.

Further provided herein is a rapid detection device that facilitates the detection of a particular biosignature in a biological sample. The device can integrate biological sample preparation with polymerase chain reaction (PCR) on a chip. The device can facilitate the detection of a particular biosignature of a vesicle in a biological sample, and an example is provided as described in Pipper et al., *Angewandte Chemie*, 47(21), p. 3900-3904 (2008), which is herein incorporated by reference in its entirety. A biosignature can be incorporated using micro-/nano-electrochemical system (MEMS/NEMS) sensors and oral fluid for diagnostic applications as described in Li et al., *Adv Dent Res* 18(1): 3-5 (2005), which is herein incorporated by reference in its entirety.

In addition to acting as binding agents for a target of interest in an assay, certain aptamers of the invention, e.g., functional group binding aptamers and/or blocking aptamers, can be used to enhance the performance of various biomarker detection techniques disclosed herein or known in the art. As described further below, such aptamers can be used in an assay that makes use of a substrate, wherein the aptamers mitigate non-specific binding to the substrate.

Particle Assays

As an alternative to planar arrays, assays using particles or microspheres, such as bead based assays are also capable of use with an aptamer of the invention. Binding agents such as aptamers and antibodies are easily conjugated with commercially available beads. See, e.g., Srinivas et al. Anal. Chem. 2011 Oct. 21, *Aptamer functionalized Microgel Particles for Protein Detection*; See also, review article on aptamers as therapeutic and diagnostic agents, Brody and Gold, Rev. Mol. Biotech 2000, 74:5-13.

Multiparametric assays or other high throughput detection assays using bead coatings with cognate ligands and reporter molecules with specific activities consistent with high sensitivity automation can be used. In a bead based assay system, a binding agent for a biomarker or vesicle, such as a capture agent (e.g. capture antibody), can be immobilized on an addressable microsphere. Each binding agent for each individual binding assay can be coupled to a distinct type of microsphere (i.e., microbead) and the assay reaction takes place on the surface of the microsphere, such as depicted in FIG. 1B. A binding agent for a vesicle can be a capture antibody coupled to a bead. Dyed microspheres with discrete fluorescence intensities are loaded separately with their appropriate binding agent or capture probes. The different bead sets carrying different binding agents can be pooled as necessary to generate custom bead arrays. Bead arrays are then incubated with the sample in a single reaction vessel to perform the assay. In some embodiments of the invention, microvesicles are directly conjugated to beads. See, e.g., FIGS. 7A-7D. The bead conjugated vesicles can be used to enrich for aptamers the bind the microvesicles. See Examples 28-33.

Bead-based assays can also be used with one or more aptamers of the invention. A bead substrate can provide a platform for attaching one or more binding agents, including aptamer(s). For multiplexing, multiple different bead sets (e.g., Illumina, Luminex) can have different binding agents (specific to different target molecules). For example, a bead can be conjugated to a binding agent, e.g., an aptamer of the invention, used to detect the presence (quantitatively or qualitatively) of an antigen of interest, or it can also be used to isolate a component present in a selected biological sample (e.g., cell, cell-fragment or vesicle comprising the target molecule to which the aptamer is configured to bind or associate). Any molecule of organic origin can be successfully conjugated to a polystyrene bead through use of commercially available kits.

One or more aptamers of the invention can be used with any bead based substrate, including but not limited to magnetic capture method, fluorescence activated cell sorting (FACS) or laser cytometry. Magnetic capture methods can include, but are not limited to, the use of magnetically activated cell sorter (MACS) microbeads or magnetic columns. Examples of bead or particle based methods that can be modified to use an aptamer of the invention include methods and bead systems described in U.S. Pat. No. 4,551,435, 4,795,698, 4,925,788, 5,108,933, 5,186,827, 5,200,084 or 5,158,871; 7,399,632; 8,124,015; 8,008,019; 7,955,802; 7,445,844; 7,274,316; 6,773,812; 6,623,526; 6,599,331; 6,057,107; 5,736,330; international patent application no. PCT/US2012/42519; PCT/US1993/04145.

Flow Cytometry

Isolation or detection of circulating biomarkers, e.g., protein antigens, from a biological sample, or of the biomarker-comprising cells, cell fragments or vesicles may also be achieved using an aptamer of the invention in a cytometry process. As a non-limiting example, aptamers of the invention can be used in an assay comprising using a particle such as a bead or microsphere. The invention provides aptamers as binding agents, which may be conjugated to the particle. Flow cytometry can be used for sorting microscopic particles suspended in a stream of fluid. As particles pass through they can be selectively charged and on their exit can be deflected into separate paths of flow. It is therefore possible to separate populations from an original mix, such as a biological sample, with a high degree of accuracy and speed. Flow cytometry allows simultaneous multiparametric analysis of the physical and/or chemical characteristics of single cells flowing through an optical/electronic detection apparatus. A beam of light, usually laser light, of a single frequency (color) is directed onto a hydrodynamically focused stream of fluid. A number of detectors are aimed at the point where the stream passes through the light beam; one in line with the light beam (Forward Scatter or FSC) and several perpendicular to it (Side Scatter or SSC) and one or more fluorescent detectors.

Each suspended particle passing through the beam scatters the light in some way, and fluorescent chemicals in the particle may be excited into emitting light at a lower frequency than the light source. This combination of scattered and fluorescent light is picked up by the detectors, and by analyzing fluctuations in brightness at each detector (one for each fluorescent emission peak), it is possible to deduce various facts about the physical and chemical structure of each individual particle. FSC correlates with the cell size and SSC depends on the inner complexity of the particle, such as shape of the nucleus, the amount and type of cytoplasmic granules or the membrane roughness. Some flow cytometers have eliminated the need for fluorescence and use only light scatter for measurement.

Flow cytometers can analyze several thousand particles every second in "real time" and can actively separate out and isolate particles having specified properties. They offer high-throughput automated quantification, and separation, of the set parameters for a high number of single cells during each analysis session. Flow cytometers can have multiple lasers and fluorescence detectors, allowing multiple labels to be used to more precisely specify a target population by their phenotype. Thus, a flow cytometer, such as a multicolor flow cytometer, can be used to detect one or more vesicles with multiple fluorescent labels or colors. In some embodiments, the flow cytometer can also sort or isolate different vesicle populations, such as by size or by different markers.

The flow cytometer may have one or more lasers, such as 1, 2, 3, 4, 5, 6, 7, 8, 9, 10 or more lasers. In some embodiments, the flow cytometer can detect more than one color or fluorescent label, such as at least 2, 3, 4, 5, 6, 7, 8, 9, 10, 11, 12, 13, 14, 15, 16, 17, 18, 19, or 20 different colors or fluorescent labels. For example, the flow cytometer can have at least 2, 3, 4, 5, 6, 7, 8, 9, 10, 11, 12, 13, 14, 15, 16, 17, 18, 19, or 20 fluorescence detectors.

Examples of commercially available flow cytometers that can be used to detect or analyze one or more vesicles, to sort or separate different populations of vesicles, include, but are not limited to the MoFlo™ XDP Cell Sorter (Beckman Coulter, Brea, Calif.), MoFlo™ Legacy Cell Sorter (Beckman Coulter, Brea, Calif.), BD FACSAria™ Cell Sorter (BD Biosciences, San Jose, Calif.), BD™ LSRII (BD Biosciences, San Jose, Calif.), and BD FACSCalibur™ (BD Biosciences, San Jose, Calif.). Use of multicolor or multi-fluor cytometers can be used in multiplex analysis of vesicles, as further described below. In some embodiments, the flow cytometer can sort, and thereby collect or sort more than one population of vesicles based one or more characteristics. For example, two populations of vesicles differ in size, such that the vesicles within each population have a similar size range and can be differentially detected or sorted. In another embodiment, two different populations of vesicles are differentially labeled.

The data resulting from flow-cytometers can be plotted in 1 dimension to produce histograms or seen in 2 dimensions as dot plots or in 3 dimensions with newer software. The regions on these plots can be sequentially separated by a series of subset extractions which are termed gates. Specific gating protocols exist for diagnostic and clinical purposes especially in relation to hematology. The plots are often made on logarithmic scales. Because different fluorescent dye's emission spectra overlap, signals at the detectors have to be compensated electronically as well as computationally. Fluorophores for labeling biomarkers may include those described in Ormerod, *Flow Cytometry* 2nd ed., Springer-Verlag, New York (1999), and in Nida et al., *Gynecologic Oncology* 2005; 4 889-894 which is incorporated herein by reference. In a multiplexed assay, including but not limited to a flow cytometry assay, one or more different target molecules can be assessed. In some embodiments, at least one of the target molecules is a biomarker, e.g., a microvesicle surface antigen, assessed using an aptamer of the invention.

Microfluidics

One or more aptamer of the invention can be conjugated to or otherwise disposed on any useful planar or bead substrate. In one aspect of the invention one or more aptamer of the invention is disposed on a microfluidic device, thereby facilitating assessing, characterizing or isolating a component of a biological sample comprising a polypeptide antigen of interest or a functional fragment thereof. For example, the circulating antigen or a cell, cell fragment or cell-derived vesicles comprising the antigen can be assessed using one or more aptamers of the invention (alternatively along with additional binding agents). Microfluidic devices, which may also be referred to as "lab-on-a-chip" systems, biomedical micro-electro-mechanical systems (bioMEMs), or multicomponent integrated systems, can be used for isolating and analyzing a vesicle. Such systems miniaturize and compartmentalize processes that allow for binding of vesicles, detection of biosignatures, and other processes.

A microfluidic device can also be used for isolation of a vesicle through size differential or affinity selection. For example, a microfluidic device can use one more channels for isolating a vesicle from a biological sample based on size or by using one or more binding agents for isolating a vesicle from a biological sample. A biological sample can be introduced into one or more microfluidic channels, which selectively allows the passage of a vesicle. The selection can be based on a property of the vesicle, such as the size, shape, deformability, or biosignature of the vesicle.

In one embodiment, a heterogeneous population of vesicles can be introduced into a microfluidic device, and one or more different homogeneous populations of vesicles can be obtained. For example, different channels can have different size selections or binding agents to select for different vesicle populations. Thus, a microfluidic device can isolate a plurality of vesicles wherein at least a subset of the plurality of vesicles comprises a different biosignature from another subset of the plurality of vesicles. For example, the microfluidic device can isolate at least 2, 3, 4, 5, 6, 7, 8, 9, 10, 15, 20, 25, 30, 40, 50, 60, 70, 80, 90, or 100 different subsets of vesicles, wherein each subset of vesicles comprises a different biosignature.

In some embodiments, the microfluidic device can comprise one or more channels that permit further enrichment or selection of a vesicle. A population of vesicles that has been enriched after passage through a first channel can be introduced into a second channel, which allows the passage of the desired vesicle or vesicle population to be further enriched, such as through one or more binding agents present in the second channel.

Array-based assays and bead-based assays can be used with microfluidic device. For example, the binding agent can be coupled to beads and the binding reaction between the beads and vesicle can be performed in a microfluidic device. Multiplexing can also be performed using a microfluidic device. Different compartments can comprise different binding agents for different populations of vesicles, where each population is of a different cell-of-origin specific vesicle population. In one embodiment, each population has a different biosignature. The hybridization reaction between the microsphere and vesicle can be performed in a microfluidic device and the reaction mixture can be delivered to a detection device. The detection device, such as a dual or multiple laser detection system can be part of the microfluidic system and can use a laser to identify each bead or microsphere by its color-coding, and another laser can detect the hybridization signal associated with each bead.

Any appropriate microfluidic device can be used in the methods of the invention. Examples of microfluidic devices that may be used, or adapted for use with vesicles, include but are not limited to those described in U.S. Pat. Nos. 7,591,936, 7,581,429, 7,579,136, 7,575,722, 7,568,399, 7,552,741, 7,544,506, 7,541,578, 7,518,726, 7,488,596, 7,485,214, 7,467,928, 7,452,713, 7,452,509, 7,449,096, 7,431,887, 7,422,725, 7,422,669, 7,419,822, 7,419,639, 7,413,709, 7,411,184, 7,402,229, 7,390,463, 7,381,471, 7,357,864, 7,351,592, 7,351,380, 7,338,637, 7,329,391, 7,323,140, 7,261,824, 7,258,837, 7,253,003, 7,238,324, 7,238,255, 7,233,865, 7,229,538, 7,201,881, 7,195,986, 7,189,581, 7,189,580, 7,189,368, 7,141,978, 7,138,062, 7,135,147, 7,125,711, 7,118,910, 7,118,661, 7,640,947, 7,666,361, 7,704,735; and International Patent Publication WO 2010/072410; each of which patents or applications are incorporated herein by reference in their entirety. Another example for use with methods disclosed herein is described in Chen et al., "*Microfluidic isolation and transcriptome analysis of serum vesicles,*" Lab on a Chip, Dec. 8, 2009 DOI: 10.1039/b916199f.

Other microfluidic devices for use with the invention include devices comprising elastomeric layers, valves and pumps, including without limitation those disclosed in U.S. Pat. Nos. 5,376,252, 6,408,878, 6,645,432, 6,719,868, 6,793,753, 6,899,137, 6,929,030, 7,040,338, 7,118,910, 7,144,616, 7,216,671, 7,250,128, 7,494,555, 7,501,245, 7,601,270, 7,691,333, 7,754,010, 7,837,946; U.S. Patent Application Nos. 2003/0061687, 2005/0084421, 2005/0112882, 2005/0129581, 2005/0145496, 2005/0201901, 2005/0214173, 2005/0252773, 2006/0006067; and EP Patent Nos. 0527905 and 1065378; each of which application is herein incorporated by reference. In some instances, much or all of the devices are composed of elastomeric material. Certain devices are designed to conduct thermal cycling reactions (e.g., PCR) with devices that include one or more elastomeric valves to regulate solution flow through the device. The devices can comprise arrays of reaction sites thereby allowing a plurality of reactions to be performed. Thus, the devices can be used to assess circulating microRNAs in a multiplex fashion, including microRNAs isolated from vesicles. In an embodiment, the microfluidic device comprises (a) a first plurality of flow channels formed in an elastomeric substrate; (b) a second plurality of flow channels formed in the elastomeric substrate that intersect the first plurality of flow channels to define an array of reaction sites, each reaction site located at an intersection of one of the first and second flow channels; (c) a plurality of isolation valves disposed along the first and second plurality of flow channels and spaced between the reaction sites that can be actuated to isolate a solution within each of the reaction sites from solutions at other reaction sites, wherein the isolation valves comprise one or more control channels that each overlay and intersect one or more of the flow channels; and (d) means for simultaneously actuating the valves for isolating the reaction sites from each other. Various modifications to the basic structure of the device are envisioned within the scope of the invention. MicroRNAs can be detected in each of the reaction sites by using PCR methods. For example, the method can comprise the steps of the steps of: (i) providing a microfluidic device, the microfluidic device comprising: a first fluidic channel having a first end and a second end in fluid communication with each other through the channel; a plurality of flow channels, each flow channel terminating at a terminal wall; wherein each flow channel branches from and is in fluid communication with the first fluidic channel, wherein an aqueous fluid that enters one of the flow channels from the first fluidic channel can flow out of the flow channel only through the first fluidic channel; and, an inlet in fluid communication with the first fluidic channel, the inlet for introducing a sample fluid; wherein each flow channel is associated with a valve that when closed isolates one end of the flow channel from the first fluidic channel, whereby an isolated reaction site is formed between the valve and the terminal wall; a control channel; wherein each the valve is a deflectable membrane which is deflected into the flow channel associated with the valve when an actuating force is applied to the control channel, thereby closing the valve; and wherein when the actuating force is applied to the control channel a valve in each of the flow channels is closed, so as to produce the isolated reaction site in each flow channel; (ii) introducing the sample fluid into the inlet, the sample fluid filling the flow channels; (iii) actuating the valve to separate the sample fluid into the separate portions within the flow channels; (iv) amplifying the nucleic acid in the sample fluid; (v) analyzing the portions of the sample fluid to determine whether the amplifying produced the reaction. The sample fluid can contain an amplifiable nucleic acid target, e.g., a microRNA, and the conditions can be polymerase chain reaction (PCR) conditions, so that the reaction results in a PCR product being formed.

The microfluidic device can have one or more binding agents attached to a surface in a channel, or present in a channel. For example, the microchannel can have one or more capture agents, such as a capture agent for one or more general microvesicle antigen in Table 3 or a cell-of-origin or cancer related antigen in Table 4, including without limitation EpCam, CD9, PCSA, CD63, CD81, PSMA, B7H3, PSCA, ICAM, STEAP, KLK2, SSX2, SSX4, PBP, SPDEF, and EGFR. The capture agent may be an aptamer selected by the methods of the invention. The surface of the channel can also be contacted with a blocking aptamer of the invention. In one embodiment, a microchannel surface is treated with avidin and a capture agent, such as an antibody, that is biotinylated can be injected into the channel to bind the avidin. In other embodiments, the capture agents are present in chambers or other components of a microfluidic device. The capture agents can also be attached to beads that can be manipulated to move through the microfluidic channels. In one embodiment, the capture agents are attached to magnetic beads. The beads can be manipulated using magnets.

A biological sample can be flowed into the microfluidic device, or a microchannel, at rates such as at least about 1, 2, 3, 4, 5, 6, 7, 8, 9, 10, 11, 12, 13, 14, 15, 16, 17, 18, 19, 20, 25, 30, 35, 40, 45, or 50 µl per minute, such as between about 1-50, 5-40, 5-30, 3-20 or 5-15 µl per minute. One or more vesicles can be captured and directly detected in the microfluidic device. Alternatively, the captured vesicle may be released and exit the microfluidic device prior to analysis. In another embodiment, one or more captured vesicles are lysed in the microchannel and the lysate can be analyzed, e.g., to examine payload within the vesicles. Lysis buffer can be flowed through the channel and lyse the captured vesicles. For example, the lysis buffer can be flowed into the device or microchannel at rates such as at least about a, 2, 3, 4, 5, 6, 7, 8, 9, 10, 11, 12, 13, 14, 15, 16, 17, 18, 19, 20, 25, 26, 27, 28, 29, 30, 35, 40, 45, or 50 µl per minute, such as between about 1-50, 5-40, 10-30, 5-30 or 10-35 µl per minute. The lysate can be collected and analyzed, such as performing RT-PCR, PCR, mass spectrometry, Western blotting, or other assays, to detect one or more biomarkers of the vesicle.

Phenotypes

Disclosed herein are products and processes for characterizing a phenotype using the methods and compositions of the invention. The term "phenotype" as used herein can mean any trait or characteristic that is attributed to a biomarker profile that is identified using in part or in whole the compositions and/or methods of the invention. For example, a phenotype can be a diagnostic, prognostic or theranostic determination based on a characterized biomarker profile for a sample obtained from a subject. A phenotype can be any observable characteristic or trait of, such as a disease or condition, a stage of a disease or condition, susceptibility to a disease or condition, prognosis of a disease stage or condition, a physiological state, or response/potential response to therapeutics. A phenotype can result from a subject's genetic makeup as well as the influence of environmental factors and the interactions between the two, as well as from epigenetic modifications to nucleic acid sequences.

A phenotype in a subject can be characterized by obtaining a biological sample from a subject and analyzing the sample using the compositions and/or methods of the invention. For example, characterizing a phenotype for a subject or individual can include detecting a disease or condition (including pre-symptomatic early stage detecting), determining a prognosis, diagnosis, or theranosis of a disease or condition, or determining the stage or progression of a disease or condition. Characterizing a phenotype can include identifying appropriate treatments or treatment efficacy for specific diseases, conditions, disease stages and condition stages, predictions and likelihood analysis of disease progression, particularly disease recurrence, metastatic spread or disease relapse. A phenotype can also be a clinically distinct type or subtype of a condition or disease, such as a cancer or tumor. Phenotype determination can also be a determination of a physiological condition, or an assessment of organ distress or organ rejection, such as post-transplantation. The compositions and methods described herein allow assessment of a subject on an individual basis, which can provide benefits of more efficient and economical decisions in treatment.

In an aspect, the invention relates to the analysis of biomarkers such as microvesicles to provide a diagnosis, prognosis, and/or theranosis of a disease or condition. Theranostics includes diagnostic testing that provides the ability to affect therapy or treatment of a disease or disease state. Theranostics testing provides a theranosis in a similar manner that diagnostics or prognostic testing provides a diagnosis or prognosis, respectively. As used herein, theranostics encompasses any desired form of therapy related testing, including predictive medicine, personalized medicine, integrated medicine, pharmacodiagnostics and Dx/Rx partnering. Therapy related tests can be used to predict and assess drug response in individual subjects, i.e., to provide personalized medicine. Predicting a drug response can be determining whether a subject is a likely responder or a likely non-responder to a candidate therapeutic agent, e.g., before the subject has been exposed or otherwise treated with the treatment. Assessing a drug response can be monitoring a response to a drug, e.g., monitoring the subject's improvement or lack thereof over a time course after initiating the treatment. Therapy related tests are useful to select a subject for treatment who is particularly likely to benefit from the treatment or to provide an early and objective indication of treatment efficacy in an individual subject. Thus, analysis using the compositions and methods of the invention may indicate that treatment should be altered to select a more promising treatment, thereby avoiding the great expense of delaying beneficial treatment and avoiding the financial and morbidity costs of administering an ineffective drug(s).

Thus, the compositions and methods of the invention may help predict whether a subject is likely to respond to a treatment for a disease or disorder. Characterizating a phenotype includes predicting the responder/non-responder status of the subject, wherein a responder responds to a treatment for a disease and a non-responder does not respond to the treatment. Biomarkers such as microvesicles can be analyzed in the subject and compared against that of previous subjects that were known to respond or not to a treatment. If the biomarker profile in the subject more closely aligns with that of previous subjects that were known to respond to the treatment, the subject can be characterized, or predicted, as a responder to the treatment. Similarly, if the biomarker profile in the subject more closely aligns with that of previous subjects that did not respond to the treatment, the subject can be characterized, or predicted as a non-responder to the treatment. The treatment can be for any appropriate disease, disorder or other condition, including without limitation those disclosed herein.

In some embodiments, the phenotype comprises a disease or condition such as those listed in Table 1. For example, the phenotype can comprise detecting the presence of or likelihood of developing a tumor, neoplasm, or cancer, or characterizing the tumor, neoplasm, or cancer (e.g., stage, grade, aggressiveness, likelihood of metastatis or recurrence, etc). Cancers that can be detected or assessed by methods or compositions described herein include, but are not limited to, breast cancer, ovarian cancer, lung cancer, colon cancer, hyperplastic polyp, adenoma, colorectal cancer, high grade dysplasia, low grade dysplasia, prostatic hyperplasia, prostate cancer, melanoma, pancreatic cancer, brain cancer (such as a glioblastoma), hematological malignancy, hepatocellular carcinoma, cervical cancer, endometrial cancer, head and neck cancer, esophageal cancer, gastrointestinal stromal tumor (GIST), renal cell carcinoma (RCC) or gastric cancer. The colorectal cancer can be CRC Dukes B or Dukes C-D. The hematological malignancy can be B-Cell Chronic Lymphocytic Leukemia, B-Cell Lymphoma-DLBCL, B-Cell Lymphoma-DLBCL-germinal center-like, B-Cell Lymphoma-DLBCL-activated B-cell-like, and Burkitt's lymphoma.

The phenotype can be a premalignant condition, such as actinic keratosis, atrophic gastritis, leukoplakia, erythroplasia, Lymphomatoid Granulomatosis, preleukemia, fibrosis, cervical dysplasia, uterine cervical dysplasia, xeroderma pigmentosum, Barrett's Esophagus, colorectal polyp, or other abnormal tissue growth or lesion that is likely to develop into a malignant tumor. Transformative viral infections such as HIV and HPV also present phenotypes that can be assessed according to the invention.

A cancer characterized by the methods of the invention can comprise, without limitation, a carcinoma, a sarcoma, a lymphoma or leukemia, a germ cell tumor, a blastoma, or other cancers. Carcinomas include without limitation epithelial neoplasms, squamous cell neoplasms squamous cell carcinoma, basal cell neoplasms basal cell carcinoma, transitional cell papillomas and carcinomas, adenomas and adenocarcinomas (glands), adenoma, adenocarcinoma, linitis plastica insulinoma, glucagonoma, gastrinoma, vipoma, cholangiocarcinoma, hepatocellular carcinoma, adenoid cystic carcinoma, carcinoid tumor of appendix, prolactinoma, oncocytoma, hurthle cell adenoma, renal cell carcinoma, grawitz tumor, multiple endocrine adenomas, endometrioid adenoma, adnexal and skin appendage neoplasms, mucoepidermoid neoplasms, cystic, mucinous and serous neoplasms, cystadenoma, pseudomyxoma peritonei, ductal, lobular and medullary neoplasms, acinar cell neoplasms, complex epithelial neoplasms, warthin's tumor, thymoma, specialized gonadal neoplasms, sex cord stromal tumor, thecoma, granulosa cell tumor, arrhenoblastoma, sertoli leydig cell tumor, glomus tumors, paraganglioma, pheochromocytoma, glomus tumor, nevi and melanomas, melanocytic nevus, malignant melanoma, melanoma, nodular melanoma, dysplastic nevus, lentigo maligna melanoma, superficial spreading melanoma, and malignant acral lentiginous melanoma. Sarcoma includes without limitation Askin's tumor, botryodies, chondrosarcoma, Ewing's sarcoma, malignant hemangio endothelioma, malignant schwannoma, osteosarcoma, soft tissue sarcomas including: alveolar soft part sarcoma, angiosarcoma, cystosarcoma phyllodes, dermatofibrosarcoma, desmoid tumor, desmoplastic small round cell tumor, epithelioid sarcoma, extraskeletal chondrosarcoma, extraskeletal osteosarcoma, fibrosarcoma, hemangiopericytoma, hemangiosarcoma, kaposi's sarcoma, leiomyosarcoma, liposarcoma, lymphangiosarcoma, lymphosarcoma, malignant fibrous histiocytoma, neurofibrosarcoma, rhabdomyosarcoma, and synovialsarcoma. Lymphoma and leukemia include without limitation chronic lymphocytic leukemia/small lymphocytic lymphoma, B-cell prolymphocytic leukemia, lymphoplasmacytic lymphoma (such as waldenstrom macroglobulinemia), splenic marginal zone lymphoma, plasma cell myeloma, plasmacytoma, monoclonal immunoglobulin deposition diseases, heavy chain diseases, extranodal marginal zone B cell lymphoma, also called malt lymphoma, nodal marginal zone B cell lymphoma (nmzl), follicular lymphoma, mantle cell lymphoma, diffuse large B cell lymphoma, mediastinal (thymic) large B cell lymphoma, intravascular large B cell lymphoma, primary effusion lymphoma, burkitt lymphoma/leukemia, T cell prolymphocytic leukemia, T cell large granular lymphocytic leukemia, aggressive NK cell leukemia, adult T cell leukemia/lymphoma, extranodal NK/T cell lymphoma, nasal type, enteropathy-type T cell lymphoma, hepatosplenic T cell lymphoma, blastic NK cell lymphoma, mycosis fungoides/sezary syndrome, primary cutaneous CD30-positive T cell lymphoproliferative disorders, primary cutaneous anaplastic large cell lymphoma, lymphomatoid papulosis, angioimmunoblastic T cell lymphoma, peripheral T cell lymphoma, unspecified, anaplastic large cell lymphoma, classical hodgkin lymphomas (nodular sclerosis, mixed cellularity, lymphocyte-rich, lymphocyte depleted or not depleted), and nodular lymphocyte-predominant hodgkin lymphoma. Germ cell tumors include without limitation germinoma, dysgerminoma, seminoma, nongerminomatous germ cell tumor, embryonal carcinoma, endodermal sinus turmor, choriocarcinoma, teratoma, polyembryoma, and gonadoblastoma. Blastoma includes without limitation nephroblastoma, medulloblastoma, and retinoblastoma. Other cancers include without limitation labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma), renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma.

In a further embodiment, the cancer under analysis may be a lung cancer including non-small cell lung cancer and small cell lung cancer (including small cell carcinoma (oat cell cancer), mixed small cell/large cell carcinoma, and combined small cell carcinoma), colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemia, lymphoma, myeloma, or a solid tumor.

In embodiments, the cancer comprises an acute lymphoblastic leukemia; acute myeloid leukemia; adrenocortical carcinoma; AIDS-related cancers; AIDS-related lymphoma; anal cancer; appendix cancer; astrocytomas; atypical teratoid/rhabdoid tumor; basal cell carcinoma; bladder cancer; brain stem glioma; brain tumor (including brain stem glioma, central nervous system atypical teratoid/rhabdoid tumor, central nervous system embryonal tumors, astrocytomas, craniopharyngioma, ependymoblastoma, ependymoma, medulloblastoma, medulloepithelioma, pineal parenchymal tumors of intermediate differentiation, supratentorial primitive neuroectodermal tumors and pineoblastoma); breast cancer; bronchial tumors; Burkitt lymphoma; cancer of unknown primary site; carcinoid tumor; carcinoma of unknown primary site; central nervous system atypical teratoid/rhabdoid tumor; central nervous system embryonal tumors; cervical cancer; childhood cancers; chordoma; chronic lymphocytic leukemia; chronic myelogenous leukemia; chronic myeloproliferative disorders; colon cancer; colorectal cancer; craniopharyngioma; cutaneous T-cell lymphoma; endocrine pancreas islet cell tumors; endometrial cancer; ependymoblastoma; ependymoma; esophageal cancer; esthesioneuroblastoma; Ewing sarcoma; extracranial germ cell tumor; extragonadal germ cell tumor; extrahepatic bile duct cancer; gallbladder cancer; gastric (stomach) cancer; gastrointestinal carcinoid tumor; gastrointestinal stromal cell tumor; gastrointestinal stromal tumor (GIST); gestational trophoblastic tumor; glioma; hairy cell leukemia; head and neck cancer; heart cancer; Hodgkin lymphoma; hypopharyngeal cancer; intraocular melanoma; islet cell tumors; Kaposi sarcoma; kidney cancer; Langerhans cell histiocytosis; laryngeal cancer; lip cancer; liver cancer; malignant fibrous histiocytoma bone cancer; medulloblastoma; medulloepithelioma; melanoma; Merkel cell carcinoma; Merkel cell skin carcinoma; mesothelioma; metastatic squamous neck cancer with occult primary; mouth cancer; multiple endocrine neoplasia syndromes; multiple myeloma; multiple myeloma/plasma cell neoplasm; mycosis fungoides; myelodysplastic syndromes; myeloproliferative neoplasms; nasal cavity cancer; nasopharyngeal cancer; neuroblastoma; Non-Hodgkin lymphoma; nonmelanoma skin cancer; non-small cell lung cancer; oral cancer; oral cavity cancer; oropharyngeal cancer; osteosarcoma; other brain and spinal cord tumors; ovarian cancer; ovarian epithelial cancer; ovarian germ cell tumor; ovarian low malignant potential tumor; pancreatic cancer; papillomatosis; paranasal sinus cancer; parathyroid cancer; pelvic cancer; penile cancer; pharyngeal cancer; pineal parenchymal tumors of intermediate differentiation; pineoblastoma; pituitary tumor; plasma cell neoplasm/multiple myeloma; pleuropulmonary blastoma; primary central nervous system (CNS) lymphoma; primary hepatocellular liver cancer; prostate cancer; rectal cancer; renal cancer; renal cell (kidney) cancer; renal cell cancer; respiratory tract cancer; retinoblastoma; rhabdomyosarcoma; salivary gland cancer; Sézary syndrome; small cell lung cancer; small intestine cancer; soft tissue sarcoma; squamous cell carcinoma; squamous neck cancer; stomach (gastric) cancer; supratentorial primitive neuroectodermal tumors; T-cell lymphoma; testicular cancer; throat cancer; thymic carcinoma; thymoma; thyroid cancer; transitional cell cancer; transitional cell cancer of the renal pelvis and ureter; trophoblastic tumor; ureter cancer; urethral cancer; uterine cancer; uterine sarcoma; vaginal cancer; vulvar cancer; Waldenström macroglobulinemia; or Wilm's tumor. The methods of the invention can be used to characterize these and other cancers. Thus, characterizing a phenotype can be providing a diagnosis, prognosis or theranosis of one of the cancers disclosed herein.

In some embodiments, the cancer comprises an acute myeloid leukemia (AML), breast carcinoma, cholangiocarcinoma, colorectal adenocarcinoma, extrahepatic bile duct adenocarcinoma, female genital tract malignancy, gastric adenocarcinoma, gastroesophageal adenocarcinoma, gastrointestinal stromal tumors (GIST), glioblastoma, head and neck squamous carcinoma, leukemia, liver hepatocellular carcinoma, low grade glioma, lung bronchioloalveolar carcinoma (BAC), lung non-small cell lung cancer (NSCLC), lung small cell cancer (SCLC), lymphoma, male genital tract malignancy, malignant solitary fibrous tumor of the pleura (MSFT), melanoma, multiple myeloma, neuroendocrine tumor, nodal diffuse large B-cell lymphoma, non epithelial ovarian cancer (non-EOC), ovarian surface epithelial carcinoma, pancreatic adenocarcinoma, pituitary carcinomas, oligodendroglioma, prostatic adenocarcinoma, retroperitoneal or peritoneal carcinoma, retroperitoneal or peritoneal sarcoma, small intestinal malignancy, soft tissue tumor, thymic carcinoma, thyroid carcinoma, or uveal melanoma. The methods of the invention can be used to characterize these and other cancers. Thus, characterizing a phenotype can be providing a diagnosis, prognosis or theranosis of one of the cancers disclosed herein.

The phenotype can also be an inflammatory disease, immune disease, or autoimmune disease. For example, the disease may be inflammatory bowel disease (IBD), Crohn's disease (CD), ulcerative colitis (UC), pelvic inflammation, vasculitis, psoriasis, diabetes, autoimmune hepatitis, Multiple Sclerosis, Myasthenia Gravis, Type I diabetes, Rheumatoid Arthritis, Psoriasis, Systemic Lupus Eiythematosis (SLE), Hashimoto's Thyroiditis, Grave's disease, Ankylosing Spondylitis Sjogren Disease, CREST syndrome, Scleroderma, Rheumatic Disease, organ rejection, Primary Sclerosing Cholangitis, or sepsis.

The phenotype can also comprise a cardiovascular disease, such as atherosclerosis, congestive heart failure, vulnerable plaque, stroke, or ischemia. The cardiovascular disease or condition can be high blood pressure, stenosis, vessel occlusion or a thrombotic event.

The phenotype can also comprise a neurological disease, such as Multiple Sclerosis (MS), Parkinson's Disease (PD), Alzheimer's Disease (AD), schizophrenia, bipolar disorder, depression, autism, Prion Disease, Pick's disease, dementia, Huntington disease (HD), Down's syndrome, cerebrovascular disease, Rasmussen's encephalitis, viral meningitis, neurospsychiatric systemic lupus erythematosus (NPSLE), amyotrophic lateral sclerosis, Creutzfeldt-Jacob disease, Gerstmann-Straussler-Scheinker disease, transmissible spongiform encephalopathy, ischemic reperfusion damage (e.g. stroke), brain trauma, microbial infection, or chronic fatigue syndrome. The phenotype may also be a condition such as fibromyalgia, chronic neuropathic pain, or peripheral neuropathic pain.

The phenotype may also comprise an infectious disease, such as a bacterial, viral or yeast infection. For example, the disease or condition may be Whipple's Disease, Prion Disease, cirrhosis, methicillin-resistant *Staphylococcus aureus*, HIV, hepatitis, syphilis, meningitis, malaria, tuberculosis, or influenza. Viral proteins, such as HIV or HCV-like particles can be assessed in a vesicle, to characterize a viral condition.

The phenotype can also comprise a perinatal or pregnancy related condition (e.g. preeclampsia or preterm birth), metabolic disease or condition, such as a metabolic disease or condition associated with iron metabolism. For example, hepcidin can be assayed in a vesicle to characterize an iron deficiency. The metabolic disease or condition can also be diabetes, inflammation, or a perinatal condition.

The compositions and methods of the invention can be used to characterize these and other diseases and disorders that can be assessed via biomarkers. Thus, characterizing a phenotype can be providing a diagnosis, prognosis or theranosis of one of the diseases and disorders disclosed herein.

Subject

One or more phenotypes of a subject can be determined by analyzing one or more vesicles, such as vesicles, in a biological sample obtained from the subject. A subject or patient can include, but is not limited to, mammals such as bovine, avian, canine, equine, feline, ovine, porcine, or primate animals (including humans and non-human primates). A subject can also include a mammal of importance due to being endangered, such as a Siberian tiger; or economic importance, such as an animal raised on a farm for consumption by humans, or an animal of social importance to humans, such as an animal kept as a pet or in a zoo. Examples of such animals include, but are not limited to, carnivores such as cats and dogs; swine including pigs, hogs and wild boars; ruminants or ungulates such as cattle, oxen, sheep, giraffes, deer, goats, bison, camels or horses. Also included are birds that are endangered or kept in zoos, as well as fowl and more particularly domesticated fowl, i.e. poultry, such as turkeys and chickens, ducks, geese, guinea fowl. Also included are domesticated swine and horses (including race horses). In addition, any animal species connected to commercial activities are also included such as those animals connected to agriculture and aquaculture and other activities in which disease monitoring, diagnosis, and therapy selection are routine practice in husbandry for economic productivity and/or safety of the food chain.

The subject can have a pre-existing disease or condition, such as cancer. Alternatively, the subject may not have any known pre-existing condition. The subject may also be non-responsive to an existing or past treatment, such as a treatment for cancer.

Samples

A sample used and/or assessed via the compositions and methods of the invention includes any relevant biological sample that can be used for biomarker assessment, including without limitation sections of tissues such as biopsy or tissue removed during surgical or other procedures, bodily fluids, autopsy samples, frozen sections taken for histological purposes, and cell cultures. Such samples include blood and blood fractions or products (e.g., serum, buffy coat, plasma, platelets, red blood cells, and the like), sputum, malignant effusion, cheek cells tissue, cultured cells (e.g., primary cultures, explants, and transformed cells), stool, urine, other biological or bodily fluids (e.g., prostatic fluid, gastric fluid, intestinal fluid, renal fluid, lung fluid, cerebrospinal fluid, and the like), etc. The sample can comprise biological material that is a fresh frozen & formalin fixed paraffin embedded (FFPE) block, formalin-fixed paraffin embedded, or is within an RNA preservative+formalin fixative. More than one sample of more than one type can be used for each patient.

The sample used in the methods described herein can be a formalin fixed paraffin embedded (FFPE) sample. The FFPE sample can be one or more of fixed tissue, unstained slides, bone marrow core or clot, core needle biopsy, malignant fluids and fine needle aspirate (FNA). In an embodiment, the fixed tissue comprises a tumor containing formalin fixed paraffin embedded (FFPE) block from a surgery or biopsy. In another embodiment, the unstained slides comprise unstained, charged, unbaked slides from a paraffin block. In another embodiment, bone marrow core or clot comprises a decalcified core. A formalin fixed core and/or clot can be paraffin-embedded. In still another embodiment, the core needle biopsy comprises 1, 2, 3, 4, 5, 6, 7, 8, 9, 10 or more, e.g., 3-4, paraffin embedded biopsy samples. An 18 gauge needle biopsy can be used. The malignant fluid can comprise a sufficient volume of fresh pleural/ascitic fluid to produce a 5×5×2 mm cell pellet. The fluid can be formalin fixed in a paraffin block. In an embodiment, the core needle biopsy comprises 1, 2, 3, 4, 5, 6, 7, 8, 9, 10 or more, e.g., 4-6, paraffin embedded aspirates.

A sample may be processed according to techniques understood by those in the art. A sample can be without limitation fresh, frozen or fixed cells or tissue. In some embodiments, a sample comprises formalin-fixed paraffin-embedded (FFPE) tissue, fresh tissue or fresh frozen (FF) tissue. A sample can comprise cultured cells, including primary or immortalized cell lines derived from a subject sample. A sample can also refer to an extract from a sample from a subject. For example, a sample can comprise DNA, RNA or protein extracted from a tissue or a bodily fluid. Many techniques and commercial kits are available for such purposes. The fresh sample from the individual can be treated with an agent to preserve RNA prior to further processing, e.g., cell lysis and extraction. Samples can include frozen samples collected for other purposes. Samples can be associated with relevant information such as age, gender, and clinical symptoms present in the subject; source of the sample; and methods of collection and storage of the sample. A sample is typically obtained from a subject.

A biopsy comprises the process of removing a tissue sample for diagnostic or prognostic evaluation, and to the tissue specimen itself. Any biopsy technique known in the art can be applied to the molecular profiling methods of the present invention. The biopsy technique applied can depend on the tissue type to be evaluated (e.g., colon, prostate, kidney, bladder, lymph node, liver, bone marrow, blood cell, lung, breast, etc.), the size and type of the tumor (e.g., solid or suspended, blood or ascites), among other factors. Representative biopsy techniques include, but are not limited to, excisional biopsy, incisional biopsy, needle biopsy, surgical biopsy, and bone marrow biopsy. An "excisional biopsy" refers to the removal of an entire tumor mass with a small margin of normal tissue surrounding it. An "incisional biopsy" refers to the removal of a wedge of tissue that includes a cross-sectional diameter of the tumor. Molecular profiling can use a "core-needle biopsy" of the tumor mass, or a "fine-needle aspiration biopsy" which generally obtains a suspension of cells from within the tumor mass. Biopsy techniques are discussed, for example, in Harrison's Principles of Internal Medicine, Kasper, et al., eds., 16th ed., 2005, Chapter 70, and throughout Part V.

Standard molecular biology techniques known in the art and not specifically described are generally followed as in Sambrook et al., Molecular Cloning: A Laboratory Manual, Cold Spring Harbor Laboratory Press, New York (1989), and as in Ausubel et al., Current Protocols in Molecular Biology, John Wiley and Sons, Baltimore, Md. (1989) and as in Perbal, A Practical Guide to Molecular Cloning, John Wiley & Sons, New York (1988), and as in Watson et al., Recombinant DNA, Scientific American Books, New York and in Birren et al (eds) Genome Analysis: A Laboratory Manual Series, Vols. 1-4 Cold Spring Harbor Laboratory Press, New York (1998) and methodology as set forth in U.S.

Pat. Nos. 4,666,828; 4,683,202; 4,801,531; 5,192,659 and 5,272,057 and incorporated herein by reference. Polymerase chain reaction (PCR) can be carried out generally as in PCR Protocols: A Guide to Methods and Applications, Academic Press, San Diego, Calif. (1990).

The biological sample assessed using the compositions and methods of the invention can be any useful bodily or biological fluid, including but not limited to peripheral blood, sera, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen (including prostatic fluid), Cowper's fluid or pre-ejaculatory fluid, female ejaculate, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, other lavage fluids, cells, cell culture, or a cell culture supernatant A biological sample may also include the blastocyl cavity, umbilical cord blood, or maternal circulation which may be of fetal or maternal origin. The biological sample may also be a cell culture, tissue sample or biopsy from which vesicles and other circulating biomarkers may be obtained. For example, cells of interest can be cultured and vesicles isolated from the culture. In various embodiments, biomarkers or more particularly biosignatures disclosed herein can be assessed directly from such biological samples (e.g., identification of presence or levels of nucleic acid or polypeptide biomarkers or functional fragments thereof) using various methods, such as extraction of nucleic acid molecules from blood, plasma, serum or any of the foregoing biological samples, use of protein or antibody arrays to identify polypeptide (or functional fragment) biomarker(s), as well as other array, sequencing, PCR and proteomic techniques known in the art for identification and assessment of nucleic acid and polypeptide molecules. In addition, one or more components present in such samples can be first isolated or enriched and further processed to assess the presence or levels of selected biomarkers, to assess a given biosignature (e.g., isolated microvesicles prior to profiling for protein and/or nucleic acid biomarkers).

Table 1 presents a non-limiting listing of diseases, conditions, or biological states and corresponding biological samples that may be used for analysis according to the methods of the invention.

TABLE 1

Examples of Biological Samples for Various Diseases, Conditions, or Biological States

| Illustrative Disease, Condition or Biological State | Illustrative Biological Samples |
|---|---|
| Cancers/neoplasms affecting the following tissue types/bodily systems: breast, lung, ovarian, colon, rectal, prostate, pancreatic, brain, bone, connective tissue, glands, skin, lymph, nervous system, endocrine, germ cell, genitourinary, hematologic/blood, bone marrow, muscle, eye, esophageal, fat tissue, thyroid, pituitary, spinal cord, bile duct, heart, gall bladder, bladder, testes, cervical, endometrial, renal, ovarian, digestive/gastrointestinal, stomach, head and neck, liver, leukemia, respiratory/thoracic, cancers of unknown primary (CUP) | Tumor, blood, serum, plasma, cerebrospinal fluid (CSF), urine, sputum, ascites, synovial fluid, semen, nipple aspirates, saliva, bronchoalveolar lavage fluid, tears, oropharyngeal washes, feces, peritoneal fluids, pleural effusion, sweat, tears, aqueous humor, pericardial fluid, lymph, chyme, chyle, bile, stool water, amniotic fluid, breast milk, pancreatic juice, cerumen, Cowper's fluid or pre-ejaculatory fluid, female ejaculate, interstitial fluid, menses, mucus, pus, sebum, vaginal lubrication, vomit |
| Neurodegenerative/neurological disorders: Parkinson's disease, Alzheimer's Disease and multiple sclerosis, Schizophrenia, and bipolar disorder, spasticity disorders, epilepsy | Blood, serum, plasma, CSF, urine |
| Cardiovascular Disease: atherosclerosis, cardiomyopathy, endocarditis, vunerable plaques, infection | Blood, serum, plasma, CSF, urine |
| Stroke: ischemic, intracerebral hemorrhage, subarachnoid hemorrhage, transient ischemic attacks (TIA) | Blood, serum, plasma, CSF, urine |
| Pain disorders: peripheral neuropathic pain and chronic neuropathic pain, and fibromyalgia, | Blood, serum, plasma, CSF, urine |
| Autoimmune disease: systemic and localized diseases, rheumatic disease, Lupus, Sjogren's syndrome | Blood, serum, plasma, CSF, urine, synovial fluid |
| Digestive system abnormalities: Barrett's esophagus, irritable bowel syndrome, ulcerative colitis, Crohn's disease, Diverticulosis and Diverticulitis, Celiac Disease | Blood, serum, plasma, CSF, urine |
| Endocrine disorders: diabetes mellitus, various forms of Thyroiditis, adrenal disorders, pituitary disorders | Blood, serum, plasma, CSF, urine |
| Diseases and disorders of the skin: psoriasis | Blood, serum, plasma, CSF, urine, synovial fluid, tears |
| Urological disorders: benign prostatic hypertrophy (BPH), polycystic kidney disease, interstitial cystitis | Blood, serum, plasma, urine |
| Hepatic disease/injury: Cirrhosis, induced hepatotoxicity (due to exposure to natural or synthetic chemical sources) | Blood, serum, plasma, urine |
| Kidney disease/injury: acute, sub-acute, chronic conditions, Podocyte injury, focal segmental glomerulosclerosis | Blood, serum, plasma, urine |

TABLE 1-continued

Examples of Biological Samples for Various Diseases, Conditions, or Biological States

| Illustrative Disease, Condition or Biological State | Illustrative Biological Samples |
|---|---|
| Endometriosis | Blood, serum, plasma, urine, vaginal fluids |
| Osteoporosis | Blood, serum, plasma, urine, synovial fluid |
| Pancreatitis | Blood, serum, plasma, urine, pancreatic juice |
| Asthma | Blood, serum, plasma, urine, sputum, bronchiolar lavage fluid |
| Allergies | Blood, serum, plasma, urine, sputum, bronchiolar lavage fluid |
| Prion-related diseases | Blood, serum, plasma, CSF, urine |
| Viral Infections: HIV/AIDS | Blood, serum, plasma, urine |
| Sepsis | Blood, serum, plasma, urine, tears, nasal lavage |
| Organ rejection/transplantation | Blood, serum, plasma, urine, various lavage fluids |
| Differentiating conditions: adenoma versus hyperplastic polyp, irritable bowel syndrome (IBS) versus normal, classifying Dukes stages A, B, C, and/or D of colon cancer, adenoma with low-grade hyperplasia versus high-grade hyperplasia, adenoma versus normal, colorectal cancer versus normal, IBS versus. ulcerative colitis (UC) versus Crohn's disease (CD), | Blood, serum, plasma, urine, sputum, feces, colonic lavage fluid |
| Pregnancy related physiological states, conditions, or affiliated diseases: genetic risk, adverse pregnancy outcomes | Maternal serum, plasma, amniotic fluid, cord blood |

The methods of the invention can be used to characterize a phenotype using a blood sample or blood derivative. Blood derivatives include plasma and serum. Blood plasma is the liquid component of whole blood, and makes up approximately 55% of the total blood volume. It is composed primarily of water with small amounts of minerals, salts, ions, nutrients, and proteins in solution. In whole blood, red blood cells, leukocytes, and platelets are suspended within the plasma. Blood serum refers to blood plasma without fibrinogen or other clotting factors (i.e., whole blood minus both the cells and the clotting factors).

The biological sample may be obtained through a third party, such as a party not performing the analysis of the biomarkers, whether direct assessment of a biological sample or by profiling one or more vesicles obtained from the biological sample. For example, the sample may be obtained through a clinician, physician, or other health care manager of a subject from which the sample is derived. Alternatively, the biological sample may obtained by the same party analyzing the vesicle. In addition, biological samples be assayed, are archived (e.g., frozen) or ortherwise stored in under preservative conditions.

Furthermore, a biological sample can comprise a vesicle or cell membrane fragment that is derived from a cell of origin and available extracellularly in a subject's biological fluid or extracellular milieu.

Methods of the invention can include assessing one or more vesicles, including assessing vesicle populations. A vesicle, as used herein, is a membrane vesicle that is shed from cells. Vesicles or membrane vesicles include without limitation: circulating microvesicles (cMVs), microvesicle, exosome, nanovesicle, dexosome, bleb, blebby, prostasome, microparticle, intralumenal vesicle, membrane fragment, intralumenal endosomal vesicle, endosomal-like vesicle, exocytosis vehicle, endosome vesicle, endosomal vesicle, apoptotic body, multivesicular body, secretory vesicle, phospholipid vesicle, liposomal vesicle, argosome, texasome, secresome, tolerosome, melanosome, oncosome, or exocytosed vehicle. Furthermore, although vesicles may be produced by different cellular processes, the methods of the invention are not limited to or reliant on any one mechanism, insofar as such vesicles are present in a biological sample and are capable of being characterized by the methods disclosed herein. Unless otherwise specified, methods that make use of a species of vesicle can be applied to other types of vesicles. Vesicles comprise spherical structures with a lipid bilayer similar to cell membranes which surrounds an inner compartment which can contain soluble components, sometimes referred to as the payload. In some embodiments, the methods of the invention make use of exosomes, which are small secreted vesicles of about 40-100 nm in diameter. For a review of membrane vesicles, including types and characterizations, see Thery et al., *Nat Rev Immunol.* 2009 August; 9(8):581-93. Some properties of different types of vesicles include those in Table 2:

TABLE 2

| | Vesicle Properties | | | | | |
|---|---|---|---|---|---|---|
| Feature | Exosomes | Microvesicles | Ectosomes | Membrane particles | Exosome-like vesicles | Apoptotic vesicles |
| Size | 50-100 nm | 100-1,000 nm | 50-200 nm | 50-80 nm | 20-50 nm | 50-500 nm |
| Density in sucrose | 1.13-1.19 g/ml | | | 1.04-1.07 g/ml | 1.1 g/ml | 1.16-1.28 g/ml |
| EM appearance | Cup shape | Irregular shape, electron dense | Bilamellar round structures | Round | Irregular shape | Heterogeneous |

TABLE 2-continued

Vesicle Properties

| Feature | Exosomes | Microvesicles | Ectosomes | Membrane particles | Exosome-like vesicles | Apoptotic vesicles |
|---|---|---|---|---|---|---|
| Sedimentation | 100,000 g | 10,000 g | 160,000-200,000 g | 100,000-200,000 g | 175,000 g | 1,200 g, 10,000 g, 100,000 g |
| Lipid composition | Enriched in cholesterol, sphingomyelin and ceramide; contains lipid rafts; expose PPS | Expose PPS | Enriched in cholesterol and diacylglycerol; expose PPS | | No lipid rafts | |
| Major protein markers | Tetraspanins (e.g., CD63, CD9), Alix, TSG101 | Integrins, selectins and CD40 ligand | CR1 and proteolytic enzymes; no CD63 | CD133; no CD63 | TNFRI | |
| Intracellular origin | Internal compartments (endosomes) | Plasma membrane | Plasma membrane | Plasma membrane | | |

Abbreviations:
phosphatidylserine (PPS);
electron microscopy (EM)

Vesicles include shed membrane bound particles, or "microparticles," that are derived from either the plasma membrane or an internal membrane. Vesicles can be released into the extracellular environment from cells. Cells releasing vesicles include without limitation cells that originate from, or are derived from, the ectoderm, endoderm, or mesoderm. The cells may have undergone genetic, environmental, and/or any other variations or alterations. For example, the cell can be tumor cells. A vesicle can reflect any changes in the source cell, and thereby reflect changes in the originating cells, e.g., cells having various genetic mutations. In one mechanism, a vesicle is generated intracellularly when a segment of the cell membrane spontaneously invaginates and is ultimately exocytosed (see for example, Keller et al., Immunol. Lett. 107 (2): 102-8 (2006)). Vesicles also include cell-derived structures bounded by a lipid bilayer membrane arising from both herniated evagination (blebbing) separation and sealing of portions of the plasma membrane or from the export of any intracellular membrane-bounded vesicular structure containing various membrane-associated proteins of tumor origin, including surface-bound molecules derived from the host circulation that bind selectively to the tumor-derived proteins together with molecules contained in the vesicle lumen, including but not limited to tumor-derived microRNAs or intracellular proteins. Blebs and blebbing are further described in Charras et al., Nature Reviews Molecular and Cell Biology, Vol. 9, No. 11, p. 730-736 (2008). A vesicle shed into circulation or bodily fluids from tumor cells may be referred to as a "circulating tumor-derived vesicle." When such vesicle is an exosome, it may be referred to as a circulating-tumor derived exosome (CTE). In some instances, a vesicle can be derived from a specific cell of origin. CTE, as with a cell-of-origin specific vesicle, typically have one or more unique biomarkers that permit isolation of the CTE or cell-of-origin specific vesicle, e.g., from a bodily fluid and sometimes in a specific manner. For example, a cell or tissue specific markers are used to identify the cell of origin. Examples of such cell or tissue specific markers are disclosed herein and can further be accessed in the Tissue-specific Gene Expression and Regulation (TiGER) Database, available at bioinfo.wilmer.jhu.edu/tiged; Liu et al. (2008) TiGER: a database for tissue-specific gene expression and regulation. BMC Bioinformatics. 9:271; TissueDistributionDBs, available at genome.dkfz-heidelberg.de/menu/tissue_db/index.html.

A vesicle can have a diameter of greater than about 10 nm, 20 nm, or 30 nm. A vesicle can have a diameter of greater than 40 nm, 50 nm, 100 nm, 200 nm, 500 nm, 1000 nm, 1500 nm, 2000 nm or greater than 10,000 nm. A vesicle can have a diameter of about 20-2000 nm, about 20-1500 nm, about 30-1000 nm, about 30-800 nm, about 30-200 nm, or about 30-100 nm. In some embodiments, the vesicle has a diameter of less than 10,000 nm, 2000 nm, 1500 nm, 1000 nm, 800 nm, 500 nm, 200 nm, 100 nm, 50 nm, 40 nm, 30 nm, 20 nm or less than 10 nm. As used herein the term "about" in reference to a numerical value means that variations of 10% above or below the numerical value are within the range ascribed to the specified value. Typical sizes for various types of vesicles are shown in Table 2. Vesicles can be assessed to measure the diameter of a single vesicle or any number of vesicles. For example, the range of diameters of a vesicle population or an average diameter of a vesicle population can be determined. Vesicle diameter can be assessed using methods known in the art, e.g., imaging technologies such as electron microscopy. In an embodiment, a diameter of one or more vesicles is determined using optical particle detection. See, e.g., U.S. Pat. No. 7,751,053, entitled "Optical Detection and Analysis of Particles" and issued Jul. 6, 2010; and U.S. Pat. No. 7,399,600, entitled "Optical Detection and Analysis of Particles" and issued Jul. 15, 2010.

In some embodiments, the methods of the invention comprise assessing vesicles directly such as in a biological sample without prior isolation, purification, or concentration from the biological sample. For example, the amount of vesicles in the sample can by itself provide a biosignature that provides a diagnostic, prognostic or theranostic determination. Alternatively, the vesicle in the sample may be isolated, captured, purified, or concentrated from a sample prior to analysis. As noted, isolation, capture or purification as used herein comprises partial isolation, partial capture or partial purification apart from other components in the sample. Vesicle isolation can be performed using various techniques as described herein, e.g., chromatography, filtration, centrifugation, flow cytometry, affinity capture (e.g., to a planar surface or bead), and/or using microfluidics. FIGS.

15B-15C present an overview of a method of the invention for assessing microvesicles using an aptamer pool.

Vesicles such as exosomes can be assessed to provide a phenotypic characterization by comparing vesicle characteristics to a reference. In some embodiments, surface antigens on a vesicle are assessed. The surface antigens can provide an indication of the anatomical origin and/or cellular of the vesicles and other phenotypic information, e.g., tumor status. For example, wherein vesicles found in a patient sample, e.g., a bodily fluid such as blood, serum or plasma, are assessed for surface antigens indicative of colorectal origin and the presence of cancer. The surface antigens may comprise any informative biological entity that can be detected on the vesicle membrane surface, including without limitation surface proteins, lipids, carbohydrates, and other membrane components. For example, positive detection of colon derived vesicles expressing tumor antigens can indicate that the patient has colorectal cancer. As such, methods of the invention can be used to characterize any disease or condition associated with an anatomical or cellular origin, by assessing, for example, disease-specific and cell-specific biomarkers of one or more vesicles obtained from a subject.

In another embodiment, the methods of the invention comprise assessing one or more vesicle payload to provide a phenotypic characterization. The payload with a vesicle comprises any informative biological entity that can be detected as encapsulated within the vesicle, including without limitation proteins and nucleic acids, e.g., genomic or cDNA, mRNA, or functional fragments thereof, as well as microRNAs (miRs). In addition, methods of the invention are directed to detecting vesicle surface antigens (in addition or exclusive to vesicle payload) to provide a phenotypic characterization. For example, vesicles can be characterized by using binding agents (e.g., antibodies or aptamers) that are specific to vesicle surface antigens, and the bound vesicles can be further assessed to identify one or more payload components disclosed therein. As described herein, the levels of vesicles with surface antigens of interest or with payload of interest can be compared to a reference to characterize a phenotype. For example, overexpression in a sample of cancer-related surface antigens or vesicle payload, e.g., a tumor associated mRNA or microRNA, as compared to a reference, can indicate the presence of cancer in the sample. The biomarkers assessed can be present or absent, increased or reduced based on the selection of the desired target sample and comparison of the target sample to the desired reference sample. Non-limiting examples of target samples include: disease; treated/not-treated; different time points, such as a in a longitudinal study; and non-limiting examples of reference sample: non-disease; normal; different time points; and sensitive or resistant to candidate treatment(s).

Biomarkers

Figure 15A:
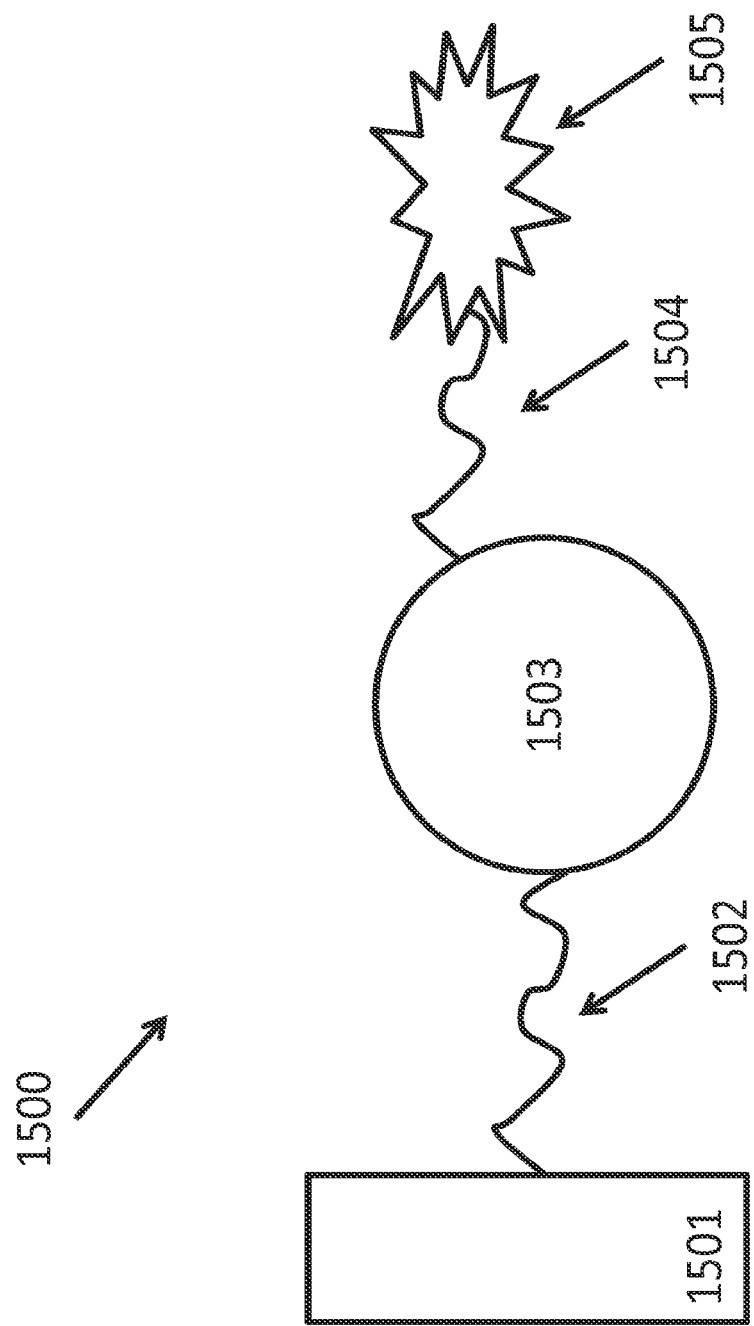
FIGS. 15A-B illustrate use of aptamers in methods of characterizing a phenotype.

As described herein, the methods and compositions of the invention can be used in assays to detect the presence or level of one or more biomarker of interest. The biomarker can be any useful biomarker disclosed herein or known to those of skill in the art. In an embodiment, the biomarker comprises a protein or polypeptide. As used herein, "protein," "polypeptide" and "peptide" are used interchangeably unless stated otherwise. The biomarker can be a nucleic acid, including DNA, RNA, and various subspecies of any thereof as disclosed herein or known in the art. The biomarker can comprise a lipid. The biomarker can comprise a carbohydrate. The biomarker can also be a complex, e.g., a complex comprising protein, nucleic acids, lipids and/or carbohydrates. In some embodiments, the biomarker comprises a microvesicle. In an embodiment, the invention provides a method wherein a pool of aptamers is used to assess the presence and/or level of a population of microvesicles of interest without knowing the precise microvesicle antigen targeted by each member of the pool. See, e.g., FIGS. 15B-C. In other cases, biomarkers associated with microvesicles are assessed according to the methods of the invention. See, e.g., FIGS. 1A-1F; FIG. 15A.

A biosignature comprising more than one biomarker can comprise one type of biomarker or multiple types of biomarkers. As a non-limiting example, a biosignature can comprise multiple proteins, multiple nucleic acids, multiple lipids, multiple carbohydrates, multiple biomarker complexes, multiple microvesicles, or a combination of any thereof. For example, the biosignature may comprise one or more microvesicle, one or more protein, and one or more microRNA, wherein the one or more protein and/or one or more microRNA is optionally in association with the microvesicle as a surface antigen and/or payload, as appropriate.

In some embodiments, vesicles are detected using vesicle surface antigens. A commonly expressed vesicle surface antigen can be referred to as a "housekeeping protein," or general vesicle biomarker. The biomarker can be CD63, CD9, CD81, CD82, CD37, CD53, Rab-5b, Annexin V or MFG-E8. Tetraspanins, a family of membrane proteins with four transmembrane domains, can be used as general vesicle biomarkers. The tetraspanins include CD151, CD53, CD37, CD82, CD81, CD9 and CD63. There have been over 30 tetraspanins identified in mammals, including the TSPAN1 (TSP-1), TSPAN2 (TSP-2), TSPAN3 (TSP-3), TSPAN4 (TSP-4, NAG-2), TSPAN5 (TSP-5), TSPAN6 (TSP-6), TSPAN7 (CD231, TALLA-1, A15), TSPAN8 (CO-029), TSPAN9 (NET-5), TSPAN10 (Oculospanin), TSPAN11 (CD151-like), TSPAN12 (NET-2), TSPAN13 (NET-6), TSPAN14, TSPAN15 (NET-7), TSPAN16 (TM4-B), TSPAN17, TSPAN18, TSPAN19, TSPAN20 (UP1b, UPK1B), TSPAN21 (UP1a, UPK1A), TSPAN22 (RDS, PRPH2), TSPAN23 (ROM1), TSPAN24 (CD151), TSPAN25 (CD53), TSPAN26 (CD37), TSPAN2? (CD82), TSPAN28 (CD81), TSPAN29 (CD9), TSPAN30 (CD63), TSPAN31 (SAS), TSPAN32 (TSSC6), TSPAN33, and TSPAN34. Other commonly observed vesicle markers include those listed in Table 3. One or more of these proteins can be useful biomarkers for the characterizing a phenotype using the subject methods and compositions.

TABLE 3

| Proteins Observed in Vesicles from Multiple Cell Types | |
| --- | --- |
| Class | Protein |
| Antigen Presentation | MHC class I, MHC class II, Integrins, Alpha 4 beta 1, Alpha M beta 2, Beta 2 |
| Immunoglobulin family | ICAM1/CD54, P-selection |
| Cell-surface peptidases | Dipeptidylpeptidase IV/CD26, Aminopeptidase n/CD13 |
| Tetraspanins | CD151, CD53, CD37, CD82, CD81, CD9 and CD63 |
| Heat-shock proteins | Hsp70, Hsp84/90 |
| Cytoskeletal proteins | Actin, Actin-binding proteins, Tubulin |

TABLE 3-continued

Proteins Observed in Vesicles from Multiple Cell Types

| Class | Protein |
|---|---|
| Membrane transport and fusion | Annexin I, Annexin II, Annexin IV, Annexin V, Annexin VI, RAB7/RAP1B/RADGDI |
| Signal transduction | Gi2alpha/14-3-3, CBL/LCK |
| Abundant membrane proteins | CD63, GAPDH, CD9, CD81, ANXA2, ENO1, SDCBP, MSN, MFGE8, EZR, GK, ANXA1, LAMP2, DPP4, TSG101, HSPA1A, GDI2, CLTC, LAMP1, Cd86, ANPEP, TFRC, SLC3A2, RDX, RAP1B, RAB5C, RAB5B, MYH9, ICAM1, FN1, RAB11B, PIGR, LGALS3, ITGB1, EHD1, CLIC1, ATP1A1, ARF1, RAP1A, P4HB, MUC1, KRT10, HLA-A, FLOT1, CD59, C1orf58, BASP1, TACSTD1, STOM |
| Other Transmembrane Proteins | Cadherins: CDH1, CDH2, CDH12, CDH3, Desmoglein, DSG1, DSG2, DSG3, DSG4, Desmocollin, DSC1, DSC2, DSC3, Protocadherins, PCDH1, PCDH10, PCDH11x, PCDH11y, PCDH12, FAT, FAT2, FAT4, PCDH15, PCDH17, PCDH18, PCDH19; PCDH20; PCDH7, PCDH8, PCDH9, PCDHA1, PCDHA10, PCDHA11, PCDHA12, PCDHA13, PCDHA2, PCDHA3, PCDHA4, PCDHA5, PCDHA6, PCDHA7, PCDHA8, PCDHA9, PCDHAC1, PCDHAC2, PCDHB1, PCDHB10, PCDHB11, PCDHB12, PCDHB13, PCDHB14, PCDHB15, PCDHB16, PCDHB17, PCDHB18, PCDHB2, PCDHB3, PCDHB4, PCDHB5, PCDHB6, PCDHB7, PCDHB8, PCDHB9, PCDHGA1, PCDHGA10, PCDHGA11, PCDHGA12, PCDHGA2; PCDHGA3, PCDHGA4, PCDHGA5, PCDHGA6, PCDHGA7, PCDHGA8, PCDHGA9, PCDHGB1, PCDHGB2, PCDHGB3, PCDHGB4, PCDHGB5, PCDHGB6, PCDHGB7, PCDHGC3, PCDHGC4, PCDHGC5, CDH9 (cadherin 9, type 2 (T1-cadherin)), CDH10 (cadherin 10, type 2 (T2-cadherin)), CDH5 (VE-cadherin (vascular endothelial)), CDH6 (K-cadherin (kidney)), CDH7 (cadherin 7, type 2), CDH8 (cadherin 8, type 2), CDH11 (OB-cadherin (osteoblast)), CDH13 (T-cadherin - H-cadherin (heart)), CDH15 (M-cadherin (myotubule)), CDH16 (KSP-cadherin), CDH17 (LI cadherin (liver-intestine)), CDH18 (cadherin 18, type 2), CDH19 (cadherin 19, type 2), CDH20 (cadherin 20, type 2), CDH23 (cadherin 23, (neurosensory epithelium)), CDH10, CDH11, CDH13, CDH15, CDH16, CDH17, CDH18, CDH19, CDH20, CDH22, CDH23, CDH24, CDH26, CDH28, CDH4, CDH5, CDH6, CDH7, CDH8, CDH9, CELSR1, CELSR2, CELSR3, CLSTN1, CLSTN2, CLSTN3, DCHS1, DCHS2, LOC389118, PCLKC, RESDA1, RET |

Any of the types of biomarkers described herein can be used and/or assessed via the subject methods and compositions. Exemplary biomarkers include without limitation those in Table 4. The markers can be detected as protein or as mRNA, which can be circulating freely or in a complex with other biological molecules. As appropriate, the markers in Table 4 can also be used for capture and/or detection of vesicles for characterizing phenotypes as disclosed herein. In some cases, multiple capture and/or detectors are used to enhance the characterization. See, e.g., FIGS. 1C-1E. The markers can be detected as vesicle surface antigens and/or vesicle payload. The "Illustrative Class" indicates indications for which the markers are known markers. Those of skill will appreciate that the markers can also be used in alternate settings in certain instances. For example, a marker which can be used to characterize one type disease may also be used to characterize another disease as appropriate. Consider a non-limiting example of a tumor marker which can be used as a biomarker for tumors from various lineages. The biomarker references in Table 4 are those commonly used in the art. Gene aliases and descriptions can be found using a variety of online databases, including GeneCards® (www.genecards.org), HUGO Gene Nomenclature (www.genenames.org), Entrez Gene (www.ncbi.nlm.nih.gov/entrez/query.fcgi?db=gene), UniProtKB/Swiss-Prot (www.uniprot.org), UniProtKB/TrEMBL (www.uniprot.org), OMIM (www.ncbi.nlm.nih.gov/entrez/query.fcgi?db=OMIM), GeneLoc (genecards.weizmann.ac.il/geneloc/), and Ensembl (www.ensembl.org). Generally, gene symbols and names below correspond to those approved by HUGO, and protein names are those recommended by UniProtKB/Swiss-Prot. Common alternatives are provided as well. In some cases, biomarkers are referred to by Ensembl reference numbers, which are of the form "ENSG" followed by a number, e.g., ENSG00000005893 which corresponds to LAMP2. In Table 4, solely for sake of brevity, "E." is sometimes used to represent "ENSG00000". For example, "E.005893 represents "ENSG00000005893." Where a protein name indicates a precursor, the mature protein is also implied. Throughout the application, gene and protein symbols may be used interchangeably and the meaning can be derived from context as necessary.

TABLE 4

Illustrative Biomarkers

| Illustrative Class | Biomarkers |
|---|---|
| Drug associated targets and prognostic markers | ABCC1, ABCG2, ACE2, ADA, ADH1C, ADH4, AGT, AR, AREG, ASNS, BCL2, BCRP, BDCA1, beta III tubulin, BIRC5, B-RAF, BRCA1, BRCA2, CA2, caveolin, CD20, CD25, CD33, CD52, CDA, CDKN2A, CDKN1A, CDKN1B, CDK2, CDW52, CES2, CK 14, CK 17, CK 5/6, c-KIT, c-Met, c-Myc, COX-2, Cyclin D1, DCK, DHFR, DNMT1, DNMT3A, DNMT3B, E-Cadherin, ECGF1, EGFR, EML4-ALK fusion, EPHA2, Epiregulin, ER, |

TABLE 4-continued

Illustrative Biomarkers

| Illustrative Class | Biomarkers |
|---|---|
| | ERBR2, ERCC1, ERCC3, EREG, ESR1, FLT1, folate receptor, FOLR1, FOLR2, FSHB, FSHPRH1, FSHR, FYN, GART, GNA11, GNAQ, GNRH1, GNRHR1, GSTP1, HCK, HDAC1, hENT-1, Her2/Neu, HGF, HIF1A, HIG1, HSP90, HSP90AA1, HSPCA, IGF-1R, IGFRBP, IGFRBP3, IGFRBP4, IGFRBP5, IL13RA1, IL2RA, KDR, Ki67, KIT, K-RAS, LCK, LTB, Lymphotoxin Beta Receptor, LYN, MET, MGMT, MLH1, MMR, MRP1, MS4A1, MSH2, MSH5, Myc, NFKB1, NFKB2, NFKBIA, NRAS, ODC1, OGFR, p16, p21, p27, p53, p95, PARP-1, PDGFC, PDGFR, PDGFRA, PDGFRB, PGP, PGR, PI3K, POLA, POLA1, PPARG, PPARGC1, PR, PTEN, PTGS2, PTPN12, RAF1, RARA, ROS1, RRM1, RRM2, RRM2B, RXRB, RXRG, SIK2, SPARC, SRC, SSTR1, SSTR2, SSTR3, SSTR4, SSTR5, Survivin, TK1, TLE3, TNF, TOP1, TOP2A, TOP2B, TS, TUBB3, TXN, TXNRD1, TYMS, VDR, VEGF, VEGFA, VEGFC, VHL, YES1, ZAP70 |
| Drug associated targets and prognostic markers | ABL1, STK11, FGFR2, ERBB4, SMARCB1, CDKN2A, CTNNB1, FGFR1, FLT3, NOTCH1, NPM1, SRC, SMAD4, FBXW7, PTEN, TP53, AKT1, ALK, APC, CDH1, C-Met, HRAS, IDH1, JAK2, MPL, PDGFRA, SMO, VHL, ATM, CSF1R, FGFR3, GNAS, ERBB2, HNF1A, JAK3, KDR, MLH1, PTPN11, RB1, RET, c-Kit, EGFR, PIK3CA, NRAS, GNA11, GNAQ, KRAS, BRAF |
| Drug associated targets and prognostic markers | ALK, AR, BRAF, cKIT, cMET, EGFR, ER, ERCC1, GNA11, HER2, IDH1, KRAS, MGMT, MGMT promoter methylation, NRAS, PDGFRA, Pgp, PIK3CA, PR, PTEN, ROS1, RRM1, SPARC, TLE3, TOP2A, TOPO1, TS, TUBB3, VHL |
| Drug associated targets and prognostic markers | AR, cMET, EGFR, ER, HER2, MGMT, Pgp, PR, PTEN, RRM1, SPARC, TLE3, TOPO1, TOP2A, TS, TUBB3, ALK, cMET, HER2, ROS1, TOP2A, BRAF, IDH2, MGMT Methylation, ABL1, AKT1, ALK, APC, ATM, BRAF, CDH1, CSF1R, CTNNB1, EGFR, ERBB2 (HER2), ERBB4, FBXW7, FGFR1, FGFR2, FLT3, GNA11, GNAQ, GNAS, HNF1A, HRAS, IDH1, JAK2, JAK3, KDR (VEGFR2), KIT, KRAS, MET, MLH1, MPL, NOTCH1, NPM1, NRAS, PDGFRA, PIK3CA, PTEN, PTPN11, RB1, RET, SMAD4, SMARCB1, SMO, STK11, TP53, VHL |
| 5-aminosalicyclic acid (5-ASA) efficacy | μ-protocadherin, KLF4, CEBPα |
| Cancer treatment associated markers | AR, AREG (Amphiregulin), BRAF, BRCA1, cKIT, cMET, EGFR, EGFR w/T790M, EML4-ALK, ER, ERBB3, ERBB4, ERCC1, EREG, GNA11, GNAQ, hENT-1, Her2, Her2 Exon 20 insert, IGF1R, Ki67, KRAS, MGMT, MGMT methylation, MSH2, MSI, NRAS, PGP (MDR1), PIK3CA, PR, PTEN, ROS1, ROS1 translocation, RRM1, SPARC, TLE3, TOPO1, TOPO2A, TS, TUBB3, VEGFR2 |
| Cancer treatment associated markers | AR, AREG, BRAF, BRCA1, cKIT, cMET, EGFR, EGFR w/T790M, EML4-ALK, ER, ERBB3, ERBB4, ERCC1, EREG, GNA11, GNAQ, Her2, Her2 Exon 20 insert, IGFR1, Ki67, KRAS, MGMT-Me, MSH2, MSI, NRAS, PGP (MDR-1), PIK3CA, PR, PTEN, ROS1 translocation, RRM1, SPARC, TLE3, TOPO1, TOPO2A, TS, TUBB3, VEGFR2 |
| Colon cancer treatment associated markers | AREG, BRAF, EGFR, EML4-ALK, ERCC1, EREG, KRAS, MSI, NRAS, PIK3CA, PTEN, TS, VEGFR2 |
| Colon cancer treatment associated markers | AREG, BRAF, EGFR, EML4-ALK, ERCC1, EREG, KRAS, MSI, NRAS, PIK3CA, PTEN, TS, VEGFR2 |
| Melanoma treatment associated markers | BRAF, cKIT, ERBB3, ERBB4, ERCC1, GNA11, GNAQ, MGMT, MGMT methylation, NRAS, PIK3CA, TUBB3, VEGFR2 |
| Melanoma treatment associated markers | BRAF, cKIT, ERBB3, ERBB4, ERCC1, GNA11, GNAQ, MGMT-Me, NRAS, PIK3CA, TUBB3, VEGFR2 |
| Ovarian cancer treatment associated markers | BRCA1, cMET, EML4-ALK, ER, ERBB3, ERCC1, hENT-1, HER2, IGF1R, PGP(MDR1), PIK3CA, PR, PTEN, RRM1, TLE3, TOPO1, TOPO2A, TS |
| Ovarian cancer treatment associated markers | BRCA1, cMET, EML4-ALK (translocation), ER, ERBB3, ERCC1, HER2, PIK3CA, PR, PTEN, RRM1, TLE3, TS |
| Breast cancer treatment associated markers | BRAF, BRCA1, EGFR, EGFR T790M, EML4-ALK, ER, ERBB3, ERCC1, HER2, Ki67, PGP (MDR1), PIK3CA, PR, PTEN, ROS1, ROS1 translocation, RRM1, TLE3, TOPO1, TOPO2A, TS |
| Breast cancer treatment associated markers | BRAF, BRCA1, EGFR w/T790M, EML4-ALK, ER, ERBB3, ERCC1, HER2, Ki67, KRAS, PIK3CA, PR, PTEN, ROS1 translocation, RRM1, TLE3, TOPO1, TOPO2A, TS |
| NSCLC cancer treatment associated markers | BRAF, BRCA1, cMET, EGFR, EGFR w/T790M, EML4-ALK, ERCC1, Her2 Exon 20 insert, KRAS, MSH2, PIK3CA, PTEN, ROS1 (trans), RRM1, TLE3, TS, VEGFR2 |
| NSCLC cancer treatment associated markers | BRAF, cMET, EGFR, EGFR w/T790M, EML4-ALK, ERCC1, Her2 Exon 20 insert, KRAS, MSH2, PIK3CA, PTEN, ROS1 translocation, RRM1, TLE3, TS |
| Mutated in cancers | AKT1, ALK, APC, ATM, BRAF, CDH1, CDKN2A, c-Kit, C-Met, CSF1R, CTNNB1, EGFR, ERBB2, ERBB4, FBXW7, FGFR1, FGFR2, FGFR3, FLT3, GNA11, GNAQ, GNAS, HNF1A, HRAS, IDH1, JAK2, JAK3, KDR, KRAS, MLH1, MPL, NOTCH1, NPM1, NRAS, PDGFRA, PIK3CA, PTEN, PTPN11, RB1, RET, SMAD4, SMARCB1, SMO, SRC, STK11, TP53, VHL |
| Mutated in cancers | ALK, BRAF, BRCA1, BRCA2, EGFR, ERRB2, GNA11, GNAQ, IDH1, IDH2, KIT, KRAS, MET, NRAS, PDGFRA, PIK3CA, PTEN, RET, SRC, TP53 |

TABLE 4-continued

Illustrative Biomarkers

| Illustrative Class | Biomarkers |
|---|---|
| Mutated in cancers | AKT1, HRAS, GNAS, MEK1, MEK2, ERK1, ERK2, ERBB3, CDKN2A, PDGFRB, IFG1R, FGFR1, FGFR2, FGFR3, ERBB4, SMO, DDR2, GRB1, PTCH, SHH, PD1, UGT1A1, BIM, ESR1, MLL, AR, CDK4, SMAD4 |
| Mutated in cancers | ABL, APC, ATM, CDH1, CSFR1, CTNNB1, FBXW7, FLT3, HNF1A, JAK2, JAK3, KDR, MLH1, MPL, NOTCH1, NPM1, PTPN11, RB1, SMARCB1, STK11, VHL |
| Mutated in cancers | ABL1, AKT1, AKT2, AKT3, ALK, APC, AR, ARAF, ARFRP1, ARID1A, ARID2, ASXL1, ATM, ATR, ATRX, AURKA, AURKB, AXL, BAP1, BARD1, BCL2, BCL2L2, BCL6, BCOR, BCORL1, BLM, BRAF, BRCA1, BRCA2, BRIP1, BTK, CARD11, CBFB, CBL, CCND1, CCND2, CCND3, CCNE1, CD79A, CD79B, CDC73, CDH1, CDK12, CDK4, CDK6, CDK8, CDKN1B, CDKN2A, CDKN2B, CDKN2C, CEBPA, CHEK1, CHEK2, CIC, CREBBP, CRKL, CRLF2, CSF1R, CTCF, CTNNA1, CTNNB1, DAXX, DDR2, DNMT3A, DOT1L, EGFR, EMSY (C11orf30), EP300, EPHA3, EPHA5, EPHB1, ERBB2, ERBB3, ERBB4, ERG, ESR1, EZH2, FAM123B (WTX), FAM46C, FANCA, FANCC, FANCD2, FANCE, FANCF, FANCG, FANCL, FBXW7, FGF10, FGF14, FGF19, FGF23, FGF3, FGF4, FGF6, FGFR1, FGFR2, FGFR3, FGFR4, FLT1, FLT3, FLT4, FOXL2, GATA1, GATA2, GATA3, GID4 (C17orf39), GNA11, GNA13, GNAQ, GNAS, GPR124, GRIN2A, GSK3B, HGF, HRAS, IDH1, IDH2, IGF1R, IKBKE, IKZF1, IL7R, INHBA, IRF4, IRS2, JAK1, JAK2, JAK3, JUN, KAT6A (MYST3), KDM5A, KDM5C, KDM6A, KDR, KEAP1, KIT, KLHL6, KRAS, LRP1B, MAP2K1, MAP2K2, MAP2K4, MAP3K1, MCL1, MDM2, MDM4, MED12, MEF2B, MEN1, MET, MITF, MLH1, MLL, MLL2, MPL, MRE11A, MSH2, MSH6, MTOR, MUTYH, MYC, MYCL1, MYCN, MYD88, NF1, NF2, NFE2L2, NFKBIA, NKX2-1, NOTCH1, NOTCH2, NPM1, NRAS, NTRK1, NTRK2, NTRK3, NUP93, PAK3, PALB2, PAX5, PBRM1, PDGFRA, PDGFRB, PDK1, PIK3CA, PIK3CG, PIK3R1, PIK3R2, PPP2R1A, PRDM1, PRKAR1A, PRKDC, PTCH1, PTEN, PTPN11, RAD50, RAD51, RAF1, RARA, RB1, RET, RICTOR, RNF43, RPTOR, RUNX1, SETD2, SF3B1, SMAD2, SMAD4, SMARCA4, SMARCB1, SMO, SOCS1, SOX10, SOX2, SPEN, SPOP, SRC, STAG2, STAT4, STK11, SUFU, TET2, TGFBR2, TNFAIP3, TNFRSF14, TOP1, TP53, TSC1, TSC2, TSHR, VHL, WISP3, WT1, XPO1, ZNF217, ZNF703 |
| Gene rearrangement in cancer | ALK, BCR, BCL2, BRAF, EGFR, ETV1, ETV4, ETV5, ETV6, EWSR1, MLL, MYC, NTRK1, PDGFRA, RAF1, RARA, RET, ROS1, TMPRSS2 |
| Cancer Related | ABL1, ACE2, ADA, ADH1C, ADH4, AGT, AKT1, AKT2, AKT3, ALK, APC, AR, ARAF, AREG, ARFRP1, ARID1A, ARID2, ASNS, ASXL1, ATM, ATR, ATRX, AURKA, AURKB, AXL, BAP1, BARD1, BCL2, BCL2L2, BCL6, BCOR, BCORL1, BCR, BIRC5 (survivin), BLM, BRAF, BRCA1, BRCA2, BRIP1, BTK, CA2, CARD11, CAV, CBFB, CBL, CCND1, CCND2, CCND3, CCNE1, CD33, CD52 (CDW52), CD79A, CD79B, CDC73, CDH1, CDK12, CDK2, CDK4, CDK6, CDK8, CDKN1B, CDKN2A, CDKN2B, CDKN2C, CEBPA, CES2, CHEK1, CHEK2, CIC, CREBBP, CRKL, CRLF2, CSF1R, CTCF, CTNNA1, CTNNB1, DAXX, DCK, DDR2, DHFR, DNMT1, DNMT3A, DNMT3B, DOT1L, EGFR, EMSY (C11orf30), EP300, EPHA2, EPHA3, EPHA5, EPHB1, ERBB2, ERBB3, ERBB4, ERBR2 (typo?), ERCC3, EREG, ERG, ESR1, ETV1, ETV4, ETV5, ETV6, EWSR1, EZH2, FAM123B (WTX), FAM46C, FANCA, FANCC, FANCD2, FANCE, FANCF, FANCG, FANCL, FBXW7, FGF10, FGF14, FGF19, FGF23, FGF3, FGF4, FGF6, FGFR1, FGFR2, FGFR3, FGFR4, FLT1, FLT3, FLT4, FOLR1, FOLR2, FOXL2, FSHB, FSHPRH1, FSHR, GART, GATA1, GATA2, GATA3, GID4 (C17orf39), GNA11, GNA13, GNAQ, GNAS, GNRH1, GNRHR1, GPR124, GRIN2A, GSK3B, GSTP1, HDAC1, HGF, HIG1, HNF1A, HRAS, HSPCA (HSP90), IDH1, IDH2, IGF1R, IKBKE, IKZF1, IL13RA1, IL2, IL2RA (CD25), IL7R, INHBA, IRF4, IRS2, JAK1, JAK2, JAK3, JUN, KAT6A (MYST3), KDM5A, KDM5C, KDM6A, KDR (VEGFR2), KEAP1, KIT, KLHL6, KRAS, LCK, LRP1B, LTB, LTBR, MAP2K1, MAP2K2, MAP2K4, MAP3K1, MAPK, MCL1, MDM2, MDM4, MED12, MEF2B, MEN1, MET, MGMT, MITF, MLH1, MLL, MLL2, MPL, MRE11A, MS4A1 (CD20), MSH2, MSH6, MTAP, MTOR, MUTYH, MYC, MYCL1, MYCN, MYD88, NF1, NF2, NFE2L2, NFKB1, NFKB2, NFKBIA, NGF, NKX2-1, NOTCH1, NOTCH2, NPM1, NRAS, NTRK1, NTRK2, NTRK3, NUP93, ODC1, OGFR, PAK3, PALB2, PAX5, PBRM1, PDGFC, PDGFRA, PDGFRB, PDK1, PGP, PGR (PR), PIK3CA, PIK3CG, PIK3R1, PIK3R2, POLA, PPARG, PPARGC1, PPP2R1A, PRDM1, PRKAR1A, PRKDC, PTCH1, PTEN, PTPN11, RAD50, RAD51, RAF1, RARA, RB1, RET, RICTOR, RNF43, ROS1, RPTOR, RRM1, RRM2, RRM2B, RUNX1, RXR, RXRB, RXRG, SETD2, SF3B1, SMAD2, SMAD4, SMARCA4, SMARCB1, SMO, SOCS1, SOX10, SOX2, SPARC, SPEN, SPOP, SRC, SST, SSTR1, SSTR2, SSTR3, SSTR4, SSTR5, STAG2, STAT4, STK11, SUFU, TET2, TGFBR2, TK1, TLE3, TMPRSS2, TNF, TNFAIP3, TNFRSF14, TOP1, TOP2, TOP2A, TOP2B, TP53, TS, TSC1, TSC2, TSHR, TUBB3, TXN, TYMP, VDR, VEGF (VEGFA), VEGFC, VHL, WISP3, WT1, XDH, XPO1, YES1, ZAP70, ZNF217, ZNF703 |
| Cytohesions | cytohesin-1 (CYTH1), cytohesin-2 (CYTH2; ARNO), cytohesin-3 (CYTH3; Grp1; ARNO3), cytohesin-4 (CYTH4) |
| Cancer/Angio | Erb 2, Erb 3, Erb 4, UNC93a, B7H3, MUC1, MUC2, MUC16, MUC17, 5T4, RAGE, VEGF A, VEGFR2, FLT1, DLL4, Epcam |
| Tissue (Breast) | BIG H3, GCDFP-15, PR(B), GPR 30, CYFRA 21, BRCA 1, BRCA 2, ESR 1, ESR2 |
| Tissue (Prostate) | PSMA, PCSA, PSCA, PSA, TMPRSS2 |
| Inflammation/Immune | MFG-E8, IFNAR, CD40, CD80, MICB, HLA-DRb, IL-17-Ra |
| Common vesicle markers | HSPA8, CD63, Actb, GAPDH, CD9, CD81, ANXA2, HSP90AA1, ENO1, YWHAZ, PDCD6IP, CFL1, SDCBP, PKN2, MSN, MFGE8, EZR, YWHAG, PGK1, EEF1A1, PPIA, GLC1F, GK, ANXA6, ANXA1, ALDOA, ACTG1, TPI1, LAMP2, HSP90AB1, DPP4, YWHAB, TSG101, PFN1, LDHB, HSPA1B, HSPA1A, GSTP1, GNAI2, GDI2, CLTC, ANXA5, YWHAQ, TUBA1A, THBS1, PRDX1, LDHA, LAMP1, CLU, CD86 |

TABLE 4-continued

Illustrative Biomarkers

| Illustrative Class | Biomarkers |
|---|---|
| Common vesicle membrane markers | CD63, GAPDH, CD9, CD81, ANXA2, ENO1, SDCBP, MSN, MFGE8, EZR, GK, ANXA1, LAMP2, DPP4, TSG101, HSPA1A, GDI2, CLTC, LAMP1, CD86, ANPEP, TFRC, SLC3A2, RDX, RAP1B, RAB5C, RAB5B, MYH9, ICAM1, FN1, RAB11B, PIGR, LGALS3, ITGB1, EHD1, CLIC1, ATP1A1, ARF1, RAP1A, P4HB, MUC1, KRT10, HLA-A, FLOT1, CD59, C1orf58, BASP1, TACSTD1, STOM |
| Common vesicle markers | MHC class I, MHC class II, Integrins, Alpha 4 beta 1, Alpha M beta 2, Beta 2, ICAM1/CD54, P-selection, Dipeptidylpeptidase IV/CD26, Aminopeptidase n/CD13, CD151, CD53, CD37, CD82, CD81, CD9, CD63, Hsp70, Hsp84/90 Actin, Actin-binding proteins, Tubulin, Annexin I, Annexin II, Annexin IV, Annexin V, Annexin VI, RAB7/RAP1B/RADGDI, Gi2alpha/14-3-3, CBL/LCK, CD63, GAPDH, CD9, CD81, ANXA2, ENO1, SDCBP, MSN, MFGE8, EZR, GK, ANXA1, LAMP2, DPP4, TSG101, HSPA1A, GDI2, CLTC, LAMP1, Cd86, ANPEP, TFRC, SLC3A2, RDX, RAP1B, RAB5C, RAB5B, MYH9, ICAM1, FN1, RAB11B, PIGR, LGALS3, ITGB1, EHD1, CLIC1, ATP1A1, ARF1, RAP1A, P4HB, MUC1, KRT10, HLA-A, FLOT1, CD59, C1orf58, BASP1, TACSTD1, STOM |
| Vesicle markers | A33, a33 nl5, AFP, ALA, ALIX, ALP, AnnexinV, APC, ASCA, ASPH (246-260), ASPH (666-680), ASPH (A-10), ASPH (D01P), ASPH (D03), ASPH (G-20), ASPH (H-300), AURKA, AURKB, B7H3, B7H4, BCA-225, BCNP, BDNF, BRCA, CA125 (MUC16), CA-19-9, C-Bir, CD1.1, CD10, CD174 (Lewis y), CD24, CD44, CD46, CD59 (MEM-43), CD63, CD66e CEA, CD73, CD81, CD9, CDA, CDAC1 1a2, CEA, C-Erb2, C-erbB2, CRMP-2, CRP, CXCL12, CYFRA21-1, DLL4, DR3, EGFR, Epcam, EphA2, EphA2 (H-77), ER, ErbB4, EZH2, FASL, FRT, FRT c.f23, GDF15, GPCR, GPR30, Gro-alpha, HAP, HBD 1, HBD2, HER 3 (ErbB3), HSP, HSP70, hVEGFR2, iC3b, IL 6 Unc, IL-1B, IL6 Unc, IL6R, IL8, IL-8, INSIG-2, KLK2, L1CAM, LAMN, LDH, MACC-1, MAPK4, MART-1, MCP-1, M-CSF, MFG-E8, MIC1, MIF, MIS RII, MMG, MMP26, MMP7, MMP9, MS4A1, MUC1, MUC1 seq1, MUC1 seq11A, MUC17, MUC2, Ncam, NGAL, NPGP/NPFF2, OPG, OPN, p53, p53, PA2G4, PBP, PCSA, PDGFRB, PGP9.5, PIM1, PR (B), PRL, PSA, PSMA, PSME3, PTEN, R5-CD9 Tube 1, Reg IV, RUNX2, SCRN1, seprase, SERPINB3, SPARC, SPB, SPDEF, SRVN, STAT 3, STEAP1, TF (FL-295), TFF3, TGM2, TIMP-1, TIMP1, TIMP2, TMEM211, TMPRSS2, TNF-alpha, Trail-R2, Trail-R4, TrKB, TROP2, Tsg 101, TWEAK, UNC93A, VEGF A, YPSMA-1 |
| Vesicle markers | NSE, TRIM29, CD63, CD151, ASPH, LAMP2, TSPAN1, SNAIL, CD45, CKS1, NSE, FSHR, OPN, FTH1, PGP9, ANNEXIN 1, SPD, CD81, EPCAM, PTH1R, CEA, CYTO 7, CCL2, SPA, KRAS, TWIST1, AURKB, MMP9, P27, MMP1, HLA, HIF, CEACAM, CENPH, BTUB, INTG b4, EGFR, NACC1, CYTO 18, NAP2, CYTO 19, ANNEXIN V, TGM2, ERB2, BRCA1, B7H3, SFTPC, PNT, NCAM, MS4A1, P53, INGA3, MUC2, SPA, OPN, CD63, CD9, MUC1, UNCR3, PAN ADH, HCG, TIMP, PSMA, GPCR, RACK1, PSCA, VEGF, BMP2, CD81, CRP, PRO GRP, B7H3, MUC1, M2PK, CD9, PCSA, PSMA |
| Vesicle markers | TFF3, MS4A1, EphA2, GAL3, EGFR, N-gal, PCSA, CD63, MUC1, TGM2, CD81, DR3, MACC-1, TrKB, CD24, TIMP-1, A33, CD66 CEA, PRL, MMP9, MMP7, TMEM211, SCRN1, TROP2, TWEAK, CDACC1, UNC93A, APC, C-Erb, CD10, BDNF, FRT, GPR30, P53, SPR, OPN, MUC2, GRO-1, tsg 101, GDF15 |
| Vesicle markers | CD9, Erb2, Erb4, CD81, Erb3, MUC16, CD63, DLL4, HLA-Drpe, B7H3, IFNAR, 5T4, PCSA, MICB, PSMA, MFG-E8, Muc1, PSA, Muc2, Unc93a, VEGFR2, EpCAM, VEGF A, TMPRSS2, RAGE, PSCA, CD40, Muc17, IL-17-RA, CD80 |
| Benign Prostate Hyperplasia (BPH) | BCMA, CEACAM-1, HVEM, IL-1 R4, IL-10 Rb, Trappin-2, p53, hsa-miR-329, hsa-miR-30a, hsa-miR-335, hsa-miR-152, hsa-miR-151-5p, hsa-miR-200a, hsa-miR-145, hsa-miR-29a, hsa-miR-106b, hsa-miR-595, hsa-miR-142-5p, hsa-miR-99a, hsa-miR-20b, hsa-miR-373, hsa-miR-502-5p, hsa-miR-29b, hsa-miR-142-3p, hsa-miR-663, hsa-miR-423-5p, hsa-miR-15a, hsa-miR-888, hsa-miR-361-3p, hsa-miR-365, hsa-miR-10b, hsa-miR-199a-3p, hsa-miR-181a, hsa-miR-19a, hsa-miR-125b, hsa-miR-760, hsa-miR-7a, hsa-miR-671-5p, hsa-miR-7c, hsa-miR-1979, hsa-miR-103 |
| Metastatic Prostate Cancer | hsa-miR-100, hsa-miR-1236, hsa-miR-1296, hsa-miR-141, hsa-miR-146b-5p, hsa-miR-17*, hsa-miR-181a, hsa-miR-200b, hsa-miR-20a*, hsa-miR-23a*, hsa-miR-331-3p, hsa-miR-375, hsa-miR-452, hsa-miR-572, hsa-miR-574-3p, hsa-miR-577, hsa-miR-582-3p, hsa-miR-937, miR-10a, miR-134, miR-141, miR-200b, miR-30a, miR-32, miR-375, miR-495, miR-564, miR-570, miR-574-3p, miR-885-3p |
| Metastatic Prostate Cancer | hsa-miR-200b, hsa-miR-375, hsa-miR-141, hsa-miR-331-3p, hsa-miR-181a, hsa-miR-574-3p |
| Prostate Cancer | hsa-miR-574-3p, hsa-miR-141, hsa-miR-432, hsa-miR-326, hsa-miR-2110, hsa-miR-181a-2*, hsa-miR-107, hsa-miR-301a, hsa-miR-484, hsa-miR-625* |
| Metastatic Prostate Cancer | hsa-miR-582-3p, hsa-miR-20a*, hsa-miR-375, hsa-miR-200b, hsa-miR-379, hsa-miR-572, hsa-miR-513a-5p, hsa-miR-577, hsa-miR-23a*, hsa-miR-1236, hsa-miR-609, hsa-miR-17*, hsa-miR-130b, hsa-miR-619, hsa-miR-624*, hsa-miR-198 |
| Metastatic Prostate Cancer | FOX01A, SOX9, CLNS1A, PTGDS, XPO1, LETMD1, RAD23B, ABCC3, APC, CHES1, EDNRA, FRZB, HSPG2, TMPRSS2_ETV1 fusion |
| Prostate Cancer | hsa-let-7b, hsa-miR-107, hsa-miR-1205, hsa-miR-1270, hsa-miR-130b, hsa-miR-141, hsa-miR-143, hsa-miR-148b*, hsa-miR-150, hsa-miR-154*, hsa-miR-181a*, hsa-miR-181a-2*, hsa-miR-18a*, hsa-miR-19b-1*, hsa-miR-204, hsa-miR-2110, hsa-miR-215, hsa-miR-217, hsa-miR-219-2-3p, hsa-miR-23b*, hsa-miR-299-5p, hsa-miR-301a, hsa-miR-301a, hsa-miR-326, hsa-miR-331-3p, hsa-miR-365*, hsa-miR-373*, hsa-miR-424, hsa-miR-424*, hsa-miR-432, hsa-miR-450a, hsa-miR-451, hsa-miR-484, hsa-miR-497, hsa-miR-517*, hsa-miR-517a, hsa-miR-518f, hsa-miR-574-3p, hsa-miR-595, hsa-miR-617, hsa-miR-625*, hsa-miR-628-5p, hsa-miR-629, hsa-miR-634, hsa-miR-769-5p, hsa-miR-93, hsa-miR-96 |
| Prostate Cancer | CD9, PSMA, PCSA, CD63, CD81, B7H3, IL 6, OPG-13, IL6R, PA2G4, EZH2, RUNX2, SERPINB3, EpCam |

TABLE 4-continued

Illustrative Biomarkers

| Illustrative Class | Biomarkers |
|---|---|
| Prostate Cancer | A33, a33 n15, AFP, ALA, ALIX, ALP, AnnexinV, APC, ASCA, ASPH (246-260), ASPH (666-680), ASPH (A-10), ASPH (D01P), ASPH (D03), ASPH (G-20), ASPH (H-300), AURKA, AURKB, B7H3, B7H4, BCA-225, BCNP, BDNF, BRCA, CA125 (MUC16), CA-19-9, C-Bir, CD1.1, CD10, CD174 (Lewis y), CD24, CD44, CD46, CD59 (MEM-43), CD63, CD66e CEA, CD73, CD81, CD9, CDA, CDAC1 1a2, CEA, C-Erb2, C-erbB2, CRMP-2, CRP, CXCL12, CYFRA21-1, DLL4, DR3, EGFR, Epcam, EphA2, EphA2 (H-77), ER, ErbB4, EZH2, FASL, FRT, FRT c.f23, GDF15, GPCR, GPR30, Gro-alpha, HAP, HBD 1, HBD2, HER 3 (ErbB3), HSP, HSP70, hVEGFR2, iC3b, IL 6 Unc, IL-1B, IL6 Unc, IL6R, IL8, IL-8, INSIG-2, KLK2, L1CAM, LAMN, LDH, MACC-1, MAPK4, MART-1, MCP-1, M-CSF, MFG-E8, MIC1, MIF, MIS RII, MMG, MMP26, MMP7, MMP9, MS4A1, MUC1, MUC1 seq1, MUC1 seq11A, MUC17, MUC2, Ncam, NGAL, NPGP/NPFF2, OPG, OPN, p53, p53, PA2G4, PBP, PCSA, PDGFRB, PGP9.5, PIM1, PR (B), PRL, PSA, PSMA, PSME3, PTEN, R5-CD9 Tube 1, Reg IV, RUNX2, SCRN1, seprase, SERPINB3, SPARC, SPB, SPDEF, SRVN, STAT 3, STEAP1, TF (FL-295), TFF3, TGM2, TIMP-1, TIMP1, TIMP2, TMEM211, TMPRSS2, TNF-alpha, Trail-R2, Trail-R4, TrKB, TROP2, Tsg 101, TWEAK, UNC93A, VEGF A, YPSMA-1 |
| Prostate Cancer Vesicle Markers | 5T4, ACTG1, ADAM10, ADAM15, ALDOA, ANXA2, ANXA6, APOA1, ATP1A1, BASP1, C1orf58, C20orf114, C8B, CAPZA1, CAV1, CD151, CD2AP, CD59, CD9, CD9, CFL1, CFP, CHMP4B, CLTC, COTL1, CTNND1, CTSB, CTSZ, CYCS, DPP4, EEF1A1, EHD1, ENO1, F11R, F2, F5, FAM125A, FNBP1L, FOLH1, GAPDH, GLB1, GPX3, HIST1H1C, HIST1H2AB, HSP90AB1, HSPA1B, HSPA8, IGSF8, ITGB1, ITIH3, JUP, LDHA, LDHB, LUM, LYZ, MFGE8, MGAM, MMP9, MYH2, MYL6B, NME1, NME2, PABPC1, PABPC4, PACSIN2, PCBP2, PDCD6IP, PRDX2, PSA, PSMA, PSMA1, PSMA2, PSMA4, PSMA6, PSMA7, PSMB1, PSMB2, PSMB3, PSMB4, PSMB5, PSMB6, PSMB8, PTGFRN, RPS27A, SDCBP, SERINC5, SH3GL1, SLC3A2, SMPDL3B, SNX9, TACSTD1, TCN2, THBS1, TPI1, TSG101, TUBB, VDAC2, VPS37B, YWHAG, YWHAQ, YWHAZ |
| Prostate Cancer Vesicle Markers | FLNA, DCRN, HER 3 (ErbB3), VCAN, CD9, GAL3, CDADC1, GM-CSF, EGFR, RANK, CSA, PSMA, ChickenIgY, B7H3, PCSA, CD63, CD3, MUC1, TGM2, CD81, S100-A4, MFG-E8, Integrin, NK-2R(C-21), PSA, CD24, TIMP-1, IL6 Unc, PBP, PIM1, CA-19-9, Trail-R4, MMP9, PRL, EphA2, TWEAK, NY-ESO-1, Mammaglobin, UNC93A, A33, AURKB, CD41, XAGE-1, SPDEF, AMACR, seprase/FAP, NGAL, CXCL12, FRT, CD66e CEA, SIM2 (C-15), C-Bir, STEAP, PSIP1/LEDGF, MUC17, hVEGFR2, ERG, MUC2, ADAM10, ASPH (A-10), CA125, Gro-alpha, Tsg 101, SSX2, Trail-R4 |
| Prostate Cancer Vesicle Markers | NT5E (CD73), A33, ABL2, ADAM10, AFP, ALA, ALIX, ALPL, AMACR, Apo J/CLU, ASCA, ASPH (A-10), ASPH (D01P), AURKB, B7H3, B7H4, BCNP, BDNF, CA125 (MUC16), CA-19-9, C-Bir (Flagellin), CD10, CD151, CD24, CD3, CD41, CD44, CD46, CD59(MEM-43), CD63, CD66e CEA, CD81, CD9, CDA, CDADC1, C-erbB2, CRMP-2, CRP, CSA, CXCL12, CXCR3, CYFRA21-1, DCRN, DDX-1, DLL4, EGFR, EpCAM, EphA2, ERG, EZH2, FASL, FLNA, FRT, GAL3, GATA2, GM-CSF, Gro-alpha, HAP, HER3 (ErbB3), HSP70, HSPB1, hVEGFR2, iC3b, IL-1B, IL6 R, IL6 Unc, IL7 R alpha/CD127, IL8, INSIG-2, Integrin, KLK2, Label, LAMN, Mammaglobin, M-CSF, MFG-E8, MIF, MIS RII, MMP7, MMP9, MS4A1, MUC1, MUC17, MUC2, Ncam, NDUFB7, NGAL, NK-2R(C-21), NY-ESO-1, p53, PBP, PCSA, PDGFRB, PIM1, PRL, PSA, PSIP1/LEDGF, PSMA, RAGE, RANK, Reg IV, RUNX2, S100-A4, seprase/FAP, SERPINB3, SIM2 (C-15), SPARC, SPC, SPDEF, SPP1, SSX2, SSX4, STEAP, STEAP4, TFF3, TGM2, TIMP-1, TMEM211, Trail-R2, Trail-R4, TrKB (poly), Trop2, Tsg 101, TWEAK, UNC93A, VCAN, VEGF A, wnt-5a(C-16), XAGE, XAGE-1 |
| Prostate Vesicle Membrane | ADAM 9, ADAM10, AGR2, ALDOA, ALIX, ANXA1, ANXA2, ANXA4, ARF6, ATP1A3, B7H3, BCHE, BCL2L14 (Bcl G), BCNP1, BDKRB2, BDNFCAV1—Caveolin1, CCR2 (CC chemokine receptor 2, CD192), CCR5 (CC chemokine receptor 5), CCT2 (TCP1-beta), CD10, CD151, CD166/ALCAM, CD24, CD283/TLR3, CD41, CD46, CD49d (Integrin alpha 4, ITGA4), CD63, CD81, CD9, CD90/THY1, CDH1, CDH2, CDKN1A cyclin-dependent kinase inhibitor (p21), CGA gene (coding for the alpha subunit of glycoprotein hormones), CLDN3—Claudin3, COX2 (PTGS2), CSE1L (Cellular Apoptosis Susceptibility), CXCR3, Cytokeratin 18, Eag1 (KCNH1), EDIL3 (del-1), EDNRB—Endothelial Receptor Type B, EGFR, EpoR, EZH2 (enhancer of Zeste Homolog2), EZR, FABP5, Farnesyltransferase/geranylgeranyl diphosphate synthase 1 (GGPS1), Fatty acid synthase (FASN), FTL (light and heavy), GAL3, GDF15—Growth Differentiation Factor 15, GloI, GM-CSF, GSTP1, H3F3A, HGF (hepatocyte growth factor), hK2/Kif2a, HSP90AA1, HSPA1A/HSP70-1, HSPB1, IGFBP-2, IGFBP-3, IL1alpha, IL-6, IQGAP1, ITGAL (Integrin alpha L chain), Ki67, KLK1, KLK10, KLK11, KLK12, KLK13, KLK14, KLK15, KLK4, KLK5, KLK6, KLK7, KLK8, KLK9, Lamp-2, LDH-A, LGALS3BP, LGALS8, MMP 1, MMP 2, MMP 25, MMP 3, MMP10, MMP-14/MT1-MMP, MMP7, MTA1nAnS, Nav1.7, NKX3-1, Notch1, NRP1/CD304, PAP (ACPP), PGP, PhIP, PIP3/BPNT1, PKM2, PKP1 (plakophilin1), PKP3 (plakophilin3), Plasma chromogranin-A (CgA), PRDX2, Prostate secretory protein (PSP94)/β-Microseminoprotein (MSP)/IGBF, PSAP, PSMA, PSMA1, PTENPTPN13/PTPL1, RPL19, seprase/FAPSET, SLC3A2/CD98, SRVN, STEAP1, Syndecan/CD138, TGFB, TGM2, TIMP-1TLR4 (CD284), TLR9 (CD289), TMPRSS1/hepsin, TMPRSS2, TNFR1, TNFα, Transferrin receptor/CD71/TRFR, Trop2 (TACSTD2), TWEAK uPA (urokinase plasminoge activator) degrades extracellular matrix, uPAR (uPA receptor)/CD87, VEGFR1, VEGFR2 |
| Prostate Vesicle Markers | ADAM 34, ADAM 9, AGR2, ALDOA, ANXA1, ANXA 11, ANXA4, ANXA 7, ANXA2, ARF6, ATP1A1, ATP1A2, ATP1A3, BCHE, BCL2L14 (Bcl G), BDKRB2, CA215, CAV1—Caveolin1, CCR2 (CC chemokine receptor 2, CD192), CCR5 (CC chemokine receptor 5), CCT2 (TCP1-beta), CD166/ALCAM, CD49b (Integrin alpha 2, ITGA4), CD90/THY1, CDH1, CDH2, CDKN1A cyclin-dependent kinase inhibitor (p21), CGA gene (coding for the |

TABLE 4-continued

Illustrative Biomarkers

| Illustrative Class | Biomarkers |
|---|---|
| | alpha subunit of glycoprotein hormones), CHMP4B, CLDN3—Claudin3, CLSTN1 (Calsyntenin-1), COX2 (PTGS2), CSE1L (Cellular Apoptosis Susceptibility), Cytokeratin 18, Eag1 (KCNH1) (plasma membrane-K+-voltage gated channel), EDIL3 (del-1), EDNRB—Endothelial Receptor Type B, Endoglin/CD105, ENOX2—Ecto-NOX disulphide Thiol exchanger 2, EPCA-2 Early prostate cancer antigen2, EpoR, EZH2 (enhancer of Zeste Homolog2), EZR, FABP5, Farnesyltransferase/geranylgeranyl diphosphate synthase 1 (GGPS1), Fatty acid synthase (FASN, plasma membrane protein), FTL (light and heavy), GDF15—Growth Differentiation Factor 15, GloI, GSTP1, H3F3A, HGF (hepatocyte growth factor), hK2 (KLK2), HSP90AA1, HSPA1A/HSP70-1, IGFBP-2, IGFBP-3, IL1alpha, IL-6, IQGAP1, ITGAL (Integrin alpha L chain), Ki67, KLK1, KLK10, KLK11, KLK12, KLK13, KLK14, KLK15, KLK4, KLK5, KLK6, KLK7, KLK8, KLK9, Lamp-2, LDH-A, LGALS3BP, LGALS8, MFAP5, MMP 1, MMP 2, MMP 24, MMP 25, MMP 3, MMP10, MMP-14/MT1-MMP, MTA1, nAnS, Nav1.7, NCAM2—Neural cell Adhesion molecule 2, NGEP/D-TMPP/IPCA-5/ANO7, NKX3-1, Notch1, NRP1/CD304, PGP, PAP (ACPP), PCA3—Prostate cancer antigen 3, Pdia3/ERp57, PhIP, phosphatidylethanolamine (PE), PIP3, PKP1 (plakophilin1), PKP3 (plakophilin3), Plasma chromogranin-A (CgA), PRDX2, Prostate secretory protein (PSP94)/β-Microseminoprotein (MSP)/IGBF, PSAP, PSMA1, PTEN, PTGFRN, PTPN13/PTPL1, PKM2, RPL19, SCA-1/ATXN1, SERINC5/TPO1, SET, SLC3A2/CD98, STEAP1, STEAP-3, SRVN, Syndecan/CD138, TGFB, Tissue Polypeptide Specific antigen TPS, TLR4 (CD284), TLR9 (CD289), TMPRSS1/hepsin, TMPRSS2, TNFR1, TNFα, CD283/TLR3, Transferrin receptor/CD71/TRFR, uPA (urokinase plasminoge activator), uPAR (uPA receptor)/CD87, VEGFR1, VEGFR2 |
| Prostate Cancer Treatment | hsa-miR-1974, hsa-miR-27b, hsa-miR-103, hsa-miR-146a, hsa-miR-22, hsa-miR-382, hsa-miR-23a, hsa-miR-376c, hsa-miR-335, hsa-miR-142-5p, hsa-miR-221, hsa-miR-142-3p, hsa-miR-151-3p, hsa-miR-21, hsa-miR-16 |
| Prostate Cancer | let-7d, miR-148a, miR-195, miR-25, miR-26b, miR-329, miR-376c, miR-574-3p, miR-888, miR-9, miR1204, miR-16-2*, miR-497, miR-588, miR-614, miR-765, miR92b*, miR-938, let-7f-2*, miR-300, miR-523, miR-525-5p, miR-1182, miR-1244, miR-520d-3p, miR-379, let-7b, miR-125a-3p, miR-1296, miR-134, miR-149, miR-150, miR-187, miR-32, miR-324-3p, miR-324-5p, miR-342-3p, miR-378, miR-378*, miR-384, miR-451, miR-455-3p, miR-485-3p, miR-487a, miR-490-3p, miR-502-5p, miR-548a-5p, miR-550, miR-562, miR-593, miR-593*, miR-595, miR-602, miR-603, miR-654-5p, miR-877*, miR-886-5p, miR-125a-5p, miR-140-3p, miR-192, miR-196a, miR-2110, miR-212, miR-222, miR-224*, miR-30b*, miR-499-3p, miR-505* |
| Prostate (PCSA + cMVs) | miR-182, miR-663, miR-155, mirR-125a-5p, miR-548a-5p, miR-628-5p, miR-517*, miR-450a, miR-920, hsa-miR-619, miR-1913, miR-224*, miR-502-5p, miR-888, miR-376a, miR-542-5p, miR-30b*, miR-1179 |
| Prostate Cancer | miR-183-96-182 cluster (miRs-183, 96 and 182), metal ion transporter such as hZIP1, SLC39A1, SLC39A2, SLC39A3, SLC39A4, SLC39A5, SLC39A6, SLC39A7, SLC39A8, SLC39A9, SLC39A10, SLC39A11, SLC39A12, SLC39A13, SLC39A14 |
| Prostate Cancer | RAD23B, FBP1, TNFRSF1A, CCNG2, NOTCH3, ETV1, BID, SIM2, LETMD1, ANXA1, miR-519d,miR-647 |
| Prostate Cancer | RAD23B, FBP1, TNFRSF1A, NOTCH3, ETV1, BID, SIM2, ANXA1, BCL2 |
| Prostate Cancer | ANPEP, ABL1, PSCA, EFNA1, HSPB1, INMT, TRIP13 |
| Prostate Cancer | E2F3, c-met, pRB, EZH2, e-cad, CAXII, CAIX, HIF-1α, Jagged, PIM-1, hepsin, RECK, Clusterin, MMP9, MTSP-1, MMP24, MMP15, IGFBP-2, IGFBP-3, E2F4, caveolin, EF-1A, Kallikrein 2, Kallikrein 3, PSGR |
| Prostate Cancer | A2ML1, BAX, C10orf47, C1orf162, CSDA, EIFC3, ETFB, GABARAPL2, GUK1, GZMH, HIST1H3B, HLA-A, HSP90AA1, NRGN, PRDX5, PTMA, RABAC1, RABAGAP1L, RPL22, SAP18, SEPW1, SOX1 |
| Prostate Cancer | NY-ESO-1, SSX-2, SSX-4, XAGE-lb, AMACR, p90 autoantigen, LEDGF |
| Prostate Cancer | A33, ABL2, ADAM10, AFP, ALA, ALIX, ALPL, ApoJ/CLU, ASCA, ASPH(A-10), ASPH(D01P), AURKB, B7H3, B7H3, B7H4, BCNP, BDNF, CA125(MUC16), CA-19-9, C-Bir, CD10, CD151, CD24, CD41, CD44, CD46, CD59(MEM-43), CD63, CD63, CD66eCEA, CD81, CD81, CD9, CD9, CDA, CDADC1, CRMP-2, CRP, CXCL12, CXCR3, CYFRA21-1, DDX-1, DLL4, DLL4, EGFR, Epcam, EphA2, ErbB2, ERG, EZH2, FASL, FLNA, FRT, GAL3, GATA2, GM-CSF, Gro-alpha, HAP, HER3(ErbB3), HSP70, HSPB1, hVEGFR2, iC3b, IL-1B, IL6R, IL6Unc, IL7Ralpha/CD127, IL8, INSIG-2, Integrin, KLK2, LAMN, Mammoglobin, M-CSF, MFG-E8, MIF, MISRII, MMP7, MMP9, MUC1, Muc1, MUC17, MUC2, Ncam, NDUFB7, NGAL, NK-2R(C-21), NT5E (CD73), p53, PBP, PCSA, PCSA, PDGFRB, PIM1, PRL, PSA, PSA, PSMA, PSMA, RAGE, RANK, RegIV, RUNX2, S100-A4, seprase/FAP, SERPINB3, SIM2(C-15), SPARC, SPC, SPDEF, SPP1, STEAP, STEAP4, TFF3, TGM2, TIMP-1, TMEM211, Trail-R2, Trail-R4, TrKB(poly), Trop2, Tsg101, TWEAK, UNC93A, VEGFA, wnt-5a(C-16) |
| Prostate Vesicles | CD9, CD63, CD81, PCSA, MUC2, MFG-E8 |
| Prostate Cancer | miR-148a, miR-329, miR-9, miR-378*, miR-25, miR-614, miR-518c*, miR-378, miR-765, let-7f-2*, miR-574-3p, miR-497, miR-32, miR-379, miR-520g, miR-542-5p, miR-342-3p, miR-1206, miR-663, miR-222 |
| Prostate Cancer | hsa-miR-877*, hsa-miR-593, hsa-miR-595, hsa-miR-300, hsa-miR-324-5p, hsa-miR-548a-5p, hsa-miR-329, hsa-miR-550, hsa-miR-886-5p, hsa-miR-603, hsa-miR-490-3p, hsa-miR-938, hsa-miR-149, hsa-miR-150, hsa-miR-1296, hsa-miR-384, hsa-miR-487a, hsa-miRPlus-C1089, hsa-miR-485-3p, hsa-miR-525-5p |
| Prostate Cancer | hsa-miR-451, hsa-miR-223, hsa-miR-593*, hsa-miR-1974, hsa-miR-486-5p, hsa-miR-19b, hsa-miR-320b, hsa-miR-92a, hsa-miR-21, hsa-miR-675*, hsa-miR-16, hsa-miR-876-5p, hsa-miR-144, hsa-miR-126, hsa-miR-137, hsa-miR-1913, hsa-miR-29b-1*, hsa-miR-15a, hsa-miR-93, hsa-miR-1266 |

TABLE 4-continued

Illustrative Biomarkers

| Illustrative Class | Biomarkers |
|---|---|
| Inflammatory Disease | miR-588, miR-1258, miR-16-2*, miR-938, miR-526b, miR-92b*, let-7d, miR-378*, miR-124, miR-376c, miR-26b, miR-1204, miR-574-3p, miR-195, miR-499-3p, miR-2110, miR-888 |
| Prostate Cancer | A33, ADAM10, AMACR, ASPH (A-10), AURKB, B7H3, CA125, CA-19-9, C-Bir, CD24, CD3, CD41, CD63, CD66e CEA, CD81, CD9, CDADC1, CSA, CXCL12, DCRN, EGFR, EphA2, ERG, FLNA, FRT, GAL3, GM-CSF, Gro-alpha, HER 3 (ErbB3), hVEGFR2, IL6 Unc, Integrin, Mammaglobin, MFG-E8, MMP9, MUC1, MUC17, MUC2, NGAL, NK-2R(C-21), NY-ESO-1, PBP, PCSA, PIM1, PRL, PSA, PSIP1/LEDGF, PSMA, RANK, S100-A4, seprase/FAP, SIM2 (C-15), SPDEF, SSX2, STEAP, TGM2, TIMP-1, Trail-R4, Tsg 101, TWEAK, UNC93A, VCAN, XAGE-1 |
| Prostate Cancer | A33, ADAM10, ALIX, AMACR, ASCA, ASPH (A-10), AURKB, B7H3, BCNP, CA125, CA-19-9, C-Bir (Flagellin), CD24, CD3, CD41, CD63, CD66e CEA, CD81, CD9, CDADC1, CRP, CSA, CXCL12, CYFRA21-1, DCRN, EGFR, EpCAM, EphA2, ERG, FLNA, GAL3, GATA2, GM-CSF, Gro alpha, HER3 (ErbB3), HSP70, hVEGFR2, iC3b, IL-1B, IL6 Unc, IL8, Integrin, KLK2, Mammaglobin, MFG-E8, MMP7, MMP9, MS4A1, MUC1, MUC17, MUC2, NGAL, NK-2R(C-21), NY-ESO-1, p53, PBP, PCSA, PIM1, PRL, PSA, PSMA, RANK, RUNX2, S100-A4, seprase/FAP, SERPINB3, SIM2 (C-15), SPC, SPDEF, SSX2, SSX4, STEAP, TGM2, TIMP-1, TRAIL R2, Trail-R4, Tsg 101, TWEAK, VCAN, VEGF A, XAGE |
| Prostate Vesicles | EpCam, CD81, PCSA, MUC2, MFG-E8 |
| Prostate Vesicles | CD9, CD63, CD81, MMP7, EpCAM |
| Prostate Cancer | let-7d, miR-148a, miR-195, miR-25, miR-26b, miR-329, miR-376c, miR-574-3p, miR-888, miR-9, miR1204, miR-16-2*, miR-497, miR-588, miR-614, miR-765, miR92b*, miR-938, let-7f-2*, miR-300, miR-523, miR-525-5p, miR-1182, miR-1244, miR-520d-3p, miR-379, let-7b, miR-125a-3p, miR-1296, miR-134, miR-149, miR-150, miR-187, miR-32, miR-324-3p, miR-324-5p, miR-342-3p, miR-378, miR-378*, miR-384, miR-451, miR-455-3p, miR-485-3p, miR-487a, miR-490-3p, miR-502-5p, miR-548a-5p, miR-550, miR-562, miR-593, miR-593*, miR-595, miR-602, miR-603, miR-654-5p, miR-877*, miR-886-5p, miR-125a-5p, miR-140-3p, miR-192, miR-196a, miR-2110, miR-212, miR-222, miR-224*, miR-30b*, miR-499-3p, miR-505* |
| Prostate Cancer | STAT3, EZH2, p53, MACC1, SPDEF, RUNX2, YB-1, AURKA, AURKB |
| Prostate Cancer (Ensembl ENSG identifiers) | E.001036, E.001497, E.001561, E.002330, E.003402, E.003756, E.004838, E.005471, E.005882, E.005893, E.006210, E.006453, E.006625, E.006695, E.006756, E.007264, E.007952, E.008118, E.008196, E.009694, E.009830, E.010244, E.010256, E.010278, E.010539, E.010810, E.011052, E.011114, E.011143, E.011304, E.011451, E.012061, E.012779, E.014216, E.014257, E.015133, E.015171, E.015479, E.015676, E.016402, E.018189, E.018699, E.020922, E.022976, E.023909, E.026508, E.026559, E.029363, E.029725, E.030582, E.033030, E.035141, E.036257, E.036448, E.038002, E.039068, E.039560, E.041353, E.044115, E.047410, E.047597, E.048544, E.048828, E.049239, E.049246, E.049883, E.051596, E.051620, E.052795, E.053108, E.054118, E.054938, E.056097, E.057252, E.057608, E.058729, E.059122, E.059378, E.059691, E.060339, E.060688, E.061794, E.061918, E.062485, E.063241, E.063244, E.064201, E.064489, E.064655, E.064886, E.065054, E.065057, E.065308, E.065427, E.065457, E.065485, E.065526, E.065548, E.065978, E.066455, E.066557, E.067248, E.067369, E.067704, E.068724, E.068885, E.069535, E.069712, E.069849, E.069869, E.069956, E.070501, E.070785, E.070814, E.071246, E.071626, E.071859, E.072042, E.072071, E.072110, E.072506, E.073050, E.073350, E.073584, E.073756, E.074047, E.074071, E.074964, E.075131, E.075239, E.075624, E.075651, E.075711, E.075856, E.075886, E.076043, E.076248, E.076554, E.076864, E.077097, E.077147, E.077312, E.077514, E.077522, E.078269, E.078295, E.078808, E.078902, E.079246, E.079313, E.079785, E.080572, E.080823, E.081087, E.081138, E.081181, E.081721, E.081842, E.082212, E.082258, E.082556, E.083093, E.083720, E.084234, E.084463, E.085224, E.085733, E.086062, E.086205, E.086717, E.087087, E.087301, E.088888, E.088899, E.088930, E.088992, E.089048, E.089127, E.089154, E.089177, E.089248, E.089280, E.089902, E.090013, E.090060, E.090565, E.090612, E.090615, E.090674, E.090861, E.090889, E.091140, E.091483, E.091542, E.091732, E.092020, E.092199, E.092421, E.092621, E.092820, E.092871, E.092978, E.093010, E.094755, E.095139, E.095380, E.095485, E.095627, E.096060, E.096384, E.099331, E.099715, E.099783, E.099785, E.099800, E.099821, E.099899, E.099917, E.099956, E.100023, E.100056, E.100065, E.100084, E.100142, E.100191, E.100216, E.100242, E.100271, E.100284, E.100299, E.100311, E.100348, E.100359, E.100393, E.100399, E.100401, E.100412, E.100442, E.100575, E.100577, E.100583, E.100601, E.100603, E.100612, E.100632, E.100714, E.100739, E.100796, E.100802, E.100815, E.100823, E.100836, E.100883, E.101057, E.101126, E.101152, E.101222, E.101246, E.101265, E.101365, E.101439, E.101557, E.101639, E.101654, E.101811, E.101812, E.101901, E.102030, E.102054, E.102103, E.102158, E.102174, E.102241, E.102290, E.102316, E.102362, E.102384, E.102710, E.102780, E.102904, E.103035, E.103067, E.103175, E.103194, E.103449, E.103479, E.103591, E.103599, E.103855, E.103978, E.104064, E.104067, E.104131, E.104164, E.104177, E.104228, E.104331, E.104365, E.104419, E.104442, E.104611, E.104626, E.104723, E.104760, E.104805, E.104812, E.104823, E.104824, E.105127, E.105220, E.105221, E.105281, E.105379, E.105402, E.105404, E.105409, E.105419, E.105428, E.105486, E.105514, E.105518, E.105618, E.105705, E.105723, E.105939, E.105948, E.106049, E.106078, E.106128, E.106153, E.106346, E.106392, E.106554, E.106565, E.106603, E.106633, E.107104, E.107164, E.107404, E.107485, E.107551, E.107581, E.107623, E.107798, E.107816, E.107833, E.107890, E.107897, E.107968, E.108296, E.108312, E.108375, E.108387, E.108405, E.108417, E.108465, E.108561, E.108582, E.108639, E.108641, |

TABLE 4-continued

Illustrative Biomarkers

| Illustrative Class | Biomarkers |
|---|---|
| | E.108848, E.108883, E.108953, E.109062, E.109184, E.109572, E.109625, E.109758, E.109790, E.109814, E.109846, E.109956, E.110063, E.110066, E.110104, E.110107, E.110321, E.110328, E.110921, E.110955, E.111057, E.111218, E.111261, E.111335, E.111540, E.111605, E.111647, E.111785, E.111790, E.111801, E.111907, E.112039, E.112081, E.112096, E.112110, E.112144, E.112232, E.112234, E.112473, E.112578, E.112584, E.112715, E.112941, E.113013, E.113163, E.113282, E.113368, E.113441, E.113448, E.113522, E.113580, E.113645, E.113719, E.113739, E.113790, E.114054, E.114127, E.114302, E.114331, E.114388, E.114491, E.114861, E.114867, E.115053, E.115221, E.115234, E.115239, E.115241, E.115257, E.115339, E.115540, E.115541, E.115561, E.115604, E.115648, E.115738, E.115758, E.116044, E.116096, E.116127, E.116254, E.116288, E.116455, E.116478, E.116604, E.116649, E.116726, E.116754, E.116833, E.117298, E.117308, E.117335, E.117362, E.117411, E.117425, E.117448, E.117480, E.117592, E.117593, E.117614, E.117676, E.117713, E.117748, E.117751, E.117877, E.118181, E.118197, E.118260, E.118292, E.118513, E.118523, E.118640, E.118898, E.119121, E.119138, E.119318, E.119321, E.119335, E.119383, E.119421, E.119636, E.119681, E.119711, E.119820, E.119888, E.119906, E.120159, E.120328, E.120337, E.120370, E.120656, E.120733, E.120837, E.120868, E.120915, E.120948, E.121022, E.121057, E.121068, E.121104, E.121390, E.121671, E.121690, E.121749, E.121774, E.121879, E.121892, E.121903, E.121940, E.121957, E.122025, E.122033, E.122126, E.122507, E.122566, E.122705, E.122733, E.122870, E.122884, E.122952, E.123066, E.123080, E.123143, E.123154, E.123178, E.123416, E.123427, E.123595, E.123901, E.123908, E.123983, E.123992, E.124143, E.124164, E.124181, E.124193, E.124216, E.124232, E.124529, E.124562, E.124570, E.124693, E.124749, E.124767, E.124788, E.124795, E.124831, E.124942, E.125246, E.125257, E.125304, E.125352, E.125375, E.125445, E.125492, E.125676, E.125753, E.125798, E.125844, E.125868, E.125901, E.125944, E.125995, E.126062, E.126267, E.126653, E.126773, E.126777, E.126814, E.126858, E.126883, E.126934, E.126945, E.126952, E.127022, E.127328, E.127329, E.127399, E.127415, E.127554, E.127616, E.127720, E.127824, E.127884, E.127914, E.127946, E.127948, E.128050, E.128311, E.128342, E.128609, E.128626, E.128683, E.128708, E.128881, E.129315, E.129351, E.129355, E.129514, E.129636, E.129657, E.129757, E.129810, E.129990, E.130175, E.130177, E.130193, E.130255, E.130299, E.130305, E.130338, E.130340, E.130402, E.130413, E.130612, E.130713, E.130764, E.130770, E.130810, E.130826, E.130935, E.131351, E.131467, E.131473, E.131771, E.131773, E.132002, E.132275, E.132323, E.132382, E.132475, E.132481, E.132589, E.132646, E.132716, E.132881, E.133313, E.133315, E.133687, E.133835, E.133863, E.133874, E.133961, E.134077, E.134138, E.134207, E.134248, E.134308, E.134444, E.134452, E.134548, E.134684, E.134759, E.134809, E.134851, E.134955, E.135052, E.135297, E.135298, E.135387, E.135390, E.135476, E.135486, E.135525, E.135597, E.135679, E.135740, E.135829, E.135842, E.135870, E.135900, E.135914, E.135926, E.135940, E.135999, E.136044, E.136068, E.136152, E.136169, E.136280, E.136371, E.136383, E.136450, E.136521, E.136527, E.136574, E.136710, E.136750, E.136807, E.136874, E.136875, E.136930, E.136933, E.136935, E.137055, E.137124, E.137312, E.137409, E.137497, E.137513, E.137558, E.137601, E.137727, E.137776, E.137806, E.137814, E.137815, E.137948, E.137955, E.138028, E.138031, E.138041, E.138050, E.138061, E.138069, E.138073, E.138095, E.138160, E.138294, E.138347, E.138363, E.138385, E.138587, E.138594, E.138621, E.138674, E.138756, E.138757, E.138760, E.138772, E.138796, E.139211, E.139405, E.139428, E.139517, E.139613, E.139626, E.139684, E.139697, E.139874, E.140263, E.140265, E.140326, E.140350, E.140374, E.140382, E.140451, E.140481, E.140497, E.140632, E.140678, E.140694, E.140743, E.140932, E.141002, E.141012, E.141258, E.141378, E.141425, E.141429, E.141522, E.141543, E.141639, E.141744, E.141873, E.141994, E.142025, E.142208, E.142515, E.142606, E.142698, E.142765, E.142864, E.142875, E.143013, E.143294, E.143321, E.143353, E.143374, E.143375, E.143390, E.143578, E.143614, E.143621, E.143633, E.143771, E.143797, E.143816, E.143889, E.143924, E.143933, E.143947, E.144136, E.144224, E.144306, E.144381, E.144410, E.144485, E.144566, E.144671, E.144741, E.144935, E.145020, E.145632, E.145741, E.145833, E.145888, E.145907, E.145908, E.145919, E.145990, E.146067, E.146070, E.146281, E.146433, E.146457, E.146535, E.146701, E.146856, E.146966, E.147044, E.147127, E.147130, E.147133, E.147140, E.147231, E.147257, E.147403, E.147475, E.147548, E.147697, E.147724, E.148158, E.148396, E.148488, E.148672, E.148737, E.148835, E.149182, E.149218, E.149311, E.149480, E.149548, E.149646, E.150051, E.150593, E.150961, E.150991, E.151092, E.151093, E.151247, E.151304, E.151491, E.151690, E.151715, E.151726, E.151779, E.151806, E.152086, E.152207, E.152234, E.152291, E.152359, E.152377, E.152409, E.152422, E.152582, E.152763, E.152818, E.152942, E.153113, E.153140, E.153391, E.153904, E.153936, E.154099, E.154127, E.154380, E.154639, E.154723, E.154781, E.154832, E.154864, E.154889, E.154957, E.155368, E.155380, E.155508, E.155660, E.155714, E.155959, E.155980, E.156006, E.156194, E.156282, E.156304, E.156467, E.156515, E.156603, E.156650, E.156735, E.156976, E.157064, E.157103, E.157502, E.157510, E.157538, E.157551, E.157637, E.157764, E.157827, E.157992, E.158042, E.158290, E.158321, E.158485, E.158545, E.158604, E.158669, E.158715, E.158747, E.158813, E.158863, E.158901, E.158941, E.158987, E.159147, E.159184, E.159348, E.159363, E.159387, E.159423, E.159658, E.159692, E.159761, E.159921, E.160049, E.160226, E.160285, E.160294, E.160633, E.160685, E.160691, E.160789, E.160862, E.160867, E.160948, E.160972, E.161202, E.161267, E.161649, E.161692, E.161714, E.161813, E.161939, E.162069, E.162298, E.162385, E.162437, E.162490, E.162613, E.162641, E.162694, E.162910, E.162975, E.163041, E.163064, E.163110, |

TABLE 4-continued

Illustrative Biomarkers

| Illustrative Class | Biomarkers |
|---|---|
| | E.163257, E.163468, E.163492, E.163530, E.163576, E.163629, E.163644, E.163749, E.163755, E.163781, E.163825, E.163913, E.163923, E.163930, E.163932, E.164045, E.164051, E.164053, E.164163, E.164244, E.164270, E.164300, E.164309, E.164442, E.164488, E.164520, E.164597, E.164749, E.164754, E.164828, E.164916, E.164919, E.164924, E.165084, E.165119, E.165138, E.165215, E.165259, E.165264, E.165280, E.165359, E.165410, E.165496, E.165637, E.165646, E.165661, E.165688, E.165695, E.165699, E.165792, E.165807, E.165813, E.165898, E.165923, E.165934, E.166263, E.166266, E.166329, E.166337, E.166341, E.166484, E.166526, E.166596, E.166598, E.166710, E.166747, E.166833, E.166860, E.166946, E.166971, E.167004, E.167085, E.167110, E.167113, E.167258, E.167513, E.167552, E.167553, E.167604, E.167635, E.167642, E.167658, E.167699, E.167744, E.167751, E.167766, E.167772, E.167799, E.167815, E.167969, E.167978, E.167987, E.167996, E.168014, E.168036, E.168066, E.168071, E.168148, E.168298, E.168393, E.168575, E.168653, E.168746, E.168763, E.168769, E.168803, E.168916, E.169087, E.169093, E.169122, E.169189, E.169213, E.169242, E.169410, E.169418, E.169562, E.169592, E.169612, E.169710, E.169763, E.169789, E.169807, E.169826, E.169957, E.170017, E.170027, E.170037, E.170088, E.170144, E.170275, E.170310, E.170315, E.170348, E.170374, E.170381, E.170396, E.170421, E.170430, E.170445, E.170549, E.170632, E.170703, E.170743, E.170837, E.170854, E.170906, E.170927, E.170954, E.170959, E.171121, E.171155, E.171180, E.171202, E.171262, E.171302, E.171345, E.171428, E.171488, E.171490, E.171492, E.171540, E.171643, E.171680, E.171723, E.171793, E.171861, E.171953, E.172115, E.172283, E.172345, E.172346, E.172466, E.172590, E.172594, E.172653, E.172717, E.172725, E.172733, E.172831, E.172867, E.172893, E.172939, E.173039, E.173230, E.173366, E.173473, E.173540, E.173585, E.173599, E.173714, E.173726, E.173805, E.173809, E.173826, E.173889, E.173898, E.173905, E.174021, E.174100, E.174332, E.174842, E.174996, E.175063, E.175110, E.175166, E.175175, E.175182, E.175198, E.175203, E.175216, E.175220, E.175334, E.175416, E.175602, E.175866, E.175946, E.176102, E.176105, E.176155, E.176171, E.176371, E.176515, E.176900, E.176971, E.176978, E.176994, E.177156, E.177239, E.177354, E.177409, E.177425, E.177459, E.177542, E.177548, E.177565, E.177595, E.177628, E.177674, E.177679, E.177694, E.177697, E.177731, E.177752, E.177951, E.178026, E.178078, E.178104, E.178163, E.178175, E.178187, E.178234, E.178381, E.178473, E.178741, E.178828, E.178950, E.179091, E.179115, E.179119, E.179348, E.179388, E.179776, E.179796, E.179869, E.179912, E.179981, E.180035, E.180198, E.180287, E.180318, E.180667, E.180869, E.180979, E.180998, E.181072, E.181163, E.181222, E.181234, E.181513, E.181523, E.181610, E.181773, E.181873, E.181885, E.181924, E.182013, E.182054, E.182217, E.182271, E.182318, E.182319, E.182512, E.182732, E.182795, E.182872, E.182890, E.182944, E.183048, E.183092, E.183098, E.183128, E.183207, E.183292, E.183431, E.183520, E.183684, E.183723, E.183785, E.183831, E.183856, E.184007, E.184047, E.184113, E.184156, E.184254, E.184363, E.184378, E.184470, E.184481, E.184508, E.184634, E.184661, E.184697, E.184708, E.184735, E.184840, E.184916, E.185043, E.185049, E.185122, E.185219, E.185359, E.185499, E.185554, E.185591, E.185619, E.185736, E.185860, E.185896, E.185945, E.185972, E.186198, E.186205, E.186376, E.186472, E.186575, E.186591, E.186660, E.186814, E.186834, E.186868, E.186889, E.187097, E.187323, E.187492, E.187634, E.187764, E.187792, E.187823, E.187837, E.187840, E.188021, E.188171, E.188186, E.188739, E.188771, E.188846, E.189060, E.189091, E.189143, E.189144, E.189221, E.189283, E.196236, E.196419, E.196436, E.196497, E.196504, E.196526, E.196591, E.196700, E.196743, E.196796, E.196812, E.196872, E.196975, E.196993, E.197081, E.197157, E.197217, E.197223, E.197299, E.197323, E.197353, E.197451, E.197479, E.197746, E.197779, E.197813, E.197837, E.197857, E.197872, E.197969, E.197976, E.198001, E.198033, E.198040, E.198087, E.198131, E.198156, E.198168, E.198205, E.198216, E.198231, E.198265, E.198366, E.198431, E.198455, E.198563, E.198586, E.198589, E.198712, E.198721, E.198732, E.198783, E.198793, E.198804, E.198807, E.198824, E.198841, E.198951, E.203301, E.203795, E.203813, E.203837, E.203879, E.203908, E.204231, E.204316, E.204389, E.204406, E.204560, E.204574 |
| Prostate Markers (Ensembl ENSG identifiers) | E.005893 (LAMP2), E.006756 (ARSD), E.010539 (ZNF200), E.014257 (ACPP), E.015133 (CCDC88C), E.018699 (TTC27), E.044115 (CTNNA1), E.048828 (FAM120A), E.051620 (HEBP2), E.056097 (ZFR), E.060339 (CCAR1), E.063241 (ISOC2), E.064489 (MEF2BNB-MEF2B), E.064886 (CHI3L2), E.066455 (GOLGA5), E.069535 (MAOB), E.072042 (RDH11), E.072071 (LPHN1), E.074047 (GLI2), E.076248 (UNG), E.076554 (TPD52), E.077147 (TM9SF3), E.077312 (SNRPA), E.081842 (PCDHA6), E.086717 (PPEF1), E.088888 (MAVS), E.088930 (XRN2), E.089902 (RCOR1), E.090612 (ZNF268), E.092199 (HNRNPC), E.095380 (NANS), E.099783 (HNRNPM), E.100191 (SLC5A4), E.100216 (TOMM22), E.100242 (SUN2), E.100284 (TOM1), E.100401 (RANGAP1), E.100412 (ACO2), E.100836 (PABPN1), E.102054 (RBBP7), E.102103 (PQBP1), E.103599 (IQCH), E.103978 (TMEM87A), E.104177 (MYEF2), E.104228 (TRIM35), E.105428 (ZNRF4), E.105518 (TMEM205), E.106603 (C7orf44; COA1), E.108405 (P2RX1), E.111057 (KRT18), E.111218 (PRMT8), E.112081 (SRSF3), E.112144 (ICK), E.113013 (HSPA9), E.113368 (LMNB1), E.115221 (ITGB6), E.116096 (SPR), E.116754 (SRSF11), E.118197 (DDX59), E.118898 (PPL), E.119121 (TRPM6), E.119711 (ALDH6A1), E.120656 (MEF2BNB-MEF2B), E.121671 (CRY2), E.121774 (KHDRBS1), E.122126 (OCRL), E.122566 (HNRNPA2B1), E.123901 (GPR83), E.124562 (SNRPC), E.124788 (ATXN1), E.124795 (DEK), E.125246 (CLYBL), E.126883 (NUP214), E.127616 (SMARCA4), E.127884 (ECHS1), E.128050 (PAICS), E.129351 (ILF3), E.129757 (CDKN1C), E.130338 (TULP4), E.130612 (CYP2G1P), E.131351 (HAUS8), E.131467 (PSME3), E.133315 (MACROD1), E.134452 |

TABLE 4-continued

Illustrative Biomarkers

| Illustrative Class | Biomarkers |
|---|---|
| | (FBXO18), E.134851 (TMEM165), E.135940 (COX5B), E.136169 (SETDB2), E.136807 (CDK9), E.137727 (ARHGAP20), E.138031 (ADCY3), E.138050 (THUMPD2), E.138069 (RAB1A), E.138594 (TMOD3), E.138760 (SCARB2), E.138796 (HADH), E.139613 (SMARCC2), E.139684 (ESD), E.140263 (SORD), E.140350 (ANP32A), E.140632 (GLYR1), E.142765 (SYTL1), E.143621 (ILF2), E.143933 (CALM2), E.144410 (CPO), E.147127 (RAB41), E.151304 (SRFBP1), E.151806 (GUF1), E.152207 (CYSLTR2), E.152234 (ATP5A1), E.152291 (TGOLN2), E.154723 (ATP5J), E.156467 (UQCRB), E.159387 (IRX6), E.159761 (C16orf86), E.161813 (LARP4), E.162613 (FUBP1), E.162694 (EXTL2), E.165264 (NDUFB6), E.167113 (COQ4), E.167513 (CDT1), E.167772 (ANGPTL4), E.167978 (SRRM2), E.168916 (ZNF608), E.169763 (PRYP3), E.169789 (PRY), E.169807 (PRY2), E.170017 (ALCAM), E.170144 (HNRNPA3), E.170310 (STX8), E.170954 (ZNF415), E.170959 (DCDC5), E.171302 (CANT1), E.171643 (S100Z), E.172283 (PRYP4), E.172590 (MRPL52), E.172867 (KRT2), E.173366 (TLR9), E.173599 (PC), E.177595 (PIDD), E.178473 (UCN3), E.179981 (TSHZ1), E.181163 (NPM1), E.182319 (Tyrosine-protein kinase SgK223), E.182795 (C1orf116), E.182944 (EWSR1), E.183092 (BEGAIN), E.183098 (GPC6), E.184254 (ALDH1A3), E.185619 (PCGF3), E.186889 (TMEM17), E.187837 (HIST1H1C), E.188771 (C11orf34), E.189060 (H1F0), E.196419 (XRCC6), E.196436 (NPIPL2), E.196504 (PRPF40A), E.196796, E.196993, E.197451 (HNRNPAB), E.197746 (PSAP), E.198131 (ZNF544), E.198156, E.198732 (SMOC1), E.198793 (MTOR), E.039068 (CDH1), E.173230 (GOLGB1), E.124193 (SRSF6), E.140497 (SCAMP2), E.168393 (DTYMK), E.184708 (EIF4ENIF1), E.124164 (VAPB), E.125753 (VASP), E.118260 (CREB1), E.135052 (GOLM1), E.010244 (ZNF207), E.010278 (CD9), E.047597 (XK), E.049246 (PER3), E.069849 (ATP1B3), E.072506 (HSD17B10), E.081138 (CDH7), E.099785 (MARCH2), E.104331 (IMPAD1), E.104812 (GYS1), E.120868 (APAF1), E.123908 (EIF2C2), E.125492 (BARHL1), E.127328 (RAB3IP), E.127329 (PTPRB), E.129514 (FOXA1), E.129657 (SEC14L1), E.129990 (SYT5), E.132881 (RSG1), E.136521 (NDUFB5), E.138347 (MYPN), E.141429 (GALNT1), E.144566 (RAB5A), E.151715 (TMEM45B), E.152582 (SPEF2), E.154957 (ZNF18), E.162385 (MAGOH), E.165410 (CFL2), E.168298 (HIST1H1E), E.169418 (NPR1), E.178187 (ZNF454), E.178741 (COX5A), E.179115 (FARSA), E.182732 (RGS6), E.183431 (SF3A3), E.185049 (WHSC2), E.196236 (XPNPEP3), E.197217 (ENTPD4), E.197813, E.203301, E.116833 (NR5A2), E.121057 (AKAP1), E.005471 (ABCB4), E.071859 (FAM50A), E.084234 (APLP2), E.101222 (SPEF1), E.103175 (WFDC1), E.103449 (SALL1), E.104805 (NUCB1), E.105514 (RAB3D), E.107816 (LZTS2), E.108375 (RNF43), E.109790 (KLHL5), E.112039 (FANCE), E.112715 (VEGFA), E.121690 (DEPDC7), E.125352 (RNF113A), E.134548 (C12orf39), E.136152 (COG3), E.143816 (WNT9A), E.147130 (ZMYM3), E.148396 (SEC16A), E.151092 (NGLY1), E.151779 (NBAS), E.155508 (CNOT8), E.163755 (HPS3), E.166526 (ZNF3), E.172733 (PURG), E.176371 (ZSCAN2), E.177674 (AGTRAP), E.181773 (GPR3), E.183048 (SLC25A10; MRPL12 SLC25A10), E.186376 (ZNF75D), E.187323 (DCC), E.198712 (MT-CO2), E.203908 (C6orf221; KHDC3L), E.001497 (LAS1L), E.009694 (ODZ1), E.080572 (CXorf41; PIH1D3), E.083093 (PALB2), E.089048 (ESF1), E.100065 (CARD10), E.100739 (BDKRB1), E.102904 (TSNAXIP1), E.104824 (HNRNPL), E.107404 (DVL1), E.110066 (SUV420H1), E.120328 (PCDHB12), E.121903 (ZSCAN20), E.122025 (FLT3), E.136930 (PSMB7), E.142025 (DMRTC2), E.144136 (SLC20A1), E.146535 (GNA12), E.147140 (NONO), E.153391 (INO80C), E.164919 (COX6C), E.171540 (OTP), E.177951 (BET1L), E.179796 (LRRC3B), E.197479 (PCDHB11), E.198804 (MT-CO1), E.086205 (FOLH1), E.100632 (ERH), E.100796 (SMEK1), E.104760 (FGL1), E.114302 (PRKAR2A), E.130299 (GTPBP3), E.133961 (NUMB), E.144485 (HES6), E.167085 (PHB), E.167635 (ZNF146), E.177239 (MAN1B1), E.184481 (FOXO4), E.188171 (ZNF626), E.189221 (MAOA), E.157637 (SLC38A10), E.100883 (SRP54), E.105618 (PRPF31), E.119421 (NDUFA8), E.170837 (GPR27), E.168148 (HIST3H3), E.135525 (MAP7), E.174996 (KLC2), E.018189 (RUFY3), E.183520 (UTP11L), E.173905 (GOLIM4), E.165280 (VCP), E.022976 (ZNF839), E.059691 (PET112), E.063244 (U2AF2), E.075651 (PLD1), E.089177 (KIF16B), E.089280 (FUS), E.094755 (GABRP), E.096060 (FKBP5), E.100023 (PPIL2), E.100359 (SGSM3), E.100612 (DHRS7), E.104131 (EIF3J), E.104419 (NDRG1), E.105409 (ATP1A3), E.107623 (GDF10), E.111335 (OAS2), E.113522 (RAD50), E.115053 (NCL), E.120837 (NFYB), E.122733 (KIAA1045), E.123178 (SPRYD7), E.124181 (PLCG1), E.126858 (RHOT1), E.128609 (NDUFA5), E.128683 (GAD1), E.130255 (RPL36), E.133874 (RNF122), E.135387 (CAPRIN1), E.135999 (EPC2), E.136383 (ALPK3), E.139405 (C12orf52), E.141012 (GALNS), E.143924 (EML4), E.144671 (SLC22A14), E.145741 (BTF3), E.145907 (G3BP1), E.149311 (ATM), E.153113 (CAST), E.157538 (DSCR3), E.157992 (KRTCAP3), E.158901 (WFDC8), E.165259 (HDX), E.169410 (PTPN9), E.170421 (KRT8), E.171155 (C1GALT1C1), E.172831 (CES2), E.173726 (TOMM20), E.176515, E.177565 (TBL1XR1), E.177628 (GBA), E.179091 (CYC1), E.189091 (SF3B3), E.197299 (BLM), E.197872 (FAM49A), E.198205 (ZXDA), E.198455 (ZXDB), E.082212 (ME2), E.109956 (B3GAT1), E.169710 (FASN), E.011304 (PTBP1), E.057252 (SOAT1), E.059378 (PARP12), E.082258 (CCNT2), E.087301 (TXNDC16), E.100575 (TIMM9), E.101152 (DNAJC5), E.101812 (H2BFM), E.102384 (CENPI), E.108641 (B9D1), E.119138 (KLF9), E.119820 (YIPF4), E.125995 (ROMO1), E.132323 (ILKAP), E.134809 (TIMM10), E.134955 (SLC37A2), E.135476 (ESPL1), E.136527 (TRA2B), E.137776 (SLTM), E.139211 (AMIGO2), E.139428 (MMAB), E.139874 (SSTR1), E.143321 (HDGF), E.164244 (PRRC1), E.164270 (HTR4), E.165119 (HNRNPK), E.165637 (VDAC2), E.165661 (QSOX2), E.167258 (CDK12), E.167815 (PRDX2), E.168014 (C2CD3), E.168653 (NDUFS5), E.168769 (TET2), E.169242 (EFNA1), E.175334 (BANF1), E.175416 (CLTB), E.177156 (TALDO1), E.180035 (ZNF48), E.186591 (UBE2H), E.187097 (ENTPD5), E.188739 (RBM34), E.196497 (IPO4), E.197323 |

TABLE 4-continued

Illustrative Biomarkers

| Illustrative Class | Biomarkers |
|---|---|
| | (TRIM33), E.197857 (ZNF44), E.197976 (AKAP17A), E.064201 (TSPAN32), E.088992 (TESC), E.092421 (SEMA6A), E.100601 (ALKBH1), E.101557 (USP14), E.103035 (PSMD7), E.106128 (GHRHR), E.115541 (HSPE1), E.121390 (PSPC1), E.124216 (SNAI1), E.130713 (EXOSC2), E.132002 (DNAJB1), E.139697 (SBNO1), E.140481 (CCDC33), E.143013 (LMO4), E.145020 (AMT), E.145990 (GFOD1), E.146070 (PLA2G7), E.164924 (YWHAZ), E.165807 (PPP1R36), E.167751 (KLK2), E.169213 (RAB3B), E.170906 (NDUFA3), E.172725 (CORO1B), E.174332 (GLIS1), E.181924 (CHCHD8), E.183128 (CALHM3), E.204560 (DHX16), E.204574 (ABCF1), E.146701 (MDH2), E.198366 (HIST1H3A), E.081181 (ARG2), E.185896 (LAMP1), E.077514 (POLD3), E.099800 (TIMM13), E.100299 (ARSA), E.105419 (MEIS3), E.108417 (KRT37), E.113739 (STC2), E.125868 (DSTN), E.145908 (ZNF300), E.168575 (SLC20A2), E.182271 (TMIGD1), E.197223 (C1D), E.186834 (HEXIM1), E.001561 (ENPP4), E.011451 (WIZ), E.053108 (FSTL4), E.064655 (EYA2), E.065308 (TRAM2), E.075131 (TIPIN), E.081087 (OSTM1), E.092020 (PPP2R3C), E.096384 (HSP90AB1), E.100348 (TXN2), E.100577 (GSTZ1), E.100802 (C14orf93), E.101365 (IDH3B), E.101654 (RNMT), E.103067 (ESRP2), E.104064 (GABPB1), E.104823 (ECH1), E.106565 (TMEM176B), E.108561 (C1QBP), E.115257 (PCSK4), E.116127 (ALMS1), E.117411 (B4GALT2), E.119335 (SET), E.120337 (TNFSF18), E.122033 (MTIF3), E.122507 (BBS9), E.122870 (BICC1), E.130177 (CDC16), E.130193 (C8orf55; THEM6), E.130413 (STK33), E.130770 (ATPIF1), E.133687 (TMTC1), E.136874 (STX17), E.137409 (MTCH1), E.139626 (ITGB7), E.141744 (PNMT), E.145888 (GLRA1), E.146067 (FAM193B), E.146433 (TMEM181), E.149480 (MTA2), E.152377 (SPOCK1), E.152763 (WDR78), E.156976 (EIF4A2), E.157827 (FMNL2), E.158485 (CD1B), E.158863 (FAM160B2), E.161202 (DVL3), E.161714 (PLCD3), E.163064 (EN1), E.163468 (CCT3), E.164309 (CMYA5), E.164916 (FOXK1), E.165215 (CLDN3), E.167658 (EEF2), E.170549 (IRX1), E.171680 (PLEKHG5), E.178234 (GALNT11), E.179869 (ABCA13), E.179912 (R3HDM2), E.180869 (C1orf180), E.180979 (LRRC57), E.182872 (RBM10), E.183207 (RUVBL2), E.184113 (CLDN5), E.185972 (CCIN), E.189144 (ZNF573), E.197353 (LYPD2), E.197779 (ZNF81), E.198807 (PAX9), E.100442 (FKBP3), E.111790 (FGFR1OP2), E.136044 (APPL2), E.061794 (MRPS35), E.065427 (KARS), E.068885 (IFT80), E.104164 (PLDN; BLOC1S6), E.105127 (AKAP8), E.123066 (MED13L), E.124831 (LRRFIP1), E.125304 (TM9SF2), E.126934 (MAP2K2), E.130305 (NSUN5), E.135298 (BAI3), E.135900 (MRPL44), E.136371 (MTHFS), E.136574 (GATA4), E.140326 (CDAN1), E.141378 (PTRH2), E.141543 (EIF4A3), E.150961 (SEC24D), E.155368 (DBI), E.161649 (CD300LG), E.161692 (DBF4B), E.162437 (RAVER2), E.163257 (DCAF16), E.163576 (EFHB), E.163781 (TOPBP1), E.163913 (IFT122), E.164597 (COG5), E.165359 (DDX26B), E.165646 (SLC18A2), E.169592 (INO80E), E.169957 (ZNF768), E.171492 (LRRC8D), E.171793 (CTPS; CTPS1), E.171953 (ATPAF2), E.175182 (FAM131A), E.177354 (C10orf71), E.181610 (MRPS23), E.181873 (IBA57), E.187792 (ZNF70), E.187823 (ZCCHC16), E.196872 (C2orf55; KIAA1211L), E.198168 (SVIP), E.160633 (SAFB), E.177697 (CD151), E.181072 (CHRM2), E.012779 (ALOX5), E.065054 (SLC9A3R2), E.074071 (MRPS34), E.100815 (TRIP11), E.102030 (NAA10), E.106153 (CHCHD2), E.126814 (TRMT5), E.126952 (NXF5), E.136450 (SRSF1), E.136710 (CCDC115), E.137124 (ALDH1B1), E.143353 (LYPLAL1), E.162490 (C1orf187; DRAXIN), E.167799 (NUDT8), E.171490 (RSL1D1), E.173826 (KCNH6), E.173898 (SPTBN2), E.176900 (OR51T1), E.181513 (ACBD4), E.185554 (NXF2), E.185945 (NXF2B), E.108848 (LUC7L3), E.029363 (BCLAF1), E.038002 (AGA), E.108312 (UBTF), E.166341 (DCHS1), E.054118 (THRAP3), E.135679 (MDM2), E.166860 (ZBTB39), E.183684 (THOC4; ALYREF), E.004838 (ZMYND10), E.007264 (MATK), E.020922 (MRE11A), E.041353 (RAB27B), E.052795 (FNIP2), E.075711 (DLG1), E.087087 (SRRT), E.090060 (PAPOLA), E.095139 (ARCN1), E.099715 (PCDH11Y), E.100271 (TTLL1), E.101057 (MYBL2), E.101265 (RASSF2), E.101901 (ALG13), E.102290 (PCDH11X), E.103194 (USP10), E.106554 (CHCHD3), E.107833 (NPM3), E.110063 (DCPS), E.111540 (RAB5B), E.113448 (PDE4D), E.115339 (GALNT3), E.116254 (CHD5), E.117425 (PTCH2), E.117614 (SYF2), E.118181 (RPS25), E.118292 (C1orf54), E.119318 (RAD23B), E.121022 (COPS5), E.121104 (FAM117A), E.123427 (METTL21B), E.125676 (THOC2), E.132275 (RRP8), E.137513 (NARS2), E.138028 (CGREF1), E.139517 (LNX2), E.143614 (GATAD2B), E.143889 (HNRPLL), E.145833 (DDX46), E.147403 (RPL10), E.148158 (SNX30), E.151690 (MFSD6), E.153904 (DDAH1), E.154781 (C3orf19), E.156650 (KAT6B), E.158669 (AGPAT6), E.159363 (ATP13A2), E.163530 (DPPA2), E.164749 (HNF4G), E.165496 (RPL10L), E.165688 (PMPCA), E.165792 (METTL17), E.166598 (HSP90B1), E.168036 (CTNNB1), E.168746 (C20orf62), E.170381 (SEMA3E), E.171180 (OR2M4), E.171202 (TMEM126A), E.172594 (SMPDL3A), E.172653 (C17orf66), E.173540 (GMPPB), E.173585 (CCR9), E.173809 (TDRD12), E.175166 (PSMD2), E.177694 (NAALADL2), E.178026 (FAM211B; C22orf36), E.184363 (PKP3), E.187634 (SAMD11), E.203837 (PNLIPRP3), E.169122 (FAM110B), E.197969 (VPS13A), E.136068 (FLNB), E.075856 (SART3), E.081721 (DUSP12), E.102158 (MAGT1), E.102174 (PHEX), E.102316 (MAGED2), E.104723 (TUSC3), E.105939 (ZC3HAV1), E.108883 (EFTUD2), E.110328 (GALNTL4), E.111785 (RIC8B), E.113163 (COL4A3BP), E.115604 (IL18R1), E.117362 (APH1A), E.117480 (FAAH), E.124767 (GLO1), E.126267 (COX6B1), E.130175 (PRKCSH), E.135926 (TMBIM1), E.138674 (SEC31A), E.140451 (PIF1), E.143797 (MBOAT2), E.149646 (C20orf152), E.157064 (NMNAT2), E.160294 (MCM3AP), E.165084 (C8orf34), E.166946 (CCNDBP1), E.170348 (TMED10), E.170703 (TTLL6), E.175198 (PCCA), E.180287 (PLD5), E.183292 (MIR5096), E.187492 (CDHR4), E.188846 (RPL14), E.015479 (MATR3), E.100823 (APEX1), E.090615 (GOLGA3), E.086062 (B4GALT1), E.138385 (SSB), E.140265 (ZSCAN29), E.140932 (CMTM2), E.167969 (ECI1), E.135486 |

TABLE 4-continued

Illustrative Biomarkers

| Illustrative Class | Biomarkers |
|---|---|
| | (HNRNPA1), E.137497 (NUMA1), E.181523 (SGSH), E.099956 (SMARCB1), E.049883 (PTCD2), E.082556 (OPRK1), E.090674 (MCOLN1), E.107164 (FUBP3), E.108582 (CPD), E.109758 (HGFAC), E.111605 (CPSF6), E.115239 (ASB3), E.121892 (PDS5A), E.125844 (RRBP1), E.130826 (DKC1), E.132481 (TRIM47), E.135390 (ATP5G2), E.136875 (PRPF4), E.138621 (PPCDC), E.145632 (PLK2), E.150051 (MKX), E.153140 (CETN3), E.154127 (UBASH3B), E.156194 (PPEF2), E.163825 (RTP3), E.164053 (ATRIP), E.164442 (CITED2), E.168066 (SF1), E.170430 (MGMT), E.175602 (CCDC85B), E.177752 (YIPF7), E.182512 (GLRX5), E.188186 (C7orf59), E.198721 (ECI2), E.204389 (HSPA1A), E.010256 (UQCRC1), E.076043 (REXO2), E.102362 (SYTL4), E.161939 (C17orf49), E.173039 (RELA), E.014216 (CAPN1), E.054938 (CHRDL2), E.065526 (SPEN), E.070501 (POLB), E.078808 (SDF4), E.083720 (OXCT1), E.100084 (HIRA), E.101246 (ARFRP1), E.102241 (HTATSF1), E.103591 (AAGAB), E.104626 (ERI1), E.105221 (AKT2), E.105402 (NAPA), E.105705 (SUGP1), E.106346 (USP42), E.108639 (SYNGR2), E.110107 (PRPF19), E.112473 (SLC39A7), E.113282 (CLINT1), E.115234 (SNX17), E.115561 (CHMP3), E.119906 (FAM178A), E.120733 (KDM3B), E.125375 (ATP5S), E.125798 (FOXA2), E.127415 (IDUA), E.129810 (SGOL1), E.132382 (MYBBP1A), E.133313 (CNDP2), E.134077 (THUMPD3), E.134248 (HBXIP), E.135597 (REPS1), E.137814 (HAUS2), E.138041 (SMEK2), E.140382 (HMG20A), E.143578 (CREB3L4), E.144224 (UBXN4), E.144306 (SCRN3), E.144741 (SLC25A26), E.145919 (BOD1), E.146281 (PM20D2), E.152359 (POC5), E.152409 (JMY), E.154889 (MPPE1), E.157551 (KCNJ15), E.157764 (BRAF), E.158987 (RAPGEF6), E.162069 (CCDC64B), E.162910 (MRPL55), E.163749 (CCDC158), E.164045 (CDC25A), E.164300 (SERINC5), E.165898 (ISCA2), E.167987 (VPS37C), E.168763 (CNNM3), E.170374 (SP7), E.171488 (LRRC8C), E.178381 (ZFAND2A), E.180998 (GPR137C), E.182318 (ZSCAN22), E.198040 (ZNF84), E.198216 (CACNA1E), E.198265 (HELZ), E.198586 (TLK1), E.203795 (FAM24A), E.204231 (RXRB), E.123992 (DNPEP), E.184634 (MED12), E.181885 (CLDN7), E.186660 (ZFP91), E.126777 (KTN1), E.080823 (MOK), E.101811 (CSTF2), E.124570 (SERPINB6), E.148835 (TAF5), E.158715 (SLC45A3), E.110955 (ATP5B), E.127022 (CANX), E.142208 (AKT1), E.128881 (TTBK2), E.147231 (CXorf57), E.006210 (CX3CL1), E.009830 (POMT2), E.011114 (BTBD7), E.065057 (NTHL1), E.068724 (TTC7A), E.073584 (SMARCE1), E.079785 (DDX1), E.084463 (WBP11), E.091140 (DLD), E.099821 (POLRMT), E.101126 (ADNP), E.104442 (ARMC1), E.105486 (LIG1), E.110921 (MVK), E.113441 (LNPEP), E.115758 (ODC1), E.116726 (PRAMEF12), E.119681 (LTBP2), E.136933 (RABEPK), E.137815 (RTF1), E.138095 (LRPPRC), E.138294 (MSMB), E.141873 (SLC39A3), E.142698 (C1orf94), E.143390 (RFX5), E.148488 (ST8SIA6), E.148737 (TCF7L2), E.151491 (EPS8), E.152422 (XRCC4), E.154832 (CXXC1), E.158321 (AUTS2), E.159147 (DONSON), E.160285 (LSS), E.160862 (AZGP1), E.160948 (VPS28), E.160972 (PPP1R16A), E.165934 (CPSF2), E.167604 (NFKBID), E.167766 (ZNF83), E.168803 (ADAL), E.169612 (FAM103A1), E.171262 (FAM98B), E.172893 (DHCR7), E.173889 (PHC3), E.176971 (FIBIN), E.177548 (RABEP2), E.179119 (SPTY2D1), E.184378 (ACTRT3), E.184508 (HDDC3), E.185043 (CIB1), E.186814 (ZSCAN30), E.186868 (MAPT), E.196812 (ZSCAN16), E.198563 (DDX39B), E.124529 (HIST1H4B), E.141002 (TCF25), E.174100 (MRPL45), E.109814 (UGDH), E.138756 (BMP2K), E.065457 (ADAT1), E.105948 (TTC26), E.109184 (DCUN1D4), E.125257 (ABCC4), E.126062 (TMEM115), E.142515 (KLK3), E.144381 (HSPD1), E.166710 (B2M), E.198824 (CHAMP1), E.078902 (TOLLIP), E.099331 (MYO9B), E.102710 (FAM48A), E.107485 (GATA3), E.120948 (TARDBP), E.187764 (SEMA4D), E.103855 (CD276), E.117751 (PPP1R8), E.173714 (WFIKKN2), E.172115 (CYCS), E.005882 (PDK2), E.007952 (NOX1), E.008118 (CAMK1G), E.012061 (ERCC1), E.015171 (ZMYND11), E.036257 (CUL3), E.057608 (GDI2), E.058729 (RIOK2), E.071246 (VASH1), E.073050 (XRCC1), E.073350 (LLGL2), E.079246 (XRCC5), E.085733 (CTTN), E.091542 (ALKBH5), E.091732 (ZC3HC1), E.092621 (PHGDH), E.099899 (TRMT2A), E.099917 (MED15), E.101439 (CST3), E.103479 (RBL2), E.104611 (SH2D4A), E.105281 (SLC1A5), E.106392 (C1GALT1), E.107104 (KANK1), E.107798 (LIPA), E.108296 (CWC25), E.109572 (CLCN3), E.112110 (MRPL18), E.113790 (EHHADH), E.115648 (MLPH), E.117308 (GALE), E.117335 (CD46), E.118513 (MYB), E.118640 (VAMP8), E.119321 (FKBP15), E.122705 (CLTA), E.123983 (ACSL3), E.124232 (RBPJL), E.125901 (MRPS26), E.127399 (LRRC61), E.127554 (GFER), E.128708 (HAT1), E.129355 (CDKN2D), E.130340 (SNX9), E.130935 (NOL11), E.131771 (PPP1R1B), E.133863 (TEX15), E.134207 (SYT6), E.136935 (GOLGA1), E.141425 (RPRD1A), E.143374 (TARS2), E.143771 (CNIH4), E.146966 (DENND2A), E.148672 (GLUD1), E.150593 (PDCD4), E.153936 (HS2ST1), E.154099 (DNAAF1), E.156006 (NAT2), E.156282 (CLDN17), E.158545 (ZC3H18), E.158604 (TMED4), E.158813 (EDA), E.159184 (HOXB13), E.161267 (BDH1), E.163492 (CCDC141), E.163629 (PTPN13), E.164163 (ABCE1), E.164520 (RAET1E), E.165138 (ANKS6), E.165923 (AGBL2), E.166484 (MAPK7), E.166747 (AP1G1), E.166971 (AKTIP), E.167744 (NTF4), E.168071 (CCDC88B), E.169087 (HSPBAP1), E.170396 (ZNF804A), E.170445 (HARS), E.170632 (ARMC10), E.170743 (SYT9), E.171428 (NAT1), E.172346 (CSDC2), E.173805 (HAP1), E.175175 (PPM1E), E.175203 (DCTN2), E.177542 (SLC25A22), E.177679 (SRRM3), E.178828 (RNF186), E.182013 (PNMAL1), E.182054 (IDH2), E.182890 (GLUD2), E.184156 (KCNQ3), E.184697 (CLDN6), E.184735 (DDX53), E.184840 (TMED9), E.185219 (ZNF445), E.186198 (SLC51B), E.186205 (MOSC1; MARC1), E.189 143 (CLDN4), E.196700 (ZNF512B), E.196743 (GM2A), E.198087 (CD2AP), E.198951 (NAGA), E.204406 (MBD5), E.002330 (BAD), E.105404 (RABAC1), E.114127 (XRN1), E.117713 (ARID1A), E.123143 (PKN1), E.130764 (LRRC47), E.131773 (KHDRBS3), E.137806 (NDUFAF1), E.142864 (SERBP1), E.158747 (NBL1), E.175063 (UBE2C), E.178104 (PDE4DIP), E.186472 (PCLO), E.069956 (MAPK6), |

TABLE 4-continued

Illustrative Biomarkers

| Illustrative Class | Biomarkers |
|---|---|
| | E.112941 (PAPD7), E.116604 (MEF2D), E.142875 (PRKACB), E.147133 (TAF1), E.157510 (AFAP1L1), E.006625 (GGCT), E.155980 (KIF5A), E.134444 (KIAA1468), E.107968 (MAP3K8), E.117592 (PRDX6), E.123154 (WDR83), E.135297 (MTO1), E.135829 (DHX9), E.149548 (CCDC15), E.152086 (TUBA3E), E.167553 (TUBA1C), E.169826 (CSGALNACT2), E.171121 (KCNMB3), E.198033 (TUBA3C), E.147724 (FAM135B), E.170854 (MINA), E.006695 (COX10), E.067369 (TP53BP1), E.089248 (ERP29), E.112096 (SOD2), E.138073 (PREB), E.146856 (AGBL3), E.159423 (ALDH4A1), E.171345 (KRT19), E.172345 (STARD5), E.111647 (UHRF1BP1L), E.117877 (CD3EAP), E.155714 (PDZD9), E.156603 (MED19), E.075886 (TUBA3D), E.167699 (GLOD4), E.121749 (TBC1D15), E.090861 (AARS), E.093010 (COMT), E.117676 (RPS6KA1), E.157502 (MUM1L1), E.159921 (GNE), E.169562 (GJB1), E.179776 (CDH5), E.071626 (DAZAP1), E.085224 (ATRX), E.116478 (HDAC1), E.117298 (ECE1), E.176171 (BNIP3), E.177425 (PAWR), E.179348 (GATA2), E.187840 (EIF4EBP1), E.033030 (ZCCHC8), E.049239 (H6PD), E.060688 (SNRNP40), E.075239 (ACAT1), E.095627 (TDRD1), E.109625 (CPZ), E.113719 (ERGIC1), E.126773 (C14orf135; PCNXL4), E.149218 (ENDOD1), E.162975 (KCNF1), E.183785 (TUBA8), E.198589 (LRBA), E.105379 (ETFB), E.011052 (NME2), E.011143 (MKS1), E.048544 (MRPS10), E.062485 (CS), E.114054 (PCCB), E.138587 (MNS1), E.155959 (VBP1), E.181222 (POLR2A), E.183723 (CMTM4), E.184661 (CDCA2), E.204316 (MRPL38), E.140694 (PARN), E.035141 (FAM136A), E.095485 (CWF19L1), E.115540 (MOB4), E.123595 (RAB9A), E.140678 (ITGAX), E.141258 (SGSM2), E.158941 (KIAA1967), E.169189 (NSMCE1), E.198431 (TXNRD1), E.016402 (IL20RA), E.112234 (FBXL4), E.125445 (MRPS7), E.128342 (LIF), E.164051 (CCDC51), E.175866 (BAIAP2), E.102780 (DGKH), E.203813 (HIST1H3H), E.198231 (DDX42), E.030582 (GRN), E.106049 (HIBADH), E.130810 (PPAN), E.132475 (H3F3B), E.158290 (CUL4B), E.166266 (CUL5), E.026559 (KCNG1), E.059122 (FLYWCH1), E.107897 (ACBD5), E.121068 (TBX2), E.125944 (HNRNPR), E.134308 (YWHAQ), E.137558 (PI15), E.137601 (NEK1), E.147548 (WHSC1L1), E.149182 (ARFGAP2), E.159658 (KIAA0494), E.165699 (TSC1), E.170927 (PKHD1), E.186575 (NF2), E.188021 (UBQLN2), E.167552 (TUBA1A), E.003756 (RBM5), E.134138 (MEIS2), E.008196 (TFAP2B), E.079313 (REXO1), E.089127 (OAS1), E.106078 (COBL), E.113645 (WWC1), E.116288 (PARK7), E.121940 (CLCC1), E.136280 (CCM2), E.141639 (MAPK4), E.147475 (ERLIN2), E.155660 (PDIA4), E.162298 (SYVN1), E.176978 (DPP7), E.176994 (SMCR8), E.178175 (ZNF366), E.196591 (HDAC2), E.127824 (TUBA4A), E.163932 (PRKCD), E.143375 (CGN), E.076864 (RAP1GAP), E.138772 (ANXA3), E.163041 (H3F3A), E.165813 (C10orf118), E.166337 (TAF10), E.178078 (STAP2), E.184007 (PTP4A2), E.167004 (PDIA3), E.039560 (RAI14), E.119636 (C14orf45), E.140374 (ETFA), E.143633 (C1orf131), E.144935 (TRPC1), E.156735 (BAG4), E.159348 (CYB5R1), E.170275 (CRTAP), E.172717 (FAM71D), E.172939 (OXSR1), E.176105 (YES1), E.078295 (ADCY2), E.119888 (EPCAM), E.141522 (ARHGDIA), E.184047 (DIABLO), E.109062 (SLC9A3R1), E.170037 (CNTROB), E.066557 (LRRC40), E.074964 (ARHGEF10L), E.078269 (SYNJ2), E.090013 (BLVRB), E.100142 (POLR2F), E.100399 (CHADL), E.104365 (IKBKB), E.111261 (MANSC1), E.111907 (TPD52L1), E.112578 (BYSL), E.121957 (GPSM2), E.122884 (P4HA1), E.124693 (HIST1H3B), E.126653 (NSRP1), E.130402 (ACTN4), E.138757 (G3BP2), E.150991 (UBC), E.164828 (SUN1), E.175216 (CKAP5), E.176155 (CCDC57), E.177459 (C8orf47), E.183856 (IQGAP3), E.185122 (HSF1), E.122952 (ZWINT), E.151093 (OXSM), E.067704 (IARS2), E.088899 (ProSAP-interacting protein 1), E.091483 (FH), E.114388 (NPRL2), E.114861 (FOXP1), E.135914 (HTR2B), E.197837 (HIST4H4), E.127720 (C12orf26; METTL25), E.123416 (TUBA1B), E.047410 (TPR), E.117748 (RPA2), E.133835 (HSD17B4), E.067248 (DHX29), E.121879 (PIK3CA), E.132589 (FLOT2), E.136750 (GAD2), E.160780 (LMNA), E.166329, E.170088 (TMEM192), E.175946 (KLHL38), E.178163 (ZNF518B), E.182217 (HIST2H4B), E.184470 (TXNRD2), E.110321 (EIF4G2), E.171861 (RNMTL1), E.065978 (YBX1), E.115738 (ID2), E.143294 (PRCC), E.158042 (MRPL17), E.169093 (ASMTL), E.090565 (RAB11FIP3), E.185591 (SP1), E.156304 (SCAF4), E.092978 (GPATCH2), E.100056 (DGCR14), E.100583 (SAMD15), E.105723 (GSK3A), E.107551 (RASSF4), E.107581 (EIF3A), E.107890 (ANKRD26), E.110104 (CCDC86), E.112584 (FAM120B), E.113580 (NR3C1), E.114491 (UMPS), E.137312 (FLOT1), E.137955 (RABGGTB), E.141994 (DUS3L), E.147044 (CASK), E.152818 (UTRN), E.180667 (YOD1), E.184916 (JAG2), E.196526 (AFAP1), E.198783 (ZNF830), E.108465 (CDK5RAP3), E.156515 (HK1), E.036448 (MYOM2), E.061918 (GUCY1B3), E.070785 (EIF2B3), E.116044 (NFE2L2), E.128311 (TST), E.131473 (ACLY), E.132716 (DCAF8), E.138363 (ATIC), E.166596 (WDR16), E.170027 (YWHAG), E.174021 (GNG5), E.203879 (GDI1), E.160049 (DFFA), E.010810 (FYN), E.051596 (THOC3), E.006453 (BAI1-associated protein 2-like 1), E.126945 (HNRNPH2), E.165695 (AK8), E.069869 (NEDD4), E.111801 (BTN3A3), E.112232 (KHDRBS2), E.128626 (MRPS12), E.129636 (ITFG1), E.137948 (BRDT), E.147257 (GPC3), E.155380 (SLC16A1), E.159692 (CTBP1), E.166833 (NAV2), E.172466 (ZNF24), E.175110 (MRPS22), E.176102 (CSTF3), E.179388 (EGR3), E.185359 (HGS), E.198001 (IRAK4), E.100603 (SNW1), E.162641 (AKNAD1), E.069712 (KIAA1107), E.073756 (PTGS2), E.077522 (ACTN2), E.101639 (CEP192), E.106633 (GCK), E.115241 (PPM1G), E.116649 (SRM), E.120370 (GORAB), E.124143 (ARHGAP40), E.127948 (POR), E.129315 (CCNT1), E.132646 (PCNA), E.135740 (SLC9A5), E.151726 (ACSL1), E.154380 (ENAH), E.157103 (SLC6A1), E.163930 (BAP1), E.164488 (DACT2), E.164754 (RAD21), E.175220 (ARHGAP1), E.180318 (ALX1), E.181234 (TMEM132C), E.197081 (IGF2R), E.092871 (RFFL), E.163644 (PPM1K), E.171723 (GPHN), E.108953 (YWHAE), E.072110 (ACTN1), E.077097 (TOP2B), E.090889 (KIF4A), E.114331 (ACAP2), E.114867 (EIF4G1), E.117593 (DARS2), E.118523 (CTGF), E.120915 (EPHX2), E.134759 (ELP2), |

TABLE 4-continued

Illustrative Biomarkers

| Illustrative Class | Biomarkers |
|---|---|
| | E.138061 (CYP1B1), E.140743 (CDR2), E.151247 (EIF4E), E.152942 (RAD17), E.160685 (ZBTB7B), E.163923 (RPL39L), E.167642 (SPINT2), E.167996 (FTH1), E.185736 (ADARB2), E.198841 (KTI12), E.185860 (C1orf110), E.160226 (C21orf2), E.070814 (TCOF1), E.124749 (COL21A1), E.154639 (CXADR), E.065485 (PDIA5), E.023909 (GCLM), E.100714 (MTHFD1), E.108387 (SEPT4), E.160867 (FGFR4), E.134684 (YARS), E.123080 (CDKN2C), E.065548 (ZC3H15), E.116455 (WDR77), E.117448 (AKR1A1), E.100393 (EP300), E.138160 (KIF11), E.166263 (STXBP4), E.173473 (SMARCC1), E.124942 (AHNAK), E.174842 (GLMN), E.180198 (RCC1), E.185499 (MUC1), E.143947 (RPS27A), E.170315 (UBB), E.003402 (CFLAR), E.137055 (PLAA), E.142606 (MMEL1), E.147697 (GSDMC), E.163110 (PDLIM5), E.135842 (FAM129A), E.160691 (SHC1), E.197157 (SND1), E.029725 (RABEP1), E.127946 (HIP1), E.001036 (FUCA2), E.109846 (CRYAB), E.183831 (ANKRD45), E.189283 (FHIT), E.092820 (EZR), E.104067 (TJP1), E.120159 (C9orf82; CAAP1), E.154864 (PIEZO2), E.196975 (ANXA4), E.105220 (GPI), E.127914 (AKAP9), E.135870 (RC3H1), E.026508 (CD44), E.089154 (GCN1L1), E.100311 (PDGFB), E.119383 (PPP2R4), E.075624 (ACTB), E.177409 (SAMD9L), E.177731 (FLII), E.015676 (NUDCD3), E.146457 (WTAP), E.178950 (GAK), E.167110 (GOLGA2) |
| Prostate vesicle | LAMP2, ACPP, CTNNA1, HEBP2, ISOC2, HNRNPC, HNRNPM, TOMM22, TOM1, ACO2, KRT18, HSPA9, LMNB1, SPR, PPL, ALDH6A1, HNRNPA2B1, ATXN1, SMARCA4, ECHS1, PAICS, ILF3, PSME3, COX5B, RAB1A, SCARB2, HADH, ESD, SORD, ILF2, CALM2, ATP5A1, TGOLN2, ANGPTL4, ALCAM, KRT2, PC, NPM1, C1orf116, GPC6, ALDH1A3, HIST1H1C, XRCC6, HNRNPAB, PSAP, CDH1, SCAMP2, VASP, CD9, ATP1B3, HSD17B10, APAF1, EIF2C2, RAB5A, CFL2, FARSA, XPNPEP3, ENTPD4, APLP2, NUCB1, RAB3D, VEGFA, HPS3, TSNAXIP1, HNRNPL, PSMB7, GNA12, NONO, FOLH1, PRKAR2A, PHB, HIST3H3, MAP7, VCP, U2AF2, FUS, FKBP5, NDRG1, ATP1A3, NCL, RPL36, KRT8, C1GALT1C1, FASN, PTBP1, TXNDC16, DNAJC5, SLC37A2, HNRNPK, VDAC2, PRDX2, TALDO1, USP14, PSMD7, HSPE1, DNAJB1, YWHAZ, RAB3B, CORO1B, MDH2, HIST1H3A, LAMP1, STC2, DSTN, SLC20A2, ENPP4, WIZ, HSP90AB1, IDH3B, ECH1, C1QBP, SET, TNFSF18, ITGB7, SPOCK1, EIF4A2, CCT3, CLDN3, EEF2, LRRC57, RUVBL2, CLDN5, APPL2, TM9SF2, EIF4A3, DBI, DBF4B, SVIP, CD151, ALOX5, SLC9A3R2, RAB27B, DLG1, ARCN1, CHCHD3, RAB5B, RPS25, RPL10, DDAH1, HSP90B1, CTNNB1, PSMD2, PKP3, FLNB, EFTUD2, GLO1, PRKCSH, TMBIM1, SEC31A, TMED10, RPL14, MATR3, APEX1, B4GALT1, HNRNPA1, CPD, HSPA1A, CAPN1, CHRDL2, SPEN, SDF4, NAPA, SYNGR2, CHMP3, CNDP2, CCDC64B, SERINC5, VPS37C, DNPEP, CLDN7, KTN1, SERPINB6, ATP5B, CANX, AKT1, TTBK2, DDX1, DLD, LNPEP, LTBP2, LRPPRC, EPS8, AZGP1, VPS28, DHCR7, CIB1, DDX39B, HIST1H4B, UGDH, HSPD1, B2M, TOLLIP, CD276, CYCS, CUL3, GDI2, LLGL2, XRCC5, CTTN, PHGDH, CST3, RBL2, SLC1A5, CD46, VAMP8, CLTA, ACSL3, MRPS26, SNX9, GLUD1, TMED4, PTPN13, AP1G1, SYT9, DCTN2, IDH2, GLUD2, TMED9, CLDN4, GM2A, CD2AP, MBD5, SERBP1, NBL1, PRKACB, GGCT, PRDX6, DHX9, TUBA3E, TUBA1C, TUBA3C, ERP29, SOD2, KRT19, TUBA3D, AARS, COMT, MUM1L1, CDH5, ECE1, ACAT1, ENDOD1, TUBA8, ETFB, NME2, CS, VBP1, RAB9A, TXNRD1, LIF, BAIAP2, HIST1H3H, GRN, HIBADH, H3F3B, CUL4B, HNRNPR, YWHAQ, PKHD1, TUBA1A, PARK7, ERLIN2, PDIA4, TUBA4A, PRKCD, ANXA3, H3F3A, PTP4A2, PDIA3, ETFA, CYB5R1, CRTAP, OXSR1, YES1, EPCAM, ARHGDIA, DIABLO, SLC9A3R1, BLVRB, P4HA1, HIST1H3B, ACTN4, UBC, FH, HIST4H4, TUBA1B, HSD17B4, PIK3CA, FLOT2, LMNA, TMEM192, HIST2H4B, YBX1, EIF3A, FLOT1, UTRN, HK1, ACLY, ATIC, YWHAG, GNG5, GDI1, HNRNPH2, NEDD4, BTN3A3, SLC16A1, HGS, ACTN2, SRM, PCNA, ACSL1, RAD21, ARHGAP1, IGF2R, YWHAE, ACTN1, EIF4G1, EPHX2, EIF4E, FTH1, CXADR, MTHFD1, AKR1A1, STXBP4, AHNAK, MUC1, RPS27A, UBB, PDLIM5, FAM129A, SND1, FUCA2, CRYAB, EZR, TJP1, ANXA4, GPI, AKAP9, CD44, GCN1L1, ACTB, FLII, NUDCD3 |
| Prostate Cancer vesicles | EGFR, GLUD2, ANXA3, APLP2, BclG, Coiflin 2/cfL2, DCTN-50/DCTN2, DDAH1, ESD, FARSLA, GITRL, PRKCSH, SLC20A2, Synaptogyrin 2/SYNGR2, TM9SF2, Calnexin, TOMM22, NDRG1, RPL10, RPL14, USP14, VDAC2, LLGL2, CD63, CD81, uPAR/CD87, ADAM 9, BDKRB2, CCR5, CCT2 (TCP1-beta), PSMA, PSMA1, HSPB1, VAMP8, Rab1A, B4GALT1, Aspartyl Aminopeptidase/Dnpep, ATPase Na+/K+ beta 3/ATP1B3, BDNF, ATPB, beta 2 Microglobulin, Calmodulin 2/CALM2, CD9, XRCC5/ Ku80, SMARCA4, TOM1, Cytochrome C, Hsp10/HSPE1, COX2/PTGS2, Claudin 4/ CLDN4, Cytokeratin 8, Cortactin/CTTN, DBF4B/DRF1, ECH1, ECHS1, GOLPH2, ETS1, DIP13B/appl2, EZH2/KMT6, GSTP1, hK2/Kif2a, IQGAP1, KLK13, Lamp-2, GM2A, Hsp40/DNAJB1, HADH/HADHSC, Hsp90B, Nucleophosmin, p130/RBL2, PHGDH, RAB3B, ANXA1, PSMD7, PTBP1, Rab5a, SCARB2, Stanniocalcin 2/STC2, TGN46/ TGOLN2, TSNAXIP1, ANXA2, CD46, KLK14, IL1alpha, hnRNP C1 + C2, hnRNP A1, hnRNP A2B1, Claudin 5, CORO1B, Integrin beta 7, CD41, CD49d, CDH2, COX5b, IDH2, ME1, PhIP, ALDOA, EDNRB/EDN3, MTA1, NKX3-1, TMPRSS2, CD10, CD24, CDH1, ADAM10, B7H3, CD276, CHRDL2, SPOCK1, VEGFA, BCHE, CD151, CD166/ALCAM, CSE1L, GPC6, CXCR3, GAL3, GDF15, IGFBP-2, HGF, KLK12, ITGAL, KLK7, KLK9, MMP 2, MMP 25, MMP10, TNFR1, Notch 1, PAP - same as ACPP, PTPN13/PTPL1, seprase/FAP, TNFRI, TWEAK, VEGFR2, E-Cadherin, Hsp60, CLDN3—Claudin3, KLK6, KLK8, EDIL3 (del-1), APE1, MMP 1, MMP3, nAnS, PSP94/MSP/IGBF, PSAP, RPL19, SET, TGFB, TGM2, TIMP-1, TNFRII, MDH2, PKP1, Cystatin C, Trop2/TACSTD2, CCR2/ CD192, hnRNP M1-M4, CDKN1A, CGA, Cytokeratin 18, EpoR, GGPS1, FTL (light and heavy), GM-CSF, HSP90AA1, IDH3B, MKI67/Ki67, LTBP2, KLK1, KLK4, KLK5, LDH-A, Nav1.7/SCN9A, NRP1/CD304, PIP3/BPNT1, PKP3, CgA, PRDX2, SRVN, ATPase Na+/K+ alpha 3/ATP1A3, SLC3A2/CD98, U2AF2, TLR4 (CD284), TMPRSS1, TNFα, |

TABLE 4-continued

Illustrative Biomarkers

| Illustrative Class | Biomarkers |
|---|---|
| | uPA, GloI, ALIX, PKM2, FABP5, CAV1, TLR9/CD289, ANXA4, PLEKHC1/Kindlin-2, CD71/TRFR, MBD5, SPEN/RBM15, LGALS8, SLC9A3R2, ENTPD4, ANGPTL4, p97/VCP, TBX5, PTEN, Prohibitin, LSP1, HOXB13, DDX1, AKT1, ARF6, EZR, H3F3A, CIB1, Ku70 (XRCC6), KLK11, TMBIM6, SYT9, APAF1, CLDN7, MATR3, CD90/THY1, Tollip, NOTCH4, 14-3-3 zeta/beta, ATP5A1, DLG1, GRP94, FKBP5/FKBP51, LAMP1, LGALS3BP, GDI2, HSPA1A, NCL, KLK15, Cytokeratin basic, EDN-3, AGR2, KLK10, BRG1, FUS, Histone H4, hnRNP L, Catenin Alpha 1, hnRNP K (F45)*, MMP7*, DBI*, beta catenin, CTH, CTNND2, Ataxin 1, Proteasome 20S beta 7, ADE2, EZH2, GSTP1, Lamin B1, Coatomer Subunit Delta, ERAB, Mortalin, PKM2, IGFBP-3, CTNND1/delta 1-catenin/p120-catenin, PKA R2, NONO, Sorbitol Dehydrogenase, Aconitase 2, VASP, Lipoamide Dehydrogenase, AP1G1, GOLPH2, ALDH6A1, AZGP1, Ago2, CNDP2, Nucleobindin-1, SerpinB6, RUVBL2, Proteasome 19S 10B, SH3PX1, SPR, Destrin, MDM4, FLNB, FASN, PSME |
| Prostate Cancer vesicles | 14-3-3 zeta/beta, Aconitase 2, ADAM 9, ADAM10, ADE2, AFM, Ago2, AGR2, AKT1, ALDH1A3, ALDH6A1, ALDOA, ALIX, ANGPTL4, ANXA1, ANXA2, ANXA3, ANXA3, ANXA4, AP1G1, APAF1, APE1, APLP2, APLP2, ARF6, Aspartyl Aminopeptidase/Dnpep, Ataxin 1, ATP5A1, ATPase Na+/K+ alpha 3/ATP1A3, ATPase Na+/K+ beta 3/ATP1B3, ATPase Na+/K+ beta 3/ATP1B3, ATPB, AZGP1, B4GALT1, B7H3, BCHE, BclG, BDKRB2, BDNF, BDNF, beta 2 Microglobulin, beta catenin, BRG1, CALM2, Calmodulin 2/CALM2, Calnexin, Calpain 1, Catenin Alpha 1, CAV1, CCR2/CD192, CCR5, CCT2 (TCP1-beta), CD10, CD151, CD166/ALCAM, CD24, CD276, CD41, CD46, CD49d, CD63, CD71/TRFR, CD81, CD9, CD9, CD90/THY1, CDH1, CDH2, CDKN1A, CGA, CgA, CHRDL2, CIB1, CIB1, Claudin 4/CLDN4, Claudin 5, CLDN3, CLDN3—Claudin3, CLDN4, CLDN7, CNDP2, Coatomer Subunit Delta, Cofilin 2/cfL2, CORO1B, Cortactin/CTTN, COX2/PTGS2, COX5b, CSE1L, CTH, CTNND1/delta 1-catenin/p120-catenin, CTNND2, CXCR3, CYCS, Cystatin C, Cytochrome C, Cytokeratin 18, Cytokeratin 8, Cytokeratin basic, DBF4B/DRF1, DBI*, DCTN-50/DCTN2, DDAH1, DDAH1, DDX1, Destrin, DIP13B/appl2, DIP13B/appl2, DLG1, Dnpep, E-Cadherin, ECH1, ECHS1, ECHS1, EDIL3 (del-1), EDN-3, EDNRB/EDN3, EGFR, EIF4A3, ENTPD4, EpoR, EpoR, ERAB, ESD, ESD, ETS1, ETS1, ETS-2, EZH2, EZH2/KMT6, EZR, FABP5, FARSLA, FASN, FKBP5/FKBP51, FLNB, FTL (light and heavy), FUS, GAL3, gamma-catenin, GDF15, GDI2, GGPS1, GGPS1, GITRL, GloI, GLUD2, GM2A, GM-CSF, GOLM1/GOLPH2 Mab; clone 3B10, GOLPH2, GOLPH2, GPC6, GRP94, GSTP1, GSTP1, H3F3A, HADH/HADHSC, HGF, HIST1H3A, Histone H4, hK2/Kif2a, hnRNP A1, hnRNP A2B1, hnRNP C1 + C2, hnRNP K (F45)*, hnRNP L, hnRNP M1-M4, HOXB13, Hsp10/HSPE1, Hsp40/DNAJB1, Hsp60, HSP90AA1, Hsp90B, HSPA1A, HSPB1, IDH2, IDH3B, IDH3B, IGFBP-2, IGFBP-3, IgG1, IgG2A, IgG2B, IL1alpha, IL1alpha, Integrin beta 7, IQGAP1, ITGAL, KLHL12/C3IP1, KLK1, KLK10, KLK11, KLK12, KLK13, KLK14, KLK15, KLK4, KLK5, KLK6, KLK7, KLK8, KLK9, Ku70 (XRCC6), Lamin B1, LAMP1, Lamp-2, LDH-A, LGALS3BP, LGALS8, Lipoamide Dehydrogenase, LLGL2, LSP1, LSP1, LTBP2, MATR3, MBD5, MDH2, MDM4, ME1, MKI67/Ki67, MMP 1, MMP 2, MMP 25, MMP10, MMP-14/MT1-MMP, MMP3, MMP7*, Mortalin, MTA1, nAnS, nAnS, Nav1.7/SCN9A, NCL, NDRG1, NKX3-1, NONO, Notch1, NOTCH4, NRP1/CD304, Nucleobindin-1, Nucleophosmin, p130/RBL2, p97/VCP, PAP - same as ACPP, PHGDH, PhIP, PIP3/BPNT1, PKA R2, PKM2, PKM2, PKP1, PKP3, PLEKHC1/Kindlin-2, PRDX2, PRKCSH, Prohibitin, Proteasome 19S 10B, Proteasome 20S beta 7, PSAP, PSMA, PSMA1, PSMA1, PSMD7, PSMD7, PSME3, PSP94/MSP/IGBF, PTBP1, PTEN, PTPN13/PTPL1, Rab1A, RAB3B, Rab5a, Rad51b, RPL10, RPL10, RPL14, RPL14, RPL19, RUVBL2, SCARB2, seprase/FAP, SerpinB6, SET, SH3PX1, SLC20A2, SLC3A2/CD98, SLC9A3R2, SMARCA4, Sorbitol Dehydrogenase, SPEN/RBM15, SPOCK1, SPR, SRVN, Stanniocalcin 2/STC2, STEAP1, Synaptogyrin 2/SYNGR2, Syndecan, SYNGR2, SYT9, TAF1B/GRHL1, TBX5, TGFB, TGM2, TGN46/TGOLN2, TIMP-1, TLR3, TLR4 (CD284), TLR9/CD289, TM9SF2, TMBIM6, TMPRSS1, TMPRSS2, TNFR1, TNFRI, TNFRII, TNFSF18/GITRL, TNFα, TNFα, Tollip, TOM1, TOMM22, Trop2/TACSTD2, TSNAXIP1, TWEAK, U2AF2, uPA, uPAR/CD87, USP14, USP14, VAMP8, VASP, VDAC2, VEGFA, VEGFR1/FLT1, VEGFR2, VPS28, XRCC5/Ku80, XRCC5/Ku80 |
| Prostate Vesicles/General Vesicles | EpCAM/TROP-1, HSA, Fibrinogen, GAPDH, Cholesterol Oxidase, MMP7, Complement Factor D/Adipsin, E-Cadherin, Transferrin Antibody, eNOS, IgM, CD9, Apolipoprotein B (Apo B), Ep-CAM, TBG, Kallekerin 3, IgA, IgG, Annexin V, IgG, Pyruvate Carboxylase, trypsin, AFP, TNF RI/TNFRSF1A, Aptamer CAR023, Aptamer CAR024, Aptamer CAR025, Aptamer CAR026 |
| Ribonucleoprotein complexes & vesicles | GW182, Ago2, miR-let-7a, miR-16, miR-22, miR-148a, miR-451, miR-92a, CD9, CD63, CD81 |
| Prostate Cancer vesicles | PCSA, Muc2, Adam10 |
| Prostate Cancer vesicles | Alkaline Phosphatase (AP), CD63, MyoD1, Neuron Specific Enolase, MAP1B, CNPase, Prohibitin, CD45RO, Heat Shock Protein 27, Collagen II, Laminin B1/b1, Gai1, CDw75, bcl-XL, Laminin-s, Ferritin, CD21, ADP-ribosylation Factor (ARF-6) |
| Prostate Cancer vesicles | CD56/NCAM-1, Heat Shock Protein 27/hsp27, CD45RO, MAP1B, MyoD1, CD45/T200/LCA, CD3zeta, Laminin-s, bcl-XL, Rad18, Gai1, Thymidylate Synthase, Alkaline Phosphatase (AP), CD63, MMP-16/MT3-MMP, Cyclin C, Neuron Specific Enolase, SIRP a1, Laminin B1/b1, Amyloid Beta (APP), SODD (Silencer of Death Domain), CDC37, Gab-1, E2F-2, CD6, Mast Cell Chymase, Gamma Glutamylcysteine Synthetase (GCS) |

TABLE 4-continued

Illustrative Biomarkers

| Illustrative Class | Biomarkers |
|---|---|
| Prostate Cancer vesicles | EpCAM, MMP7, PCSA, BCNP, ADAM10, KLK2, SPDEF, CD81, MFGE8, IL-8 |
| Prostate Cancer vesicles | EpCAM, KLK2, PBP, SPDEF, SSX2, SSX4 |
| Prostate Cancer vesicles | ADAM-10, BCNP, CD9, EGFR, EpCam, IL1B, KLK2, MMP7, p53, PBP, PCSA, SERPINB3, SPDEF, SSX2, SSX4 |
| Androgen Receptor (AR) pathway members in cMVs | GTF2F1, CTNNB1, PTEN, APPL1, GAPDH, CDC37, PNRC1, AES, UXT, RAN, PA2G4, JUN, BAG1, UBE2I, HDAC1, COX5B, NCOR2, STUB1, HIPK3, PXN, NCOA4 |
| EGFR1 pathway members in cMVs | RALBP1, SH3BGRL, RBBP7, REPS1, SNRPD2, CEBPB, APPL1, MAP3K3, EEF1A1, GRB2, RAC1, SNCA, MAP2K3, CEBPA, CDC42, SH3KBP1, CBL, PTPN6, YWHAB, FOXO1, JAK1, KRT8, RALGDS, SMAD2, VAV1, NDUFA13, PRKCB1, MYC, JUN, RFXANK, HDAC1, HIST3H3, PEBP1, PXN, TNIP1, PKN2 |
| TNF-alpha pathway members in cMVs | BCL3, SMARCE1, RPS11, CDC37, RPL6, RPL8, PAPOLA, PSMC1, CASP3, AKT2, MAP3K7IP2, POLR2L, TRADD, SMARCA4, HIST3H3, GNB2L1, PSMD1, PEBP1, HSPB1, TNIP1, RPS13, ZFAND5, YWHAQ, COMMD1, COPS3, POLR1D, SMARCC2, MAP3K3, BIRC3, UBE2D2, HDAC2, CASP8, MCM7, PSMD7, YWHAG, NFKBIA, CAST, YWHAB, G3BP2, PSMD13, FBL, RELB, YWHAZ, SKP1, UBE2D3, PDCD2, HSP90AA1, HDAC1, KPNA2, RPL30, GTF2I, PFDN2 |
| Colorectal cancer | CD9, EGFR, NGAL, CD81, STEAP, CD24, A33, CD66E, EPHA2, Ferritin, GPR30, GPR110, MMP9, OPN, p53, TMEM211, TROP2, TGM2, TIMP, EGFR, DR3, UNC93A, MUC17, EpCAM, MUC1, MUC2, TSG101, CD63, B7H3 |
| Colorectal cancer | DR3, STEAP, epha2, TMEM211, unc93A, A33, CD24, NGAL, EpCam, MUC17, TROP2, TETS |
| Colorectal cancer | A33, AFP, ALIX, ALX4, ANCA, APC, ASCA, AURKA, AURKB, B7H3, BANK1, BCNP, BDNF, CA-19-9, CCSA-2, CCSA-3&4, CD10, CD24, CD44, CD63, CD66 CEA, CD66e CEA, CD81, CD9, CDA, C-Erb2, CRMP-2, CRP, CRTN, CXCL12, CYFRA21-1, DcR3, DLL4, DR3, EGFR, Epcam, EphA2, FASL, FRT, GAL3, GDF15, GPCR (GPR110), GPR30, GRO-1, HBD 1, HBD2, HNP1-3, IL-1B, IL8, IMP3, L1CAM, LAMN, MACC-1, MGC20553, MCP-1, M-CSF, MIC1, MIF, MMP7, MMP9, MS4A1, MUC1, MUC17, MUC2, Ncam, NGAL, NNMT, OPN, p53, PCSA, PDGFRB, PRL, PSMA, PSME3, Reg IV, SCRN1, Sept-9, SPARC, SPON2, SPR, SRVN, TFF3, TGM2, TIMP-1, TMEM211, TNF-alpha, TPA, TPS, Trail-R2, Trail-R4, TrKB, TROP2, Tsg 101, TWEAK, UNC93A, VEGFA |
| Colorectal cancer | miR 92, miR 21, miR 9, miR 491 |
| Colorectal cancer | miR-127-3p, miR-92a, miR-486-3p, miR-378 |
| Colorectal cancer | TMEM211, MUC1, CD24 and/or GPR110 (GPCR 110) |
| Colorectal cancer | hsa-miR-376c, hsa-miR-215, hsa-miR-652, hsa-miR-582-5p, hsa-miR-324-5p, hsa-miR-1296, hsa-miR-28-5p, hsa-miR-190, hsa-miR-590-5p, hsa-miR-202, hsa-miR-195 |
| Colorectal cancer vesicle markers | A26C1A, A26C1B, A2M, ACAA2, ACE, ACOT7, ACP1, ACTA1, ACTA2, ACTB, ACTBL2, ACTBL3, ACTC1, ACTG1, ACTG2, ACTN1, ACTN2, ACTN4, ACTR3, ADAM10, ADSL, AGR2, AGR3, AGRN, AHCY, AHNAK, AKR1B10, ALB, ALDH16A1, ALDH1A1, ALDOA, ANXA1, ANXA11, ANXA2, ANXA2P2, ANXA4, ANXA5, ANXA6, AP2A1, AP2A2, APOA1, ARF1, ARF3, ARF4, ARF5, ARF6, ARHGDIA, ARPC3, ARPC5L, ARRDC1, ARVCF, ASCC3L1, ASNS, ATP1A1, ATP1A2, ATP1A3, ATP1B1, ATP4A, ATP5A1, ATP5B, ATP5I, ATP5L, ATP5O, ATP6AP2, B2M, BAIAP2, BAIAP2L1, BRI3BP, BSG, BUB3, C1orf58, C5orf32, CAD, CALM1, CALM2, CALM3, CAND1, CANX, CAPZA1, CBR1, CBR3, CCT2, CCT3, CCT4, CCT5, CCT6A, CCT7, CCT8, CD44, CD46, CD55, CD59, CD63, CD81, CD82, CD9, CDC42, CDH1, CDH17, CEACAM5, CFL1, CFL2, CHMP1A, CHMP2A, CHMP4B, CKB, CLDN3, CLDN4, CLDN7, CLIC1, CLIC4, CLSTN1, CLTC, CLTCL1, CLU, COL12A1, COPB1, COPB2, CORO1C, COX4I1, COX5B, CRYZ, CSPG4, CSRP1, CST3, CTNNA1, CTNNB1, CTNND1, CTTN, CYFIP1, DCD, DERA, DIP2A, DIP2B, DIP2C, DMBT1, DPEP1, DPP4, DYNC1H1, EDIL3, EEF1A1, EEF1A2, EEF1AL3, EEF1G, EEF2, EFNB1, EGFR, EHD1, EHD4, EIF3EIP, EIF3I, EIF4A1, EIF4A2, ENO1, ENO2, ENO3, EPHA2, EPHA5, EPHB1, EPHB2, EPHB3, EPHB4, EPPK1, ESD, EZR, F11R, F5, F7, FAM125A, FAM125B, FAM129B, FASLG, FASN, FAT, FCGBP, FER1L3, FKBP1A, FLNA, FLNB, FLOT1, FLOT2, G6PD, GAPDH, GARS, GCN1L1, GDI2, GK, GMDS, GNA13, GNAI2, GNAI3, GNAS, GNB1, GNB2, GNB2L1, GNB3, GNB4, GNG12, GOLGA7, GPA33, GPI, GPRC5A, GSN, GSTP1, H2AFJ, HADHA, hCG_1757335, HEPH, HIST1H2AB, HIST1H2AE, HIST1H2AJ, HIST1H2AK, HIST1H4A, HIST1H4B, HIST1H4C, HIST1H4D, HIST1H4E, HIST1H4F, HIST1H4H, HIST1H4I, HIST1H4J, HIST1H4K, HIST1H4L, HIST2H2AC, HIST2H4A, HIST2H4B, HIST3H2A, HIST4H4, HLA-A, HLA-A29.1, HLA-B, HLA-C, HLA-E, HLA-H, HNRNPA2B1, HNRNPH2, HPCAL1, HRAS, HSD17B4, HSP90AA1, HSP90AA2, HSP90AA4P, HSP90AB1, HSP90AB2P, HSP90AB3P, HSP90B1, HSPA1A, HSPA1B, HSPA1L, HSPA2, HSPA4, HSPA5, HSPA6, HSPA7, HSPA8, HSPA9, HSPD1, HSPE1, HSPG2, HYOU1, IDH1, IFITM1, IFITM2, IFITM3, IGH@, IGHG1, IGHG2, IGHG3, IGHG4, IGHM, IGHV4-31, IGK@, IGKC, IGKV1-5, IGKV2-24, IGKV3-20, IGSF3, IGSF8, IQGAP1, IQGAP2, ITGA2, ITGA3, ITGA6, ITGAV, ITGB1, ITGB4, JUP, KIAA0174, KIAA1199, KPNB1, KRAS, KRT1, KRT10, KRT13, KRT14, KRT15, KRT16, KRT17, KRT18, KRT19, KRT2, KRT20, KRT24, KRT25, KRT27, KRT28, KRT3, KRT4, KRT5, KRT6A, KRT6B, KRT6C, KRT7, KRT75, KRT76, KRT77, KRT79, KRT8, KRT9, LAMA5, LAMP1, LDHA, LDHB, LFNG, LGALS3, LGALS3BP, LGALS4, LIMA1, LIN7A, LIN7C, LOC100128936, LOC100130553, LOC100133382, LOC100133739, LOC284889, LOC388524, LOC388720, LOC442497, LOC653269, LRP4, LRPPRC, LRSAM1, LSR, LYZ, MAN1A1, MAP4K4, MARCKS, MARCKSL1, METRNL, MFGE8, MICA, MIF, MINK1, MITD1, MMP7, MOBKL1A, MSN, MTCH2, MUC13, MYADM, |

TABLE 4-continued

Illustrative Biomarkers

| Illustrative Class | Biomarkers |
|---|---|
| | MYH10, MYH11, MYH14, MYH9, MYL6, MYL6B, MYO1C, MYO1D, NARS, NCALD, NCSTN, NEDD4, NEDD4L, NME1, NME2, NOTCH1, NQO1, NRAS, P4HB, PCBP1, PCNA, PCSK9, PDCD6, PDCD6IP, PDIA3, PDXK, PEBP1, PFN1, PGK1, PHB, PHB2, PKM2, PLEC1, PLEKHB2, PLSCR3, PLXNA1, PLXNB2, PPIA, PPIB, PPP2R1A, PRDX1, PRDX2, PRDX3, PRDX5, PRDX6, PRKAR2A, PRKDC, PRSS23, PSMA2, PSMC6, PSMD11, PSMD3, PSME3, PTGFRN, PTPRF, PYGB, QPCT, QSOX1, RAB10, RAB11A, RAB11B, RAB13, RAB14, RAB15, RAB1A, RAB1B, RAB2A, RAB33B, RAB35, RAB43, RAB4B, RAB5A, RAB5B, RAB5C, RAB6A, RAB6B, RAB7A, RAB8A, RAB8B, RAC1, RAC3, RALA, RALB, RAN, RANP1, RAP1A, RAP1B, RAP2A, RAP2B, RAP2C, RDX, REG4, RHOA, RHOC, RHOG, ROCK2, RP11-631M21.2, RPL10A, RPL12, RPL6, RPL8, RPLP0, RPLP0-like, RPLP1, RPLP2, RPN1, RPS13, RPS14, RPS15A, RPS16, RPS18, RPS20, RPS21, RPS27A, RPS3, RPS4X, RPS4Y1, RPS4Y2, RPS7, RPS8, RPSA, RPSAP15, RRAS, RRAS2, RUVBL1, RUVBL2, S100A10, S100A11, S100A14, S100A16, S100A6, S100P, SDC1, SDC4, SDCBP, SDCBP2, SERINC1, SERINC5, SERPINA1, SERPINF1, SETD4, SFN, SLC12A2, SLC12A7, SLC16A1, SLC1A5, SLC25A4, SLC25A5, SLC25A6, SLC29A1, SLC2A1, SLC3A2, SLC44A1, SLC7A5, SLC9A3R1, SMPDL3B, SNAP23, SND1, SOD1, SORT1, SPTAN1, SPTBN1, SSBP1, SSR4, TACSTD1, TAGLN2, TBCA, TCEB1, TCP1, TF, TFRC, THBS1, TJP2, TKT, TMED2, TNFSF10, TNIK, TNKS1BP1, TNPO3, TOLLIP, TOMM22, TPI1, TPM1, TRAP1, TSG101, TSPAN1, TSPAN14, TSPAN15, TSPAN6, TSPAN8, TSTA3, TTYH3, TUBA1A, TUBA1B, TUBA1C, TUBA3C, TUBA3D, TUBA3E, TUBA4A, TUBA4B, TUBAS, TUBB, TUBB2A, TUBB2B, TUBB2C, TUBB3, TUBB4, TUBB4Q, TUBB6, TUFM, TXN, UBA1, UBA52, UBB, UBC, UBE2N, UBE2V2, UGDH, UQCRC2, VAMP1, VAMP3, VAMP8, VCP, VIL1, VPS25, VPS28, VPS35, VPS36, VPS37B, VPS37C, WDR1, YWHAB, YWHAE, YWHAG, YWHAH, YWHAQ, YWHAZ |
| Colorectal Cancer | hsa-miR-16, hsa-miR-25, hsa-miR-125b, hsa-miR-451, hsa-miR-200c, hsa-miR-140-3p, hsa-miR-658, hsa-miR-370, hsa-miR-1296, hsa-miR-636, hsa-miR-502-5p |
| Breast cancer | miR-21, miR-155, miR-206, miR-122a, miR-210, miR-21, miR-155, miR-206, miR-122a, miR-210, let-7, miR-10b, miR-125a, miR-125b, miR-145, miR-143, miR-145, miR-1b |
| Breast cancer | GAS5 |
| Breast cancer | ER, PR, HER2, MUC1, EGFR, KRAS, B-Raf, CYP2D6, hsp70, MART-1, TRP, HER2, hsp70, MART-1, TRP, HER2, ER, PR, Class III b-tubulin, VEGFA, ETV6-NTRK3, BCA-225, hsp70, MART1, ER, VEGFA, Class III b-tubulin, HER2/neu (e.g., for Her2+ breast cancer), GPR30, ErbB4 (JM) isoform, MPR8, MISIIR, CD9, EphA2, EGFR, B7H3, PSM, PCSA, CD63, STEAP, CD81, ICAM1, A33, DR3, CD66e, MFG-E8, TROP-2, Mammaglobin, Hepsin, NPGP/NPFF2, PSCA, 5T4, NGAL, EpCam, neurokinin receptor-1 (NK-1 or NK-1R), NK-2, Pai-1, CD45, CD10, HER2/ERBB2, AGTR1, NPY1R, MUC1, ESA, CD133, GPR30, BCA225, CD24, CA15.3 (MUC1 secreted), CA27.29 (MUC1 secreted), NMDAR1, NMDAR2, MAGEA, CTAG1B, NY-ESO-1, SPB, SPC, NSE, PGP9.5, progesterone receptor (PR) or its isoform (PR(A) or PR(B)), P2RX7, NDUFB7, NSE, GAL3, osteopontin, CHI3L1, IC3b, mesothelin, SPA, AQP5, GPCR, hCEA-CAM, PTP IA-2, CABYR, TMEM211, ADAM28, UNC93A, MUC17, MUC2, IL10R-beta, BCMA, HVEM/TNFRSF14, Trappin-2, Elafin, ST2/IL1 R4, TNFRF14, CEACAM1, TPA1, LAMP, WF, WH1000, PECAM, BSA, TNFR |
| Breast cancer | CD9, MIS Rii, ER, CD63, MUC1, HER3, STAT3, VEGFA, BCA, CA125, CD24, EPCAM, ERB B4 |
| Breast cancer | CD10, NPGP/NPFF2, HER2/ERBB2, AGTR1, NPY1R, neurokinin receptor-1 (NK-1 or NK-1R), NK-2, MUC1, ESA, CD133, GPR30, BCA225, CD24, CA15.3 (MUC1 secreted), CA27.29 (MUC1 secreted), NMDAR1, NMDAR2, MAGEA, CTAG1B, NY-ESO-1 |
| Breast cancer | SPB, SPC, NSE, PGP9.5, CD9, P2RX7, NDUFB7, NSE, GAL3, osteopontin, CHI3L1, EGFR, B7H3, IC3b, MUC1, mesothelin, SPA, PCSA, CD63, STEAP, AQP5, CD81, DR3, PSM, GPCR, EphA2, hCEA-CAM, PTP IA-2, CABYR, TMEM211, ADAM28, UNC93A, A33, CD24, CD10, NGAL, EpCam, MUC17, TROP-2, MUC2, IL10R-beta, BCMA, HVEM/TNFRSF14, Trappin-2 Elafin, ST2/IL1 R4, TNFRF14, CEACAM1, TPA1, LAMP, WF, WH1000, PECAM, BSA, TNFR |
| Breast cancer | BRCA, MUC-1, MUC 16, CD24, ErbB4, ErbB2 (HER2), ErbB3, HSP70, Mammaglobin, PR, PR(B), VEGFA |
| Breast cancer | CD9, HSP70, Gal3, MIS, EGFR, ER, ICB3, CD63, B7H4, MUC1, DLL4, CD81, ERB3, VEGF, BCA225, BRCA, CA125, CD174, CD24, ERB2, NGAL, GPR30, CYFRA21, CD31, cMET, MUC2, ERBB4 |
| Breast cancer | CD9, EphA2, EGFR, B7H3, PSMA, PCSA, CD63, STEAP, CD81, STEAP1, ICAM1 (CD54), PSMA, A33, DR3, CD66e, MFG-8e, TMEM211, TROP-2, EGFR, Mammoglobin, Hepsin, NPGP/NPFF2, PSCA, 5T4, NGAL, NK-2, EpCam, NK-1R, PSMA, 5T4, PAI-1, CD45 |
| Breast cancer | PGP9.5, CD9, HSP70, gal3-b2c10, EGFR, iC3b, PSMA, PCSA, CD63, MUC1, DLL4, CD81, B7-H3, HER 3 (ErbB3), MART-1, PSA, VEGF A, TIMP-1, GPCR GPR110, EphA2, MMP9, mmp7, TMEM211, UNC93a, BRCA, CA125 (MUC16), Mammaglobin, CD174 (Lewis y), CD66e CEA, CD24 c.sn3, C-erbB2, CD10, NGAL, epcam, CEA (carcinoembryonic Antigen), GPR30, CYFRA21-1, OPN, MUC17, hVEGFR2, MUC2, NCAM, ASPH, ErbB4, SPB, SPC, CD9, MS4A1, EphA2, MIS RII, HER2 (ErbB2), ER, PR (B), MRP8, CD63, B7H4, TGM2, CD81, DR3, STAT 3, MACC-1, TrKB, IL 6 Unc, OPG - 13, IL6R, EZH2, SCRN1, TWEAK, SERPINB3, CDAC1, BCA-225, DR3, A33, NPGP/NPFF2, TIMP1, BDNF, FRT, Ferritin heavy chain, seprase, p53, LDH, HSP, ost, p53, CXCL12, HAP, CRP, Gro-alpha, Tsg 101, GDF15 |

TABLE 4-continued

Illustrative Biomarkers

| Illustrative Class | Biomarkers |
|---|---|
| Breast cancer | CD9, HSP70, Gal3, MIS (RII), EGFR, ER, ICB3, CD63, B7H4, MUC1, CD81, ERB3, MART1, STAT3, VEGF, BCA225, BRCA, CA125, CD174, CD24, ERB2, NGAL, GPR30, CYFRA21, CD31, cMET, MUC2, ERB4, TMEM211 |
| Breast Cancer | 5T4 (trophoblast), ADAM10, AGER/RAGE, APC, APP (β-amyloid), ASPH (A-10), B7H3 (CD276), BACE1, BAI3, BRCA1, BDNF, BIRC2, C1GALT1, CA125 (MUC16), Calmodulin 1, CCL2 (MCP-1), CD9, CD10, CD127 (IL7R), CD174, CD24, CD44, CD63, CD81, CEA, CRMP-2, CXCR3, CXCR4, CXCR6, CYFRA 21, derlin 1, DLL4, DPP6, E-CAD, EpCaM, EphA2 (H-77), ER(1) ESR1 α, ER(2) ESR2 β, Erb B4, Erbb2, erb3 (Erb-B3), PA2G4, FRT (FLT1), Gal3, GPR30 (G-coupled ER1), HAP1, HER3, HSP-27, HSP70, IC3b, IL8, insig, junction plakoglobin, Keratin 15, KRAS, Mammaglobin, MART1, MCT2, MFGE8, MMP9, MRP8, Muc1, MUC17, MUC2, NCAM, NG2 (CSPG4), Ngal, NHE-3, NT5E (CD73), ODC1, OPG, OPN, p53, PARK7, PCSA, PGP9.5 (PARK5), PR(B), PSA, PSMA, RAGE, STXBP4, Survivin, TFF3 (secreted), TIMP1, TIMP2, TMEM211, TRAF4 (scaffolding), TRAIL-R2 (death Receptor 5), TrkB, Tsg 101, UNC93a, VEGF A, VEGFR2, YB-1, VEGFR1, GCDPF-15 (PIP), BigH3 (TGFb1-induced protein), 5HT2B (serotonin receptor 2B), BRCA2, BACE 1, CDH1—cadherin |
| Breast Cancer | AK5.2, ATP6V1B1, CRABP1 |
| Breast Cancer | DST.3, GATA3, KRT81 |
| Breast Cancer | AK5.2, ATP6V1B1, CRABP1, DST.3, ELF5, GATA3, KRT81, LALBA, OXTR, RASL10A, SERHL, TFAP2A.1, TFAP2A.3, TFAP2C, VTCN1 |
| Breast Cancer | TRAP; Renal Cell Carcinoma; Filamin; 14.3.3, Pan; Prohibitin; c-fos; Ang-2; GSTmu; Ang-1; FHIT; Rad51; Inhibin alpha; Cadherin-P; 14.3.3 gamma; p18INK4c; P504S; XRCC2; Caspase 5; CREB-Binding Protein; Estrogen Receptor; IL17; Claudin 2; Keratin 8; GAPDH; CD1; Keratin, LMW; Gamma Glutamylcysteine Synthetase(GCS)/Glutamate-cysteine Ligase; a-B-Crystallin; Pax-5; MMP-19; APC; IL-3; Keratin 8 (phospho-specific Ser73); TGF-beta 2; ITK; Oct-2/; DJ-1; B7-H2; Plasma Cell Marker; Rad18; Estriol; Chk1; Prolactin Receptor; Laminin Receptor; Histone H1; CD45RO; GnRH Receptor; IP10/CRG2; Actin, Muscle Specific; S100; Dystrophin; Tubulin-a; CD3zeta; CDC37; GABA a Receptor 1; MMP-7 (Matrilysin); Heregulin; Caspase 3; CD56/NCAM-1; Gastrin 1; SREBP-1 (Sterol Regulatory Element Binding Protein-1); MLH1; PGP9.5; Factor VIII Related Antigen; ADP-ribosylation Factor (ARF-6); MHC II (HLA-DR) Ia; Survivin; CD23; G-CSF; CD2; Calretinin; Neuron Specific Enolase; CD165; Calponin; CD95/Fas; Urocortin; Heat Shock Protein 27/hsp27; Topo II beta; Insulin Receptor; Keratin 5/8; sm; Actin, skeletal muscle; CA19-9; GluR1; GRIP1; CD79a mb-1; TdT; HRP; CD94; CCK-8; Thymidine Phosphorylase; CD57; Alkaline Phosphatase (AP); CD59/MACIF/MIRL/Protectin; GLUT-1; alpha-1-antitrypsin; Presenillin; Mucin 3 (MUC3); pS2; 14-3-3 beta; MMP-13 (Collagenase-3); Fli-1; mGluR5; Mast Cell Chymase; Laminin B1/b1; Neurofilament (160 kDa); CNPase; Amylin Peptide; Gai1; CD6; alpha-1-antichymotrypsin; E2F-2; MyoD1 |
| Ductal carcinoma in situ (DCIS) | Laminin B1/b1; E2F-2; TdT; Apolipoprotein D; Granulocyte; Alkaline Phosphatase (AP); Heat Shock Protein 27/hsp27; CD95/Fas; pS2; Estriol; GLUT-1; Fibronectin; CD6; CCK-8; sm; Factor VIII Related Antigen; CD57; Plasminogen; CD71/Transferrin Receptor; Keratin 5/8; Thymidine Phosphorylase; CD45/T200/LCA; Epithelial Specific Antigen; Macrophage; CD10; MyoD1; Gai1; bcl-XL; hPL; Caspase 3; Actin, skeletal muscle; IP10/CRG2; GnRH Receptor; p35nck5a; ADP-ribosylation Factor (ARF-6); Cdk4 ; alpha-1-antitrypsin; IL17; Neuron Specific Enolase; CD56/NCAM-1; Prolactin Receptor; Cdk7; CD79a mb-1; Collagen IV; CD94; Myeloid Specific Marker; Keratin 10; Pax-5; IgM (m-Heavy Chain); CD45RO; CA19-9; Mucin 2; Glucagon; Mast Cell Chymase; MLH1; CD1; CNPase; Parkin; MHC II (HLA-DR) Ia; B7-H2; Chk1; Lambda Light Chain; MHC II (HLA-DP and DR); Myogenin; MMP-7 (Matrilysin); Topo II beta; CD53; Keratin 19; Rad18; Ret Oncoprotein; MHC II (HLA-DP); E3-binding protein (ARM1); Progesterone Receptor; Keratin 8; IgG; IgA; Tubulin; Insulin Receptor Substrate-1; Keratin 15; DR3; IL-3; Keratin 10/13; Cyclin D3; MHC I (HLA25 and HLA-Aw32); Calmodulin; Neurofilament (160 kDa) |
| Ductal carcinoma in situ (DCIS) v. other Breast cancer | Macrophage; Fibronectin; Granulocyte; Keratin 19; Cyclin D3; CD45/T200/LCA; EGFR; Thrombospondin; CD81/TAPA-1; Ruv C; Plasminogen; Collagen IV; Laminin B1/b1; CD10; TdT; Filamin; bcl-XL; 14.3.3 gamma; 14.3.3, Pan; p170; Apolipoprotein D; CD71/Transferrin Receptor; FHIT |
| Breast cancer | 5HT2B, 5T4 (trophoblast), ACO2, ACSL3, ACTN4, ADAM10, AGR2, AGR3, ALCAM, ALDH6A1, ANGPTL4, ANO9, AP1G1, APC, APEX1, APLP2, APP (_-amyloid), ARCN1, ARHGAP35, ARL3, ASAH1, ASPH (A-10), ATP1B1, ATP1B3, ATP5I, ATP5O, ATXN1, B7H3, BACE1, BAI3, BAIAP2, BCA-200, BDNF, BigH3, BIRC2, BLVRB, BRCA, BST2, C1GALT1, C1GALT1C1, C20orf3, CA125, CACYBP, Calmodulin, CAPN1, CAPNS1, CCDC64B, CCL2 (MCP-1), CCT3, CD10(BD), CD127 (IL7R), CD174, CD24, CD44, CD80, CD86, CDH1, CDH5, CEA, CFL2, CHCHD3, CHMP3, CHRDL2, CIB1, CKAP4, COPA, COX5B, CRABP2, CRIP1, CRISPLD1, CRMP-2, CRTAP, CTLA4, CUL3, CXCR3, CXCR4, CXCR6, CYB5B, CYB5R1, CYCS, CYFRA 21, DBI, DDX23, DDX39B, derlin 1, DHCR7, DHX9, DLD, DLL4, DNAJB1, DPP6, DSTN, eCadherin, EEF1D, EEF2, EFTUD2, EIF4A2, EIF4A3, EpCaM, EphA2, ER(1) ESR1_, ER(2) ESR2_, Erb B4, Erb2, erb3 (Erb-B3?), ERLIN2, ESD, FARSA, FASN, FEN1, FKBP5, FLNB, FOXP3, FUS, Gal3, GCDPF-15, GCNT2, GNA12, GNG5, GNPTG, GPC6, GPD2, GPER (GPR30), GSPT1, H3F3B, H3F3C, HADH, HAP1, HER3, HIST1H1C, HIST1H2AB, HIST1H3A, HIST1H3C, HIST1H3D, HIST1H3E, HIST1H3F, HIST1H3G, HIST1H3H, HIST1H3I, HIST1H3J, HIST2H2BF, HIST2H3A, HIST2H3C, HIST2H3D, HIST3H3, HMGB1, HNRNPA2B1, HNRNPAB, HNRNPC, HNRNPD, HNRNPH2, HNRNPK, HNRNPL, HNRNPM, HNRNPU, HPS3, HSP-27, HSP70, HSP90B1, HSPA1A, HSPA2, HSPA9, HSPE1, IC3b, IDE, IDH3B, IDO1, IFI30, IL1RL2, IL7, IL8, ILF2, ILF3, IQCG, ISOC2, IST1, ITGA7, ITGB7, junction plakoglobin, Keratin 15, KRAS, KRT19, KRT2, KRT7, KRT8, KRT9, |

TABLE 4-continued

Illustrative Biomarkers

| Illustrative Class | Biomarkers |
|---|---|
| | KTN1, LAMP1, LMNA, LMNB1, LNPEP, LRPPRC, LRRC57, Mammaglobin, MAN1A1, MAN1A2, MART1, MATR3, MBD5, MCT2, MDH2, MFGE8, MFGE8, MGP, MMP9, MRP8, MUC1, MUC17, MUC2, MYO5B, MYOF, NAPA, NCAM, NCL, NG2 (CSPG4), Ngal, NHE-3, NME2, NONO, NPM1, NQO1, NT5E (CD73), ODC1, OPG, OPN (SC), OS9, p53, PACSIN3, PAICS, PARK7, PARVA, PC, PCNA, PCSA, PD-1, PD-L1, PD-L2, PGP9.5, PHB, PHB2, PIK3C2B, PKP3, PPL, PR(B)?, PRDX2, PRKCB, PRKCD, PRKDC, PSA, PSAP, PSMA, PSMB7, PSMD2, PSME3, PYCARD, RAB1A, RAB3D, RAB7A, RAGE, RBL2, RNPEP, RPL14, RPL27, RPL36, RPS25, RPS4X, RPS4Y1, RPS4Y2, RUVBL2, SET, SHMT2, SLAIN1, SLC39A14, SLC9A3R2, SMARCA4, SNRPD2, SNRPD3, SNX33, SNX9, SPEN, SPR, SQSTM1, SSBP1, ST3GAL1, STXBP4, SUB1, SUCLG2, Survivin, SYT9, TFF3 (secreted), TGOLN2, THBS1, TIMP1, TIMP2, TMED10, TMED4, TMED9, TMEM211, TOM1, TRAF4 (scaffolding), TRAIL-R2, TRAP1, TrkB, Tsg 101, TXNDC16, U2AF2, UEVLD, UFC1, UNC93a, USP14, VASP, VCP, VDAC1, VEGFA, VEGFR1, VEGFR2, VPS37C, WIZ, XRCC5, XRCC6, YB-1, YWHAZ |
| Lung cancer | Pgrmc1 (progesterone receptor membrane component 1)/sigma-2 receptor, STEAP, EZH2 |
| Lung cancer | Prohibitin, CD23, Amylin Peptide, HRP, Rad51, Pax-5, Oct-3/, GLUT-1, PSCA, Thrombospondin, FHIT, a-B-Crystallin, LewisA, Vacular Endothelial Growth Factor(VEGF), Hepatocyte Factor Homologue-4, Flt-4, GluR6/7, Prostate Apoptosis Response Protein-4, GluR1, Fli-1, Urocortin, S100A4, 14-3-3 beta, P504S, HDAC1, PGP9.5, DJ-1, COX2, MMP-19, Actin, skeletal muscle, Claudin 3, Cadherin-P, Collagen IX, p27Kip1, Cathepsin D, CD30 (Reed-Sternberg Cell Marker), Ubiquitin, FSH-b, TrxR2, CCK-8, Cyclin C, CD138, TGF-beta 2, Adrenocorticotrophic Hormone, PPAR-gamma, Bcl-6, GLUT-3, IGF-I, mRANKL, Fas-ligand, Filamin, Calretinin, O ct-1, Parathyroid Hormone, Claudin 5, Claudin 4, Raf-1 (Phospho-specific), CDC14A Phosphatase, Mitochondria, APC, Gastrin 1, Ku (p80), Gai1, XPA, Maltose Binding Protein, Melanoma (gp100), Phosphotyrosine, Amyloid A, CXCR4/Fusin, Hepatic Nuclear Factor-3B, Caspase 1, HPV 16-E7, Axonal Growth Cones, Lck, Ornithine Decarboxylase, Gamma Glutamylcysteine Synthetase(GCS)/Glutamate-cysteine Ligase, ERCC1, Calmodulin, Caspase 7 (Mch 3), CD137 (4-1BB), Nitric Oxide Synthase, brain (bNOS), E2F-2, IL-10R, L-Plastin, CD18, Vimentin, CD50/ICAM-3, Superoxide Dismutase, Adenovirus Type 5 E1A, PHAS-I, Progesterone Receptor (phospho-specific) - Serine 294, MHC II (HLA-DQ), XPG, ER Ca+2 ATPase2, Laminin-s, E3-binding protein (ARM1), CD45RO, CD1, Cdk2, MMP-10 (Stromilysin-2), sm, Surfactant Protein B (Pro), Apolipoprotein D, CD46, Keratin 8 (phospho-specific Ser73), PCNA, PLAP, CD20, Syk, LH, Keratin 19, ADP-ribosylation Factor (ARF-6), Int-2 Oncoprotein, Luciferase, AIF (Apoptosis Inducing Factor), Grb2, bcl-X, CD16, Paxillin, MHC II (HLA-DP and DR), B-Cell, p21WAF1, MHC II (HLA-DR), Tyrosinase, E2F-1, Pds1, Calponin, Notch, CD26/DPP IV, SV40 Large T Antigen, Ku (p70/p80), Perforin, XPF, SIM Ag (SIMA-4D3), Cdk1/p34cdc2, Neuron Specific Enolase, b-2-Microgulin, DNA Polymerase Beta, Thyroid Hormone Receptor, Human, Alkaline Phosphatase (AP), Plasma Cell Marker, Heat Shock Protein 70/hsp70, TRP75/gp75, SRF (Serum Response Factor), Laminin B1/b1, Mast Cell Chymase, Caldesmon, CEA/CD66e, CD24, Retinoid X Receptor (hRXR), CD45/T200/LCA, Rabies Virus, Cytochrome c, DR3, bcl-XL, Fascin, CD71/Transferrin Receptor |
| Lung Cancer | miR-497 |
| Lung Cancer | Pgrmc1 |
| Ovarian Cancer | CA-125, CA 19-9, c-reactive protein, CD95(also called Fas, Fas antigen, Fas receptor, FasR, TNFRSF6, APT1 or APO-1), FAP-1, miR-200 microRNAs, EGFR, EGFRvIII, apolipoprotein AI, apolipoprotein CIII, myoglobin, tenascin C, MSH6, claudin-3, claudin-4, caveolin-1, coagulation factor III, CD9, CD36, CD37, CD53, CD63, CD81, CD136, CD147, Hsp70, Hsp90, Rab13, Desmocollin-1, EMP-2, CK7, CK20, GCDF15, CD82, Rab-5b, Annexin V, MFG-E8, HLA-DR. MiR-200 microRNAs (miR-200a, miR-200b, miR-200c), miR-141, miR-429, JNK, Jun |
| Prostate Cancer v normal | AQP2, BMP5, C16orf86, CXCL13, DST, ERCC1, GNAO1, KLHL5, MAP4K1, NELL2, PENK, PGF, POU3F1, PRSS21, SCML1, SEMG1, SMARCD3, SNAI2, TAF1C, TNNT3 |
| Prostate Cancer v Breast Cancer | ADRB2, ARG2, C22orf32, CYorf14, EIF1AY, FEV, KLK2, KLK4, LRRC26, MAOA, NLGN4Y, PNPLA7, PVRL3, SIM2, SLC30A4, SLC45A3, STX19, TRIM36, TRPM8 |
| Prostate Cancer v Colorectal Cancer | ADRB2, BAIAP2L2, C19orf33, CDX1, CEACAM6, EEF1A2, ERN2, FAM110B, FOXA2, KLK2, KLK4, LOC389816, LRRC26, MIPOL1, SLC45A3, SPDEF, TRIM31, TRIM36, ZNF613 |
| Prostate Cancer v Lung Cancer | ASTN2, CAB39L, CRIP1, FAM110B, FEV, GSTP1, KLK2, KLK4, LOC389816, LRRC26, MUC1, PNPLA7, SIM2, SLC45A3, SPDEF, TRIM36, TRPV6, ZNF613 |
| Prostate Cancer | miRs-26a + b, miR-15, miR-16, miR-195, miR-497, miR-424, miR-206, miR-342-5p, miR-186, miR-1271, miR-600, miR-216b, miR-519 family, miR-203 |
| Integrins | ITGA1 (CD49a, VLA1), ITGA2 (CD49b, VLA2), ITGA3 (CD49c, VLA3), ITGA4 (CD49d, VLA4), ITGA5 (CD49e, VLA5), ITGA6 (CD49f, VLA6), ITGA7 (FLJ25220), ITGA8, ITGA9 (RLC), ITGA10, ITGA11 (HsT18964), ITGAD (CD11D, FLJ39841), ITGAE (CD103, HUMINAE), ITGAL (CD11a, LFA1A), ITGAM (CD11b, MAC-1), ITGAV (CD51, VNRA, MSK8), ITGAW, ITGAX (CD11c), ITGB1 (CD29, FNRB, MSK12, MDF20), ITGB2 (CD18, LFA-1, MAC-1, MFI7), ITGB3 (CD61, GP3A, GPIIIa), ITGB4 (CD104), ITGB5 (FLJ26658), ITGB6, ITGB7, ITGB8 |
| Glycoprotein | GpIa-IIa, GpIIb-IIIa, GpIIIb, GpIb, GpIX |
| Transcription factors | STAT3, EZH2, p53, MACC1, SPDEF, RUNX2, YB-1 |
| Kinases | AURKA, AURKB |
| Disease Markers | 6Ckine, Adiponectin, Adrenocorticotropic Hormone, Agouti-Related Protein, Aldose Reductase, Alpha-1-Antichymotrypsin, Alpha-1-Antitrypsin, Alpha-1-Microglobulin, Alpha- |

TABLE 4-continued

Illustrative Biomarkers

| Illustrative Class | Biomarkers |
|---|---|
| | 2-Macroglobulin, Alpha-Fetoprotein, Amphiregulin, Angiogenin, Angiopoietin-2, Angiotensin-Converting Enzyme, Angiotensinogen, Annexin A1, Apolipoprotein A-I, Apolipoprotein A-II, Apolipoprotein A-IV, Apolipoprotein B, Apolipoprotein C-I, Apolipoprotein C-III, Apolipoprotein D, Apolipoprotein E, Apolipoprotein H, Apolipoprotein(a), AXL Receptor Tyrosine Kinase, B cell-activating Factor, B Lymphocyte Chemoattractant, Bcl-2-like protein 2, Beta-2-Microglobulin, Betacellulin, Bone Morphogenetic Protein 6, Brain-Derived Neurotrophic Factor, Calbindin, Calcitonin, Cancer Antigen 125, Cancer Antigen 15-3, Cancer Antigen 19-9, Cancer Antigen 72-4, Carcinoembryonic Antigen, Cathepsin D, CD 40 antigen, CD40 Ligand, CD5 Antigen-like, Cellular Fibronectin, Chemokine CC-4, Chromogranin-A, Ciliary Neurotrophic Factor, Clusterin, Collagen IV, Complement C3, Complement Factor H, Connective Tissue Growth Factor, Cortisol, C-Peptide, C-Reactive Protein, Creatine Kinase-MB, Cystatin-C, Endoglin, Endostatin, Endothelin-1, EN-RAGE, Eotaxin-1, Eotaxin-2, Eotaxin-3, Epidermal Growth Factor, Epiregulin, Epithelial cell adhesion molecule, Epithelial-Derived Neutrophil-Activating Protein 78, Erythropoietin, E-Selectin, Ezrin, Factor VII, Fas Ligand, FASLG Receptor, Fatty Acid-Binding Protein (adipocyte), Fatty Acid-Binding Protein (heart), Fatty Acid-Binding Protein (liver), Ferritin, Fetuin-A, Fibrinogen, Fibroblast Growth Factor 4, Fibroblast Growth Factor basic, Fibulin-1C, Follicle-Stimulating Hormone, Galectin-3, Gelsolin, Glucagon, Glucagon-like Peptide 1, Glucose-6-phosphate Isomerase, Glutamate-Cysteine Ligase Regulatory subunit, Glutathione S-Transferase alpha, Glutathione S-Transferase Mu 1, Granulocyte Colony-Stimulating Factor, Granulocyte-Macrophage Colony-Stimulating Factor, Growth Hormone, Growth-Regulated alpha protein, Haptoglobin, HE4, Heat Shock Protein 60, Heparin-Binding EGF-Like Growth Factor, Hepatocyte Growth Factor, Hepatocyte Growth Factor Receptor, Hepsin, Human Chorionic Gonadotropin beta, Human Epidermal Growth Factor Receptor 2, Immunoglobulin A, Immunoglobulin E, Immunoglobulin M, Insulin, Insulin-like Growth Factor I, Insulin-like Growth Factor-Binding Protein 1, Insulin-like Growth Factor-Binding Protein 2, Insulin-like Growth Factor-Binding Protein 3, Insulin-like Growth Factor Binding Protein 4, Insulin-like Growth Factor Binding Protein 5, Insulin-like Growth Factor Binding Protein 6, Intercellular Adhesion Molecule 1, Interferon gamma, Interferon gamma Induced Protein 10, Interferon-inducible T-cell alpha chemoattractant, Interleukin-1 alpha, Interleukin-1 beta, Interleukin-1 Receptor antagonist, Interleukin-2, Interleukin-2 Receptor alpha, Interleukin-3, Interleukin-4, Interleukin-5, Interleukin-6, Interleukin-6 Receptor, Interleukin-6 Receptor subunit beta, Interleukin-7, Interleukin-8, Interleukin-10, Interleukin-11, Interleukin-12 Subunit p40, Interleukin-12 Subunit p70, Interleukin-13, Interleukin-15, Interleukin-16, Interleukin-25, Kallikrein 5, Kallikrein-7, Kidney Injury Molecule-1, Lactoylglutathione lyase, Latency-Associated Peptide of Transforming Growth Factor beta 1, Lectin-Like Oxidized LDL Receptor 1, Leptin, Luteinizing Hormone, Lymphotactin, Macrophage Colony-Stimulating Factor 1, Macrophage Inflammatory Protein-1 alpha, Macrophage Inflammatory Protein-1 beta, Macrophage Inflammatory Protein-3 alpha, Macrophage inflammatory protein 3 beta, Macrophage Migration Inhibitory Factor, Macrophage-Derived Chemokine, Macrophage-Stimulating Protein, Malondialdehyde-Modified Low-Density Lipoprotein, Maspin, Matrix Metalloproteinase-1, Matrix Metalloproteinase-2, Matrix Metalloproteinase-3, Matrix Metalloproteinase-7, Matrix Metalloproteinase-9, Matrix Metalloproteinase-9, Matrix Metalloproteinase-10, Mesothelin, MHC class I chain-related protein A, Monocyte Chemotactic Protein 1, Monocyte Chemotactic Protein 2, Monocyte Chemotactic Protein 3, Monocyte Chemotactic Protein 4, Monokine Induced by Gamma Interferon, Myeloid Progenitor Inhibitory Factor 1, Myeloperoxidase, Myoglobin, Nerve Growth Factor beta, Neuronal Cell Adhesion Molecule, Neuron-Specific Enolase, Neuropilin-1, Neutrophil Gelatinase-Associated Lipocalin, NT-proBNP, Nucleoside diphosphate kinase B, Osteopontin, Osteoprotegerin, Pancreatic Polypeptide, Pepsinogen I, Peptide YY, Peroxiredoxin-4, Phosphoserine Aminotransferase, Placenta Growth Factor, Plasminogen Activator Inhibitor 1, Platelet-Derived Growth Factor BB, Pregnancy-Associated Plasma Protein A, Progesterone, Proinsulin (inc. Total or Intact), Prolactin, Prostasin, Prostate-Specific Antigen (inc. Free PSA), Prostatic Acid Phosphatase, Protein S100-A4, Protein S100-A6, Pulmonary and Activation-Regulated Chemokine, Receptor for advanced glycosylation end products, Receptor tyrosine-protein kinase erbB-3, Resistin, S100 calcium-binding protein B, Secretin, Serotransferrin, Serum Amyloid P-Component, Serum Glutamic Oxaloacetic Transaminase, Sex Hormone-Binding Globulin, Sortilin, Squamous Cell Carcinoma Antigen-1, Stem Cell Factor, Stromal cell-derived Factor-1, Superoxide Dismutase 1 (soluble), T Lymphocyte-Secreted Protein I-309, Tamm-Horsfall Urinary Glycoprotein, T-Cell-Specific Protein RANTES, Tenascin-C, Testosterone, Tetranectin, Thrombomodulin, Thrombopoietin, Thrombospondin-1, Thyroglobulin, Thyroid-Stimulating Hormone, Thyroxine-Binding Globulin, Tissue Factor, Tissue Inhibitor of Metalloproteinases 1, Tissue type Plasminogen activator, TNF-Related Apoptosis-Inducing Ligand Receptor 3, Transforming Growth Factor alpha, Transforming Growth Factor beta-3, Transthyretin, Trefoil Factor 3, Tumor Necrosis Factor alpha, Tumor Necrosis Factor beta, Tumor Necrosis Factor Receptor I, Tumor necrosis Factor Receptor 2, Tyrosine kinase with Ig and EGF homology domains 2, Urokinase-type Plasminogen Activator, Urokinase-type plasminogen activator Receptor, Vascular Cell Adhesion Molecule-1, Vascular Endothelial Growth Factor, Vascular endothelial growth Factor B, Vascular Endothelial Growth Factor C, Vascular endothelial growth Factor D, Vascular Endothelial Growth Factor Receptor 1, Vascular Endothelial Growth Factor Receptor 2, Vascular endothelial growth Factor Receptor 3, Vitamin K-Dependent Protein S, Vitronectin, von Willebrand Factor, YKL-40 |
| Disease Markers | Adiponectin, Adrenocorticotropic Hormone, Agouti-Related Protein, Alpha-1-Antichymotrypsin, Alpha-1-Antitrypsin, Alpha-1-Microglobulin, Alpha-2-Macroglobulin, |

TABLE 4-continued

Illustrative Biomarkers

| Illustrative Class | Biomarkers |
|---|---|
| | Alpha-Fetoprotein, Amphiregulin, Angiopoietin-2, Angiotensin-Converting Enzyme, Angiotensinogen, Apolipoprotein A-I, Apolipoprotein A-II, Apolipoprotein A-IV, Apolipoprotein B, Apolipoprotein C-I, Apolipoprotein C-III, Apolipoprotein D, Apolipoprotein E, Apolipoprotein H, Apolipoprotein(a), AXL Receptor Tyrosine Kinase, B Lymphocyte Chemoattractant, Beta-2-Microglobulin, Betacellulin, Bone Morphogenetic Protein 6, Brain-Derived Neurotrophic Factor, Calbindin, Calcitonin, Cancer Antigen 125, Cancer Antigen 19-9, Carcinoembryonic Antigen, CD 40 antigen, CD40 Ligand, CD5 Antigen-like, Chemokine CC-4, Chromogranin-A, Ciliary Neurotrophic Factor, Clusterin, Complement C3, Complement Factor H, Connective Tissue Growth Factor, Cortisol, C-Peptide, C-Reactive Protein, Creatine Kinase-MB, Cystatin-C, Endothelin-1, EN-RAGE, Eotaxin-1, Eotaxin-3, Epidermal Growth Factor, Epiregulin, Epithelial-Derived Neutrophil-Activating Protein 78, Erythropoietin, E-Selectin, Factor VII, Fas Ligand, FASLG Receptor, Fatty Acid-Binding Protein (heart), Ferritin, Fetuin-A, Fibrinogen, Fibroblast Growth Factor 4, Fibroblast Growth Factor basic, Follicle-Stimulating Hormone, Glucagon, Glucagon-like Peptide 1, Glutathione S-Transferase alpha, Granulocyte Colony-Stimulating Factor, Granulocyte-Macrophage Colony-Stimulating Factor, Growth Hormone, Growth-Regulated alpha protein, Haptoglobin, Heat Shock Protein 60, Heparin-Binding EGF-Like Growth Factor, Hepatocyte Growth Factor, Immunoglobulin A, Immunoglobulin E, Immunoglobulin M, Insulin, Insulin-like Growth Factor I, Insulin-like Growth Factor-Binding Protein 2, Intercellular Adhesion Molecule 1, Interferon gamma, Interferon gamma Induced Protein 10, Interleukin-1 alpha, Interleukin-1 beta, Interleukin-1 Receptor antagonist, Interleukin-2, Interleukin-3, Interleukin-4, Interleukin-5, Interleukin-6, Interleukin-6 Receptor, Interleukin-7, Interleukin-8, Interleukin-10, Interleukin-11, Interleukin-12 Subunit p40, Interleukin-12 Subunit p70, Interleukin-13, Interleukin-15, Interleukin-16, Interleukin-25, Kidney Injury Molecule-1, Lectin-Like Oxidized LDL Receptor 1, Leptin, Luteinizing Hormone, Lymphotactin, Macrophage Colony-Stimulating Factor 1, Macrophage Inflammatory Protein-1 alpha, Macrophage Inflammatory Protein-1 beta, Macrophage Inflammatory Protein-3 alpha, Macrophage Migration Inhibitory Factor, Macrophage-Derived Chemokine, Malondialdehyde-Modified Low-Density Lipoprotein, Matrix Metalloproteinase-1, Matrix Metalloproteinase-2, Matrix Metalloproteinase-3, Matrix Metalloproteinase-7, Matrix Metalloproteinase-9, Matrix Metalloproteinase-9, Matrix Metalloproteinase-10, Monocyte Chemotactic Protein 1, Monocyte Chemotactic Protein 2, Monocyte Chemotactic Protein 3, Monocyte Chemotactic Protein 4, Monokine Induced by Gamma Interferon, Myeloid Progenitor Inhibitory Factor 1, Myeloperoxidase, Myoglobin, Nerve Growth Factor beta, Neuronal Cell Adhesion Molecule, Neutrophil Gelatinase-Associated Lipocalin, NT-proBNP, Osteopontin, Pancreatic Polypeptide, Peptide YY, Placenta Growth Factor, Plasminogen Activator Inhibitor 1, Platelet-Derived Growth Factor BB, Pregnancy-Associated Plasma Protein A, Progesterone, Proinsulin (inc. Intact or Total), Prolactin, Prostate-Specific Antigen (inc. Free PSA), Prostatic Acid Phosphatase, Pulmonary and Activation-Regulated Chemokine, Receptor for advanced glycosylation end products, Resistin, S100 calcium-binding protein B, Secretin, Serotransferrin, Serum Amyloid P-Component, Serum Glutamic Oxaloacetic Transaminase, Sex Hormone-Binding Globulin, Sortilin, Stem Cell Factor, Superoxide Dismutase 1 (soluble), T Lymphocyte-Secreted Protein I-309, Tamm-Horsfall Urinary Glycoprotein, T-Cell-Specific Protein RANTES, Tenascin-C, Testosterone, Thrombomodulin, Thrombopoietin, Thrombospondin-1, Thyroid-Stimulating Hormone, Thyroxine-Binding Globulin, Tissue Factor, Tissue Inhibitor of Metalloproteinases 1, TNF-Related Apoptosis-Inducing Ligand Receptor 3, Transforming Growth Factor alpha, Transforming Growth Factor beta-3, Transthyretin, Trefoil Factor 3, Tumor Necrosis Factor alpha, Tumor Necrosis Factor beta, Tumor necrosis Factor Receptor 2, Vascular Cell Adhesion Molecule-1, Vascular Endothelial Growth Factor, Vitamin K-Dependent Protein S, Vitronectin, von Willebrand Factor |
| Oncology | 6Ckine, Aldose Reductase, Alpha-Fetoprotein, Amphiregulin, Angiogenin, Annexin A1, B cell-activating Factor, B Lymphocyte Chemoattractant, Bcl-2-like protein 2, Betacellulin, Cancer Antigen 125, Cancer Antigen 15-3, Cancer Antigen 19-9, Cancer Antigen 72-4, Carcinoembryonic Antigen, Cathepsin D, Cellular Fibronectin, Collagen IV, Endoglin, Endostatin, Eotaxin-2, Epidermal Growth Factor, Epiregulin, Epithelial cell adhesion molecule, Ezrin, Fatty Acid-Binding Protein (adipocyte), Fatty Acid-Binding Protein (liver), Fibroblast Growth Factor basic, Fibulin-1C, Galectin-3, Gelsolin, Glucose-6-phosphate Isomerase, Glutamate-Cysteine Ligase Regulatory subunit, Glutathione S-Transferase Mu 1, HE4, Heparin-Binding EGF-Like Growth Factor, Hepatocyte Growth Factor, Hepatocyte Growth Factor Receptor, Hepsin, Human Chorionic Gonadotropin beta, Human Epidermal Growth Factor Receptor 2, Insulin-like Growth Factor-Binding Protein 1, Insulin-like Growth Factor-Binding Protein 2, Insulin-like Growth Factor-Binding Protein 3, Insulin-like Growth Factor Binding Protein 4, Insulin-like Growth Factor Binding Protein 5, Insulin-like Growth Factor Binding Protein 6, Interferon gamma Induced Protein 10, Interferon-inducible T-cell alpha chemoattractant, Interleukin-2 Receptor alpha, Interleukin-6, Interleukin-6 Receptor subunit beta, Kallikrein 5, Kallikrein-7, Lactoylglutathione lyase, Latency-Associated Peptide of Transforming Growth Factor beta 1, Leptin, Macrophage inflammatory protein 3 beta, Macrophage Migration Inhibitory Factor, Macrophage-Stimulating Protein, Maspin, Matrix Metalloproteinase-2, Mesothelin, MHC class I chain-related protein A, Monocyte Chemotactic Protein 1, Monokine Induced by Gamma Interferon, Neuron-Specific Enolase, Neuropilin-1, Neutrophil Gelatinase-Associated Lipocalin, Nucleoside diphosphate kinase B, Osteopontin, Osteoprotegerin, Pepsinogen I, Peroxiredoxin-4, Phosphoserine Aminotransferase, Placenta Growth Factor, Platelet-Derived Growth Factor BB, Prostasin, Protein S100-A4, Protein S100-A6, Receptor tyrosine-protein kinase erbB-3, Squamous Cell Carcinoma Antigen-1, Stromal cell-derived Factor-1, Tenascin-C, Tetranectin, |

TABLE 4-continued

Illustrative Biomarkers

| Illustrative Class | Biomarkers |
|---|---|
| | Thyroglobulin, Tissue type Plasminogen activator, Transforming Growth Factor alpha, Tumor Necrosis Factor Receptor I, Tyrosine kinase with Ig and EGF homology domains 2, Urokinase-type Plasminogen Activator, Urokinase-type plasminogen activator Receptor, Vascular Endothelial Growth Factor, Vascular endothelial growth Factor B, Vascular Endothelial Growth Factor C, Vascular endothelial growth Factor D, Vascular Endothelial Growth Factor Receptor 1, Vascular Endothelial Growth Factor Receptor 2, Vascular endothelial growth Factor Receptor 3, YKL-40 |
| Disease | Adiponectin, Alpha-1-Antitrypsin, Alpha-2-Macroglobulin, Alpha-Fetoprotein, Apolipoprotein A-I, Apolipoprotein C-III, Apolipoprotein H, Apolipoprotein(a), Beta-2-Microglobulin, Brain-Derived Neurotrophic Factor, Calcitonin, Cancer Antigen 125, Cancer Antigen 19-9, Carcinoembryonic Antigen, CD 40 antigen, CD40 Ligand, Complement C3, C-Reactive Protein, Creatine Kinase-MB, Endothelin-1, EN-RAGE, Eotaxin-1, Epidermal Growth Factor, Epithelial-Derived Neutrophil-Activating Protein 78, Erythropoietin, Factor VII, Fatty Acid-Binding Protein (heart), Ferritin, Fibrinogen, Fibroblast Growth Factor basic, Granulocyte Colony-Stimulating Factor, Granulocyte-Macrophage Colony-Stimulating Factor, Growth Hormone, Haptoglobin, Immunoglobulin A, Immunoglobulin E, Immunoglobulin M, Insulin, Insulin-like Growth Factor I, Intercellular Adhesion Molecule 1, Interferon gamma, Interleukin-1 alpha, Interleukin-1 beta, Interleukin-1 Receptor antagonist, Interleukin-2, Interleukin-3, Interleukin-4, Interleukin-5, Interleukin-6, Interleukin-7, Interleukin-8, Interleukin-10, Interleukin-12 Subunit p40, Interleukin-12 Subunit p70, Interleukin-13, Interleukin-15, Interleukin-16, Leptin, Lymphotactin, Macrophage Inflammatory Protein-1 alpha, Macrophage Inflammatory Protein-1 beta, Macrophage-Derived Chemokine, Matrix Metalloproteinase-2, Matrix Metalloproteinase-3, Matrix Metalloproteinase-9, Monocyte Chemotactic Protein 1, Myeloperoxidase, Myoglobin, Plasminogen Activator Inhibitor 1, Pregnancy-Associated Plasma Protein A, Prostate-Specific Antigen (inc. Free PSA), Prostatic Acid Phosphatase, Serum Amyloid P-Component, Serum Glutamic Oxaloacetic Transaminase, Sex Hormone-Binding Globulin, Stem Cell Factor, T-Cell- Specific Protein RANTES, Thrombopoietin, Thyroid-Stimulating Hormone, Thyroxine-Binding Globulin, Tissue Factor, Tissue Inhibitor of Metalloproteinases 1, Tumor Necrosis Factor alpha, Tumor Necrosis Factor beta, Tumor Necrosis Factor Receptor 2, Vascular Cell Adhesion Molecule-1, Vascular Endothelial Growth Factor, von Willebrand Factor |
| Neurological | Alpha-1-Antitrypsin, Apolipoprotein A-I, Apolipoprotein A-II, Apolipoprotein B, Apolipoprotein C-I, Apolipoprotein H, Beta-2-Microglobulin, Betacellulin, Brain-Derived Neurotrophic Factor, Calbindin, Cancer Antigen 125, Carcinoembryonic Antigen, CD5 Antigen-like, Complement C3, Connective Tissue Growth Factor, Cortisol, Endothelin-1, Epidermal Growth Factor Receptor, Ferritin, Fetuin-A, Follicle-Stimulating Hormone, Haptoglobin, Immunoglobulin A, Immunoglobulin M, Intercellular Adhesion Molecule 1, Interleukin-6 Receptor, Interleukin-7, Interleukin-10, Interleukin-11, Interleukin-17, Kidney Injury Molecule-1, Luteinizing Hormone, Macrophage-Derived Chemokine, Macrophage Migration Inhibitory Factor, Macrophage Inflammatory Protein-1 alpha, Matrix Metalloproteinase-2, Monocyte Chemotactic Protein 2, Peptide YY, Prolactin, Prostatic Acid Phosphatase, Serotransferrin, Serum Amyloid P-Component, Sortilin, Testosterone, Thrombopoietin, Thyroid-Stimulating Hormone, Tissue Inhibitor of Metalloproteinases 1, TNF-Related Apoptosis-Inducing Ligand Receptor 3, Tumor necrosis Factor Receptor 2, Vascular Endothelial Growth Factor, Vitronectin |
| Cardiovascular | Adiponectin, Apolipoprotein A-I, Apolipoprotein B, Apolipoprotein C-III, Apolipoprotein D, Apolipoprotein E, Apolipoprotein H, Apolipoprotein(a), Clusterin, C-Reactive Protein, Cystatin-C, EN-RAGE, E-Selectin, Fatty Acid-Binding Protein (heart), Ferritin, Fibrinogen, Haptoglobin, Immunoglobulin M, Intercellular Adhesion Molecule 1, Interleukin-6, Interleukin-8, Lectin-Like Oxidized LDL Receptor 1, Leptin, Macrophage Inflammatory Protein-1 alpha, Macrophage Inflammatory Protein-1 beta, Malondialdehyde-Modified Low-Density Lipoprotein, Matrix Metalloproteinase-1, Matrix Metalloproteinase-10, Matrix Metalloproteinase-2, Matrix Metalloproteinase-3, Matrix Metalloproteinase-7, Matrix Metalloproteinase-9, Monocyte Chemotactic Protein 1, Myeloperoxidase, Myoglobin, NT-proBNP, Osteopontin, Plasminogen Activator Inhibitor 1, P-Selectin, Receptor for advanced glycosylation end products, Serum Amyloid P-Component, Sex Hormone-Binding Globulin, T-Cell-Specific Protein RANTES, Thrombomodulin, Thyroxine-Binding Globulin, Tissue Inhibitor of Metalloproteinases 1, Tumor Necrosis Factor alpha, Tumor necrosis Factor Receptor 2, Vascular Cell Adhesion Molecule-1, von Willebrand Factor |
| Inflammatory | Alpha-1-Antitrypsin, Alpha-2-Macroglobulin, Beta-2-Microglobulin, Brain-Derived Neurotrophic Factor, Complement C3, C-Reactive Protein, Eotaxin-1, Factor VII, Ferritin, Fibrinogen, Granulocyte-Macrophage Colony-Stimulating Factor, Haptoglobin, Intercellular Adhesion Molecule 1, Interferon gamma, Interleukin-1 alpha, Interleukin-1 beta, Interleukin-1 Receptor antagonist, Interleukin-2, Interleukin-3, Interleukin-4, Interleukin-5, Interleukin-6, Interleukin-7, Interleukin-8, Interleukin-10, Interleukin-12 Subunit p40, Interleukin-12 Subunit p70, Interleukin-15, Interleukin-17, Interleukin-23, Macrophage Inflammatory Protein-1 alpha, Macrophage Inflammatory Protein-1 beta, Matrix Metalloproteinase-2, Matrix Metalloproteinase-3, Matrix Metalloproteinase-9, Monocyte Chemotactic Protein 1, Stem Cell Factor, T-Cell-Specific Protein RANTES, Tissue Inhibitor of Metalloproteinases 1, Tumor Necrosis Factor alpha, Tumor Necrosis Factor beta, Tumor necrosis Factor Receptor 2, Vascular Cell Adhesion Molecule-1, Vascular Endothelial Growth Factor, Vitamin D-Binding Protein, von Willebrand Factor |
| Metabolic | Adiponectin, Adrenocorticotropic Hormone, Angiotensin-Converting Enzyme, Angiotensinogen, Complement C3 alpha des arg, Cortisol, Follicle-Stimulating Hormone, Galanin, Glucagon, Glucagon-like Peptide 1, Insulin, Insulin-like Growth Factor I, Leptin, |

TABLE 4-continued

Illustrative Biomarkers

| Illustrative Class | Biomarkers |
|---|---|
| | Luteinizing Hormone, Pancreatic Polypeptide, Peptide YY, Progesterone, Prolactin, Resistin, Secretin, Testosterone |
| Kidney | Alpha-1-Microglobulin, Beta-2-Microglobulin, Calbindin, Clusterin, Connective Tissue Growth Factor, Creatinine, Cystatin-C, Glutathione S-Transferase alpha, Kidney Injury Molecule-1, Microalbumin, Neutrophil Gelatinase-Associated Lipocalin, Osteopontin, Tamm-Horsfall Urinary Glycoprotein, Tissue Inhibitor of Metalloproteinases 1, Trefoil Factor 3, Vascular Endothelial Growth Factor |
| Cytokines | Granulocyte-Macrophage Colony-Stimulating Factor, Interferon gamma, Interleukin-2, Interleukin-3, Interleukin-4, Interleukin-5, Interleukin-6, Interleukin-7, Interleukin-8, Interleukin-10, Macrophage Inflammatory Protein-1 alpha, Macrophage Inflammatory Protein-1 beta, Matrix Metalloproteinase-2, Monocyte Chemotactic Protein 1, Tumor Necrosis Factor alpha, Tumor Necrosis Factor beta, Brain-Derived Neurotrophic Factor, Eotaxin-1, Intercellular Adhesion Molecule 1, Interleukin-1 alpha, Interleukin-1 beta, Interleukin-1 Receptor antagonist, Interleukin-12 Subunit p40, Interleukin-12 Subunit p70, Interleukin-15, Interleukin-17, Interleukin-23, Matrix Metalloproteinase-3, Stem Cell Factor, Vascular Endothelial Growth Factor |
| Protein | 14.3.3 gamma, 14.3.3 (Pan), 14-3-3 beta, 6-Histidine, a-B-Crystallin, Acinus, Actin beta, Actin (Muscle Specific), Actin (Pan), Actin (skeletal muscle), Activin Receptor Type II, Adenovirus, Adenovirus Fiber, Adenovirus Type 2 E1A, Adenovirus Type 5 E1A, ADP-ribosylation Factor (ARF-6), Adrenocorticotrophic Hormone, AIF (Apoptosis Inducing Factor), Alkaline Phosphatase (AP), Alpha Fetoprotein (AFP), Alpha Lactalbumin, alpha-1-antichymotrypsin, alpha-1-antitrypsin, Amphiregulin, Amylin Peptide, Amyloid A, Amyloid A4 Protein Precursor, Amyloid Beta (APP), Androgen Receptor, Ang-1, Ang-2, APC, APC11, APC2, Apolipoprotein D, A-Raf, ARC, Ask1/MAPKKK5, ATM, Axonal Growth Cones, b Galactosidase, b-2-Microglobulin, B7-H2, BAG-1, Bak, Bax, B-Cell, B-cell Linker Protein (BLNK), Bcl10/CIPER/CLAP/mE10, bcl-2a, Bcl-6, bcl-X, bcl-XL, Bim (BOD), Biotin, Bonzo/STRL33/TYMSTR, Bovine Serum Albumin, BRCA2 (aa 1323-1346), BrdU, Bromodeoxyuridine (BrdU), CA125, CA19-9, c-Abl, Cadherin (Pan), Cadherin-E, Cadherin-P, Calcitonin, Calcium Pump ATPase, Caldesmon, Calmodulin, Calponin, Calretinin, Casein, Caspase 1, Caspase 2, Caspase 3, Caspase 5, Caspase 6 (Mch 2), Caspase 7 (Mch 3), Caspase 8 (FLICE), Caspase 9, Catenin alpha, Catenin beta, Catenin gamma, Cathepsin D, CCK-8, CD1, CD10, CD100/Leukocyte Semaphorin, CD105, CD106/VCAM, CD115/c-fms/CSF-1R/M-CSFR, CD137 (4-1BB), CD138, CD14, CD15, CD155/PVR (Polio Virus Receptor), CD16, CD165, CD18, CD1a, CD1b, CD2, CD20, CD21, CD23, CD231, CD24, CD25/IL-2 Receptor a, CD26/DPP IV, CD29, CD30 (Reed-Sternberg Cell Marker), CD32/Fcg Receptor II, CD35/CR1, CD36GPIIIb/GPIV, CD3zeta, CD4, CD40, CD42b, CD43, CD45/T200/LCA, CD45RB, CD45RO, CD46, CD5, CD50/ICAM-3, CD53, CD54/ICAM-1, CD56/NCAM-1, CD57, CD59/MACIF/MIRL/Protectin, CD6, CD61/Platelet Glycoprotein IIIA, CD63, CD68, CD71/Transferrin Receptor, CD79a mb-1, CD79b, CD8, CD81/TAPA-1, CD84, CD9, CD94, CD95/Fas, CD98, CDC14A Phosphatase, CDC25C, CDC34, CDC37, CDC47, CDC6, cdh1, Cdk1/p34cdc2, Cdk2, Cdk3, Cdk4, Cdk5, Cdk7, Cdk8, CDw17, CDw60, CDw75, CDw78, CEA/CD66e, c-erbB-2/HER-2/neu Ab-1 (21N), c-erbB-4/HER-4, c-fos, Chk1, Chorionic Gonadotropin beta (hCG-beta), Chromogranin A, CIDE-A, CIDE-B, CITED1, c-jun, Clathrin, claudin 11, Claudin 2, Claudin 3, Claudin 4, Claudin 5, CLAUDIN 7, Claudin-1, CNPase, Collagen II, Collagen IV, Collagen IX, Collagen VII, Connexin 43, COX2, CREB, CREB-Binding Protein, *Cryptococcus neoformans*, c-Src, Cullin-1 (CUL-1), Cullin-2 (CUL-2), Cullin-3 (CUL-3), CXCR4/Fusin, Cyclin B1, Cyclin C, Cyclin D1, Cyclin D3, Cyclin E, Cyclin E2, Cystic Fibrosis Transmembrane Regulator, Cytochrome c, D4-GDI, Daxx, DcR1, DcR2/TRAIL-R4/TRUNDD, Desmin, DFF40 (DNA Fragmentation Factor 40)/CAD, DFF45/ICAD, DJ-1, DNA Ligase I, DNA Polymerase Beta, DNA Polymerase Gamma, DNA Primase (p49), DNA Primase (p58), DNA-PKcs, DP-2, DR3, DR5, Dysferlin, Dystrophin, E2F-1, E2F-2, E2F-3, E2F-4, E2F-5, E3-binding protein (ARM1), EGFR, EMA/CA15-3/MUC-1, Endostatin, Epithelial Membrane Antigen (EMA/CA15-3/MUC-1), Epithelial Specific Antigen, ER beta, ER Ca+2 ATPase2, ERCC1, Erk1, ERK2, Estradiol, Estriol, Estrogen Receptor, Exo1, Ezrin/p81/80K/Cytovillin, F.VIII/VWF, Factor VIII Related Antigen, FADD (FAS-Associated death domain-containing protein), Fascin, Fas-ligand, Ferritin, FGF-1, FGF-2, FHIT, Fibrillin-1, Fibronectin, Filaggrin, Filamin, FITC, Fli-1, FLIP, Flk-1/KDR/VEGFR2, Flt-1/VEGFR1, Flt-4, Fra2, FSH, FSH-b, Fyn, Ga0, Gab-1, GABA a Receptor 1, GAD65, Gai1, Gamma Glutamyl Transferase (gGT), Gamma Glutamylcysteine Synthetase(GCS)/Glutamate-cysteine Ligase, GAPDH, Gastrin 1, GCDFP-15, G-CSF, GFAP, Glicentin, Glucagon, Glucose-Regulated Protein 94, GluR 2/3, GluR1, GluR4, GluR6/7, GLUT-1, GLUT-3, Glycogen Synthase Kinase 3b (GSK3b), Glycophorin A, GM-CSF, GnRH Receptor, Golgi Complex, Granulocyte, Granzyme B, Grb2, Green Fluorescent Protein (GFP), GRIP1, Growth Hormone (hGH), GSK-3, GST, GSTmu, *H. Pylori*, HDAC1, HDJ-2/DNAJ, Heat Shock Factor 1, Heat Shock Factor 2, Heat Shock Protein 27/hsp27, Heat Shock Protein 60/hsp60, Heat Shock Protein 70/hsp70, Heat Shock Protein 75/hsp75, Heat Shock Protein 90a/hsp86, Heat Shock Protein 90b/hsp84, *Helicobacter pylori*, Heparan Sulfate Proteoglycan, Hepatic Nuclear Factor-3B, Hepatocyte, Hepatocyte Factor Homologue-4, Hepatocyte Growth Factor, Heregulin, HIF-1a, Histone H1, hPL, HPV 16, HPV 16-E7, HRP, Human Sodium Iodide Symporter (hNIS), I-FLICE/CASPER, IFN gamma, IgA, IGF-1R, IGF-I, IgG, IgM (m-Heavy Chain), I-Kappa-B Kinase b (IKKb), IL-1 alpha, IL-1 beta, IL-10, IL-10R, IL17, IL-2, IL-3, IL-30, IL-4, IL-5, IL-6, IL-8, Inhibin alpha, Insulin, Insulin Receptor, Insulin Receptor Substrate-1, Int-2 Oncoprotein, Integrin beta5, Interferon-a(II), Interferon-g, Involucrin, IP10/CRG2, IPO-38 Proliferation Marker, IRAK, ITK, JNK Activating kinase (JKK1), Kappa Light Chain, Keratin 10, Keratin 10/13, Keratin |

TABLE 4-continued

Illustrative Biomarkers

| Illustrative Class | Biomarkers |
|---|---|
| | 14, Keratin 15, Keratin 16, Keratin 18, Keratin 19, Keratin 20, Keratin 5/6/18, Keratin 5/8, Keratin 8, Keratin 8 (phospho-specific Ser73), Keratin 8/18, Keratin (LMW), Keratin (Multi), Keratin (Pan), Ki67, Ku (p70/p80), Ku (p80), L1 Cell Adhesion Molecule, Lambda Light Chain, Laminin B1/b1, Laminin B2/g1, Laminin Receptor, Laminin-s, Lck, Lck (p56lck), Leukotriene (C4, D4, E4), LewisA, LewisB, LH, L-Plastin, LRP/MVP, Luciferase, Macrophage, MADD, MAGE-1, Maltose Binding Protein, MAP1B, MAP2a, b, MART-1/Melan-A, Mast Cell Chymase, Mcl-1, MCM2, MCM5, MDM2, Medroxyprogesterone Acetate (MPA), Mek1, Mek2, Mek6, Mekk-1, Melanoma (gp100), mGluR1, mGluR5, MGMT, MHC I (HLA25 and HLA-Aw32), MHC I (HLA-A), MHC I (HLA-A, B, C), MHC I (HLA-B), MHC II (HLA-DP and DR), MHC II (HLA-DP), MHC II (HLA-DQ), MHC II (HLA-DR), MHC II (HLA-DR) Ia, Microphthalmia, Milk Fat Globule Membrane Protein, Mitochondria, MLH1, MMP-1 (Collagenase-I), MMP-10 (Stromilysin-2), MMP-11 (Stromelysin-3), MMP-13 (Collagenase-3), MMP-14/MT1-MMP, MMP-15/MT2-MMP, MMP-16/MT3-MMP, MMP-19, MMP-2 (72 kDa Collagenase IV), MMP-23, MMP-7 (Matrilysin), MMP-9 (92 kDa Collagenase IV), Moesin, mRANKL, Muc-1, Mucin 2, Mucin 3 (MUC3), Mucin 5AC, MyD88, Myelin/Oligodendrocyte, Myeloid Specific Marker, Myeloperoxidase, MyoD1, Myogenin, Myoglobin, Myosin Smooth Muscle Heavy Chain, Nck, Negative Control for Mouse IgG1, Negative Control for Mouse IgG2a, Negative Control for Mouse IgG3, Negative Control for Mouse IgM, Negative Control for Rabbit IgG, Neurofilament, Neurofilament (160 kDa), Neurofilament (200 kDa), Neurofilament (68 kDa), Neuron Specific Enolase, Neutrophil Elastase, NF kappa B/p50, NF kappa B/p65 (Rel A), NGF-Receptor (p75NGFR), brain Nitric Oxide Synthase (bNOS), endothelial Nitric Oxide Synthase (eNOS), nm23, NOS-i, NOS-u, Notch, Nucleophosmin (NPM), NuMA, O ct-1, Oct-2/, Oct-3/, Ornithine Decarboxylase, Osteopontin, p130, p130cas, p14ARF, p15INK4b, p16INK4a, p170, p170/MDR-1, p18INK4c, p19ARF, p19Skp1, p21WAF1, p27Kip1, p300/CBP, p35nck5a, P504S, p53, p57Kip2 Ab-7, p63 (p53 Family Member), p73, p73a, p73a/b, p95VAV, Parathyroid Hormone, Parathyroid Hormone Receptor Type 1, Parkin, PARP, PARP (Poly ADP-Ribose Polymerase), Pax-5, Paxillin, PCNA, PCTAIRE2, PDGF, PDGFR alpha, PDGFR beta, Pds1, Perform, PGP9.5, PHAS-I, PHAS-II, Phospho-Ser/Thr/Tyr, Phosphotyrosine, PLAP, Plasma Cell Marker, Plasminogen, PLC gamma 1, PMP-22, *Pneumocystis jiroveci*, PPAR-gamma, PR3 (Proteinase 3), Presenillin, Progesterone, Progesterone Receptor, Progesterone Receptor (phospho-specific) - Serine 190, Progesterone Receptor (phospho-specific) - Serine 294, Prohibitin, Prolactin, Prolactin Receptor, Prostate Apoptosis Response Protein-4, Prostate Specific Acid Phosphatase, Prostate Specific Antigen, pS2, PSCA, Rabies Virus, RAD1, Rad51, Raf1, Raf-1 (Phospho-specific), RAIDD, Ras, Rad18, Renal Cell Carcinoma, Ret Oncoprotein, Retinoblastoma, Retinoblastoma (Rb) (Phospho-specific Serine608), Retinoic Acid Receptor (b), Retinoid X Receptor (hRXR), Retinol Binding Protein, Rhodopsin (Opsin), ROC, RPA/p32, RPA/p70, Ruv A, Ruv B, Ruv C, S100, S100A4, S100A6, SHP-1, SIM Ag (SIMA-4D3), SIRP a1, sm, SODD (Silencer of Death Domain), Somatostatin Receptor-I, SRC1 (Steroid Receptor Coactivator-1) Ab-1, SREBP-1 (Sterol Regulatory Element Binding Protein-1), SRF (Serum Response Factor), Stat-1, Stat3, Stat5, Stat5a, Stat5b, Stat6, Streptavidin, Superoxide Dismutase, Surfactant Protein A, Surfactant Protein B, Surfactant Protein B (Pro), Survivin, SV40 Large T Antigen, Syk, Synaptophysin, Synuclein, Synuclein beta, Synuclein pan, TACE (TNF-alpha converting enzyme)/ADAM17, TAG-72, tau, TdT, Tenascin, Testosterone, TGF beta 3, TGF-beta 2, Thomsen-Friedenreich Antigen, Thrombospondin, Thymidine Phosphorylase, Thymidylate Synthase, Thymine Glycols, Thyroglobulin, Thyroid Hormone Receptor beta, Thyroid Hormone Receptor, Thyroid Stimulating Hormone (TSH), TID-1, TIMP-1, TIMP-2, TNF alpha, TNFa, TNR-R2, Topo II beta, Topoisomerase IIa, Toxoplasma Gondii, TR2, TRADD, Transforming Growth Factor a, Transglutaminase II, TRAP, Tropomyosin, TRP75/gp75, TrxR2, TTF-1, Tubulin, Tubulin-a, Tubulin-b, Tyrosinase, Ubiquitin, UCP3, uPA, Urocortin, Vacular Endothelial Growth Factor(VEGF), Vimentin, Vinculin, Vitamin D Receptor (VDR), von Hippel-Lindau Protein, Wnt-1, Xanthine Oxidase, XPA, XPF, XPG, XRCC1, XRCC2, ZAP-70, Zip kinase |
| Known Cancer Genes | ABL1, ABL2, ACSL3, AF15Q14, AF1Q, AF3p21, AF5q31, AKAP9, AKT1, AKT2, ALDH2, ALK, ALO17, APC, ARHGEF12, ARHH, ARID1A, ARID2, ARNT, ASPSCR1, ASXL1, ATF1, ATIC, ATM, ATRX, BAP1, BCL10, BCL11A, BCL11B, BCL2, BCL3, BCL5, BCL6, BCL7A, BCL9, BCOR, BCR, BHD, BIRC3, BLM, BMPR1A, BRAF, BRCA1, BRCA2, BRD3, BRD4, BRIP1, BTG1, BUB1B, C12orf9, C15orf21, C15orf55, C16orf75, CANT1, CARD11, CARS, CBFA2T1, CBFA2T3, CBFB, CBL, CBLB, CBLC, CCNB1IP1, CCND1, CCND2, CCND3, CCNE1, CD273, CD274, CD74, CD79A, CD79B, CDH1, CDH11, CDK12, CDK4, CDK6, CDKN2A, CDKN2a(p14), CDKN2C, CDX2, CEBPA, CEP1, CHCHD7, CHEK2, CHIC2, CHN1, CIC, CIITA, CLTC, CLTCL1, CMKOR1, COL1A1, COPEB, COX6C, CREB1, CREB3L1, CREB3L2, CREBBP, CRLF2, CRTC3, CTNNB1, CYLD, D10S170, DAXX, DDB2, DDIT3, DDX10, DDX5, DDX6, DEK, DICER1, DNMT3A, DUX4, EBF1, EGFR, EIF4A2, ELF4, ELK4, ELKS, ELL, ELN, EML4, EP300, EPS15, ERBB2, ERCC2, ERCC3, ERCC4, ERCC5, ERG, ETV1, ETV4, ETV5, ETV6, EVI1, EWSR1, EXT1, EXT2, EZH2, FACL6, FAM22A, FAM22B, FAM46C, FANCA, FANCC, FANCD2, FANCE, FANCF, FANCG, FBXO11, FBXW7, FCGR2B, FEV, FGFR1, FGFR1OP, FGFR2, FGFR3, FH, FHIT, FIP1L1, FLI1, FLJ27352, FLT3, FNBP1, FOXL2, FOXO1A, FOXO3A, FOXP1, FSTL3, FUBP1, FUS, FVT1, GAS7, GATA1, GATA2, GATA3, GMPS, GNA11, GNAQ, GNAS, GOLGA5, GOPC, GPC3, GPHN, GRAF, HCMOGT-1, HEAB, HERPUD1, HEY1, HIP1, HIST1H4I, HLF, HLXB9, HMGA1, HMGA2, HNRNPA2B1, HOOK3, HOXA11, HOXA13, HOXA9, HOXC11, HOXC13, HOXD11, HOXD13, HRAS, HRPT2, HSPCA, HSPCB, IDH1, IDH2, IGH@, IGK@, IGL@, IKZF1, IL2, IL21R, IL6ST, IL7R, IRF4, IRTA1, ITK, JAK1, JAK2, JAK3, |

TABLE 4-continued

Illustrative Biomarkers

| Illustrative Class | Biomarkers |
|---|---|
| | JAZF1, JUN, KDM5A, KDM5C, KDM6A, KDR, KIAA1549, KIT, KLK2, KRAS, KTN1, LAF4, LASP1, LCK, LCP1, LCX, LHFP, LIFR, LMO1, LMO2, LPP, LYL1, MADH4, MAF, MAFB, MALT1, MAML2, MAP2K4, MDM2, MDM4, MDS1, MDS2, MECT1, MED12, MEN1, MET, MITF, MKL1, MLF1, MLH1, MLL, MLL2, MLL3, MLLT1, MLLT10, MLLT2, MLLT3, MLLT4, MLLT6, MLLT7, MN1, MPL, MSF, MSH2, MSH6, MSI2, MSN, MTCP1, MUC1, MUTYH, MYB, MYC, MYCL1, MYCN, MYD88, MYH11, MYH9, MYST4, NACA, NBS1, NCOA1, NCOA2, NCOA4, NDRG1, NF1, NF2, NFE2L2, NFIB, NFKB2, NIN, NKX2-1, NONO, NOTCH1, NOTCH2, NPM1, NR4A3, NRAS, NSD1, NTRK1, NTRK3, NUMA1, NUP214, NUP98, OLIG2, OMD, P2RY8, PAFAH1B2, PALB2, PAX3, PAX5, PAX7, PAX8, PBRM1, PBX1, PCM1, PCSK7, PDE4DIP, PDGFB, PDGFRA, PDGFRB, PER1, PHOX2B, PICALM, PIK3CA, PIK3R1, PIM1, PLAG1, PML, PMS1, PMS2, PMX1, PNUTL1, POU2AF1, POU5F1, PPARG, PPP2R1A, PRCC, PRDM1, PRDM16, PRF1, PRKAR1A, PRO1073, PSIP2, PTCH, PTEN, PTPN11, RAB5EP, RAD51L1, RAF1, RALGDS, RANBP17, RAP1GDS1, RARA, RB1, RBM15, RECQL4, REL, RET, ROS1, RPL22, RPN1, RUNDC2A, RUNX1, RUNXBP2, SBDS, SDH5, SDHB, SDHC, SDHD, SEPT6, SET, SETD2, SF3B1, SFPQ, SFRS3, SH3GL1, SIL, SLC45A3, SMARCA4, SMARCB1, SMO, SOCS1, SOX2, SRGAP3, SRSF2, SS18, SS18L1, SSH3BP1, SSX1, SSX2, SSX4, STK11, STL, SUFU, SUZ12, SYK, TAF15, TAL1, TAL2, TCEA1, TCF1, TCF12, TCF3, TCF7L2, TCL1A, TCL6, TET2, TFE3, TFEB, TFG, TFPT, TFRC, THRAP3, TIF1, TLX1, TLX3, TMPRSS2, TNFAIP3, TNFRSF14, TNFRSF17, TNFRSF6, TOP1, TP53, TPM3, TPM4, TPR, TRA@, TRB@, TRD@, TRIM27, TRIM33, TRIP11, TSC1, TSC2, TSHR, TTL, U2AF1, USP6, VHL, VTI1A, WAS, WHSC1, WHSC1L1, WIF1, WRN, WT1, WTX, XPA, XPC, XPO1, YWHAE, ZNF145, ZNF198, ZNF278, ZNF331, ZNF384, ZNF521, ZNF9, ZRSR2 |
| Known Cancer Genes | AR, androgen receptor; ARPC1A, actin-related protein complex 2/3 subunit A; AURKA, Aurora kinase A; BAG4, BCl-2 associated anthogene 4; Bcl2l2, BCl-2 like 2; BIRC2, Baculovirus IAP repeat containing protein 2; CACNA1E, calcium channel voltage dependent alpha-1E subunit; CCNE1, cyclin E1; CDK4, cyclin dependent kinase 4; CHD1L, chromodomain helicase DNA binding domain 1-like; CKS1B, CDC28 protein kinase 1B; COPS3, COP9 subunit 3; DCUN1D1, DCN1 domain containing protein 1; DYRK2, dual specificity tyrosine phosphorylation regulated kinase 2; EEF1A2, eukaryotic elongation transcription factor 1 alpha 2; EGFR, epidermal growth factor receptor; FADD, Fas-associated via death domain; FGFR1, fibroblast growth factor receptor 1, GATA6, GATA binding protein 6; GPC5, glypican 5; GRB7, growth factor receptor bound protein 7; MAP3K5, mitogen activated protein kinase kinase kinase 5; MED29, mediator complex subunit 5; MITF, microphthalmia associated transcription factor; MTDH, metadherin; NCOA3, nuclear receptor coactivator 3; NKX2-1, NK2 homeobox 1; PAK1, p21/CDC42/RAC1-activated kinase 1; PAX9, paired box gene 9; PIK3CA, phosphatidylinositol-3 kinase catalytic a; PLA2G10, phopholipase A2, group X; PPM1D, protein phosphatase magnesium-dependent 1D; PTK6, protein tyrosine kinase 6; PRKCI, protein kinase C iota; RPS6KB1, ribosomal protein s6 kinase 70 kDa; SKP2, s-phase kinase associated protein; SMURF1, sMAD specific E3 ubiquitin protein ligase 1; SHH, sonic hedgehog homologue; STARD3, sTAR-related lipid transfer domain containing protein 3; YWHAQ, tyrosine 3-monooxygenase/tryptophan 5-monooxygenase activation protein, zeta isoform; ZNF217, zinc finger protein 217 |
| Mitotic Related Cancer Genes | Aurora kinase A (AURKA); Aurora kinase B (AURKB); Baculoviral IAP repeat-containing 5, survivin (BIRC5); Budding uninhibited by benzimidazoles 1 homolog (BUB1); Budding uninhibited by benzimidazoles 1 homolog beta, BUBR1 (BUB1B); Budding uninhibited by benzimidazoles 3 homolog (BUB3); CDC28 protein kinase regulatory subunit 1B (CKS1B); CDC28 protein kinase regulatory subunit 2 (CKS2); Cell division cycle 2 (CDC2)/CDK1 Cell division cycle 20 homolog (CDC20); Cell division cycle-associated 8, borealin (CDCA8); Centromere protein F, mitosin (CENPF); Centrosomal protein 110 kDa (CEP110); Checkpoint with forkhead and ring finger domains (CHFR); Cyclin B1 (CCNB1); Cyclin B2 (CCNB2); Cytoskeleton-associated protein 5 (CKAP5/ch-TOG); Microtubule-associated protein RP/EB family member 1. End-binding protein 1, EB1 (MAPRE1); Epithelial cell transforming sequence 2 oncogene (ECT2); Extra spindle poles like 1, separase (ESPL1); Forkhead box M1 (FOXM1); H2A histone family, member X (H2AFX); Kinesin family member 4A (KIF4A); Kinetochore-associated 1 (KNTC1/ROD); Kinetochore-associated 2; highly expressed in cancer 1 (KNTC2/HEC1); Large tumor suppressor, homolog 1 (LATS1); Large tumor suppressor, homolog 2 (LATS2); Mitotic arrest deficient-like 1; MAD1 (MAD1L1); Mitotic arrest deficient-like 2; MAD2 (MAD2L1); Mps1 protein kinase (TTK); Never in mitosis gene a-related kinase 2 (NEK2); Ninein, GSKSb interacting protein (NIN); Non-SMC condensin I complex, subunit D2 (NCAPD2/CNAP1); Non-SMC condensin I complex, subunit H (NACPH/CAPH); Nuclear mitotic apparatus protein 1 (NUMA1); Nucleophosmin (nucleolar phosphoprotein B23, numatrin); (NPM1); Nucleoporin (NUP98); Pericentriolar material 1 (PCM1); Pituitary tumor-transforming 1, securin (PTTG1); Polo-like kinase 1 (PLK1); Polo-like kinase 4 (PLK4/SAK); Protein (peptidylprolyl cis/trans isomerase) NIMA-interacting 1 (PIN1); Protein regulator of cytokinesis 1 (PRC1); RAD21 homolog (RAD21); Ras association (RalGDS/AF-6); domain family 1 (RASSF1); Stromal antigen 1 (STAG1); Synuclein-c, breast cancer-specific protein 1 (SNCG, BCSG1); Targeting protein for Xklp2 (TPX2); Transforming, acidic coiled-coil containing protein 3 (TACC3); Ubiquitin-conjugating enzyme E2C (UBE2C); Ubiquitin-conjugating enzyme E2I (UBE2I/UBC9); ZW10 interactor, (ZWINT); ZW10, kinetochore-associated homolog (ZW10); Zwilch, kinetochore-associated homolog (ZWILCH) |

TABLE 4-continued

Illustrative Biomarkers

| Illustrative Class | Biomarkers |
|---|---|
| Ribonucleoprotein complexes | Argonaute family member, Ago1, Ago2, Ago3, Ago4, GW182 (TNRC6A), TNRC6B, TNRC6C, HNRNPA2B1, HNRPAB, ILF2, NCL (Nucleolin), NPM1 (Nucleophosmin), RPL10A, RPL5, RPLP1, RPS12, RPS19, SNRPG, TROVE2, apolipoprotein, apolipoprotein A, apo A-I, apo A-II, apo A-IV, apo A-V, apolipoprotein B, apo B48, apo B100, apolipoprotein C, apo C-I, apo C-II, apo C-III, apo C-IV, apolipoprotein D (ApoD), apolipoprotein E (ApoE), apolipoprotein H (ApoH), apolipoprotein L, APOL1, APOL2, APOL3, APOL4, APOL5, APOL6, APOLD1 |
| Cytokine Receptors | 4-1BB, ALCAM, B7-1, BCMA, CD14, CD30, CD40 Ligand, CEACAM-1, DR6, Dtk, Endoglin, ErbB3, E-Selectin, Fas, Flt-3L, GITR, HVEM, ICAM-3, IL-1 R4, IL-1 RI, IL-10 Rbeta, IL-17R, IL-2Rgamma, IL-21R, LIMPII, Lipocalin-2, L-Selectin, LYVE-1, MICA, MICB, NRG1-beta1, PDGF Rbeta, PECAM-1, RAGE, TIM-1, TRAIL R3, Trappin-2, uPAR, VCAM-1, XEDAR |
| Prostate and colorectal cancer vesicles | ErbB3, RAGE, Trail R3 |
| Colorectal cancer vesicles | IL-1 alpha, CA125, Filamin, Amyloid A |
| Colorectal cancer v adenoma vesicles | Involucrin, CD57, Prohibitin, Thrombospondin, Laminin B1/b1, Filamin, 14.3.3 gamma, 14.3.3 Pan |
| Colorectal adenoma vesicles | Involucrin, Prohibitin, Laminin B1/b1, IL-3, Filamin, 14.3.3 gamma, 14.3.3 Pan, MMP-15/ MT2-MMP, hPL, Ubiquitin, and mRANKL |
| Brain cancer vesicles | Prohibitin, CD57, Filamin, CD18, b-2-Microgulbulin, IL-2, IL-3, CD16, p170, Keratin 19, Pds1, Glicentin, SRF (Serum Response Factor), E3-binding protein (ARM1), Collagen II, SRC1 (Steroid Receptor Coactivator-1) Ab-1, Caldesmon, GFAP, TRP75/gp75, alpha-1-antichymotrypsin, Hepatic Nuclear Factor-3B, PLAP, Tyrosinase, NF kappa B/p50, Melanoma (gp100), Cyclin E, 6-Histidine, Mucin 3 (MUC3), TdT, CD21, XPA, Superoxide Dismutase, Glycogen Synthase Kinase 3b (GSK3b), CD54/ICAM-1, Thrombospondin, Gai1, CD79a mb-1, IL-1 beta, Cytochrome c, RAD1, bcl-X, CD50/ICAM-3, Neurofilament, Alkaline Phosphatase (AP), ER Ca+2 ATPase2, PCNA, F.VIII/VWF, SV40 Large T Antigen, Paxillin, Fascin, CD165, GRIP1, Cdk8, Nucleophosmin (NPM), alpha-1-antitrypsin, CD32/Fcg Receptor II, Keratin 8 (phospho-specific Ser73), DR5, CD46, TID-1, MHC II (HLA-DQ), Plasma Cell Marker, DR3, Calmodulin, AIF (Apoptosis Inducing Factor), DNA Polymerase Beta, Vitamin D Receptor (VDR), Bcl10/CIPER/CLAP/mE10, Neuron Specific Enolase, CXCR4/Fusin, Neurofilament (68 kDa), PDGFR, beta, Growth Hormone (hGH), Mast Cell Chymase, Ret Oncoprotein, and Phosphotyrosine |
| Melanoma vesicles | Caspase 5, Thrombospondin, Filamin, Ferritin, 14.3.3 gamma, 14.3.3 Pan, CD71/Transferrin Receptor, and Prostate Apoptosis Response Protein-4 |
| Head and neck cancer vesicles | 14.3.3 Pan, Filamin, 14.3.3 gamma, CD71/Transferrin Receptor, CD30, Cdk5, CD138, Thymidine Phosphorylase, Ruv 5, Thrombospondin, CD1, Von Hippel-Lindau Protein, CD46, Rad51, Ferritin, c-Abl, Actin, Muscle Specific, LewisB |
| Membrane proteins | carbonic anhydrase IX, B7, CCCL19, CCCL21, CSAp, HER-2/neu, BrE3, CD1, CD1a, CD2, CD3, CD4, CD5, CD8, CD11A, CD14, CD15, CD16, CD18, CD19, CD20, CD21, CD22, CD23, CD25, CD29, CD30, CD32b, CD33, CD37, CD38, CD40, CD40L, CD44, CD45, CD46, CD52, CD54, CD55, CD59, CD64, CD67, CD70, CD74, CD79a, CD80, CD83, CD95, CD126, CD133, CD138, CD147, CD154, CEACAM5, CEACAM-6, alpha-fetoprotein (AFP), VEGF, ED-B fibronectin, EGP-1, EGP-2, EGF receptor (ErbB1), ErbB2, ErbB3, Factor H, FHL-1, Flt-3, folate receptor, Ga 733, GROB, HMGB-1, hypoxia inducible factor (HIF), HM1.24, HER-2/neu, insulin-like growth factor (ILGF), IFN-γ, IFN-α, IL-β, IL-2R, IL-4R, IL-6R, IL-13R, IL-15R, IL-17R, IL-18R, IL-2, IL-6, IL-8, IL-12, IL-15, IL-17, IL-18, IL-25, IP-10, IGF-1R, Ia, HM1.24, gangliosides, HCG, HLA-DR, CD66a-d, MAGE, mCRP, MCP-1, MIP-1A, MIP-1B, macrophage migration-inhibitory factor (MIF), MUC1, MUC2, MUC3, MUC4, MUC5, placental growth factor (P1GF), PSA (prostate-specific antigen), PSMA, PSMA dimer, PAM4 antigen, NCA-95, NCA-90, A3, A33, Ep-CAM, KS-1, Le(y), mesothelin, S100, tenascin, TAC, Tn antigen, Thomas-Friedenreich antigens, tumor necrosis antigens, tumor angiogenesis antigens, TNF-α, TRAIL receptor (R1 and R2), VEGFR, RANTES, T101, cancer stem cell antigens, complement factors C3, C3a, C3b, C5a, C5 |
| Cluster of Differentiation (CD) proteins | CD1, CD2, CD3, CD4, CD5, CD6, CD7, CD8, CD9, CD10, CD11a, CD11b, CD11c, CD12w, CD13, CD14, CD15, CD16, CDw17, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42, CD43, CD44, CD45, CD46, CD47, CD48, CD49a, CD49b, CD49c, CD49d, CD49e, CD49f, CD53, CD54, CD55, CD56, CD57, CD58, CD59, CD61, CD62E, CD62L, CD62P, CD63, CD68, CD69, CD71, CD72, CD73, CD74, CD80, CD81, CD82, CD83, CD86, CD87, CD88, CD89, CD90, CD91, CD95, CD96, CD100, CD103, CD105, CD106, CD107, CD107a, CD107b, CD109, CD117, CD120, CD127, CD133, CD134, CD135, CD138, CD141, CD142, CD143, CD144, CD147, CD151, CD152, CD154, CD156, CD158, CD163, CD165, CD166, CD168, CD184, CDw186, CD195, CD197, CD209, CD202a, CD220, CD221, CD235a, CD271, CD303, CD304, CD309, CD326 |
| Interleukin (IL) proteins | IL-1, IL-2, IL-3, IL-4, IL-5, IL-6, IL-7, IL-8 or CXCL8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-35, IL-36 |
| IL receptors | CD121a/IL1R1, CD121b/IL1R2, CD25/IL2RA, CD122/IL2RB, CD132/IL2RG, CD123/IL3RA, CD131/IL3RB, CD124/IL4R, CD132/IL2RG, CD125/IL5RA, CD131/IL3RB, CD126/IL6RA, CD130/IR6RB, CD127/IL7RA, CD132/IL2RG, CXCR1/IL8RA, CXCR2/IL8RB/CD128, CD129/IL9R, CD210/IL10RA, CDW210B/IL10RB, IL11RA, CD212/IL12RB1, IR12RB2, IL13R, IL15RA, CD4, |

TABLE 4-continued

Illustrative Biomarkers

| Illustrative Class | Biomarkers |
|---|---|
| | CDw217/IL17RA, IL17RB, CDw218a/IL18R1, IL20R, IL20R, IL21R, IL22R, IL23R, IL20R, LY6E, IL20R1, IL27RA, IL28R, IL31RA |
| Mucin (MUC) proteins | MUC1, MUC2, MUC3A, MUC3B, MUC4, MUC5AC, MUC5B, MUC6, MUC7, MUC8, MUC12, MUC13, MUC15, MUC16, MUC17, MUC19, and MUC20 |
| MUC1 isoforms | mucin-1 isoform 2 precursor or mature form (NP_001018016.1), mucin-1 isoform 3 precursor or mature form (NP_001018017.1), mucin-1 isoform 5 precursor or mature form (NP_001037855.1), mucin-1 isoform 6 precursor or mature form (NP_001037856.1), mucin-1 isoform 7 precursor or mature form (NP_001037857.1), mucin-1 isoform 8 precursor or mature form (NP_001037858.1), mucin-1 isoform 9 precursor or mature form (NP_001191214.1), mucin-1 isoform 10 precursor or mature form (NP_001191215.1), mucin-1 isoform 11 precursor or mature form (NP_001191216.1), mucin-1 isoform 12 precursor or mature form (NP_001191217.1), mucin-1 isoform 13 precursor or mature form (NP_001191218.1), mucin-1 isoform 14 precursor or mature form (NP_001191219.1), mucin-1 isoform 15 precursor or mature form (NP_001191200.1), mucin-1 isoform 16 precursor or mature form (NP_001191201.1), mucin-1 isoform 17 precursor or mature form (NP_001191202.1), mucin-1 isoform 18 precursor or mature form (NP_001191203.1), mucin-1 isoform 19 precursor or mature form (NP_001191204.1), mucin-1 isoform 20 precursor or mature form (NP_001191205.1), mucin-1 isoform 21 precursor or mature form (NP_001191206.1), mucin-1 isoform 1 precursor or mature form (NP_002447.4), ENSP00000357380, ENSP00000357377, ENSP00000389098, ENSP00000357374, ENSP00000357381, ENSP00000339690, ENSP00000342814, ENSP00000357383, ENSP00000357375, ENSP00000338983, ENSP00000343482, ENSP00000406633, ENSP00000388172, ENSP00000357378, P15941-1, P15941-2, P15941-3, P15941-4, P15941-5, P15941-6, P15941-7, P15941-8, P15941-9, P15941-10, secreted isoform, membrane bound isoform, CA 27.29 (BR 27.29), CA 15-3, PAM4 reactive antigen, underglycosylated isoform, unglycosylated isoform, CanAg antigen |
| MUC1 interacting proteins | ABL1, SRC, CTNND1, ERBB2, GSK3B, JUP, PRKCD, APC, GALNT1, GALNT10, GALNT12, JUN, LCK, OSGEP, ZAP70, CTNNB1, EGFR, SOS1, ERBB3, ERBB4, GRB2, ESR1, GALNT2, GALNT4, LYN, TP53, C1GALT1, C1GALT1C1, GALNT3, GALNT6, GCNT1, GCNT4, MUC12, MUC13, MUC15, MUC17, MUC19, MUC2, MUC20, MUC3A, MUC4, MUC5B, MUC6, MUC7, MUCL1, ST3GAL1, ST3GAL3, ST3GAL4, ST6GALNAC2, B3GNT2, B3GNT3, B3GNT4, B3GNT5, B3GNT7, B4GALT5, GALNT11, GALNT13, GALNT14, GALNT5, GALNT8, GALNT9, ST3GAL2, ST6GAL1, ST6GALNAC4, GALNT15, MYOD1, SIGLEC1, IKBKB, TNFRSF1A, IKBKG, MUC1 |
| Tumor markers | Alphafetoprotein (AFP), Carcinoembryonic antigen (CEA), CA-125, MUC-1, Epithelial tumor antigen (ETA), Tyrosinase, Melanoma-associated antigen (MAGE), p53 |
| Tumor markers | Alpha fetoprotein (AFP), CA15-3, CA27-29, CA19-9, CA-125, Calretinin, Carcinoembryonic antigen, CD34, CD99, CD117, Chromogranin, Cytokeratin (various types), Desmin, Epithelial membrane protein (EMA), Factor VIII, CD31 FL1, Glial fibrillary acidic protein (GFAP), Gross cystic disease fluid protein (GCDFP-15), HMB-45, Human chorionic gonadotropin (hCG), immunoglobulin, inhibin, keratin (various types), PTPRC (CD45), lymphocyte marker (various types), MART-1 (Melan-A), Myo D1, muscle-specific actin (MSA), neurofilament, neuron-specific enolase (NSE), placental alkaline phosphatase (PLAP), prostate-specific antigen, S100 protein, smooth muscle actin (SMA), synaptophysin, thyroglobulin, thyroid transcription factor-1, Tumor M2-PK, vimentin |
| Cell adhesion molecule (CAMs) | Immunoglobulin superfamily CAMs (IgSF CAMs), N-CAM (Myelin protein zero), ICAM (1, 5), VCAM-1, PE-CAM, L1-CAM, Nectin (PVRL1, PVRL2, PVRL3), Integrins, LFA-1 (CD11a + CD18), Integrin alphaXbeta2 (CD11c + CD18), Macrophage-1 antigen (CD11b + CD18), VLA-4 (CD49d + CD29), Glycoprotein IIb/IIIa (ITGA2B + ITGB3), Cadherins, CDH1, CDH2, CDH3, Desmosomal, Desmoglein (DSG1, DSG2, DSG3, DSG4), Desmocollin (DSC1, DSC2, DSC3), Protocadherin, PCDH1, T-cadherin, CDH4, CDH5, CDH6, CDH8, CDH11, CDH12, CDH15, CDH16, CDH17, CDH9, CDH10, Selectins, E-selectin, L-selectin, P-selectin, Lymphocyte homing receptor: CD44, L-selectin, integrin (VLA-4, LFA-1), Carcinoembryonic antigen (CEA), CD22, CD24, CD44, CD146, CD164 |
| Annexins | ANXA1; ANXA10; ANXA11; ANXA13; ANXA2; ANXA4; ANXA5; ANXA6; ANXA7; ANXA8; ANXA8L1; ANXA8L2; ANXA9 |
| Cadherins ("calcium-dependent adhesion") | CDH1, CDH2, CDH12, CDH3, Deomoglein, DSG1, DSG2, DSG3, DSG4, Desmocollin, DSC1, DSC2, DSC3, Protocadherins, PCDH1, PCDH10, PCDH11x, PCDH11y, PCDH12, FAT, FAT2, FAT4, PCDH15, PCDH17, PCDH18, PCDH19; PCDH20; PCDH7, PCDH8, PCDH9, PCDHA1, PCDHA10, PCDHA11, PCDHA12, PCDHA13, PCDHA2, PCDHA3, PCDHA4, PCDHA5, PCDHA6, PCDHA7, PCDHA8, PCDHA9, PCDHAC1, PCDHAC2, PCDHB1, PCDHB10, PCDHB11, PCDHB12, PCDHB13, PCDHB14, PCDHB15, PCDHB16, PCDHB17, PCDHB18, PCDHB2, PCDHB3, PCDHB4, PCDHB5, PCDHB6, PCDHB7, PCDHB8, PCDHB9, PCDHGA1, PCDHGA10, PCDHGA11, PCDHGA12, PCDHGA2; PCDHGA3, PCDHGA4, PCDHGA5, PCDHGA6, PCDHGA7, PCDHGA8, PCDHGA9, PCDHGB1, PCDHGB2, PCDHGB3, PCDHGB4, PCDHGB5, PCDHGB6, PCDHGB7, PCDHGC3, PCDHGC4, PCDHGC5, CDH9 (cadherin 9, type 2 (T1-cadherin)), CDH10 (cadherin 10, type 2 (T2-cadherin)), CDH5 (VE-cadherin (vascular endothelial)), CDH6 (K-cadherin (kidney)), CDH7 (cadherin 7, type 2), CDH8 (cadherin 8, type 2), CDH11 (OB-cadherin (osteoblast)), CDH13 (T-cadherin - H-cadherin (heart)), CDH15 (M-cadherin (myotubule)), CDH16 (KSP-cadherin), CDH17 (LI cadherin (liver-intestine)), CDH18 (cadherin 18, type 2), CDH19 (cadherin 19, type 2), CDH20 (cadherin 20, type 2), CDH23 (cadherin 23, (neurosensory epithelium)), CDH10, CDH11, CDH13, CDH15, CDH16, CDH17, CDH18, CDH19, CDH20, CDH22, CDH23, CDH24, CDH26, CDH28, CDH4, CDH5, CDH6, CDH7, CDH8, CDH9, CELSR1, CELSR2, CELSR3, CLSTN1, CLSTN2, CLSTN3, DCHS1, DCHS2, LOC389118, PCLKC, RESDA1, RET |

TABLE 4-continued

Illustrative Biomarkers

| Illustrative Class | Biomarkers |
| --- | --- |
| ECAD (CDH1) downregulators | SNAI1/SNAIL, ZFHX1B/SIP1, SNAI2/SLUG, TWIST1, DeltaEF1 |
| ECAD upregulators | AML1, p300, HNF3 |
| ECAD interacting proteins | ACADVL, ACTG1, ACTN1, ACTN4, ACTR3, ADAM10, ADAM9, AJAP1, ANAPC1, ANAPC11, ANAPC4, ANAPC7, ANK2, ANP32B, APC2, ARHGAP32, ARPC2, ARVCF, BOC, C1QBP, CA9, CASP3, CASP8, CAV1, CBLL1, CCNB1, CCND1, CCT6A, CDC16, CDC23, CDC26, CDC27, CDC42, CDH2, CDH3, CDK5R1, CDON, CDR2, CFTR, CREBBP, CSE1L, CSNK2A1, CTNNA1, CTNNB1, CTNND1, CTNND2, DNAJA1, DRG1, EGFR, EP300, ERBB2, ERBB2IP, ERG, EZR, FER, FGFR1, FOXM1, FRMD5, FYN, GBAS, GNA12, GNA13, GNB2L1, GSK3B, HDAC1, HDAC2, HSP90AA1, HSPA1A, HSPA1B, HSPD1, IGHA1, IQGAP1, IRS1, ITGAE, ITGB7, JUP, KIFC3, KLRG1, KRT1, KRT9, LIMA1, LMNA, MAD2L2, MAGI1, MAK, MDM2, MET, MYO6, MYO7A, NDRG1, NEDD9, NIPSNAP1, NKD2, PHLPP1, PIP5K1C, PKD1, PKP4, PLEKHA7, POLR2E, PPP1CA, PRKD1, PSEN1, PTPN1, PTPN14, PTPRF, PTPRM, PTPRQ, PTTG1, PVR, PVRL1, RAB8B, RRM2, SCRIB, SET, SIX1, SKI, SKP2, SRC, TACC3, TAS2R13, TGM2, TJP1, TK1, TNS3, TTK, UBC, USP9X, VCL, VEZT, XRCC5, YAP1, YES1, ZC3HC1 |
| Epithelial-mesenchymal transition (EMT) | SERPINA3, ACTN1, AGR2, AKAP12, ALCAM, AP1M2, AXL, BSPRY, CCL2, CDH1, CDH2, CEP170, CLDN3, CLDN4, CNN3, CYP4X1, DNMT3A, DSG3, DSP, EFNB2, EHF, ELF3, ELF5, ERBB3, ETV5, FLRT3, FOSB, FOSL1, FOXC1, FX YD 5, GPDIL, HMGA1, HMGA2, HOPX, IFI16, IGFBP2, IHH, IKBIP, IL-11, IL-18, IL6, IL8, ITGA5, ITGB3, LAMB1, LCN2, MAP7, MB, MMP7, MMP9, MPZL2, MSLN, MTA3, MTSS1, OCLN, PCOLCE2, PECAM1, PLAUR, PLXNB1, PPL, PPP1R9A, RASSF8, SCNN1A, SERPINB2, SERPINE1, SFRP1, SH3YL1, SLC27A2, SMAD7, SNAI1, SNAI2, SPARC, SPDEF, SRPX, STAT5A, TBX2, TJP3, TMEM125, TMEM45B, TWIST1, VCAN, VIM, VWF, XBP1, YBX1, ZBTB10, ZEB1, ZEB2 |

Examples of additional biomarkers that can be incorporated into the methods and compositions of the invention include without limitation those disclosed in International Patent Application Nos. PCT/US2012/042519, filed Jun. 14, 2012 and PCT/US2012/050030, filed Aug. 8, 2012.

In various embodiments of the invention, the biomarkers or biosignature used to detect or assess any of the conditions or diseases disclosed herein can comprise one or more biomarkers in one of several different categories of markers, wherein the categories include without limitation one or more of: 1) disease specific biomarkers; 2) cell- or tissue-specific biomarkers; 3) vesicle-specific markers (e.g., general vesicle biomarkers); 4. angiogenesis-specific biomarkers; and 5) immunomodulatory biomarkers. Examples of such markers are disclosed herein and known to a person having ordinary skill in the art. Furthermore, a biomarker known in the art that is characterized to have a role in a particular disease or condition can be adapted for use as a target in compositions and methods of the invention. In further embodiments, such biomarkers that are associated with vesicles can be all vesicle surface markers, or a combination of vesicle surface markers and vesicle payload markers (i.e., molecules enclosed by a vesicle). The biomarkers assessed can be from a combination of sources. For example, a disease or disorder may be detected or characterized by assessing a combination of proteins, nucleic acids, vesicles, circulating biomarkers, biomarkers from a tissue sample, and the like. In addition, as noted herein, the biological sample assessed can be any biological fluid, or can comprise individual components present within such biological fluid (e.g., vesicles, nucleic acids, proteins, or complexes thereof).

EpCAM is a pan-epithelial differentiation antigen that is expressed on many tumor cells. It is intricately linked with the Cadherin-Catenin pathway and hence the fundamental WNT pathway responsible for intracellular signalling and polarity. It has been used as an immunotherapeutic target in the treatment of gastrointestinal, urological and other carcinomas. (Chaudry M A, Sales K, Ruf P, Lindhofer H, Winslet M C (April 2007). Br. J. Cancer 96 (7): 1013-9.). It is expressed in undifferentiated pluripotent stem cells. EpCAM is a member of a family that includes at least two type I membrane proteins and functions as a homotypic calcium-independent cell adhesion molecule. Mutations in this gene result in congenital tufting enteropathy. EpCAM has been observed on the surface of microvesicles derived from cancer cell of various lineages. EpCAM is used as an exemplary surface antigen in various examples herein. One of skill will appreciate that various embodiments and examples using EpCAM can also be applied to other biomarkers, including other microvesicle surface antigens.

Therapeutics

As used herein "therapeutically effective amount" refers to an amount of a composition that relieves (to some extent, as judged by a skilled medical practitioner) one or more symptoms of the disease or condition in a mammal Additionally, by "therapeutically effective amount" of a composition is meant an amount that returns to normal, either partially or completely, physiological or biochemical parameters associated with or causative of a disease or condition. A clinician skilled in the art can determine the therapeutically effective amount of a composition in order to treat or prevent a particular disease condition, or disorder when it is administered, such as intravenously, subcutaneously, intraperitoneally, orally, or through inhalation. The precise amount of the composition required to be therapeutically effective will depend upon numerous factors, e.g., such as the specific activity of the active agent, the delivery device employed, physical characteristics of the agent, purpose for the administration, in addition to many patient specific considerations. But a determination of a therapeutically effective amount is within the skill of an ordinarily skilled clinician upon the appreciation of the disclosure set forth herein.

The terms "treating," "treatment," "therapy," and "therapeutic treatment" as used herein refer to curative therapy, prophylactic therapy, or preventative therapy. An example of "preventative therapy" is the prevention or lessening the chance of a targeted disease (e.g., cancer or other proliferative disease) or related condition thereto. Those in need of treatment include those already with the disease or condition as well as those prone to have the disease or condition to be prevented. The terms "treating," "treatment," "therapy," and "therapeutic treatment" as used herein also describe the management and care of a mammal for the purpose of combating a disease, or related condition, and includes the administration of a composition to alleviate the symptoms, side effects, or other complications of the disease, condition. Therapeutic treatment for cancer includes, but is not limited to, surgery, chemotherapy, radiation therapy, gene therapy, and immunotherapy.

As used herein, the term "agent" or "drug" or "therapeutic agent" refers to a chemical compound, a mixture of chemical compounds, a biological macromolecule, or an extract made from biological materials such as bacteria, plants, fungi, or animal (particularly mammalian) cells or tissues that are suspected of having therapeutic properties. The agent or drug can be purified, substantially purified or partially purified. An "agent" according to the present invention, also includes a radiation therapy agent or a "chemotherapuetic agent."

As used herein, the term "diagnostic agent" refers to any chemical used in the imaging of diseased tissue, such as, e.g., a tumor.

As used herein, the term "chemotherapuetic agent" refers to an agent with activity against cancer, neoplastic, and/or proliferative diseases, or that has ability to kill cancerous cells directly.

As used herein, "pharmaceutical formulations" include formulations for human and veterinary use with no significant adverse toxicological effect. "Pharmaceutically acceptable formulation" as used herein refers to a composition or formulation that allows for the effective distribution of the nucleic acid molecules of the instant invention in the physical location most suitable for their desired activity.

As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated.

Aptamer-Toxin Conjugates as a Cancer Therapeutic

Extensive previous work has developed the concept of antibody-toxin conjugates ("immunoconjugates") as potential therapies for a range of indications, mostly directed at the treatment of cancer with a primary focus on hematological tumors. A variety of different payloads for targeted delivery have been tested in pre-clinical and clinical studies, including protein toxins, high potency small molecule cytotoxics, radioisotopes, and liposome-encapsulated drugs. While these efforts have successfully yielded three FDA-approved therapies for hematological tumors, immunoconjugates as a class (especially for solid tumors) have historically yielded disappointing results that have been attributable to multiple different properties of antibodies, including tendencies to develop neutralizing antibody responses to non-humanized antibodies, limited penetration in solid tumors, loss of target binding affinity as a result of toxin conjugation, and imbalances between antibody half-life and toxin conjugate half-life that limit the overall therapeutic index (reviewed by Reff and Heard, Critical Reviews in Oncology/Hematology, 40 (2001):25-35).

Aptamers are functionally similar to antibodies, except their absorption, distribution, metabolism, and excretion ("ADME") properties are intrinsically different and they generally lack many of the immune effector functions generally associated with antibodies (e.g., antibody-dependent cellular cytotoxicity, complement-dependent cytotoxicity). In comparing many of the properties of aptamers and antibodies previously described, several factors suggest that toxin-delivery via aptamers offers several concrete advantages over delivery with antibodies, ultimately affording them better potential as therapeutics. Several examples of the advantages of toxin-delivery via aptamers over antibodies are as follows:

1) Aptamer-toxin conjugates are entirely chemically synthesized. Chemical synthesis provides more control over the nature of the conjugate. For example, the stoichiometry (ratio of toxins per aptamer) and site of attachment can be precisely defined. Different linker chemistries can be readily tested. The reversibility of aptamer folding means that loss of activity during conjugation is unlikely and provides more flexibility in adjusting conjugation conditions to maximize yields.

2) Smaller size allows better tumor penetration. Poor penetration of antibodies into solid tumors is often cited as a factor limiting the efficacy of conjugate approaches. See Colcher, D., Goel, A., Pavlinkova, G., Beresford, G., Booth, B., Batra, S. K. (1999) "Effects of genetic engineering on the pharmacokinetics of antibodies," Q. J. Nucl. Med., 43: 132-139. Studies comparing the properties of unPEGylated anti-tenascin C aptamers with corresponding antibodies demonstrate efficient uptake into tumors (as defined by the tumor:blood ratio) and evidence that aptamer localized to the tumor is unexpectedly long-lived ($t_{1/2}$>12 hours) (Hicke, B. J., Stephens, A. W., "Escort aptamers: a delivery service for diagnosis and therapy", J. Clin. Invest., 106:923-928 (2000)).

3) Tunable PK. Aptamer half-life/metabolism can be easily tuned to match properties of payload, optimizing the ability to deliver toxin to the tumor while minimizing systemic exposure. Appropriate modifications to the aptamer backbone and addition of high molecular weight PEGs should make it possible to match the half-life of the aptamer to the intrinsic half-life of the conjugated toxin/linker, minimizing systemic exposure to non-functional toxin-bearing metabolites (expected if $t_{1/2}$ (aptamer)<<$t_{1/2}$ (toxin)) and reducing the likelihood that persisting unconjugated aptamer will functionally block uptake of conjugated aptamer (expected if $t_{1/2}$ (aptamer)>>$t_{1/2}$ (toxin)).

4) Relatively low material requirements. It is likely that dosing levels will be limited by toxicity intrinsic to the cytotoxic payload. As such, a single course of treatment will likely entail relatively small (<100 mg) quantities of aptamer, reducing the likelihood that the cost of oligonucleotide synthesis will be a barrier for aptamer-based therapies.

5) Parenteral administration is preferred for this indication. There will be no special need to develop alternative formulations to drive patient/physician acceptance.

Aptamer Identification Methods

Nucleic acid sequences fold into secondary and tertiary motifs particular to their nucleotide sequence. These motifs position the positive and negative charges on the nucleic acid sequences in locations that enable the sequences to bind to specific locations on target molecules, e.g., proteins and other amino acid sequences. These binding sequences are known in the field as aptamers. Due to the trillions of possible unique nucleotide sequences in even a relatively short stretch of nucleotides (e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides), a large variety of motifs can be generated, resulting in aptamers for almost any desired protein or other target.

Aptamers are created by randomly generating oligonucleotides of a specific length, typically 20-80 base pairs long, e.g., 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or 80 base pairs. These random oligonucleotides are then incubated with the protein target of interest. After several wash steps, the oligonucleotides that bind to the target are collected and amplified. The amplified aptamers are then added to the target and the process is repeated, often 15-20 times. A common version of this process known to those of skill in the art as the SELEX method.

The end result comprises one or more aptamer with high affinity to the target. The invention provides further processing of such resulting aptamers that can be use to provide desirable characteristics: 1) competitive binding assays to identify aptamers to a desired epitope; 2) motif analysis to identify high affinity binding aptamers in silico; and 3) microvesicle based aptamer selection assays to identify aptamers that can be used to detect a particular disease. The invention also provides use of the aptamers to detect a target of interest, e.g., to detect a biological entity such as a protein, nucleic acid, or microvesicle. Aptamers of the invention may bind to functional groups of interest, e.g., carboxyl groups, for use as blocking agents, negative controls, and the like. The methods are described in more detail below and further in the Examples.

The invention further contemplates aptamer sequences that are highly homologous to the sequences that are discovered by the methods of the invention. "High homology" typically refers to a homology of 40% or higher, preferably 60% or higher, more preferably 80% or higher, even more preferably 85%, 90%, 91%, 92%, 93%, 94%, 95%, 96%, 97%, 98%, 99% or higher between a polynucleotide sequence sequence and a reference sequence. In an embodiment, the reference sequence comprises the sequence of one or more aptamer provided herein. Percent homologies (also referred to as percent identity) are typically carried out between two optimally aligned sequences. Methods of alignment of sequences for comparison are well-known in the art. Optimal alignment of sequences and comparison can be conducted, e.g., using the algorithm in "Wilbur and Lipman, Proc Natl Acad Sci USA 80: 726-30 (1983)". Homology calculations can also be performed using BLAST, which can be found on the NCBI server at: www.ncbi.nlm.nih.gov/BLAST/(Altschul S F, et al, Nucleic Acids Res. 1997; 25(17):3389-402; Altschul S F, et al, J Mol. Biol. 1990; 215(3):403-10). In the case of an isolated polynucleotide which is longer than or equivalent in length to the reference sequence, e.g., a sequence identified by the methods herein, the comparison is made with the full length of the reference sequence. Where the isolated polynucleotide is shorter than the reference sequence, e.g., shorter than a sequence identified by the methods herein, the comparison is made to a segment of the reference sequence of the same length (excluding any loop required by the homology calculation).

The invention further contemplates aptamer sequences that are functional fragments of the sequences that are discovered by the methods of the invention. In the context of an aptamer sequence, a "functional fragment" of the aptamer sequence may comprise a subsequence that binds to the same target as the full length sequence. In some instances, a candidate aptamer sequence is from a member of a library that contains a 5' leader sequences and/or a 3' tail sequence. Such leader sequences or tail sequences may serve to facilitate primer binding for amplification or capture, etc. In these embodiments, the functional fragment of the full length sequence may comprise the subsequence of the candidate aptamer sequence absent the leader and/or tail sequences.

Competitive Antibody Addition

Known aptamer production methods may involve eluting all bound aptamers from the target sequence. In some cases, this is not sufficient to identify the desired aptamer sequence. For example, when trying to replace an antibody in an assay, it may be desirable to only collect aptamers that bind to the specific epitope of the antibody being replaced. The invention provides a method comprising addition of an antibody that is to be replaced to the aptamer/target reaction in order to allow for the selective collection of aptamers which bind to the antibody epitope. In an embodiment, the method comprises incubating a reaction mixture comprising randomly generated oligonucleotides with a target of interest, removing unbound aptamers from the reaction mixture that do not bind the target, adding an antibody to the reaction mixture that binds to that epitope of interest, and collecting the aptamers that are displaced by the antibody. The target can be a protein.

Figure 2A:
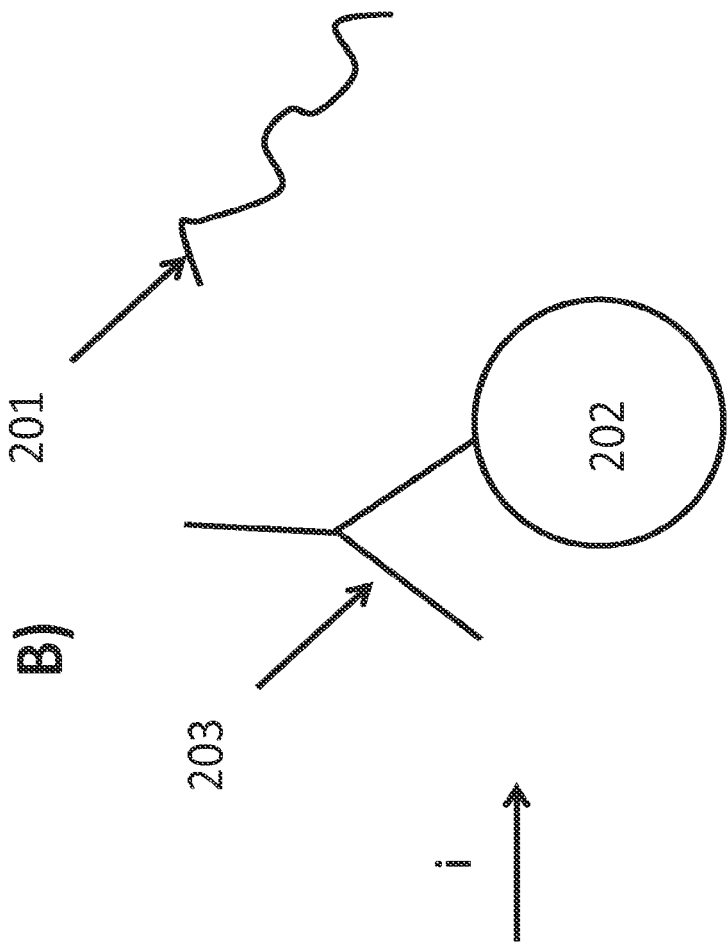
FIGS. 2A-2B illustrate a competitive assay selection strategy. A random pool of nucleic acid aptamer candidates (the library) are incubated with a target of interest 202. Multiple rounds of binding can be performed wherein: 1) the library is incubated with the target; 2) the library-target mixture is washed to remove unbound aptamer candidates; 3) bound aptamer candidates are eluted from the target; and 4) the eluted aptamer candidates are again added to the target and allowed to bind.
Figure 2B:
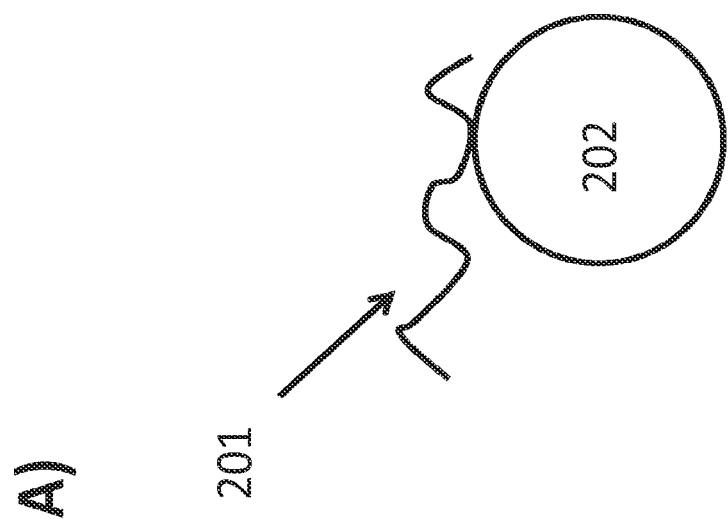

FIGS. 2A-2B illustrate a competitive assay selection strategy. A random pool of nucleic acid aptamer candidates (the library) are incubated with a target of interest 202. Multiple rounds of binding can be performed wherein: 1) the library is incubated with the target; 2) the library-target mixture is washed to remove unbound aptamer candidates; 3) bound aptamer candidates are eluted from the target; and 4) the eluted aptamer candidates are again added to the target and allowed to bind. FIG. 2A illustrates aptamer candidate 201 bound to target 202. In step i), a competing antibody 203 is then added to the reaction. FIG. 2B illustrates candidate antibody 203 competing with aptamer candidate 201 at the epitope of the antibody. Aptamer candidate 201 is displaced by the antibody and then collected.

Competitive Binding

As described herein, aptamers can be identified against a target of interest. A competitive binding scheme 30 can be used to identify aptamers against a target of interest, as outlined in FIG. 3. An analyte of interest, e.g., a biological entity such as a protein or microvesicle, is captured to a substrate 31. The substrate can be, e.g., a planar substrate or bead. The analyte can be captured covalently or non-covalently, e.g., the analyte can be captured using an antibody, aptamer, or streptavidin-biotin linkage. The captured analyte is contacted with a pool of oligonucleotide aptamer candidates 32. In an embodiment, the pool comprises randomly generated oligonucleotides, e.g., at least 10, $10^2$, $10^3$, $10^4$, $10^5$, $10^6$, $10^7$, $10^8$, $10^9$, $10^{10}$, $10^{11}$, $10^{12}$, $10^{13}$, $10^{23}$, $10^{15}$, $10^{16}$, $10^{17}$, $10^{18}$, $10^{19}$ or at least $10^{20}$ oligonucleotides. The oligonucleotides bind to various components in the mixture, including the analyte, the substrate, the capture agent (e.g., antibody (Ab), aptamer, etc), reaction tube or well, biological debris, etc 33. Oligonucleotides that bind the analyte comprise aptamer candidates to the target of interest 34. Unbound oligonucleotides are removed via washing 35. After this step, the reaction mixture comprises the capture analyte bound by aptamer candidates. A ligand that recognizes a specific epitope, e.g., an antibody, is contacted with the reaction mixture 37. The ligand disassociates aptamer candidates bound to the same epitope as the ligand via competition for the epitope 38. The disassociated aptamer candidates are collected and amplified 39. Steps 32-39 are repeated a set number of times, n, e.g., 1, 2, 3, 4, 5, 6, 7, 8, 9, 10, 11, 12, 13, 14, 15, 16, 17, 18, 19 or 20 times, to further enrich the aptamer candidates with those that bind to the same epitope as the ligand. After the repeated cycles, the remaining aptamers are assessed by sequencing, and other characterizations 310 as described herein.

Control screening is performed in parallel with the above method. Any aptamer identified via the control screening are discarded. Controls analytes include without limitation bare substrate incubated with the analyte, bare substrate without the analyte, and the method performed with a control ligand, such as an antibody that does not bind a target of interest.

The ligand can be an antibody to a biomarker of interest. The method may be used to identify an aptamer to substitute for an antibody in a biological assay. For example, the aptamer may be produced more reproducibly and efficiently than an equivalent antibody. The biomarker may be any useful biomarker, including without limitation a biomarker in Table 3 or 4. In an embodiment, the biomarker is a microvesicle surface antigen selected from Table 3 or 4.

In an embodiment, the invention provides a method of selecting a group of aptamers, comprising: (a) contacting a pool of aptamer candidates to a sample comprising a target molecule; (b) removing unbound aptamer candidates; (c) contacting the sample with a ligand to the target molecule; and (d) isolating aptamer candidates that are disassociated from the target molecule by competition with the ligand, thereby selecting the group of aptamers that bind the same target as the ligand. The target molecule may be a protein. The protein can be a microvesicle surface antigen. The surface antigen may be isolated from a microvesicle or remain embedded within a microvesicle membrane. The target molecule may be directly or indirectly tethered to a substrate. For example, the target molecule can be a protein that is bound by an antibody or aptamer on the substrate surface. In another example, the target molecule is a surface antigen of a microvesicle and the microvesicle is tethered to the substrate.

The ligand used to displace the aptamer candidates may comprise a small molecule or protein. In some embodiment, the ligand comprises an antibody. Thus the method can be used to identify aptamers that bind the same epitope as an antibody.

As described herein, steps (a)-(d) can be repeated 1, 2, 3, 4, 5, 6, 7, 8, 9, 10, 11, 12, 13, 14, 15, 16, 17, 18, 19 or 20 times, wherein the aptamer candidates isolated in the step (d) are used the pool of aptamer candidates input into step (a) in each iteration. This iterative process is used to further enrich the pool of aptamer candidates with those that bind the same target as the ligand.

The members of the selected group of aptamers may be identified for further characterization. In some embodiments, the identifying is performed by high throughput sequencing (HTS). The HTS can be Next Generation sequencing.

Motif Analysis

In most aptamer experiments, multiple aptamer sequences are identified that bind to the target. These aptamers will have various binding affinities. It can be time consuming and laborious to generate quantities of these many aptamers sufficient to assess the affinities of each. To identify large numbers of aptamers with the highest affinities without physically screening large subsets, the invention provides a method comprising the analysis of the two dimensional structure of one or more high affinity aptamers to the target of interest. In an embodiment, the method comprises screening the database for aptamers that have similar two-dimensional structures, or motifs, but not necessarily similar primary sequences. In an embodiment, the method comprises identifying a high affinity aptamer using traditional methods such as disclosed herein or known in the art (e.g. surface plasmon resonance binding assay, see, e.g., FIG. 4), approximating the two-dimensional structure of the high affinity aptamer, and identifying aptamers from a pool of sequences that are predicted to have a similar two-dimensional structure to the high affinity aptamer. The method thereby provides a pool of candidates that also bind the target of interest. The two-dimensional structure of an oligo can be predicting using methods known in the art, e.g., via free energy ($\Delta G$) calculations performed using a commercially available software program such as Vienna or mFold, for example as described in Mathews, D., Sabina, J., Zucker, M. & Turner, H. Expanded sequence dependence of thermodynamic parameters provides robust prediction of RNA secondary structure. J. Mol. Biol. 288, 911-940 (1999); Hofacker et al., Monatshefte f Chemie 125: 167-188 (1994); and Hofacker, I. L. Vienna RNA secondary structure server. Nucleic Acids Res. 31, 3429-3431 (2003), the contents of which are incorporated herein by reference in their entirety. See FIGS. 5A-5B. The pool of sequences can be sequenced from a pool of randomly generated aptamer candidates using a high-throughput sequencing platform, such as the Ion Torrent platform from Life Technologies. Identifying aptamers from a pool of sequences that are predicted to have a similar two-dimensional structure to the high affinity aptamer may comprise loading the resulting sequences into the software program of choice to identify members of the pool of sequences with similar two-dimensional structures as the high affinity aptamer. The affinities of the pool of sequences can then be determined in situ, e.g., surface plasmon resonance binding assay or the like.

Aptamer Subtraction Methods

In order to develop an assay to detect a disease, for example, cancer, one typically screens a large population of known biomarkers from normal and diseased patients in order to identify markers that correlate with disease. This process only works if discriminating markers are already described. In order to address this problem, the invention provides a method comprising subtracting out non-discriminating aptamers from a large pool of aptamers by incubating them initially with non-target microvesicles or cells. The non-target cells can be normal cells or microvesicles shed therefrom. The aptamers that did not bind to the normal microvesicles or cells are then incubated with diseased microvesicles or cells. The aptamers that bind to the diseased microvesicles or cells but that did not bind to the normal cells are then possible candidates for an assay to detect the disease. This process is independent of knowing the existence of a particular marker in the diseased sample.

Subtraction methods can be used to identify aptamers that preferentially recognize a desired population of targets. In an embodiment, the subtraction method is used to identify aptamers that preferentially recognize target from a diseased target population over a control (e.g., normal or non-diseased) population. The diseased target population may be a population of vesicles from a diseased individual or individuals, whereas the control population comprises vesicles from a non-diseased individual or individuals. The disease can be a cancer or other disease disclosed herein or known in the art. Accordingly, the method provides aptamers that preferentially identify disease targets versus control targets.

Circulating microvesicles are isolated from control plasma, e.g., plasma from "normal" individuals that are absent a disease of interest, such as an absence of cancer. Vesicles in the plasma are isolated using a method disclosed herein or as known in the art. For example, vesicles can be isolated from the plasma by one of the following methods: filtration, ExoQuick reagent, ultracentrifugation, using a molecular crowding reagent (e.g., TEXIS from Life Technologies), affinity isolation, affinity selection, or a combination of any of these methods. The microvesicles isolated in each case will be a mixture of vesicle types and will be various sizes with the exception of the ultracentrifugation methods, which has a tendency to produce exosomal-sized vesicles. Randomly generated oligonucleotide libraries (e.g., produced as described in Example 1 below) are incubated with the isolated normal vesicles. The aptamers that do not bind to these vesicles are isolated, e.g., by spinning down the vesicles and collecting the supernatant containing the non-binding aptamers. These non-binding aptamers are then contacted with vesicles isolated from diseased patients (e.g., using the same methods as described above) to allow the aptamers to recognize the disease vesicles. Next, aptamers that are bound to the diseased vesicles are collected. In an embodiment, the vesicles are isolated then lysed using a chaotropic agent (e.g., SDS or a similar detergent), and the aptamers are then captured by running the lysis mixture over an affinity column. The affinity column may comprise streptavidin beads in the case of biotin conjugated aptamer pools. The isolated aptamers are the amplified. The process can then repeated, e.g., 1, 2, 3, 4, 5, 6, 7, 8, 9, 10, 11, 12, 13, 14, 15, 16, 17, 18, 19 or 20 or more times.

In one aspect of the invention, an aptamer profile is identified that can be used to characterize a biological sample of interest. In an embodiment, a pool of randomly generated oligonucleotides, e.g., at least 10, $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$ or at least $10^{20}$ oligonucleotides, is contacted with a biological component or target of interest from a control population. The oligonucleotides that do not bind the biological component or target of interest from the control population are isolated and then contacted with a biological component or target of interest from a test population. The oligonucleotides that bind the biological component or target of interest from the test population are retained. The retained oligonucleotides can be used to repeat the process by contacting the retained oligonucleotides with the biological component or target of interest from the control population, isolating the retained oligonucleotides that do not bind the biological component or target of interest from the control population, and again contacting these isolated oligonucleotides with the biological component or target of interest from the test population and isolating the binding oligonucleotides. The "component" or "target" can be anything that is present in sample to which the oligonucleotides are capable of binding (e.g., polypeptides, peptide, nucleic acid molecules, carbodyhrates, lipids, etc.). The process is then repeated, e.g., 1, 2, 3, 4, 5, 6, 7, 8, 9, 10 or more times. The resulting oligonucleotides comprise aptamers that can differentially detect the test population versus the control. These aptamers provide an aptamer profile, which comprises a biosignature that is determined using one or more aptamer, e.g., a biosignature comprising a presense or level of the component or target which is detected using the one or more aptamer.

Figure 6:
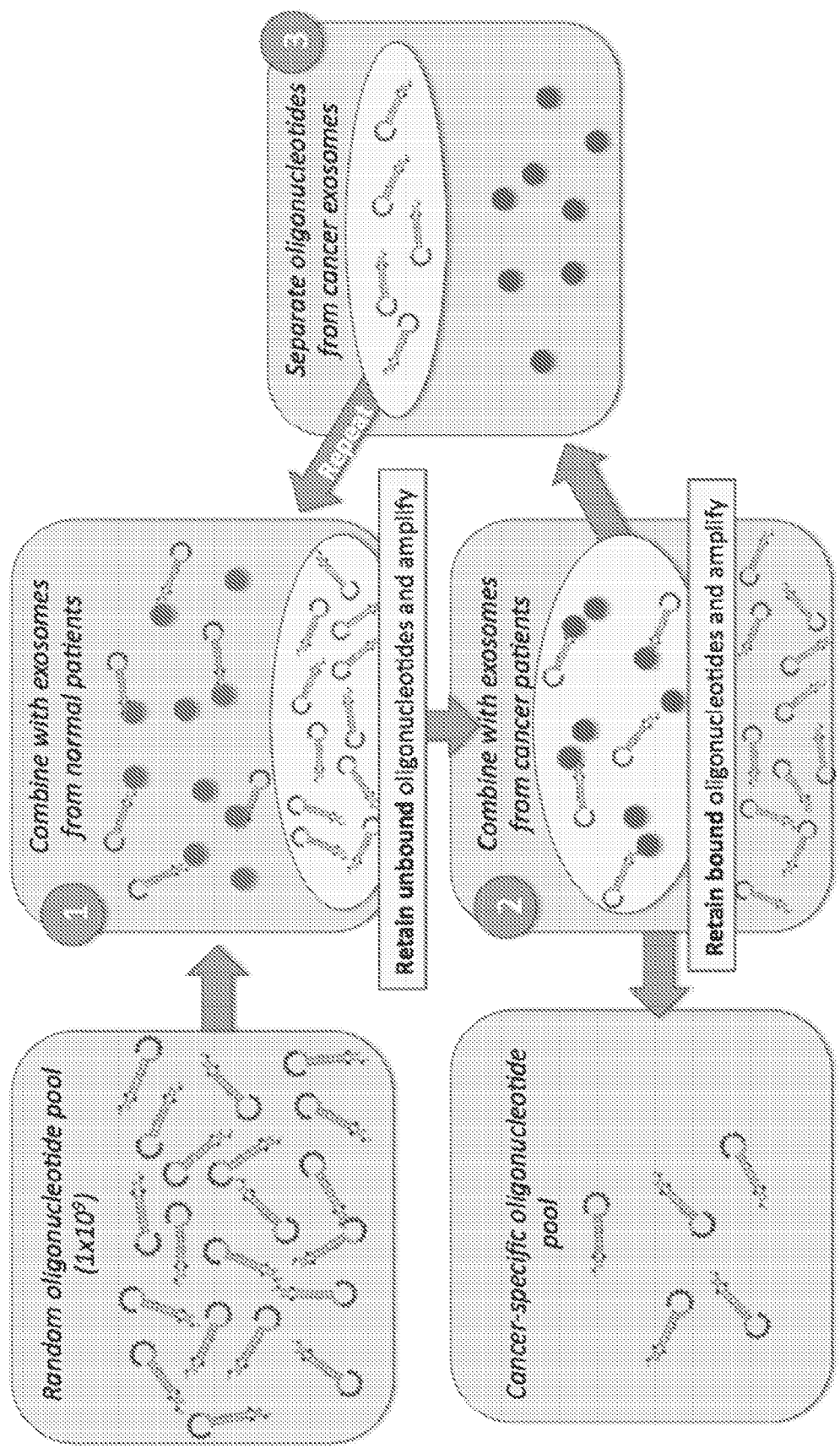
FIG. 6 illustrates a process for producing a target-specific set of aptamers using a cell subtraction method, wherein the target is a biomarker associated with a specific disease. In Step 1, a random pool of oligonucleotides are contacted with a biological sample from a normal patient. In Step 2, the oligos that did not bind in Step 1 are added to a biological sample isolated from diseased patients. The bound oligos from this step are then eluted, captured via their biotin linkage and then combined again with normal biological sample. The unbound oligos are then added again to disease-derived biological sample and isolated. This process can be repeated iteratively. The final eluted aptamers are tested against patient samples to measure the sensitivity and specificity of the set. Biological samples can include blood, including plasma or serum, or other components of the circulatory system, such as microvesicles.

An exemplary process is illustrated in FIG. 6, which demonstrates the method to identify aptamer that preferentially recognize cancer vesicles using vesicles from normal (non-cancer) individuals as a control. In the figure, exosomes are exemplified but one of skill will appreciate that other microvesicles can be used in the same manner. The resulting aptamers can provide a profile that can differentially detect the cancer vesicles from the normal vesicles. One of skill will appreciate that the same steps can be used to derive an aptamer profile to characterize any disease or condition of interest.

In an embodiment, the invention provides an isolated polynucleotide identified by the methods above. The invention further provides an isolated polynucleotide having a nucleotide sequence that is at least 60% identical to the nucleotide sequence identified by the methods above. More preferably, the isolated nucleic acid molecule is at least 65%, 70%, 75%, 80%, 85%, 90%, 91%, 92%, 93%, 94%, 95%, 96%, 97%, 98%, 99% or more, identical to the nucleotide sequence identified by the methods above. In the case of an isolated polynucleotide which is longer than or equivalent in length to the reference sequence, e.g., a sequence identified by the methods above, the comparison is made with the full length of the reference sequence. Where the isolated polynucleotide is shorter than the reference sequence, e.g., shorter than a sequence identified by the methods above, the comparison is made to a segment of the reference sequence of the same length (excluding any loop required by the homology calculation).

In a related aspect, the invention provides a method of characterizing a biological phenotype using an aptamer profile. The aptamer profile can be determined using the method above. The aptamer profile can be determined for a test sample and compared to a control aptamer profile. The phenotype may be a disease or disorder such as a cancer. Characterizing the phenotype can include without limitation providing a diagnosis, prognosis, or theranosis. Thus, the aptamer profile can provide a diagnostic, prognostic and/or theranostic readout for the subject from whom the test sample is obtained.

In another embodiment, an aptamer profile is determined for a test sample by contacting a pool of aptamer molecules to the test sample, contacting the same pool of aptamers to a control sample, and identifying one or more aptamer molecules that differentially bind a component or target in the test sample but not in the control sample (or vice versa). A "component" or "target" as used in the context of the biological test sample or control sample can be anything that is present in sample to which the aptamers are capable of binding (e.g., polypeptides, peptide, nucleic acid molecules, carbodyhrates, lipids, etc.). For example, if a sample is a plasma or serum sample, the aptamer molecules may bind a polypeptide biomarker that is solely expressed or differentially expressed (over- or underexpressed) in a disease state as compared to a non-diseased subject. Comparison of the aptamer profile in the test sample as compared to the control sample may be based on qualitative and quantitative measure of aptamer binding (e.g., binding versus no binding, or level of binding in test sample versus different level of binding in the reference control sample).

In an aspect, the invention provides a method of identifying a target-specific aptamer profile, comprising contacting a biological test sample with a pool of aptamer molecules, contacting the pool to a control biological sample, identifying one or more aptamers that bind to a component in said test sample but not to the control sample, thereby identifying an aptamer profile for said biological test sample. In an embodiment, a pool of aptamers is selected against a disease sample and compared to a reference sample, the aptamers in a subset that bind to a component(s)

in the disease sample but not in the reference sample can be sequenced using conventional sequencing techniques to identify the subset that bind, thereby identifying an aptamer profile for the particular disease sample. In this way, the aptamer profile provides an individualized platform for detecting disease in other samples that are screened. Furthermore, by selecting an appropriate reference or control sample, the aptamer profile can provide a diagnostic, prognostic and/or theranostic readout for the subject from whom the test sample is obtained.

In a related aspect, the invention provides a method of selecting a pool of aptamers, comprising: (a) contacting a biological control sample with a pool of oligonucleotides; (b) isolating a first subset of the pool of oligonucleotides that do not bind the biological control sample; (c) contacting the biological test sample with the first subset of the pool of oligonucleotides; and (d) isolating a second subset of the pool of oligonucleotides that bind the biological test sample, thereby selecting the pool of aptamers. The pool of oligonucleotides may comprise any number of desired sequences, e.g., at least 10, $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$ or at least $10^{20}$ oligonucleotides may be present in the starting pool. Steps (a)-(d) may be repeated to further hone the pool of aptamers. In an embodiment, these steps are repeated at least 1, 2, 3, 4, 5, 6, 7, 8, 9, 10, 11, 12, 13, 14, 15, 16, 17, 18, 19 or at least 20 times.

As described herein, the biological test sample and biological control sample may comprise microvesicles. In an embodiment, the biological test sample and optionally biological control sample comprise a bodily fluid. The bodily fluid may comprise without limitation peripheral blood, sera, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, Cowper's fluid, pre-ejaculatory fluid, female ejaculate, sweat, fecal matter, hair, tears, cyst fluid, pleural fluid, peritoneal fluid, malignant fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates or other lavage fluids. The biological test sample and optionally biological control may also comprise a tumor sample, e.g., cells from a tumor or tumor tissue. In other embodiments, the biological test sample and optionally biological control sample comprise a cell culture medium. In embodiments, the biological test sample comprises a diseased sample and the biological control sample comprises a non-diseased sample. Accordingly, the pool of aptamers may be used to provide a diagnostic, prognostic and/or theranostic readout a disease.

As noted, the invention can be used to assess microvesicles. Microvesicles are powerful biomarkers because the vesicles provide one biological entity that comprises multiple pieces of information. For example as described, a vesicle can have multiple surface antigens, each of which provides complementary information. Consider a cancer marker and a tissue specific marker. If both markers are individually present in a sample, e.g., both are circulating proteins or nucleic acids, it may not be ascertainable whether the cancer marker and the tissue specific marker are derived from the same anatomical locale. However, if both the cancer marker and the tissue specific marker are surface antigens on a single microvesicle, the vesicle itself links the two markers and provides an indication of a disease (via the cancer marker) and origin of the disease (via the tissue specific marker). Furthermore, the vesicle can have any number of surface antigens and also payload that can be assessed. Accordingly, the invention provides a method for identifying binding agents comprising contacting a plurality of extracellular microvesicles with a randomly generated library of binding agents, identifying a subset of the library of binding agents that have an affinity to one or more components of the extracellular microvesicles. The binding agents may comprise aptamers, antibodies, and/or any other useful type of binding agent disclosed herein or known in the art.

In a related aspect, the invention provides a method for identifying a plurality of target ligands comprising, (a) contacting a reference microvesicle population with a plurality of ligands that are capable of binding one or more microvesicle surface markers, (b) isolating a plurality of reference ligands, wherein the plurality of reference ligands comprise a subset of the plurality of ligands that do not have an affinity for the reference microvesicle population; (c) contacting one or more test microvesicle with the plurality of reference ligands; and (d) identifying a subset of ligands from the plurality of reference ligands that form complexes with a surface marker on the one or more test microvesicle, thereby identifying the plurality of target ligands. The term "ligand" can refer a molecule, or a molecular group, that binds to another chemical entity to form a larger complex. Accordingly, a binding agent comprises a ligand. The plurality of ligands may comprise aptamers, antibodies and/or other useful binding agents described herein or known in the art.

The invention further provides kits comprising one or more reagent to carry out the methods above. In an embodiment, the one or more reagent comprises a library of potential binding agents that comprises one or more of an aptamer, antibody, and other useful binding agents described herein or known in the art.

Substrate-Sample Complexes

The invention contemplates multiple variations of the method to identify a binding agent that is specific for or binds to a target molecule present in a sample. The binding agent in the context of any of the embodiments herein can be any molecular that is capable of binding to a desired target molecule. Examples of such binding agents are disclosed herein below. Any of the embodiments herein can include a method to identify various types of binding agents that are capable of binding to one or more components present in a biological sample tested. In further embodiments, the specific target to which a binding agent binds or associates is characterized as described above.

In an aspect, the invention provides a method comprising: (a) contacting a substrate with a biological sample to allow formation of a substrate-biological sample complex; (b) contacting the complex with a plurality of candidate binding agents; and (c) identifying one or more binding agent that binds to or associates with the complex, thereby selecting one or more binding agent.

In any of the embodiments herein, the binding agent can be any appropriate binding agent, including those described herein such a nucleic acid, DNA molecule, RNA molecule, antibody, antibody fragment, aptamer, peptoid, zDNA, peptide nucleic acid (PNA), locked nucleic acid (LNA), lectin, peptide, dendrimer, membrane protein labeling agent, chemical compound, or a combination thereof. In an embodiment, the binding agent comprises an antibody, antibody conjugate, antibody fragment, and/or aptamer. In some embodiments, the binding agent comprises a polypeptide, peptide or a nucleic acid molecule. For example, the binding agent can be an aptamer. The polypeptide can be an antibody or functional fragment thereof.

The biological sample may comprise a tissue sample or cell culture sample, a bodily fluid or any component of an animal or human subject that can be isolated for assessment. In any of the embodiments herein, the bodily fluid comprises peripheral blood, sera, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, female ejaculate, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, umbilical cord blood, or a derivative of any thereof. The biological sample of these or other origins may comprise a heterogeneous microvesicle population or a homogeneous microvesicle population.

In some embodiments, the biological sample comprises a concentrated plasma sample, a serum sample, a clarified serum sample, or a clarified plasma sample. The biological sample of these or other origins may comprise a heterogeneous microvesicle population or a homogeneous microvesicle population. As used in the context of microvesicles, the term "heterogenous" means the microvesicle population may comprise microvesicles that are of different cellular or tissue origin, are produced through different biological or cellular mechanisms, and/or comprise microvesicles of different sizes as discussed herein. As used in the context of microvesicles, the term "homogeneous" means without limitation, that the microvesicle population comprise microvesicles that are of the same cellular or tissue origin, are produced through the same biological or cellular mechanisms and/or comprise microvesicles of the same size range as discussed herein. In a non-limiting example, a homogeneous microvesicle population can be obtained from a heterogeneous microvesicle population by subjecting the heterogeneous microvesicle population to affinity isolation or size exclusion methodology.

As used herein, a "clarified" serum or "clarified" plasma sample has reduced levels of one or more abundant protein as compared to an unclarified sample. In such cases, the one or more abundant protein comprises a blood protein. For example, the one or more abundant protein may comprise one or more of albumin, IgG, transferrin, fibrinogen, fibrin, IgA, α2-Marcroglobulin, IgM, α1-Antitrypsin, complement C3, haptoglobulin, apolipoprotein A1, A3 and B; α1-Acid Glycoprotein, ceruloplasmin, complement C4, C1q, IgD, prealbumin (transthyretin), plasminogen, a derivative of any thereof, and a combination thereof. The one or more abundant protein may comprise one or more of Albumin, Immunoglobulins, Fibrinogen, Prealbumin, Alpha 1 antitrypsin, Alpha 1 acid glycoprotein, Alpha 1 fetoprotein, Haptoglobin, Alpha 2 macroglobulin, Ceruloplasmin, Transferrin, complement proteins C3 and C4, Beta 2 microglobulin, Beta lipoprotein, Gamma globulin proteins, C-reactive protein (CRP), Lipoproteins (chylomicrons, VLDL, LDL, HDL), other globulins (types alpha, beta and gamma), Prothrombin, Mannose-binding lectin (MBL), a derivative of any thereof, and a combination thereof.

The one or more abundant protein can be depleted using methods known in the art or disclosed herein. For example, abundant proteins can be separated in whole or in part by chromatography methods (size exclusion, ion exchange, immunoaffinity, etc), immunoaffinity, precipitation, or a combination thereof. In some embodiments, selectively depleting the one or more abundant protein comprises contacting the biological sample with thromboplastin. This step can serve to precipitate fibrinogen, thereby facilitating its removal.

The one or more abundant protein is preferably depleted to a level that improves the performance of downstream processing steps. For example, selectively depleting the one or more abundant protein from the biological sample may comprise depleting at least 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% or 100% of the one or more abundant protein.

The substrate-biological sample complex can comprise a linkage between the substrate and a component of the sample. Any useful method of crosslinking disclosed herein or known in the art can be used. In any of the embodiments herein, the linkage can comprise a cross-link. Any useful method of cross-linking as disclosed herein or known in the art may be used. In an embodiment, the cross-link comprises a photocrosslink, an imidoester crosslinker, dimethyl suberimidate, a lipid crosslinker, an N-Hydroxysuccinimide-ester crosslinker, bissulfosuccinimidyl suberate (BS3), an aldehyde, acrolein, crotonaldehyde, formaldehyde, a carbodiimide crosslinker, N,N'-dicyclohexylcarbodiimide (DDC), N,N'-diisopropylcarbodiimide (DIC), 1-Ethyl-3-[3-dimethylaminopropyl]cathodiimide hydrochloride (EDC or EDAC), Succinimidyl-4-(N-maleimidomethyl)cyclohexane-1-carboxylate (SMCC), a Sulfosuccinimidyl-4-(N-maleimidomethyl)cyclohexane-1-carboxylate (Sulfo-SMCC), a Sulfo-N-hydroxysuccinimidyl-2-(6-[biotinamido]-2-(p-azido benzamido)-hexanoamido)ethyl-1,3'-dithioproprionate (Sulfo-SBED), 2-[N2-(4-Azido-2,3,5,6-tetrafluorobenzoyl)-N6-(6-biotin-amidocaproyl)-L-lysinyl]ethylmethanethiosulfonate (Mts-Atf-Biotin; available from Thermo Fisher Scientific Inc, Rockford Ill.), 2-{N2-[N6-(4-Azido-2,3,5,6-tetrafluorobenzoyl-6-aminocaproyl)-N6-(6-biotinamidocaproyl)-L-lysinylamido]}ethyl methanethiosultonate (Mts-Atf-LC-Biotin; available from Thermo Fisher Scientific Inc), a photoreactive amino acid (e.g., L-Photo-Leucine and L-Photo-Methionine, see, e.g., Suchanek, M., et al. (2005). Photo-leucine and photo-methionine allow identification of protein-protein interactions. Nat. Methods 2:261-267), an N-Hydroxysuccinimide (NHS) crosslinker, an NHS-Azide reagent (e.g., NHS-Azide, NHS-PEG4-Azide, NHS-PEG12-Azide; each available from Thermo Fisher Scientific, Inc.), an NHS-Phosphine reagent (e.g., NHS-Phosphine, Sulfo-NHS-Phosphine; each available from Thermo Fisher Scientific, Inc.), or any combination or modification thereof.

In any of the embodiments herein, the substrate is directly crosslinked to a sample component, e.g., a microvesicle. Any useful moiety on the surface of the microvesicle can be a target of the linkage, e.g., a surface protein, carbohydrate or lipid moiety. In other embodiments, the substrate is linked to the microvesicle via a linker.

In any of the embodiments herein, the substrate and sample may be linked through a linker that comprises additional components that provide functional linkage, where for example the linker has the same or two different components at each end (e.g., formula of X-linker-X or X-LINKER-Y), wherein "X" and "Y" represent functional moieties that are configured to bind or associate with a substrate and a component present in the biological sample. Thus, it will be evident that in some instances X and Y are the same or different functional moieties. Non-limiting examples of such functional moieties for linking, crosslinking or interchelating with a desired target moiety are disclosed herein. The linker may be a nucleic acid or peptide molecule (e.g., providing an arm that reduces or prevents steric hinderance). The linker may also be a chemical backbone that itself terminates in functional groups that are available for covalent linkage to a specified chemical group present on the selected substrate (e.g. bead) and the selected sample (e.g., microvesicles). The linker can comprise a functionalized lipid. Useful functionalized lipids include without limitation 16:0 Biotinyl PE 1,2-dipalmitoyl-sn-glycero-3-phosphoethanolamine-N-(biotinyl) (sodium salt), 18:1 Biotinyl PE 1,2-dioleoyl-sn-glycero-3-phosphoethanolamine-N-(biotinyl) (sodium salt), 16:0 Biotinyl Cap PE 1,2-dipalmitoyl-sn-glycero-3-phosphoethanolamine-N-(cap biotinyl) (sodium salt) or 18:1 Biotinyl Cap PE 1,2-dioleoyl-sn-glycero-3-phosphoethanolamine-N-(cap biotinyl) (sodium salt), Biotin Sphingosine, Biotin SIP, 12:0 Biotinyl MG, 18:1-12:0 Biotin DG, 12:0 N-Biotinyl Fatty Acid, 18:1-12:0 Biotin PS, 18:1-12:0 Biotin PA, 18:1-12:0 Biotin PE, 18:1-12:0 Biotin PC, 18:1-12:0 Biotin CA, 12:0 Biotinyl LPA, 18:1-12:0 Biotin PIP3, 12:0 Biotinyl Coenzyme A, all of which are available from Avanti Polar Lipids, Inc. (Alabaster, Ala.). The functional lipid may serve as a lipid or membrance anchor.

For illustration, in an X-LINKER-Y example, the X is a moiety capable of binding or associating strongly with substrate (e.g., bead, plate, array) and Y is a moiety of capable of binding to a component of the biological sample such as a cell, microvesicle, etc. X can be a conventional cross-linker, such amine/carbonyl specific compounds as described herein or known in the art. Y can also be a conventional cross-linker, such amine/carbonyl specific compounds as described herein or known in the art. In other embodiments, Y is a lipid-membrane specific moiety. Y may be configured to embed within a lipid membrane of a vesicle, cell or other biological entity.

In addition to the functional lipids described above, other useful membrane anchor entities include without limitation diacyl glycerols, diacyl phosphoglycerols (phospholipids) and sterols, dialkyl glycerols, dialkyl- or diacyl-1-amino-2, 3-dihydroxypropanes, long-chain alkyls or acyls with 8 to 25 carbon atoms, sphingolipids, ceramides, phospholipids, glycosyl phosphatidylinositol (GPI) membrane anchor sequences, glycophospholipid membrane anchors, membrane receptor fragments, protein-binding receptors, metal-chelating receptors, immunoglobulin Fc-binding receptors, cytokine or growth factor-binding receptors, drug-binding receptors, lipid mimicking receptors, transmembrane receptors, synthetic protein-binding receptors, synthetic metal-chelating receptors, synthetic immunoglobulin Fc-binding receptors, synthetic cytokine or growth factor-binding receptors, synthetic drug-binding receptors, synthetic lipid mimicking receptors, synthetic transmembrane receptors, proteins, peptides, peptidomimetics, phospholipids, sphingolipids, steroids, cholesterol, dihydrocholesterol, ergosterol, brassicasterol, cholesterylamine, dihydrocholesterylamine, ergosteiylamine, brassicasterylamine, 3-cholesterylamine, 3-dihydrocholesterylamine, 3-ergosterylamine, 3-brassicasterylamine 3β-cholesterylamine, 3β-dihydrocholesterylamine, 3β-ergosterylamine, 3β-brassicasterylamine, and derivatives of any thereof. The term "derivative" may be used to refer to a molecule that contains at least the portion of that allows the molecule to insert into a lipid membrane. Examples of derivatives of cholesterol include cholesteryl esters and cholesteryl carbamates. Examples of derivatives of 3β-cholesterylamine include, without limitation, N-alkyl, N-aryl, and N-acyl 3β-cholesterylamines. Still other useful membrane anchoring moieties and methods of use are described in the following references, each of which is incorporated by reference herein in its entirety: Nizard et al., "Anchoring Antibodies to Membranes Using a Diphtheria Toxin T Domain-ZZ Fusion Protein as a pH Sensitive Membrane Anchor," FEBs Letters 433:83-88, 1998; Nizard et al., "Prolonged Display or Rapid Internalization of the IgG-Binding Protein ZZ Anchored to the Surface of Cells Using the Diphtheria Toxin T Domain," Protein Engineering 14(6):439-446, 2001; Caras et al., "Signal peptide for protein secretion directing glycophospholipid membrane anchor attachment", Science, vol. 243:1196-1198 (1989); Lin et al., "Expression of T Cell Antigen Receptor Heterodimers in a Lipid-Linked Form," Science Reports, 1990; 249:677-679; Hussey, Stephen L., et al., "A Synthetic Membrane-Anchored Antigen Efficiently Promotes Uptake of Antifluorescein Antibodies and Associated Protein a by Mammalian Cells", J. Am. Chem. Soc., 2001, vol. 123, pp. 12712-12713; U.S. Patent Application 2006/0068388 A1; U.S. Pat. Nos. 7,083,958, 7,160,856, 7,288,368, 7,371,404, 7,407,947, 7,514,400, 7,611,863, 7,858,117, 7,947,647, 8,013,131, 8,048,448, 8,088,601, 8,198,230; PCT Patent Applications PCT/US98/15124 (WO 99/05255), WO 00/59474, PCT/NZ02/00214 (WO 03/034074), PCT/NZ03/00059 (WO 03/087346).

The invention further comprises identification of the binding agent identified by the method herein. Methods of identifying biological entities are known in the art. For example, nucleic acids can be identified by sequencing (Sanger, NextGen, etc).

In another aspect, the invention provides a composition of matter comprising a substrate-microvesicle complex, wherein the substrate is synthetic. As used in the context of a substrate-microvesicle complex, the term "synthetic" means that the substrate is man-made. The substrate can be a bead (e.g., a magnetic bead, a polystyrene bead, etc.), a planar substrate, or other useful substrate disclosed herein or known in the art. The composition can be used in the methods above to identify binding agents. The composition can also be used to provide normalization in an assay comprising a substrate. As a non-limiting example, a bead linked to a microvesicle can be used to provide normalization in an assay wherein microvesicles in a biological sample are captured and detected using beads.

In an embodiment, the sample comprises a microvesicle bound to a substrate. The method can then be used to identify aptamers and/or other binding agents that bind a microvesicle, including without limitation a microvesicle surface antigen. Microvesicles can be bound to a substrate using various methods, e.g.: 1) direct conjugation; 2) lipid anchoring; 3) antibody binding; and 4) aptamer binding. See schematics in FIGS. 7A-D. FIG. 7A illustrates direct conjugation of a carboxylated microsphere to a vesicle surface antigen. FIG. 7B illustrates anchoring of a microvesicle to a microsphere via a biotin functionalized lipid anchor. FIG. 7C illustrates antibody binding to a vesicle surface antigen, wherein the antibody is conjugated to a carboxylated microsphere. FIG. 7D illustrates aptamer binding to a vesicle surface antigen, wherein the aptamer is conjugated to a carboxylated microsphere. Substrate attached microvesicles produced by the method can be used to screen an aptamer library against the microvesicle as described herein. FIGS. 8-10 illustrate use of microvesicle-substrate complexes to screen aptamer libraries. FIGS. 11-12 present images of microbead-conjugated microvesicles.

In an aspect, the invention provides a method of producing a stable substrate-microvesicle complex, comprising contacting a substrate with a microvesicle, wherein the substrate is functionalized with a chemical group capable of binding directly to at least one component present on the surface of the microvesicle. The substrate may be a bead, a well, a matrix, e.g., a gel matrix in a column, or a planar substrate. The chemical group can comprise any useful chemical group that can link a microvesicle to a bead, such as those described above. For example, the chemical group may comprise without limitation a peptoid, zDNA, peptide nucleic acid (PNA), locked nucleic acid (LNA), lectin, peptide/polypeptide, dendrimer, membrane protein labeling agent, chemical compound, a photocrosslink, an imidoester crosslinker, dimethyl suberimidate, a lipid crosslinker, an N-Hydroxysuccinimide-ester crosslinker, bissulfosuccinimidyl suberate (BS3), an aldehyde, acrolein, crotonaldehyde, formaldehyde, a carbodiimide crosslinker, N,N'-dicyclohexylcarbodiimide (DDC), N,N'-diisopropylcarbodiimide (DIC), 1-Ethyl-3-[3-dimethylaminopropyl]carbodiimide hydrochloride (EDC or EDAC), Succinimidyl-4-(N-maleimidomethyl)cyclohexane-1-carboxylate (SMCC), a Sulfo-succinimidyl-4-(N-maleimidomethyl)cyclohexane-1-carboxylate (Sulfo-SMCC), a Sulfo-N-hydroxysuccinimidyl-2-(6-[biotinamido]-2-(p-azido benzamido)-hexanoamido) ethyl-1,3'-dithioproprionate (Sulfo-SBED), 2-[N2-(4-Azido-2,3,5,6-tetrafluorobenzoyl)-N6-(6-biotin-amidocaproyl)-L-lysinyl]ethyl methanethiosulfonate (Mts-Atf-Biotin; available from Thermo Fisher Scientific Inc, Rockford Ill.), 2-{N2-[N6-(4-Azido-2,3,5,6-tetrafluorobenzoyl-6-amino-caproyl)-N6-(6-biotinamidocaproyl)-L-lysinylamido]}ethyl methanethiosultonate (Mts-Atf-LC-Biotin; available from Thermo Fisher Scientific Inc), a photoreactive amino acid (e.g., L-Photo-Leucine and L-Photo-Methionine, see, e.g., Suchanek, M., et al. (2005). Photo-leucine and photo-methionine allow identification of protein-protein interactions. Nat. Methods 2:261-267), an N-Hydroxysuccinimide (NHS) crosslinker, an NHS-Azide reagent (e.g., NHS-Azide, NHS-PEG4-Azide, NHS-PEG12-Azide; each available from Thermo Fisher Scientific, Inc.), an NHS-Phosphine reagent (e.g., NHS-Phosphine, Sulfo-NHS-Phosphine; each available from Thermo Fisher Scientific, Inc.), or a combination thereof. The chemical group may not include antibodies or aptamers. The chemical group may comprise a functional group such as disclosed herein, including without limitation a hydrocarbon, a halogen, a group containing oxygen (i.e., C—O bonds), a group containing nitrogen, a group containing sulfur, a group containing phosphorus, a group containing boron, a carboxyl group, an amino group, a hydroxyl group, a hydrazide group, a chloromethyl group, or a combination thereof. The at least one component may comprise any useful biological component such as disclosed herein, including without limitation a peptide, polypeptide, protein, lipid, carbohydrate, a derivative thereof, or a combination thereof.

Figure 10A:
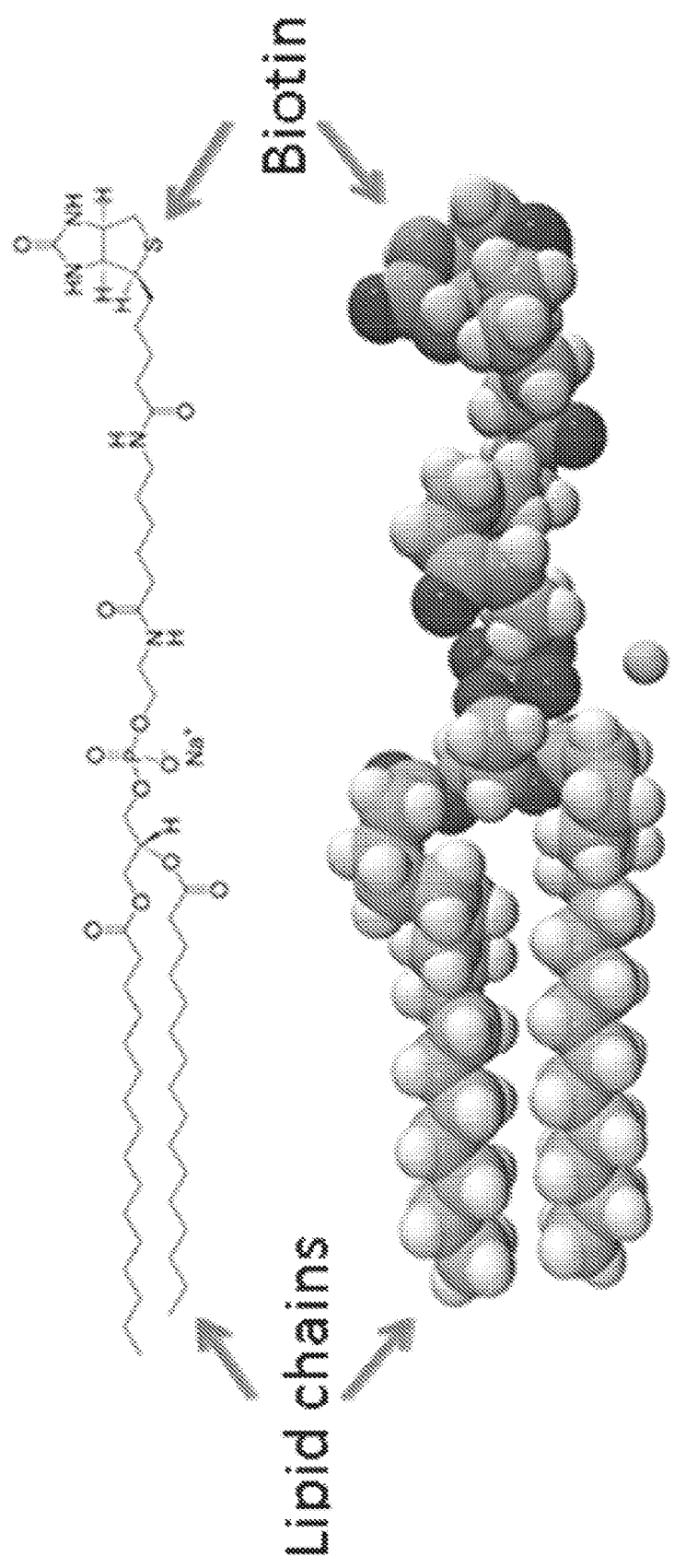
Figure 10B:
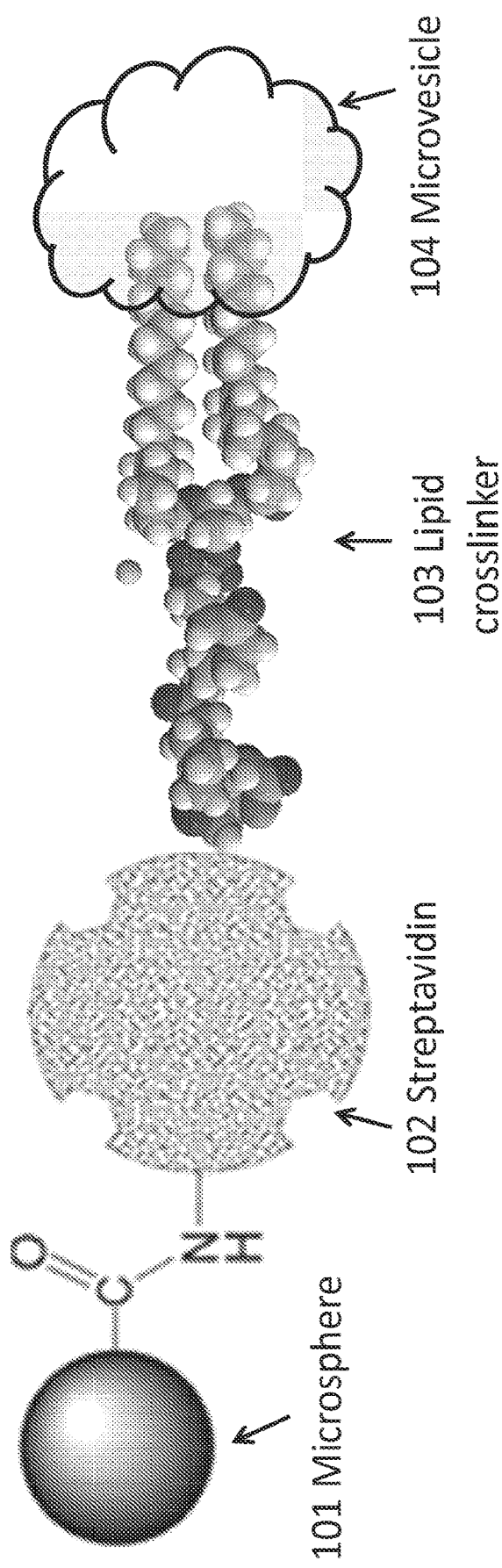
FIG. 10B illustrates biotin functionalized lipid anchoring of microvesicles to the microspheres. As shown, a carboxylated microsphere 101 is conjugated to streptavidin 102. The crosslinker 103 is bound to the streptavidin via a biotin moiety (see FIG. 10A). Finally, the lipid linker 103 is embedded in the lipid bilayer membrane of the microvesicle 104.

In a related aspect, the invention provides a method of isolating a microvesicle from a sample comprising, contacting a biological sample to a substrate disposed with a lipid moiety that is capable of forming a complex with a microvesicle, partitioning any complex formed from the sample, thereby isolating the microvesicle. The invention also provides an isolated complex comprising a synthetic substrate directly bound to a lipid moiety that is complexed to a microvesicle such as in FIG. 10B. One aspect of the invention is incorporation of a lipid moiety (also referred to as "lipid anchor" into a fixed substrate, such as a planar sheet or sphere which is then utilized as a reagent to separate or isolate a microvesicle from a source biological sample (FIG. 10B). The substrate is bound to the lipid anchor through direct covalent linkage (such as through a amide linkage) or the lipid anchor is functionalized to bind to the substrate indirectly, such as by using streptavidin or avidin (FIG. 10B). The biological sample used in methods of the invention can be any biological liquid from a subject or from cell culture, including but not limited to blood, plasma, serum, cell culture media (whether crude or clarified). Examples of lipid anchors that can be incorporated into practicing methods of the invention or manufacture of compositions of the invention include those disclosed herein or in United States Patent Application Publications having the following reference numbers: 2013/0035371, 2012/0264810, 2012/0101148, 2012/0027803; or U.S. Pat. No. 6,986,902, the specification for each of which is incorporated herein by reference in its entirety.

The invention further provides kits comprising one or more reagent to carry out the methods above. In an embodiment, the one or more reagent comprises a library of potential binding agents that comprises one or more of an aptamer, antibody, and other useful binding agents described herein or known in the art. In another embodiment, the one or more reagent comprises an aptamer identified by the methods above. In still another embodiment, the one or more reagent comprises a substrate-microvesicle complex and/or a reagent that is part of such complex, e.g., a linker or cross linker as described herein. The kit may comprise components disclosed herein useful for forming microvesicle-substrate complexes by various methods, e.g., via direct conjugation, lipid anchoring, antibody binding, and/or aptamer binding.

Negative and Positive Aptamer Selection

Aptamers can be used in various biological assays, including numerous types of assays which rely on a binding agent. For example, aptamers can be used instead of or along side antibodies in immune-based assays. The invention provides an aptamer screening method that identifies aptamers that do not bind to any surfaces (substrates, tubes, filters, beads, other antigens, etc.) throughout the assay steps and bind specifically to an antigen of interest. The assay relies on negative selection to remove aptamers that bind non-target antigen components of the final assay. The negative selection is followed by positive selection to identify aptamers that bind the desired antigen.

In an aspect, the invention provides a method of identifying an aptamer specific to a target of interest, comprising (a) contacting a pool of candidate aptamers with one or more assay components, wherein the assay components do not comprise the target of interest; (b) recovering the members of the pool of candidate aptamers that do not bind to the one or more assay components in (a); (c) contacting the members of the pool of candidate aptamers recovered in (b) with the target of interest in the presence of one or more confounding target; and (d) recovering a candidate aptamer that binds to the target of interest in step (c), thereby identifying the aptamer specific to the target of interest. In the method, steps (a) and (b) provide negative selection to remove aptamers that bind non-target entities. Conversely, steps (c) and (d) provide positive selection by identifying aptamers that bind the target of interest but not other confounding targets, e.g., other antigens that may be present in a biological sample which comprises the target of interest. The pool of candidate aptamers may comprise at least 10, $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$ or at least $10^{20}$ nucleic acid sequences. One means of performing the method is illustrated in detail in Example 9.

In some embodiments, steps (a)-(b) are optional. In other embodiments, steps (a)-(b) are repeated at least 1, 2, 3, 4, 5, 6, 7, 8, 9, 10, 11, 12, 13, 14, 15, 16, 17, 18, 19 or at least 20 times before positive selection in step (c) is performed. The positive selection can also be performed in multiple rounds. Steps (c)-(d) can be repeated at least 1, 2, 3, 4, 5, 6, 7, 8, 9, 10, 11, 12, 13, 14, 15, 16, 17, 18, 19 or at least 20 times before identifying the aptamer specific to the target of interest. Multiple rounds may provide improved stringency of selection.

In some embodiments, the one or more assay components contacted with the aptamer pool during negative selection comprise one or more of a substrate, a bead, a planar array, a column, a tube, a well, or a filter. One of skill will appreciate that the assay components can include any substance that may be part of a biological assay.

The target of interest can be any appropriate entity that can be detected when recognized by an aptamer. In an embodiment, the target of interest comprises a protein or polypeptide. As used herein, "protein," "polypeptide" and "peptide" are used interchangeably unless stated otherwise. The target of interest can be a nucleic acid, including DNA, RNA, and various subspecies of any thereof as disclosed herein or known in the art. The target of interest can comprise a lipid. The target of interest can comprise a carbohydrate. The target of interest can also be a complex, e.g., a complex comprising protein, nucleic acids, lipids and/or carbohydrates. In some embodiments, the target of interest comprises a microvesicle. In such cases, the aptamer can be a binding agent to a microvesicle surface antigen, e.g., a protein. General microvesicle surface antigens include tetraspanin, CD9, CD63, CD81, CD63, CD9, CD81, CD82, CD37, CD53, Rab-5b, Annexin V, and MFG-E8. Additional general microvesicle surface antigens are provided in Table 3 herein.

The microvesicle surface antigen can also be a biomarker of a disease or disorder. In such cases, the aptamer may be used to provide a diagnosis, prognosis or theranosis of the disease or disorder. For example, the one or more protein may comprise one or more of PSMA, PCSA, B7H3, EpCam, ADAM-10, BCNP, EGFR, IL1B, KLK2, MMP7, p53, PBP, SERPINB3, SPDEF, SSX2, and SSX4. These markers can be used detect a prostate cancer. Additional microvesicle surface antigens are provided in Tables 3-4 herein.

The one or more confounding target can be an antigen other than the target of interest. For example, a confounding target can be another entity that may be present in a sample to be assayed. As a non-limiting example, consider that the sample to be assessed is a plasma sample from an individual. The target of interest may be a protein, e.g., a microvesicle surface antigen, which is present in the sample. In this case, a confounding target could be selected from any other antigen that is likely to be present in the plasma sample. Accordingly, the positive selection should provide candidate aptamers that recognize the target of interest but have minimal, if any, interactions with the confounding targets. In some embodiments, the target of interest and the one or more confounding target comprise the same type of biological entity, e.g., all protein, all nucleic acid, all carbohydrate, or all lipids. As a non-limiting example, the target of interest can be a protein selected from the group consisting of SSX4, SSX2, PBP, KLK2, SPDEF, and EpCAM, and the one or more confounding target comprises the other members of this group. In other embodiments, the target of interest and the one or more confounding target comprise different types of biological entities, e.g., any combination of protein, nucleic acid, carbohydrate, and lipids. The one or more confounding targets may also comprise different types of biological entities, e.g., any combination of protein, nucleic acid, carbohydrate, and lipids.

In an embodiment, the invention provides an isolated polynucleotide, or a fragment thereof, identified by the methods above. The invention further provides an isolated polynucleotide having a nucleotide sequence that is at least 60% identical to the nucleotide sequence identified by the methods above. More preferably, the isolated nucleic acid molecule is at least 65%, 70%, 75%, 80%, 85%, 90%, 91%, 92%, 93%, 94%, 95%, 96%, 97%, 98%, 99% or more, identical to the nucleotide sequence identified by the methods above. In the case of an isolated polynucleotide which is longer than or equivalent in length to the reference sequence, e.g., a sequence identified by the methods above, the comparison is made with the full length of the reference sequence. Where the isolated polynucleotide is shorter than the reference sequence, e.g., shorter than a sequence identified by the methods above, the comparison is made to a segment of the reference sequence of the same length (excluding any loop required by the homology calculation).

In a related aspect, the invention provides a method of selecting a group of aptamers, comprising: (a) contacting a pool of aptamers to a population of microvesicles from a first sample; (b) enriching a subpool of aptamers that show affinity to the population of microvesicles from the first sample; (c) contacting the subpool to a second population of microvesicles from a second sample; and (d) depleting a second subpool of aptamers that show affinity to the second population of microvesicles from the second sample, thereby selecting the group of aptamers that have preferential affinity for the population of microvesicles from the first sample.

The first sample and/or second sample may comprise a biological fluid such as disclosed herein. For example, the biological fluid may include without limitation blood, a blood derivative, plasma, serum or urine. The first sample and/or second sample may also be derived from a cell culture.

In an embodiment, the first sample comprises a cancer sample and the second sample comprises a control sample, such as a non-cancer sample. The first sample and/or and the second sample may each comprise a pooled sample. For example, the first sample and/or second sample can comprise bodily fluid from 2, 3, 4, 5, 6, 7, 8, 9, 10, 11, 12, 13, 14, 15, 16, 17, 18, 19, 20, 25, 30, 40, 50, 60, 70, 80, 90, 100 or more than 100 individuals. In such cases, the members of a pool may be chosen to represent a desired phenotype. In a non-limiting example, the members of the first sample pool may be from patients with a cancer and the members of the second sample pool may be from non-cancer controls.

Steps (a)-(d) can be repeated a desired number of times in order to further enrich the pool in aptamers that have preferential affinity for the population of microvesicles from the first sample. For example, steps (a)-(d) can be repeated 1, 2, 3, 4, 5, 6, 7, 8, 9, 10, 11, 12, 13, 14, 15, 16, 17, 18, 19, 20 or more than 20 times. The output from step (d) can be used as the input to repeated step (a). In embodiment, the first sample and/or second sample are replaced with a different sample before repeating steps (a)-(d). In a non-limiting example, members of a first sample pool may be from patients with a cancer and members of a second sample pool may be from non-cancer controls. During subsequent repetitions of steps (a)-(d), the first sample pool may comprise samples from different cancer patients than in the prior round/s. Similarly, the second sample pool may comprise samples from different controls than in the prior round/s.

The method may further comprise identifying the members of the selected group of aptamers, e.g., by DNA sequencing. The sequencing may be performed by Next Generation sequencing as desired.

The method may also comprise identifying the targets of the selected group of aptamers. Methods to identify aptamer targets are disclosed herein.

Figure 13A:
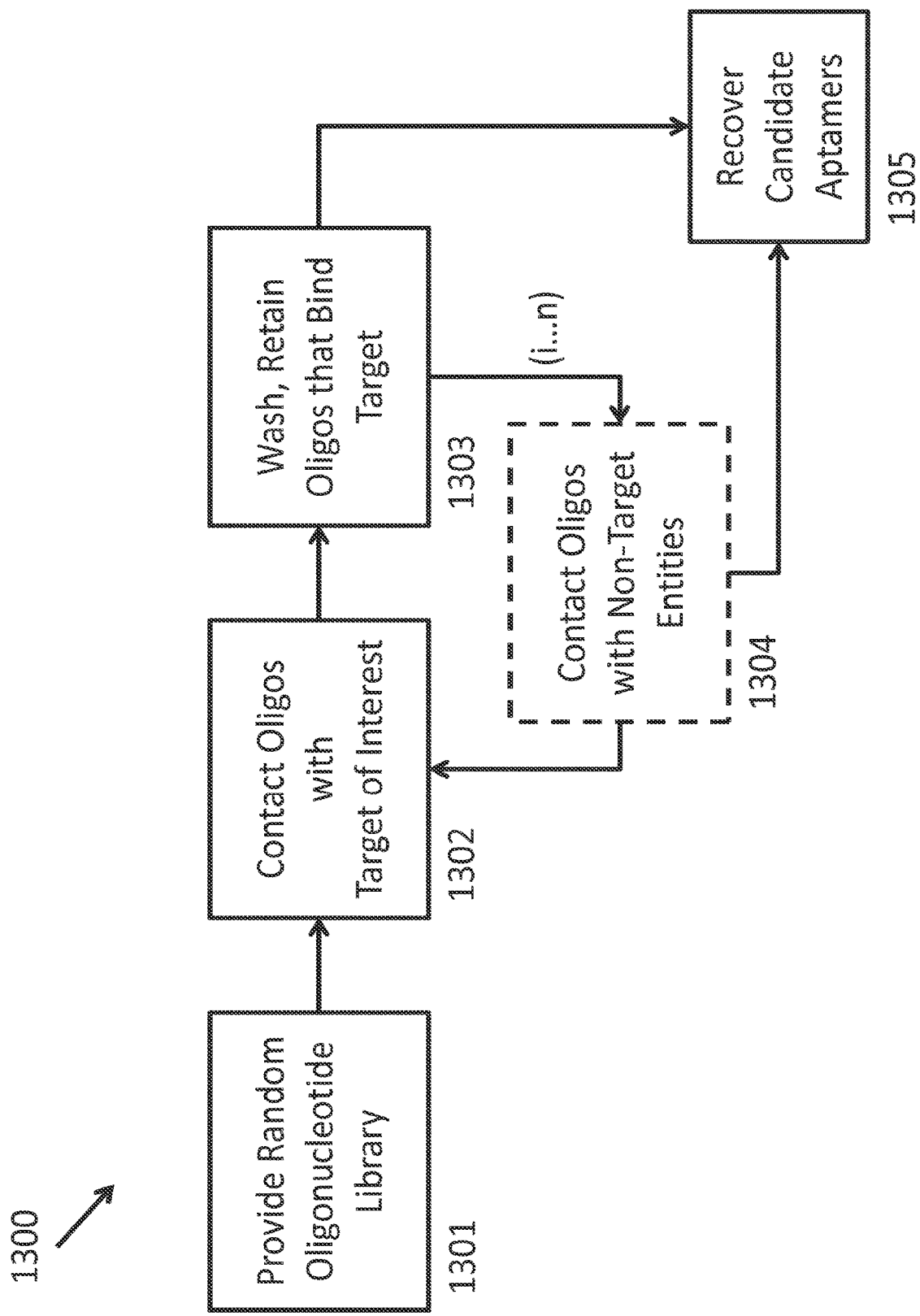

FIG. 13A illustrates a scheme 1300 for positive and optionally negative rounds of screening an oligonucleotide library against a target of interest. A library pool of oligo candidates is provided 1301. The pool of oligo candidate aptamers may comprise any number of desired members, e.g., at least $10, 10^2, 10^3, 10^4, 10^5, 10^6, 10^7, 10^8, 10^9, 10^{10}, 10^{11}, 10^{12}, 10^{13}, 10^{14}, 10^{15}, 10^{16}, 10^{17}, 10^{18}, 10^{19}$ or at least $10^{20}$ nucleic acid sequences. To perform positive selection, the oligos are contacted with the target of interest 1302. The target of interest can be any appropriate entity that can be detected when recognized by an aptamer. The target of interest may comprise a protein or polypeptide, a nucleic acid, including DNA, RNA, and various subspecies thereof, a lipid, a carbohydrate, a complex, e.g., a complex comprising protein, nucleic acids, lipids and/or carbohydrates. In some embodiments, the target of interest comprises a microvesicle. The target may be immobilized to a substrate using methods disclosed herein (see, e.g., Examples 28-31) or known in the art. The mixture is washed to remove unbound oligos and then oligos are disassociated from the washed mixture and collected 1303. The collected oligos can be used as input to a new round of target binding, which can be repeated any number of times (indicated as 1 . . . n). For example, positive selection can be repeated 1, 2, 3, 4, 5, 6, 7, 8, 9, 10, 11, 12, 13, 14, 15, 16, 17, 18, 19, 20 or more than 20 times. Between rounds of positive selection, negative selection is optionally performed wherein oligos are contacted with one or more non-target entity 1304. The non-target entity can be any entity that may interfere with specific binding of the resulting aptamers to the target of interest, including without limitation other biological entities, non-disease specific targets, and various assay components (substrates, tubes, etc.). During negative selection, oligos that do not bind the one or more non-target entity are retained and used as input to a new round of positive selection 1302. This step serves to remove oligos that have an affinity for the non-target entities. The oligos collected after the desired numbers of rounds of positive selection 1303 and/or negative selection 1304 are collected as candidate aptamers which are indicated to bind the target of interest 1305.

FIG. 13B illustrates one such scheme for selection of aptamers against cancer samples versus non-cancer control samples. The scheme shows 8 cancer samples (Ca1-Ca8) and 7 control samples (nCa1-nCa7) each consisting of individual samples or pooled samples. Seven different selections (Selection 1-Selection 7) are run in parallel. In each Selection, an input pool of candidate aptamers is enriched for aptamers against one of the cancer samples ("positive selection"), and then the pool is depleted of aptamers against one of the control samples ("negative selection"). This process is repeated as indicated. The ordering of the samples is altered in each Selection to avoid selection bias. The aptamers remaining after the last round of positive selection comprise the selected aptamers, which can then be further developed, e.g., as part of an assay to differentiate cancer from non-cancer samples. The aptamer pools can be sequenced after each round to track enrichment, depletion, potential issues, etc.

Aptamer Target Identification

The methods and kits above can be used to identify binding agents that differentiate between two biomarker populations. The invention further provides methods of identifying the targets of the binding agents, as described in this section. For example, the methods may further comprise identifying a surface marker of a target microvesicle that is recognized by the binding agent.

In an embodiment, the invention provides a method of identifying a target of a binding agent comprising: (a) contacting the binding agent with the target to bind the target with the binding agent, wherein the target comprises a surface antigen of a microvesicle; (b) disrupting the microvesicle under conditions which do not disrupt the binding of the target with the binding agent; (c) isolating the complex between the target and the binding agent; and (d) identifying the target bound by the binding agent. The binding agent can be a binding agent identified by the methods above, e.g., an aptamer, ligand, antibody, or other useful binding agent that can differentiate between two populations of biomarkers.

Figure 14:
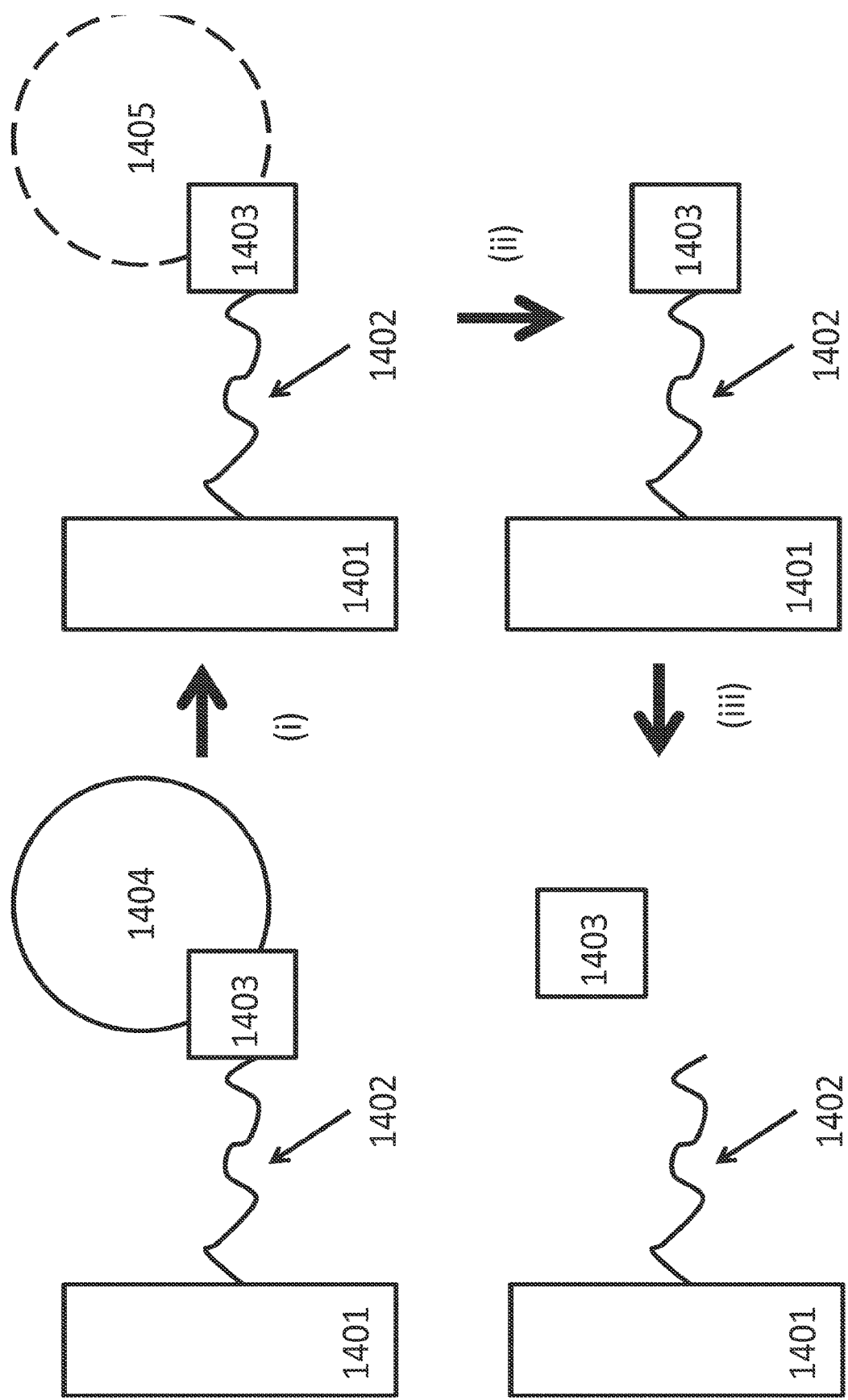
FIG. 14 comprises a schematic for identifying a target of a selected aptamer, such as an aptamer selected by the above process. The figure shows a binding agent 1402, here an aptamer for purposes of illustration, tethered to a substrate 1401. The binding agent 1402 can be covalently attached to substrate 1401. The binding agent 1402 may also be non-covalently attached. For example, binding agent 1402 can comprise a label which can be attracted to the substrate, such as a biotin group which can form a complex with an avidin/streptavidin molecule that is covalently attached to the substrate. The binding agent 1402 binds to a surface antigen 1403 of microvesicle 1404. In the step signified by arrow (i), the microvesicle is disrupted while leaving the complex between the binding agent 1402 and surface antigen 1403 intact. Disrupted microvesicle 1405 is removed, e.g., via washing or buffer exchange, in the step signified by arrow (ii). In the step signified by arrow (iii), the surface antigen 1403 is released from the binding agent 1402. The surface antigen 1403 can be analyzed to determine its identity.

An illustrative schematic for carrying on the method is shown in FIG. 14. The figure shows a binding agent 1402, here an aptamer for purposes of illustration, tethered to a substrate 1401. The binding agent 1402 can be covalently attached to substrate 1401. The binding agent 1402 may also be non-covalently attached. For example, binding agent 1402 can comprise a label which can be attracted to the substrate, such as a biotin group which can form a complex with an avidin/streptavidin molecule that is covalently attached to the substrate. This can allow a complex to be formed between the aptamer and the microvesicle while in solution, followed by capture of the aptamer using the biotin label. The binding agent 1402 binds to a surface antigen 1403 of microvesicle 1404. In the step signified by arrow (i), the microvesicle is disrupted while leaving the complex between the binding agent 1402 and surface antigen 1403 intact. Disrupted microvesicle 1405 is removed, e.g., via washing or buffer exchange, in the step signified by arrow (ii). In the step signified by arrow (iii), the surface antigen 1403 is released from the binding agent 1402. The surface antigen 1403 can be analyzed to determine its identity using methods disclosed herein and/or known in the art. The target of the method can be any useful biological entity associated with a microvesicle. For example, the target may comprise a protein, nucleic acid, lipid or carbohydrate, or other biological entity disclosed herein or known in the art.

In some embodiments of the method, the target is cross-linked to the binding agent prior disrupting the microvesicle. Without being bound by theory, this step may assist in maintaining the complex between the binding agent and the target while the vesicle is disrupted. Any useful method of crosslinking disclosed herein or known in the art can be used. In embodiments, the cross-linking comprises photo-crosslinking, an imidoester crosslinker, dimethyl suberimidate, an N-Hydroxysuccinimide-ester crosslinker, bissulfosuccinimidyl suberate (BS3), an aldehyde, acrolein, crotonaldehyde, formaldehyde, a carbodiimide crosslinker, N,N'-dicyclohexylcarbodiimide (DDC), N,N'-diisopropylcarbodiimide (DIC), 1-Ethyl-3-[3-dimethylaminopropyl] carbodiimide hydrochloride (EDC or EDAC), Succinimidyl-4-(N-maleimidomethyl)cyclohexane-1-carboxylate (SMCC), a Sulfosuccinimidyl-4-(N-maleimidomethyl)cyclohexane-1-carboxylate (Sulfo-SMCC), a Sulfo-N-hydroxysuccinimidyl-2-(6-[biotinamido]-2-(p-azido benzamido)-hexanoamido)ethyl-1,3'-dithioproprionate (Sulfo-SBED), 2-[N2-(4-Azido-2,3,5,6-tetrafluorobenzoyl)-N6-(6-biotinamidocaproyl)-L-lysinyl]ethylmethanethiosulfonate (Mts- Atf-Biotin; available from Thermo Fisher Scientific Inc, Rockford Ill.), 2-{N2-[N6-(4-Azido-2,3,5,6-tetrafluorobenzoyl-6-amino-caproyl)-N6-(6-biotinamidocaproyl)-L-lysinylamido]}ethyl methanethiosultonate (Mts-Atf-LC-Biotin; available from Thermo Fisher Scientific Inc), a photoreactive amino acid (e.g., L-Photo-Leucine and L-Photo-Methionine, see, e.g., Suchanek, M., et al. (2005). Photoleucine and photo-methionine allow identification of protein-protein interactions. Nat. Methods 2:261-267), an N-Hydroxysuccinimide (NHS) crosslinker, an NHS-Azide reagent (e.g., NHS-Azide, NHS-PEG4-Azide, NHS-PEG12-Azide; each available from Thermo Fisher Scientific, Inc.), an NHS-Phosphine reagent (e.g., NHS-Phosphine, Sulfo-NHS-Phosphine; each available from Thermo Fisher Scientific, Inc.), or any combination or modification thereof.

A variety of methods can be used to disrupt the microvesicle. For example, the vesicle membrane can be disrupted using mechanical forces, chemical agents, or a combination thereof. In embodiments, disrupting the microvesicle comprises use of one or more of a detergent, a surfactant, a solvent, an enzyme, or any useful combination thereof. The enzyme may comprise one or more of lysozyme, lysostaphin, zymolase, cellulase, mutanolysin, a glycanase, a protease, and mannase. The detergent or surfactant may comprise one or more of a octylthioglucoside (OTG), octyl beta-glucoside (OG), a nonionic detergent, Triton X, Tween 20, a fatty alcohol, a cetyl alcohol, a stearyl alcohol, cetostearyl alcohol, an oleyl alcohol, a polyoxyethylene glycol alkyl ether (Brij), octaethylene glycol monododecyl ether, pentaethylene glycol monododecyl ether, a polyoxypropylene glycol alkyl ether, a glucoside alkyl ether, decyl glucoside, lauryl glucoside, octyl glucoside, a polyoxyethylene glycol octylphenol ethers, a polyoxyethylene glycol alkylphenol ether, nonoxynol-9, a glycerol alkyl ester, glyceryl laurate, a polyoxyethylene glycol sorbitan alkyl esters, polysorbate, a sorbitan alkyl ester, cocamide MEA, cocamide DEA, dodecyldimethylamine oxide, a block copolymers of polyethylene glycol and polypropylene glycol, poloxamers, polyethoxylated tallow amine (POEA), a zwitterionic detergent, 3-[(3-cholamidopropyl)dimethylammonio]-1-propanesulfonate (CHAPS), a linear alkylbenzene sulfonate (LAS), a alkyl phenol ethoxylate (APE), cocamidopropyl hydroxysultaine, a betaine, cocamidopropyl betaine, lecithin, an ionic detergent, sodium dodecyl sulfate (SDS), cetrimonium bromide (CTAB), cetyl trimethylammonium chloride (CTAC), octenidine dihydrochloride, cetylpyridinium chloride (CPC), benzalkonium chloride (BAC), benzethonium chloride (BZT), 5-Bromo-5-nitro-1,3-dioxane, dimethyldioctadecylammonium chloride, dioctadecyldimethylammonium bromide (DODAB), sodium deoxycholate, nonyl phenoxypolyethoxylethanol (Tergitol-type NP-40; NP-40), ammonium lauryl sulfate, sodium laureth sulfate (sodium lauryl ether sulfate (SLES)), sodium myreth sulfate, an alkyl carboxylate, sodium stearate, sodium lauroyl sarcosinate, a carboxylate-based fluorosurfactant, perfluorononanoate, perfluorooctanoate (PFOA or PFO), and a biosurfactant. Mechanical methods of disruption that can be used comprise without limitation mechanical shear, bead milling, homogenation, microfluidization, sonication, French Press, impingement, a colloid mill, decompression, osmotic shock, thermolysis, freeze-thaw, desiccation, or any combination thereof.

As shown in FIG. 14, the binding agent may be tethered to a substrate. The binding agent can be tethered before or after the complex between the binding agent and target is formed. The substrate can be any useful substrate such as disclosed herein or known in the art. In an embodiment, the substrate comprises a microsphere. In another embodiment, the substrate comprises a planar substrate. The binding agent can also be labeled. Isolating the complex between the target and the binding agent may comprise capturing the binding agent via the label. For example, the label can be a biotin label. In such cases, the binding agent can be attached to the substrate via a biotin-avidin binding event.

Methods of identifying the target after release from the binding agent will depend on the type of target of interest. For example, when the target comprises a protein, identifying the target may comprise use of mass spectrometry (MS), peptide mass fingerprinting (PMF; protein fingerprinting), sequencing, N-terminal amino acid analysis, C-terminal amino acid analysis, Edman degradation, chromatography, electrophoresis, two-dimensional gel electrophoresis (2D gel), antibody array, and immunoassay. Nucleic acids can be identified by sequencing.

One of skill will appreciate that the method can be used to identify any appropriate target, including those not associated with a vesicle. For example, with respect to the FIG. 14, all steps except for the step signified by arrow (i) (i.e., disrupting the microvesicle), could be performed for a circulating target such as a protein, nucleic acid, lipid, carbohydrate, or combination thereof.

Sample Characterization

The aptamers of the invention can be used to characterize a biological sample. For example, an aptamer can be used to bind a biomarker in the sample. The presence or level of the bound biomarker can indicate a characteristic of the example, such as a diagnosis, prognosis or theranosis of a disease or disorder associated with the sample.

In an aspect, the invention provides a method of characterizing a disease or disorder, comprising: (a) contacting a biological test sample with one or more aptamer of the invention; (b) detecting a presence or level of a complex between the one or more aptamer and the target bound by the one or more aptamer in the biological test sample formed in step (a); (c) contacting a biological control sample with the one or more aptamer; (d) detecting a presence or level of a complex between the one or more aptamer and the target bound by the one or more aptamer in the biological control sample formed in step (c); and (e) comparing the presence or level detected in steps (b) and (d), thereby characterizing the disease or disorder. The one or more aptamer can comprise any aptamer useful for characterizing the disease or disorder, e.g., the aptamers comprising any of SEQ ID NOs. 1-241535 herein, a useful modification, or a functional fragment thereof.

The biological test sample and biological control sample can each comprise a tissue sample, a cell culture, or a biological fluid. In some embodiments, the biological test sample and biological control sample comprise the same sample type, e.g., both are tissue samples or both are fluid samples. In other embodiments, different sample types may be used for the test and control samples. For example, the control sample may comprise an engineered or otherwise artificial sample.

The biological fluid may comprise a bodily fluid. The bodily fluid may include without limitation one or more of peripheral blood, sera, plasma, ascites, urine, cerebrospinal fluid (CSF), sputum, saliva, bone marrow, synovial fluid, aqueous humor, amniotic fluid, cerumen, breast milk, bronchoalveolar lavage fluid, semen, prostatic fluid, cowper's fluid or pre-ejaculatory fluid, female ejaculate, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, or umbilical cord blood. In some embodiments, the bodily fluid comprises blood, serum or plasma.

The biological fluid may comprise microvesicles. For example, the biological fluid can be a tissue, cell culture, or bodily fluid which comprises microvesicles released from cells in the sample. The microvesicles can be circulating microvesicles.

The one or more aptamer can bind a target biomarker, e.g., a biomarker useful in characterizing the sample. The biomarker may comprise a polypeptide or fragment thereof, or other useful biomarker described herein or known in the art (lipid, carbohydrate, complex, nucleic acid, etc). In embodiments, the polypeptide or fragment thereof is soluble or membrane bound. Membrane bound polypeptides may comprise a cellular surface antigen or a microvesicle surface antigen. The biomarker can be a biomarker selected from Table 3 or Table 4.

The characterizing can comprises a diagnosis, prognosis or theranosis of the disease or disorder. Various diseases and disorders can be characterized using the compositions and methods of the invention, including without limitation a cancer, a premalignant condition, an inflammatory disease, an immune disease, an autoimmune disease or disorder, a cardiovascular disease or disorder, a neurological disease or disorder, an infectious disease, and/or pain. See section herein "Phenotypes" for further details. In embodiments, the disease or disorder comprises a proliferative or neoplastic disease or disorder. For example, the disease or disorder can be a cancer. In some embodiments, the cancer comprises a breast cancer, ovarian cancer, prostate cancer, lung cancer, colorectal cancer, melanoma, or brain cancer.

FIG. 15A is a schematic 1500 showing an assay configuration that can be used to detect and/or quantify a target of interest using one or more aptamer of the invention. Capture aptamer 1502 is attached to substrate 1501. The substrate can be a planar substrate, well, microbead, or other useful substrate as disclosed herein or known in the art. Target of interest 1503 is bound by capture aptamer 1502. The target of interest can be any appropriate entity that can be detected when recognized by an aptamer or other binding agent. The target of interest may comprise a protein or polypeptide, a nucleic acid, including DNA, RNA, and various subspecies thereof, a lipid, a carbohydrate, a complex, e.g., a complex comprising protein, nucleic acids, lipids and/or carbohydrates. In some embodiments, the target of interest comprises a microvesicle. The target of interest can be a microvesicle surface antigen. The target of interest may be a biomarker, including a vesicle associated biomarker, in Tables 3 or 4. The microvesicle input can be isolated from a sample using various techniques as described herein, e.g., chromatography, filtration, centrifugation, flow cytometry, affinity capture (e.g., to a planar surface, column or bead), and/or using microfluidics. Detection aptamer 1504 is also bound to target of interest 1503. Detection aptamer 1504 carries label 1505 which can be detected to identify target captured to substrate 1501 via capture aptamer 1502. The label can be a fluorescent, radiolabel, enzyme, or other detectable label as disclosed herein. Either capture aptamer 1502 or detection aptamer 1504 can be substituted with another binding agent, e.g., an antibody. For example, the target may be captured with an antibody and detected with an aptamer, or vice versa. When the target of interest comprises a complex, the capture and detection agents (aptamer, antibody, etc) can recognize the same or different targets. For example, when the target is a microvesicle, the capture agent may recognize one microvesicle surface antigen while the detection agent recognizes another microvesicle surface antigen. Alternately, the capture and detection agents can recognize the same surface antigen.

The above configuration comprises a "sandwich" assay format which may comprise an immunoassay format such as ELISA or microbead assay. In other embodiments, target of interest 1503 is not captured to a substrate but is detected in solution. In such cases, detector aptamer 1504 can be contacted with the target of interest and detected directly in solution, e.g., using a flow cytometry assay or the like.

Aptamer Pools to Characterize a Sample

In an aspect, the invention provides a method of characterizing a sample by contacting the sample with a pool of different aptamers, and determining the frequency at which various aptamers in the pool bind the sample. For example, a pool of aptamers is identified that preferentially bind to microvesicles from cancer patients as compared to non-cancer patients. A test sample, e.g., from a patient suspected of having the cancer, is collected and contacted with the pool of aptamers. Aptamers that bind the test sample are eluted from the test sample, collected and identified, and the composition of the bound aptamers is compared to those known to bind cancer samples. Various sequencing, amplification and hybridization techniques can be used to identify the eluted aptamers. When a large pool of aptamers is used, aptamer identification may be performed by high throughput sequencing or via hybridization. If the test sample is bound by the aptamer pool in a similar manner (e.g., as determined by bioinformatics classification methods) to the microvesicles from cancer patients, then the test sample is indicative of cancer as well. Using this method, a pool of aptamers that bind one or more microvesicle antigen can be used to characterize the sample without necessarily knowing the precise target of each member of the pool of aptamers. Examples 23-24 herein illustrates an embodiment of the invention.

In an aspect, the invention provides a method for characterizing a condition for a test sample comprising: contacting a microvesicle sample with a plurality of oligonucleotide aptamers capable of binding one or more target(s) present in said microvesicle sample, identifying a set of oligonucleotides that form a complex with the sample wherein the set is predetermined to characterize a condition for the sample, thereby characterizing a condition for a sample.

In an related aspect, the invention provides a method for identifying a set of oligonucleotide aptamers associated with a test sample, comprising: (a) contacting a microvesicle sample with a plurality of oligonucleotides, isolating a set of oligonucleotides that form a complex with the microvesicle sample, (b) determining sequence and/or copy number for each of the oligonucleotides, thereby identifying a set of oligonucleotides associated with the test sample.

In still another related aspect, the invention provides a method of diagnosing a sample as cancerous or predisposed to be cancerous, comprising contacting a microvesicle sample with a plurality of oligonucleotide aptamers that are predetermined to preferentially form a complex with microvesicles from a cancer sample as compared to microvesicles from a non-cancer sample.

The oligonucleotides can be identified by sequencing, e.g., by dye termination (Sanger) sequencing or high throughput methods. High throughput methods can comprise techniques to rapidly sequence a large number of nucleic acids, including next generation techniques such as Massively parallel signature sequencing (MPSS; Polony sequencing; 454 pyrosequencing; Illumina (Solexa)

sequencing; SOLiD sequencing; Ion Torrent semiconductor sequencing; DNA nanoball sequencing; Heliscope single molecule sequencing; Single molecule real time (SMRT) sequencing, or other methods such as Nanopore DNA sequencing; Tunnelling currents DNA sequencing; Sequencing by hybridization; Sequencing with mass spectrometry; Microfluidic Sanger sequencing; Microscopy-based techniques; RNAP sequencing; In vitro virus high-throughput sequencing. The oligonucleotides may also be identified by hybridization techniques. For example, a microarray having addressable locals to hybridize and thereby detect the various members of the pool can be used.

The plurality or pool of oligonucleotide aptamers can comprise any desired number of oligonucleotide aptamers to allow characterization of the sample. In various embodiments, the pool comprises at least 2, 3, 4, 5, 6, 7, 8, 9, 10, 11, 12, 13, 14, 15, 16, 17, 18, 19, 20, 25, 30, 40, 50, 60, 70, 80, 90, 100, 150, 200, 250, 300, 350, 400, 450, 500, 600, 700, 800, 900, 1000, 2000, 3000, 4000, 5000, 6000, 7000, 8000, 9000, or at least 10000 different oligonucleotide members.

The plurality of oligonucleotide aptamers can be preselected through one or more steps of positive or negative selection, wherein positive selection comprises selection of oligonucleotides against a sample having substantially similar characteristics compared to the test sample, and wherein negative selection comprises selection of oligonucleotides against a sample having substantially different characteristics compared to the test sample. Substantially similar characteristics mean that the samples used for positive selection are representative of the test sample in one or more characteristic of interest. For example, the samples used for positive selection can be from cancer patients or cell lines and the test sample can be a sample from a patient having or suspected to have a cancer. Substantially different characteristics mean that the samples used for negative selection differ from the test sample in one or more characteristic of interest. For example, the samples used for negative selection can be from individuals or cell lines that do not have cancer (e.g., "normal" or otherwise "control" samples) and the test sample can be a sample from a patient having or suspected to have a cancer. The cancer can be a breast cancer, ovarian cancer, prostate cancer, lung cancer, colorectal cancer, melanoma, brain cancer, or other cancer.

By selecting samples representative of the desired phenotypes to detect and/or distinguish, the characterizing can comprise a diagnosis, prognosis or theranosis for any number of diseases or disorders. Various diseases and disorders can be characterized using the compositions and methods of the invention, including without limitation a cancer, a premalignant condition, an inflammatory disease, an immune disease, an autoimmune disease or disorder, a cardiovascular disease or disorder, a neurological disease or disorder, an infectious disease, and/or pain. See section herein "Phenotypes" for further details. In embodiments, the disease or disorder comprises a proliferative or neoplastic disease or disorder. For example, the disease or disorder can be a cancer. In some embodiments, the cancer comprises a breast cancer, ovarian cancer, prostate cancer, lung cancer, colorectal cancer, melanoma, or brain cancer.

Figure 15B:
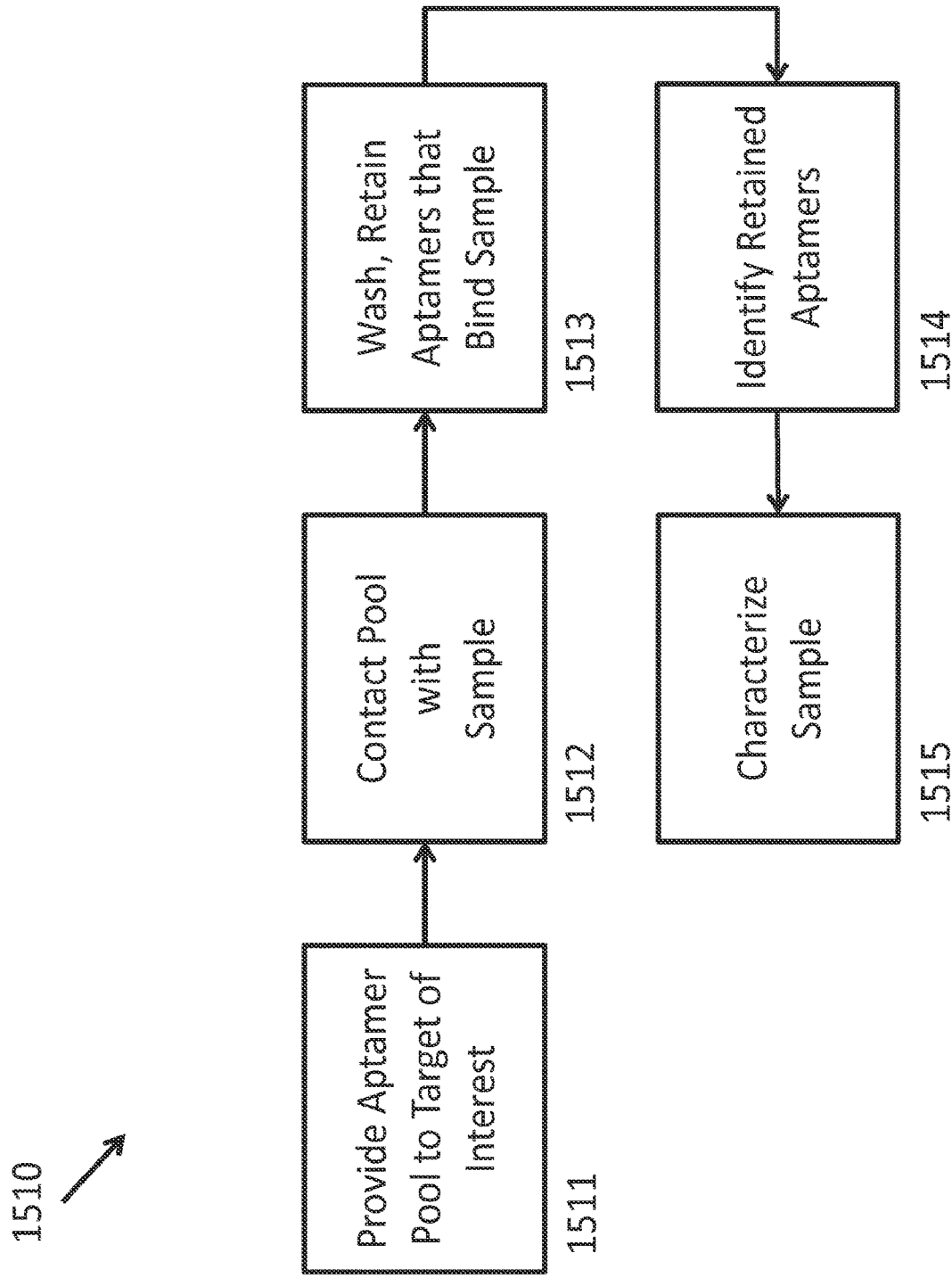

FIG. 15B is a schematic 1510 showing use of an aptamer pool to characterize a phenotype of a sample, such as those listed above. A pool of aptamers to a target of interest is provided 1511. For example, the pool of aptamers can be enriched to target one or more microvesicle. The members of the pool may bind different targets (e.g., a microvesicle surface antigen) or different epitopes of the same target present on the one or more microvesicle. The pool is contacted with a test sample to be characterized 1512. For example, the test sample may be a biological sample from an individual having or suspected of having a given disease or disorder. The mixture is washed to remove unbound aptamers. The remaining aptamers are eluted or otherwise disassociated from the sample and collected 1513. The collected aptamers are identified, e.g., by sequencing or hybridization. The presence and/or copy number of the identified is used to characterize the phenotype 1514. For example, the pool of aptamers may be chosen as aptamers that preferentially recognize microvesicles shed from cancer cells. The method can be employed to detect whether the sample retains aptamers that bind the cancer-related microvesicles, thereby allowing the sample to be characterized as cancerous or not.

Figure 15C:
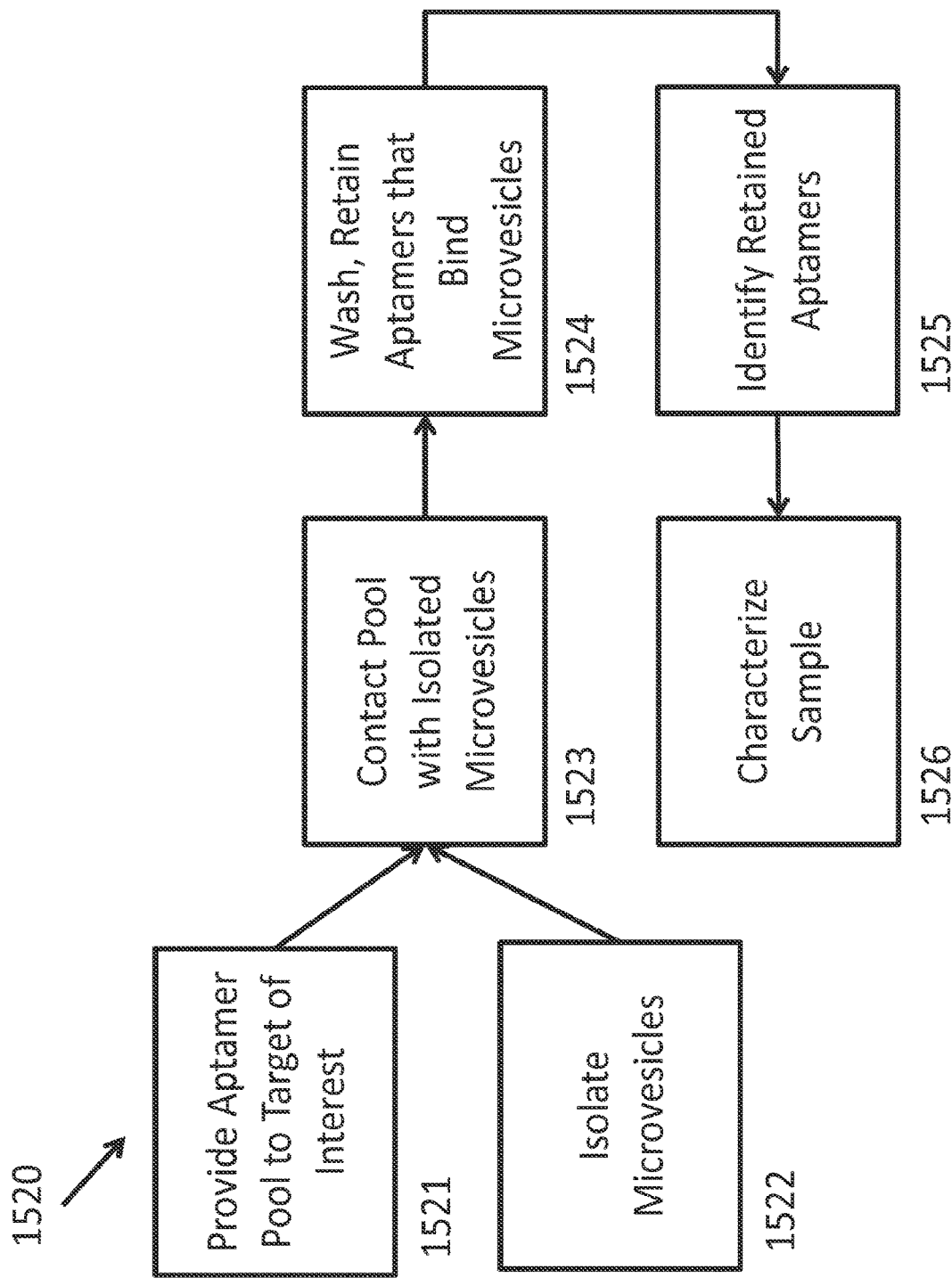
FIG. 15C is a schematic 1520 showing an implementation of the method in FIG. 15B. A pool of aptamers identified as binding a microvesicle population is provided 1521. The input sample comprises microvesicles that are isolated from a test sample 1522. The pool is contacted with the isolated microvesicles to be characterized 1523. The mixture is washed to remove unbound aptamers and the remaining aptamers are disassociated and collected 1525. The collected aptamers are identified and the identity of the retained aptamers is used to characterize the phenotype 1526.

FIG. 15C is a schematic 1520 showing an implementation of the method in FIG. 15B. A pool of aptamers identified as binding a microvesicle population is provided 1521. The microvesicle population can be isolated from a sample using various techniques as described herein, e.g., chromatography, filtration, ultrafiltration, centrifugation, ultracentrifugation, flow cytometry, affinity capture (e.g., to a planar surface, column or bead), and/or using microfluidics. The input sample comprises microvesicles that are isolated from a test sample 1522. For example, the test sample may be a biological sample from an individual having or suspected of having a given disease or disorder. The pool is contacted with the isolated microvesicles to be characterized 1523. The mixture is washed to remove unbound aptamers and the remaining aptamers are eluted or otherwise disassociated from the sample and collected 1524. The collected aptamers are identified 1525 and the presence and/or copy number of the retained aptamers is used to characterize the phenotype 1526 as above.

In an alternate embodiment to FIG. 15C, the pool of aptamers 1520 is directly contacted with a biological sample that comprises or is expected to comprise microvesicles. Microvesicles are thereafter isolated from the sample and the mixture is washed to remove unbound aptamers and the remaining aptamers are disassociated and collected 1524. The following steps are performed as above. As an example of this alternate configuration, a biological sample, e.g., a blood, serum or plasma sample, is directly contacted with the pool of aptamers. Microvesicles are then isolated by various techniques disclosed herein, including without limitation ultracentrifugation, ultrafiltration, flow cytometry, affinity isolation or the like. Remaining aptamers are then identified, e.g., by sequencing, hybridization or amplification.

In a related aspect, the invention provides a composition of matter comprising a plurality of oligonucleotides that can be used to carry out the methods comprising use of an aptamer pool to characterize a phenotype. The plurality of oligonucleotides can comprise any of those described herein, including one or more of SEQ ID NOs. 1-241535. In some embodiments, the plurality of oligonucleotides are selected from SEQ ID NOs. 1-230810. In still other embodiments, the plurality of oligonucleotides are selected from SEQ ID NOs. 230811-230899. The plurality of oligonucleotides can be selected from SEQ ID NOs. 230900-230927, or from SEQ ID NOs. 231018-241535. The composition may comprise any one of these sequences. The selected oligonucleotides may be capable of binding to a plurality of targets present in a biological sample. In some embodiments of the invention, the composition comprises at least 2, 3, 4, 5, 6, 7, 8, 9, 10, 11, 12, 13, 14, 15, 16, 17, 18, 19, 20, 25, 30, 40, 50, 60, 70, 80, 90, 100, 200, 300, 400, 500, 600, 700, 800, 900, 1000, 2000, 3000, 4000, 5000, 6000, 7000, 8000, 9000, 10000 or all oligonucleotides listed in SEQ ID NOs. 231018-241535. The composition may comprise at least 2, 3, 4, 5, 6, 7, 8, 9, 10, 11, 12, 13, 14, 15, 16, 17, 18, 19, 20, 25, 30, 40, 50, 60, 70, 80, 90, 100, 200, 300, 400, 500, 600, 700, 800, 900, 1000, 2000, 3000, 4000, 5000, 6000, 7000, 8000, 9000, 10000 or all oligonucleotides listed in SEQ ID NOs. 231018-241535. The composition of matter may also comprise one or more oligonucleotides set forth in any of Tables 23-24 which are capable of binding to a plurality of targets present in a biological sample. For example, the composition may comprise at least 1, 2, 3, 4, 5, 6, 7, 8, 9, 10, 11, 12, 13, 14, 15, 16, 17, 18, 19 or 20 oligonucleotides listed in Table 23 or Table 24. The oligonucleotides may be used in the subject methods to characterize a cancer sample, including without limitation a breast cancer sample or prostate cancer sample.

In a related aspect, the invention provides a method of performing high-throughput sequencing comprising: performing at least one (i) negative selection or (ii) one positive selection of a plurality of oligonucleotides with a microvesicle sample; obtaining a set of oliognucleotides to provide a negative binder subset or positive binder subset of the plurality of oligonucleotides, wherein the negative binder subset of the plurality of oligonucleotides does not bind the microvesicle sample and wherein the positive binder subset of the plurality of oligonucleotides does bind the microvesicle sample; contacting the negative binder subset or positive binder subset with a test sample; eluting oligonucleotides that bound to the test sample to provide a plurality of eluate oligonucleotides; and performing high-throughput sequencing of the plurality of eluate oligonucleotides to identify sequence and/or copy number of the members of the plurality of eluate oligonucleotides. Negative and positive selection of the plurality of oligonucleotides using microvesicle sample can be performed as disclosed herein. The aptamer profile revealed by the sequence and/or copy number of the members of the plurality of eluate oligonucleotides can be used to characterize a phenotype of the test sample as described herein.

In a similar aspect, the invention provides a method for identifying oligonucleotides specific for a test sample. The method comprises: (a) enriching a plurality of oligonucleotides for a sample to provide a set of oligonucleotides predetermined to form a complex with a target sample; (b) contacting the plurality in (a) with a test sample to allow formation of complexes of oligonucleotides with test sample; (c) recovering oligonucleotides that formed complexes in (b) to provide a recovered subset of oligonucleotides; and (d) profiling the recovered subset of oligonucleotides by high-throughput sequencing or hybridization, thereby identifying oligonucleotides specific for a test sample. The test sample may comprise a plurality of microvesicles. The oligonucleotides may comprise RNA, DNA or both. In some embodiment, the method further comprises performing informatics analysis to identify a subset of oligonucleotides comprising sequence identity of at least 50%, 55%, 60%, 65%, 70%, 75%, 80%, 85%, 90%, 91%, 92%, 93%, 94%, 95%, 96%, 97%, 98%, or at least 99% to the oligonucleotides predetermined to form a complex with the target sample.

The invention further provides a kit to facilitate use of an aptamer pool to characterize a phenotype. The kit may comprise a reagent for carrying out the subject methodology. Relatedly, the invention provides for use of a reagent for carrying out such methods. The reagent may comprise an aptamer, a pool of aptamers, or a composition comprising such aptamers as described above.

Nucleic Acid Negative Controls

In another aspect, the invention provides a negative control composition comprising a non-target binding nucleic acid and a substrate. The non-target binding nucleic acid can be provided by the selection methods of the invention described above, wherein the nucleic acid is identified as a non-target binding aptamer. For example, the non-binding aptamer can be identified as a non-target binding aptamer during positive selection. In some embodiments, the non-binding aptamer is predicted to have minimal if any secondary structure. Once a nucleic acid sequence is identified, its sequence can be analyzed using a software program to estimate its two-dimensional folding structure. Well-known sequence alignment programs and algorithms for motif identification can be used to identify sequence motifs and reduce the dimensionality of even large data sets of sequences. Further, software programs such as Vienna and mfold are well-known to those skilled in the art of aptamer selection and can be used to further group sequences based on secondary structure motifs (shared shapes).

The non-target binding nucleic acid can be associated with the substrate. The association can be via covalent or non-covalent binding. In some embodiments, the non-target binding nucleic acid is conjugated to the substrate. A detection assay as described herein or known in the art can be performed using the composition as a negative control. The negative control can be used in any appropriate manner. For example, when using a microtiter plate or planar array (see, e.g., FIG. 1A), a well or an area of the array can be contacted with the non-target binding nucleic acid. The assay can be performed and any signal resulting from the area of the array contacted with the non-target binding nucleic acid can be subtracted from the assay signal derived from the target. Similarly, a when using a microbead array in an assay (see, e.g., FIG. 1B), a portion of beads can be included in the assay that are contacted with the non-target binding nucleic acid. The assay can be performed and any signal resulting from the beads contacted with the non-target binding nucleic acid can be subtracted from the assay signal derived from the target. As noted, the non-target binding nucleic acid may or may not be conjugated to the substrate as desired.

In an embodiment, the non-target binding, negative control nucleic acid of the invention comprises a nucleic acid having a sequence at least 50, 55, 60, 65, 70, 75, 80, 85, 90, 91, 92, 93, 94, 95, 96, 97, 98, 99, or 100% homologous to a sequence selected from the group consisting of any of SEQ ID NOs. 230938-231008. For example, the nucleic acid can have a sequence at least 91, 92, 93, 94, 95, 96, 97, 98, 99, or 100% homologous to a sequence selected from the group consisting of any of SEQ ID NOs. 230938-231008. The nucleic acid can have the sequence of any of SEQ ID NOs. 230938-231008, e.g., SEQ ID NO. 230938. The nucleic acid can be used as a negative control nucleic acid according to the methods and compositions of the invention.

In a related aspect, the invention provides a method of detecting a presence or level of a biological entity in a biological sample suspected of containing the biological entity, comprising: (a) providing a composition comprising a substrate and a negative control composition as described above, wherein the substrate comprises one or more binding agent to the biological entity; (b) contacting the biological sample with the composition provided in step (a); (c) detecting a target signal corresponding to the amount of biological entity recognized by the one or more binding agent in step (b); and (d) normalizing the target signal detected in step (c) to a control signal corresponding to the amount of signal produced by the negative control composition, thereby detecting the presence or level of the biological entity in the biological sample. As noted, normalizing the target signal may comprise subtracting the control signal from the target signal.

The one or more binding agent can be an antibody, aptamer, or other appropriate binding agent disclosed herein or known in the art. Similarly, the biological entity can be any appropriate biomarker disclosed herein or known in the art. In an embodiment, the biological entity comprises a protein. In another embodiment, the biological entity comprises a microvesicle. In such case, the one or more binding agent can be specific to a microvesicle surface antigen. The microvesicle surface antigen may be an antigen disclosed herein, e.g., in Tables 3-4. In some embodiments, the microvesicle surface antigen is a biomarker of a disease or disorder. Accordingly, the method may provide a diagnosis, prognosis or theranosis of the disease or disorder.

In an embodiment, the invention provides an isolated polynucleotide, or a fragment thereof, identified by the methods above. The invention further provides an isolated polynucleotide having a nucleotide sequence that is at least 60% identical to the nucleotide sequence identified by the methods above. More preferably, the isolated nucleic acid molecule is at least 65%, 70%, 75%, 80%, 85%, 90%, 91%, 92%, 93%, 94%, 95%, 96%, 97%, 98%, 99% or more, identical to the nucleotide sequence identified by the methods above. In the case of an isolated polynucleotide which is longer than or equivalent in length to the reference sequence, e.g., a sequence identified by the methods above, the comparison is made with the full length of the reference sequence. Where the isolated polynucleotide is shorter than the reference sequence, e.g., shorter than a sequence identified by the methods above, the comparison is made to a segment of the reference sequence of the same length (excluding any loop required by the homology calculation).

In an aspect, the invention provides negative control aptamers wherein the aptamer sequences comprise scrambled versions of a target binding nucleic acid. For example, aptamers herein are disclosed that bind proteins (e.g., EpCAM, PSMA) or microvesicles (e.g., prostate and breast cancer microvesicles). A negative control for any of the target binding aptamers can be a randomly scrambled sequence thereof.

The invention further provides a kit for carrying out the methods of the invention. As further described below, the kit may comprise one or more reagent for carrying out the method. In certain embodiments, the one or more reagent comprises the non-target binding, negative control nucleic acid or the negative control composition. The kit may comprise the substrate and/or a binding agent of interest to a target of interest. The negative control composition may be used to normalize a signal produced by binding of a binding agent and a target of interest.

Blocking Aptamers

In some embodiments, the nucleic acids of the invention serve as a blocking agent for the substrate. Following a coupling reaction between a substrate and a desired molecule or entity, e.g., a binding agent, blocking agents can be applied to the substrate to minimize non-specific interactions between the coated substrate and non-target molecules. Blocking agents can be selected to minimize nonspecific interactions but not interfere with any desired interactions, such as specific interaction between a molecule of interest conjugated to the substrate and another molecule of interest in a test solution. Commonly used blockers include BSA (bovine serum albumin), casein (a milk-based protein), pepticase (hydrolyzed casein), non-ionic surfactants (e.g., Tween® 20 and Triton® X-100), non-reacting antibodies or fragments thereof (e.g., off-species), FSG (fish skin gelatin), pure gelatin or a gelatin hydrolase, PEG (polyethylene glycol), non-reacting sera, non-reacting protein, and various commercially available blockers known to those in the art. A non-reacting protein refers to a protein that should have minimal, if any, interaction with components of an assay.

Figure 16A:
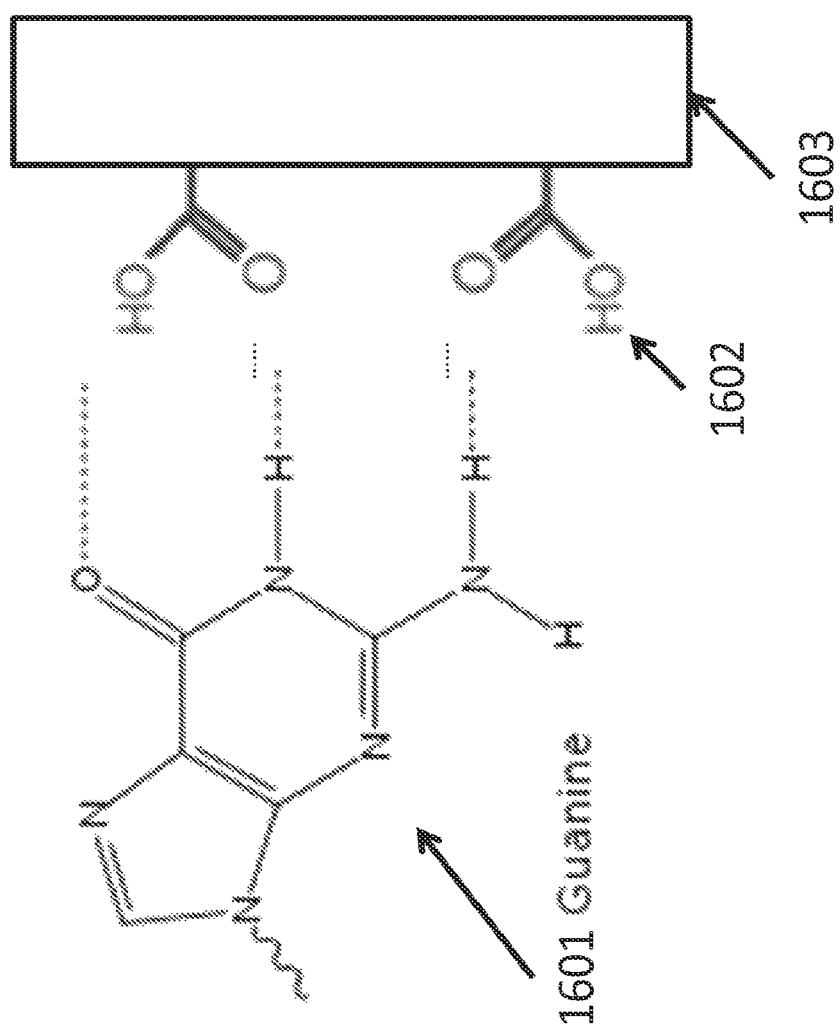
FIG. 16A illustrates hydrogen bonding between a portion of an aptamer 1601 to carboxyl groups 1602 attached to a planar substrate 1603.
Figure 16B:
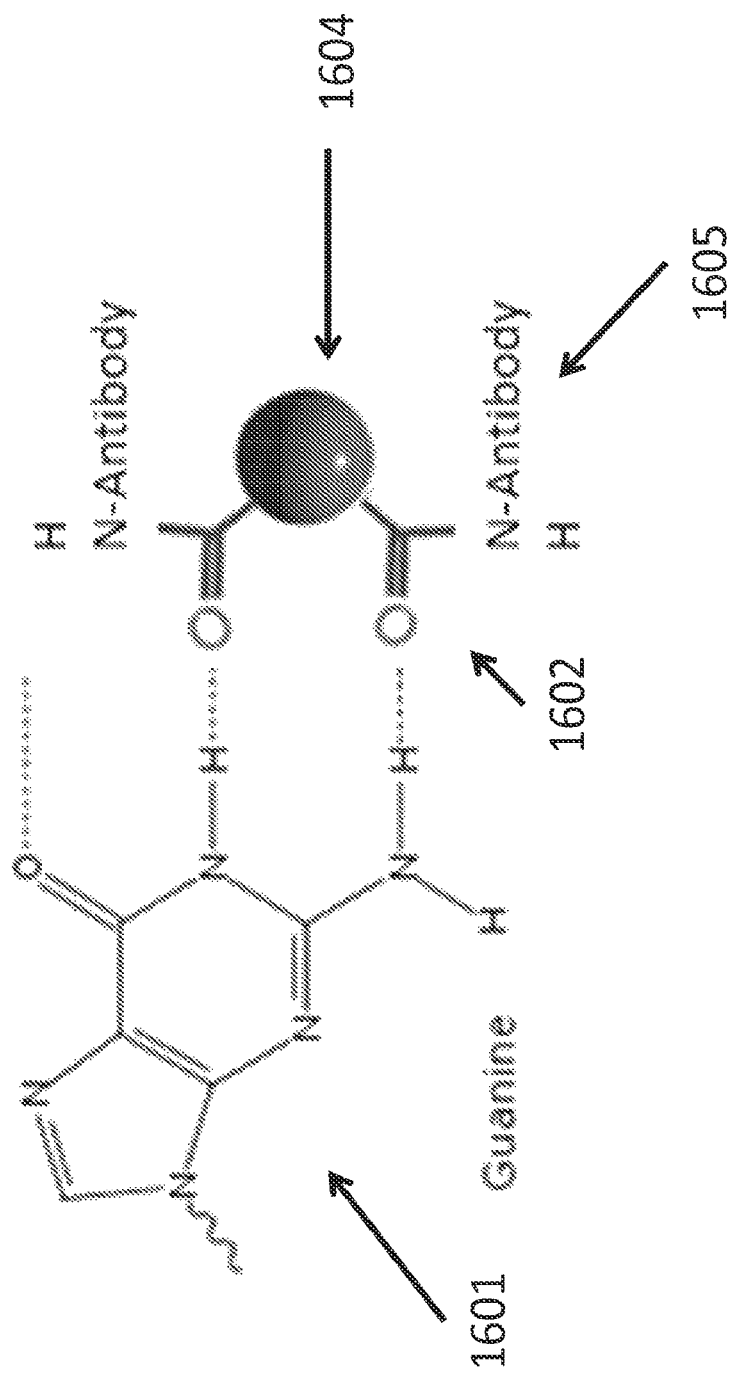
FIG. 16B illustrates hydrogen bonding between a portion of an aptamer 1601 to carboxyl groups 1602 attached to a microsphere substrate 1604. Carboxyl groups 1602 are further attached to an antibody 1605.

FIGS. 16A-16B illustrate use of an aptamer to block an unconjugated carboxyl group on a substrate. FIG. 16A illustrates hydrogen bonding between a portion of an aptamer 1601 to carboxyl groups 1602 attached to a planar substrate 1603. FIG. 16B illustrates hydrogen bonding between a portion of an aptamer 1601 to carboxyl groups 1602 attached to a microsphere substrate 1604. Carboxyl groups 1602 are further attached to an antibody 1605. Guanine is the only one nucleotide which can form two hydrogen bounds.

In an aspect, the invention provides a non-binding nucleic acid. The non-binding nucleic acid can be selected to have minimal, if any, interaction with components of an assay of interest. For example, the non-binding nucleic acid can have minimal, if any, interaction with the target molecules of an assay of interest. However, the blocking aptamer may bind other assay components, e.g., substrates, tubes, beads, etc, thereby minimizing interaction between the target molecules and any assay components other than the binding agents specific for the target molecules. The invention also provides blocking compositions comprising the non-binding nucleic acid and one or more blocking component selected from the group consisting of BSA (bovine serum albumin), casein (a milk-based protein), pepticase (hydrolyzed casein), non-ionic surfactants (e.g., Tween® 20 and Triton® X-100), non-reacting antibodies or fragments thereof (e.g., off-species), FSG (fish skin gelatin), pure gelatin or a gelatin hydrolase, PEG (polyethylene glycol), non-reacting sera, non-reacting protein, and various commercially available blockers known to those in the art.

In an embodiment, the non-binding nucleic acid comprises a sequence at least 50, 55, 60, 65, 70, 75, 80, 85, 90, 91, 92, 93, 94, 95, 96, 97, 98, 99, or 100% homologous to a sequence selected from the group consisting of any of SEQ ID NOs. 230938-231008. For example, the nucleic acid can have a sequence at least 91, 92, 93, 94, 95, 96, 97, 98, 99, or 100% homologous to a sequence selected from the group consisting of any of SEQ ID NOs. 230938-231008. The nucleic acid can have the sequence of any of SEQ ID NOs. 230938-231008, e.g., SEQ ID NO. 230938.

In a related aspect, the invention provides a method comprising contacting the non-binding nucleic acid with a substrate to block the substrate, contacting a biological sample with the blocked substrate, and detecting binding of one or more biological entity to the substrate. The non-binding nucleic acid can be included in a blocking composition provided above. The substrate can also be a substrate such as described herein, including without limitation a planar substrate or a microsphere. Such blocking can inhibit in full or in part undesired binding events.

The invention further provides a kit for carrying out the methods of the invention. As further described below, the kit may comprise one or more reagent for carrying out the method. In certain embodiments, the one or more reagent comprises the non-binding nucleic acid or the blocking composition. The kit may comprise the substrate and/or a binding agent of interest to a target of interest. The non-binding nucleic acid or the blocking composition may be used for blocking the substrate.

In an embodiment, the invention provides an isolated polynucleotide, or a fragment thereof, identified by the methods above. The invention further provides an isolated polynucleotide having a nucleotide sequence that is at least 60% identical to the nucleotide sequence identified by the methods above. More preferably, the isolated nucleic acid molecule is at least 65%, 70%, 75%, 80%, 85%, 90%, 91%, 92%, 93%, 94%, 95%, 96%, 97%, 98%, 99% or more, identical to the nucleotide sequence identified by the methods above. In the case of an isolated polynucleotide which is longer than or equivalent in length to the reference sequence, e.g., a sequence identified by the methods above, the comparison is made with the full length of the reference sequence. Where the isolated polynucleotide is shorter than the reference sequence, e.g., shorter than a sequence identified by the methods above, the comparison is made to a segment of the reference sequence of the same length (excluding any loop required by the homology calculation).

In some embodiments, blocking aptamers are selected that bind to functional groups, e.g., functional groups that are present on one or more component of a biological assay. Such functional group binding aptamers are described in further detail below.

Functional Group Binding Aptamers

In an aspect, the invention provides an aptamer capable of binding a functional group of interest. Functional groups as used herein are groups of atoms or bonds within molecules that are responsible for the characteristic chemical reactions of those molecules. The same functional group will undergo the same or similar chemical reaction(s) regardless of the size of the molecule it is a part of. However, its relative reactivity can be modified by nearby functional groups. A "moiety" can be a functional group or can be comprised of one or more functional groups.

The atoms of functional groups are linked to each other and to the rest of the molecule by covalent bonds. When the group of covalently bound atoms bears a net charge, the group can be referred to as a polyatomic ion or a complex ion. Any subgroup of atoms of a compound also may be called a radical, and if a covalent bond is broken homolytically, the resulting fragment radicals are referred as free radicals.

Aptamers of the invention can be directed to various functional groups of interest. The functional group may include without limitation hydrocarbons, halogens, groups containing oxygen (i.e., C—O bonds), groups containing nitrogen, groups containing sulfur, groups containing phosphorus, or groups containing boron. Illustrative hydrocarbons include without limitation alkanes, alkenes, alkynes, benzene derivatives, toluene derivatives, branched or ring alkanes, carbocations and carboanions. Illustrative halogens include without limitation haloalkanes, fluoroalkanes, chloroalkanes, bromoalkanes and iodoalkanes. Illustrative groups containing oxygen include without limitation alcohols, ketones, aldehydes, acyl halides, carbonates, carboxylates, carboxylic acids, esters, hydroperoxides, ethers, hemiacetals, hemiketals, acetals, ketals, orthoesters, and orthocarbonates. Illustrative groups containing nitrogen include without limitation amides, amines, imines, imides, azides, azo compounds, cyanates, nitrates, nitriles, nitrites, nitro compounds, nitroso compounds, and pyridine derivatives. Illustrative groups containing sulfur include without limitation thiols, sulfides, disulfides, sulfoxides, sulfones, sulfunic acids, sulfonic acids, thiocyantes, isothyanates, thiones, and thials. Illustrative groups containing phosphorus include without limitation phosphines, phosphanes, phosphonic acids, phosphates, and phosphodiesters. Illustrative groups containing boron include without limitation boronic acids, boronic esters, borinic acids and borinic esters.

The aptamers of the invention can be directed to one or more functional groups selected from the group consisting of acetals, acyl groups, acyl halides, alkenyl groups, alkoxides, alkoxy groups, alkynyl groups, amides, amine oxides, amines, carbodiimides, carboximidates, carboxylic acids, cyanamides, cyanates, dithiocarbamates, enols, esters, ethers, hydrazines, hydrazones, hydroxamic acids, imides, isocyanates, isocyanides, isothiocyanates, ketals, ketenes, ketones, leaving groups, nitriles, organohalides, organophosphorus, orthoesters, oximes, phosphonofluoridates, phosphonothioates, phosphoramidothioates, phosphorodithioates, phosphorofluoridates, phosphorothioates, protecting groups, pyrophosphates, semicarbazides, semicarbazones, sulfamates, sulfonate esters, sulfones, sulfonic acids, sulfonyl groups, sulfoximines, sulfuryl compounds, thioamides, thiocyanates, thioesters, thiolates, thiones, thiophosphoryl compounds, and thiosulfinates.

The aptamers of the invention can be directed to one or more functional group selected from the group consisting of acetal, acetoxy group, acetylide, acid anhydride, activating group, acyl chloride, acyl halide, acylal, acyloin, acylsilane, alcohol, aldehyde, aldimine, alkane, alkene, alkoxide, alkyl cycloalkane, alkyl nitrites, alkyne, allene, amide, amidine, aminal, amine oxide, azide, azine, aziridine, azoxy, bifunctional, bisthiosemicarbazone, biuret, boronic acid, carbamate, cathamino, carbazide, cathene, carbinol, carbonate ester, carbonyl, carboxamide, carboximidate, carboxylic acid, chloroformate, cumulene, cyanate ester, cyanimide, cyanohydrin, deactivating groups, depside, diazo, diol, dithiocarbamate, enamine, enediyne, enol, enol ether, enone, enyne, episulfide, epoxide, ester, ether, fluorosulfonate, halohydrin, haloketone, hemiacetal, hemiaminal, hemithioacetal, hydrazide, hydrazone, hydroxamic acid, hydroxyl, hydroxylamine, imine, iminium, isothiouronium, ketene, ketenimine, ketone, ketyl, lactam, lactol, lactone, methine, methyl group, nitrate, nitrile ylide, nitrilimine, nitro compound, nitroamine, nitronate, nitrone, nitronium ion, nitrosamine, nitroso, orthoester, osazone, oxaziridine, oxime, n-oxoammonium salt, peroxide, peroxy acid, persistent carbene, phenols, phosphaalkene, phosphaalkyne, phosphate, phosphinate, phosphine, phosphine oxide, phosphinite, phosphonate, phosphonite, phosphonium, phosphorane, s-nitrosothiol, schiff base, selenol, selenonic acid, selone, semicarbazide, semicarbazone, silyl enol ether, silyl ether, sulfenamide, sulfenic acid, sulfenyl chloride, sulfide, sulfilimine, sulfinamide, sulfinic acid, sulfite ester, sulfonamide, sulfonanilide, sulfonate, sulfonyl, sulfonyl halide, sulfoxide, sulfuryl, sultone, tellurol, thial, thioacetal, thioamide, thiocathamate, thiocarboxy, thiocyanate, thioester, thioether, thioketal, thioketone, thiol, thiolactone, thiourea, tosylhydrazone, triazene, triol, urea, vanillyl, xanthate, ylide, and ynolate.

The functional group can be tethered to the surface of a substrate to facilitate the covalent attachment of other molecules to the surface of the substrate. For example, the substrate may be carboxyl-modified, amino-modified, hydroxyl-modified, hydrazide-modified and/or chloromethyl-modified.

In an embodiment, the aptamer binds to a carboxyl group. The aptamer can have a high GC content, e.g., greater than 50%, 60%, 70%, 80%, 90%, 95% or more GC content. The nucleic acid sequence of the aptamer may be a nucleic acid having a sequence at least 50, 55, 60, 65, 70, 75, 80, 85, 90, 91, 92, 93, 94, 95, 96, 97, 98, 99, or 100% homologous to a sequence selected from the group consisting of any of SEQ ID NOs. 230938-231008. For example, the nucleic acid can have a sequence at least 91, 92, 93, 94, 95, 96, 97, 98, 99, or 100% homologous to a sequence selected from the group consisting of any of SEQ ID NOs. 230938-231008. The nucleic acid can have the sequence of any of SEQ ID NOs. 230938-231008, e.g., the aptamer can have the sequence of SEQ ID NO. 230938.

In some embodiments, the aptamer is further modified to comprise at least one chemical modification. The chemical modification can be selected from the group consisting: of a chemical substitution at a sugar position; a chemical substitution at a phosphate position; and a chemical substitution at a base position of the nucleic acid. The chemical modification can also be selected from the group consisting of: incorporation of a modified nucleotide, 3' capping, conjugation to an amine linker, conjugation to a high molecular weight, non-immunogenic compound, conjugation to a lipophilic compound, conjugation to a drug, conjugation to a cytotoxic moiety, and labeling with a radioisotope. The cytotoxic moiety can be conjugated to the 5' end of the aptamer, it can be conjugated to the 3' end of the aptamer, or a cytotoxic moiety can be conjugated to both ends of the aptamer. In some embodiments, the cytotoxic moiety is encapsulated in a nanoparticle, e.g., a liposome, dendrimer, and/or comb polymer. In other embodiments, the cytotoxic moiety comprises a small molecule cytotoxic moiety. The small molecule cytotoxic moiety can be selected from the group consisting of vinblastine hydrazide, calicheamicin, vinca alkaloid, a cryptophycin, a tubulysin, dolastatin-10, dolastatin-15, auristatin E, rhizoxin, epothilone B, epithilone D, taxoids, maytansinoids, and variants and derivatives of any thereof. The cytotoxic moiety can also be a protein toxin. In embodiments, the protein toxin is selected from the group consisting of diphtheria toxin, ricin, abrin, gelonin, and *Pseudomonas* exotoxin A. The radioisotope can be selected from the group consisting of yttrium-90, indium-111, iodine-131, lutetium-177, copper-67, rhenium-186, rhenium-188, bismuth-212, bismuth-213, astatine-211, and actinium-225. The non-immunogenic, high molecular weight compound can be a polyalkylene glycol, such as polyethylene glycol.

In another aspect, the invention provides a composition comprising an aptamer of the invention, e.g., as described above, and a substrate. As described herein, the substrate can be any physically separable solid to which a binding agent can be directly or indirectly attached including, but not limited to, surfaces provided by microarrays and wells, particles such as beads, columns, optical fibers, wipes, glass and modified or functionalized glass, quartz, mica, diazotized membranes (paper or nylon), polyformaldehyde, cellulose, cellulose acetate, paper, ceramics, metals, metalloids, semiconductive materials, quantum dots, coated beads or particles, other chromatographic materials, magnetic particles; plastics (including acrylics, polystyrene, copolymers of styrene or other materials, polypropylene, polyethylene, polybutylene, polyurethanes, Teflon material, etc.), polysaccharides, nylon or nitrocellulose, resins, silica or silica-based materials including silicon and modified silicon, carbon, metals, inorganic glasses, plastics, ceramics, conducting polymers (including polymers such as polypyrole and polyindole); micro or nano structured surfaces such as nucleic acid tiling arrays, nanotube, nanowire, or nanoparticulate decorated surfaces; or porous surfaces or gels such as methacrylates, aciylamides, sugar polymers, cellulose, silicates, or other fibrous or stranded polymers. In addition, as is known the art, the substrate may be coated using passive or chemically-derivatized coatings with any number of materials, including polymers, such as dextrans, aciylamides, gelatins or agarose. The substrate can also be coated with a functional group to facilitate covalent attachment to the surface of any desired molecules. Such coatings can facilitate the use of the array with a biological sample. The substrate can be in any useful form. In an embodiment, the substrate is a planar substrate. For example, the substrate can be the well of a plate, or a microarray. In another embodiment, the substrate is a microsphere. For example, the substrate can be a magnetic or fluorescently labeled microsphere or bead.

In an embodiment, the substrate of the composition comprises a carboxyl group. For example, the surface of the substrate can be coated with a functional group such as a carboxyl group. The aptamer can be bound to the carboxyl group. In an embodiment, the aptamer binds the carboxyl group via hydrogen binding.

In some embodiments, the aptamer serves as a blocking agent for the substrate. Following a coupling reaction between a substrate and a desired molecule or entity, e.g., a binding agent, blocking agents can be applied to the substrate to minimize non-specific interactions between the coated substrate and non-target molecules. Blocking agents can be selected to minimize nonspecific interactions but not interfere with any desired interactions, such as specific interaction between a molecule of interest conjugated to the substrate and another molecule of interest in a test solution. Commonly used blockers include BSA (bovine serum albumin), casein (a milk based protein), pepticase (hydrolyzed casein), non-ionic surfactants (e.g., Tween® 20 and Triton® X-100), non-reacting antibodies or fragments thereof (e.g., off-species), FSG (fish skin gelatin), pure gelatin or a gelatin hydrolase, PEG (polyethylene glycol), non-reacting sera, and various commercially available blockers known to those in the art.

In an embodiment, the substrate comprises a binding agent. The binding agent can be a nucleic acid, protein, or other molecule that can bind to a target of interest, e.g., a biological entity. In preferred embodiment, the binding agent has specificity for the target of interest. The binding agent can comprise DNA, RNA, monoclonal antibodies, polyclonal antibodies, Fabs, Fab', single chain antibodies, synthetic antibodies, aptamers (DNA/RNA), peptoids, zDNA, peptide nucleic acids (PNAs), locked nucleic acids (LNAs), lectins, synthetic or naturally occurring chemical compounds (including but not limited to drugs, labeling reagents), dendrimers, or a combination thereof. For example, the binding agent can be an antibody or an aptamer. In embodiments of the invention, the binding agent comprises a membrane protein labeling agent. See, e.g., the membrane protein labeling agents disclosed in Alroy et al., US. Patent Publication US 2005/0158708.

The composition can comprise further entities. In embodiments, the composition comprises a biological entity. For example, the biological entity can be a nucleic acid/polynucleotide, a protein, or a microvesicle. In an embodiment, the protein is associated with a microvesicle. For example, the protein can be a microvesicle surface antigen. The protein can also be a microvesicle payload. The microvesicle surface antigen and/or payload may be a biomarker disclosed herein, e.g., in Tables 3-4.

Figure 17A:
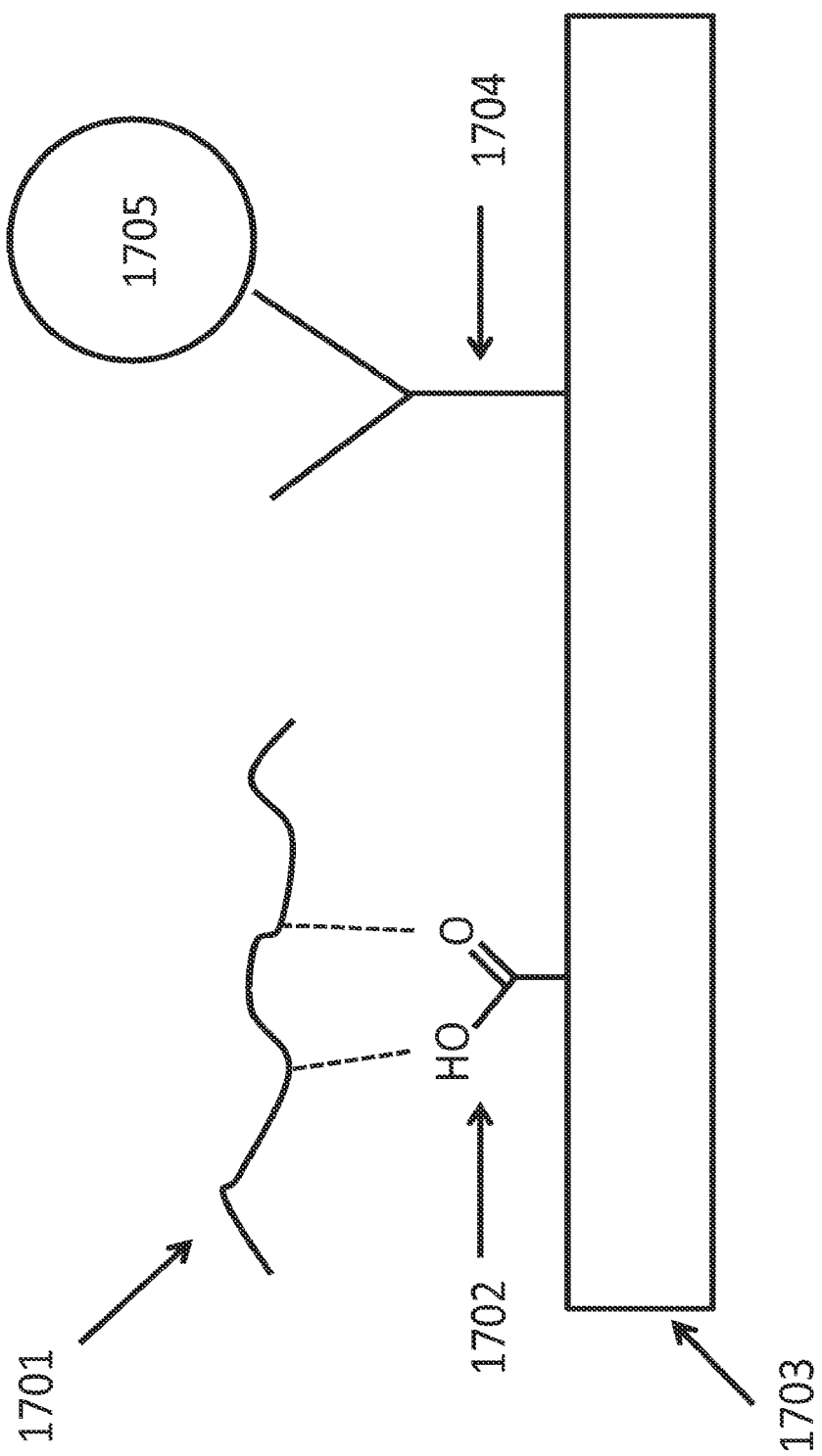
FIG. 17A and FIG. 17B illustrate hydrogen bonding between a portion of an aptamer 1701 to carboxyl groups 1702 attached to a substrate 1703.
Figure 17B:
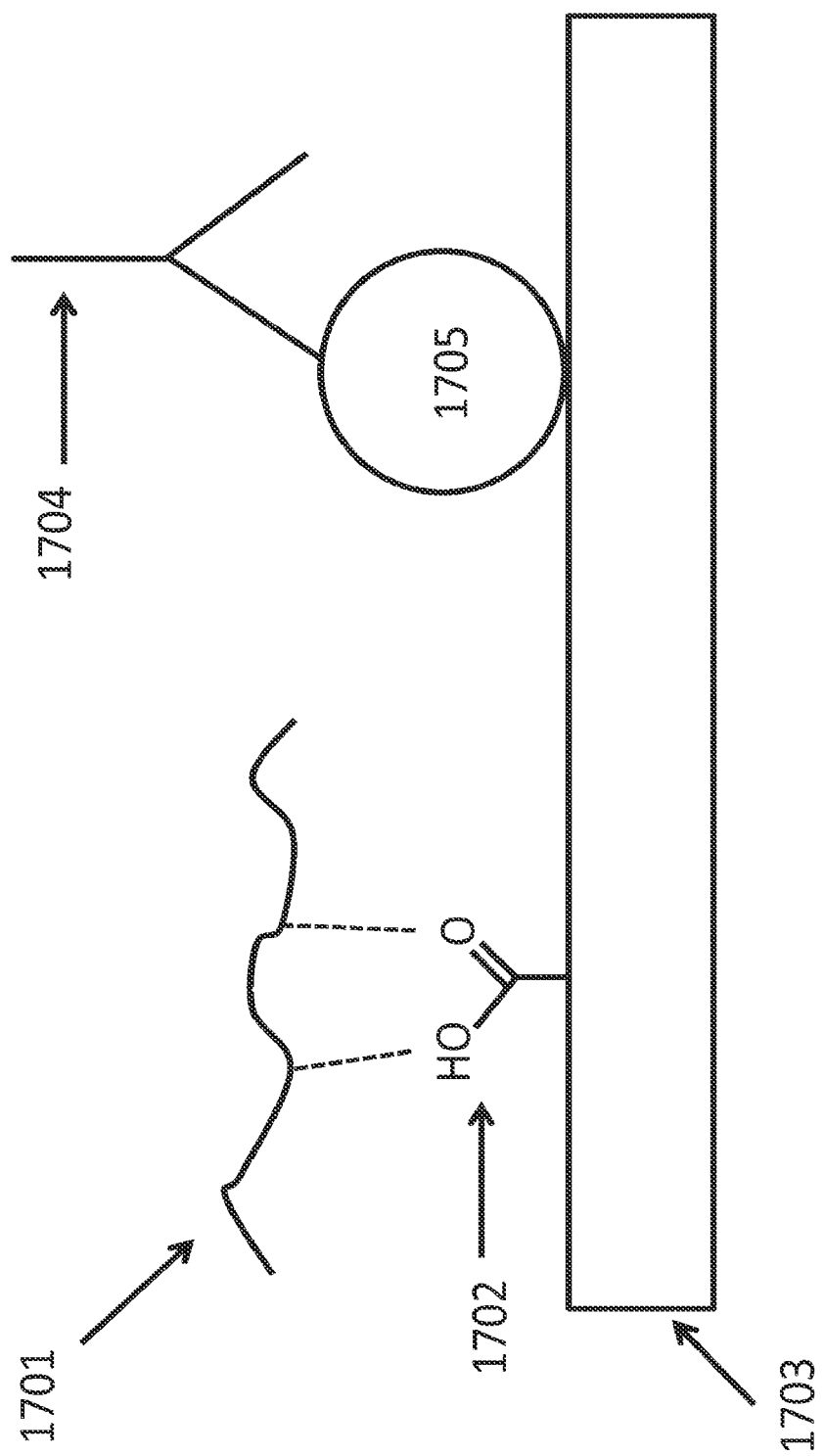
Figures 18A, 18B, 18C, 18D:
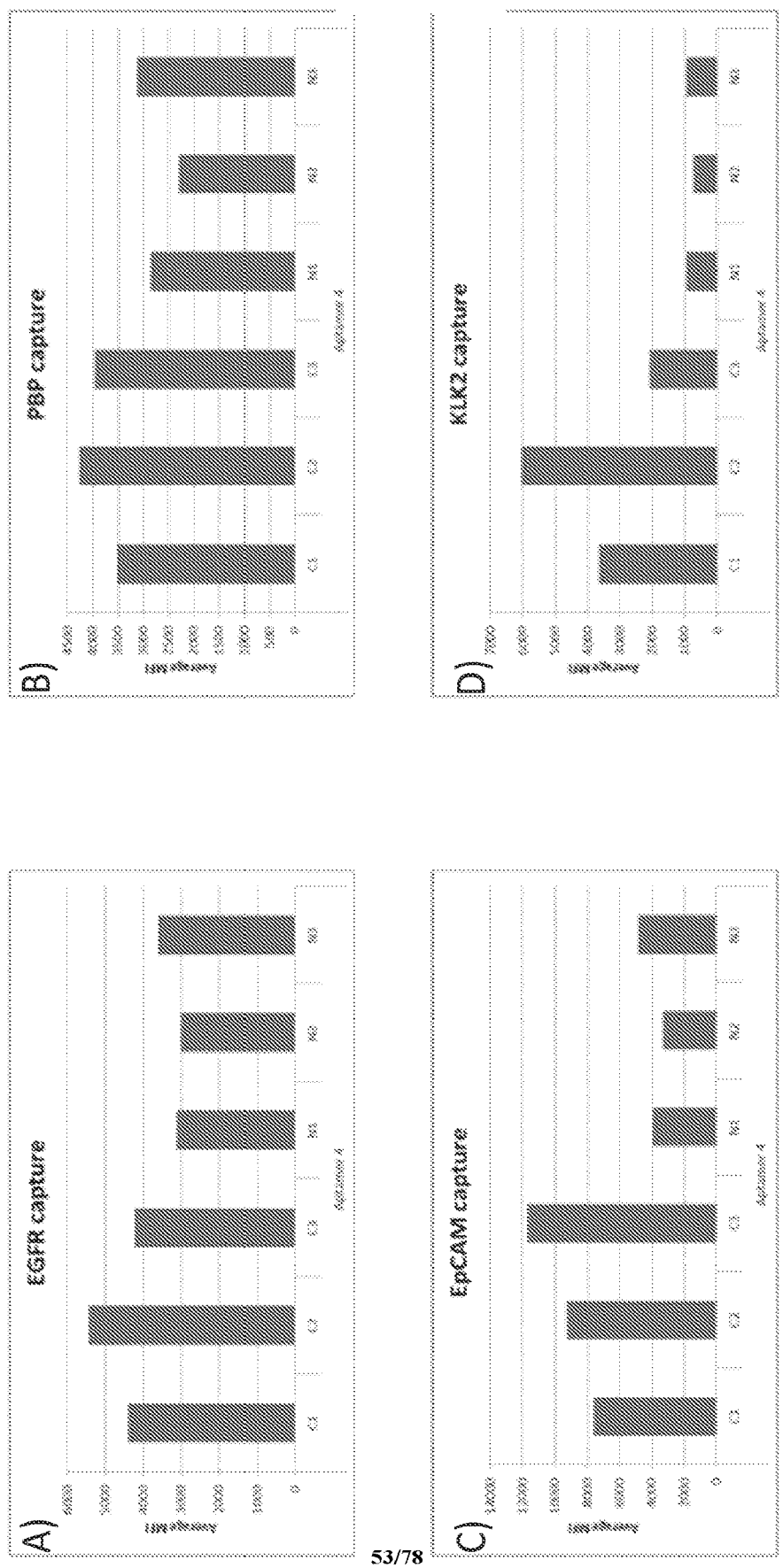
FIGS. 18A-18D illustrate the use of an anti-EpCAM aptamer (Aptamer 4; SEQ ID NO. 1) to detect a microvesicle population. Vesicles in patient plasma samples were captured using bead-conjugated antibodies to the indicated microvesicle surface antigens.

An exemplary configuration of a composition of the invention is shown in FIG. 17A. FIG. 17A illustrates hydrogen bonding between a portion of an aptamer 1701 to carboxyl groups 1702 attached to a substrate 1703. Binding agent 1704 is also attached to the substrate 1703. The binding agent has specificity for target 1705, which may be any appropriate biological entity described herein or known in the art, such as a protein, nucleic acid, microvesicle, cell, or a portion of any thereof. Without being bound by theory, the aptamer 1701 may serve to block some or all undesired binding of the target 1705, or any other molecule or entity, to the substrate 1703. FIG. 17B shows an alternate configuration wherein a biological entity of interest is bound to the substrate 1703.

As described further below, the invention provides a kit comprising an aptamer or composition of the invention, such as those described above.

In still another aspect, the invention provides a method comprising contacting the aptamer of the invention with a substrate. The aptamer can be an aptamer of the invention such as described above. The substrate can also be a substrate such as described above, including a planar substrate, or a microsphere. The substrate may comprise a carboxyl group. For example, the surface of the substrate can be functionalized with carboxyl moieties. In embodiments, the aptamer is bound to the carboxyl group. The aptamer can be bound to the carboxyl group via hydrogen bonding. Without being bound by theory, the aptamer may serve to block carboxyl groups on the substrate from undesired binding events.

In an embodiment, the substrate comprises a binding agent. The binding agent can be any binding agent disclosed herein or known in the art that can be attached via covalent or non-covalent bonds to the substrate. In some embodiments, the binding agent comprises an antibody or aptamer.

The method of contacting the aptamer of the invention with a substrate may further comprise contacting the substrate with a sample comprising a target of the binding agent. One possible configuration for the method is shown in FIG. 17A. As shown in FIG. 17A, the target 1705 is recognized by the binding agent 1704 while the carboxyl group 1702 is masked by the aptamer 1701. In embodiments, the surface of substrate 1703 is covered by carboxyl groups 1702 to facilitate covalent attachment of binding agent 1704 to the substrate. After attachment of binding agent 1704 to substrate 1703, the aptamer 1701 can be applied to block any unconjugated carboxyl group 1702. Finally, the blocked substrate 1703 can be contacted with a sample comprising the target 1705. The method may enhance the ability to detect binding events between the binding agent 1704 and target 1705. For example, blocking by the aptamer may reduce any non-specific binding events with the substrate 1703 that could interfere with specific binding between the binding agent 1704 and target 1705. Alternately, blocking by the aptamer may reduce any non-specific binding events between the target 1705 and the substrate 1703. One of skill will appreciate that both mechanisms may operate simultaneously. FIG. 17B shows an alternate configuration wherein a biological entity of interest is bound to the substrate 1703.

In an embodiment, the invention provides an isolated polynucleotide, or a fragment thereof, identified by the methods above. The invention further provides an isolated polynucleotide having a nucleotide sequence that is at least 60% identical to the nucleotide sequence identified by the methods above. More preferably, the isolated nucleic acid molecule is at least 65%, 70%, 75%, 80%, 85%, 90%, 91%, 92%, 93%, 94%, 95%, 96%, 97%, 98%, 99% or more, identical to the nucleotide sequence identified by the methods above. In the case of an isolated polynucleotide which is longer than or equivalent in length to the reference sequence, e.g., a sequence identified by the methods above, the comparison is made with the full length of the reference sequence. Where the isolated polynucleotide is shorter than the reference sequence, e.g., shorter than a sequence identified by the methods above, the comparison is made to a segment of the reference sequence of the same length (excluding any loop required by the homology calculation).

The invention further provides a kit for carrying out the methods of the invention. As further described below, the kit may comprise one or more reagent for carrying out the method. In certain embodiments, the one or more reagent comprises the aptamer and/or the substrate.

In another aspect, the invention provides a method of detecting a presence or level of a biological entity in a biological sample suspected of containing the biological entity. The method comprises: (a) providing a composition comprising one or more binding agent specific to the biological entity attached to a carboxylated substrate, wherein the carboxylated substrate is bound to the aptamer provided by the invention; (b) contacting the biological sample with the composition provided in step (a); and (c) detecting whether the biological entity is recognized by the one or more binding agent in step (b), thereby detecting the presence or level of the biological entity in the biological sample. One possible configuration for the method is shown in FIG. 17A. As shown in FIG. 17A, the target 1705 is recognized by the binding agent 1704 while the carboxyl group 1702 is masked by the aptamer 1701. In embodiments, the surface of substrate 1703 is covered by carboxyl groups 1702 to facilitate covalent attachment of binding agent 1704 to the substrate. After attachment of binding agent 1704 to substrate 1703, the aptamer 1701 can be applied to block any unconjugated carboxyl group 1702. Finally, the blocked substrate 1703 can be contacted with a sample comprising the target 1705. The method may enhance the ability to detect binding events between the binding agent 1704 and target 1705. For example, blocking by the aptamer may reduce any non-specific binding events with the substrate 1703 that could interfere with specific binding between the binding agent 1704 and target 1705. Alternately, blocking by the aptamer may reduce any non-specific binding events between the target 1705 and the substrate 1703. One of skill will appreciate that both mechanisms may operate simultaneously. FIG. 17B shows an alternate configuration wherein a biological entity of interest is bound to the substrate 1703.

The biological entity can be any appropriate entity that can be detected when recognized by the binding agent. In an embodiment, the biological entity comprises a protein or polypeptide. As used herein, "protein," "polypeptide" and "peptide" are used interchangeably unless stated otherwise. The biological entity can be a nucleic acid, including DNA, RNA, and various subspecies of any thereof as disclosed herein or known in the art. The biological entity can comprise a lipid. The biological entity can comprise a carbohydrate. The biological entity can also be a complex, e.g., a complex comprising protein, nucleic acids, lipids and/or carbohydrates. In some embodiments, the biological entity comprises a microvesicle. In such cases, the binding agent can be a binding agent to a microvesicle surface antigen, e.g., a protein. General microvesicle surface antigens include tetraspanin, CD9, CD63, CD81, CD63, CD9, CD81, CD82, CD37, CD53, Rab-5b, Annexin V, and MFG-E8. Additional general microvesicle surface antigens are provided in Table 3 herein.

The microvesicle surface antigen can also be a biomarker of a disease or disorder. The method may provide a diagnosis, prognosis or theranosis of the disease or disorder. For example, the one or more protein may comprise one or more of PSMA, PCSA, B7H3, EpCam, ADAM-10, BCNP, EGFR, IL1B, KLK2, MMP7, p53, PBP, SERPINB3, SPDEF, SSX2, and SSX4. These markers can be used detect a prostate cancer. Additional microvesicle surface antigens are provided in Tables 3-4 herein.

The invention further provides a kit for carrying out the methods of the invention. As further described below, the kit may comprise one or more reagent for carrying out the method. In certain embodiments, the one or more reagent comprises the aptamer, the substrate, and/or the binding agent. The kit may comprise the substrate coated with the carboxyl group, instructions for conjugating a binding agent of interest to the substrate, and the aptamer. The aptamer may be used for blocking any unconjugated carboxyl groups.

In a related aspect, the invention provides a method for enhancing binding comprising: (a) contacting a substrate with an aptamer capable of binding a carboxyl group, wherein the substrate also comprises one or more selected nucleic acid or polypeptide molecules; and (b) contacting the substrate with a binding agent capable of binding the nucleic acid or polypeptide molecule, whereby the aptamer binding to the carboxyl group enhances the binding of the binding agent to the nucleic acid or polypeptide molecule. The aptamer can be an aptamer of the invention, e.g., an aptamer having a sequence selected from SEQ ID NOs. 230938-231008. The substrate can be a substrate such as described herein or known in the art, including planar substrates or microspheres/beads. An illustrative schematic is shown in FIG. 17A and FIG. 17B. With respect to FIG. 17A, the substrate 1703 comprises the one or more selected nucleic acid or polypeptide molecules 1704, which in this illustration represents an antibody. The aptamer 1701 is shown binding a carboxyl group 1702 on the surface of the substrate 1703. The binding agent 1705 is a molecule or entity that binds the one or more selected nucleic acid or polypeptide molecules 1704. With respect to FIG. 17B, the substrate 1703 comprises the one or more selected nucleic acid or polypeptide molecules 1705, which in this illustration represents a target entity, e.g., a protein or microvesicle. The aptamer 1701 is shown binding a carboxyl group 1702 on the surface of the substrate 1703. The binding agent 1704 is an antibody specific for the one or more selected nucleic acid or polypeptide molecule 1705. One of skill will appreciate that various binding agents can be used as disclosed herein or known in the art.

The nucleic acid or polypeptide can be covalently bound to a carboxyl group via an amide linkage. A amide bond, or peptide bond, is a covalent chemical bond formed between two molecules when the carboxyl group of one molecule reacts with the amino group of the other molecule, causing the release of a molecule of water.

The aptamers of the invention can be identified using any useful selection methodology. For example, an aptamer can be identified using SELEX or variants thereof, such as described in Pan and Clawson, Primer-free aptamer selection using a random DNA library. Methods Mol Biol. 2010; 629:369-85; which publication is herein incorporated by reference in its entirety. The aptamer can be identified using negative and positive selection methods such as described herein. The aptamer can be identified using the method described by Mei, H, et al. Functional-group specific aptamers indirectly recognizing compounds with alkyl amino group. Anal Chem. 2012 Sep. 4; 84(17):7323-9. Epub 2012 Aug. 21; which publication is herein incorporated by reference in its entirety.

Kits

The invention also provides a kit comprising one or more reagent to carry out the methods of the invention. For example, the one or more reagent can be the one or more aptamer, a buffer, blocker, enzyme, or combination thereof. The one or more reagent may comprise any useful reagents for carrying out the subject methods, including without limitation aptamer libraries, substrates such as microbeads or planar arrays or wells, reagents for biomarker and/or microvesicle isolation, aptamers directed to specific targets, aptamer pools that facilitate detection of a biomarker/microvesicle population, reagents such as primers for nucleic acid sequencing or amplification, arrays for nucleic acid hybridization, detectable labels, solvents or buffers and the like, various linkers, various assay components, blockers, and the like. The one or more reagent may also comprise various compositions provided by the invention. In an embodiment, the one or more reagent comprises one or more aptamer of the invention. The one or more reagent can comprise a substrate, such as a planar substrate, column or bead. The kit can contain instructions to carry out various assays using the one or more reagent.

In an embodiment, the kit comprises an aptamer or composition provided herein. The kit can be configured to carry out the methods provided herein. For example, the kit can include an aptamer of the invention, a substrate, or both an aptamer of the invention and a substrate.

In an embodiment, the kit is configured to carry out an assay. For example, the kit can contain one or more reagent and instructions for detecting the presence or level of a biological entity in a biological sample. In such cases, the kit can include one or more binding agent to a biological entity of interest. The one or more binding agent can be bound to a substrate.

In an embodiment, the kit comprises a set of aptamers that provide a particular aptamer profile for a biological sample. An aptamer profile can include, without limitation, a profile that can be used to characterize a particular disease or disorder. For example, the disease or disorder can be a proliferative disease or disorder, including without limitation a cancer.

Example 1: Identification of DNA Oligonucleotides that Bind a Target

The target is affixed to a solid substrate, such as a glass slide or a magnetic bead. For a magnetic bead preparation, beads are incubated with a concentration of target protein ranging from 0.1 to 1 mg/ml. The target protein is conjugated to the beads according to a chemistry provided by the particular bead manufacturer. Typically, this involves coupling via an N-hydroxysuccinimide (NHS) functional group process. Unoccupied NHS groups are rendered inactive following conjugation with the target.

Randomly generated oligonucleotides (oligos) of a certain length, such as 32 base pairs long, are added to a container holding the stabilized target. Each oligo contains 6 thymine nucleotides (a "thymine tail") at either the 5 or 3 prime end, along with a single molecule of biotin conjugated to the thymine tail. Additional molecules of biotin could be added. Each oligo is also manufactured with a short stretch of nucleotides on each end (5-10 base pairs long) corresponding to amplification primers for PCR ("primer tails"). The sequences of a large pool of 32-mer aptamers are shown in SEQ ID NOs. 1-230810. The sequences are shown absent the thymine tails or primer tails.

The oligonucleotides are incubated with the target at a specified temperature and time in phosphate-buffered saline (PBS) at 37 degrees Celsius in 500 microliter reaction volume.

The target/oligo combination is washed 1-10 times with buffer to remove unbound oligo. The number of washes increases with each repetition of the process (as noted below).

The oligos bound to the target are eluted using a buffer containing a chaotropic agent such as 7 M urea or 1% SDS and collected using the biotin tag. The oligos are amplified using the polymerase chain reaction using primers specific to 5' and 3' sequences added to the randomized region of the oligos. The amplified oligos are added to the target again for another round of selection. This process is repeated as necessary to observe binding enrichment.

Example 2: Competitive Assay

The process is performed as in Example 1 above, except that a known ligand to the target, such as an antibody, is used to elute the bound oligo species (as opposed to or in addition to the chaotropic agent). In this case, anti-EpCAM antibody from Santa Cruz Biotechnology, Inc. was used to elute the aptamers from the target EpCAM.

Example 3: Screening and Affinity Analysis

Aptamers generated from the binding assays described above are sequenced using a high-throughput sequencing platform, such as the Ion Torrent from Life Technologies:

Library Preparation—Aptamers were pooled after ligating barcodes and adapter sequences (Life Technologies) according to manufacturer protocols. In brief, equimolar pools of the aptamers were made using the following steps: Analyzed an aliquot of each library with a Bioanalyzer™ instrument and Agilent DNA 1000 Kit or Agilent High Sensitivity Kit, as appropriate for the final library concentration. The molar concentration (nmol/L) of each amplicon library was determined using the commercially available software (Agilent).

An equimolar pool of the library was prepared at the highest possible concentration.

The combined concentration of the pooled library stock was calculated.

The template dilution factor of the library pool was determined using the following equation: Template Dilution Factor=(Library pool concentration [pM])/26 pM).

Template Preparation—Using a freshly diluted library, the aptamer pool resulting from binding assays provided above were sequenced using conventional sequencing protocols. High throughput (NextGen) sequencing methods can be used as desired. The aptamer pool sequences are identified in SEQ ID NOs. 1-230810.

Twenty aptamers were selected based on direct or competitive assays assessing binding to EpCAM (as described above). See Example 7 and Table 8 for the selected sequences.

Affinity Measurements—These twenty aptamers were then tested for binding affinity using an in vitro binding platform. SPR can be used for this step, e.g., a Biacore SPR machine using the T200 control software, as follows:

Dilute the antigen to a concentration of 32 nM.

Prepare necessary dilutions for kinetics, starting at 32 nM prepare two-fold dilutions of antigen down to 0.5 nM.

The Biacore 200 control software is programmed with the following conditions: Solution: HBS-EP+ Buffer; Number of cycles: 3; Contact time: 120 s; Flow rate: 30 μl/min; Dissociation time: 300 s; Solution: Glycine-HCl pH 2.5; Contact time: 120 s; Flow rate: 20 μl/min; Stabilization period: 0 s. The binding affinities of these aptamers are then measured using the SPR assay above, or an alternate in vitro assay assessing the aptamer for a desired function.

Figure 4:
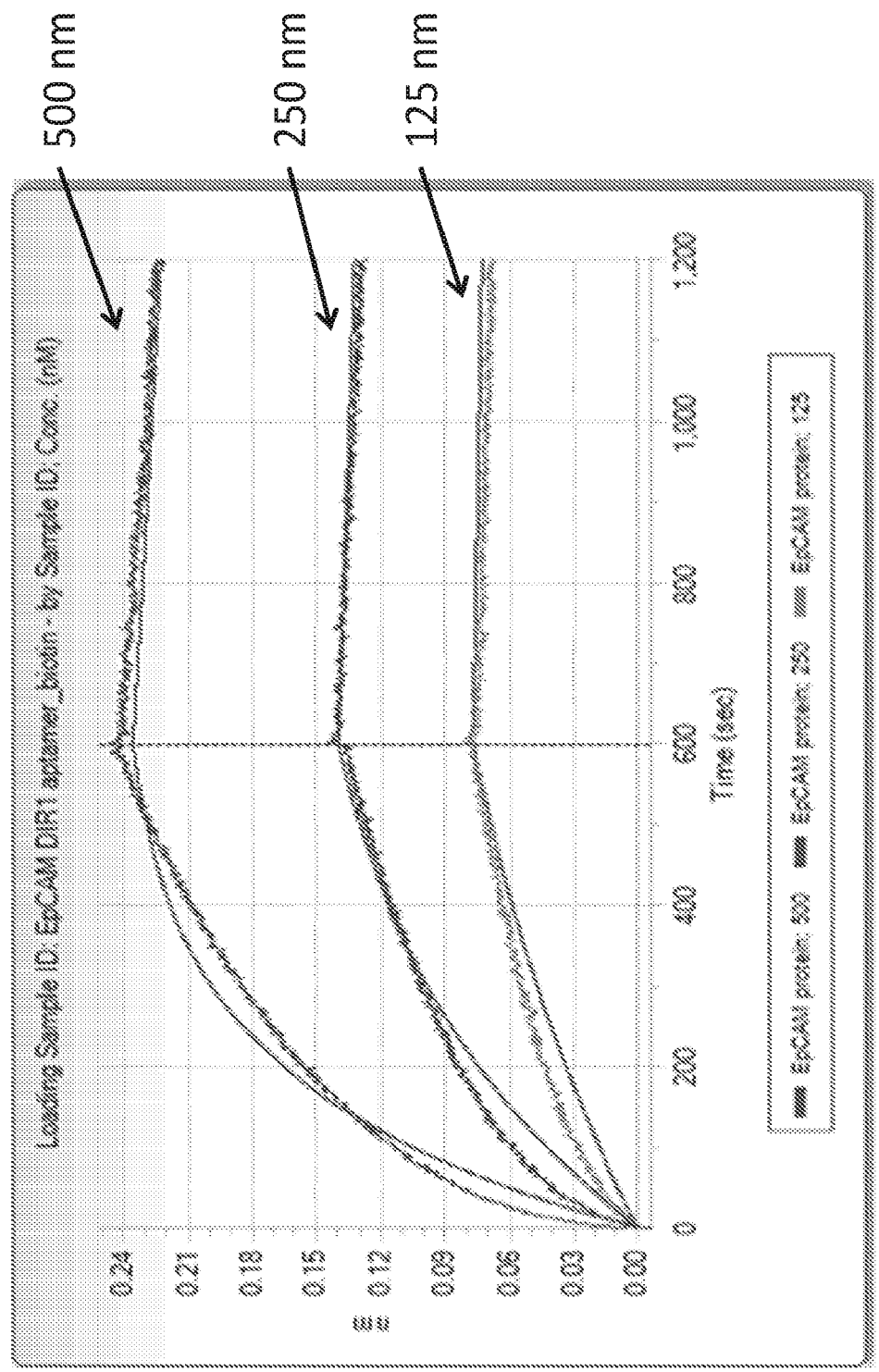
FIG. 4 illustrates results from a binding assay showing the binding affinity of an exemplary aptamer (Aptamer ID BTX176881 (SEQ ID NO. 98883)) to the target EpCAM protein at various target concentrations. The aptamer to be tested is fixed to a substrate using a biotin tail and is incubated with various concentrations of target (125, 250 and 500 nM, as indicated in the figure). The test is performed on a surface plasmon resonance machine (SPR). The SPR machine detects association and disassociation of the aptamer and the target. Target is applied until the association and disassociation events are equal, resulting in a plateau of the curve. The equations describing the curve at each concentration can then be used to calculate the $K_D$ of the aptamer (see Table 5).
Figure 5B:
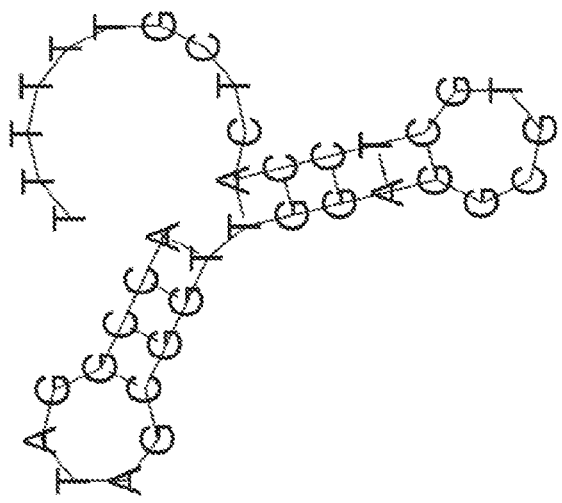
FIGS. 5A-5B illustrate aptamer nucleotide sequences and corresponding secondary structure prediction.
Figure 5A:
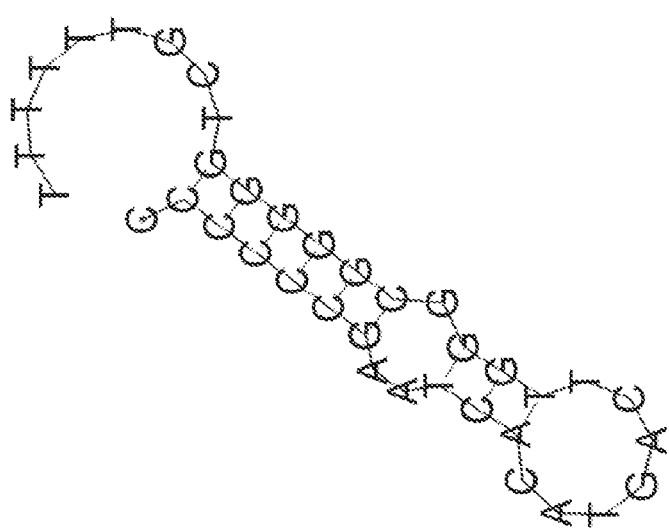

FIG. 4 shows the SPR data for aptamer BTX176881 (SEQ ID NO: 98883). The figure comprises an association and dissociation graph of 1:1 fitting model of the biotinylated aptamers to EpCAM protein at the indicated concentrations (nM). Table 5 shows the calculated $K_d$ values from the SPR measurements that are illustrated in FIG. 4. In addition, Table 5 shows the SPR data and calculated $K_d$ values for BTX187269 (SEQ ID NO: 109271) and Aptamer 4 (SEQ ID NO. 1).

TABLE 5

Calculated $K_D$ values from SPR measurements

| Immobilized aptamer | Analyte | Conc (nM) | Response | $K_d$ (nM) | Full $R^2$ | Full $Chi^2$ |
|---|---|---|---|---|---|---|
| BTX176881 | EpCAM | 500 | 0.2434 | 8.40 | 0.989322 | 0.179008 |
| (SEQ ID No: | protein | 250 | 0.136 | 8.40 | 0.989322 | 0.179008 |
| 98883) | | 100 | 0.0776 | 8.40 | 0.989322 | 0.179008 |
| BTX187269 | EpCAM | 500 | 0.2575 | 7.12 | 0.990323 | 0.215697 |
| (SEQ ID NO: | protein | 250 | 0.1584 | 7.12 | 0.990323 | 0.215697 |
| 109271) | | 100 | 0.0551 | 7.12 | 0.990323 | 0.215697 |
| Aptamer 4 | EpCAM | 500 | 0.2742 | 10.10 | 0.986276 | 0.299279 |
| (SEQ ID NO. 1) | protein | 250 | 0.1618 | 10.10 | 0.986276 | 0.299279 |
| | | 100 | 0.0809 | 10.10 | 0.986276 | 0.299279 |

*$K_d$, $R^2$ and $Chi^2$ values by Global fitting for single reference method.

Example 4: Motif Analysis

The process in the Examples above is followed to identity a high affinity aptamer to a target of interest. Once a high affinity aptamer is identified, its sequence is then analyzed using a software program to estimate its two-dimensional folding structure. Well-known sequence alignment programs and algorithms for motif identification can be used to identify sequence motifs and reduce the dimensionality of even large data sets of sequences. Further, software programs such as Vienna and mfold are well-known to those skilled in the art of aptamer selection and can be used to further group sequences based on secondary structure motifs (shared shapes). See FIGS. 5A-5B for example structure predictions. Shared secondary structure of course, does not guarantee identical three-dimensional structure. Therefore "wet-lab" validation of aptamers is still useful as no one set of in silico tools has yet been able to accurately predict the optimal aptamer among a set of aptamer candidates.

Using the same software, the sequences produced in high-throughput sequencing of a pool of candidate aptamers (produced as described in Example 1 above) are analyzed for structural motifs similar to the high-affinity aptamer. The structure comparisons are based on free energy calculations performed using Vienna. Tables 6 and 7 present an illustrative selection of free energy calculations for the top twenty library members calculated to have high identity to Aptamer 4 (SEQ ID NO. 1) and Oligo6 (SEQ ID NO. 230810), respectively. In Tables 6 and 7, the column "Identity" indicates the identical alignment proportion of Aptamer 4 to the indicated library sequences. The identity value comprises the result of pairwise alignment divided by number of nucleotides in the alignment. The column "mfeCode" comprises "dot-bracket notation" output from Vienna 2.0.7. Pseudo-knot free secondary structures can be represented in the space-efficient dot-bracket notation, which is used throughout the Vienna RNA package. Briefly, a structure on a sequence of length n is represented by a string of equal length consisting of matching brackets and dots. A base pair between base i and j is represented by a '(' at position i and a ')' at position j, and unpaired bases are represented by dots. Further information on the mfeCode dot-bracket notation is available at rna.tbi.univie.ac.at/help.html. The column "mfeValue" in Tables 6 and 7 provides the minimum free energy calculation as calculated with Vienna 2.0.7 with default parameter file.

TABLE 6

Identity and Secondary Structure Comparison to Aptamer 4

| ID | Sequence( 5'→3') | Identity | mfeCode | mfe Value (kcal/mol) |
|---|---|---|---|---|
| Aptamer4 (SEQ ID NO. 1) | CCCCCCGAATCACATGACTTGGGCGGGGGTCG | 1 | (((((((((.(((.....)).))))).))).....  | -13.5 |
| BTX175447 (SEQ ID NO. 97449) | CCCCCCGAATCACATGACTTGGGCGGGGGTCG | 1 | (((((((((.(((.....)).))))).))).....  | -13.5 |
| BTX100359 (SEQ ID NO. 22361) | CCGCCAGCATAACTGACTAGTGCTGTCTTTTT | 0.78125 | ....(((((..........))))))....... | -6 |
| BTX6393 (SEQ ID NO. 160929) | CCGGCCATCACTGCCTTTAACGTGGTGGTTTT | 0.75 | ..((((((((..........))))))))).. | -10.7 |
| BTX141572 (SEQ ID NO. 63574) | TCCTCACGAATGTGACTGACGTGGGGTTTTAC | 0.75 | .(((((((...........))))))).....  | -9.3 |
| BTX53793 (SEQ ID NO. 208329) | TCTCCTGAATGTGTTGTTCGGGGATGTTTTGT | 0.75 | ..((((((((.....)))))))).......... | -7.8 |
| BTX176890 (SEQ ID NO. 98892) | CCGCGCTACATCACATGCTGGGGCAGGTCGCC | 0.75 | ((((.(((((((...))).)))).)).))..... | -7.5 |
| BTX34119 (SEQ ID NO. 188655) | ACCGAACAGTGTCGGGCGGGGTGGAGGTGTTT | 0.75 | .(((...(.......)...)))............ | -5.1 |
| BTX4758 (SEQ ID NO. 159294) | CCCACGCTACACCTGGCGAGCGTTCGTTTTTT | 0.75 | ....(((((.....))))).............. | -5 |
| BTX175446 (SEQ ID NO. 97448) | CCCCCCGAATCACAGGTTGGTCCGTTGAAATT | 0.75 | (((..((..........))..))..........  | -2.9 |
| BTX6079 (SEQ ID NO. 160615) | CCGCGATCCACGTAAGGTTCGGGGGTCTCTTT | 0.71875 | ((.(((.((.......)).))).))......... | -10.6 |
| BTX112777 (SEQ ID NO. 34779) | CTGGGTCCTGTTGGGCTGGGGTCGGTCTTGAT | 0.71875 | ((.(((((....))))).))............. | -10.4 |
| BTX18213 (SEQ ID NO. 172749) | TAGCCCGCCAGATACTTGGGTGGGAATCCTTT | 0.71875 | ....((((((..........))))))........ | -10.2 |
| BTX186007 (SEQ ID NO. 108009) | CTCTGCTCAATGCGTGGGCTGGGGCGGTCAGT | 0.71875 | ..(((((((...((....))..))))))).....  | -10.1 |
| BTX178871 (SEQ ID NO. 100873) | CCTTGAAGACTGGGCGCTGGTCCTAGCTCTTT | 0.71875 | ....(((((((((((.....).))))).))))))  | -9.7 |
| BTX27728 (SEQ ID NO. 182264) | GCGCTGGAACTCGTGACAGTGCGTGGCGTTTT | 0.71875 | ((((((..........)))))))..........  | -8.8 |
| BTX39166 (SEQ ID NO. 193702) | CCAGCCCTGGATCCCATTGACCTCGGGGATTG | 0.71875 | .(((((((((.((......)).).)))))).))) | -7.6 |
| BTX79672 (SEQ ID NO. 1674) | AATCACCGATGGGCGGGAATCACGTGTTGGT | 0.71875 | ....(((((((.(.((....)).).))))))))  | -7.6 |

TABLE 6-continued

Identity and Secondary Structure Comparison to Aptamer 4

| ID | Sequence( 5'→3') | Identity | mfeCode | mfe Value (kcal/mol) |
|---|---|---|---|---|
| BTX13384 (SEQ ID NO. 167920) | GCGACGCATGTGTTGTGCT GTGCTCGTGTTTT | 0.71875 | ((((.(((((((.....)).)))))))).... | -7.5 |
| BTX4712 (SEQ ID NO. 159248) | CCCACAATCGACAGCGAAC TTGGGGGGTGCGG | 0.71875 | ((((...(((....)))...)))))........ | -7.5 |

In total, 880 sequences had an identity score of 0.65 or higher as compared to Aptamer4. The SEQ ID NOs. of these sequences ordered by identity to Aptamer4 from high to low are 1, 83833, 404, 192457, 46196, 181195, 85436, 159336, 174291, 83832, 188968, 14201, 91259, 95567, 87637, 152235, 164943, 208225, 37604, 173781, 229801, 162649, 141236, 229277, 197636, 208288, 222015, 46488, 41404, 20282, 37215, 164674, 88106, 230291, 222830, 86840, 106217, 153548, 69938, 22919, 148527, 23133, 62644, 150047, 195461, 165410, 95492, 187335, 143568, 229624, 211801, 89529, 49853, 86203, 229309, 148998, 227639, 12831, 207967, 83812, 100031, 24403, 44443, 86417, 85531, 177048, 222142, 224357, 191046, 25876, 176402, 78410, 169614, 170692, 220915, 227125, 88394, 211129, 167260, 21437, 95247, 229151, 1344, 18302, 94815, 105377, 130159, 47458, 77703, 229665, 446, 6632, 222154, 5925, 89185, 166992, 82685, 190696, 227012, 165589, 140293, 165488, 184824, 22443, 89500, 139968, 26382, 223375, 21852, 175936, 191752, 227183, 229246, 28597, 79173, 218544, 90815, 115055, 118391, 147334, 228629, 63019, 112671, 14867, 31453, 49788, 83331, 170600, 182781, 65037, 77839, 219756, 22498, 169879, 84231, 87890, 87951, 93241, 95274, 25145, 229605, 229647, 145760, 5602, 5944, 129548, 229432, 148342, 165400, 62962, 71321, 130354, 227261, 96175, 1923, 3602, 88544, 112311, 229170, 168079, 195903, 203783, 129930, 208300, 215426, 224543, 227717, 82099, 221395, 10847, 61398, 99233, 165100, 208999, 15946, 44819, 164778, 190331, 224367, 181869, 221786, 229009, 67955, 87277, 202044, 63204, 97683, 119091, 127373, 176380, 2790, 182858, 226993, 40773, 86822, 149227, 189749, 223226, 109, 7382, 142902, 190403, 2511, 14476, 125189, 224206, 86454, 130486, 147726, 108815, 18082, 190843, 45237, 83778, 191228, 229117, 96465, 171461, 186224, 82242, 176191, 181376, 184432, 147735, 214179, 159297, 2709, 45318, 105849, 171053, 222127, 52894, 125871, 164642, 84142, 45997, 86837, 94742, 130073, 175675, 222007, 112130, 221515, 127575, 141509, 525, 173934, 201340, 135715, 209835, 23712, 83926, 6015, 215164, 206485, 5690, 50212, 118847, 61503, 202365, 225979, 8859, 45779, 176358, 113963, 45463, 66945, 188869, 15231, 22936, 84157, 12271, 58672, 135632, 180563, 200213, 12292, 74327, 88219, 163713, 208378, 229071, 3089, 12468, 140336, 155915, 331, 115507, 206325, 225180, 230194, 21183, 113125, 229023, 41920, 105992, 210427, 213341, 76296, 104423, 146335, 178047, 228984, 12604, 83530, 90950, 185519, 222186, 222283, 27831, 88097, 116409, 154939, 168206, 5549, 195919, 217797, 22658, 154805, 171036, 214987, 225767, 62979, 85662, 222046, 224554, 226930, 227276, 27161, 166910, 202893, 8124, 8714, 23847, 39241, 27746, 165206, 166056, 423, 36640, 86849, 137280, 190114, 202287, 230304, 5179, 6067, 6505, 6611, 41483, 37479, 45749, 107382, 117315, 202535, 29748, 82654, 84060, 87907, 157362, 206589, 223382, 28495, 44462, 62270, 100524, 173820, 192490, 222297, 1390, 19210, 22495, 118163, 133889, 179659, 192074, 204965, 2461, 77762, 106037, 166379, 167776, 182280, 228707, 808, 47456, 152081, 222818, 229813, 148355, 148387, 167853, 167857, 187723, 357, 163173, 175586, 224340, 12254, 24110, 158863, 199558, 228579, 500, 85061, 94630, 162650, 165617, 168065, 222121, 228609, 51102, 112611, 125773, 190879, 215724, 227812, 229506, 442, 12284, 36658, 44057, 95079, 97943, 167653, 177081, 204180, 209922, 18882, 62824, 89180, 107532, 131610, 179747, 181924, 208078, 208690, 631, 46216, 96215, 105283, 150525, 166187, 227449, 103425, 185880, 837, 26023, 157638, 165823, 175971, 228232, 230020, 36086, 61478, 171159, 177192, 196612, 215002, 225782, 84127, 88107, 111059, 147670, 149254, 166308, 175530, 206924, 221620, 2514, 2717, 23418, 51045, 83895, 83974, 84095, 84146, 86150, 104166, 106868, 152996, 185740, 222844, 229172, 229254, 27401, 160516, 165619, 172635, 189302, 220615, 221183, 229356, 230021, 83828, 124068, 152013, 181636, 190744, 194448, 195157, 196263, 215307, 229390, 229807, 28160, 33150, 84689, 150169, 170181, 175758, 202239, 1872, 7459, 22350, 39454, 82329, 101757, 151736, 162225, 7946, 83756, 159512, 164932, 185169, 217855, 229824, 7381, 45608, 55427, 85522, 92756, 94362, 149604, 166378, 166572, 185619, 1200, 20260, 20952, 22787, 78128, 80744, 108103, 116667, 129831, 130067, 168581, 178969, 208724, 222116, 8122, 144078, 164779, 218167, 220960, 22637, 24612, 24944, 106584, 156344, 167262, 222022, 228813, 44051, 77865, 82089, 88152, 93245, 94935, 152153, 190789, 200547, 201908, 225916, 1323, 2837, 10181, 22043, 25177, 26567, 93412, 104099, 127374, 130454, 147664, 150419, 177674, 183092, 9715, 12644, 22918, 40833, 77732, 82992, 83365, 210202, 229833, 3976, 11015, 13524, 65438, 90954, 98759, 148864, 163106, 163192, 74660, 79359, 83110, 95108, 95525, 112590, 171072, 172776, 183058, 224159, 226062, 228518, 12809, 15906, 23455, 42107, 76961, 91318, 129989, 137160, 155158, 177958, 2759, 46018, 48333, 78031, 86611, 128087, 135823, 180253, 191245, 209093, 230546, 20542, 63496, 71991, 83901, 142432, 171932, 227515, 61337, 160422, 172960, 173608, 189801, 210407, 216678, 229101, 65755, 79467, 94134, 98247, 197374, 202491, 225597, 77739, 94166, 95667, 151387, 168443, 187779, 220937, 5921, 7576, 148846, 177037, 190387, 190580, 190594, 229692, 12103, 32693, 92399, 114220, 163673, 223983, 652, 5953, 22926, 45297, 119857, 181369, 190352, 227216, 173208, 191585, 207218, 214989, 229099, 229137, 19556, 20676, 20726, 55409, 63187, 82431, 83731, 91667, 108942, 167838, 208244, 208660, 226483, 486, 98243, 147746, 186732, 190125, 222129, 13059, 47113, 63281, 63816, 147364, 191597, 194319, 226191, 80867, 88703, 141125, 165353, 7836, 44100, 84750, 97305, 151159, 163292, 166160, 174457, 187346, 206359, 212868, 3743, 4210, 7231, 77720, 101878, 151668, 158168, 203331, 226481, 12095, 51060, 78232, 85545, 145684, 164617, 169839, 180765, 203890, 209861, 222276, 12511, 120891, 163107, 171003, 176280, 20466, 195366, 222140, 72978, 141852, 158096, 162904, 2767, 8748, 105451, 111950, 229203, 229612, 6031, 12231, 93001, 172784, 174080, 195635, 222160, 2077, 148220, 190414, 207102, 84111, 89221, 177736, 222281, 51841, 83873, 112121, 129029, 130969, 147734, 148231, 148343, 152004, 172491, 192443, 200375, 230195, 165471, 169651, 87960, 230440, 83966, 101115, 158138, 191593, 191892, 229621, 13073, 31147, 44055, 71915, 905, 130121, 130286, 83984, 94826, 201315, 2654, 3052, 5288, 62828, 109159, 45345, 57797, 77490, 83203, 150059, 180295, 210195, 227209, 229074, 7529, 86462, 87778, 130059, 229341, 83520, 14855, 45242, 51014, 89143, 163311, 164805, 206146, 210232, 156377, 172805, 192953, 4313, 22875, 63708, 77497, 165430, 187428, 190477, 105395, 176513, 172889, 217595, 2587, 75016, 193089, 12089, 211658, 61730, 61745, 63353, 83986, 84548, 94951, 124283, 229118.

TABLE 7

| | Identity and Secondary Structure Comparison to Oligo6 | | | |
|---|---|---|---|---|
| ID | Sequence (5'→3') | Identity | mfeCode | mfe Value (kcal/mol) |
| BTX28676 (SEQ ID NO. 183212) | GGCGCAGGGGGGGCCCAG AGTATGGGGCCTG | 1 | ..........(((.((((.....)))).))). | -12.2 |
| Oligo6 (SEQ ID NO. 230810) | GGCGCAGGGGGGGCCCAG AGTATGGGGCCTG | 1 | ..........(((.((((.....)))).))). | -12.2 |
| BTX165089 (SEQ ID NO. 87091) | ATCGCCCAGGGCAGCCAAG AGATGGGCCCTGC | 0.75 | ......(((((((...(((......)))))))))))). | -12.5 |
| BTX125376 (SEQ ID NO. 47378) | GCTTGGGAGGTGGGCCTGG TAGTGTGGGCCTG | 0.75 | ..........(((((((......)))))))). | -9.7 |
| BTX148478 (SEQ ID NO. 70480) | TTACAGCCCAGGTGGGGA GATGGAGGGCCTG | 0.75 | .....((((...............)))).... | -6 |
| BTX54083 (SEQ ID NO. 208619) | TGACGCAGGCGGCCGATAG TCATGGGAAGGCT | 0.75 | ......((.(...((.((....)).))...).)) | -5 |
| BTX138117 (SEQ ID NO. 60119) | TAGCGAGGGATGTGCCAGA GCAAGGGGCGATG | 0.75 | ..........(((.((.........)).))).... | -4.6 |
| BTX151736 (SEQ ID NO. 73738) | TTTTGGTGGTTTTGGGCAC AGAGATCCGCCTT | 0.71875 | ....(((((((((((....))))))..)))))... | -9.4 |
| BTX165901 (SEQ ID NO. 87903) | ATGATTTCTGGCGCTGGGC AGGCGGCGTACTG | 0.71875 | ..........(((((((......)))))))..... | -8.7 |
| BTX45567 (SEQ ID NO. 200103) | GATATTTTGGCGCTGGGGT ACTAACGGGGGCT | 0.71875 | ........(((.((.(.........).)).))) | -7.9 |
| BTX102652 (SEQ ID NO. 24654) | CCTCGTTGGAGAAGGGGTG CCGGGTATTGGCT | 0.71875 | ((((..........)))).(((((......)))). | -7.6 |
| BTX139961 (SEQ ID NO. 61963) | TCAGCTCAGGTCGGGGCCT CGAGTAGGGTCGT | 0.71875 | ...(((((((((....))))).)))))........ | -7.6 |
| BTX168333 (SEQ ID NO. 90335) | ATTTTTGGAGGCGTCGGCC ACTTAGGCGCCCT | 0.71875 | ........((((....(((......))).)))) | -7.2 |
| BTX164283 (SEQ ID NO. 86825) | ATATCTTGTCTGCATGGAG GGCAATGGTGGCG | 0.71875 | .((((((((((.......)))))))))).... | -6.8 |
| BTX118000 (SEQ ID NO. 40002) | GATGGGCGCAGGAGGGGGC AGAGCTTCACCTA | 0.71875 | .........(((...(((((...)))))).))). | -6.5 |
| BTX56414 (SEQ ID NO. 210950) | TTTTGGTTGTAAGCATGCG ATGGCGATATGCT | 0.71875 | ...........(((((((((....)).))))))) | -6.3 |
| BTX143000 (SEQ ID NO. 65002) | TCGGTGCACGGGAGTGAGC AGGTAGGGGCTCG | 0.71875 | (((.....)))...(((((........))))) | -6 |
| BTX183604 (SEQ ID NO. 105605) | CGTTGGTTTTGGCGAGTTG GGCGCGTGTGCGT | 0.71875 | ((((......))))......(((((....)))) | -5.9 |
| BTX90485 (SEQ ID NO. 12487) | ATTTTGGCTCAATAGAGAC TCAGAGTGCGGCC | 0.71875 | (((((((((((....))).).)))))))...... | -5.8 |
| BTX151550 (SEQ ID NO. 72552) | TTTGGGCTATGGGGTGCGC GAATGAGGCATTG | 0.71875 | ((((.((.........)).)))).......... | -5.4 |

In total, 548 sequences had an identity score of 0.65 or higher as compared to Oligo6. The SEQ ID NOs. of these sequences ordered by identity to Oligo6 from high to low are 153288, 230810, 72324, 28200, 53868, 181518, 42357, 57489, 73227, 172055, 2952, 44405, 75929, 71429, 20006, 184108, 47784, 92897, 220240, 57283, 52420, 140995, 146820, 169084, 39855, 146442, 147185, 181215, 56691, 75368, 53201, 146451, 147211, 63615, 228278, 173786, 46890, 75306, 107324, 221968, 14758, 47455, 135584, 30860, 33832, 43355, 120959, 131982, 146257, 229669, 52947, 140895, 37532, 161060, 167186, 115635, 199581, 32146, 152683, 56718, 147067, 220159, 49808, 50500, 176682, 154788, 201850, 3316, 146032, 147160, 155055, 48737, 139597, 72670, 207849, 170684, 54938, 3636, 128263, 156447, 145935, 51375, 116222, 119142, 127442, 142254, 153286, 155023, 22541, 46005, 182785, 205662, 61165, 144596, 51275, 177954, 48823, 219645, 3084, 8721, 146275, 17565, 57305, 118912, 146989, 206013, 128221, 40437, 55270, 192802, 92525, 183937, 220230, 43550, 46880, 56462, 193987, 152961, 162432, 43249, 157821, 56686, 103350, 57509, 147179, 204595, 144580, 91355, 155573, 50702, 96578, 229726, 33377, 146294, 144529, 38645, 53968, 174050, 42652, 107918, 209673, 131257, 175795, 182083, 39709, 51680, 145326, 202876, 139743, 133866, 221057, 47843, 135884, 194660, 80602, 5151, 69290, 49106, 41372, 50054, 119798, 201995, 27833, 213489, 2552, 103757, 139126, 205965, 21565, 109594, 139143, 95213, 168594, 8295, 107746, 48633, 51565, 121759, 124806, 165297, 8858, 168415, 205374, 36291, 38832, 188342, 65224, 51894, 136891, 182808, 50398, 134134, 161741, 214580, 52534, 88648, 111909, 130891, 144347, 145899, 33191, 35279, 125042, 178432, 1128, 15284, 28047, 62081, 72359, 144383, 166893, 177544, 27186, 33119, 53848, 56247, 10318, 13463, 112272, 138972, 15079, 24082, 36118, 55252, 127295, 144690, 10788, 14263, 74803, 179469, 221824, 52269, 136543, 72810, 108106, 134688, 13605, 34744, 107781, 183957, 195805, 14823, 17943, 20827, 35634, 40892, 51368, 54007, 117928, 179645, 205008, 223768, 15354, 40102, 48730, 103308, 213735, 13491, 36202, 39617, 54305, 55719, 79126, 144251, 181386, 199426, 24145, 48970, 85613, 108868, 126137, 160451, 182602, 196198, 202593, 205100, 205178, 221276, 120234, 5534, 15236, 50585, 84864, 129328, 219741, 156356, 86591, 11670, 29721, 54364, 71545, 74815, 131589, 139261, 146096, 50285, 71392, 114854, 152931, 169999, 8242, 57478, 62417, 111260, 182506, 17688, 34796, 43260, 146362, 157911, 175343, 5282, 45570, 52948, 56261, 57527, 79678, 128070, 170101, 85036, 103923, 106792, 146449, 156276, 195604, 196920, 3796, 40839, 50916, 51342, 52751, 116864, 135801, 140220, 193642, 196275, 220855, 226649, 1694, 11775, 43184, 107072, 151999, 184762, 6175, 150549, 182543, 200143, 203039, 98018, 112499, 134073, 136233, 147188, 182640, 206111, 22684, 34862, 53055, 72815, 181471, 197260, 203774, 14892, 23173, 49134, 55035, 55769, 130459, 131392, 214574, 223101, 36256, 51551, 51755, 137626, 143652, 146917, 219821, 69499, 143367, 34770, 105892, 122539, 128264, 144806, 152945, 181300, 204421, 204755, 42340, 56630, 147194, 170809, 188435, 209724, 213559, 23949, 54193, 67388, 179249, 211115, 31368, 34502, 51837, 57080, 94239, 133863, 178270, 216886, 131090, 139144, 205199, 40207, 54308, 55444, 56625, 56828, 90681, 126395, 128352, 146092, 146416, 161065, 200089, 53369, 56071, 127939, 178282, 37651, 39118, 39693, 47389, 61289, 73185, 132055, 145917, 181354, 199583, 218281, 10820, 133779, 141303, 200009, 54698, 70129, 91825, 168148, 202370, 213819, 220132, 93335, 145481, 199400, 54628, 178071, 202831, 57710, 73719, 143175, 146419, 161948, 180016, 14543, 66627, 57374, 89825, 124215, 155543, 181422, 205448, 205630, 49108, 55482, 57015, 98225, 146453, 218426, 103338, 179980, 207727, 178323, 27665, 55329, 96775, 136240, 144944, 180598, 93933, 146163, 183627, 13029, 103967, 127930, 147087, 176958, 54661, 122836, 183775, 193643, 205616, 48939, 102882, 157197, 17752, 28989, 74331, 154261, 39112, 43618, 140934, 185185, 138825, 138909, 143865, 147257, 67515, 205974, 24649, 55488, 75948, 122503, 23338, 39818, 89053, 90410, 137944, 158565, 53667, 110669, 41983, 155574, 199831, 7910, 183865, 52679, 54099, 157927, 42198, 220071, 223787, 54235, 98792, 146366, 178495, 146625, 78716, 121036.

Aptamers with similar motifs are chosen and manufactured using the oligo synthesizer. The affinity of promising candidates is determined using SPR as in Example 3.

Example 5: Microvesicle-Based Aptamer Subtraction Assay

This Example presents a process of depleting an aptamer pool of aptamers that recognize biomarkers found in a biological sample. The method can be used to deplete aptamers that recognize microvesicles from healthy individuals. The depleted aptamers provide a pool of aptamers that can be screened against microvesicles from diseased individuals, thereby identifying aptamers that preferentially recognize disease versus healthy.

Aptamer Pool Subtraction

Circulating microvesicles are isolated from normal plasma (e.g., from individuals without cancer) using one of the following methods: 1) Isolation using the ExoQuick reagent according to manufacturer's protocol; 2) Ultracentrifugation comprising spin at 50,000 to 150,000 g for 1 to 20 hours then resuspending the pellet in PBS; 3) Isolation using the TEXIS reagent from Life Technologies according to manufacturer's protocol; and 4) filtration methodology. The filtration method is described in more detail as follows:

Place syringe and filter (1.2 μm Acrodisc Syringe Filter Versapor Membrane Non-Pyrogenic Ref: 4190, Pall Life Sciences) on open 7 ml 150K MWCO column (Pierce concentrators, 150K MWCO (molecular weight cut off) 7 ml. Part number: 89922). Fill open end of syringe with 5.2 ml of filtered 1×PBS prepared in sterile molecular grade water.

Pipette patient plasma (900-1000 μl) into the PBS in the syringe, pipette mix twice Filter the plasma into the 7 ml 150K MWCO column.

Centrifuge 7 ml 150K MWCO columns at 2000×g at 20° C. (16° C. to 24° C.) for 1 hour.

After 1 hour spin, pour the flow-through into 10% bleach to be discarded.

Visually inspect sample volume. If plasma concentrate is above the 8.5 ml graduation on the concentrator tube, continue to spin plasma sample at 10 minute increments at 2000×g at 20° C. (16° C. to 24° C.) checking volume after each spin until plasma concentrate is between 8.0 and 8.5 mls.

Pipette mix slowly on the column a minimum of 6 times and adjust pipette to determine plasma concentrate volume. If volume is between 100 μl and Target Volume, transfer plasma concentrate to previously labeled co-polymer 1.5 ml tube. If volume is still greater than Target Volume, repeat the above centrifugation step.

Pour ~45 mls of filtered 1×PBS prepared in sterile molecular grade water into 50 ml conical tube for use in the next step.

Add the appropriate amount of filtered 1×PBS to reconstitute the sample to the Target Volume.

The microvesicles produced using any of the isolation methods will comprise a mixture of vesicle types and will be various sizes with the exception of the ultracentrifugation methods, which tends to isolate exosomes.

Randomly generated oligonucleotides (produced as described in Example 1 above) are incubated with the isolated normal vesicles in PBS overnight at room temperature or at 4 degrees Celsius.

The aptamers that do not bind to these vesicles are isolated by spinning down the vesicles at 50,000 to 150,000×g for 1 to 20 hours and collecting the supernatant.

The aptamer oligonucleotides are collected from the supernatant by running the mixture over a column containing streptavidin-coated beads. These aptamers are then added to vesicles isolated from diseased patients (using the same methods as above) and incubated overnight in PBS at room temperature or 4 degrees Celsius.

The vesicles are then spun at 50,000 to 150,000×g for 1 to 20 hours and the supernatant is discarded. The vesicles are resuspended in PBS and lysed using SDS or some similar detergent.

The aptamers are then captured by running the lysis mixture over a column of streptavidin-coated beads. The isolated aptamers are then subjected to a round of PCR to amplify the products.

The process is then repeated for a set number of times, e.g., five or more times. The remaining aptamer pool has been depleted of aptamers that recognize microvesicles found in "normal" plasma. Accordingly, this method can be used to enrich the pool in aptamers that recognize cancer vesicles. See FIG. 6.

Example 6: Aptamer Target Identification

The Example above presents a method of identifying disease-specific aptamers. The Example further presents methods of identifying the targets of the disease-specific aptamers.

An aptamer identified according to the method in Example 5 is tethered to a microbead. The aptamer has shown the ability to preferentially recognize cancer vesicles versus controls. The microbead is incubated with a biological sample comprising cancer vesicles under conditions such that the aptamer can bind to the antigen it recognizes on the cancer microvesicle surface. Once the complex has formed, the aptamer is photo-crosslinked to the antigen. The vesicle is then disrupted using a surfactant, thereby leaving the aptamer-target complex tethered to the microbead. The microbeads are washed and recovered. The crosslinks are disrupted thereby releasing the target into solution. The beads are spun from solution and the target is further concentrated and isolated using size exclusion chromatography. The purified target is subjected to mass spectrometry for identification. See FIG. 14 for illustrative schematic.

Example 7: Illustrative Aptamer Sequences

The following Tables comprise illustrative aptamers of the invention. The aptamers were part of the pool of random aptamers described in Example 1. It is understood that the nucleotide sequences that are disclosed in Table 8 can be modified to the extent that resulting modifications result in an aptamer having about 50, 55, 60, 65, 70, 75, 80, 85, 90, 95, 96, 97, 98, and 99 percent homology to the disclosed sequence and retain the functionality of binding to EpCAM antigen or functional fragments thereof. As used in the context of any defined numerical unit, the term "about" means variance of 10% above or below that numerical unit and all units in between. Modifications indicated in Table 8 were made to the aptamer pools in order to allow conjugation of the aptamer sequence. One of skill will appreciate that the thymine tail or similar moiety can be conjugated to either end of the aptamer.

TABLE 8

Illustrative EpCAM Aptamers

| Aptamer ID | Sequence | Modifications | SEQ ID NO. |
|---|---|---|---|
| BTX176881 | 5'-CCG CGC AGA TAT ACA ACG TAC CTC TGT GCG CA | 3' tail comprising 6 thymines and a biotin moiety | 98883 |
| BTX187269 | 5'-CTG TGA GGC GTA CTG CGG TGA GCC TCT CAT TA | 3' tail comprising 6 thymines and a biotin moiety | 109271 |
| BTX221708 | 5'-TGC AAG CTG CTA ATC AGC GAT GCT CTT TGG AG | 3' tail comprising 6 thymines and a biotin moiety | 143710 |
| APTAMER 4 | 5'-CCC CCC GAA TCA CAT GAC TTG GGC GGG GGT CG | 3' tail comprising 6 thymines and a biotin moiety | 1 |
| BTX222490 | 5'-TGC GCG TCT ATA AGT GCG CGA GCG GGC TTC CC | 3' tail comprising 6 thymines and a biotin moiety | 144492 |
| BTX196339 | 5'-GCG AGC CTA TGC ACC ATC TAG GTG TTG TGG CA | 3' tail comprising 6 thymines and a biotin moiety | 118341 |
| BTX214537 | 5'-TAT CGA TCG CAT CTA TGT GAT CGC TTA ACC GT | 3' tail comprising 6 thymines and a biotin moiety | 136539 |
| Aptamer 8 | 5'-AAT CGT TAG TCA CTA TTC GTC CAT AGT AGT GAC A | 3' tail comprising 6 thymines and a biotin moiety | 230811 |
| BTX201159 | 5'-GGC GGC GAC CAT TGT TGG TTT GGT GTC GCT GG | 3' tail comprising 6 thymines and a biotin moiety | 123161 |
| BTX219183 | 5'-TCG TGG CAA AGG CCG ATT CAC CCA TGC CGG GT | 3' tail comprising 6 thymines and a biotin moiety | 141185 |

TABLE 8-continued

Illustrative EpCAM Aptamers

| Aptamer ID | Sequence | Modifications | SEQ ID NO. |
|---|---|---|---|
| BTX80419 | 5'-ACA CGG GCC TTC TTG GCA CGA GCC ATG GGG CT | 3' tail comprising 6 thymines and a biotin moiety | 2421 |
| BTX145792 | 5'-TGC GTC ACT CTC GCG ATC AAG ATC ATT GAT CT | 3' tail comprising 6 thymines and a biotin moiety | 67794 |
| BTX135844 | 5'-GTT GCT GTC TAG CAA CGA CGC AAA CTG CAA CG | 3' tail comprising 6 thymines and a biotin moiety | 57846 |
| BTX85875 | 5'-AGC GGG GCA TCG GCG TTG GCG AAC CGA CGG CG | 3' tail comprising 6 thymines and a biotin moiety | 7877 |
| BTX120273 | 5'-GCC AGG CGT ATC CGC ATC CGA TGG GCT CGG GC | 3' tail comprising 6 thymines and a biotin moiety | 42275 |
| Aptamer 16 | 5'-TTT CAA GGC ACT CGT GTT CCC GAC ATG AGT G | 3' tail comprising 6 thymines and a biotin moiety | 230812 |
| BTX119687 | 5'-GCA TCG ATG CGT CCC CGC GGC GGC CAG CCG AT | 3' tail comprising 6 thymines and a biotin moiety | 41689 |
| BTX111579 | 5'-CTC GGT GCT GGA GTT TTG TAA CTC GCG TAC CG | 3' tail comprising 6 thymines and a biotin moiety | 33581 |
| Oligo6 | 5'-GGC GCA GGG GGG GGC CCA GAG TAT GGG GCC TG | 5' tail comprising 6 thymines and a biotin moiety | 230810 |
| BTX28596 (also referred to as Oligo4B) | 5'-GGC CGC GCA TTC TCT GCC GGC TGG TGT ACG GT | 5' tail comprising 6 thymines and a biotin moiety | 183132 |

Example 8: Detection of Microvesicles Using Anti-EpCAM Aptamers

Aptamers can be used as binding agents to detect a biomarker. In this Example, aptamers are used as binding agents to detect EpCAM protein associated with microvesicles.

FIGS. 18A-18D illustrate the use of an anti-EpCAM aptamer (Aptamer 4; SEQ ID NO. 1) to detect a microvesicle population in plasma samples. Plasma samples were obtained from three men with prostate cancer and three men without prostate cancer (referred to as controls or normals). Antibodies to the following microvesicle surface protein antigens of interest were conjugated to microbeads (Luminex Corp, Austin, Tex.): A) EGFR (epidermal growth factor receptor); B) PBP (prostatic binding protein; also known as PEBP1 (phosphatidylethanolamine binding protein 1)); C) EpCAM (epithelial cell adhesion molecule); and D) KLK2 (kallikrein-related peptidase 2). Microvesicles in the plasma samples were captured using the bead-conjugated antibodies. Fluorescently labeled Aptamer 4 was used as a detector in the microbead assay. FIGS. 18A-18D show the average median fluorescence values (MFI values) detected for the bead-captured and Aptamer 4 detected microvesicles. Each plot individually shows the three cancer (C1-C3) and three normal samples (N1-N3). These data show that, on average, the prostate cancer samples have higher levels of microvesicles containing the target proteins than the normals.

Example 9: Negative and Positive Selection of Aptamers

Aptamers can be used in various biological assays, including numerous types of assays which rely on a binding agent. For example, aptamers can be used instead of antibodies in immune-based assays. This Example provides an aptamer screening method that identifies aptamers that do not bind to any surfaces (substrates, tubes, filters, beads, other antigens, etc.) throughout the assay steps and bind specifically to an antigen of interest. The assay relies on negative selection to remove aptamers that bind non-target antigen components of the final assay. The negative selection is followed by positive selection to identify aptamers that bind the desired antigen.

Preliminary experiments were done with five DNA aptamer libraries with $10^{15}$ sequences each and variable lengths (60, 65, 70, 75, 80-mers) were pre-amplified and strand separated so that forward strand (non-biotinylated) serves as an aptamer. Multiple rounds of negative selection and positive selection were performed. Before each round, the recovered aptamer products were PCR amplified and strand separated using standard methodology.

The aptamer library and primers used to amplify the recovered aptamers after each round of selection are shown in Table 9. In the aptamer library sequences, 20N-40N refer to the number of random nucleotides in the library sequence.

TABLE 9

Aptamer Library and PCR Primers

| Identity | Sequence (5' → 3') | SEQ ID NO. |
|---|---|---|
| Forward primer | 5'-ATCCAGAGTGACGCAGCA | 230813 |
| Forward primer | 5'-ACTAAGCCACCGTGTCCA | 230814 |

TABLE 9-continued

Aptamer Library and PCR Primers

| Identity | Sequence (5' → 3') | SEQ ID NO. |
|---|---|---|
| Reverse primer | 5'-biotin-ATCCAGAGTGACGCAGCA | 230815 |
| Reverse primer | 5'-biotin-ACTAAGCCACCGTGTCCA | 230816 |
| 60-mer aptamer library | 5'-ATCCAGAGTGACGCAGCA-20n-TGGACACGGTGGCTTAGT | 230817 |
| 65-mer aptamer library | 5'-ATCCAGAGTGACGCAGCA-25n-TGGACACGGTGGCTTAGT | 230818 |
| 70-mer aptamer library | 5'-ATCCAGAGTGACGCAGCA-30n-TGGACACGGTGGCTTAGT | 230819 |
| 75-mer aptamer library | 5'-ATCCAGAGTGACGCAGCA-35n-TGGACACGGTGGCTTAGT | 230820 |
| 80-mer aptamer library | 5'-ATCCAGAGTGACGCAGCA-40n-TGGACACGGTGGCTTAGT | 230821 |

Selections were performed as follows:

Negative Selection

1. Prepare bead negative Selection Mix: Incubate 1200 non-magnetic beads with standard blocking agent for 20 min.
2. Add 50 µl of aptamer library (5 libraries total) to a PCR strip tube with 4.5 µl of each bead mixture. Incubate for 2 h at 37° C. with agitation at 550 rpm.
3. Pre-wet filter plate (1.2 µm, Millipore) with PBS-BN buffer. Add 150 µl PBS-BN.
4. Transfer samples from the PCR strip tubes to the filter plate, incubate for 1 h at room temperature with agitation at 550 rpm.
5. Collect flow-through from filter plate into a collection (NBS) plate using a vacuum manifold.
6. Concentrate and clean samples to remove excess materials as desired.

The negative selection process is repeated up to 6-7 times.

Positive Selection

Before starting, conjugate the protein biomarkers of interest (SSX4, SSX2, PBP, KLK2, SPDEF) to desired non-magnetic microbeads using conditions known in the art. The recombinant purified starting material included: SPDEF recombinant protein from Novus Biologicals (Littleton, Colo., USA), catalog number H00025803-P01; KLK2 recombinant protein from Novus, catalog number H00003817-P02; SSX2 recombinant protein from Novus, catalog number H00006757-P01; PBP recombinant protein from Fitzgerald Industries International (Action, Mass., USA), catalog number 30R-1382; SSX4 recombinant protein from GenWay Biotech, Inc. (San Diego, Calif., USA), catalog number GWB-E219AC.

1. Bead blocking: Incubate a desired number of each bead (8400× number of aptamer libraries (5)× an overage factor of (1.2)) with a starting block for 20 min.
2. Mix 50 µl of each aptamer library sample to PCR strip tubes add 2.3 µl of bead sample with particular antigen. Incubate for 2 h at 37° C. with agitation at 550 rpm.
3. Pre-wet filter plate (1.2 µm, Millipore) with PBS-BN buffer. Add 150 µl PBS-BN.
4. Transfer samples from the PCR strip tubes to the filter plate, incubate for 1 h at room temperature with agitation at 550 rpm.
5. Wash 3× with PBS-BN, add 50 µl of PBS and collect samples from the top of the filter to the 1.5 ml tubes.

The positive selection is repeated up to 16 times. Certain rounds of positive selection have additional steps to treat the recovered RNA (i.e., remaining aptamer candidates) as follows:

Round 8 of Positive Selection was Modified as Follows:

1. After the third wash (PBS-BN) 25 µl of sample were collected from the top of the filter into 1.5 ml tubes.
2. The filter plate was incubated at 45° C. for ~10 min and washed immediately using vacuum. The plate was washed three more times with PBS-BN.
3. 50 µl of PBS were added to the plate and step 2 was repeated.
4. After the last wash, 25 µl of PBS was added to the wells. The samples were mixed well and collected from the top of the filter into 1.5 ml tubes.

Round 9 of Positive Selection was Modified as Follows:

1. After the final wash in step 5), 5 µg/ml Streptavidin-PE was added to the aptamer mixture and incubated for 30 min at room temperature with agitation at 550 rpm.
2. Samples on filter plate were washed 3× with PBS-BN (+ additional 500 mM NaCl).
3. One additional wash with regular PBS-BN was performed.
4. 50 µl of PBS was added to the samples followed by collection as above into 1.5 ml tubes.
5. Samples stored at −20° C.

Round 14 of Positive Selection was Modified as Follows:

Before start this round, the antigens of interest (SSX4, SSX2, PBP, KLK2, SPDEF) were conjugated to carboxylated magnetic beads using methods known in the art.

1. Bead blocking: take desired number of each non-magnetic bead (3000× number of aptamer libraries (5)× an overage factor of 1.2), add starting block (3:1, blocking per 1200 beads), make 5 mixes of 4 antigens and supplement each with different target antigen conjugated to magnetic beads (see Table 10 below, wherein the antigens are conjugated to non-magnetic beads except as indicated), incubate 20 min.

TABLE 10

Bead blocking mixtures

| Blocking Mix | Non-magnetic bead antigens | Magnetic bead antigens |
|---|---|---|
| 1 | SSX4 + PBP + KLK2 + SPDEF | SSX2 |
| 2 | SSX2 + PBP + KLK2 + SPDEF | SSX4 |
| 3 | SSX2 + SSX4 + KLK2 + SPDEF | PBP |
| 4 | SSX2 + SSX4 + PBP + SPDEF | KLK2 |
| 5 | SSX2 + SSX4 + PBP + KLK2 | SPDEF |

2. Add 50 µl of aptamer libraries to PCR strip tubes, add bead mixtures with target antigen on magnetic beads to the tubes with pre-selected corresponding aptamer library and incubate for 2 h at 37° C. with agitation at 550 rpm.

3. Pre-wet filter plate with PBS-BN buffer, add 150 µl PBS-BN.

4. Transfer samples from PCR strip tubes to filter plate, incubate 1 h room temperature with agitation at 550 rpm.

5. After last (standard) wash, add 5 µg/ml Streptavidin-PE, incubate for 30 min room temperature with agitation at 550 rpm;

6. Wash 3× with PBS-BN (+ additional 500 mM NaCl).

7. Perform one additional wash with regular PBS-BN.

8. 50 µl of PBS was added to the samples followed by collection as above into 1.5 ml tubes.

9. Remove the magnetic beads using a magnetic stand, and replace with fresh PBS buffer.

10. Samples stored at −20° C. for subsequent DNA extraction and strand separation.

Optional steps implemented in the later round of positive selection are intended to increase stringency of aptamer binding (e.g., increased heat or salt concentration).

Figure 19A:
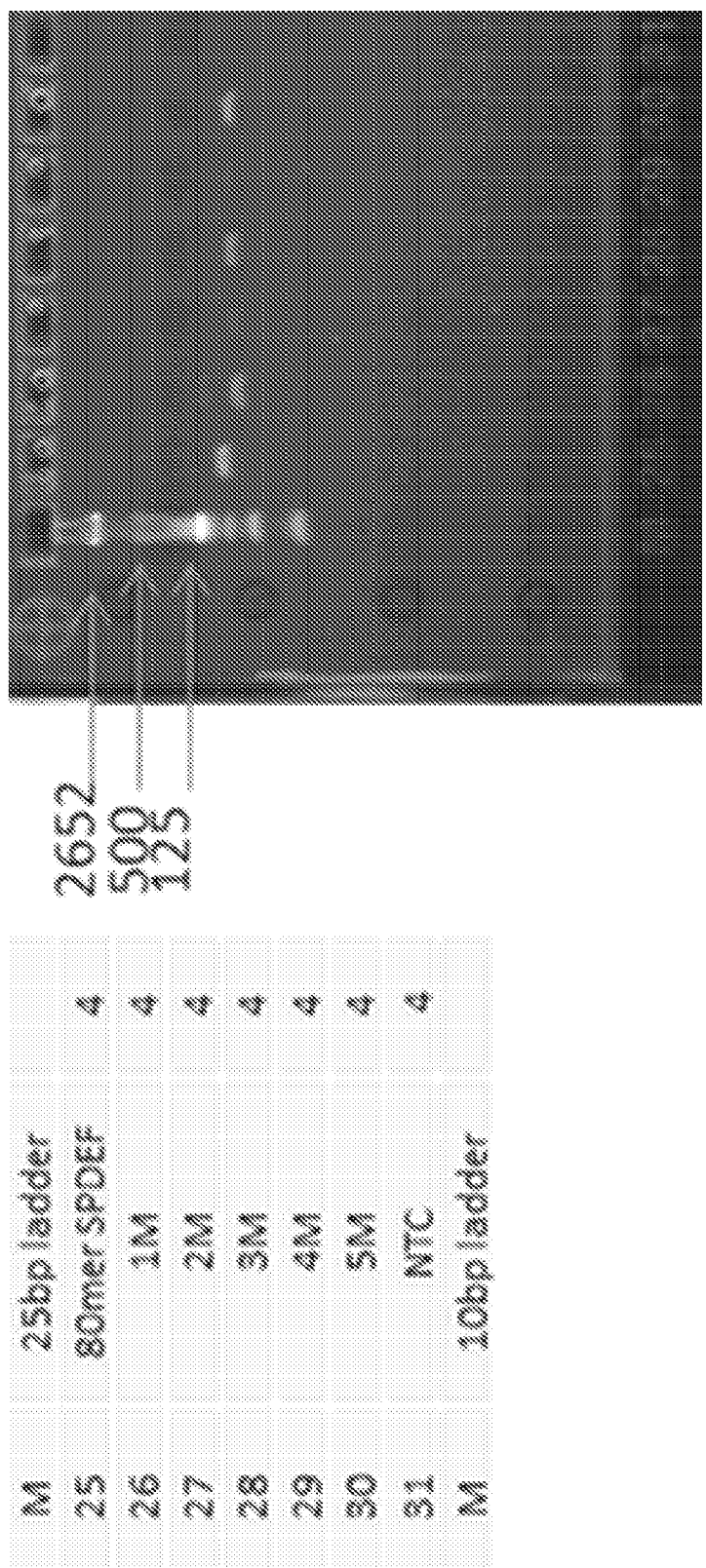
FIGS. 19A-19E illustrate selection of aptamers to antigens of interest. See Example 9. Five DNA aptamer libraries (labeled 1M-5M) after negative selection as described herein were incubated with mixture of 4 antigens (SSX2, SSX4, PBP, KLK2) conjugated to microbeads and supplemented with SPDEF antigen conjugated to magnetic beads. Samples were processed according to a positive section protocol as described herein. After collecting the magnetic beads, bound DNA aptamers were extracted from beads and re-amplified.
Figure 19B:
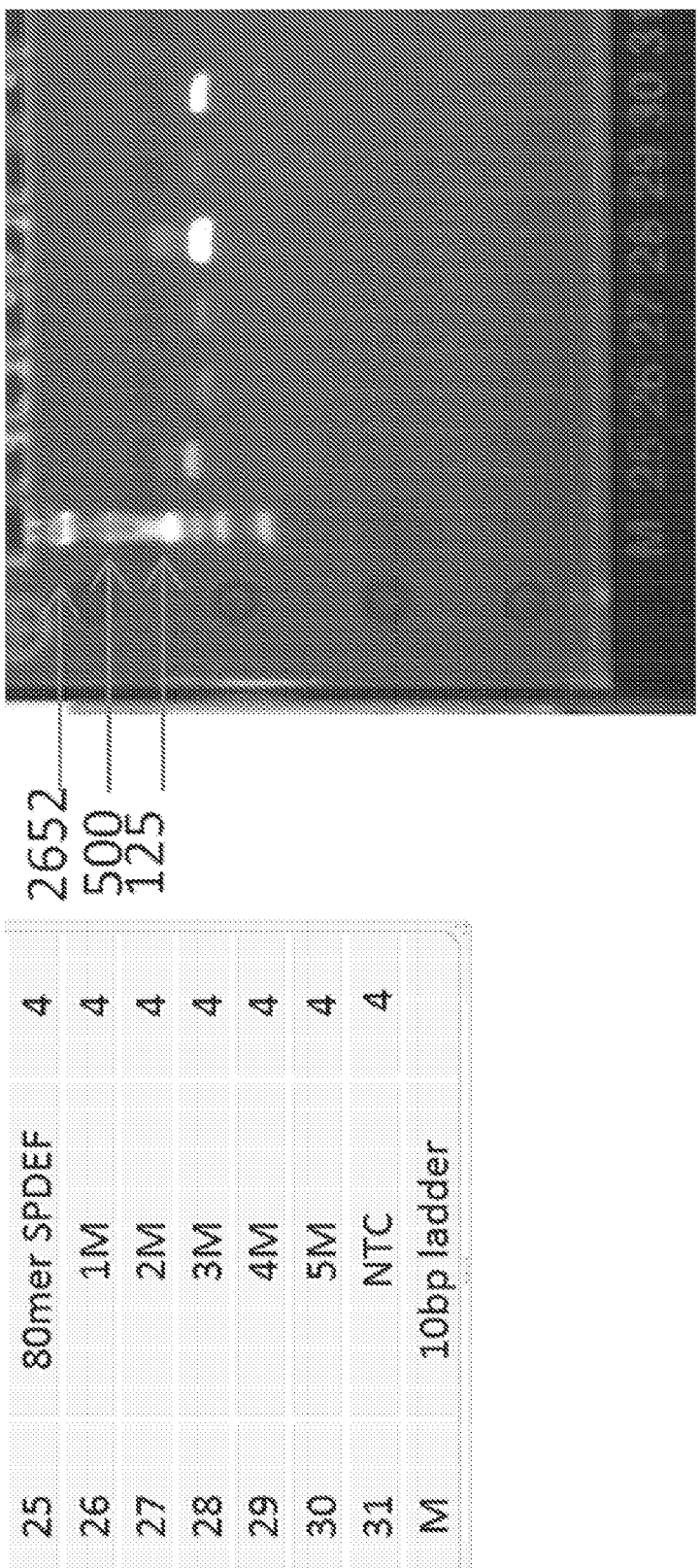
Figure 19C:
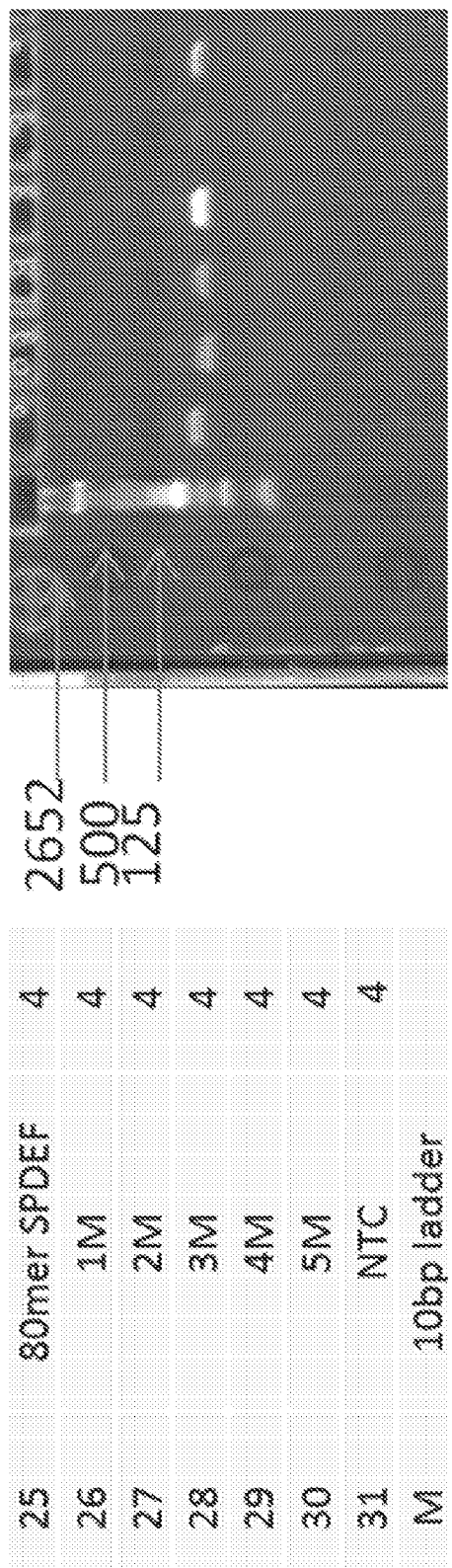

FIGS. 19A-19E illustrate selection of aptamers to antigens of interest during positive selection. Three rounds of negative selection had been performed previously. FIGS. 19A-19C illustrate five DNA aptamer libraries (labeled 1M-5M) selected for binding to SPDEF. After negative selection, the libraries were incubated with mixture of 4 antigens (SSX2, SSX4, PBP, KLK2) conjugated to microbeads and supplemented with SPDEF antigen conjugated to magnetic beads. Samples were processed according to the positive section protocol above. After collecting the magnetic beads, bound DNA aptamers were extracted from beads and re-amplified. FIGS. 19A-19C illustrate aptamers recovered from each starting library after one (FIG. 19A), two (FIG. 19B), and three rounds (FIG. 19C) of positive selection.

Figure 19D:
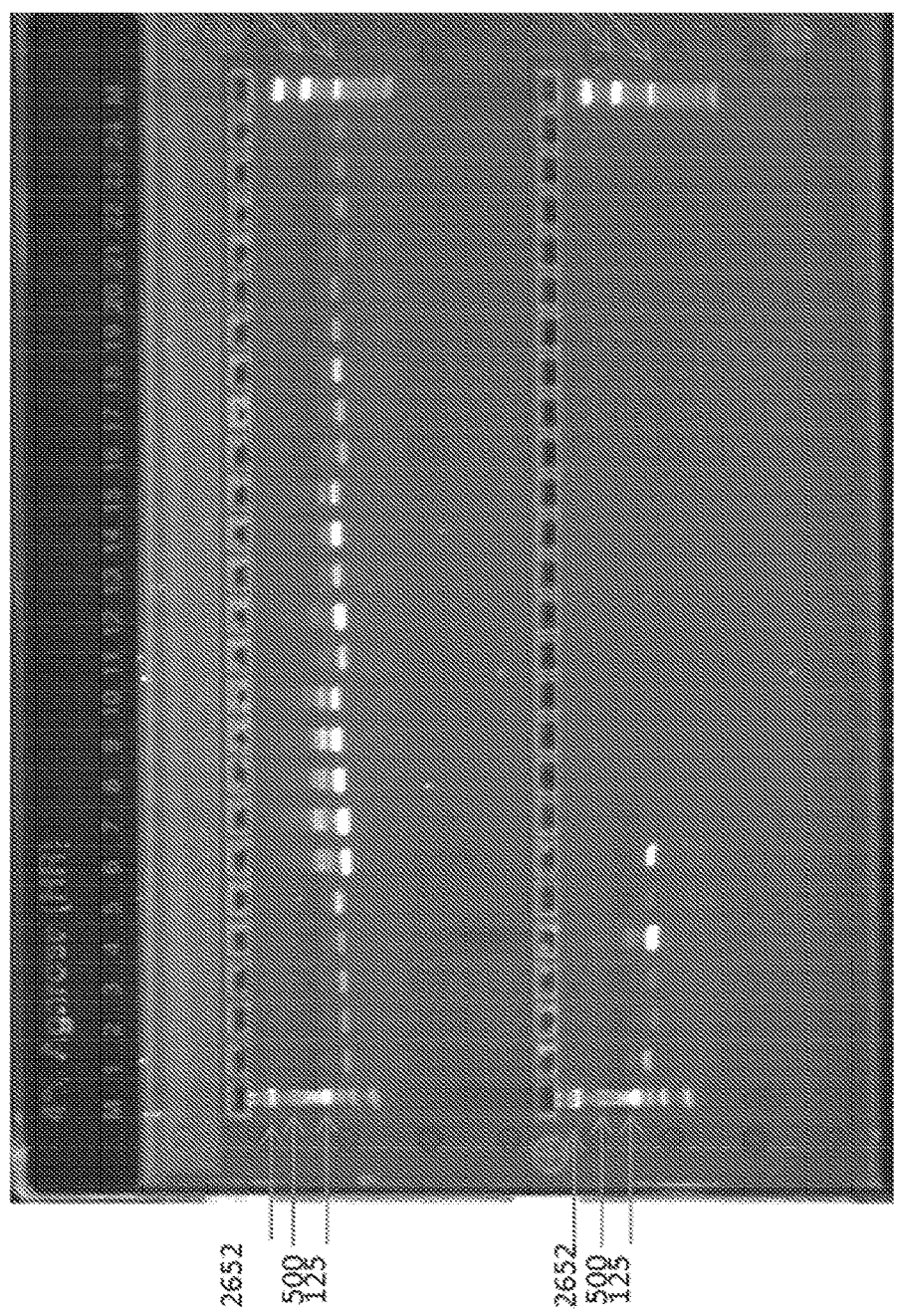
Figure 19E:
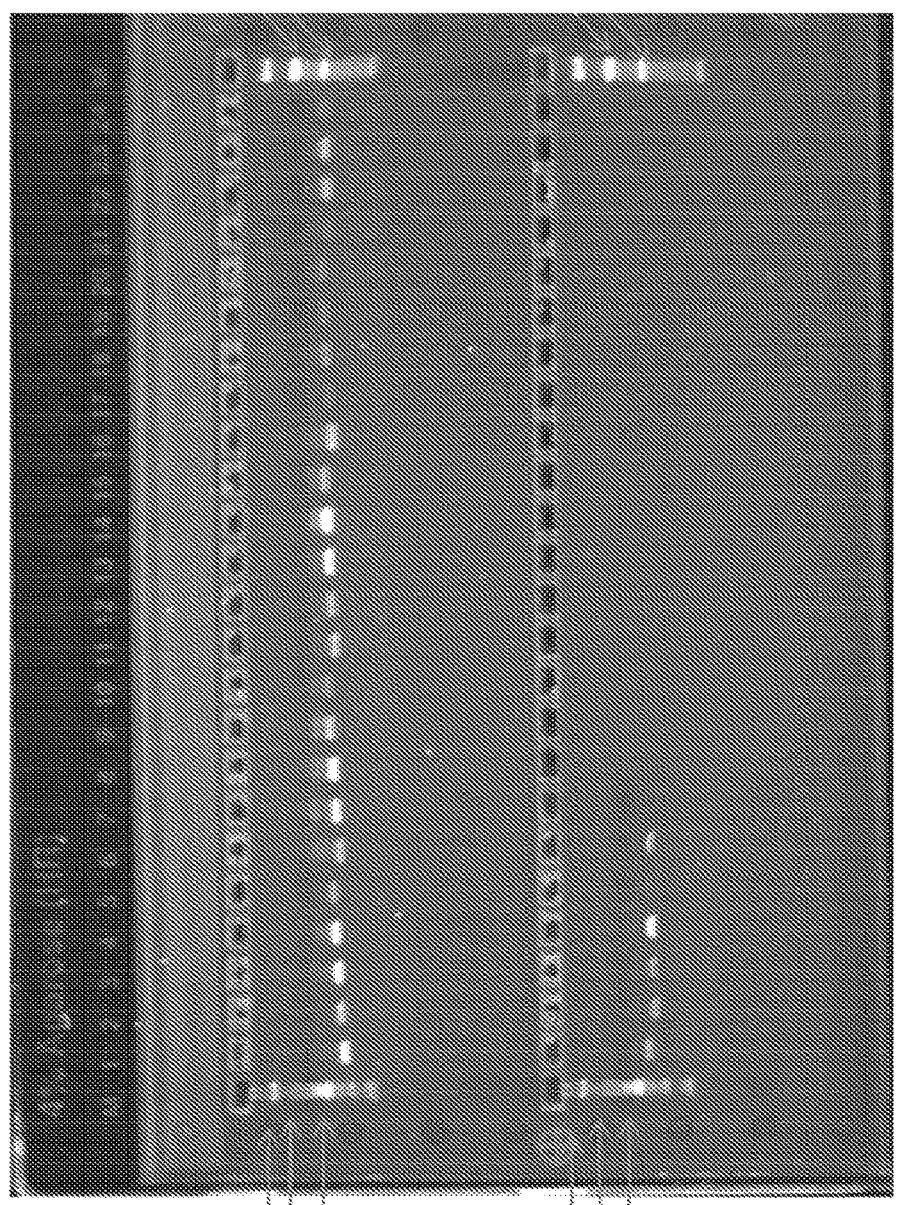

FIGS. 19D-19E illustrate screening 25 aptamer libraries after the 13th round of positive selection against specific antigen (5 libraries per each of SSX2, SSX4, PBP, KLK2 and SPDEF antigens). The aptamer selection after this round was modified with the inclusion of confounding antigens per the round 13 modifications described above. DNA aptamers bound to magnetic beads conjugated to the aptamers of interest were extracted from beads and re-amplified. The recovered libraries are shown in FIG. 19D. FIG. 19E shows the libraries after an addition round of selection and stringent wash.

Example 10: Strand Separation

After each round of selection in the Example above, the recovered aptamer pool was amplified using PCR with standard protocols. The PCR products were captured and strand separated using methodology presented in this Example.

Negative Selection Strand Separation

Prepare 20 µL/PCR of Streptavidin magnetic beads (Thermo Scientific, Rockford, Ill., USA) by placing on magnet for 1 min. Remove storage buffer completely. Wash 3 times with PBS-T. Resuspend in equivalent volume of PBS-T as at the start. Aliquot 20 µL/well in all relevant aptamer wells (25/plate) in a 96 well plate.

Add an additional 80 µL of PBS-T/well.

Add remaining PCR contents for each respective aptamer in appropriate well. Incubate at room temperature for 15 minutes with mild agitation. Place plates on magnet. Remove supernatant and discard. Wash 3× with 150 µL PBS.

After final wash, place on magnet and remove PBS. Add 50 µL of 0.1 M NaOH and incubate for 5 minutes at room temperature. Following the incubation, remove the strand-separated aptamer in solution and place in new 96-well leaving the complementary strand immobilized on the beads. Neutralize the solution with the addition of 5 µL of 1 M HCl. Bring volume up to 100 µL with 45 µL of water.

Ethanol precipitate by adding 1/10 volume of 3 M Sodium acetate pH 5.2 and 3× volumes of 95% ethanol.

Add 1.25 µL of glycogen (Roche 20 µg/µL) and spin at room temperature for 15 minutes. Discard supernatant and allow pellet to dry.

Resuspend in appropriate buffer for next round of selection.

Positive Selection Strand Separation

1. Aliquot each sample into a 1.7 ml Eppendorf tube.

2. Pre-aliquot into labeled tubes 5 µL 1M HCl. There should be one tube/sample.

3. If sample volume is −38 µL, add 420 µL of 0.05% Tween in 1×PBS (to prepare add 250 µL of Tween into 500 mL of Hyclone PBS and mix well-pipet tween slowly-material is viscous).

4. Prepare streptavidin beads, 40 µL per sample is needed (keep beads pooled in a tube for washes). If performing 25 strand separations-aliquot 540 µL of beads×2 tubes (includes overage). Vortex beads well before preparing them, there should be no clumps evident.

5. Place beads on magnet and wait for the solution to clear.

6. Remove supernatant without disturbing the beads.

7. Add 1 mL 0.05% Tween in 1×PBS to the beads and mix off the magnet. Replace on the magnet after mixing and wait for the solution to clear.

8. Remove supernatant without disturbing the beads.

9. Repeat steps 7 and 8. Resuspend beads in tween-PBS solution in the same volume aliquoted previously 10. Vortex beads well off the magnet, and add 40 µL to each of the samples.

11. Cap the samples tightly and place on rotator for 15 minutes at room temperature.

12. Place samples back on the magnet to wash away unbound sample.

13. Add 1 mL 0.05% Tween in 1×PBS to each tube, aiming towards the magnetic wall. Wait for the solution to clear.

14. Remove supernatant without disturbing the beads.

15. Repeat steps 12 and 13. Make sure no remaining solution remains in the tube.

16. Off the magnet, add 50 µL of 0.1M NaOH to each sample.

17. Place tubes on Mix Mate for 5 minutes at 350 RPM room temperature.

18. After 5 minutes, place the tubes on the magnet.

19. After the beads clear and are stuck to the magnet, remove supernatant and add to appropriately labeled 5 µL HCl tubes (these should have been aliquoted and labeled prior to start of the strand separation). This should neutralize the solution. The solution should be slightly cloudy.

20. Bring the volume up to 100 μL in each tube by adding 45 μL of molecular grade RNase/DNase free water. Place samples briefly on ice.

21. Add 11 μL of 3M sodium acetate to each tube. This might clear some of the solution.

22. Add 350 μL of 95% ethanol to each tube.

23. Add 1.25 μL of glycogen to each tube, there should be a faint whitish trail that can be seen.

24. Mix by inversion 10×.

25. Centrifuge ethanol tubes for a minimum of 16 minutes at max speed at room temp.

26. When centrifugation is complete, remove ethanol from tubes, careful to not disturb the pellet. Use a p1000 first, followed up with a p200.

27. Let samples air dry for ~5 minutes or until ethanol residue is gone. Do not let air dry too long.

28. Resuspend samples in 55 μL 25 mM HEPES in PBS-BN.

29. Let sit for ~2 minutes and vortex sample and spin it down.

30. Aliquot 5 μl into tubes labeled with positive selection, the round number, date, sample number, and 'post-Amp'. Freeze at −20° C.

31. The remaining 50 μL is used for the next round of selection.

Example 11: Discovery and Characterization of Anti-EpCAM Aptamers

Figures 20A, 20B:
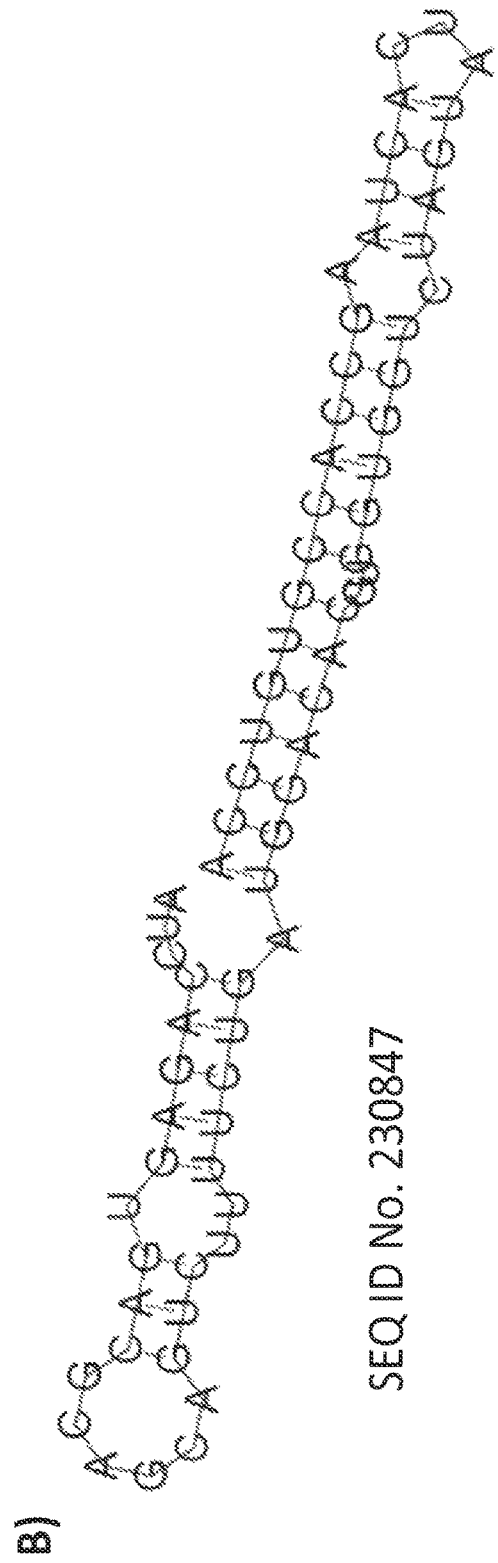
FIG. 20A illustrates the sequence of EPCAM aptamer CAR003 (SEQ ID NO. 230822).
FIG. 20B illustrates the optimal secondary structure of CAR003 with a minimum free energy ($\Delta G$) of −30.00 kcal/mol. For purposes of illustration, the aptamer is shown as an RNA aptamer (SEQ ID NO. 230847) corresponding to the DNA sequence in FIG. 20A.

In this Example, an aptamer to EpCAM identified using the technique in Examples 9-10 above is characterized. After selection for a pool of EpCAM binding aptamers as described above, the aptamer library was sequenced using the Ion Torrent standard protocol (Life Technologies, Carlsbad, Calif.). Lead candidates were selected as those having (a) high abundant motifs across all read sequences with full expected length product and (b) strong secondary structure (FIG. 20B).

Aptamers were selected for EPCAM protein conjugated to MicroPlex beads in competition with SSX4, SSX2, PBP, KLK2, and SPDEF recombinant proteins. A portion of the aptamers was selected in initial rounds against EpCAM that was attached to an Fc tag, and after round 8 the selection was switched to EPCAM with a Histidine tag. Another portion of the aptamers was selected in initial rounds against EpCAM that was attached to a Histidine tag, and after round 8 the selection was switched to EPCAM with an Fc tag. Methods of using Fc and histidine tags for protein purification and capture are known to those of skill in the art. A number of representative sequences obtained from these procedures are shown in Table 11. In Table 11, the sequences are shown 5' to 3' from left to right, wherein each complete sequence consists of the indicated 5' leader sequence followed by the indicated Variable Sequence followed by the indicated 3' tail sequence. Each sequence is derived from a library having a leader and tail (see Table 9) with a variable sequence between. The table indicates whether the identified sequence comprises a biotin moiety on the 5' or 3' end. It is understood that the nucleotide sequences that are disclosed in Table 11 can also be modified to the extent that resulting modifications result in an aptamer having about 50, 55, 60, 65, 70, 75, 80, 85, 90, 95, 96, 97, 98, and 99 percent homology to the disclosed sequence and retain the functionality of binding to EpCAM antigen or functional fragments thereof.

TABLE 11

EpCAM aptamer candidate sequences

| ID | SEQ ID NO. | 5'-Leader | Variable Sequence | Tail-3' |
|---|---|---|---|---|
| CAR003.2_5'-B | 230822 | Biotin-ATCCAGAGT GACGCAGCA | GTCTTTTCTGATGGAC ACGTGGTGGTCTAGT ATC | TGGACAC GGTGGCT TAGT |
| CAR003.2_3'-B | 230823 | ATCCAGAGT GACGCAGCA | GTCTTTTCTGATGGAC ACGTGGTGGTCTAGT ATC | TGGACAC GGTGGCT TAGT-Biotin |
| CAR008.2_5'-B | 230824 | Biotin-ATCCAGAGT GACGCAGCA | TCCCCCCCGATCCCC GACCATACCATGAAT GTATTATCTT | TGGACAC GGTGGCT TAGT |
| CAR008.2_3'-B | 230825 | ATCCAGAGT GACGCAGCA | TCCCCCCCGATCCCC GACCATACCATGAAT GTATTATCTT | TGGACAC GGTGGCT TAGT-Biotin |
| CAR009.2_5'-B | 230826 | Biotin-ATCCAGAGT GACGCAGCA | TAACCCGCAACCACC CATCACTGCCTGCTA CTATA | TGGACAC GGTGGCT TAGT |
| CAR009.2_3'-B | 230827 | ATCCAGAGT GACGCAGCA | TAACCCGCAACCACC CATCACTGCCTGCTA CTATA | TGGACAC GGTGGCT TAGT-Biotin |
| CAR010.2_5'-B | 230828 | Biotin-ATCCAGAGT GACGCAGCA | TGTGATGAGGGGGGT TTTCGATAGG | TGGACAC GGTGGCT TAGT |
| CAR010.2_3'-B | 230829 | ATCCAGAGT GACGCAGCA | TGTGATGAGGGGGGT TTTCGATAGG | TGGACAC GGTGGCT TAGT-Biotin |
| CAR011_5'-B | 230830 | Biotin-ATCCAGAGT GACGCAGCA | CCACCACCCGCCTAC TGCTAGTTACTTGGG TAGTT | TGGACAC GGTGGCT TAGT |
| CAR011_3'-B | 230831 | ATCCAGAGT GACGCAGCA | CCACCACCCGCCTAC TGCTAGTTACTTGGG TAGTT | TGGACAC GGTGGCT TAGT-Biotin |
| CAR012_5'-B | 230832 | Biotin-ATCCAGAGT GACGCAGCA | TTGGACCGGGGCTT GGCAATTTCGACCTA ACATC | TGGACAC GGTGGCT TAGT |
| CAR012_3'-B | 230833 | ATCCAGAGT GACGCAGCA | TTGGACCGGGGCTT GGCAATTTCGACCTA ACATC | TGGACAC GGTGGCT TAGT-Biotin |
| CAR013_5'-B | 230834 | Biotin-ATCCAGAGT GACGCAGCA | GGAGAGGGTGGCTTA GGGAGGTGCAAGAA GGTAGA | TGGACAC GGTGGCT TAGT |
| CAR013_3'-B | 230835 | ATCCAGAGT GACGCAGCA | GGAGAGGGTGGCTTA GGGAGGTGCAAGAA GGTAGA | TGGACAC GGTGGCT TAGT-Biotin |
| CAR014_5'-B | 230836 | Biotin-ATCCAGAGT GACGCAGCA | CATGCGGCATTCTGA GTCTGGTGCGACTTT CTGGT | TGGACAC GGTGGCT TAGT |
| CAR014_3'-B | 230837 | ATCCAGAGT GACGCAGCA | CATGCGGCATTCTGA GTCTGGTGCGACTTT CTGGT | TGGACAC GGTGGCT TAGT-Biotin |

TABLE 11-continued

EpCAM aptamer candidate sequences

| ID | SEQ ID NO. | 5'-Leader | Variable Sequence | Tail-3' |
|---|---|---|---|---|
| CAR015_ 5'-B | 230838 | Biotin-ATCCAGAGT GACGCAGCA | GATGAATTTGTATTT GGACGCGGTGGTGGT AATCA | TGGACAC GGTGGCT TAGT |
| CAR015_ 3'-B | 230839 | ATCCAGAGT GACGCAGCA | GATGAATTTGTATTT GGACGCGGTGGTGGT AATCA | TGGACAC GGTGGCT TAGT-Biotin |
| CAR016 | 230840 | Biotin-ACTAAGCCA CCGTGTCCA | ACGTAAGTATATCTG TACAA | TGCTGCG TCACTCT GGAT |
| CAR017 | 230841 | Biotin-ACTAAGCCA CCGTGTCCA | AACATCAGCTTTTAT CTTAA | TGCTGCG TCACTCT GGAT |
| CAR018 | 230842 | Biotin-ACTAAGCCA CCGTGTCCA | TGTTATAACCTACCA TTAAA | TGCTGCG TCACTCT GGAT |
| CAR019 | 230843 | Biotin-ACTAAGCCA CCGTGTCCA | ACCGTATGGTTATGT GCTCA | TGCTGCG TCACTCT GGAT |
| CAR020 | 230844 | Biotin-ACTAAGCCA CCGTGTCCA | CCATACGTCACACTT CTTTA | TGCTGCG TCACTCT GGAT |
| CAR021 | 230845 | Biotin-ACTAAGCCA CCGTGTCCA | GGTCCATCTCCTTAC ATTTT | TGCTGCG TCACTCT GGAT |
| CAR022 | 230846 | Biotin-ACTAAGCCA CCGTGTCCA | CTATGTACCAACTAT TTATA | TGCTGCG TCACTCT GGAT |

Additional aptamer candidates were chosen on the initial clonal screening and further validated on both Fc-EpCam and Histag Epcam target by titration of the aptamer and target EpCAM protein. A number of representative sequences obtained from these procedures are shown in Table 12. CAR027 and CAR028 were initially identified against Fc-EpCam target whereas CAR029 and CAR030 were initially identified against the Histag EpCam target. In Table 12, the sequences are shown 5' to 3' from left to right, wherein each complete sequence consists of the indicated 5' leader sequence followed by the indicated Variable Sequence followed by the indicated 3' tail sequence. Each sequence is derived from a library having a leader and tail (see Table 9) with a variable sequence between. The table indicates whether the identified sequence comprises a biotin moiety on the 5' or 3' end. Table 13 presents modified aptamer candidates based on the full sequences in Table 12. Rational for the modifications is listed in the table. The sequences are shortened to the extent that they retain the expected secondary structure. It is understood that the nucleotide sequences that are disclosed in Tables 12 and 13 can be modified to the extent that resulting modifications result in an aptamer having about 50, 55, 60, 65, 70, 75, 80, 85, 90, 95, 96, 97, 98, and 99 percent homology to the disclosed sequence and retain the functionality of binding to EpCAM antigen or fragments thereof.

TABLE 12

Additional EpCAM aptamer candidate sequences

| ID | SEQ ID NO. | 5'-Leader | Variable Sequence | Tail-3' |
|---|---|---|---|---|
| CAR027 | 230904 | Biotin-ACTAAGCCA CCGTGTCCA | GTGTCCCCTCCTATA GCTGC | TGCTGCGTC ACTCTGGAT |
| CAR028 | 230905 | Biotin-ACTAAGCCA CCGTGTCCA | GCGTTCCCCTACTATT TAAC | TGCTGCGTC ACTCTGGAT |
| CAR029 | 230906 | Biotin-ACTAAGCCA CCGTGTCCA | TCCTGGTTATACTCCC CTTC | TGCTGCGTC ACTCTGGAT |
| CAR030 | 230907 | Biotin-ACTAAGCCA CCGTGTCCA | TATCGCTGTTTCCTGT TATC | TGCTGCGTC ACTCTGGAT |

TABLE 13

EpCAM aptamer optimization

| ID | SEQ ID NO. | 5'-Sequence-3' | Rational |
|---|---|---|---|
| CAR032 | 230909 | Biotin-TATCGCTGTTTCCT GTTATCTGCTGCG | Shorten the CAR030 sequence according to the secondary structure |
| CAR033 | 230910 | Biotin-TCCAGTGTCCCCTC CTATAGCTGCTGCT GCGTCACTCTGG | Shorten the CAR029 sequence according to the secondary structure |
| CAR034 | 230911 | Biotin-CCAGCGTTCCCCTA CTATTTAACTGCTG | shorten the CAR028 sequence according to the secondary structure |

Aptamer Development

As an RNA aptamer, CAR003 with alternate tail sequence has the following RNA sequence (SEQ ID NO. 230847):

5'-auccagagug acgcagcagu cuuuucugau ggacacgugg uggucuagua ucacuaagcc accgugucca-3'

CAR003 (CAR003.2_5'-B, CAR003.2_3'-B) was further characterized. EpCAM aptamer CAR003 is modified as desired on the 3' end by attachment of a biotin moiety (CAR003.2_3'-B). The biotin can be used to bind the aptamer using a streptavidin-biotin system, e.g., for labeling, capture and/or anchoring. FIG. 20B illustrates the optimal secondary structure of CAR003 with a minimum free energy (ΔG) of −30.00 kcal/mol. In the illustration, the aptamer is shown as an RNA aptamer (SEQ ID NO. 230847) corresponding to the CAR003 DNA sequence (SEQ ID NOs. 230822-230823).

Synthesis and Purification.

The selected CAR003 aptamer was re-synthesized using AKTA OligoPilot 100 Synthesizer (GE Healthcare Life Sciences Corp., Piscataway, N.J.) with a 3'Biotin and final detritylation. The product was purified with anion exchange chromatography by FPLC. Several fractions after FPLC were combined as shown as the indicated Pools 1-3 in FIG.

Figure 20C:
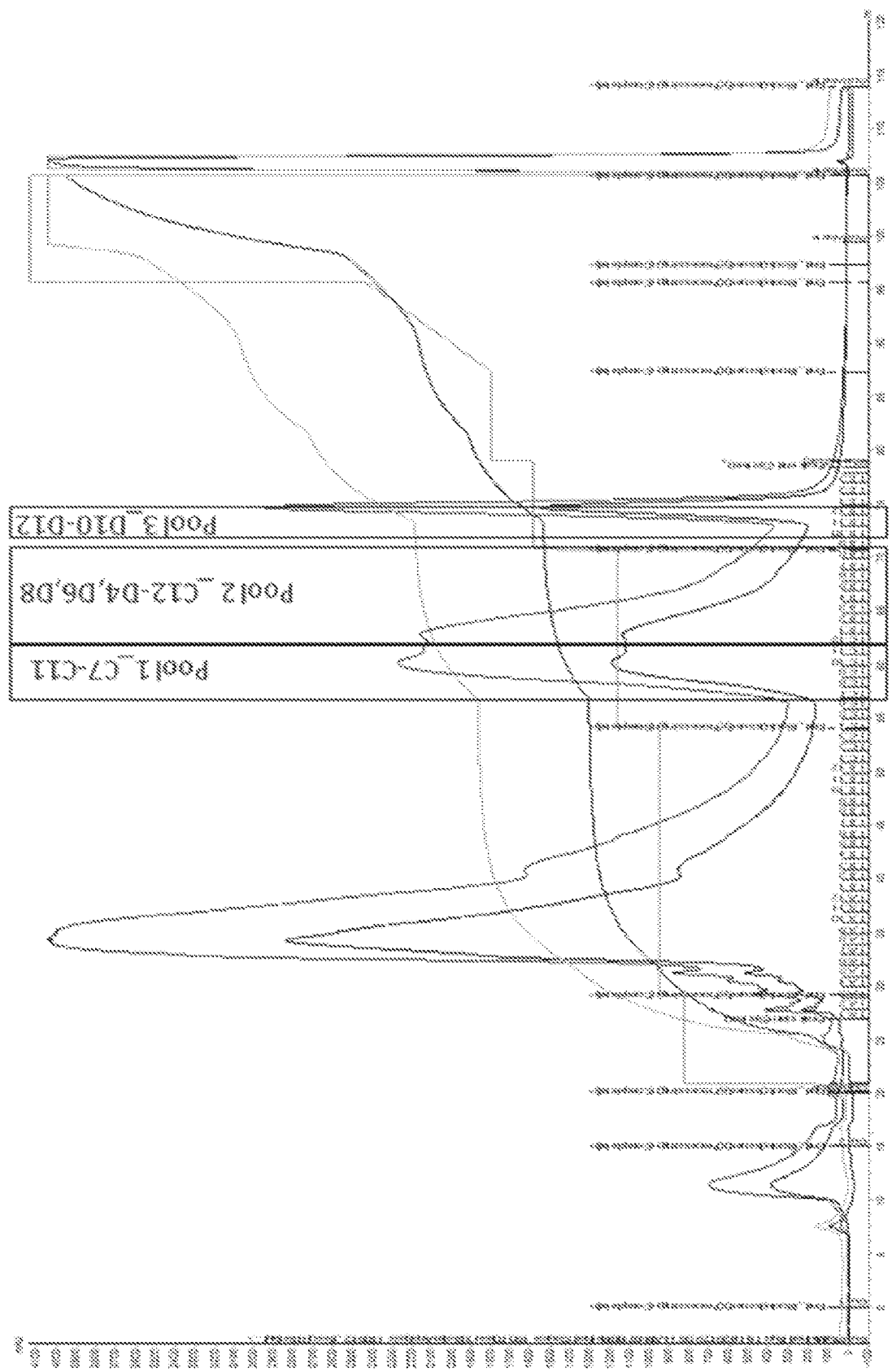
FIG. 20C illustrates aptamer pool purification. The figure comprises an FPLC chromatogram with all product and fractions assigned in pools after checking quality on gel.
Figure 20D:
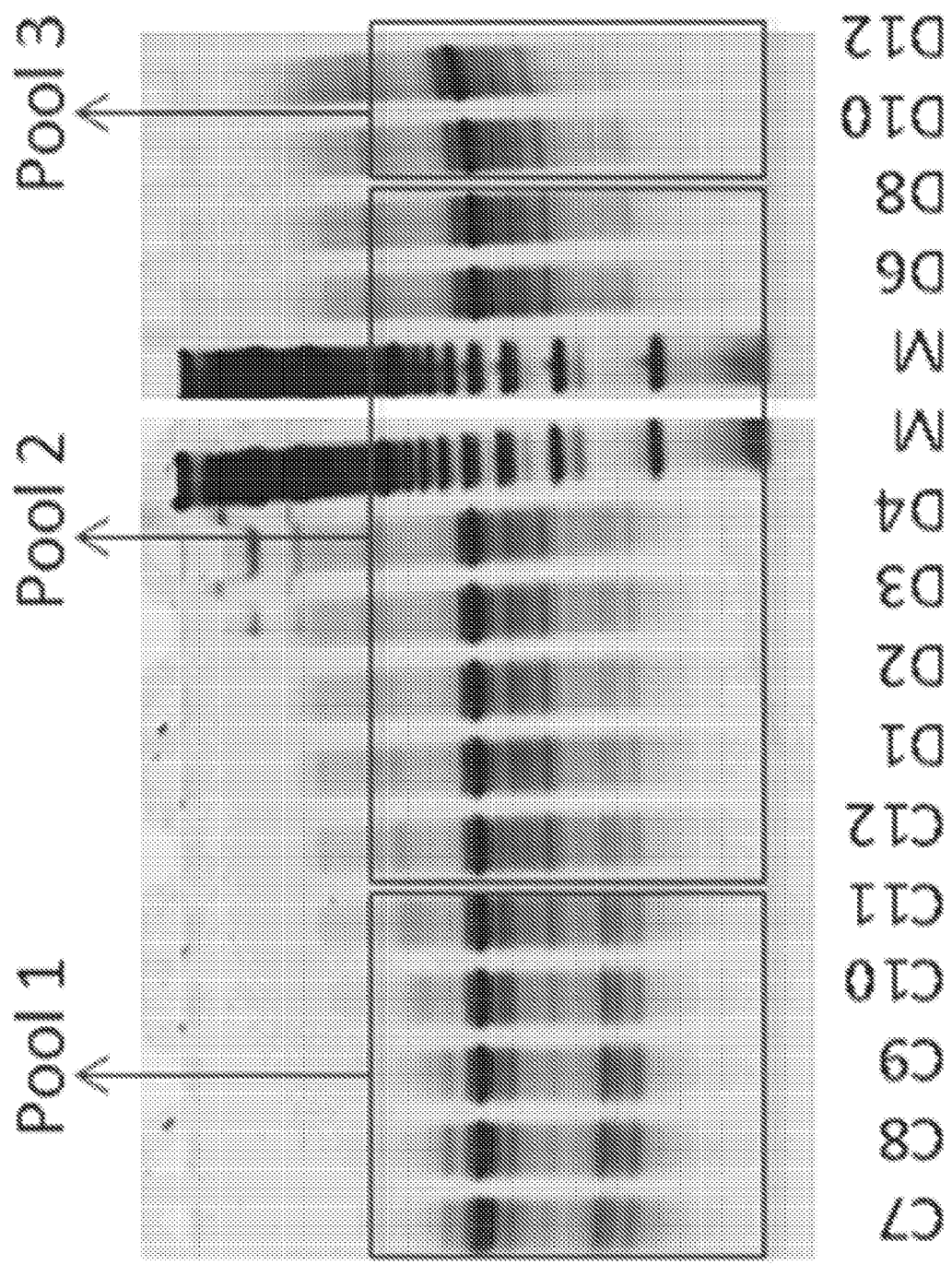
FIG. 20D illustrates a SYBR GOLD stained gel with different FPLC fractions of CAR003 aptamer after synthesis. Different fractions were combined in pools based on amount of un-finished chains in order high to low (pool 1-pool 3). The pools 1-3 correspond to those indicated in FIG. 20C.

20C. The figure comprises an FPLC chromatogram with all product and fractions assigned in pools after checking quality on gel. FIG. 20D illustrates a SYBR GOLD stained gel with different FPLC fractions of CAR003 aptamer after synthesis. Different fractions were combined in pools based on amount of unfinished chains in order high to low (pool 1-pool 3). The pools 1-3 correspond to those indicated in FIG. 20C.

CAR003 Aptamer Characterization.

Figure 20E:
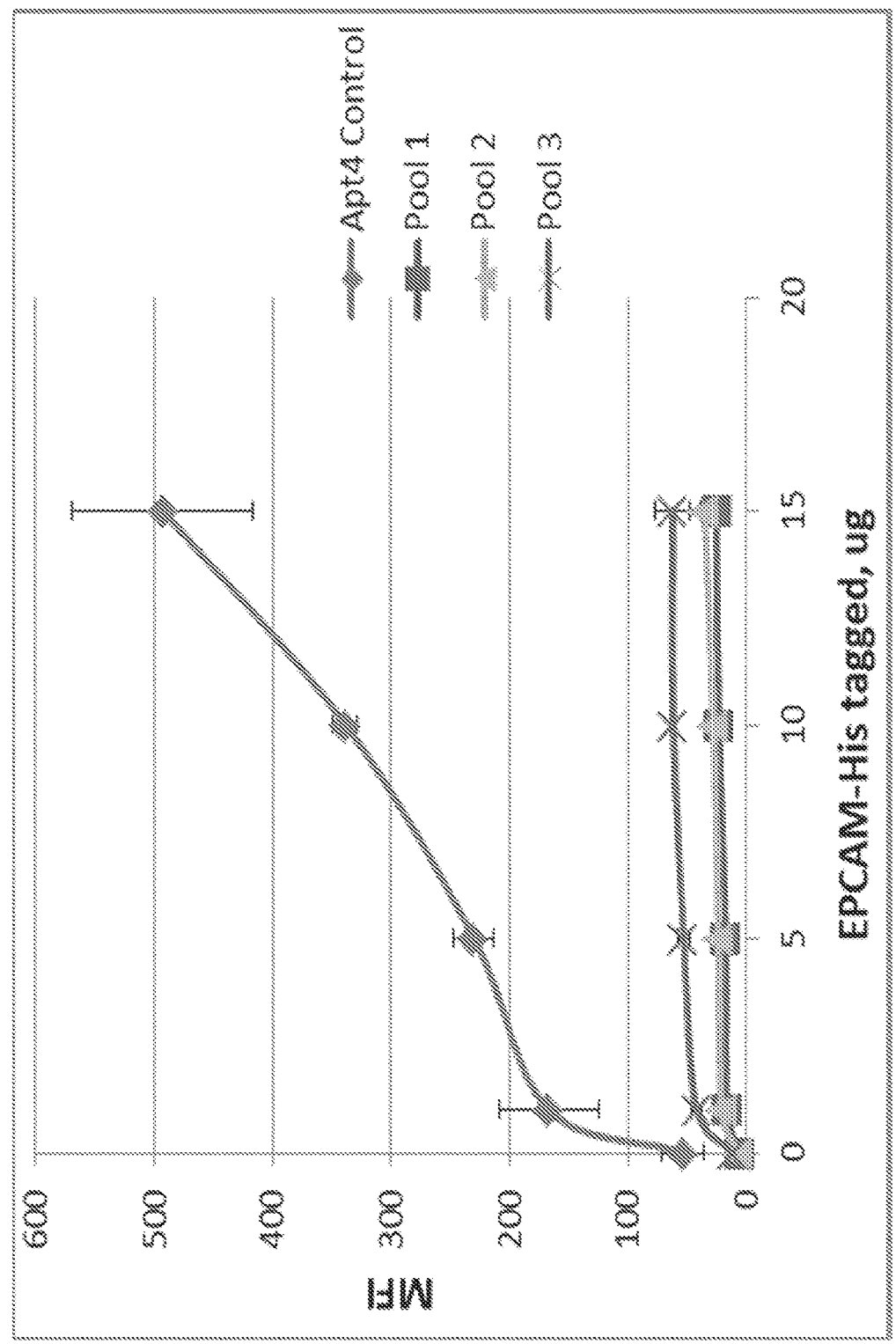
FIGS. 20E-F illustrate binding of CAR003 to EPCAM protein in 25 mM HEPES with PBS-BN (FIG. 20E) or in 25 mM HEPES with 1 mM $MgCl_2$ (FIG. 20F).
Figure 20F:
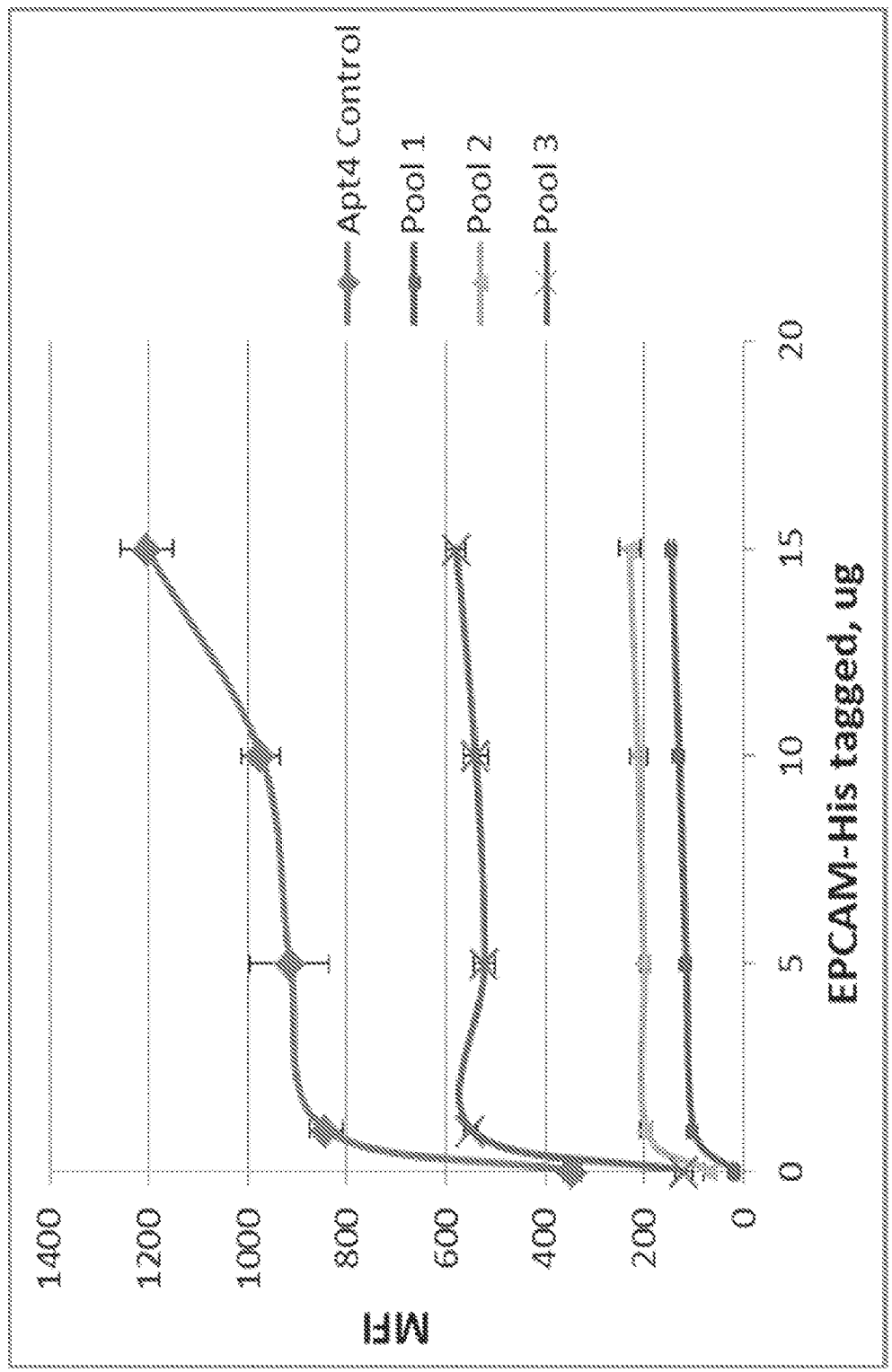

Purified CAR003 aptamer was tested for binding to recombinant EPCAM protein with a polyhistidine tag ("His tagged") using the following internally developed assay. Anti-His tag conjugated beads were mixed with EPCAM-His tagged protein. The aptamer to be tested was labeled with streptavidin-phycoerythrin (SA-PE). The EpCAM-beads and SA-PE labeled aptamers were mixed. Binding was determined as median flourescent value in a bead assay as described herein. MFI values (FIG. 20E-F) increase with increased binding of the SA-PE labeled aptamer to the recombinant EpCAM. FIGS. 20E-F illustrate binding of CAR003 to EPCAM protein in 25 mM HEPES with PBS-BN (PBS, 1% BSA, 0.05% Azide, pH 7.4) (FIG. 20E) or in 25 mM HEPES with 1 mM $MgCl_2$ (FIG. 20F). EPCAM aptamer Aptamer 4 (see above) was used for comparison. As shown in the figures, CAR003 pool 3 more efficiently binds its target in the presence of $MgCl_2$ (FIG. 20F) than in the presence of BSA (FIG. 20E).

Figure 20G:
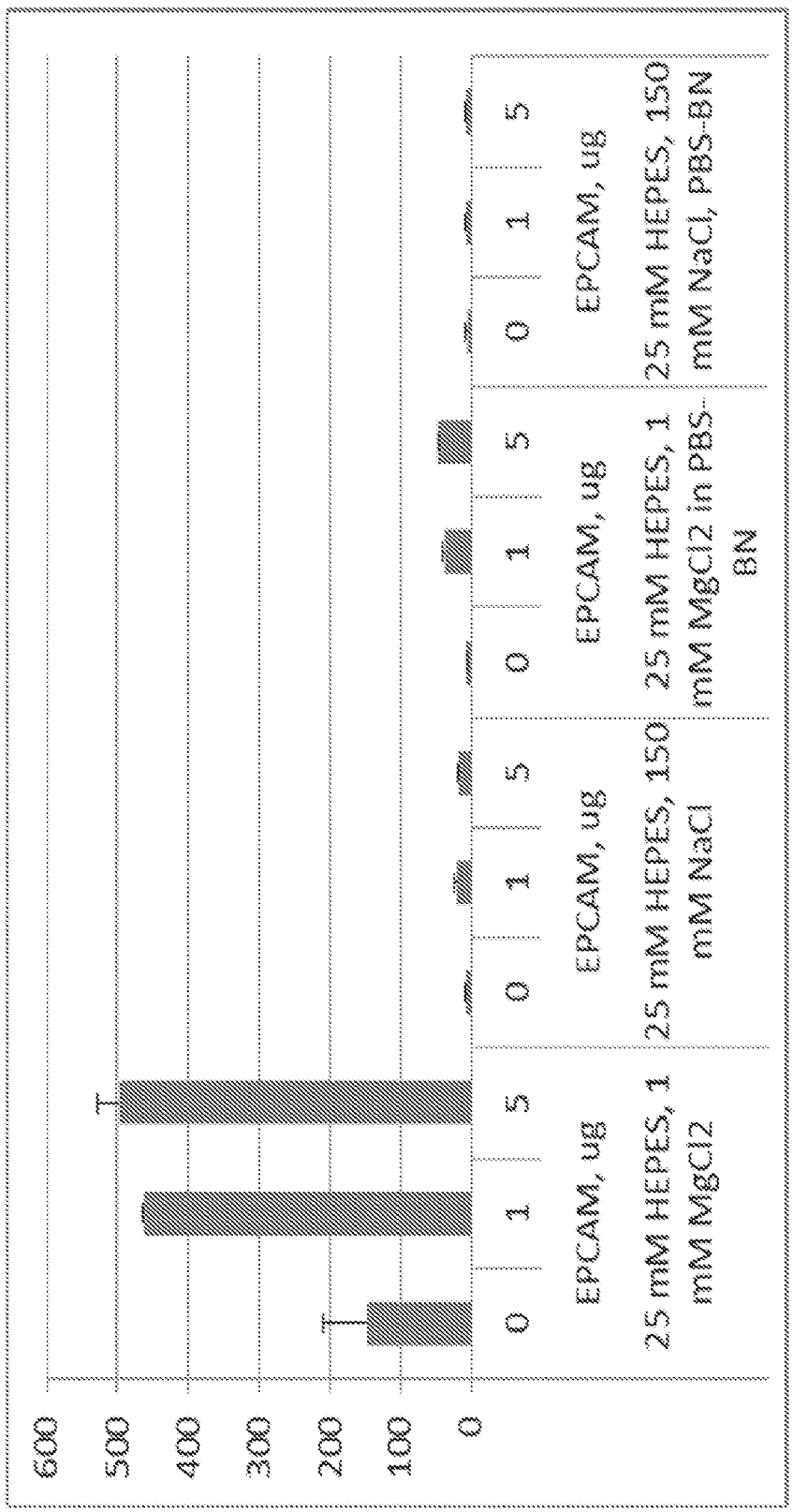
FIG. 20G illustrates CAR003 binding to EpCAM in the indicated salts with and without addition of bovine serum albumin (BSA).

To understand its performance further, CAR003 binding was tested in the presence of both BSA and $MgCl_2$ in various buffers. FIG. 20G illustrates CAR003 binding to EpCAM in the indicated salts with and without addition of bovine serum albumin (BSA). Again, CAR003 binding to EpCAM is more efficient when BSA is not present. Additionally, 150 mM NaCl was tested but did not appear to improve CAR003 performance over $MgCl_2$.

Figure 20H:
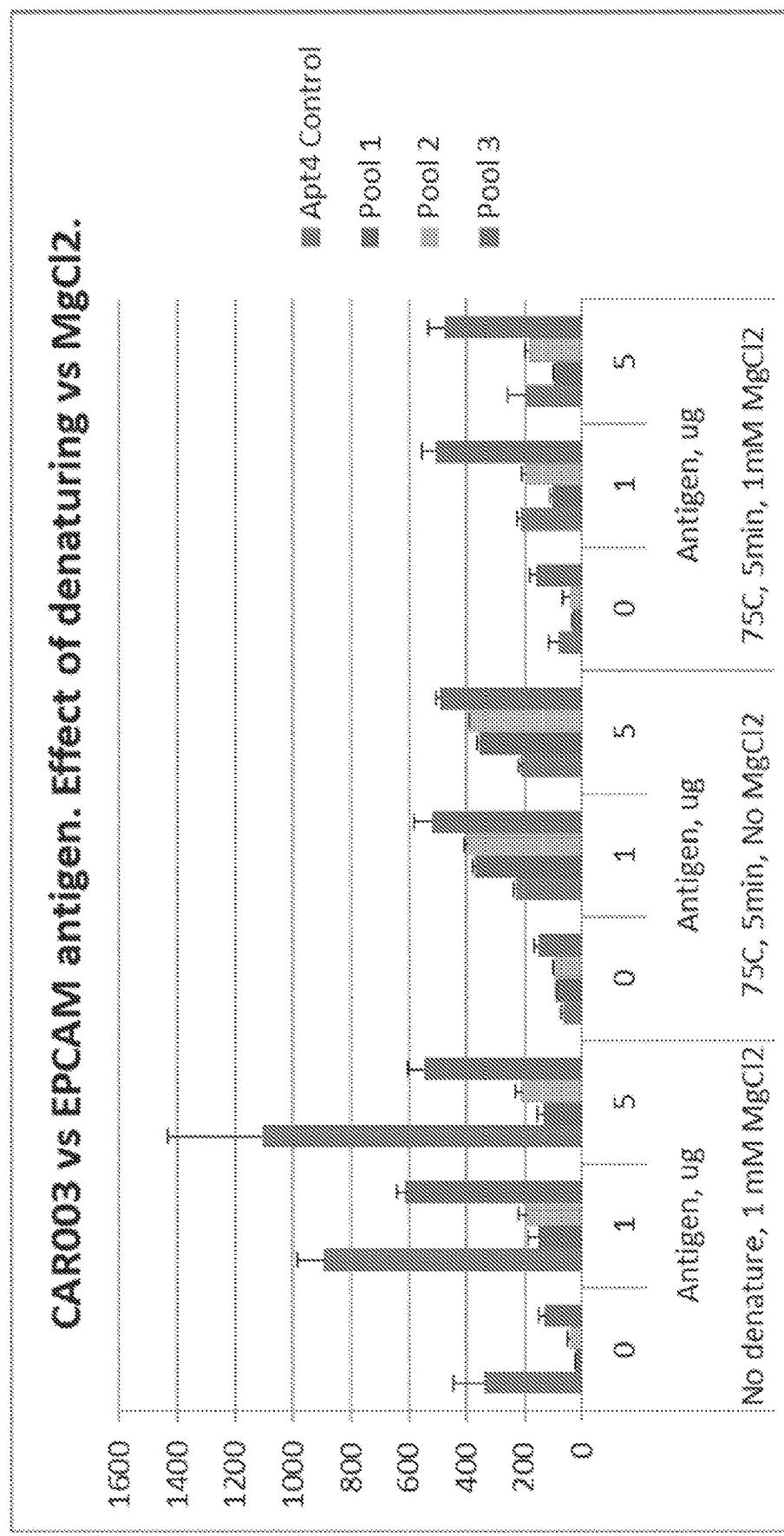
FIG. 20H illustrates the effect of denaturing on CAR003 binding to EPCAM protein. In each group of four bars, the aptamer is from left to right: Aptamer 4, CAR003 Pool 1, CAR003 Pool 2, CAR003 Pool 3.

Another factor which might influence performance of aptamer is denaturing with different salt compositions. FIG. 20H illustrates the effect of denaturing on CAR003 binding to EPCAM protein. As seen from the chart, denaturing of the aptamer has a positive effect on CAR003 binding to EpCAM similar as the effect on CAR003 from $MgCl_2$. However, denaturing in the presence of $MgCl_2$ may not synergistically improve binding of CAR003 to EpCAM. Interestingly, CAR003 appeared more stable compared to control Aptamer 4 in the conditions tested.

Figure 20I:
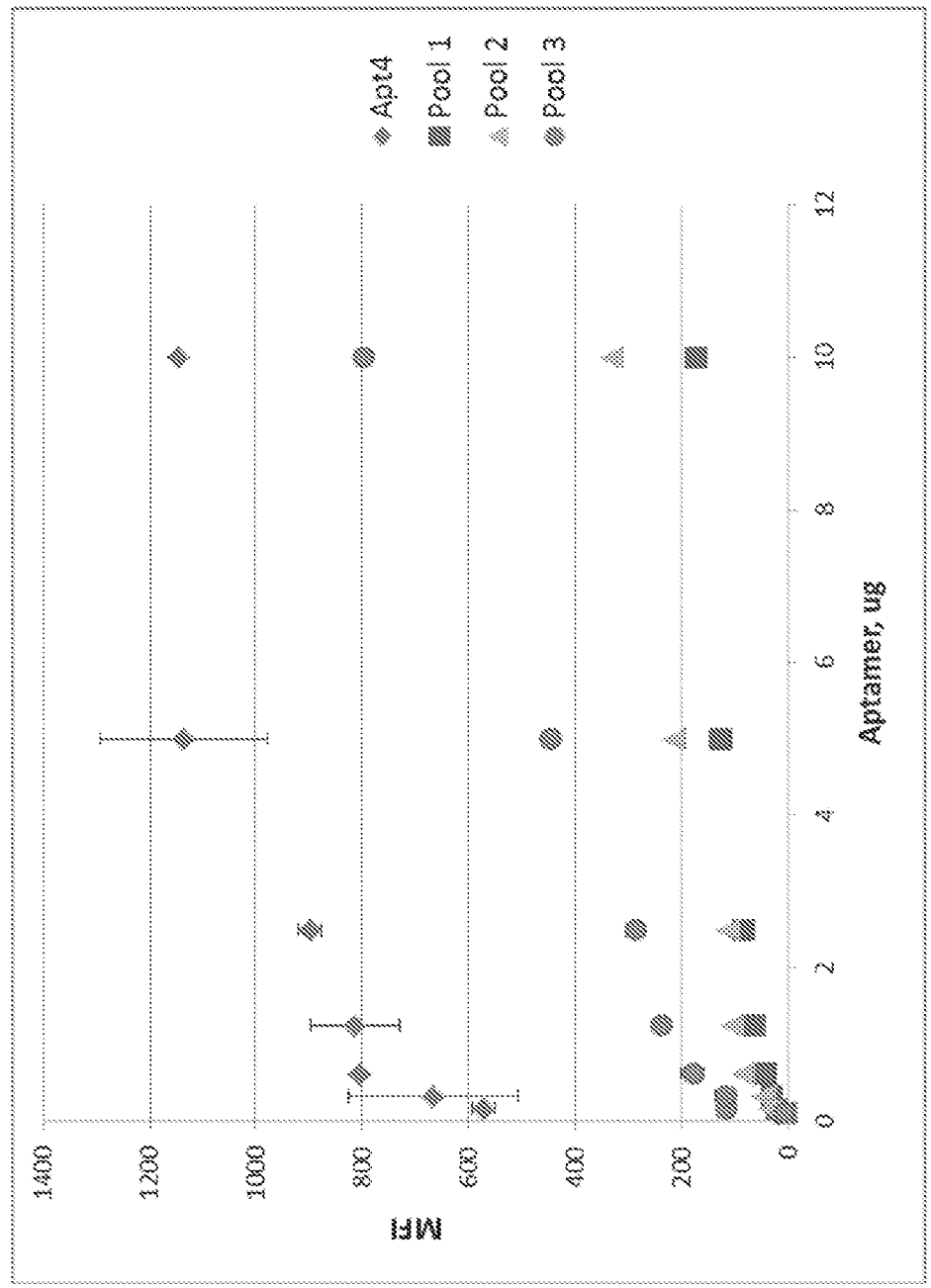
FIG. 20I illustrates titration of aptamers against EPCAM recombinant protein (constant input 5 µg).

CAR003 affinity to EpCAM in the bead assay environment was assessed in the same assay as above with aptamer titrated across a constant input of antigen. FIG. 20I illustrates titration of aptamers against EPCAM recombinant protein (constant input 5 μg). Under the conditions tested, Aptamer 4 had a higher affinity to EPCAM protein compared to CAR003 as suggested from saturation level starting at 5 μg of aptamer input.

Figure 20J:
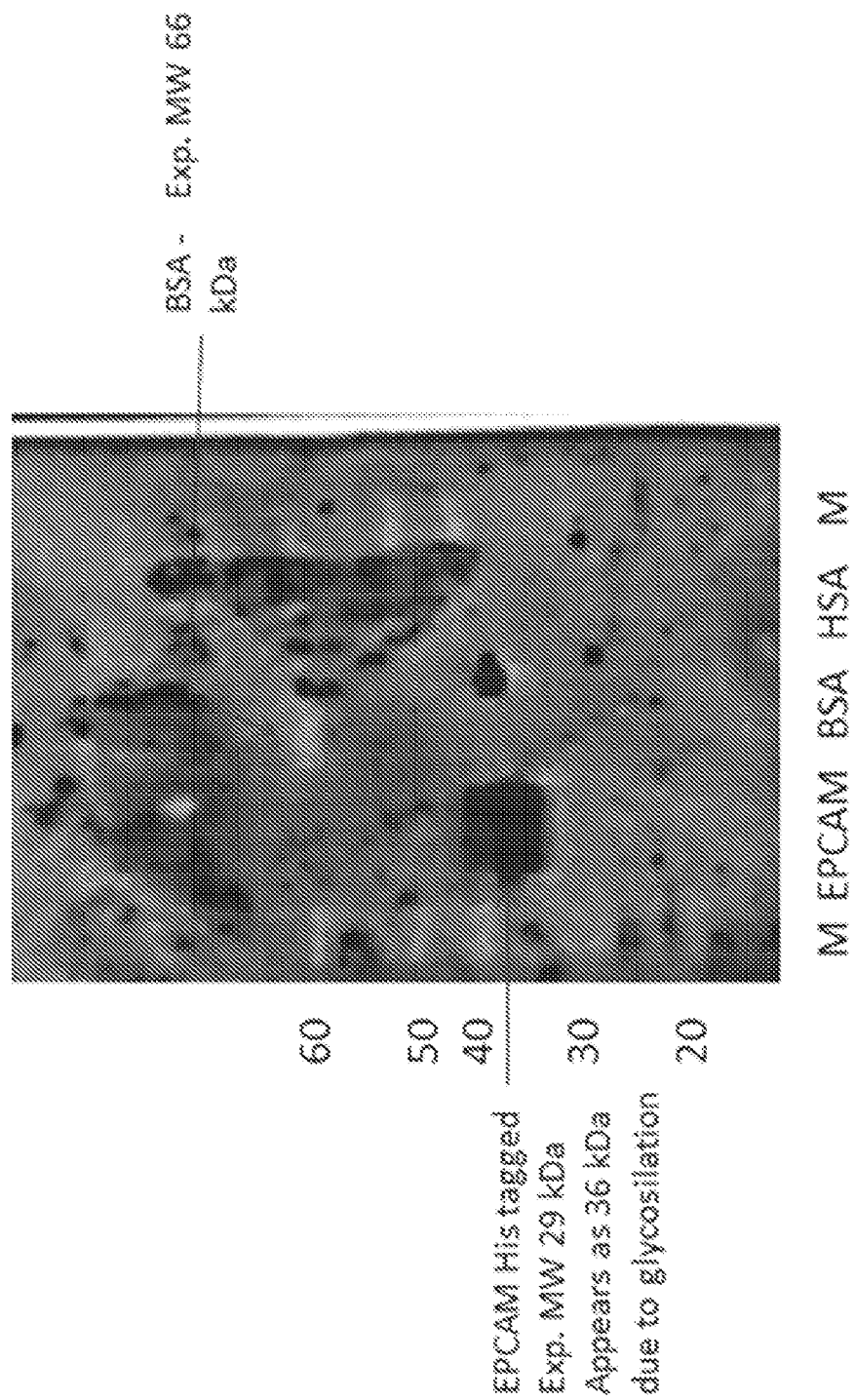
FIG. 20J illustrates a Western blot with CAR003 aptamer versus EPCAM his-tagged protein, BSA, and HSA (5 µg each). The gel was blocked 0.5% F127 and probed with ~50 µg/ml CAR003 biotinylated aptamer, fraction 3. The blot was visualized with NeutrAvidin-HRP followed by SuperSignal West Femto Chemiluminescent Substrate.
Figure 21A:
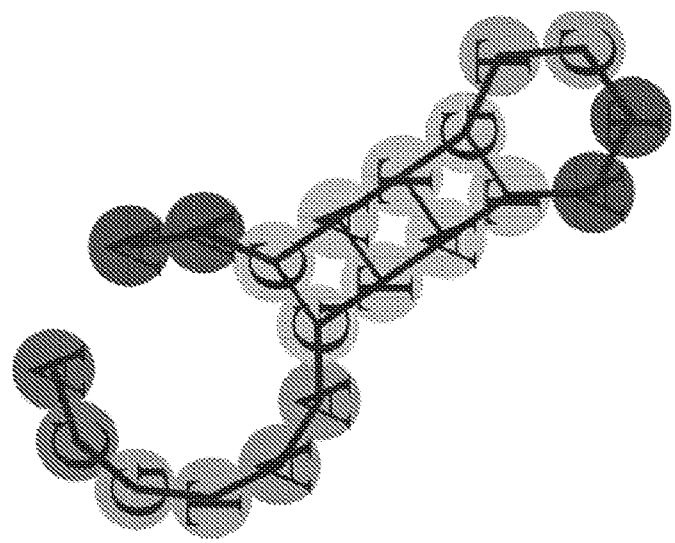
FIGS. 21A-21J show predicted secondary structure of CAR016 (SEQ ID NO. 230840) and indicated variants thereof.
Figure 21B:
Figure 21C:
Figure 21D:
Figure 21E:
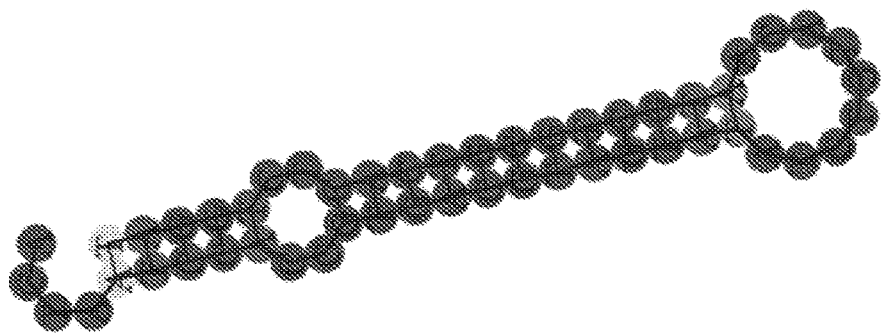
Figure 21F:
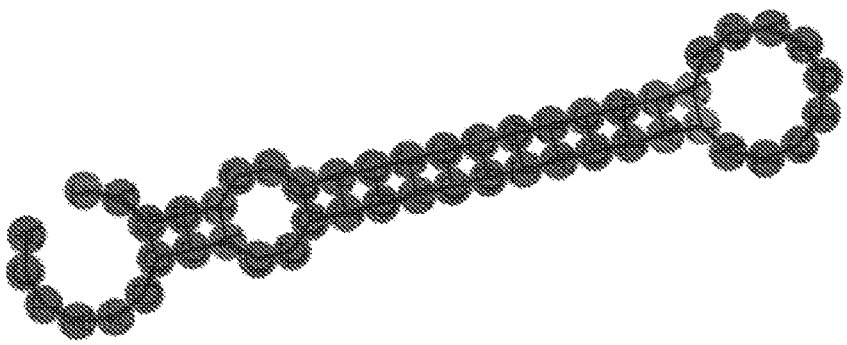
Figure 21G:
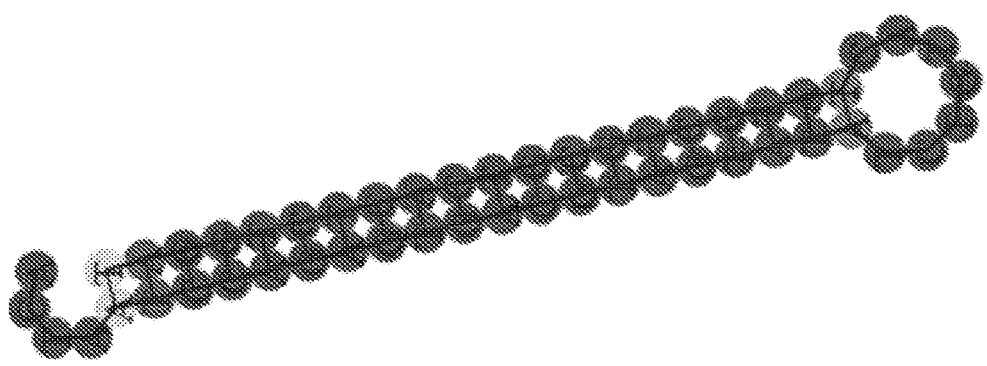
Figure 21H:
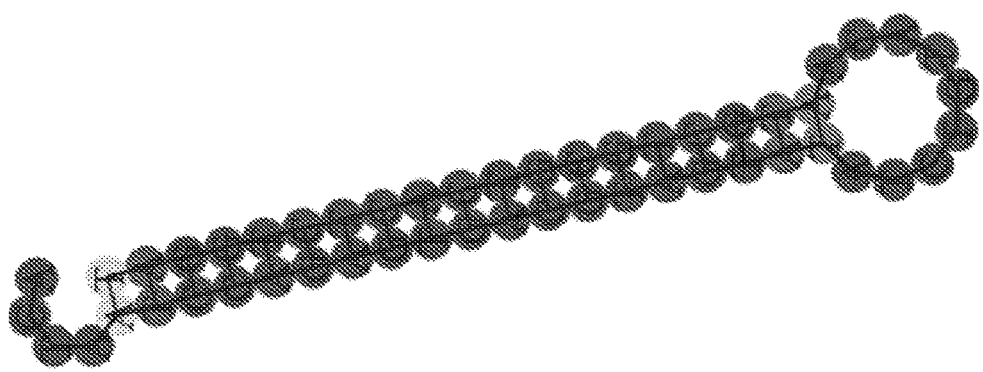
Figure 21I:
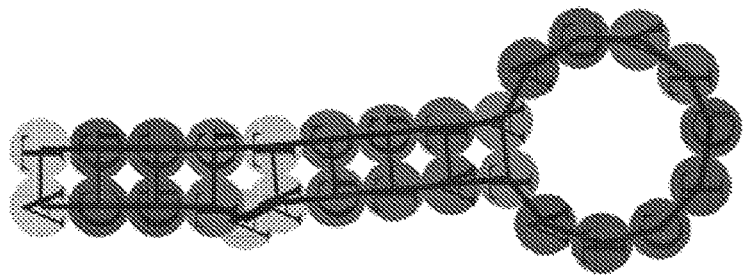
Figure 21J:
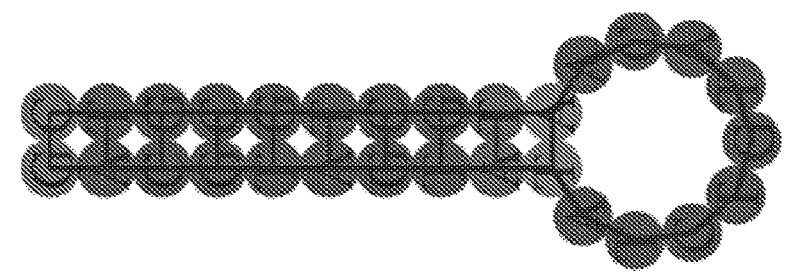

In order to evaluate specificity of CAR003, it was tested using Western Blot against EPCAM recombinant protein, and controls comprising bovine serum albumin (BSA) and human serum albumin (HSA). FIG. 20J illustrates a Western blot with CAR003 aptamer versus EPCAM his-tagged protein, BSA, and HSA (5 μg each). The gel was blocked 0.5% F127 and probed with ~50 μg/ml CAR003 biotinylated aptamer, fraction 3. The blot was visualized with NeutrAvidin-HRP followed by SuperSignal West Femto Chemiluminescent Substrate. The Western blot probed with CAR003 aptamer showed a clear preference of the aptamer to EPCAM protein over the albumins.

CAR003 Test with Plasma Samples.

Plasma samples from five prostate cancer and five normal subjects were tested with CAR003 to detect microvesicles using bead-conjugated proteins to capture the microvesicles and SA-PE labeled aptamer to detect the vesicles as described in Example 8. SA-PE labeled Aptamer 4 detector was used as control. Fold changes of Cancer over Normal are shown in Table 14. The fold changes are shown without normalization ("Raw") or with normalization to a negative control. The vesicles were captured with bead conjugated antibodies to SSX4, PBP, SPDEF, EPCAM, KLK2 and SSX2 as indicated.

TABLE 14

| | CAR003 to detect microvesicles | | | | | | |
|---|---|---|---|---|---|---|---|
| | | SSX4 | PBP | SPDEF | EPCAM | KLK2 | SSX2 |
| Raw | Standard protocol | 0.87 | 0.39 | 0.71 | 0.63 | 0.93 | 0.87 |
| | Incubation in presence of 1 mM MgCl2 and absence of PBS-BN | 0.77 | 0.39 | 0.69 | 0.6 | 0.91 | 0.81 |
| | Aptamer 4 control (standard protocol) | 0.78 | 0.67 | 0.81 | 0.72 | 1.19 | 0.79 |
| Normalized to Negative control | Standard protocol | 1.49 | 0.84 | 1.13 | 1.17 | 1.5 | 1.38 |
| | Incubation in presence of 1 mM MgCl2 and absence of PBS-BN | 1.27 | 0.83 | 1.08 | 1.1 | 1.46 | 1.29 |
| | Aptamer 4 control (standard protocol) | 1.18 | 0.96 | 1.11 | 1.04 | 1.82 | 1.1 |

Under the conditions tested, the samples detected with CAR003 had lower MFI values as compared to detection with Aptamer 4, whereas CAR003 had a better signal-to-noise ratio and showed better separation between cancer and normal samples with SSX4, SPDEF, EPCAM and SSX2 capturing markers.

Control Aptamer

The characteristics of the aptamers (size, stability, binding affinity and specificity, etc) can be compared against control aptamers specific to EpCAM or other targets. For example, the aptamers are compared to the anti-VEGF aptamer 5' biotin-CA ATT GGG CCC GTC CGT ATG GTG GGT (SEQ. ID NO. 230912) as described in Kaur and Yung, 2012.

REFERENCES

1. Müller, J., et al. "Selection of high affinity DNA-aptamer for activated protein C using capillary electrophoresis." *Research in Pharmaceutical Sciences* 7.5 (2012): S987.
2. Cerchia, L. and V. de Franciscis. "Nucleic Acid Aptamers Against Protein Kinases" *Current medicinal chemistry* 18.27 (2011): 4152-4158.
3. Wu, Jie, et al. "Identification Characterization and Application of a G-Quadruplex Structured DNA Aptamer against Cancer Biomarker Protein Anterior Gradient Homolog 2." *PloS ONE* 7.9 (2012): e46393
4. Mitkevich, Olga V., et al. "DNA aptarners detecting, generic amyloid epitopes." *Prion* 6.4 (2012): 400-406.
5. Kaur Yung L-YL (2012) Probing High Affinity Sequences of DNA Aptamer against $VEGF_{165}$. PLoS ONE 7(2): e31196. doi:10.1371/journal.pone.0031196.

Example 12: Optimization of Anti-EpCAM Aptamers

This Example demonstrates optimization of aptamer CAR016 (SEQ ID NO. 230840), which is presented above. CAR016 was the most prevalent aptamer identified in several rounds of EpCAM aptamer selection as described above (see Example 9). Its variable sequence as shown above and sequences with common motifs represented over 50% of the selected aptamer pools. Table 15 shows the most common CAR016-related variants from two independent sequencing runs (Seq Run 1 and 2) using an Ion Torrent platform after 9 rounds of selection.

TABLE 15

EpCAM aptamer screening representative sequences

| ID | SEQ ID NO. | Variable Region 5'->3' | # Occurrences Seq Run 1 | # Occurrences Seq Run 2 |
|---|---|---|---|---|
| CAR016_VAR1 | 230848 | ACGTAAGTATATCTGTACAA | 92084 | 64506 |
| CAR016_VAR2 | 230849 | ACCGTATGGTTATGTGCTCA | 11104 | 8023 |
| CAR016_VAR3 | 230850 | ACGTAAGTATATCTGCACAA | 16 | 10 |
| CAR016_VAR4 | 230851 | ACCGTATGTTTATGTGCTCA | 14 | 4 |
| CAR016_VAR5 | 230852 | ACGTAAGTATATCTGTACAG | 12 | 11 |
| CAR016_VAR6 | 230853 | ACCGTAAGTATATCTGTACA | 10 | 8 |
| CAR016_VAR7 | 230854 | CCGTAAGTATATCTGTACAA | 8 | 0 |
| CAR016_VAR8 | 230855 | ACGTAAGTATATCTGTACAC | 7 | 0 |
| CAR016_VAR9 | 230856 | ATCGTAAGTATATCTGTACA | 5 | 3 |
| CAR016_VAR10 | 230857 | ACGTATGTATATCTGTACAA | 4 | 1 |
| CAR016_VAR11 | 230858 | ACGTAAGTATATGTGTACAA | 4 | 1 |
| CAR016_VAR12 | 230859 | AACGTAAGTATATCTGTACA | 4 | 9 |
| CAR016_VAR13 | 230860 | GCGTAAGTATATCTGTACAA | 3 | 1 |
| CAR016_VAR14 | 230861 | TCGTAAGTATATCTGTACAA | 2 | 1 |
| CAR016_VAR15 | 230862 | ACGTAAGTATATCTGTACAT | 2 | 9 |
| CAR016_VAR16 | 230863 | ACGTATGGTTATGTGCTCAA | 1 | 0 |
| CAR016_VAR17 | 230864 | ACGTAAGTATATCTGTTCAA | 1 | 1 |
| CAR016_VAR18 | 230865 | ACCGTATGGTTATCTGCTCA | 1 | 0 |
| CAR016_VAR19 | 230866 | AACGTATGGTTATGTGCTCA | 1 | 0 |
| CAR016_VAR20 | 230867 | GCCGTATGGTTATGTGCTCA | 0 | 2 |
| CAR016_VAR21 | 230868 | ACCGTATGGTTATGTGTTCA | 0 | 2 |
| CAR016_VAR22 | 230869 | ACGTAAGTATATCTGTTCAA | 0 | 1 |

Together, the sequences in Table 15 can be represented by the following sequence, where [AT] specifies that either an adenine (A) or thymine (T) is present: 5'-CGTA[AT]G[TG][AT]TAT[CG]TG[TC][AT]CA (ID CAR016_CAN; SEQ ID NO. 230870).

Testing via ELISA demonstrated that CAR016 bound to EpCAM-Fc in standard ELISA plates and to EPCAM-His tagged protein in Nickel coated ELISA plates. In microbead binding assays with microvesicle coated microbeads, CAR016 had the highest mean fluorescence values between all tested aptamer candidates, including Aptamer 4. Thus, a variety of variants of CAR016 were made to test for enhanced performance. The sequence variants are shown in Table 16 and the rational behind each variant is described in Table 17. "n/a" in Table 16 indicates that the section of the aptamer is not present. Underlined nucleotides in Table 16 indicate modified nucleotides as compared to CAR016. See Table 17 for further description. Certain mutations are made to examine the effects of aptamer stability as estimated by $\Delta G$ calculations. The estimated stability of CAR016 is $\Delta G=-10.89$ kcal/mol. Lower $\Delta G$ indicates greater estimated stability. See in particular CAR016_M23 to CAR016_M27.

TABLE 16

EpCAM aptamer CAR016 mutant sequences

| ID | SEQ ID NO. | 5'-Leader | Variable Sequence Tail-3' |
|---|---|---|---|
| CAR016_M1 | 230871 | Biotin-ACTAAGCCACCGTGTATATCTGT CCA | AC<u>AC</u>AAGT TGCTGCGTCAC TCTGGAT ACAA |
| CAR016_M2 | 230872 | Biotin-ACTAAGCCACCGTGTATATCTGT CCA | ACGTAA<u>A</u>T TGCTGCGTCAC TCTGGAT ACAA |
| CAR016_M3 | 230873 | Biotin-ACTAAGCCACCGTGTA<u>GCG</u>CTGT CCA | ACGTAAGT TGCTGCGTCAC TCTGGAT ACAA |
| CAR016_M4 | 230874 | Biotin-ACTAAGCCACCGTGTATATC<u>C</u>AT CCA | ACGTAAGT TGCTGCGTCAC TCTGGAT ACAA |
| CAR016_M5 | 230875 | Biotin-ACTAAGCCACCGTGTATATCTGT CCA | ACGTAAGT TGCTGCGTCAC TCTGGAT AT<u>C</u>A |
| CAR016_M6 | 230876 | Biotin-ACTAAGCCACCGTGTA<u>GCG</u>C<u>C</u>AT CCA | AC<u>AC</u>AAT TGCTGCGTCAC TCTGGAT AT<u>C</u>A |
| CAR016_M7 | 230877 | Biotin-ACTAAGCCACCGTGTATATCTGT CCA | ACGTAAGT n/a ACAA |
| CAR016_M8 | 230878 | Biotin-ACTAAGCCACCGTGT<u>GT</u>CTTCTA CCA | AAAAAAGG TGCTGCGTCAC CGGT |
| CAR016_M9 | 230879 | Biotin-ACTAAGCCACCGTGTATATCTGT CCA | ACGTA<u>C</u>GT TGCTGCGTCAC ACAA |
| CAR016_M10 | 230880 | Biotin-ACTAAGCCACCGTGT<u>C</u>TATCTGT CCA | ACGTAAG<u>A</u> TGCTGCGTCAC ACAA |
| CAR016_M11 | 230881 | Biotin-ACTAAGCCACCGTGTATAT<u>A</u>TGT CCA | ACGTAAGT TGCTGCGTCAC TCTGGAT ACAA |
| CAR016_M12 | 230882 | Biotin-ACTAAGCCACCGTGTATATCTG<u>G</u> <u>C</u>CAA | ACGTAAGT TGCTGCGTCAC TCTGGAT |
| CAR016_M13 | 230883 | n/a | Biotin- n/a ACGTAAGT ATATCTGT ACAA |
| CAR016_M14 | 230884 | Biotin-CCGTGTCCA | ACGTAAGT TGCTGCGTC ATATCTGT ACAA |
| CAR016_M15 | 230885 | ACTAAGCCACCGTGTACGTAAGT TGCTGCGTCAC CCA | ATATCTGT TCTGGA- ACAA    Biotin |
| CAR016_M16 | 230886 | n/a | Biotin- TGCTGCGTCAC ACGTAAGT TCTGGAT ATATCTGT ACAA |
| CAR016_M17 | 230887 | n/a | ACGTAAGT TGCTGCGTCAC ATATCTGT TCTGGAT- ACAA    Biotin |
| CAR016_M18 | 230888 | Biotin-AC(dT-Biotin) AAGCCACCGTGTCCAACAA | ACGTAAGT TGCTGCGTCAC ATATCTGT TCTGGAT |
| CAR016_M19 | 230889 | Biotin-AC(dT-Biotin) AAGCCACCG (dT-Biotin) GTCCA | ACGTAAGT TGCTGCGTCAC ATATCTGT TCTGGAT ACAA |
| CAR016_M20 | 230890 | Biotin-AC(dT-Biotin) AAGCCACCG (dT-Biotin) GTCCA | ACGTAAGT TGCTGCG(dT-ATATCTGT Biotin) ACAA    CACTCTGGAT |
| CAR016_M21 | 230891 | Biotin-AC(dT-Biotin) AAGCCACCG(dT-Biotin)GTCCA | ACGTAAGT TGCTGCG(dT-ATATCTGT Biotin) ACAA    CACTCTGGAT- Biotin |
| CAR016_M22 | 230892 | Biotin-ACTAAGCCACCGTGTATATCTGT CCA | ACGTAAGT TGCTGCGTCAC TCTGGAT ACAA |
| CAR016_M23 | 230893 | Biotin-ACTAAGCCACCGTGT<u>T</u>TATCGTA CCA | ACGTAGTA TGCTGCGTCAC TCTGGAT CAA |
| CAR016_M24 | 230894 | Biotin-ACTAAGCCACCGTG | ACGTAGTA TGCTGCGTCAC TATCTGTA TCTGGAT CAA |
| CAR016_M25 | 230895 | Biotin-ACTAA<u>T</u>CCACCGTG | ACGTAGTA TGCTGCGTCAC TATCTGTA TCTGGAT CAA |
| CAR016_M26 | 230896 | Biotin-ACTAA<u>T</u>CCA<u>GA</u>GTG | ACGTAGTA TGCTGCGTCAC TATCTGTA TCTGGAT CAA |
| CAR016_M27 | 230897 | Biotin-ACTAA<u>T</u>CCA<u>GA</u>GTG | ACGTAGTA TGCTGCGTCAC TATCTGTA TCTGGAT C<u>T</u>A |
| CAR016_M28 | 230898 | Biotin-G | ACGTAGTA TGCTGCGTC TATCTGTA CAA |
| CAR016_M29 | 230899 | n/a | Biotin- TGCTGCGT ACGTAAGT ATATCTGT ACAA |

TABLE 17

EpCAM aptamer CAR016 mutant sequence rational

| ID | Explanation | Rational |
|---|---|---|
| CAR016_M1 | 3rd and 4th GT -> AC | Designed with substitutions in the constant motif sequence to challenge affinity in order to examine |

TABLE 17-continued

EpCAM aptamer CAR016 mutant sequence rational

| ID | Explanation | Rational |
|---|---|---|
| | | the minimal effective sequence and assist in design proper negative control aptamers (e.g., similar to CAR016 but do not bind EpCAM). |
| CAR016_M2 | 7th G -> A | |
| CAR016_M3 | 10, 11 and 12th TAT -> GCG | |
| CAR016_M4 | 14 and 15th TG -> CA | |
| CAR016_M5 | 18 and 19th CA -> TC | |
| CAR016_M6 | Mutations 1-5 combined | |
| CAR016_M7 | Truncated, no reverse primer | Designed to examine the role of reverse primer in aptamer affinity |
| CAR016_M8 | No abundant motif | Designed as negative control with no homology to abundant sequence |
| CAR016_M9 | 6th A -> C | Designed with substitutions in the variable motif sequence (see SEQ ID NO. 230870 above) to potentially improve affinity of aptamer. |
| CAR016_M10 | 8th and 9th TA -> AC | |
| CAR016_M11 | 13th C -> A | |
| CAR016_M12 | $15^{th}$ & 16th TA -> GC | |
| CAR016_M13 | Truncated, no primers | Designed to examine the role of variable region in the aptamer affinity. Estimated $\Delta G = -0.7$ kcal/mol |
| CAR016_M14 | Truncated, minus 9 bases from both 5' and 3' | Designed to examine the role of both forward and reverse primers in aptamer affinity. Estimated $\Delta G = -5.6$ kcal/mol. |
| CAR016_M15 | 3'-Biotin | Designed to examine the impact of 3' biotinylation on aptamer affinity. |
| CAR016_M16 | Truncated, no forward primer | Designed to examine the role of forward primer in aptamer affinity. |
| CAR016_M17 | Truncated, no forward primer, 3'-Biotin | Designed as a control for M16 with 3' biotinylation |
| CAR016_M18 | 5' + Internal biotinylation at 3rd T | Designed in order to increase sensitivity of detection which will allow to minimize aptamer input in the assay and potentially boost the information capacity of the ouput data gathered with aptamer detection on plasma samples. |
| CAR016_M19 | 5' + 2 Internal biotinylation at 3rd and 13th T | |
| CAR016_M20 | 5' + 3 Internal biotinylation at 3rd, 13th and 46th T | |
| CAR016_M21 | 5', 3" + 3 Internal biotinylation at 3rd, 13th and 46th T | |
| CAR016_M22 | No spacer between Biotin and core sequence | Designed as negative control to standard biotinylation without spacer arm between Biotin and the core sequence. |
| CAR016_M23 | 5th A deleted in variable region of CAR016 | Designed in order to probe greater stability of secondary structure. Estimated $\Delta G = -14$ kcal/mol |
| CAR016_M24 | 15, 16, 17 and 18th TCCA deleted in forward primer of M23 | Designed in order to probe greater stability of secondary structure. Estimated $\Delta G = -20.5$ kcal/mol |
| CAR016_M25 | 6th G replaced with T in forward primer of M24 | Designed in order to probe greater stability of secondary structure. Estimated $\Delta G = -22.4$ kcal/mol |
| CAR016_M26 | 10, 11th CC replaced with GA in forward primer of M25 | Designed in order to probe greater stability of secondary structure. Estimated $\Delta G = -30.1$ kcal/mol |
| CAR016_M27 | 19th A replaced with T in variable region of M26 | Designed in order to probe greater stability of secondary structure. Estimated $\Delta G = -32.4$ kcal/mol |
| CAR016_M28 | 13 bases (5'->) truncated in FP, 9 bases (<-3') truncated in RP in M24 | 2nd shortest stable aptamer. Estimated $\Delta G = -11.3$ kcal/mol |
| CAR016_M29 | CAR016 truncated: no FP; minus 9 bases at 3' in RP | The shortest stable aptamer which includes complete variable region. Estimated $\Delta G = -4.6$ kcal/mol |

As observed in Tables 16 and 17, various modifications are made across the length of the aptamers, including the 5'-leader and 3'-tail primer sequences. The aptamer variants are synthesized and binding to EpCAM is assessed using ELISA and microbead assay as described above for CAR016. Results reveal regions of the aptamer sequence that enhance or degrade the ability of the aptamer to bind specifically to EpCAM protein and EpCAM+ microvesicles. FIGS. 21A-21J show predicted secondary structures of CAR016 and the indicated CAR016 variants in Tables 16 and 17.

Example 13: Aptamers to VCAP Microvesicles

In this Example, aptamers were identified that recognize microvesicles shed by the prostate cancer VCAP cell line. VCAP microvesicles were coated onto a standard ELISA plate with a high-binding surface. After washing excess unbound microvesicles from the wells, the wells were blocked with Pluronic® F-127 (Sigma Aldrich). A 20n aptamer library (see Table 9) was incubated with the well-bound microvesicles. The wells were washed to remove unbound aptamers. The remaining VCAP microvesicles aptamers were eluted, purified, amplified, and strand separated and cleaned before next round. See detailed methodology above. The previous steps were repeated for 8 rounds. After round 8, the selected aptamer pool was subjected to IonTorrent sequencing.

Aptamers having the top frequency between total reads are shown in Table 18. In Table 18, the sequences are shown 5' to 3' from left to right, wherein each complete sequence consists of the indicated 5' leader sequence followed by the indicated Variable Sequence followed by the indicated 3' tail sequence. Each sequence is derived from a library having a leader and tail (see Table 9) with a variable sequence between. The table indicates whether the identified sequence comprises a biotin moiety on the 5' or 3' end. It is understood that the nucleotide sequences that are disclosed in Table 18 can also be modified to the extent that resulting modifications result in an aptamer having about 50, 55, 60, 65, 70, 75, 80, 85, 90, 95, 96, 97, 98, and 99 percent homology to the disclosed sequence and retain the functionality of binding to vesicle antigens or functional fragments thereof.

TABLE 18

VCAP microvesicle aptamer sequences

| ID | SEQ ID NO. | 5'-Leader | Variable Sequence | Tail-3' |
|---|---|---|---|---|
| CAR023 | 230900 | Biotin-ACTAAGCCA CCGTGTCCA | TCTTTCGTCTTGTTAT GTAT | TGCTGCGTC ACTCTGGAT |
| CAR024 | 230901 | Biotin-ACTAAGCCA CCGTGTCCA | TGTTTTCCTTCTTACC TTTA | TGCTGCGTC ACTCTGGAT |
| CAR025 | 230902 | Biotin-ACTAAGCCA CCGTGTCCA | ACCTACTATCCATTA ATTTT | TGCTGCGTC ACTCTGGAT |
| CAR026 | 230903 | Biotin-ACTAAGCCA CCGTGTCCA | ATGTTTTCCCTGTTAT TTTT | TGCTGCGTC ACTCTGGAT |
| CAR031 | 230908 | Biotin-ACTAAGCCA CCGTGTCCA | CCTATTATTAGCTTTT CTTT | TGCTGCGTC ACTCTGGAT |
| CAR035 | 230913 | Biotin-ACTAAGCCA CCGTGTCCA | TAACACTATGTCAGT TAGTA | TGCTGCGTC ACTCTGGAT |
| CAR036 | 230914 | Biotin-ACTAAGCCA CCGTGTCCA | CTTGAAATGTGATTC TTTAT | TGCTGCGTC ACTCTGGAT |
| CAR037 | 230915 | Biotin-ACTAAGCCA CCGTGTCCA | TTCCTTGTCTCCTATT CATT | TGCTGCGTC ACTCTGGAT |
| CAR038 | 230916 | Biotin-ACTAAGCCA CCGTGTCCA | TCTCTATATTACATGC TTCT | TGCTGCGTC ACTCTGGAT |
| CAR039 | 230917 | Biotin-ACTAAGCCA CCGTGTCCA | CCCTTTTTGCGATTTC TTTA | TGCTGCGTC ACTCTGGAT |
| CAR040 | 230918 | Biotin-ACTAAGCCA CCGTGTCCA | GAAGTAAGATCCTTC TGATA | TGCTGCGTC ACTCTGGAT |
| CAR041 | 230919 | Biotin-ACTAAGCCA CCGTGTCCA | ACCTTGTTGTATCCGT TATA | TGCTGCGTC ACTCTGGAT |
| CAR042 | 230920 | Biotin-ACTAAGCCA CCGTGTCCA | TTGCCTTTTCAAAGTA ATAT | TGCTGCGTC ACTCTGGAT |
| CAR043 | 230921 | Biotin-ACTAAGCCA CCGTGTCCA | TATTCCCATGTCATAT ACCT | TGCTGCGTC ACTCTGGAT |
| CAR044 | 230922 | Biotin-ACTAAGCCA CCGTGTCCA | TTGCATAGCATATTA TCTTC | TGCTGCGTC ACTCTGGAT |
| CAR045 | 230923 | Biotin-ACTAAGCCA CCGTGTCCA | TTGTTACTCTGTATCT TTAT | TGCTGCGTC ACTCTGGAT |
| CAR046 | 230924 | Biotin-ACTAAGCCA CCGTGTCCA | TTCTTTACTCTTTTCT TTTT | TGCTGCGTC ACTCTGGAT |
| CAR047 | 230925 | Biotin-ACTAAGCCA CCGTGTCCA | TCGTTTCTTCTTCACT TTAT | TGCTGCGTC ACTCTGGAT |
| CAR048 | 230926 | Biotin-ACTAAGCCA CCGTGTCCA | TGTTTCCTTCTGTTAT CTTA | TGCTGCGTC ACTCTGGAT |
| CAR049 | 230927 | Biotin-ACTAAGCCA CCGTGTCCA | TTCTCTTGCTCTCTTT CTCT | TGCTGCGTC ACTCTGGAT |

The sequences in Table 18 were the most commonly represented in the sequencing pool with two independent sequencing runs. Highest frequencies were: 1) CAR023, 18.3%; 2) CAR024, 12.7%; 3) CAR025, 9.8%; and 4) CAR026, 8.8%. CAR031 was the 5$^{th}$ most common sequence. Sequences were further validated by titration of the aptamers and target VCap exosomes.

The aptamers in Table 18 are also directly modified with a label instead of the 5' biotin moiety. For example, the biotin may be substituted with a 5' digoxigenin (NHS Ester) (abbreviated as "/5DigN/"). The digoxigenin group provides a fluorescent label. The 5' digoxigenin may be separated from the nucleotide sequence with a spacer, e.g., Int Spacer 18 (abbreviated as "/Int18/"), which is an 18-atom hexaethyleneglycol spacer and is available from Integrated DNA Technologies (IDT) Similar spacers also available from IDT which can be used include: 1) C3 Spacer, a phosphoramidite that can be incorporated internally or at the 5'-end of the oligo. Multiple C3 spacers can be added at either end of an oligo to introduce a long hydrophilic spacer arm for the attachment of fluorophores or other pendent groups; 2) PC (Photo-Cleavable) Spacer can be placed between DNA bases or between the oligo and a 5'-modifier group. It offers a 10-atom spacer arm which can be cleaved with exposure to UV light in the 300-350 nm spectral range. Cleavage releases the oligo with a 5'-phosphate group; 3) Hexanediol is a six carbon glycol spacer that is capable of blocking extension by DNA polymerases. This 3' modification is capable of supporting synthesis of longer oligos; 4) Spacer 9 is a triethylene glycol spacer that can be incorporated at the 5'-end or 3'-end of an oligo or internally. Multiple insertions can be used to create long spacer arms; and 5) The 1',2'-Dideoxyribose (dSpacer) modification is used to introduce a stable abasic site within an oligonucleotide.

Example 14: Aptamer Target Identification

In this Example, aptamers conjugated to microspheres are used to assist in determining the target of two aptamers identified by library screening methods as described above. The general approach is shown in FIG. 14. The approach is used to verify the targets of CAR029, an aptamer identified by library screening to recognize EpCAM, and CAR024, an aptamer identified by library screening to recognize an unknown target on the surface of VCAP microvesicles. See description above for both CAR029 and CAR024. In this approach, the sequences of CAR029 and CAR024 are randomly rearranged before linkage to the microspheres. The microspheres are used as controls to bind to targets that are similar but not identical to the intended target molecule.

Exemplary aptamer controls used in this study are shown in Table 19. In Table 19, the sequences are shown 5' to 3' from left to right. Each sequence is derived from random rearrangement of CAR029 or CAR024 as indicated in the aptamer ID in the table. It is understood that the nucleotide sequences that are disclosed in Table 19 can also be modified to the extent that resulting modifications result in an aptamer having about 50, 55, 60, 65, 70, 75, 80, 85, 90, 95, 96, 97, 98, and 99 percent homology to the disclosed sequence and retain the desired functionality.

TABLE 19

Negative control aptamer sequences

| ID | SEQ ID NO. | Sequence 5'->3' |
|---|---|---|
| CAR029-Neg1 | 230928 | Biotin-ACTAAGCCAC CGTGTCCACC TTCACTCCGT TATTCCTGTG CTGCGTCACT CTGGAT |
| CAR029-Neg2 | 230929 | Biotin-TGCTGCGTCA CTCTGGATCC TTCACTCCGT TATTCCTGAC TAAGCCACCG TGTCCA |
| CAR024-Neg1 | 230930 | Biotin-ACTAAGCCAC CGTGTCCACT TTACTTACTC CTTTGTTTTG CTGCGTCACT CTGGAT |
| CAR024-Neg2 | 230931 | Biotin-TGCTGCGTCA CTCTGGATCT TTACTTACTC CTTTGTTTAC TAAGCCACCG TGTCCA |

The protocol used is as follows:
1) The candidate aptamers (here, CAR029 and CAR024) and control aptamers (here, CAR029-Neg1, CAR029-Neg2, CAR024-Neg1, CAR024-Neg2) are synthesized with modifications to allow capture (here, the aptamers are biotinylated) and crosslinking (here, using the Sulfo-SBED Biotin Label Transfer Reagent and Kit, Catalog Number 33073 from Thermo Fisher Scientific Inc., Rockford, Ill., to allow photocrosslinking).
2) Each of the aptamers is individually mixed with microvesicles having the target of interest (here, VCAP microvesicles).
3) After incubation to allow the aptamers to bind target, ultraviolet light is applied to the mixtures to trigger crosslinking of the aptamers with the microvesicle targets.
4) The microvesicles are lysed, thereby releasing the crosslinked aptamer-target complex into solution.
5) The crosslinked aptamer-target complexes are captured from solution using a streptavidin coated substrate.
6) The crosslinked aptamer-target complexes for each aptamer are run individually on SDS-PAGE gel electrophoresis. The captured protein targets are visualized with Coomasie Blue staining.
7) The crosslinking and binding steps may be promiscuous so that multiple bands including the intended target but also random proteins will appear on each of the gels. The intended target will be found in a band that appears on the gel with the candidate aptamer (here, CAR029 and CAR024) but not the related negative control aptamers (here, CAR029-Neg1, CAR029-Neg2; or CAR024-Neg1, CAR024-Neg2; respectively). The bands corresponding to the target are excised from the gel.
8) Mass spectrometry (MS) is used to identify the aptamer target from the excised bands.

Example 15: Anti-PSMA Aptamers

In this Example, an aptamer library is screened for aptamers to prostate specific membrane antigen (PSMA/FOLH1/NAALADase I) protein identified using 6 rounds of positive selection as in the Examples above. After selection for a pool of PSMA binding aptamers as described above, the aptamer library was sequenced using the Ion Torrent standard protocol (Life Technologies, Carlsbad, Calif.). Lead candidates were selected for the properties such as the following: common occurrence in screened library, affinity to the target, specificity to the target, defined molecular structure, presence of favorite conformation, stability of such conformation, no or small aggregation rate at working concentrations, straight forward and reproducible synthesis and purification.

A detailed experimental protocol is presented in Example 17 below. An overview of screening parameters and protocol included the following:
1. A "6 aptamer" ssDNA library generated from forward strand synthesized DNA library by AS PCR were used. The 6 aptamer library comprised variable sequences of 10n, 20n, 25n, 30n, 35n and 40n with leader and tail sequences shown in Table 20.
2. PSMA histag conjugated onto Dynabeads.
3. Multiple rounds of positive selection were performed by mix of the PSMA-conjugated beads with diluted aptamer library in F127/PEG4000 at about 2e12 copies/selection.
4. After each round, the re-suspended beads were added directly into the PCR reaction for amplification, no elution involved.
5. After the PCR amplification, the PCR were then digested with lambda nuclease for 2 hrs and the ssDNA were purified by zymo ssDNA purification kit.
6. Total 9 rounds of selection performed. For 35n and 40n library only 6 rounds were performed since the libraries did not perform.
7. Round 6 and Round 9 selection recovery were used in PCR cloning and 30 clones from Round 6 and Round 9 each library were picked and plasmids were amplified and purified.
8. For Round 6, 180 clones were used in the initial screening. For Round 9 there are total 120 clones were used in the initial screening against target.
9. Individual ssDNA clones were amplified in mini-scale and tested in the initial screening against target protein (Histag PSMA protein) as well as non-target proteins BSA and mouse Ig. Signal/noise ratio were calculated.

10. According to the screening above, individual clones were picked and ssDNA were amplified in a midi scale, and further titrated in the ELISA format against target.

11. Sanger sequencing was performed for final clones and the sequencing data was analyzed.

Most reproducible results were observed in the 30n aptamer library. Representative sequences obtained from these procedures are shown in Table 20. In Table 20, the sequences are shown 5' to 3' from left to right, wherein each complete sequence consists of the indicated 5' leader sequence followed by the indicated Variable Sequence followed by the indicated 3' tail sequence. Each sequence is derived from a library having a leader and tail with a variable sequence between. The table indicates whether the identified sequence comprises a biotin moiety on the 5' or 3' end. It is understood that the nucleotide sequences that are disclosed in Table 20 can also be modified to the extent that resulting modifications result in an aptamer having about 50, 55, 60, 65, 70, 75, 80, 85, 90, 95, 96, 97, 98, and 99 percent homology to the disclosed sequence and retain the functionality of binding to PSMA antigen or functional fragments thereof.

TABLE 20

PSMA aptamer candidate sequences

| ID | SEQ ID NO. | 5'-Leader | Variable Sequence | Tail-3' |
|---|---|---|---|---|
| CAR050 | 230932 | Biotin-ACTAAGCCA CCGTGTCCA | CCCCCCTCTGTCTCTT GTTTCTCTTTTCTA | TGCTGCGTC ACTCTGGAT |
| CAR051 | 230933 | Biotin-ACTAAGCCA CCGTGTCCA | GCCCTATTCCCTCGCT TTCTCCCCTTTTGT | TGCTGCGTC ACTCTGGAT |
| CAR052 | 230934 | Biotin-ACTAAGCCA CCGTGTCCA | CCCGCCTGATCCAAA GTACTGACTCTGTTA | TGCTGCGTC ACTCTGGAT |
| CAR053 | 230935 | Biotin-ACTAAGCCA CCGTGTCCA | CTTCTCTATCCAGATT GCCCCTTTATTCTT | TGCTGCGTC ACTCTGGAT |

Figure 22:
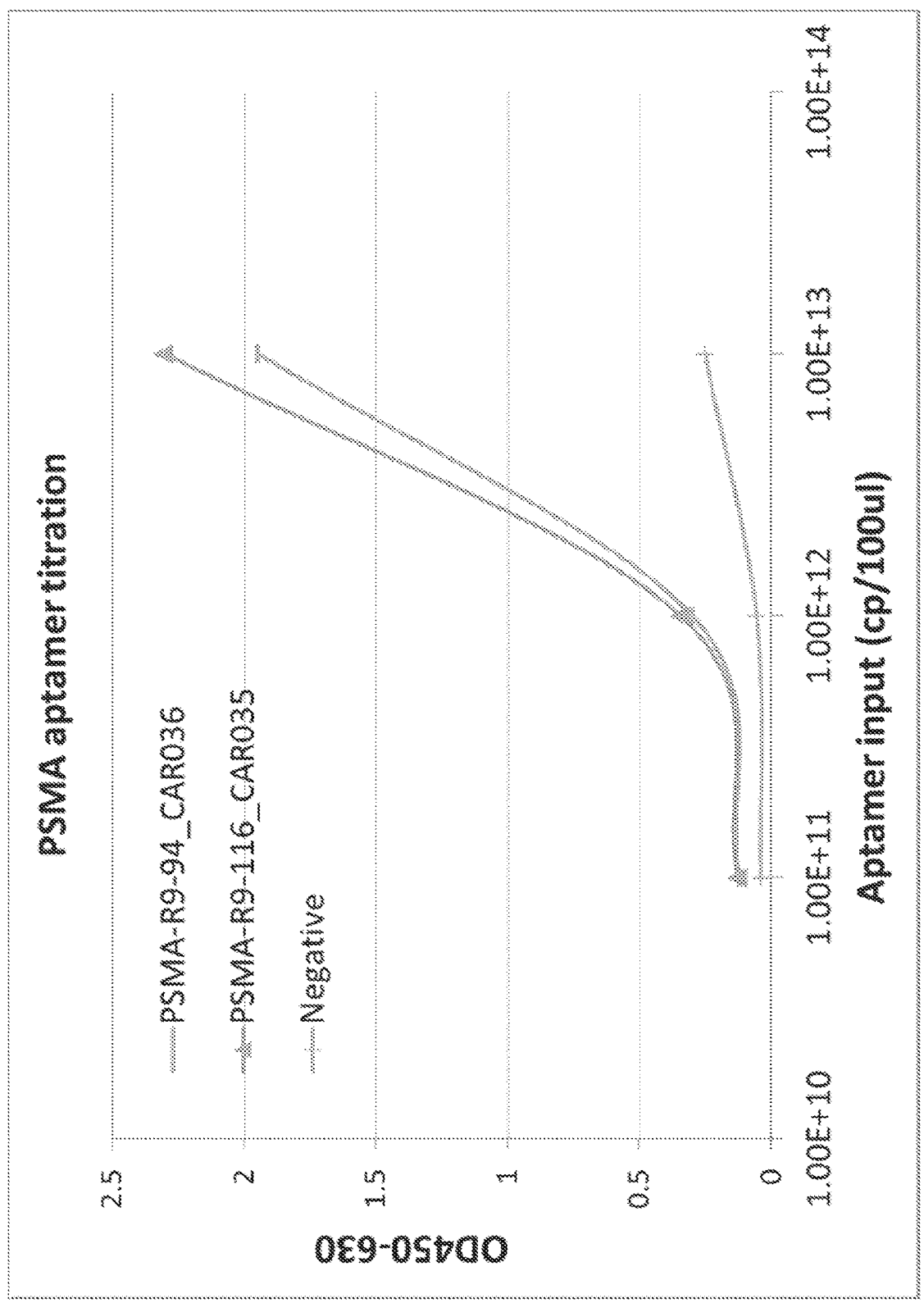
FIG. 22 illustrates binding affinity of anti-PSMA aptamer candidates CAR050 (SEQ ID NO. 230932) and CAR051 (SEQ ID NO. 230933) against PSMA protein as determined by ELISA assay against recombinant purified PSMA.

CAR050 and CAR051 were identified by cloning. The binding affinity of these two aptamers were tested against the PSMA/FOLH1/NAALADase I recombinant protein by ELISA. See FIG. 22. CAR052 and CAR053 were identified by sequencing using the Ion Torrent system after nine rounds of selection. CAR052 was the most common sequence in the torrent with 5.91% of the total read counts. CAR053, the second most common sequence, accounted for 3.34% of the total read counts.

Example 16: Competitive Isolation of Aptamers

As described herein, aptamers can be identified against a target of interest. In this Example, a competitive binding scheme is used to identify aptamers against a target of interest.

Figure 3:
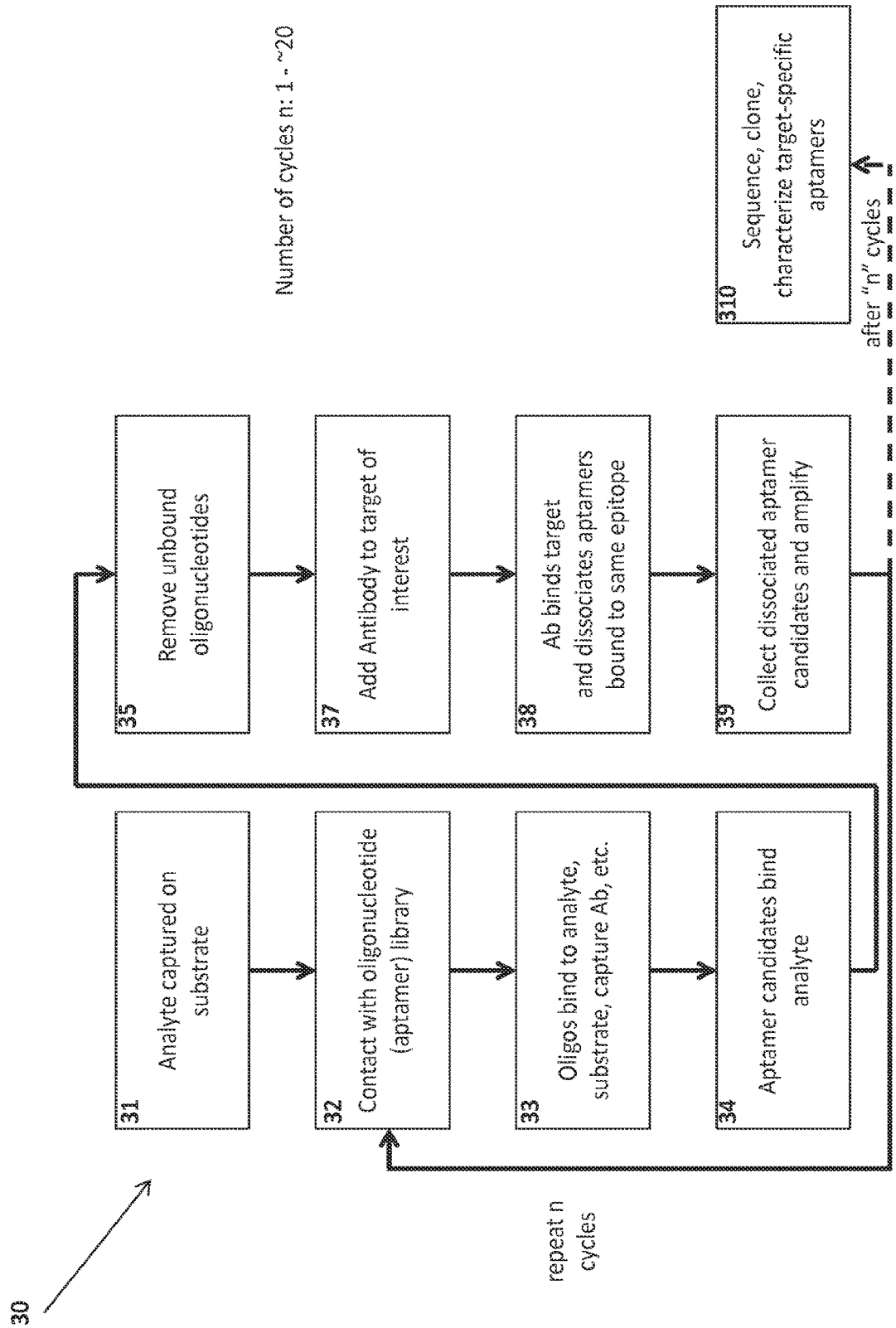
FIG. 3 presents a schematic for identifying aptamers against a target of interest.

The aptamer identification method 30 is outlined in FIG. 3. An analyte of interest, e.g., a biological entity such as a protein or microvesicle, is captured to a substrate 31. The substrate can be, e.g., a planar substrate or bead. The analyte can be captured covalently or non-covalently, e.g., the analyte can be captured using an antibody, aptamer, or streptavidin-biotin linkage. The captured analyte is contacted with a library of oligonucleotide aptamer candidates 32. The oligonucleotides bind to various components in the mixture, including the analyte, the substrate, the capture agent (e.g., antibody (Ab), aptamer, etc), reaction tube or well, biological debris, etc 33. Oligonucleotides that bind the analyte comprise aptamer candidates to the target of interest 34. Unbound oligonucleotides are removed via washing 35. After this step, the reaction mixture comprises the capture analyte bound by aptamer candidates. A ligand that recognizes a specific epitope, e.g., an antibody, is contacted with the reaction mixture 37. The ligand disassociates aptamer candidates bound to the same epitope as the ligand via competition for the epitope 38. The disassociated aptamer candidates are collected and amplified 39. Steps 32-39 are repeated a set number of times, n, e.g., 1-20 times, to further enrich the aptamer candidates with those that bind to the same epitope as the ligand After the repeated cycles, the remaining aptamers are assessed by sequencing, and other characterizations 310 as described herein.

Control screening is performed in parallel with the above method. Any aptamer identified via the control screening are discarded. Controls analytes include without limitation bare substrate incubated with the analyte, bare substrate without the analyte, and the method performed with a control ligand, such as an antibody that does not bind a target of interest.

Example 17: Aptamer Selection Protocol

This Example provides a protocol for screening an aptamer library against a protein to identify candidate aptamer that bind the protein. The protocol can be used to identify aptamer candidates that bind microvesicles by substituting the target protein with target microvesicles. Adjustments in the protocol to account for microvesicles are noted where appropriate.

Experimental Design:
1. Conjugate purified protein on the Dynabeads.
2. Positive selection (SELEX) for desired number of round
3. High throughput sequencing after select rounds (e.g., Next Generation using Ion Torrent)
4. Cloning and validation of selected clones after desired rounds The detailed Aptamer Affinity Selection protocol as follows:

Reagents:
1. Dynabeads® M-270 Carboxylic Acid ("beads") (Life Tech, 14305D)
2. Water, Molecular Biology Reagent Grade (Sigma, W4502)
3. Sulfo-NHS (Fisher Scientific, PI-24510)
4. EDC (Fisher Scientific, PI-77149)
5. MES Coupling Buffer: 0.05 M MES, pH 5.0 (pH may depend on target protein isoelectric point, pI)
   a. MES (2[N-Morpholino]ethanesulfonic acid) (Sigma, M2933)
   b. 5 N NaOH (Dilute to 1N NaOH) (Fisher, SS256-500)
6. Bead Conjugation Wash Buffer and Storage Buffer: 0.01% PBS-Tween 20
   a. PBS, pH 7.5 (Sigma, P3813)
   b. TWEEN® 20 (Sigma, 9416)
7. Target protein
   a. E.g., Histag-Epcam, C-ter Epcam, Histag-PSMA, tagless-FYN, tagless-AMACR, tagless-DBF4B
8. ELISA Wash Buffer: 0.05% PBS-Triton
9. Primary antibodies diluted in 1% PBS—B 10. Secondary antibodies diluted in 1% PBS—B 11. Aptamer library, 10n, 20n, 25n, 30n, 35n, 40n reverse library (lambda digested and purified). See Table 21, where n signifies a randomly selected nucleotide.

TABLE 21

Aptamer Library and PCR Primers

| Identity | Sequence (5'->3') | SEQ ID NO. |
|---|---|---|
| 50-mer aptamer library | 5'-actaagccaccgtgtcca-10n-tgctgcgtcactctggat | 231009 |
| 60-mer aptamer library | 5'-actaagccaccgtgtcca-20n-tgctgcgtcactctggat | 231010 |
| 65-mer aptamer library | 5'-actaagccaccgtgtcca-25n-tgctgcgtcactctggat | 231011 |
| 70-mer aptamer library | 5'-actaagccaccgtgtcca-30n-tgctgcgtcactctggat | 231012 |
| 75-mer aptamer library | 5'-actaagccaccgtgtcca-35n-tgctgcgtcactctggat | 231013 |
| 80-mer aptamer library | 5'-actaagccaccgtgtcca-40n-tgctgcgtcactctggat | 231014 |

12. 4% High Resolution E-Gel
13. Blocking and aptamer dilution buffer (0.5% F127 0.5% PEG4000 in PBS (Hyclone))
14. Washing buffer (PBS+1% BSA)
15. Phusion PCR reagents (New England Biolabs, Inc (NEB), Ipswich, Mass.)
16. AptamerPCR-F-5Phos/Aptamer-R-bio
17. Non-binding white 96 well plate. (see consumables)
18. Nanodrop.
19. Lambda exonuclease kit (NEB, 5 unit/up.
20. Sanger sequencing reagents

```
21. M13 Forward (-20) primer:
5'-GTA AAA CGA CGG CCA GT  (SEQ ID NO. 231015)

22. M13 Reverse (-27) primer:
5'-CAG GAA ACA GCT ATG AC  (SEQ ID NO. 231016)
```

23. PEG4000, PEG8000

Consumables:
1. USA Scientific co-polymer polypropylene 1.5 ml microcentrifuge tubes (USA Scientific, 1415-2500)
2. Vi-cell vials (Beckman Coulter, 723908)
3. 96-well non-binding, flat bottom white plates (Corning® Costar® #3600)
4. 96-well non-binding, round bottom white plates (Corning® Costar® #3605)
5. 96-well medium-binding flat bottom clear plate (Corning® Costar® #9017)

Equipment:
1. Magnet: DynaMag™—Spin Magnet ("magnet") (Life Tech, 12320D)
2. Vi-Cell XR—Cell Viability Analyzer
3. Veriti
4. Nanodrop
5. Centrifuge (Eppendorf, 5415)
6. Plate Magnet: Magnetic Plate Separator ("plate magnet") (Luminex, CN-0269-01)
7. MixMate
8. BioTek Synergy 2 Plate Reader Procedure:
Step 1: Target Protein Conjugation
Purpose: To co-conjugate magnetic beads with target protein and MA-PEG to block unoccupied, activated sites and to avoid non-specific aptamer binding during selection
1. Resuspend stock of beads by vortex for 2 minute.
2. Pipette desired volume of beads into copolymer tube and bring to 100 ul with 25 mM MES, pH 5 (Coupling Buffer diluted 1:1 with water).
3. Pellet the transferred beads by placing the tube on the magnet for 2 minutes and remove supernatant.
4. Add 100 ul of 25 mM MES (Coupling buffer) and shake at 800 rpm for 10 minutes.
5. Place on magnet for 1 minute and remove supernatant.
6. Repeat for a total of 2-10 minute washes with MES.
7. Immediately before use, dilute Sulfo-NHS with cold 25 mM MES to achieve a final concentration of 50 mg/ml (multiply mg×20 to achieve volume of water in ul).
8. Immediately before use, dilute EDC with cold 25 mM MES by adding 200 ul per vial to a final concentration of 50 mg/ml.
9. Add 200 ul of 50 mg/ml Sulfo-NHS and 200 ul of 50 mg/ml EDC to the beads and mix gently by vortex (800 rpm) for at least 30 minutes at RT, or 2 hours at 4° C.
10. Pellet the activated beads by placement on the magnet for 1 minute and remove supernatant.
11. Resuspend the beads in 400 ul of 25 mM MES Coupling Buffer, and mix gently by vortex (800 rpm).
12. Pellet the beads by placement on the magnet for 1 minute and remove the supernatant.
13. Repeat steps 11 and 12 for a total of two washes with 25 mM MES Coupling Buffer.
14. Resuspend the activated and washed with the target protein and mix gently by vortex.
15. Incubate for at least 30 minutes with mixing (by rotation) at room temperature.
16. Pellet the coupled beads by placement on the magnet for 1 minute and remove the supernatant.
17. Wash the beads four times with 0.01% PBS-Tween 20.
18. Pellet the supernatant and resuspend the coupled and washed beads in 200 ul of Storage Buffer and store in 500K beads/tube aliquots at −80 C.
19. Count the bead suspension using the Vi-Cell counter.
   a. Prepare a 1:100 dilution of beads: Storage Buffer by adding 14 ul of beads to 1386 ul of Storage Buffer in a Vi-Cell vial.
   b. Mix the diluted beads well by pipetting up and down several times.
   c. Transfer 700 ul of diluted beads to a new Vi-Cell vial.
   d. Read the duplicate vials for Total Cells.
   e. Determine the concentration of beads/ul by multiplying the Total Cell Count by the Dilution Factor in step 19a (i.e., 100).
   f. Determine the total yield of beads following conjugation by multiplying the concentration by the resuspension volume in step 18 (i.e., 200 ul).

Step 2a: Assess Bead Conjugation by ELISA
1. Add 200 ul of 1% PBS—B to wells of Costar, flat-bottom, non-binding plate.
2. Add 50,000 conjugated beads, seal plate, and incubate for 1 hr at room temperature (RT) with shaking at 800 rpm.
3. Place on plate magnet for 30 seconds with 800 rpm shaking Remove supernatant.
4. Remove plate from plate magnet.
5. Wash 3× with 200 ul of 0.05% PBS-Triton, 3 min each with 800 rpm shaking.

6. Place on plate magnet for 30 seconds with 800 rpm shaking Remove supernatant.

7. Add 100 ul of diluted primary antibody (AB) in 1% PBS—B to appropriate wells.

8. Seal plate well, Incubate 1 hr at 37 C with shaking, 800 rpm (on Jitterbug Change Jitterbug to original speed following one hour inc.).

9. Spin plate to collect condensation.

10. Place on plate magnet for 3 min, remove primary AB and buffer.

11. Remove plate from plate magnet.

12. Wash 3× with 200 ul of 0.05% PBS-Triton, 3 min each with 800 rpm shaking at RT.

13. Place on plate magnet for 30 seconds with 800 rpm shaking Remove supernatant.

14. Add 100 ul of diluted secondary AB in 1% PBS—B to appropriate wells.

15. Seal plate well, Incubate TIME—up to one hour—at RT with shaking, 800 rpm. NOTE: protect from light.

16. Place on plate magnet for 3 min, remove secondary AB and buffer.

17. Remove plate from plate magnet.

18. Wash 3× with 200 ul of 0.05% PBS-Triton, 3 min each with 800 rpm shaking at RT.

19. Place on plate magnet for 30 seconds with 800 rpm shaking Remove supernatant.

20. Add 100 ul of substrate (TMB), pipet mix, seal and incubate TIME—up to 30 min—with 800 rpm shaking at RT. NOTE: protect from light.

21. Add 100 ul stop solution (2N sulfuric acid), seal and incubate 1 min with 800 rpm shaking at RT.

22. Place plate on plate magnet for 3 min, then transfer supernatant to new clear plate medium-binding plate and read at 450-630 nm using micro plate reader.

Step 3: Bead Based Aptamer Screening and Selection

Purpose: affinity maturation

Use synthetic reverse aptamer library directly (input will be $10^{13}$ to $10^{15}$ if necessary)

1. Dilute the beads in 0.5% F127/PEG4000 PBS (no $MgCl_2$) buffer to 100,000 beads/50 ul (use 100,000 beads for the first round and use lower as desired amount of beads afterward for more stringency), vortex at 800 rpm for 1 hr.

2. Aliquot 50 ul with 100,000 beads into each well on the non-binding flat bottom white plate.

3. In a separate copolymer tube (USA Scientific), dilute aptamer library in appropriate 0.5% F127/PEG4000 PBS with 2 mM $MgCl_2$ to achieve proper number of aptamer copies in a total volume of 50 ul per well (input aptamer amount could be up to 10^14 for beads format)

4. Add 50 ul of diluted aptamer library to each 50 ul bead+buffer sample of the binding plate and incubate at RT with vortexing at 800 rpm for 30 min.

5. Place the plate with beads on the plate magnet for 2 min with 800 rpm shaking (the beads will concentrate in the center of the well).

6. Completely remove the buffer; leave plate on the plate magnet and tilt plate to collect liquid in corner without disturbing beads.

7. Remove plate from plate magnet and wash the beads with 200 ul of wash buffer (Using aptamer incubation buffer for the first 3 washers, then the general washing buffer is PBS—B, may increase salt concentration up to 500 mM NaCl as needed in later rounds) and vortex at 700 rpm for 1 min.

8. Place plate on plate magnet for 2 min with 700 rpm shaking. Repeat washes 10 times, a minute per wash with blocking buffer for the first 3 time, then use PBS—B (or PBS—B with increased salt buffer) for the rest.

9. After the last wash, place the plate on the plate magnet for 3 min with 700 rpm shaking, and then completely remove the buffer.

10. Re-suspend the bead with 52 ul of DNase free water, mix well by pipetting.

11. Transfer re-suspended beads to a new 1.5 ml tube (for the first round, use all in the PCR reaction)

12. Prepare PCR reaction. Use 4 (5 for the first round) reactions for each sample. Use 10 ul of re-suspended beads in 1 PCR reaction, total 4 reactions for 1 sample (Save 10 ul for cloning).

13. Aptamer recovery PCR amplification: For all libraries, the PCR can be performed with the Phusion polymerase: with PEG8000 additive, 98° C. 30 sec, cycle at 98° C. for 10 sec, 60° C. for 30 sec and 68° C. for 1 min. For 10n to 30n aptamer libraries, use as much as 30 PCR cycles. For 35n and 40n libraries, use below 25 cycles.

14. After the PCR amplification, add 10 ul of the lambda exonuclease directly to the PCR reaction, vortex and incubate at 37° C. for 2 hrs, terminated by heat up to 80° C. for 10 min and then cool back to 4° C. Before terminating the digestion, run 2 ul on a 4% High Resolution E-Gel. If there is still dsDNA band, continue the digestion, if only ssDNA band shows, terminate the digestion.

15. Zymo ssDNA purification of the lambda digested product.

16. Nanodrop (only if Zymo-purified) to quantitate adjusted to estimated 2e12 copies for the next round. (If nanodrop reading is low, qPCR is necessary to calculate the concentration of the ssDNA)

17. Repeat the desired number of rounds of selection

Step 4: Cloning and ssDNA Production and Clone Plasmid Amplification

Purpose: to separate individual aptamer colonies and obtain purified plasmid

1. Prepared the Phusion cloning PCR reaction with forward and reverse aptamer library primers without 5' or 3' modification.

2. From the recovery aptamer (on beads above), add 5 ul of the re-suspended beads into the PCR reaction.

3. PCR cycles, for all libraries, should be less than 25 cycles.

4. Add 5 ul of E-gel buffer directly into the PCR reaction, mix and load the sample to the 4% E-gel, 2 well, 20 ul/well. Run until the yellow dye closed to the end of the gel.

5. Take an image of the gel on the image device.

6. Open the gel with the E-gel opener, do not break the gel itself. Put the gel on the top of the UV box inside the image machine.

7. Slice the gel based on the estimated edge of the band vertically, turn on the UV light and quickly cut the DNA band as fast as possible (use the 365 nm UV), put the gel with the DNA band in a 1.5 ml tube.

8. Estimated the gel size, (around 100 ul-200 ul), Purify the DNA from the gel by using the Zymo Gel extraction kit according to the instruction.

9. Final elute the DNA with 10 ul DNase/RNase free water

10. According to the TOPO blunt-end cloning kit from Invitrogen: mix 2 ul of the aptamer PCR eluted product, 1 ul of salt solution and 1 ul of the vector and 2 ul of water. Mix by pipetting. Incubate at RT for 15-30 min.

1. Thaw the SOC medium and TOP10 chemical competent cells on ice; add the TOPO ligation solution above directly to the cells, mix by pipetting. Incubate on ice for 30 min.

2. Put the tube into 42° C. water bath for exactly 30 sec then immediately cool it on ice for couple minutes.

3. Add 250 ul of the SOC medium into the tube; horizontally shake the tube at 200 rpm at 37° C. for 1 hr.

4. Transfer 125 ul of the culture on at pre-warm LB agar plate with 100 ug/ml Ampicillin. Incubate at 37° C. overnight.

5. Make enough LB liquid medium and add 100 ug/ul Ampicillin stock to make 100 ug/ml LB medium. Transfer to the culture tube, 1 ml/tube.

6. Use the sterilized 20 ul tip to pick individual colonies into respective culture tubes. Shake at 300 rpm overnight at 37° C.

7. Plasmid extraction with 700 ul of the bacterial culture according to the Pure-Link plasmid mini pre protocol. Final elution to 75 ul TE (plasmid extraction could also use the Promega plasmid minipre Vacuume kit or the Genescript centrifuge plate kit, but should include a final maximal speed spin for 10 min to remove any trace chemicals).

8. Use 2 ul in 1% Egel, take image for record.

9. Estimate concentration of the plasmid prep using the Nanodrop. Adjust all the plasmid preparation to 2.5 ng/ul in water according to the calculation sheet (around 5e8 cp/ul).

Step 5: Mini-Pre of Clonal ssDNA for Initial Screening Test

Purpose: to prepare a limited quantity of single clone ssDNA and ready for the screening test.

1. For aptamer production (reverse strand), setup the PCR reaction with phosphorylated forward and biotinylated reverse aptamer library primers. Use 10 ul of the above 2.5 ng/ul plasmid solution in a 40 ul PCR reaction volume. PCR for 30 cycles.

2. After the PCR, add 10 ul of Lambda exonuclease directly to the PCR reaction, vortex and spin down, incubate at 37° C. for 2 hrs followed by 80° C. for 10 min then cool to 4° C. use 2 ul run on 4% E-gel to check if the digestion is complete. Once confirm the digestion is complete, stop the digestion and go on to the purification 3. Purify the ssDNA according to the zymo ssDNA purification kit instruction (for high throughput purpose, could use the Zymo Oligo purification kit in plate format, change the spin speed all to 5000 for all steps and maximal for the final dry spin for 10 min in the big centrifuge instead of 2000 in the manual) In both case, elute the ssDNA with 30 ul of DNase/RNase free water.

4. Estimate concentration of the ssDNA using the Nanodrop.

Step 6: Clone Screening Test

Purpose: to test affinity (positive or negative based on criteria) individual aptamer clones (ssDNA) against target as well as control protein.

1. According to the initial screening test worksheet, the day before test, coat the target protein and control protein at desired concentration, 100 ul/well on High Binding ELISA plate, at RT for 3-5 hrs.

2. Block the plate with 250 ul of 0.5% F127/PEG4000 (no MgCl2) PBS overnight at 4° C.

3. According to the Nanodrop data, chose the volume for all sample that could reach the ssDNA level at about 10e11 to 10e12/well.

4. Dilute the ssDNA in 0.5% F127/PEG4000 PBS plus final concentration of 2 mM $MgCl_2$.

5. Remove the blocking solution from the plate; wash twice with PBS, 1 min for each wash. Tap on the paper towel to remove trace liquid.

6. Add 100 ul of ssDNA dilution (10e11-10e13/well. 100 ul), incubate at RT with shaking at 800 rpm for 4 hrs.

7. Wash the plate with PBS+1% BSA for 3 times, 1 min/wash at 400-800 rpm shaking Remove the liquid and tap on the paper towel after each wash.

8. Dilute streptavidin-polyHRP at 1:1000 in PBS+1% BSA buffer, add 100 ul into each well. Incubate at RT for 1 hr with shaking 9. Wash the plate 3 times with PBS-1% BSA, tap on the paper towel to remove the trace liquid after each wash, 1 min/wash.

10. Pre-warm the Ultra ELISA substrate to RT, add 100 ul of the substrate into each well, and incubate in the dark with shaking for 30 min.

11. Stop the reaction by adding 100 ul of 2N $H_2SO_4$ and read OD450-630 by the microplate reader.

12. According to a defined criterion, (for example, OD above certain level in this standardized protocol or above the control protein), to make judgment of which clone is positive or negative.

Step 7: Mid-Scale Production of Aptamer ssDNA from Candidate Clone for Further Quantitative Evaluation Purpose: to prepare greater quantity of ssDNA from aptamer candidate clone for further confirmation of the affinity to target.

1. For aptamer production (reverse strand), setup the PCR reaction with phosphorylated forward and biotinylated reverse aptamer library primers. Use 5 ul of the above 2.5 ng/ul plasmid solution in a 40 ul PCR reaction volume, 12 reactions per sample. Run PCR amplification for 30 cycles.

2. After the PCR amplification, add 10 ul of Lambda exonuclease directly to the PCR reaction, vortex and spin down, incubate at 37° C. overnight for 2 hrs. Use 2 ul of the reaction to run on a 4% Egel to check the digestion as described above.

3. Purify the ssDNA according to the zymo ssDNA purification kit instruction (4 reactions through 1 zymo purification column). NOTE: This step uses the ssDNA purification kit, NOT the plate oligo purification kit used above.

4. Combine different elution from same sample, use Nanodrop to quantitate the ssDNA concentration.

5. Store the purified aptamer at −80° C.

Step 8: Validation Assay of Individual Aptamer Clones

Purpose: to further evaluate the selected clones in a quantitative manner.

1. For further validation test, both the target and the aptamer are titrated against each other. At least 1 non-target protein (at 1 coating concentration) is titrated against the aptamer in order to evaluate non-specific binding.

2. Coat ELISA plate wells with three different concentration of the target protein (e.g., 1 ug, 0.5 ug and 0.25 ug/ml, at 100 ul/well) as well as the non-target protein (generally 0.5 ug/ml and 100 ul/well) in PBS for 3-5 hrs. Block the plate overnight with 0.5% F127/0.5% PEG4000 (no $MgCl_2$) in PBS.

3. Dilute the aptamer over at least 4 orders of magnitude (e.g., from 10e13 to 10e10/well or 10e12 to 10e9/well depending on recovery) in the PBS with 0.5% F127/PEG4000. Add 100 ul of the aptamer dilution to the respective wells. Incubate the plate at RT at 800 rpm for 4 hrs. NOTE: If using microvesicles instead of purified protein to assess aptamer binding, incubate at 300 rpm instead of 800 rpm.

4. Wash the plate with 250 ul of PBS-1% BSA, tap on the paper towel after each wash to remove the trace liquid.

5. Dilute streptavidin-polyHRP at 1:1000 in PBS-1% BSA, add 100 ul of the solution to each well, incubate at RT with 800 rpm for 1 hr. NOTE: If using microvesicles instead of purified protein to assess aptamer binding, incubate at 300 rpm instead of 800 rpm.

6. Wash the plate 3 times with PBS-1% BSA, tap on the paper towel to remove the trace liquid.

7. Add 100 ul of UltraSubstrate (prewarm to RT at least 2 hrs before use) to each well, cover the top by the foil. Shake at 300-400 rpm for 30 min at RT. Add 100 ul of the 2N $H_2SO_4$ to stop the reaction.

8. Read OD450-630.

Step 9: Sanger Sequencing

Purpose: Obtain sequence information from the selected clones.

1. Sequencing primers: M13 Forward (−20) and M13 Reverse (−27)

2. According to the Sanger sequencing protocol, make the sequencing master mix and aliquot to 8 ul/well.

3. The mini-pre plasmid from selected clones will be used directly for the sequencing (the plasmid concentration should be at least 10 ng/ul).

4. Add 2 ul of the plasmid mini-pre sample to the respective well. Cycles as the BDT standard reaction.

5. Cleanseq the sample according to the established protocol.

6. Perform Sanger sequencing run.

7. On the FinchTV software, open the desired sequencing file (F first, if F file is not readable or quality is poor, use R file).

8. In the search bar, enter EcoRI (GAATTC) and click search.

9. The EcoRI site is 6 bases ahead of the starting of the aptamer primer sequencing if the aptamer PCR product successfully cloned into the vector. Click reverse the sequence display, from the last base on the EcoR1 site (C), the next 6 bases from the vector should be GCCCTT, the following sequence should match the either the aptamer forward pattern (ATCCAGA . . . ) or the reverse strand template (ACTAA . . . ).

10. Since the aptamer cloning direction is random, therefore, the starting of the aptamer sequence could be forward (starting as ATCCAGA . . . GCAGCA) or reverse (starting at ACTAA . . . GTCCA). When checking the sequence, identify the direction of the aptamer (forward direction or reverse).

11. Read base by base on the sequencing gram to verify the call is correct.

12. Record sequence in both forward and reverse direction.

Example 18: Aptamer Library Selection Protocol

This Example provides the protocol for SUL1 RNA library selection performed in the Example above. The protocol can be followed for other aptamer libraries and sample input as desired.

Preparation

The working space is cleaned with 80% EtOH before working.

Beads are MagPlex beads (Luminex Corp., Austin, Tex.). Other beads can be substituted as desired.

Buffers/Reagents to Prepare:
MilliQ water
100 mM $MgCl_2$
5× Transcription Buffer (200 mM Tris pH 7.9)
1×PBS
1×PBS with 3 mM $MgCl_2$
10×PBS
Selection buffer (1×PBS with 0.1% BSA and 3 mM $MgCl_2$)

Before starting with selection, remove the bead storage buffer, and wash beads with 1×PBS w/3 mM $MgCl_2$ 1 times (200 uL total in all 4 tubes). 200,000 beads per selection are used.

Binding 2'F SUL1 RNA Pool to Microvesicle Coated Magnetic Beads

Abbreviations: TK—Transcription; NTC—No template control.

Steps:
1. 1$^{st}$ Round: Mix 1 nmol purified 2'F SUL1 RNA with 20 µl of resuspended beads (conjugated with microvesicle). 10 uL of 10×PBS+1% BSA, 3 µl 100 mM $MgCl_2$, and 47 uL $H_2O$. This gives a final concentration of 1×PBS, 0.1% BSA, 3 mM $MgCl_2$.
   1.1 The addition of $MgCl_2$ in this step gives a concentration of 3 mM $MgCl_2$. This is the binding concentration for the entire process.
   1.2 Following Rounds: Mix 20 µl of transcription product (15 mM $MgCl_2$ inside) with 20 µl of washed microvesicle coated beads, plus 9 uL 10×PBS with 1% BSA, 51 uL $H_2O$. No additional $MgCl_2$ is needed because the $MgCl_2$ in the diluted transcription product (TK) provides a final concentration of 3 mM $MgCl_2$.
2. Incubate for 30 min at 37° C., shake at 1000 rpm, and pipet mix every 10 minutes.
3. Wash the beads:
   3.1 One washing cycle comprises:
      3.1.1 Remove the beads from the magnet
      3.1.2 Resuspend beads in 100 µl 1×PBS+3 mM $MgCl_2$ off the magnet.
      3.1.3 Incubate sample for 30 seconds off of the magnet.
      3.1.4 Place the sample back onto the magnet, and wait until the beads are on the side.
      3.1.5 Remove and discard the supernatant.
      3.1.6 Resuspend in 100 µl 1×PBS+3 mM $MgCl_2$+ 0.1% BSA off of the magnet.
      3.1.7 Incubate sample for 3 minutes off of the magnet.
      3.1.8 Place the sample back onto the magnet, and wait until the beads are on the side.
      3.1.9 Remove and discard the supernatant
   3.2 1$^{st}$ Round: Place bead mixture on a magnet and remove the supernatant Wash once with 100 µl 1×PBS+3 mM $MgCl_2$+0.1% BSA (by pipette mixing the beads), and discard buffer.
   3.3 Following Rounds: Increase the washing steps every second round by one more washing step up to 3 washing steps.
4. Add 55 µl MilliQ water to the bead sample.
5. Elute the RNA by incubating the bead sample for 5 min at 80° C.
   5.1 Check if there is 50 µl, if not spin the sample down to spin down the condensed water off the top.
   5.2 Transfer the supernatant to a new vial. Work quickly to avoid the strands rebinding the beads.
      5.2.1 Use 50 µl eluate for the following RT-PCR and store the rest at −20° C.

RT-PCR of Recovered Aptamer Candidates
Practice Guides
The rest of the RT-PCR sample and the TK-PCR sample is stored at −20° C.
RNA can be stored at 4° C. for ~1 h
RT-PCR product can be stored overnight at 4° C.
Proceed to the next selection cycle for optimal RNA quality immediately after transcription.
Avoid vortexing RNA
Mix on ice
Use 0.5 ml PCR tubes
Every RT-PCR should have a no-template control (NTC) with water instead of template
Do not freeze-thaw DTT more than one time
6. Prepare a Master Mix (see Table 21-A) before the first round, check it with 0.5 pmol RNA and store aliquots of 48 µl at −20° C. until usage.

TABLE 21-A

RT-PCR master mix

| Reagent | Volume (µl)/ reaction | Final concentration |
| --- | --- | --- |
| 5x Colorless GoTaq Flexi Buffer Promega cat# M890A | 20 | 1x |
| 5 x first strand buffer (Invitrogen) lot# 1300427 | 4 | 0.2 x |
| 100 mM DTT | 2 | 2 mM |
| 100 µM SUL1 F primer | 1 | 1 µM |
| 100 µM SUL1 R primer | 1 | 1 µM |
| 100 mM MgCl₂ | 1.5 | 1.5 mM |
| 25 mM (each) dNTPs | 1.2 | 300 µM |
| MilliQ water | 17.3 | |
| Total | 48 | |

7. Add 50 µl MilliQ water as negative control (NTC) (pipette this first) or 50 µl selection eluate. Pipet mix.
8. Incubate at 65° C. for 5 min.
9. After cooling to 4° C., add:
   9.1 1 µl Superscript II Reverse Transcriptase (Invitrogen, cat #18064) (200 U/µl)
   9.2 1 µl GoTaqFlexi DNA polymerase (5 units/µl) Promega cat # M8305.
PCR—Program (SARTPCR)
a) 10 min 54° C.
   (This step is only for reverse transcriptase, should more rounds be needed, do not repeat step A.)
b) 1 min 95° C.
c) 1 min 60° C.
d) 1 min 72° C.
10. Cycle steps b-d for
   10.1 1ˢᵗ round b-d 4 cycles. Run 5 µL PCR products on a 4% agarose gel.
      10.1.1 Subsequent rounds: The amount of RNA is decreased after the first round, leading to an increase in required PCR-cycles. To determine the number of cycles needed each time, check the band intensity from the agarose gel from the previous round of selection. Use that number of cycles to start the next round of RT-PCR. Note: Always check results on an agarose gel.
         10.1.1.1 Agarose gel results: product band should be seen at the target length. The band intensity should be about the same as the 50 bp ladder band (if not a little less intense). If the band is not intense enough (barely visible), cycle an appropriate amount more and re-check on an agarose gel.

Transcription
All mixing performed on ice. Prepare transcription Master Mix (Table 22) and store aliquots of 85.7 µl at −20° C. until use.
11. Verify pH of stock 200 mM Tris pH 7.9 before use. A change in pH over time may cause problems with the transcription.

TABLE 22

Transcription (TK) Master Mix for SUL1 library

| Reagent | Volume (µl) for one reaction | Volume (µl) for 20 reactions | Final concentration |
| --- | --- | --- | --- |
| 5x Transcription buffer (200 mMTris, pH 7.9) | 20 | 400 | 1x |
| 100 mM DTT | 5 | 100 | 5 mM |
| 100 mM ATP | 1 | 20 | 1 mM |
| 100 mM GTP | 1 | 20 | 1 mM |
| 100 mM 2' F-dUTP | 3 | 60 | 3 mM |
| 100 mM 2' F-dCTP | 3 | 60 | 3 mM |
| 100 mM MgCl₂ | 15 | 300 | 15 mM |
| MilliQ water | 37 | 740 | |
| Total volume | 85 | 1700 µl | |

12. Add 10 µl RT-PCR product to the mastermix.
13. Add 1 µl RNasin (40 units/µl)
   13.1 Promega Recombinant RNasin Ribonuclease Inhibitor cat # N2515/N2511
14. Add 4 µl T7 Y639F mutant polymerase (25 U/µl use: 100 U total per reaction)
15. Perform the reaction for 30 min at 37° C.
16. Use the transcription-product directly for the next selection round. If the next step is not feasible, freeze transcription product at −20 C.
Subsequent Rounds
Repeat the bead incubation, the RT-PCR and transcription as often as needed. Try to have similar band intensity of the RT-PCR product for the sample in all rounds as noted above.
Binding Assay
A binding assay is performed after desired rounds of selection to determine to assess non-specific binding of cancer selected aptamers to control beads (conjugated to supernatant from plasma ultracentrifugation, see above) and likewise for non-cancer control samples. Binding assays can also be performed to assess binding of selected aptamers against the intended target microvesicles.
Cherenkov protocol: Performed using $^{32}P$ radioactively labeled aptamer library.
Final concentration of selection buffer: 1×PBS+3 mM MgCl₂+0.01% BSA pH 7.4
Wash buffer: 1×PBS+3 mM MgCl₂ pH 7.4
1. Remove microvesicle samples from −80° C. freezer and thaw.
2. Place beads on magnet (200,000 per sample experiment), remove bead storage buffer.
3. Wash 1×200 µL for 1 minute each with 1×PBS, 3 mM MgCl₂ buffer. Pool beads to make 200,000 in one tube.
4. Resuspend beads in 70 µL of the selection buffer. (10 µl of 10×PBS, 1% BSA+3 µL 100 mM MgCl₂+57 µL H₂O per sample).
5. Add 30 µL radioactively labeled RNA aptamer library to their respective sample.
6. Incubate shaking at 1000 rpm at 37° C. for 30 min.
7. Place samples on a magnet.

8. Remove and save supernatant
9. Wash beads with 200 µL wash buffer 1×PBS 3 mM MgCl₂ pH 7.4, incubating off the magnet for 3 minute.
10. Place samples on the magnet, remove and save wash solution.
11. Repeat steps 9, 10.
12. Add 100 µL water to the sample, pipette mix.
13. Heat at 80° C. for 5 minutes.
14. Place samples on a magnet, remove supernatant, and save.
15. Resuspend beads in 100 µL water.
16. Measure radioactivity of every fraction using scintillation counter.
17. Analyze amount of background binding present.

Negative Selection

As desired, a negative selection step is added prior to incubating the aptamer library with the beads conjugated to the target microvesicles (i.e., procedure "Binding 2'F SUL1 RNA pool to microvesicle coated magnetic beads" above). The negative selection can be performed using beads conjugated to the supernatant or the input samples (e.g., plasma) after microvesicles are filtered or sedimented from the sample (referred to as "no microvesicle coated beads," "microvesicle depleted samples," or similar). The steps are:

1) Start with aptamer library product from the desired round after transcription as described above. Wash the beads before start: remove storage buffer, wash beads with 200 µL wash buffer, then replace buffer as stated below:

2) Negative selection step: Add and pipet mix 20 µl of transcription product (15 mM MgCl₂) with freshly washed 'no microvesicle' coated beads with 10 µL 10×PBS with 1% BSA, 70 µL H₂O. No additional MgCl₂ is needed because the MgCl₂ in the diluted transcription product (TK) provides a final concentration of 3 mM MgCl₂.

3) Incubate for 30 min at 37° C., shake at 1000 rpm.

4) Remove supernatant and add it to the positive selection beads (directly), which are washed microvesicle coated beads.

Continue with positive selection incubation. See Binding 2'F SUL1 RNA pool to microvesicle coated magnetic beads above, starting at step 2. Additional steps through transcription are as detailed above.

Example 19: Aptamers to Breast Cancer (BrCa) Derived Microvesicles

In this Example, an aptamer library is screened to identify aptamers that distinguish between microvesicles circulating in the blood of breast cancer patients and microvesicles circulating in the blood of healthy, control individuals (i.e., without breast cancer).

Microvesicles were isolated from plasma of a pool of 60 breast cancer patients (BrCa+). Microvesicles were also isolated from pool of 60 non-cancer samples (BrCa−). Microvesicles were isolated from the plasma using ultracentrifugation (120,000×g). Microvesicles were in the pellet from the ultracentrifugation. The supernatant from the ultracentrifugation was saved to use as a control. The microvesicles from both sample types were conjugated to MagPlex beads (Luminex Corp, Austin Tex.). Optionally, the isolated microvesicles are incubated with anti-HSA/IgG/Fibrinogen beads to remove these highly abundant blood proteins. However, the conjugation step can be optimized to favor conjugation of the microvesicles such that removal of highly abundant proteins is not strictly necessary.

The aptamer library used consisted of a 2'F SUL1 RNA aptamer library. The sequence is 5'-GG-GAGGACGAUGCGG-N40-CAGACGACUCGCUGAG-GAUCCGAGA-3' (SEQ ID NO. 231017). The aptamer library consists of three sections: Forward primer—15 nucleotides, variable region—40 nucleotides; reverse primer—25 nucleotides. All pyrimidines (C and U) were 2'Fluoro modified.

The aptamer library was incubated with either the cancer or control microvesicle-conjugated beads. Thirteen rounds of positive selection for aptamers that bind the microvesicles were performed in parallel for both types of samples. See Example 18 above for detailed protocol of the positive selection steps. Negative selection was not performed.

The aptamers that were retained from the above positive selection were sequenced using Next Generation sequencing technology consisting of Ion Torrent NGS (Life Technologies, Inc., Carlsbad, Calif.). The MiSeq system may be used also (Illumina, Inc., San Diego, Calif.). The sequences are compared to identify aptamers that are found in the cancer samples and not the control samples, and vice versa. Such aptamers provide candidates that can be used to distinguish between BrCa and non-BrCa samples.

A number of representative sequences obtained from these procedures are shown in Table 23. The sequences in the table were identified in the aptamer pools from selection against BrCa microvesicles but were not in the aptamer pools selected against non-cancer samples. In Table 23, the sequences are shown 5' to 3' from left to right, wherein each complete sequence consists of the indicated 5' leader sequence followed by the indicated Variable Sequence followed by the indicated 3' tail sequence. Each sequence is derived from a library having a leader and tail (see description above) with a variable sequence between. It is understood that the nucleotide sequences that are disclosed in Table 23 can also be modified to the extent that resulting modifications result in an aptamer having about 50, 55, 60, 65, 70, 75, 80, 85, 90, 95, 96, 97, 98, and 99 percent homology to the disclosed sequence and retain the functionality of binding to microvesicle antigens or functional fragments thereof.

TABLE 23

BrCa microvesicle aptamer candidate sequences

| ID | SEQ ID NO. | 5'-Leader | Variable Sequence Tail-3' |
|---|---|---|---|
| BRCA_APT1_RNA | 231018 | GGGAGGAC GAUGCGG | CGCGUCUUCCCCGCACAGACGACUCGCU UUGCCGCAAUUGCCAGAGGAUCCGAGA UACAUUAAUA |
| BRCA_APT2_RNA | 231020 | GGGAGGAC GAUGCGG | GUCCGGAACGCCUCGCAGACGACUCGCU AUCCUCGCAUAAUAUGAGGAUCCGAGA GAUACGUCUG |
| BRCA_APT3_RNA | 231022 | GGGAGGAC GAUGCGG | GUCCAUGGUACGCCUCAGACGACUCGCU CGAUUCCGCCCAUACGAGGAUCCGAGA AUGCAUGUAA |
| BRCA_APT4_RNA | 231024 | GGGAGGAC GAUGCGG | CACUAUCCGUUUGUCCAGACGACUCGCU CGUCCUCUUGUGGUAGAGGAUCCGAGA UUGCGCAUGC |
| BRCA_APT5_RNA | 231026 | GGGAGGAC GAUGCGG | UCUUCCAUCUGGUCGCAGACGACUCGCU CGAUACAGAAUACG GAGGAUCCGAGA AUUAACAUAAA |
| BRCA_APT6_RNA | 231028 | GGGAGGAC GAUGCGG | GAUCACGCUGCCCUUCAGACGACUCGCU UGUUUAAGGCCUUU GAGGAUCCGAGA AUACAAACGCA |

TABLE 23-continued

BrCa microvesicle aptamer candidate sequences

| ID | SEQ ID NO. | 5'-Leader | Variable Sequence | Tail-3' |
|---|---|---|---|---|
| BRCA_APT7_RNA | 231030 | GGGAGGAC GAUGCGG | UAUUCGCCAGUCACACAGACGACUCGCU UCAACUAUGAUGAC GAGGAUCCGAGA GCUUGACUGGA | |

Each sequence in Table 23 is synthesized in two variants for further investigation: 5' biotinylated and 3' biotinylated. This provides aptamer variants that can be captured at the 5' end or the 3' end as desired. The aptamers are further synthesized with each pyrimidine (C and U) 2'Fluoro modified.

The DNA sequence corresponding to each RNA sequence in Table 23 is provided in the sequence listing, where the DNA sequence directly follows its corresponding RNA sequence. For example SEQ ID NO. 231019 is the DNA sequence corresponding to RNA sequence SEQ ID NO. 231018, etc. The DNA forms of the aptamers are synthesized for further characterization as well.

The aptamers above were identified using positive selection for aptamers which recognize BrCa and non-BrCa microvesicles conjugated to microspheres.

Example 20: Additional Aptamers to Breast Cancer (BrCa) Derived Microvesicles

In this Example, an aptamer library is screened to identify aptamers that distinguish between microvesicles circulating in the blood of breast cancer patients and microvesicles circulating in the blood of healthy, control individuals (i.e., without breast cancer). The procedure uses the same samples and aptamer library as in Examples 17-19 above. Negative selection is performed before each positive selection starting after the third round of positive selection.

Negative selection serves to remove aptamers that bind soluble/abundant/non-informative and common proteins for cancer and non-cancer proteins. Negative selection include performing negative selection on the aptamer candidates selected against cancer-derived microvesicles as follows: (i) using microbeads conjugated to the supernatant from the cancer-derived plasma ultracentrifugation step (which should not contain microvesicles); (ii) using microbeads conjugated to the supernatant from the cancer-negative plasma ultracentrifugation step (which should not contain microvesicles); (iii) using microbeads conjugated to cancer-negative microvesicles. Negative selection can also be performed on the aptamer candidates selected against cancer-negative microvesicles as follows: (i) using microbeads conjugated to the supernatant from the cancer-positive plasma ultracentrifugation step (which should not contain microvesicles); (ii) using microbeads conjugated to the supernatant from the cancer-negative plasma ultracentrifugation step (which should not contain microvesicles); (iii) using microbeads conjugated to cancer-positive microvesicles. Negative selection rounds are performed between rounds of positive selection as described herein.

Microvesicles are isolated from plasma of a pool of 60 cancer-positive patients and from a pool of 60 non-cancer samples using ultracentrifugation (120,000×g). Microvesicles are found in the pellet from the ultracentrifugation. The supernatant from the ultracentrifugation is saved to use as a control. The microvesicles from both sample types are conjugated to MagPlex beads (Luminex Corp, Austin Tex.).

The aptamer library used consists of a 2'F SUL1 RNA aptamer library. The sequence is 5'-GG-GAGGACGAUGCGG-N40-CAGACGACUCGCUGAG-GAUCCGAGA-3' (SEQ ID NO. 231017), wherein the N40 signifies 40 random nucleotides. The aptamer library consists of three sections: Forward primer—15 nucleotides, variable region—40 nucleotides; reverse primer—25 nucleotides. All pyrimidines (C and U) were 2'Fluoro modified.

The aptamer library is incubated with either the cancer or control microvesicle-conjugated beads. Nine rounds of positive selection for aptamers that bind the microvesicles are performed in parallel for both types of samples. Negative selection is performed against beads conjugated to the input plasma supernatant after ultracentrifugation before positive selection in rounds 4-9. See Examples above for detailed protocol of the positive selection and negative selection steps.

The aptamers that are retained from the above positive selection are sequenced using Next Generation sequencing technology consisting of Ion Torrent NGS (Life Technologies, Inc., Carlsbad, Calif.). Any appropriate high-throughput sequencing platform such as the MiSeq system may be used for this step (Illumina, Inc., San Diego, Calif.). The sequences are compared to identify aptamers that are found in the cancer samples and not the control samples, and vice versa. Such aptamers provide candidates that can be used to distinguish between cancer and non-cancer samples.

The sequencing data is analyzed according to the following procedure:

Step 1: Sequences are ranked according to frequencies in entire aptamer pool recovered in round 9 after negative selection against beads conjugated to microvesicle-depleted cancer plasma followed by positive selection against beads conjugated to cancer microvesicles.

Step 2: Fold changes are calculated between sample noted in Step 1 and: (i) same sample after additional negative selection against microvesicle depleted cancer plasma; (ii) same sample after additional negative selection against non-cancer microvesicles; (iii) same sample after additional negative selection against microvesicles depleted non-cancer plasma.

Step 3: Sequences are ranked based on fold changes calculated in Step 2 to identify sequences which are abundant or deficient in aptamer pool selected for breast cancer derived microvesicles.

Step 4: Possible mutant sequences (e.g., due to PCR or other errors) are removed based on results of consolidation analysis.

Step 5: Sequences are identified with fold changes greater than 3 and minimum frequency 50 in all three variants (i, ii and iii in step 2).

The same selection schemes as in steps 1-5 are performed for aptamers selected against beads conjugated to non-cancer microvesicles.

The resulting sequences are synthesized in two variants for further investigation: 5' biotinylated and 3' biotinylated. This provides aptamer variants that can be captured at the 5' end or the 3' end as desired. The aptamers are further synthesized with each pyrimidine (C and U) 2'Fluoro modified. The aptamers may also be synthesized as the DNA sequence corresponding to each RNA sequence. The aptamer libraries can also be filtered based on predicted secondary sequence, free energy, and other parameters as described herein. Identified sequences are commonly overrepresented in cancer positive pools as compared to controls. However, identified sequences overrepresented in the non-cancer pools are also observed.

A number of representative sequences obtained from these procedures are shown in Table 24. The sequences in the table were identified in the aptamer pools from selection against microvesicles obtained from plasma of breast cancer patients but were not in the aptamer pools selected against non-cancer plasma samples. In Table 24, the sequences are shown 5' to 3' from left to right, wherein each complete sequence consists of the indicated 5' leader sequence followed by the indicated Variable Sequence followed by the indicated 3' tail sequence. Each sequence is derived from a library having a leader and tail (see description above) with a variable sequence between. It is understood that the nucleotide sequences that are disclosed in Table 24 can also be modified to the extent that resulting modifications result in an aptamer having about 50, 55, 60, 65, 70, 75, 80, 85, 90, 95, 96, 97, 98, and 99 percent homology to the disclosed sequence and retain the functionality of binding to microvesicle antigens or functional fragments thereof.

TABLE 24

BrCa microvesicle aptamer candidate sequences

| ID | SEQ ID NO. | 5'-Leader | Variable Sequence | Tail-3' |
|---|---|---|---|---|
| BCE8 | 231032 | GGGAGGAC GAUGCGG | UACCGCCUCAUCAUCCAGACGACUCGCUGA GGACACGACGUGUA GGAUCCGAGA UCAGUUGGCUG | |
| BCE9 | 231033 | GGGAGGAC GAUGCGG | GUUCUCGCCUCUGUCCAGACGACUCGCUGA CUCAUGGUUCGAACCGGAUCCGAGA GGUAUGCAUG | |
| BCE10 | 231034 | GGGAGGAC GAUGCGG | GCGGUUUCUUCUCCUCAGACGACUCGCUGA GACUACAUGAGAUU GGAUCCGAGA AAUAAACGCGC | |
| BCE11 | 231035 | GGGAGGAC GAUGCGG | CCGCCUCGAACACUGCAGACGACUCGCUGA ACGUCGUGGAACCUUGGAUCCGAGA CGAUUGCUAG | |
| BCE12 | 231036 | GGGAGGAC GAUGCGG | AAUCACAGUAAUUC CAGACGACUCGCUGA UGCCCCUCUGAUGAAGGAUCCGAGA ACCGGUUACUU | |
| BCE13 | 231037 | GGGAGGAC GAUGCGG | CUUAGUGAUUUCGCCCAGACGACUCGCUGA GCCCCUCUGUUUAGUGGAUCCGAGA GGCCAUUGGA | |
| BCE14 | 231038 | GGGAGGAC GAUGCGG | ACACUAUUCCGGUAACAGACGACUCGCUGA GUCAUCGUUUAACCGGGAUCCGAGA UUUGUUGCAA | |
| BCE15 | 231039 | GGGAGGAC GAUGCGG | UGCGCAACGCCUUGACAGACGACUCGCUGA UUCACUCCUACAGUGGGAUCCGAGA UGUCUAUAGA | |
| BCE16 | 231040 | GGGAGGAC GAUGCGG | AAUGUUAAGCUUAC CAGACGACUCGCUGA AUACGCCUGGGUCACGGAUCCGAGA UCUUUGUUCUG | |
| BCE17 | 231041 | GGGAGGAC GAUGCGG | GUAAAUAUUCACGU CAGACGACUCGCUGA UGAAUCGCCUUGCUCGGAUCCGAGA CUCUUAGUCUG | |
| BCE18 | 231042 | GGGAGGAC GAUGCGG | CCGCCUCGGAUCGUUCAGACGACUCGCUGA CCCAAUGGUGGUACCGGAUCCGAGA CCUAUUAAUG | |
| BCE19 | 231043 | GGGAGGAC GAUGCGG | UGUAGAUCGUUCUU CAGACGACUCGCUGA AUCCGCCUCGGUCUUGGAUCCGAGA CCCCAGGUUAA | |
| BCE20 | 231044 | GGGAGGAC GAUGCGG | AUCGUCGGGCCCUUCAGACGACUCGCUGA UUAUGAAACUUACA GGAUCCGAGA UGAAAGCGCAC | |
| BCE21 | 231045 | GGGAGGAC GAUGCGG | UAAGAGUGCACAGU CAGACGACUCGCUGA ACUGCCUCGAUCCUCGGAUCCGAGA CAUGGCUUAAG | |
| BCE22 | 231046 | GGGAGGAC GAUGCGG | GAAUUAGUACUGAC CAGACGACUCGCUGA GGCCGCCUUGAUCCUGGAUCCGAGA CCGUUAGUCUG | |
| BCE23 | 231047 | GGGAGGAC GAUGCGG | GCCCGCCUCCGAAGCCAGACGACUCGCUGA CCUCCUAAGUGCACUGGAUCCGAGA UUAAACCGCG | |
| BCE24 | 231048 | GGGAGGAC GAUGCGG | CCGCCUGGGAUCACUCAGACGACUCGCUGA CUCUACGCGUAUAAAGGAUCCGAGA UGCUCUGUCA | |
| BCE25 | 231049 | GGGAGGAC GAUGCGG | AGUCUGACCCUGUUACAGACGACUCGCUGA UGGACUACCAUAUCAGGAUCCGAGA GAAAGGUACU | |
| BCE26 | 231050 | GGGAGGAC GAUGCGG | GGUGAUCCUCCCCCCCAGACGACUCGCUGA CGCCUCGAAGAUUUGGGAUCCGAGA UGCACAUAUC | |
| BCE27 | 231051 | GGGAGGAC GAUGCGG | GCUACCAUCGUCUAGCAGACGACUCGCUGA UGAGUCACCCUUAGUGGAUCCGAGA UCAUCAAGGC | |

Figure 23A:
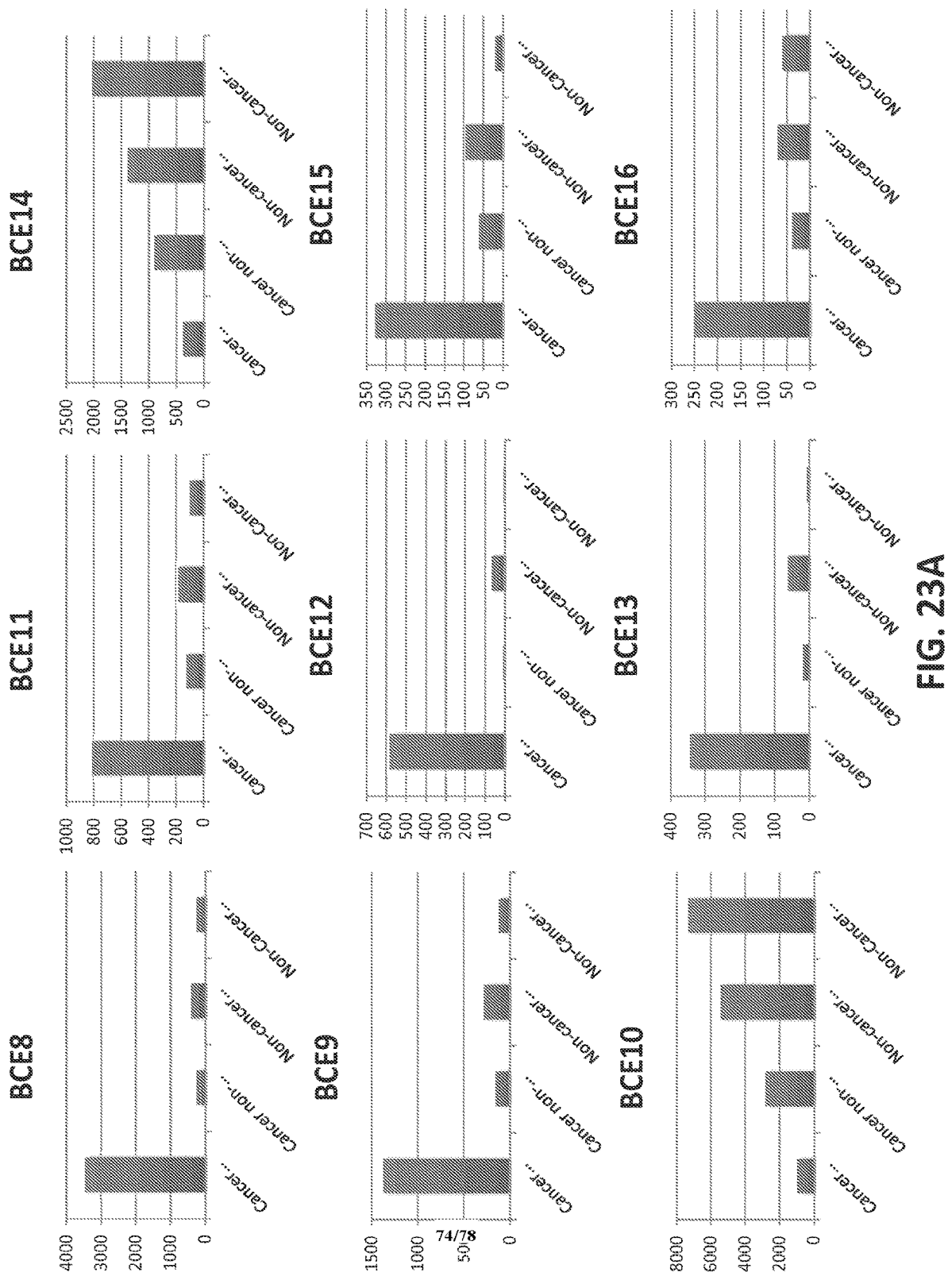
Figure 23B:
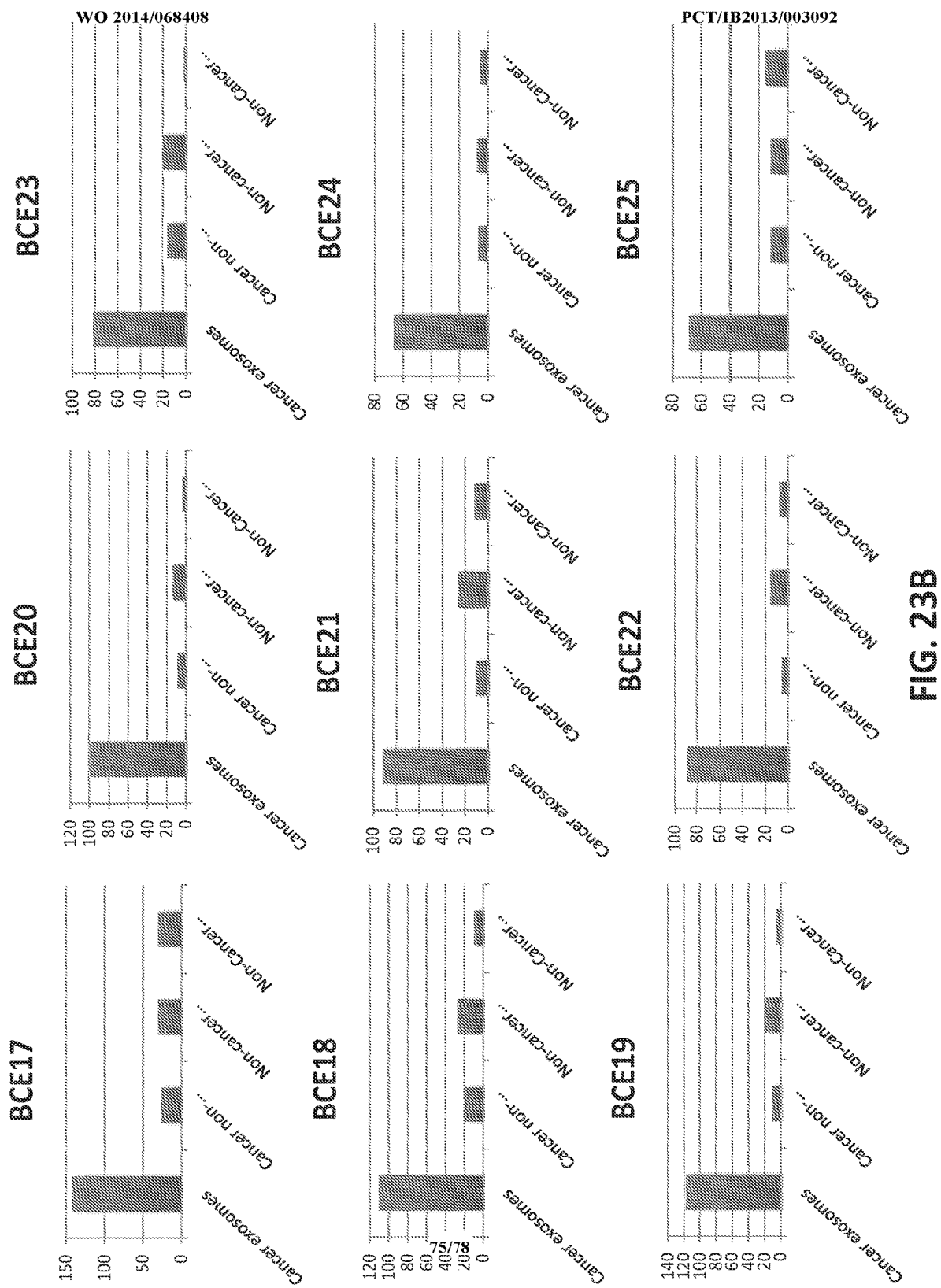

FIGS. 23A-C show binding of the indicated aptamers in Table 24 against microbeads conjugated to various input samples. The aptamer is indicated above each plot. See Table 24. The input sample is indicated on the X axis from left to right as follows: 1) Cancer Exosome: aptamer binding to microbeads conjugated to microvesicles isolated from plasma samples from breast cancer patients; 2) Cancer Non-exosome: aptamer binding to microbeads conjugated to plasma samples from breast cancer patients after removal of microvesicles by ultracentrifugation; 3) Non-Cancer Exosome: aptamer binding to microbeads conjugated to microvesicles isolated from plasma samples from normal (i.e., non breast cancer) patients; 4) Non-Cancer Non-Exosome: aptamer binding to microbeads conjugated to plasma samples from breast cancer patients after removal of microvesicles by ultracentrifugation. As shown in FIGS. 23A-C, the aptamers were each able to distinguish between the cancer microvesicle samples versus the supernatant control samples and the non-cancer microvesicles. Further, all sequences in Table 24 were observed as binding more abundantly to cancer derived microvesicles as compared to non-cancer derived microvesicles with the exception of BCE10 and BCE14, which were observed as binding more abundantly to non-cancer derived microvesicles as compared to cancer derived microvesicles.

Based on the comparisons performed in this Example, aptamers that bind different starting input are obtained, including: 1) aptamers that preferentially bind cancer-derived microvesicles over non-cancer derived microvesicles; 2) aptamers that preferentially bind non-cancer-derived microvesicles over cancer derived microvesicles; 3) aptamers that bind both non-cancer-derived microvesicles and cancer derived microvesicles (e.g., "universal" binders); and 4) aptamers that bind plasma components that have been depleted of microvesicles.

The aptamer libraries in this Example are further subjected to four rounds of additional negative and positive selection. The positive selection is performed as described in this Example. The negative selection rounds are performed using the beads conjugated to non-cancer microvesicles as negative selection for aptamers obtained by positive selection against beads conjugated to cancer microvesicles. Similarly, the negative selection rounds are performed using the beads conjugated to cancer microvesicles as negative selection for aptamers obtained by positive selection against beads conjugated to non-cancer microvesicles.

Example 21: Disease Diagnosis

This Example illustrates the use of the aptamers of the present invention to diagnose a proliferative disease.

A suitable quantity of an aptamer that binds a cancer-derived microvesicle is synthesized via chemical means known in the art. The aptamers are conjugated to a diagnostic agent suitable for detection, such as a fluorescent moiety, using a conjugation method known in the art.

The composition is applied to microvesicles isolated from blood samples taken from a test cohort of patients suffering from a proliferative disease associated with the overexpression of microvesicles, e.g., prostate, breast, or lung cancer. The composition is likewise applied to microvesicles isolated from blood samples taken from a negative control cohort, not suffering from a proliferative disease.

The use of appropriate detection techniques (e.g., microbead assay or flow cytometry) on the test cohort samples indicates the presence of disease, while the same techniques applied to the control cohort samples indicate the absence of disease.

The results show that the aptamers of the present invention are useful in diagnosing proliferative diseases.

Example 22: Therapeutic Aptamers

This Example illustrates the use of the aptamers of the present invention to treat a proliferative disease in a mouse.

A suitable quantity of an aptamer that binds a cancer-derived microvesicle is synthesized via chemical means known in the art. The aptamers are conjugated to a chemotherapeutic agent using a conjugation method known in the art. The conjugate is formulated in an aqueous composition.

The composition is administered intravenously, in one or more doses, to a test cohort of mice suffering from a proliferative disease associated with the overexpression of the microvesicles, e.g., prostate, breast, or lung cancer model. A control cohort, not suffering from a proliferative disease is administered the identical composition intravenously, according to a corresponding dosage regimen.

Pathological analysis of tumor samples and/or mouse survival indicate that mortality and/or morbidity are improved in the test cohort over the control cohort.

The results show that the aptamers of the present invention are useful in treating proliferative diseases.

Useful aptamers can be used to treat the cancer in other organisms, e.g., a human.

Example 23: Aptamer—Sequencing Detection Method

This Example illustrates the use of an aptamer pool to detect microvesicles that are indicative of a phenotype of interest. The method makes use of a pool of aptamer that have been enriched against a target of interest that is indicative of a phenotype of interest. The method in this Example allows efficient use of a library of aptamers to preferentially recognize a target entity.

For purposes of illustration, the method is described in the Example with a microvesicle target from a bodily fluid sample. One of skill will appreciate that the method can be extended to other types of target entity (e.g., cells, proteins, various other biological complexes), sample (e.g., tissue, cell culture, biopsy, other bodily fluids) and other phenotypes (other cancers, other diseases, etc) by enriching an aptamer library against the desired input samples.

General Workflow:

1) Obtain sample (plasma, serum, urine or any other biological sample) of patients with unknown medical etymology and pre-treating them accordingly to ensure availability of the target of interest (see below). Where the target of interest is a microvesicle population, the microvesicles may be isolated and optionally tethered to a solid support such as a microbead.

2) Expose sample to an aptamer pool carrying certain specificity against target of interest. As described herein, an aptamer pool carrying certain specificity against the target of interest can be enriched using various selection schemes, e.g., using non-cancer microvesicles for negative selection and cancer microvesicles for positive selection as described above. DNA or RNA aptamers can be used as desired.

3) Contact aptamer library with the sample.

4) Elute any aptamers bound to the target.

5) Sequence the eluted aptamer. Next generation sequencing methods can be used.

6) Analyze aptamer profile from the sequencing. A profile of aptamers known to bind the target of interest indicates the presence of the target within the input sample. The profile can be used to characterize the sample, e.g., as cancer or non-cancer.

Protocol Variations:

There are currently four basic protocols serving the purpose of aptamer-sequencing assay. Samples can be any biological sample.

Protocol 1:

Ultracentrifugation of 1-5 ml bodily fluid samples (e.g., plasma/serum/urine) (120K×g, no sucrose) with two washes of the precipitate to isolate microvesicles.

Measure total protein concentration of recovered sample containing the isolated microvesicles.

Conjugate the isolated microvesicles to magnetic beads (for example MagPlex beads (Luminex Corp. Austin Tex.)).

Incubate conjugated microvesicles with aptamer pool of interest.

Wash unbound aptamers by retaining beads using magnet.

Elute aptamers bound to the microvesicles.

Amplify and purify the eluted aptamers.

Aptamer sequencing (for example, Next generation methods; Ion Torrent: fusion PCR, emulsion PCR, sequencing).

Assess aptamer profile.

Protocol 2:

This alternate protocol does not include a microvesicle isolation step, microvesicles conjugation to the beads, or separate partitioning step. This may present non-specific binding of the aptamers agains the input sample.

Remove cells/debris from bodily fluid sample and dilute sample with PBS containing $MgCl_2$ (2 mM).

Pre-mix sample prepared above with aptamer library.

Ultracentrifugation of aptamer/sample mixture (120K×g, no sucrose). Wash precipitated microvesicles.

Recover precipitate and elute aptamers bound to microvesicles.

Amplify and purify the eluted aptamers.

Aptamer sequencing (for example, Next generation methods; Ion Torrent: fusion PCR, emulsion PCR, sequencing).

Assess aptamer profile.

Protocol 3:

This protocol uses filtration instead of ultracentrifugation and may require less time and sample volume.

Remove cells/debris from bodily fluid sample and dilute it with PBS containing $MgCl_2$ (2 mM).

Pre-mix sample prepared above with aptamer library.

Load sample into filter (i.e., 150K or 300K MWCO filter or any other that can eliminate unbound or unwanted aptamers). Centrifuge sample to concentrate. Concentrated sample should contain microvesicles.

Wash concentrate. Variant 1: Dilute concentrate with buffer specified above to the original volume and repeat centrifugation. Variant 2: Dilute concentrate with buffer specified above to the original volume and transfer concentrate to new filter unit and centrifuge. Repeat twice.

Recover concentrate and elute aptamers bound to microvesicles.

Amplify and purify the eluted aptamers.

Aptamer sequencing (for example, Next generation methods; Ion Torrent: fusion PCR, emulsion PCR, sequencing).

Assess aptamer profile.

Protocol 4:

Ultracentrifugation of 1-5 ml bodily fluid sample (120K×g, no sucrose) with 2 washes of the precipitate to isolate microvesicles.

Pre-mix microvesicles with aptamer pool.

Load sample into 300K MWCO filter unite and centrifuge (2000×g). Concentration rate is ~3×.

Wash concentrate. Variant 1: Dilute concentrate with buffer specified above to the original volume and centrifuge. Repeat twice. Variant 2: Dilute concentrate with buffer specified above to the original volume and transfer concentrate to new filter unit and centrifuge. Repeat twice Recover concentrate and elute aptamers bound to microvesicles.

Amplify and purify the eluted aptamers.

Aptamer sequencing (for example, Next generation methods; Ion Torrent: fusion PCR, emulsion PCR, sequencing).

Assess aptamer profile.

Example 24: Detection of Cancer Derived Microvesicle Using Aptamer Sequencing

The method in Example 23 above is used to detect microvesicles in a bodily fluid sample that are derived from cancer cells. The microvesicles may be shed from the cancer cells. The aptamer library comprises a subset of aptamers described in Examples 18-20 above that preferentially bind to microvesicles from cancer patients versus non-cancer individuals. The sequences are listed herewith as SEQ ID NOs. 231032-241535. The method is used to detect the presence or absence of microvesicles that are indicative of cancer.

The test sample comprises plasma samples that are collected from patients having or suspected of having a cancer. A test sample is a sample to be characterized by the methods of the invention. The method is performed to determine the presence or absence of cancer derived microvesicles in the circulation of the patient.

The method is further used to detect evidence of cancer prior to biopsy. The test sample comprises plasma samples that are collected from patients scheduled to undergo a biopsy. The test sample is a sample to be characterized by the methods of the invention. The method is performed to determine the presence or absence of cancer derived microvesicles in the circulation of the patient prior to biopsy. If cancer-derived microvesicles are not detected, a decision may be made to forego biopsy.

Example 25: Aptamer Selection for Microvesicles

Classic aptamer selection techniques (i.e., SELEX) are typically performed to enrich aptamers for the particular target in "clean" conditions when interference with non-target molecules (competitors) is minimized. However, various applications for the selected aptamers require that the aptamers work to bind their target in diverse environments, e.g., in a biological sample or tissue culture media with an abundance of potentially interfering molecules. In this case, such interfering molecules which were not present during the selection process may interfere with target recognition by aptamers selected in ideal conditions. This Example provides an aptamer selection process to screen an aptamer library in order to select aptamers highly specific for the targets and also able to perform in a biological sample comprising the potentially interfering molecules.

In this Example, the target comprises a microvesicle such that an aptamer library is screened for members that bind cancer-derived microvesicles as compared to normal (non-cancer controls) microvesicles. One of skill will appreciate that the method can be extended to other types of target entity (e.g., cells, proteins, various other biological complexes). The method can employ various sample types (e.g., tissue, cell culture, biopsy, other bodily fluids) and can be directed to target molecules that can be used to characterize various phenotypes (various cancers, other diseases, etc) by enriching an aptamer library against the desired input samples. In addition, the cancer and normal samples can be switched to screen for aptamers that preferentially bind the normal samples.

Variant 1: Microvesicle based aptamer selection in competition with plasma depleted from microvesicles. Workflow:

Microvesicles are isolated from cancer and normal plasma samples using ultracentrifugation. The supernatant comprising microvesicle depleted sample is stored as a negative control sample.

Capture/conjugate the isolated microvesicles to magnetic beads.

Start the aptamer screening and selection process using microvesicle conjugated beads mixed with supernatant from above (i.e., microvesicle depleted plasma). Supplement supernatant with $MgCl_2$. Aptamer screening and selection for cancer-derived and normal (non-cancer derived) microvesicles can be done in parallel. Each round consists of negative and positive selections as desired.

Since the initial aptamer library is exposed simultaneously to microvesicle targets as well as competitors (soluble proteins) from plasma, aptamers recovered from the microvesicles/beads may be more specific for the targets on microvesicle membrane. Such aptamers may perform effectively in biological samples without requiring extensive purification of the target prior to target binding/detection.

Variant 2: Aptamer selection for cancer-derived microvesicles (e.g., shed from cancer cells) in competition with microvesicles isolated from normal samples. Workflow:

Microvesicles are isolated from cancer and normal plasma samples using ultracentrifugation.

Capture/conjugate the isolated cancer-derived microvesicles to magnetic beads.

Start the aptamer screening and selection process using cancer microvesicles conjugated beads mixed with normal microvesicles (non-conjugated) supplemented with $MgCl_2$. Aptamer screening and selection is performed for the cancer-derived microvesicles only by retaining only the aptamers that are retained with the magnetic beads.

Since aptamer library will be exposed simultaneously to both types of microvesicles (cancer and normal), the method selects aptamers that preferentially bind cancer-derived microvesicles in the presence of non-cancer microvesicles.

Variant 3: Aptamer selection for cancer-derived microvesicles (e.g., shed from cancer cells) in competition with normal plasma (non microvesicles depleted). Workflow:

Microvesicles are isolated from cancer plasma samples using ultracentrifugation.

Capture/conjugate the isolated cancer-derived microvesicles to magnetic beads.

Start the aptamer screening and selection process using cancer microvesicles conjugated beads mixed with normal plasma (non-conjugated) supplemented with $MgCl_2$. Aptamer screening and selection is performed for cancer microvesicles only by retaining only the aptamers that are retained with the magnetic beads.

This approach combines advantages form Variants 1 and 2 above. Each round includes competition with normal plasma. Aptamers should be more selective for target in the presence of interfering plasma proteins and other biological entities.

Variant 4: Parallel Cancer/Normal aptamer selection on mixed beads. Workflow:

Capture/conjugate cancer-derived microvesicles to magnetic beads

Capture/conjugate normal (non-cancer) microvesicles to non-magnetic beads

Mix both bead sets and perform the aptamer screening and selection process with the starting aptamer library Separate the magnetic and non-magnetic beads after incubation with aptamer library. Use a magnet to capture the magnetic beads then centrifuge to separate the nonmagnetic beads.

Wash the separated magnetic and non-magnetic beads separately.

Elute and re-amplify aptamers from both types of beads separately.

Round 2: mix amplified aptamer pools from both types of beads and add to the mixed beads Repeat from above Advantages of variant 4 include: (i) using same aliquot of aptamer library to start the aptamer screening and selection process for both cancer and non-cancer microvesicles; (ii) using competition between cancer and non-cancer microvesicles directly in one mixture in each round; (iii) supernatant can be added as additional competitor to increase selection stringency; (iv) parallel enrichment for cancer and non-cancer specific aptamers in competition to result in aptamers identifying only normals or only cancer (since there is a choice to bind either one).

Example 26: Selection of Universal Blocking DNA Aptamers for Carboxyl Groups

Blocking buffers known in the art generally comprise a mixture of synthetic peptides, BSA, trypsinized proteins, or random DNA pools (synthetic or natural, e.g., Salmon sperm DNA). These complex mixtures may contain molecules which besides blocking effect might provide additional false targets in an assay, thereby generating false positives.

In this Example, a blocking reagent was developed to serve as a specific blocker for a carboxylated substrate. The blocking reagent comprises an aptamer with minimized cross-reactivity to any other target than carboxyl groups on the substrate.

Preliminary experiments were done with five DNA aptamer libraries with $10^{15}$ sequences each and variable lengths (60, 65, 70, 75, 80-mers) were pre-amplified and strand separated so that forward strand (non-biotinylated) serves as an aptamer. Multiple rounds of negative selection and positive selection were performed as described in Example 9 above.

To identify potential blocking aptamers, sequences commonly observed in the selection processes with different protein targets were identified. One aptamer sequence that was identified as one of the most abundant recovered from the above selection process was also identified in the final aptamer pool for each of the different target proteins. This aptamer was selected as the aptamer blocking candidate:

(SEQ ID NO. 230938)
5'-GGTGTGGTTGGGGGTGGTGGAGGTGGGGTTTGTGGTGGGA

Without being bound by theory, it is that sequences which are rich in guanine bind carboxyl groups on the substrate beads via hydrogen bonds. See FIGS. 16A and 16B. FIG. 16A illustrates hydrogen bonding between a portion of an aptamer 1601 to carboxyl groups 1602 attached to a planar substrate 1603. FIG. 16B illustrates hydrogen bonding between a portion of an aptamer 1601 to carboxyl groups 1602 attached to a microsphere substrate 1604. Carboxyl groups 1602 are further attached to an antibody 1605. Guanine is the only one nucleotide which can form two hydrogen bounds.

Testing

In order to test the blocking properties of the aptamer blocking candidate, the following experiment was performed:

To obtain the aptamer, the 40-mer PBP pool after positive selection, which contained the most of the sequence presented above, was PCR re-amplified, strand separated and ethanol precipitated. Some related sequences were also amplified but were not considered to affect the results at their lesser concentrations.

Microbeads conjugated to antibodies against the desired protein biomarkers (SSX4, PBP, SPDEF, EPCAM, KLK2, SSX2), to a negative control anti-IgG2B antibody, and to negative control aptamers (i.e., aptamers which are non-binding to any of the protein biomarkers, referred to as Neg5 and Neg9) were blocked with a solution comprising the above candidate blocking aptamer for 20 min. After incubating the antibody-conjugated microbead with the aptamer blocking candidate, standard microbead blocking solution was added and the beads were incubated for additional 20 min. The beads were then distributed into PCR strip tubes and mixed with plasma samples from patients with prostate cancer or benign prostate disorders. The mixture was incubated for 2 h at 37° C. The samples were transferred to the filter plates and mixed with a biotinylated anti-EpCAM aptamer that should recognize microvesicles captured by the antibody-conjugated microbeads. The beads were incubated with the anti-EpCAM aptamer for 1 h at room temperature.

Figure 24A:
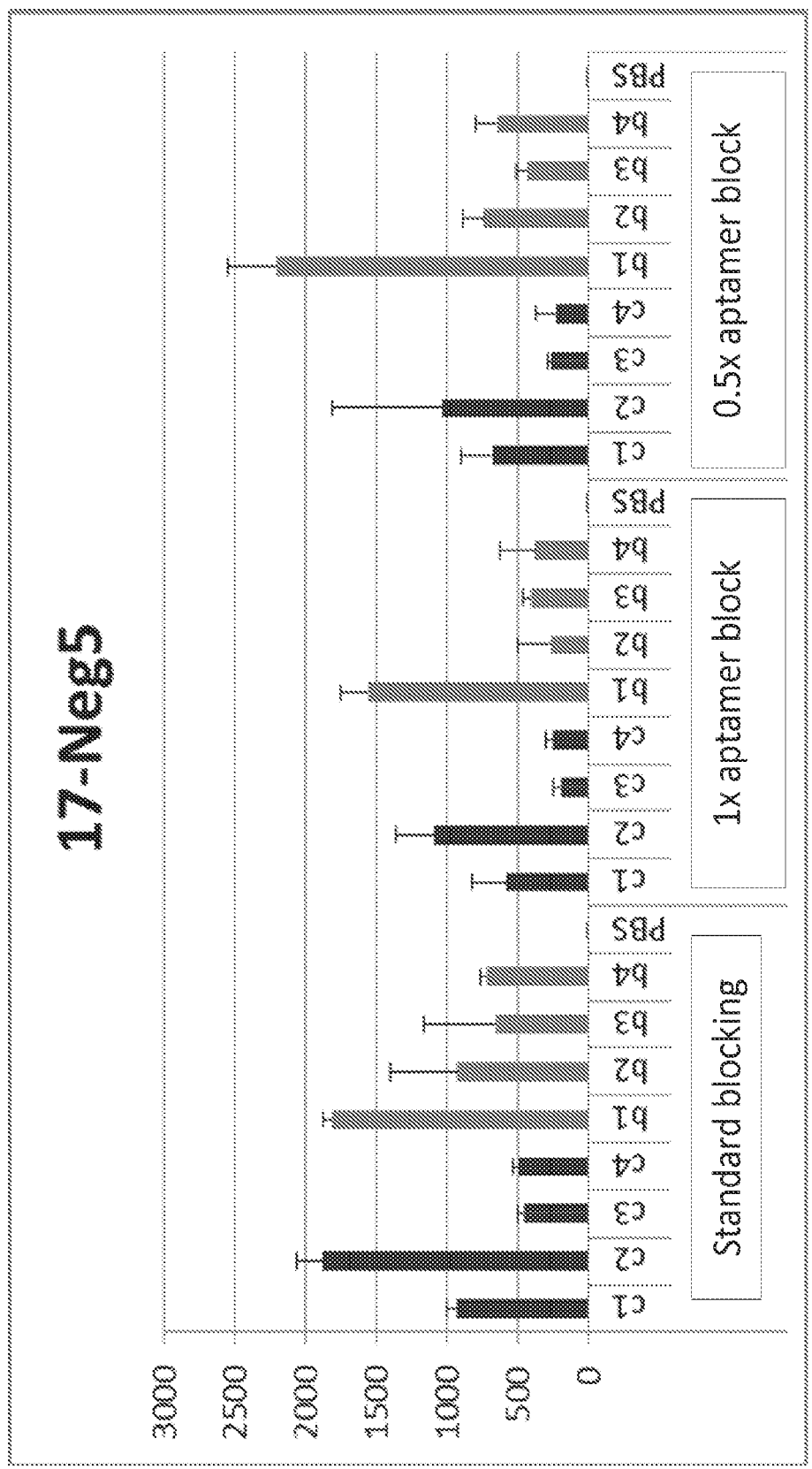
FIGS. 24A-24B illustrate detection of microvesicles in patient plasma samples. Microvesicles from the plasma samples were incubated with microbeads conjugated to antibodies to microvesicle antigens of interest. The bead-captured microvesicles were detected with a biotinylated anti-EpCAM aptamer and streptavidin-phycoerythrin (SAPE). The Y-axis shows fluorescent signal from bead-captured microvesicles. The X-axis shows bars for plasma from patients with prostate cancer (c1-c4), benign prostate conditions (b1-b4) and a PBS negative control. Different experimental conditions are indicated underneath the X-axis. Prior to incubation with the plasma samples, the antibody-conjugated beads were blocked with a standard blocking agent (StartingBlock Blocking Buffers, Thermo Fisher Scientific Inc., Rockford, Ill., USA), with the standard block and 1× concentration of a blocking aptamer of the invention (primarily SEQ ID NO. 230938), or with the standard block and 0.5× concentration of a blocking aptamer of the invention (primarily SEQ ID NO. 230938).
Figure 24B:
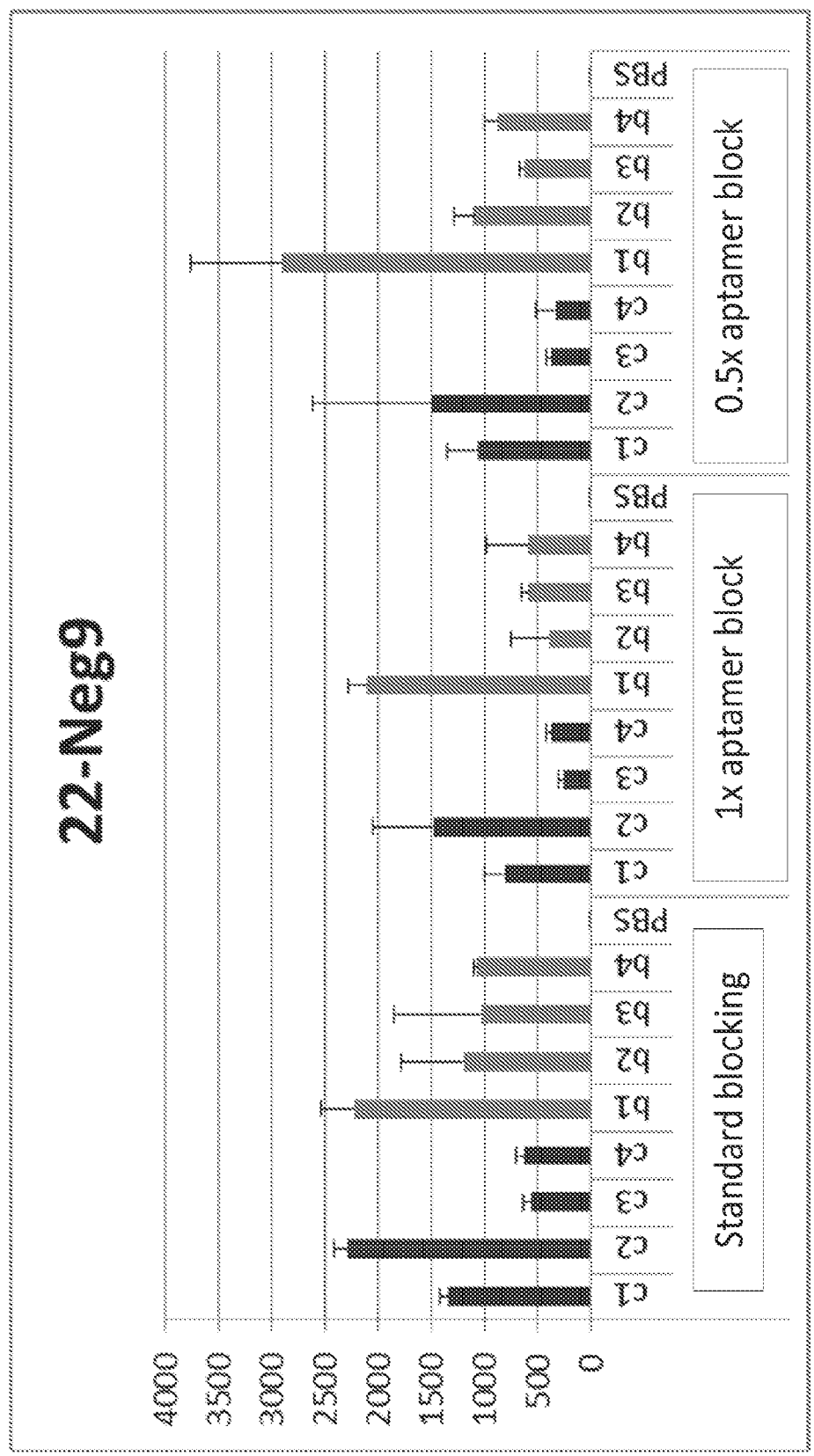

The plates were washed and Streptavidin-PE was added and samples were incubated for 30 minutes at room temperature. The plates were washed, and fluorescence of the PE in complex with the microbeads was measured with 100 µl solution of the sample. Each sample was tested in triplicate wells and results were averaged. Negative controls using an anti-IgG2b antibody and two non-binding aptamers were also run. Results are shown for the two non-binding aptamers, Neg5 and Neg9, are shown in FIGS. 24A-24B, respectively. The results as shown in FIGS. 24A-24B revealed lower background levels when beads were pre-blocked with standard blocking conditions (StartingBlock Blocking Buffers, Thermo Fisher Scientific Inc., Rockford, Ill., USA), standard blocking with 1× candidate blocking aptamer (~34 µg/ml), and to standard blocking with 0.5× aptamer blocking.

Because the blocking aptamers are rich in guanine, the experiments were repeated with a solution comprising a single guanine nucleotide only followed by the standard starting block. No improvements were observed using only the single nucleotide.

Example 27: Illustrative Blocking Aptamer Sequences

The following Table 25 comprises illustrative aptamers of the invention. The aptamers were part of the pool of aptamers described in Example 26 and were part of the common pool of blocking aptamers identified. It is understood that the nucleotide sequences that are disclosed in Table 25 can be modified to the extent that resulting modifications result in an aptamer having about 50, 55, 60, 65, 70, 75, 80, 85, 90, 95, 96, 97, 98, and 99 percent homology to the disclosed sequence and retain the functionality of binding carboxyl functional groups. As used in the context of any defined numerical unit herein, the term "about" means variance of 10% above or below that numerical unit and all units in between.

TABLE 25

Illustrative Aptamers

| Sequence 5'->3' | SEQ ID NO. |
| --- | --- |
| GGTGTGGTTG GGGGTGGTGG AGGTGGGGTT TGTGGTGGGA | 230938 |
| GGTGTGGGTT GGGGGTGGTG GAGGTGGGGT TTGTGGTGGG A | 230939 |
| GGTGTGGTTG GGGGTGGTGG AGGTGGGTTT GTGGTGGGA | 230940 |
| GGTGTGGGTT GGGGGTGGTG GAGGTGGGGT TTGTGGTGGG AG | 230941 |
| GGTGTGGGTT GGGGGTGGTG GAGGTGGGGT TTGTGGTGGG | 230942 |
| GGTGTGGGTT GGGGGTGGTG GAGGTGGGGT | 230943 |
| GGTGTGGGTT GGGGGTGGTG GAGG | 230944 |
| GGTGTGGGTT GGGGGTGGTG GAG | 230945 |
| GGTGTGGTTG GGGGTGGTGG AGGTGGGTT TGTGGTGGGA G | 230946 |
| GTGGAGGTGG GGTTTGTGGT GGGA | 230947 |
| GGGTGGTGGA GGTGGGTTTG TGGTGGGA | 230948 |
| GGTGGTGGTT GGGGGTGGTG GAGGTGGGGT TTGTGGTGGG A | 230949 |
| GTGGAGGTGG GTTTGTGGTG GGA | 230950 |
| GGGTGGTGGA GGTGGGGTTT GTGGTGGGA | 230951 |
| CGTTGAAGGT TGGGCGGTTG GGGTGTGTGG GATTGGTGGG | 230952 |
| GGTGTGGTTG GGGGTGGTGG AGGTGGGGT | 230953 |
| GTGGGGTTTG TGGTGGGA | 230954 |
| CGCCTAGAGG TCGGGTGGTT GGGGTTGTGG GATGGGGGT | 230955 |
| TGGTGTTGTC CTGTTGGCCT TTTGTTGTCG CACCCTCGCA | 230956 |
| GGTGTGGTTG GGGGTGGTGG AGGTGGGGTT TGTGGTGGG | 230957 |
| GGTGGAGGTG GGGTTTGTGG TGGGA | 230958 |
| GGTGTGGTTG GGGGTGGTGG AGG | 230959 |
| GGTGTGGTTG GGGTGGTGGA GGTGGGTTTG TGGTGGGA | 230960 |
| CTGCCTGGCA CGTCGCGTTT GTGTTCGTTG GTCGGTCAGG | 230961 |
| TGAGGGTGGG TGGTGGGTTG ATGTTGGTTG ATGGGGTGG | 230962 |
| GGTGGAGGTG GGTTTGTGGT GGGA | 230963 |
| GGTGTGGGTT GGGGTGGTGG AGG | 230964 |
| GGTGTGGGTT GGGGGTGG | 230965 |
| GGTGTTGTGG GGGTGTTTGT CG | 230966 |
| CGGTCTTGCT GGGTGGTCGT GCGGTGTTCG TGGTGGTGGT | 230967 |
| GGTGTGGTTG GGGGTGGTGGA GGTGGGGTTT GTGGTGGGA | 230968 |
| GGTGTGGTTG GGGGTGGTGG AGGTGGGTTG TGGTGGGA | 230969 |
| TGGTTGGGGG TGGTGGAGGT GGGGTTTGTG GTGGGA | 230970 |
| GGTGTGGGTT GGGGGTGGTG | 230971 |
| GGTTGGGGGT GGTGGAGGTG GGGTTTGTGG TGGGA | 230972 |
| GGTGTGGGTT GGGGTGGTGG AG | 230973 |
| GGTGTGGGTT GGGGGTGGTG GAGGTGGGGT TTG | 230974 |
| GGTGTGGTTG GGGTGGTGGA GGTGGTTGT GGTGGGA | 230975 |
| GGTTTGTGGT GGGA | 230976 |
| GGTGTGGGTT GGGGGTGGTG GAGGTGGGGT TTGTGG | 230977 |
| GTGGAGGTGG GTTGTGGTGG GA | 230978 |
| TCACGTGCTT CATTTTTGTG TTCCCTCCTC CTGCTGCGCA | 230979 |
| GGTGTGGGTT GGGGGTGGTG GAGGTGGG | 230980 |
| GTGGTGGAGG TGGGTTTGTG GTGGGA | 230981 |
| GTGGTGGAGG TGGGGTTTGT GGTGGGA | 230982 |
| GGTGTTGGTG GGGGTGTTTG TCG | 230983 |
| GGGTGGTGGA GGTGGGTTGT GGTGGGA | 230984 |
| GTGTGGTTGG GGGTGGTGGA GGTGGGTTT GTGGTGGGA | 230985 |

TABLE 25-continued

Illustrative Aptamers

| Sequence 5'->3' | SEQ ID NO. |
|---|---|
| TGGTGGGA | 230986 |
| AGGTGTGGTT GGGGGTGGTG GAGGTGGGGT TTGTGGTGGG A | 230987 |
| GTGGGTTGTG GTGGA | 230988 |
| GTGGGTTTGT GGTGGGA | 230989 |
| ACACGAACGC GCATTGTTTT CGCATCCTTC CTCCTTTCCA | 230990 |
| TGGGCGGGGG TGGTTGTATC TTCTATGGGA GGGGGTTGGC | 230991 |
| GGTGTGGGTT GGGGGTGGTG GAGGTGGGGT T | 230992 |
| GGTGTGGTTG GGGGTGGTGG AGGTGGGGTT GTGGTGGGA | 230993 |
| CGTGATGTGG GTGGGTGGTG GGCTTGGTGT GTGGGGTGG | 230994 |
| GGTGTGGGTT GGGGGTGGTG GAGGTGGGGT TGTGGTGGGA G | 230995 |
| GGTGTGGGTT GGGGTGGTGG AGGTGGGGTT TGTGGTGGGA | 230996 |
| GGTGTGGTTG GGGGTGGTGG AG | 230997 |
| GGTGTGGGTT GGGGTGGTGG AGGTGGGGT | 230998 |
| GGTGTGGTTG GGGGTGGTGG AGGTGGG | 230999 |
| GGTGTGGTTG GGGGTGGTGG AGGTGGGGTT TGTGG | 231000 |
| TGTGGTGGGA | 231001 |
| GGTGTGGGTT GGGGGTGGTG GAGGTGGGGT TTGGTGGTGG GAG | 231002 |
| GGTGTGGTTG GGGTGGTGGA GGTGGGTTGT GGTGGA | 231003 |
| GGGGTGGTGG AGGTGGGGTT TGTGGTGGGA | 231004 |
| GGTGTGGGTT GGGG | 231005 |
| GGTGTGGTTG GGGGTGGTG | 231006 |
| GCGGTCTTCG TTCGTCGTCG TGACCTCGTA TCTTTGGCTT | 231007 |
| GGTGTGGTTG GGGGTGGTGG AGGTGGGGTT TGTGGTGGA | 231008 |

Example 28: Microsphere Bound Microvesicles

Microvesicles can be bound to a substrate using various methods. In this Example, three methods are used to attach microvesicles to a substrate: 1) direct conjugation; 2) lipid anchoring; 3) antibody binding; and 4) aptamer binding. See schematics in FIGS. 7A-D. FIG. 7A illustrates direct conjugation of a carboxylated microsphere to a vesicle surface antigen. FIG. 7B illustrates anchoring of a microvesicle to a microsphere via a biotin functionalized lipid anchor. FIG. 7C illustrates antibody binding to a vesicle surface antigen, wherein the antibody is conjugated to a carboxylated microsphere. FIG. 7D illustrates aptamer binding to a vesicle surface antigen, wherein the aptamer is conjugated to a carboxylated microsphere. Microsphere attached microvesicles produced by the methods in this Example can be used to screen an aptamer library as described in the Examples above.

Figure 8A:
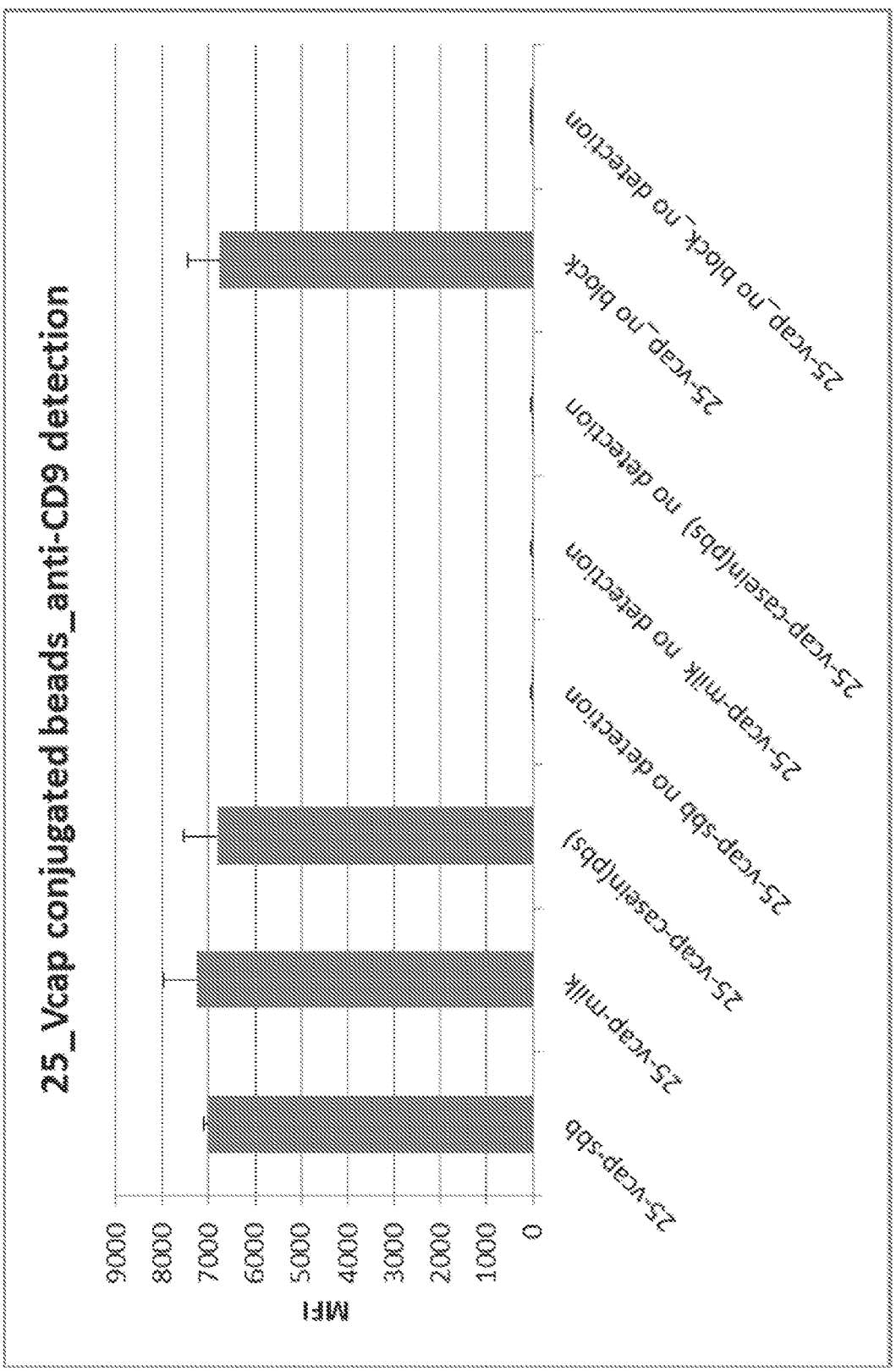
FIGS. 8A-8B illustrate detection of VCAP derived microvesicles conjugated to microspheres. The bead-conjugated vesicles were detected using MagPlex beads according to manufacturer's protocol (Luminex Corp., Austin Tex.). The microvesicles were detected with phycoerythrin (PE) labeled antibodies to CD9 (FIG. 8A) or CD63 (FIG. 8B), two common microvesicle surface proteins. The Y-axis in the figures shows median fluorescent intensity (MFI) of the detected microvesicles. Various experimental conditions are indicated along the X axis. Assays were performed with various blocking agents ("SBB": StartingBlock, Thermo Fisher Scientific Inc., Rockford, Ill.; "milk": dried milk blocking buffer; "Casein(pbs)": casein blocking buffer) or no blocking ("no block"). Controls were run without detectors where indicated.
Figure 8B:
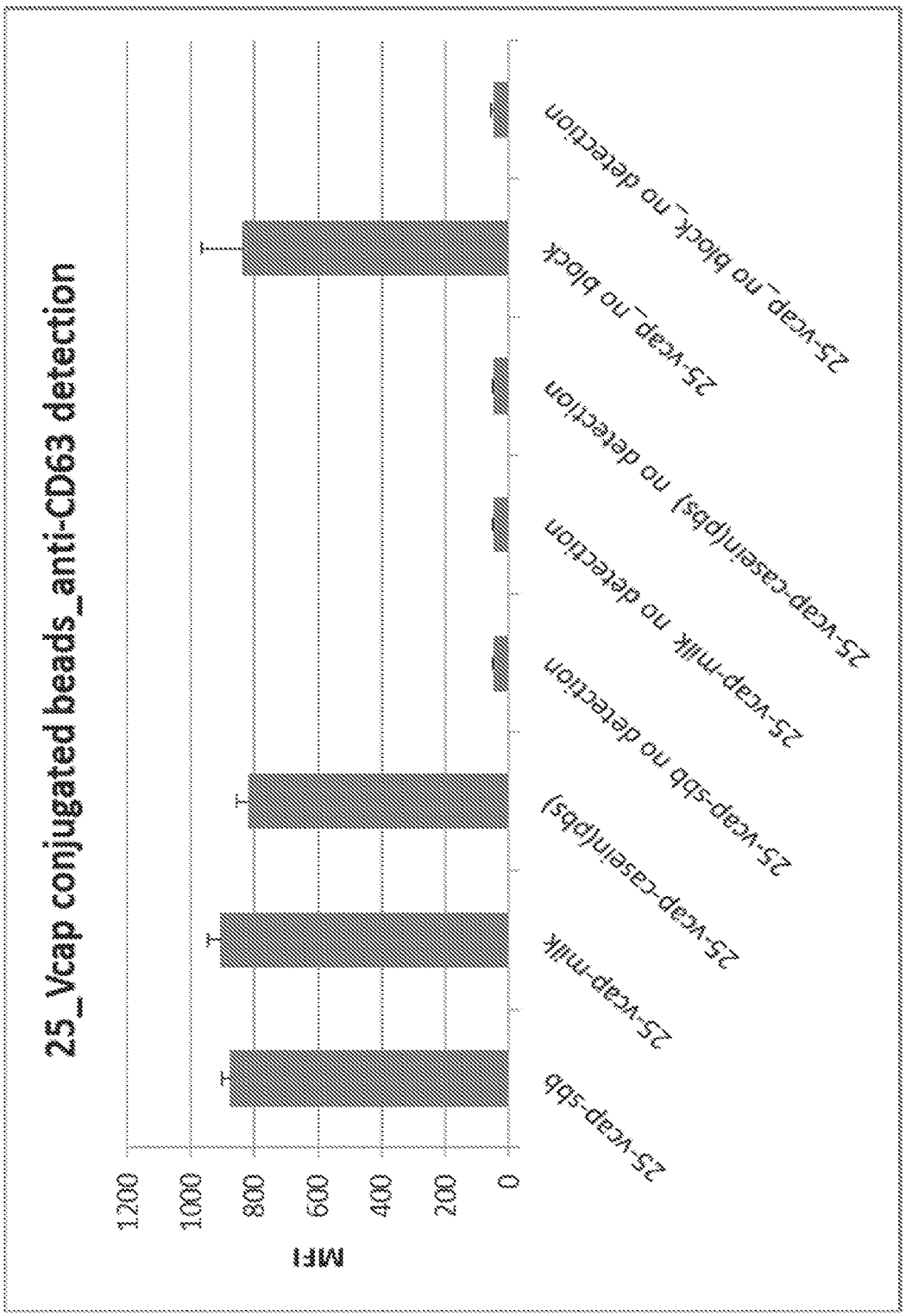

Direct Conjugation:

Direct conjugation of microvesicles to microspheres was tested using microvesicles released from the VCAP prostate cancer cell line. Protocol: VCAP microvesicles were conjugated to MagPlex beads (Luminex Corp, Austin Tex.) according to protocol established for antibodies (5 million beads, 20 µg microvesicles). See Example 29 below for detailed protocol. Isolated microvesicles were conjugated to carboxylated beads using standard two-step carbodiimide chemistry as known in the art. The MagPlex assay was performed according to manufacturer's protocol with 1200 beads per well. The beads were tested with three blocking buffers as well as without blocking to exclude any possible bead driven signals. To label the microvesicles, the beads were incubated with 5 µg/ml of PE labeled anti-tetraspanin detector antibodies (anti-CD9-PE and anti-CD63-PE) for 1 h at room temperature. Results are shown in FIGS. 8A-8B. As it seen from the figures, the bead-conjugated VCAP microvesicles were specifically detected with both detector antibodies. Further, the response to specific antibodies reflected the natural prevalence of CD9 and CD63 surface proteins in microvesicles (i.e., CD9 is more prevalent than CD63, which is reflected in the greater MFI values when using anti-CD9 detector antibodies (FIG. 8A) versus anti-CD63 detector antibodies (FIG. 8B)).

Figure 9A:
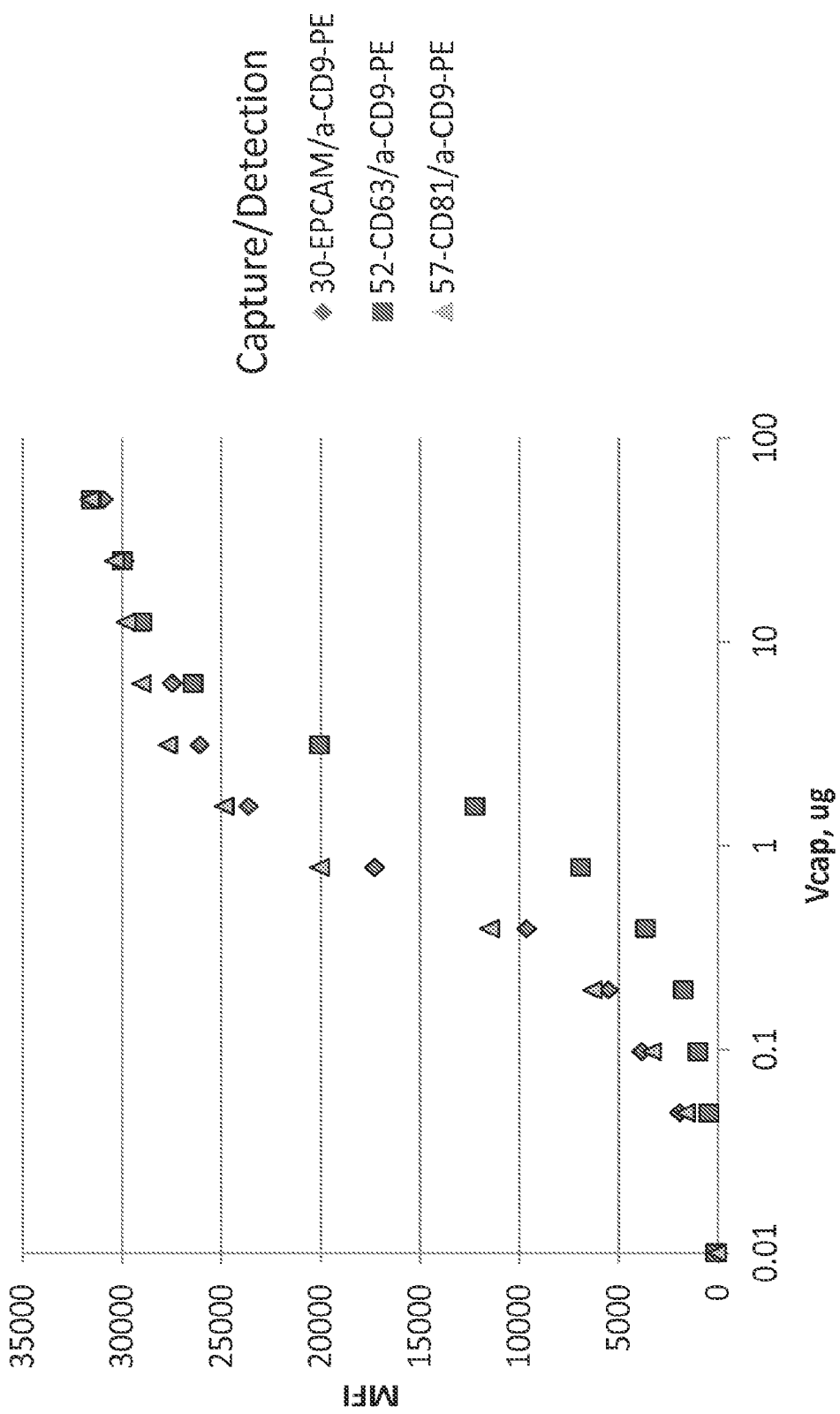
FIGS. 9A-9D illustrate capture of microvesicles using antibody-conjugated microspheres.
Figure 9B:
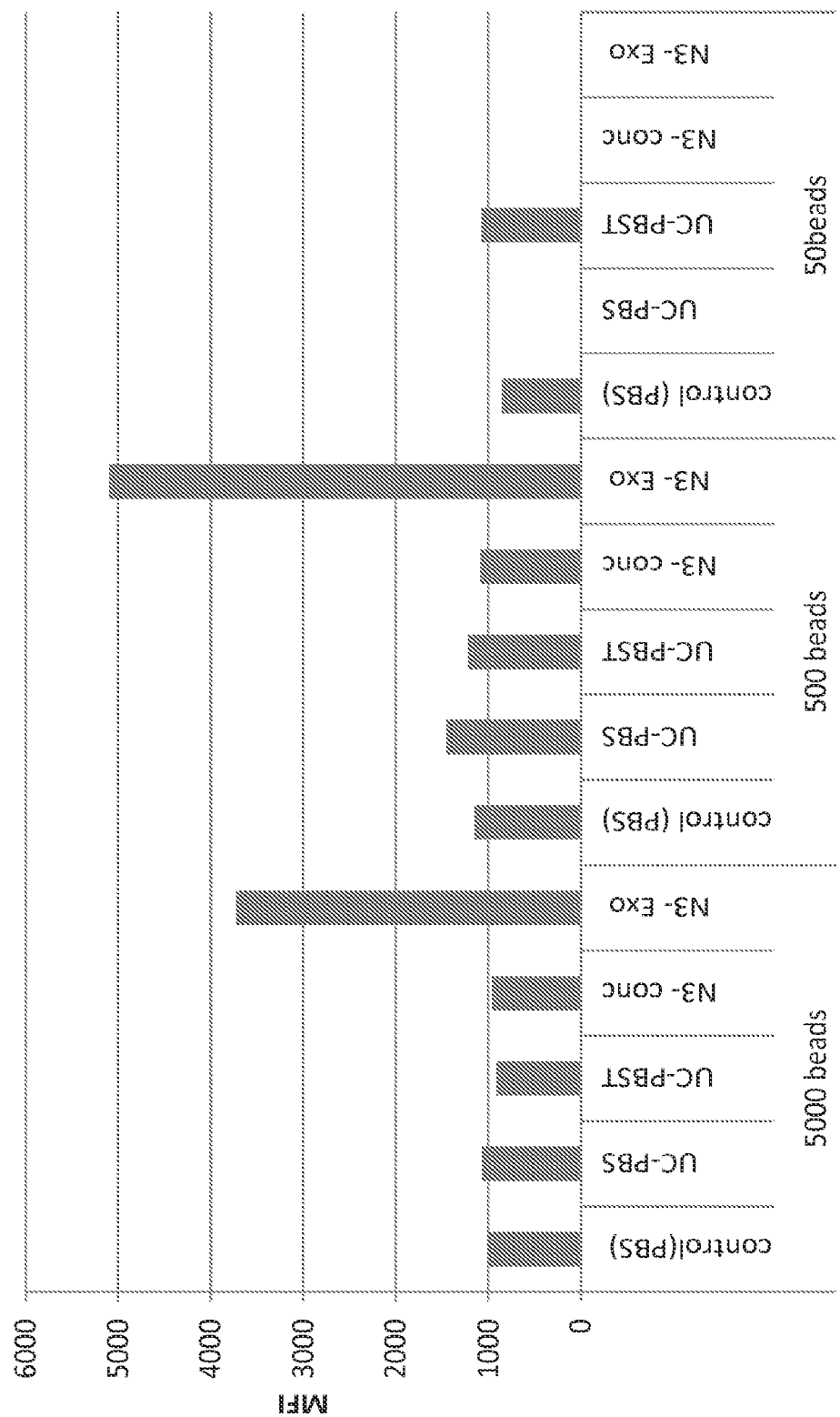
Figure 9C:
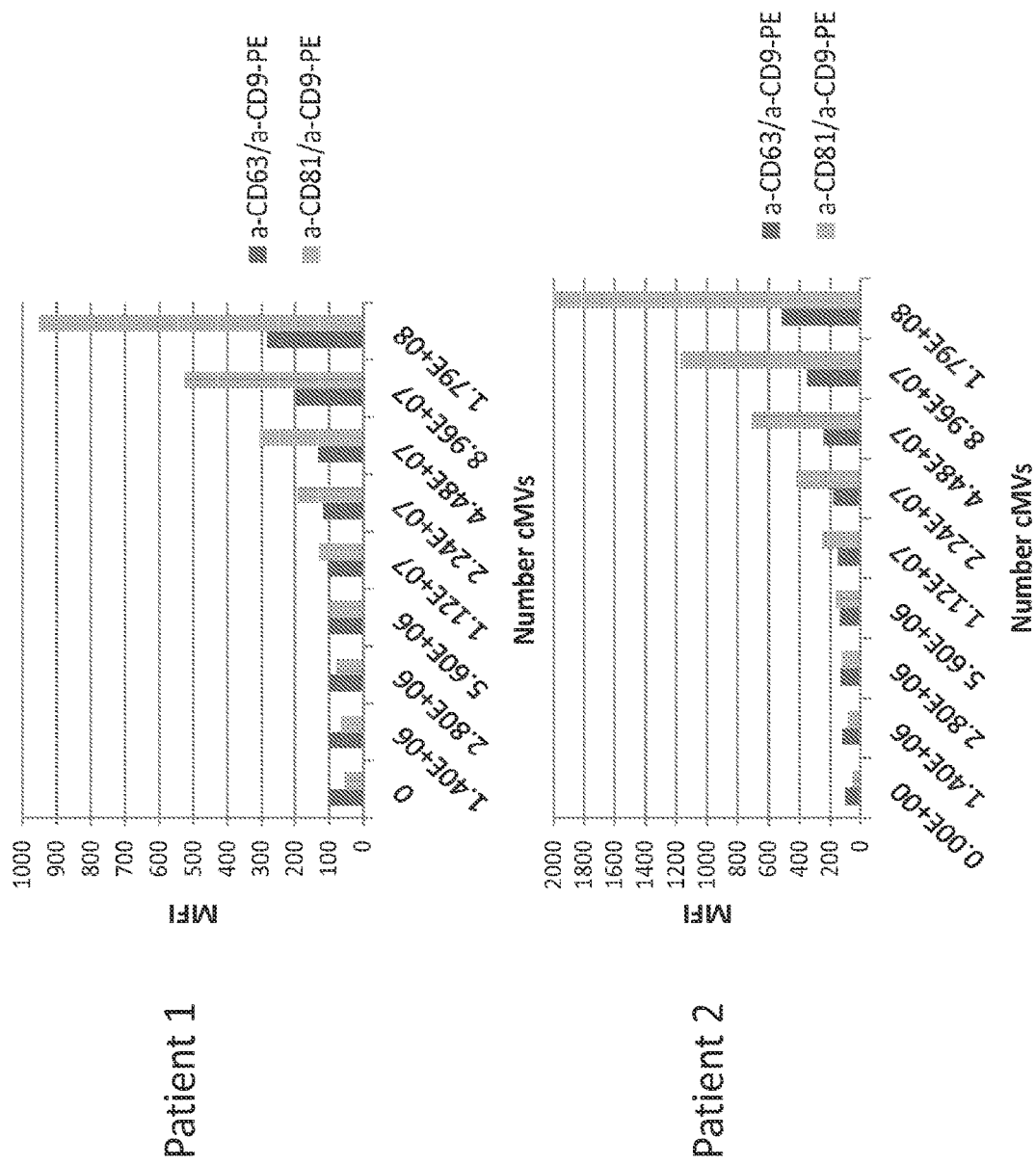
Figure 9D:
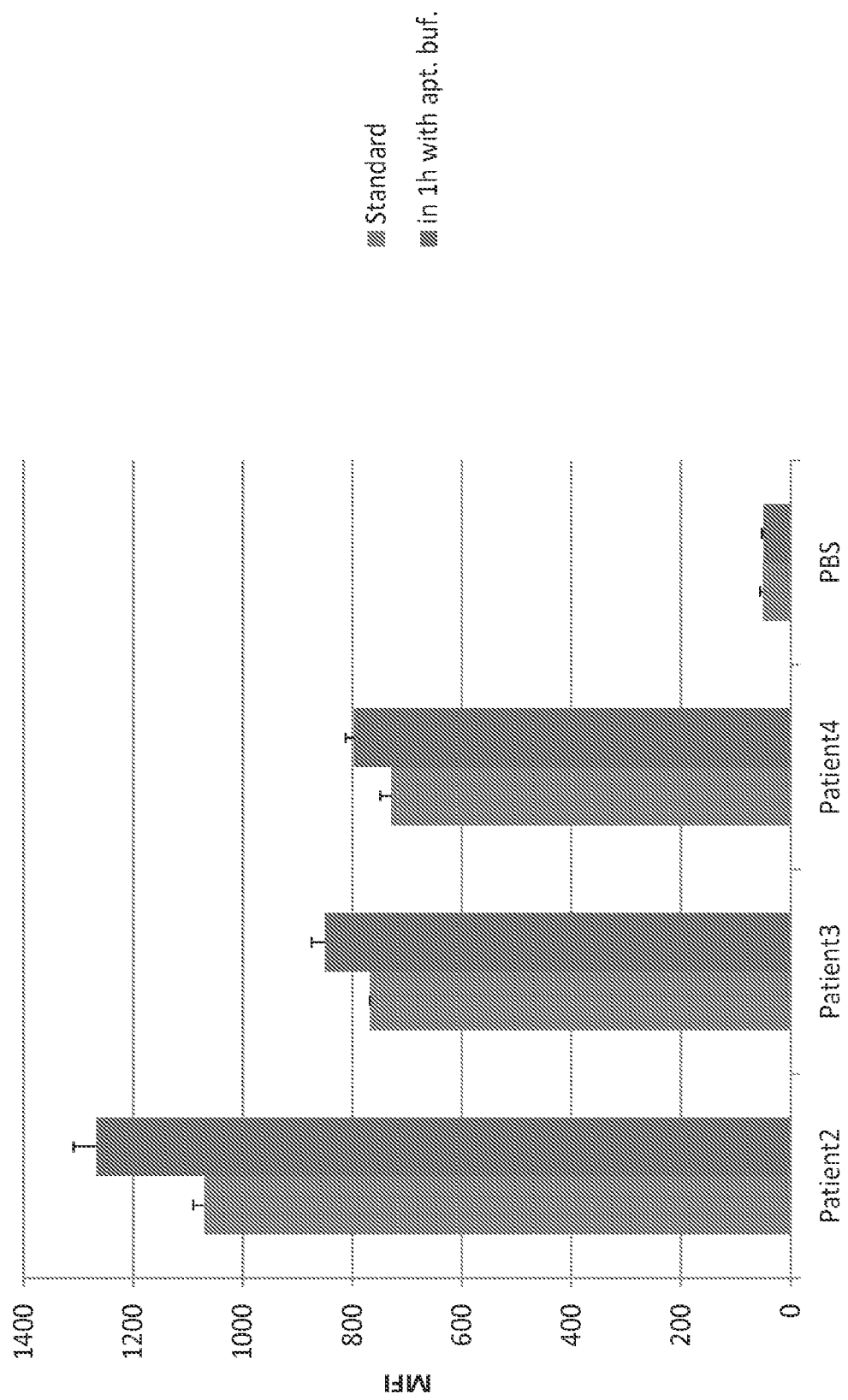

Antibody Binding:

MagPlex beads were conjugated with antibodies to EpCAM, CD63 or CD81 according to manufacturer's protocol (Luminex Corp., Austin Tex.). The microvesicles were detected with phycoerythrin (PE) labeled antibodies to CD9, a common microvesicle surface protein. The Y-axis in the figures shows median fluorescent intensity (MFI) of the detected microvesicles. Results are shown in FIGS. 9A-9E. As shown in FIGS. 9A and 9C, increasing amounts of vesicles from VCap cells (FIG. 9A) or patient plasma samples (FIG. 9C) resulted in increasing MFI signal. Sample preparation appeared to effect the signal detected, as ExoQuick isolated vesicles yielded greater signal than those isolated with ultracentrifugation or ultracentrifugation. See FIG. 9B. Finally, the antibody-captured vesicles appeared to be stably tethered to the microbeads, as shown by stable signal after prolonged incubation. See FIG. 9D.

Lipid Anchoring:

VCAP microvesicles were conjugated to microspheres using the microvesicle lipid membrane as a conjugation target. A heterobifunctional crosslinker with a lipid functional group was used as shown in FIG. 10A. The linkage between the microsphere and microvesicle using the heterobifunctional crosslinker is as shown in FIG. 10B. Streptavidin coated beads are incubated with biotin functionalized lipid (the "lipid anchor"), washed and incubated with the desired microvesicles. As shown in FIG. 10B, the attachment of the lipid anchor with the microsphere is performed by streptavidin-biotin affinity, and capturing of the microvesicles is facilitated by phospholipid analog incorporation into the vesicle lipid bilayer membrane. The protocol is as follows:

1. Wash 600 µl of Streptavidin coated magnetic beads (Pierce cat #88817) twice with phosphate buffered saline (PBS).

2. Resuspend the beads in 500 µl of PBS only (as a control) or 500 µl PBS with 1 µl of functionalized lipid moiety [1,2-dihexadecanoyl-sn-glycero-3-phosphoethanolamine-N-(cap biotinyl)] (Avanti Polar Lipids, Alabaster Ala., cat #870277X; 1:1000 dilution in water). Incubate for 30 min at 37° C. with rotation.

3. Wash the beads with UltraPure water (Invitrogen cat #10977) then twice with PBS (HyClone cat # SH30256).

4. Add 100 µg of VCAP microvesicles or human plasma to the beads with or without the lipid anchor. Raise volume to 500 µl with PBS. Incubate for 1 h at 37° C. with rotation. Store for overnight at 4° C.

5. Pipet an aliquot of the beads needed for the following experiment, wash twice with PBS.

6. Test the presence of captured microvesicles with flow cytometry (MoFlo™ XDP instrument, Beckman Coulter, Inc, Indianapolis Ind.) using microvesicle specific antibodies PE-labeled anti-human CD9 (BD Pharmingen cat #555372) and PE-labeled anti-human CD63 (BD Pharmingen cat #556020), or an isotype control PE mouse IgG1 kappa (eBioscience cat #12-4714-42).

7. Samples were incubated for 1 hour at room temperature on an Eppendorf MixMate in the dark. The beads were then washed twice and resuspended in PBS, and analyzed on MoFlo XDP or Luminex 200.

Figure 10G:
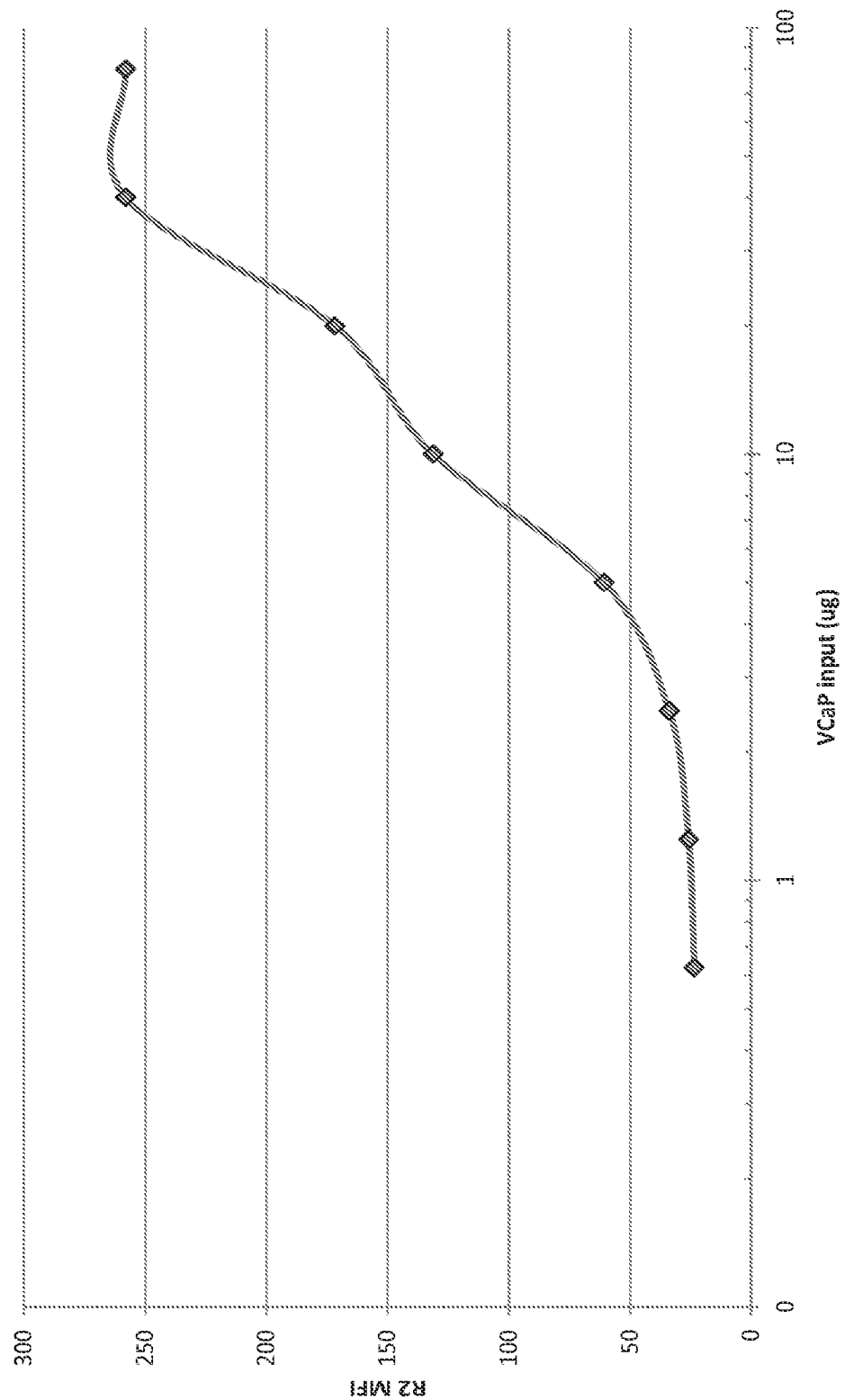
FIG. 10G illustrates titration of varying amounts of lipid-anchored vesicles detected as above.
Figure 10H:
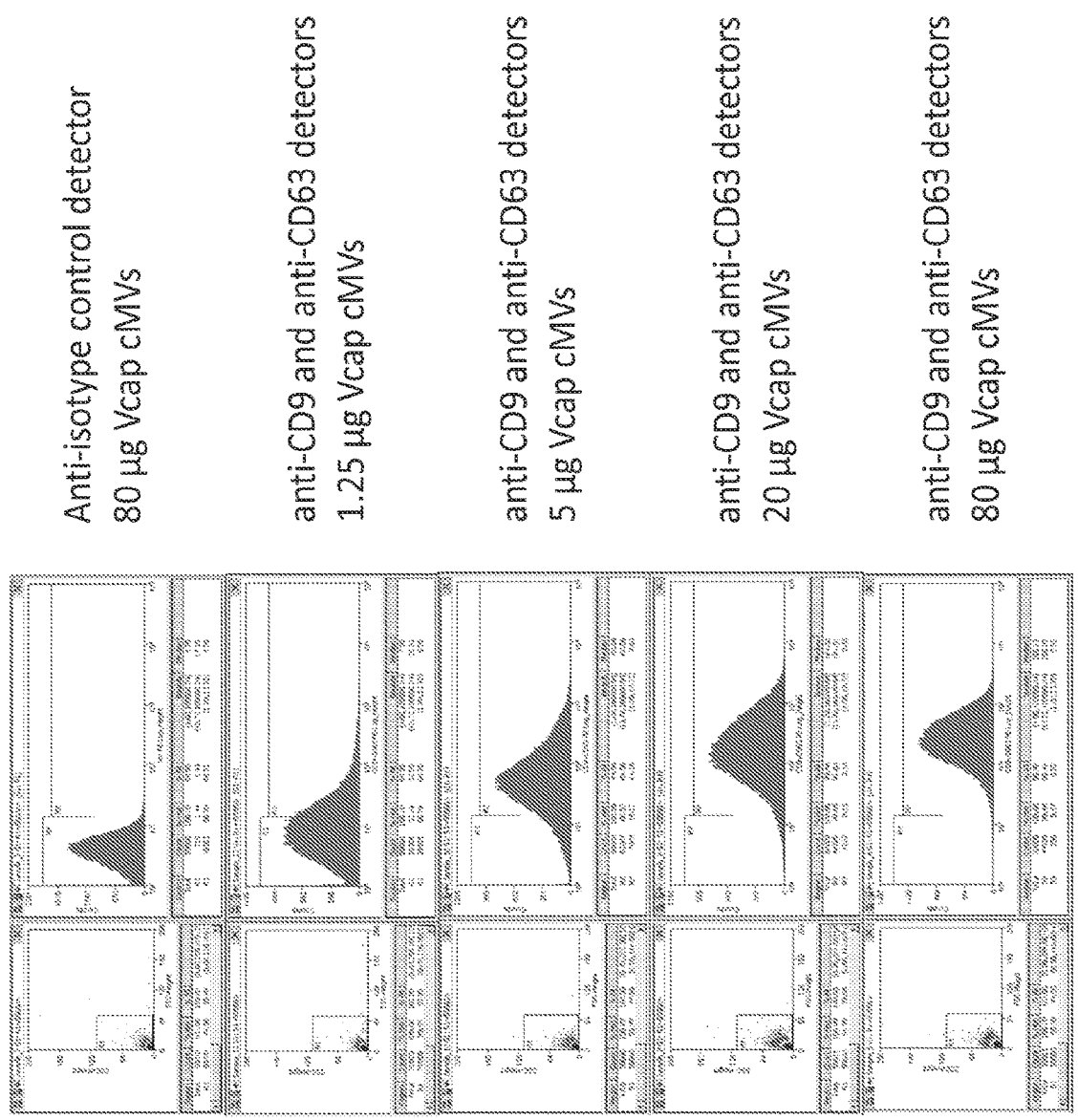
FIG. 10H illustrates another view of titration of varying amounts of lipid-anchored vesicles detected as above. The indicated amount of VCap vesicles (cMVs) were detected using either a PE labeled anti-Mouse IgG antibody as a control or PE labeled anti-CD9 and anti-CD63 antibodies.
Figure 10I:
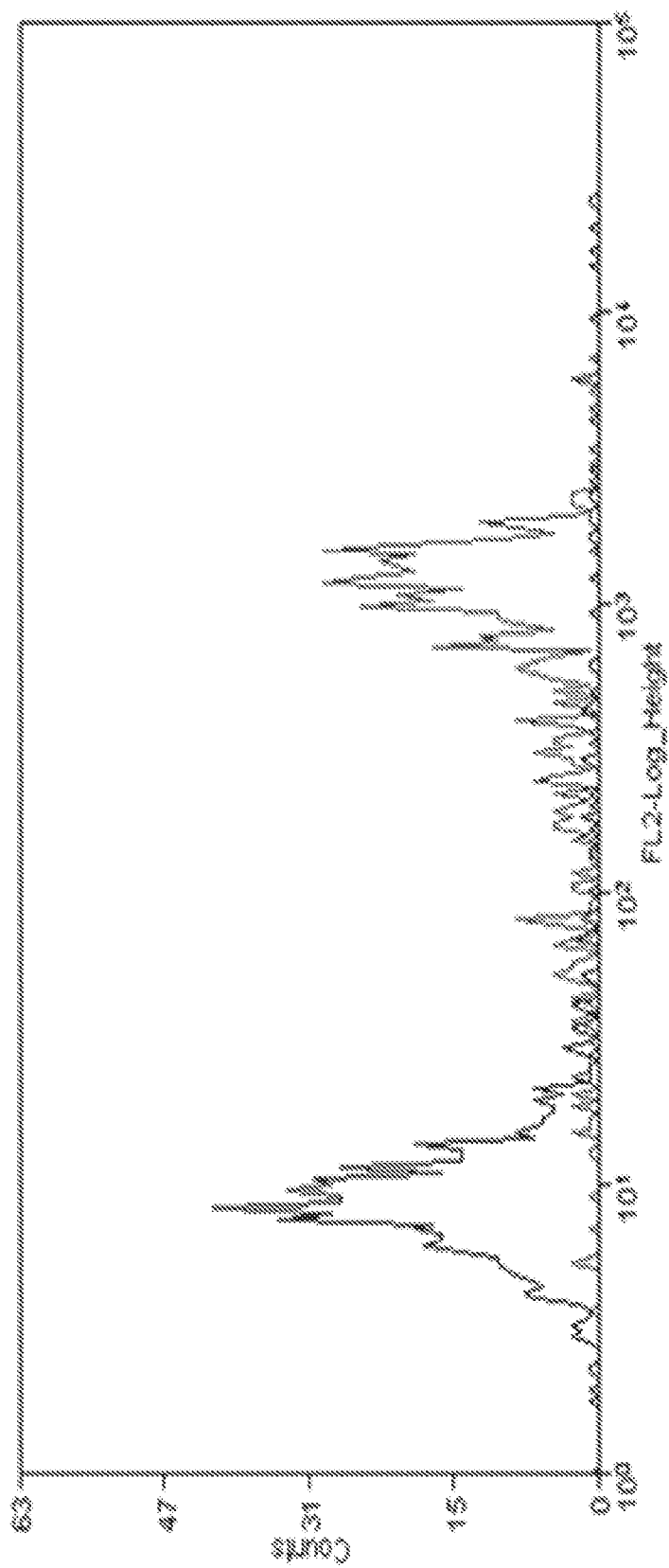
FIGS. 10I-10J illustrate capture of VCaP EVs (40 mg/mL) by lipid moiety on LumAvidin microspheres and detected with anti-CD9-PE and anti-CD63-PE by MoFlo (FIG. 10I) or with anti-CD9-PE by Luminex (FIG. 10J).

Following this protocol, VCaP microvesicles were captured by the biotinylated lipid moiety [1,2-dihexadecanoyl-sn-glycero-3-phosphoethanolamine-N-(cap biotinyl)] bound to magnetic streptavidin beads. When these microvesicles were stained with PE-labeled antibodies against the tetraspanins CD9 and CD63, the MFI of the PE signal detected by MoFlo titrated along with the input amount of VCaP microvesicles. Furthermore, the beads were saturated with microvesicles at the highest concentrations of VCaP input. See FIGS. 10C-10F for results demonstrating enrichment of bead-conjugated microvesicles in the presence of the lipid anchor. The signal derived from the lipid-anchored vesicles was correlated to the amount of vesicles, as shown in FIG. 10G and FIG. 10H.

Figure 10J:
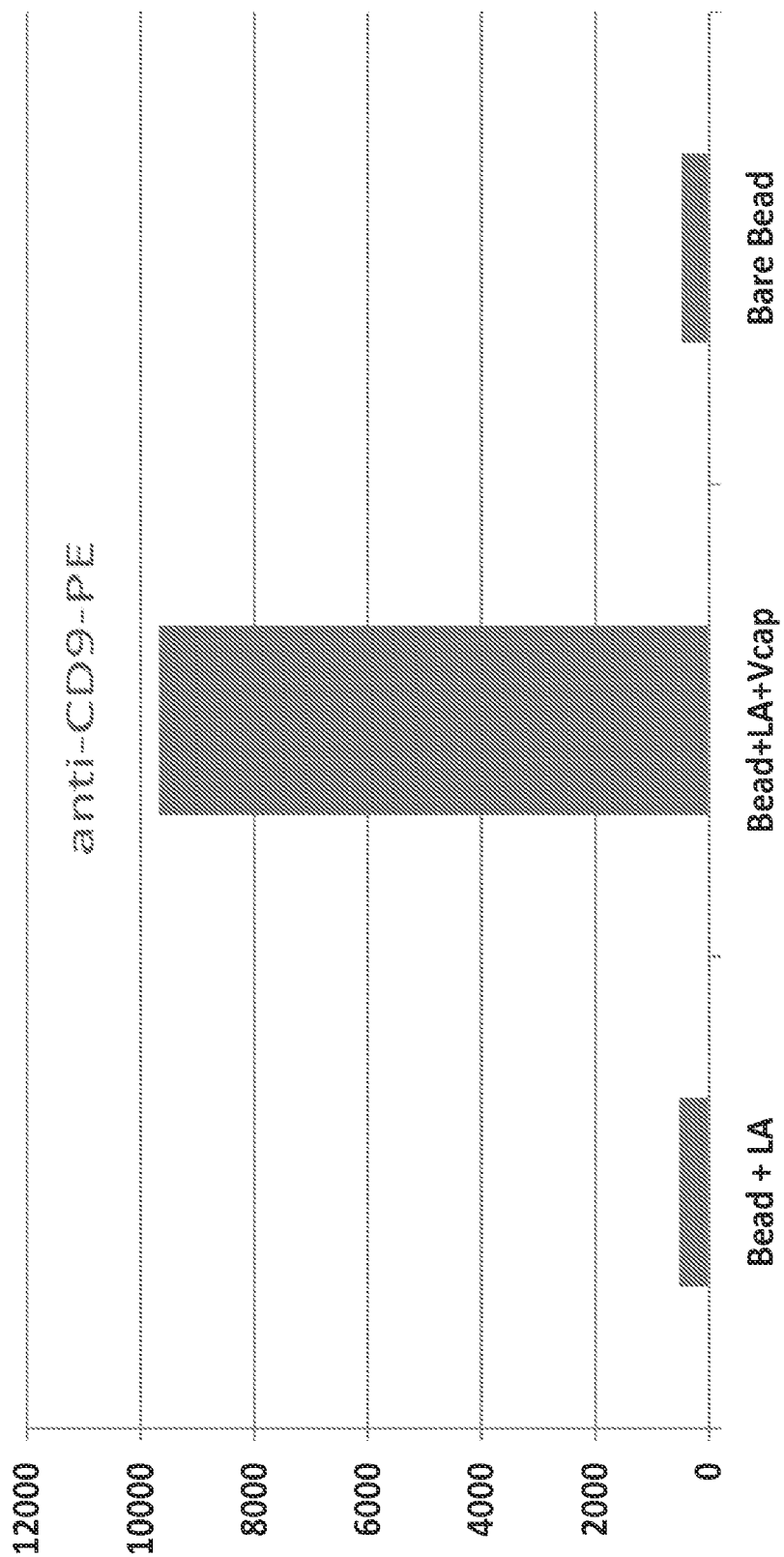

The biotinylated lipid moiety was also bound to LumAvidin beads and used to capture VCaP microvesicles, which could then be analyzed by using either traditional flow cytometry (FIG. 10I) or Luminex (FIG. 10J). Tetraspanin signal was only detected in samples containing beads bound with the lipid moiety and incubated with microvesicles; control samples containing no microvesicles or in which beads were not bound to the lipid moiety were negative for anti-CD9 signal.

Lectin Binding:

Lectins are carbohydrate-binding protein. Various lectins can be used to bind sugar moieties on the surface of microvesicles. For example, concanavalin A (ConA) is a lectin that binds specifically to certain structures found in various sugars, glycoproteins, and glycolipids, mainly internal and nonreducing terminal α-D-mannosyl and α-D-glucosyl groups. Streptavidin coated beads are incubated with biotin functionalized ConA, washed and incubated with the desired microvesicles.

Microsphere conjugated microvesicles produced by either method above can be used to screen an aptamer library as described in the Examples herein.

Effects of Sample Preparation:

Sample preparation can be optimized for the capture and/or detection of substrate-tethered microvesicles. As shown in FIG. 10K and FIG. 10L, few lipid-anchored vesicles were found when anchoring vesicles isolated from plasma samples using ultracentrifugation Similar results were observed when the plasma-derived vesicles were isolated using ExoQuick (not shown). Moreover, similar results were also observed when using microvesicles from plasma samples directly conjugated to microspheres (not shown). Without being bound by theory, it was hypothesized that highly abundant proteins in plasma samples may interfere with the microvesicle lipid anchoring or direct substrate conjugation. To test this theory, Vcap microvesicles were detected with (FIG. 10N) or without (FIG. 10M) 30 mg/ml human serum albumin (HSA) added to the samples prior to detection. These figures show that the signal of the detected vesicles was diminished in the presence of HSA.

Various methods to improve the sample preparation of blood-derived microvesicles include depletion of highly abundant proteins (e.g., HSA/IgG/Fibrinogen), removal of blood-based lipids, plasma concentration with 150k, 300K and 1000K MWCO filters to remove proteins and other interfering materials, and/or affinity isolation (e.g., immunoprecipitation or affinity chromatography) using binding agents against vesicle surface antigens. These approaches are then followed by vesicle isolation (e.g., ultracentrifugation, ultrafiltration, Exoquick).

Figures 10O, 10P:
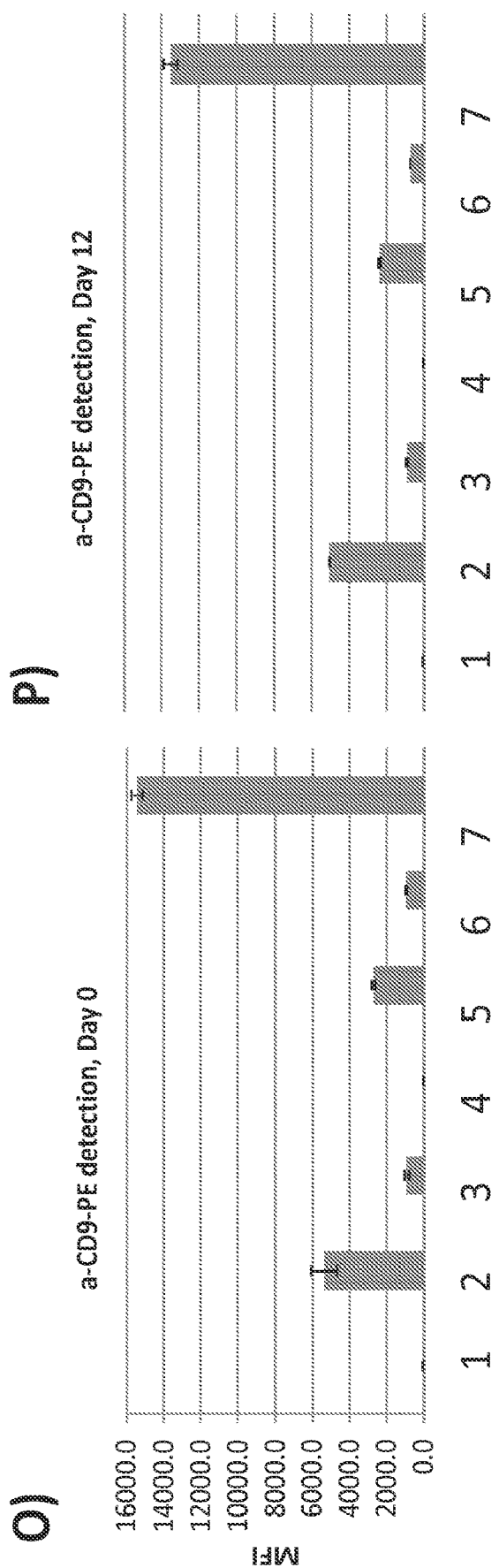

Stability:

Because the microvesicles are covalently coupled to the microbeads, there should minimal "bleeding" of conjugated microvesicles from the beads once conjugation is done and the beads are properly washed. An experiment was performed to test the stability of bead-conjugated microvesicles. Microvesicles purified using various methods were directly conjugated to microspheres as described above. The signal from the microvesicle conjugated beads were determined after storage of the conjugated beads for 2-3 days at 4° C. and again after the same beads were stored for 11-12 days at −80° C. Microvesicles were labeled with PE-conjugated anti-CD9 antibody or PE-conjugated anti-CD63 antibody. MFI values for each of the lots of beads were determined. FIGS. 10O-10P shows that minimal degradation of signal was observed before and after 12 days of storage at −80° C. using the anti-CD9 detector. Vesicles isolated using different methods were tested as indicated by conditions along the X-axis: 1) ExoQuick™ Kit (System Biosciences, Inc., Mountain View, Calif.) followed by ultrafiltration; 2) ultracentrifugation; 3) ultracentrifugation followed by Exoquick; 4) ExoQuick to ExoMir™ Kit (Bioo Scientific Corp., Austin Tex.); 5) ultrafiltered VCAP vesicle prep #1; 6) ultrafiltered VCAP vesicle prep #2; and 7) ultrafiltration followed by ultracentrifugation. Identical results were observed with the anti-CD63 detector.

Figure 11A:
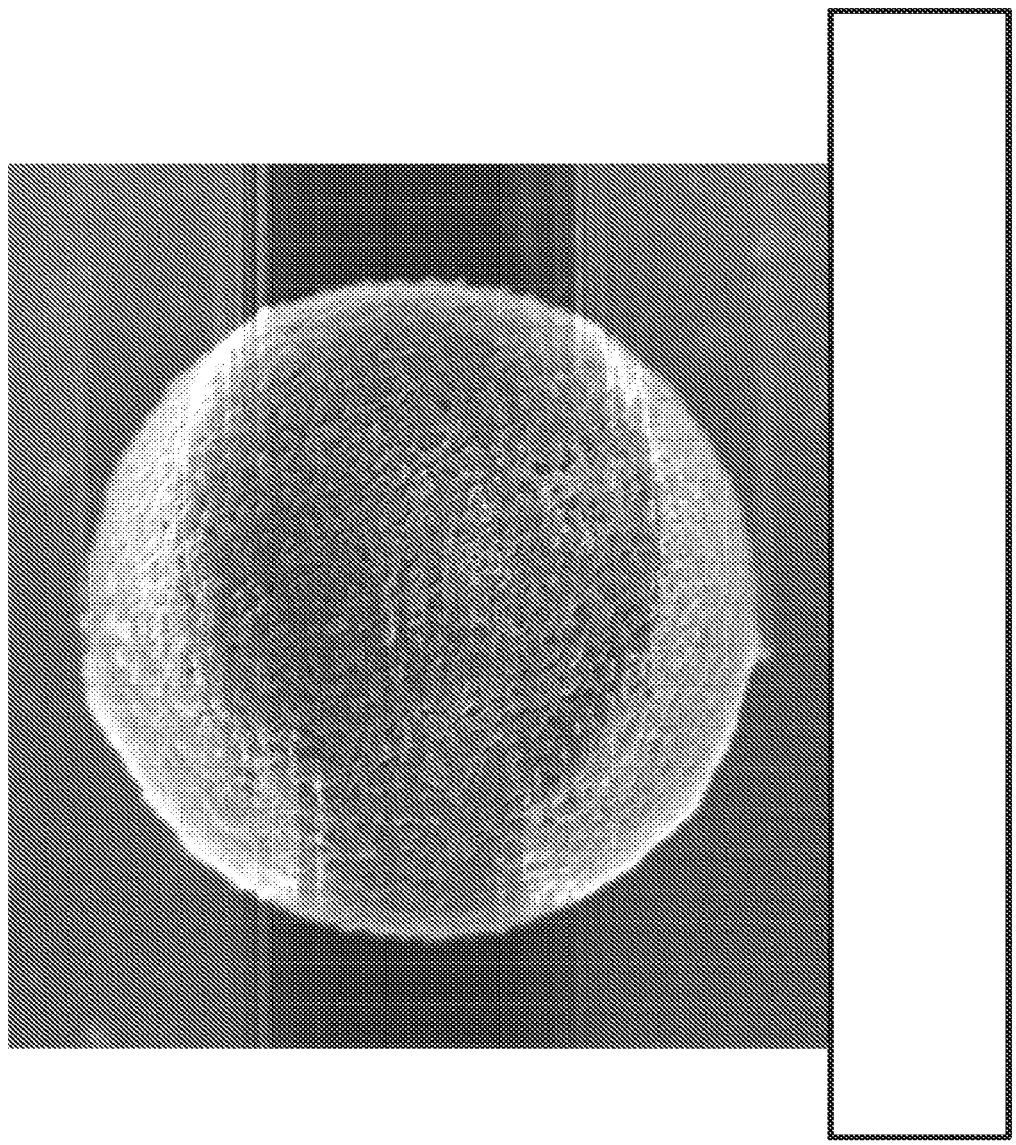
Figure 12A:
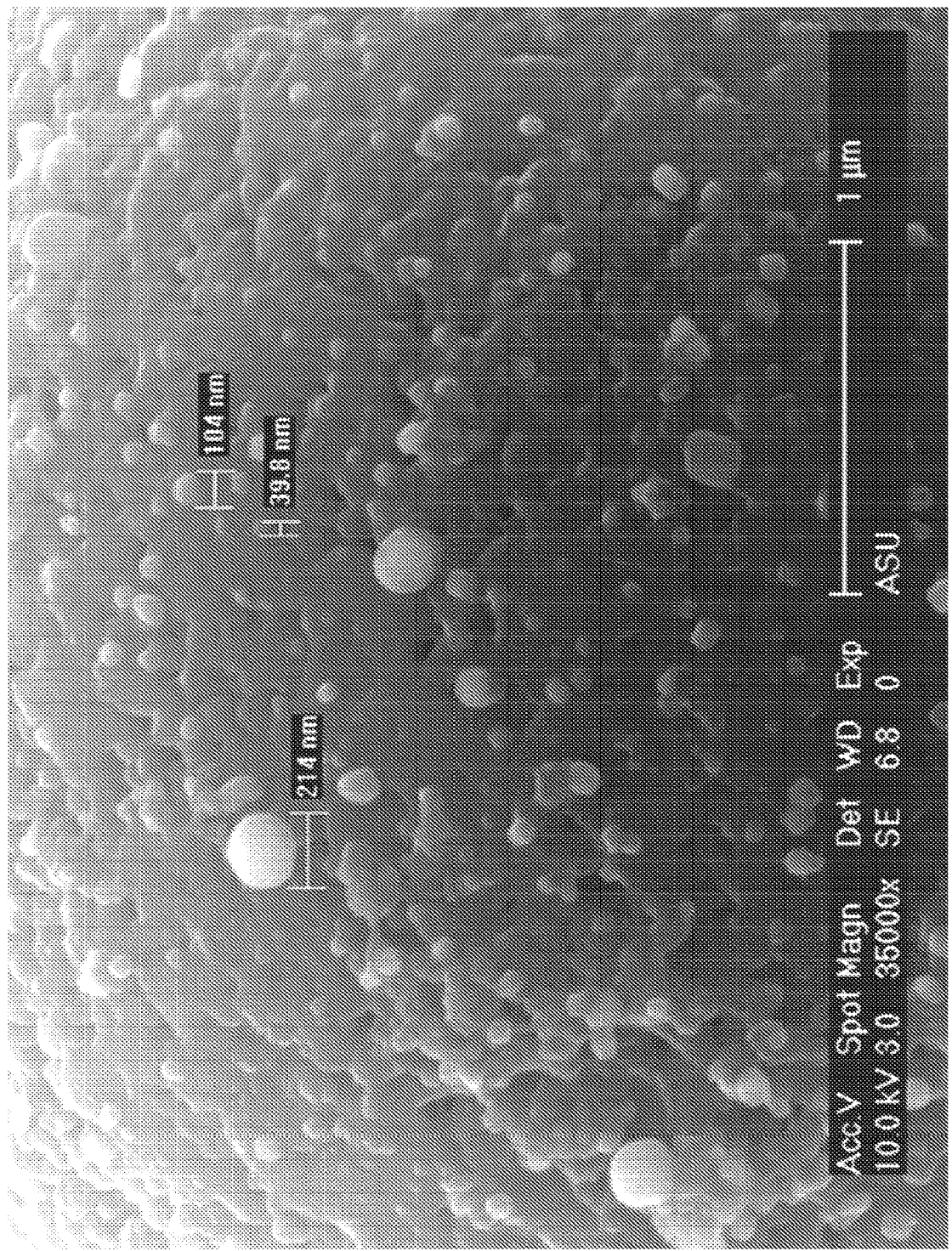
Figure 12C:
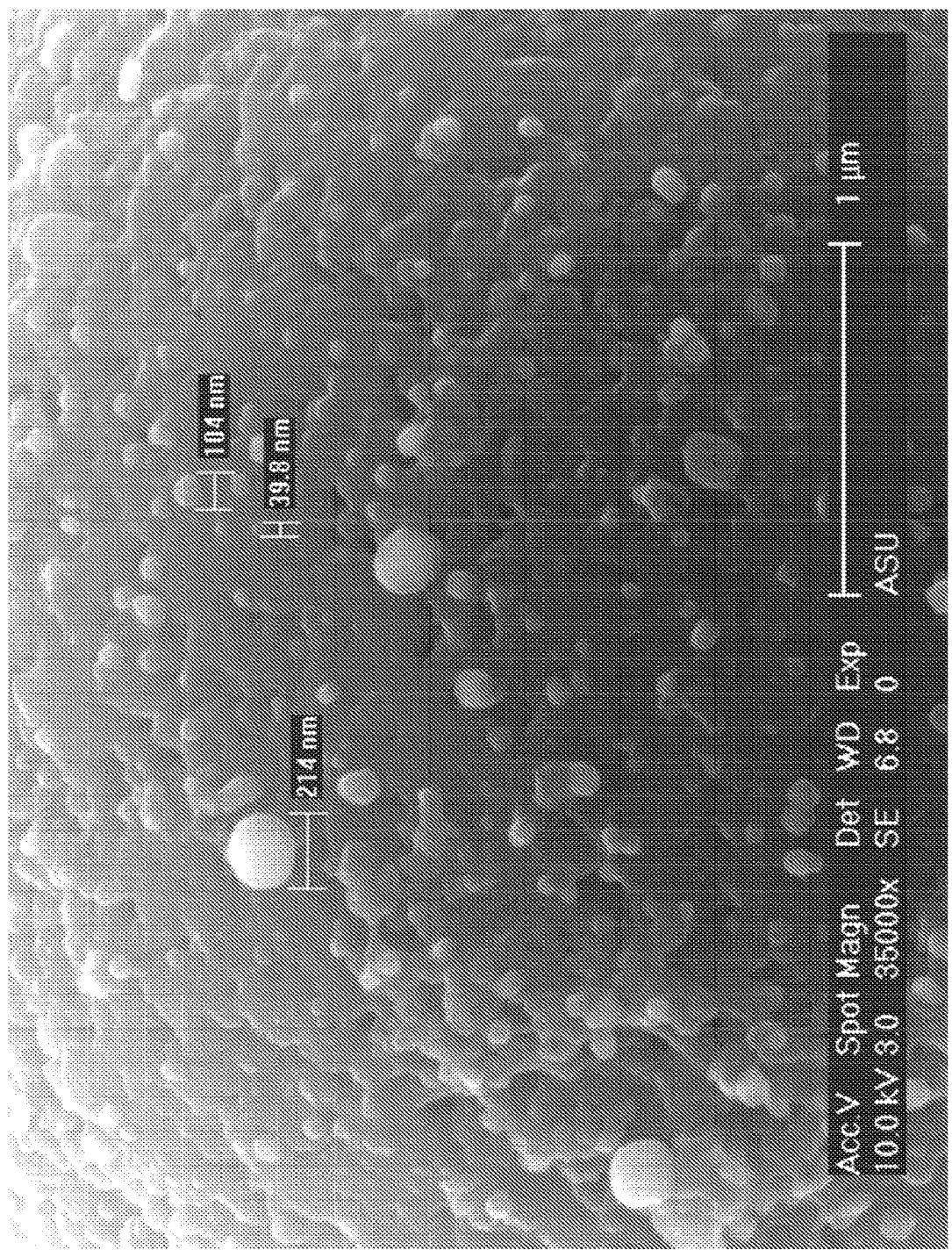
Figure 12D:
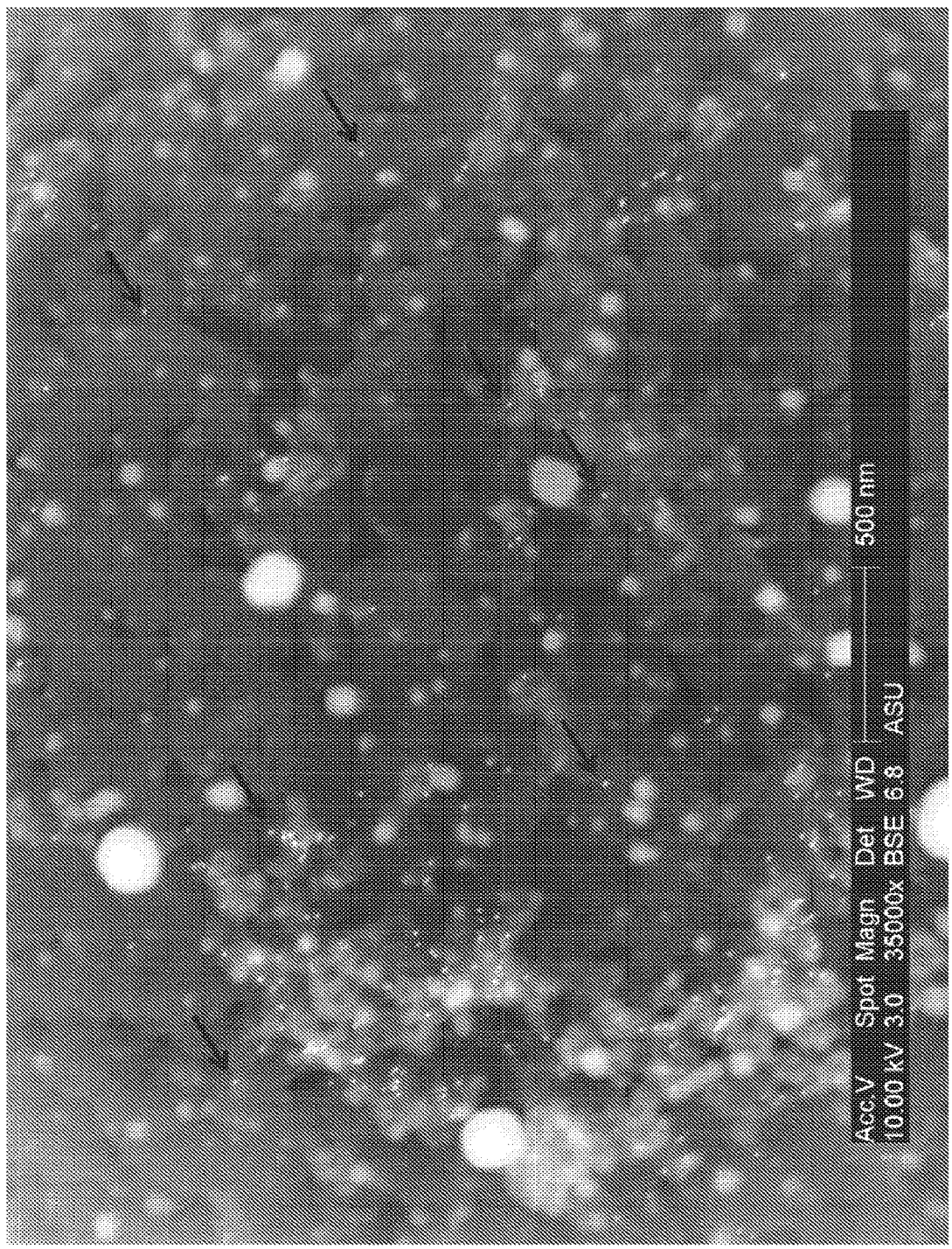
Figure 12E:
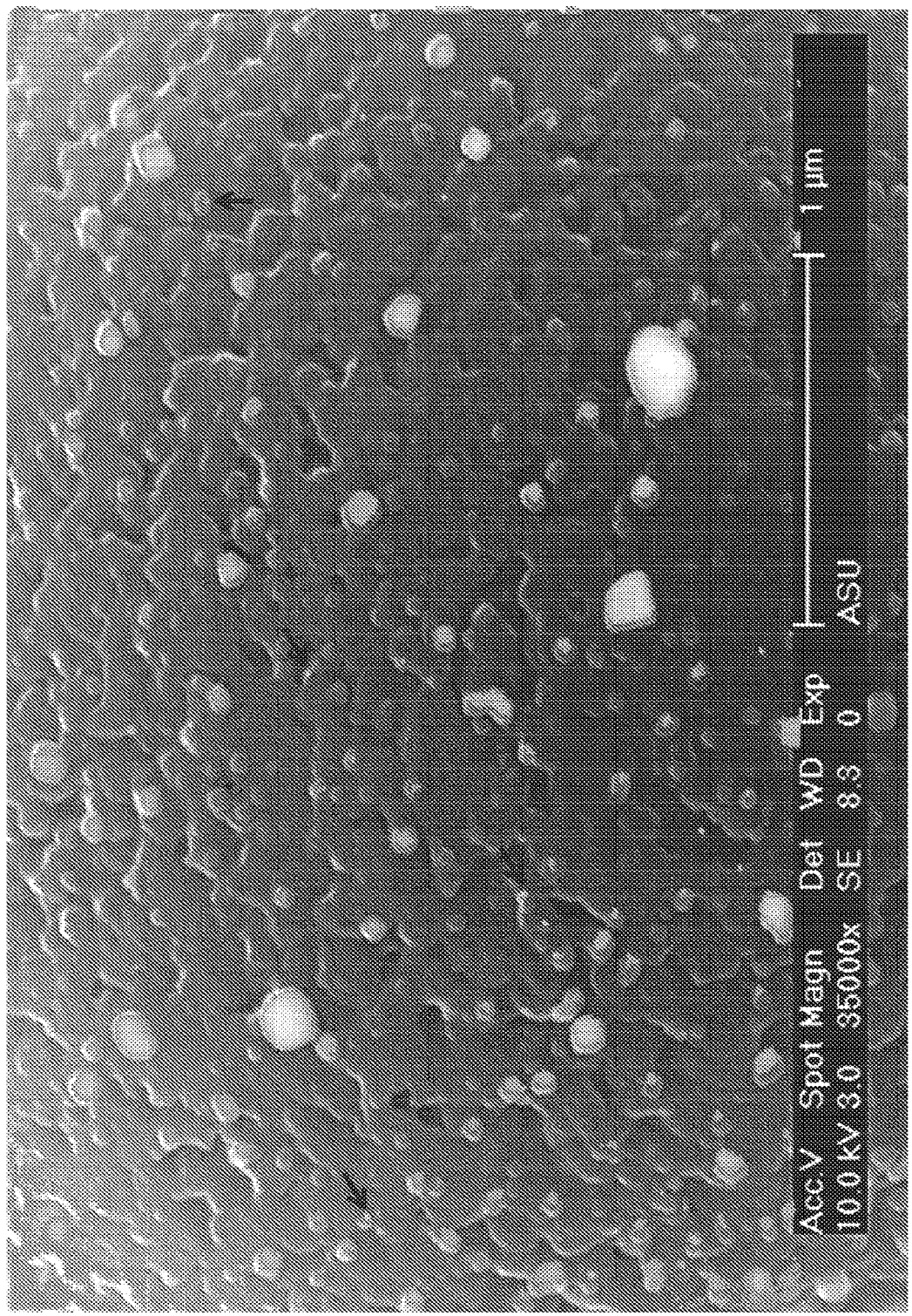

Imaging of Tethered Microvesicles:

Field emission scanning electron microscopy (FE-SEM) was used for evaluation of the alternative protocols for tethering microvesicles isolated from plasma to the surface of microspheres. FIGS. 11A-11N show the FE-SEM images. FIG. 11A shows a microsphere that has not been functionalized or conjugated. FIG. 11B shows direct conjugation of plasma microvesicles isolated using ultracentrifugation to non-magnetic beads. FIG. 11C shows a blow up of the indicated region of FIG. 11B. The arrows point to various microvesicles. FIG. 11D and FIG. 11E correspond to FIG. 11B and FIG. 11C, respectively, except that the beads are magnetic. FIGS. 11F-H show functionalized magnetic beads. FIG. 11F shows avidin conjugated beads functionalized with biotinylated ConA. FIG. 11G shows avidin conjugated beads functionalized with a biotinylated lipid anchor. FIG. 11H shows beads directly conjugated with anti-CD9 antibodies. FIG. 11I shows bead capture of plasma microvesicles isolated using ultracentrifugation to ConA functionalized beads. FIG. 11J shows a blow up of the indicated region of FIG. 11I. The arrows point to various microvesicles. FIG. 11K shows bead capture of plasma microvesicles isolated using ultracentrifugation to lipid anchor functionalized beads. FIG. 11L shows a blow up of the indicated region of FIG. 11K. The arrows point to various microvesicles. FIG. 11M shows bead capture of plasma microvesicles isolated using ultracentrifugation to lipid anchor functionalized beads. FIG. 11N shows a blow up of the indicated region of FIG. 11M. The arrows point to various microvesicles.

Summary:

All three platforms for tethering of vesicles to the microspheres (direct conjugation, antibody binding, and lipid anchor) were demonstrated using Vcap (human prostate cell line) derived microvesicles. With optimized sample conditions (e.g., removal of highly abundant proteins), similar results are observed using vesicles isolated from human plasma samples. It is surprising to obtain sufficient coupling of a complex microvesicle structure directly to beads given the potential for interference of molecular entities, including but not limited to steric interference via different sized vesicles, aggregate formation, soluble protein blocking, or vesicle fragment interference. Microsphere attached microvesicles produced by the methods in this Example can be used to screen an aptamer library as described in the Examples above.

Example 29: Protocol for Two-Step Carbodiimide Coupling of Protein or Microvesicles to Carboxylated Microspheres The protocol below is used to conjugate proteins (e.g., antibodies) or microvesicles to carboxylated microspheres (MagPlex® magnetic microspheres or MicroPlex® non-magnetic microspheres, Luminex Corporation, Austin, Tex.).

Materials:

Region 15: Luminex Catalog # MC10015-01 Lot # B28049 Exp: 2016 Dec. 16

Region 18: Luminex Catalog # MC10018-01 Lot # B29449 Exp: 2017 Mar. 14

Protocol:

Microspheres should be protected from prolonged exposure to light throughout this procedure.

1. Resuspend the stock uncoupled microsphere suspension according to the instructions described in the Product Information Sheet provided with the microspheres.
2. Transfer $5.0 \times 10^6$ of the stock microspheres to a USA Scientific microcentrifuge tube. Ratio Protein/Beads: 20 m/$5 \times 10^6$. Can be scaled down to 4 μg/$10^6$.
3. Place the tube into a magnetic separator and allow separation to occur for 60 seconds. See Technical Note 1 below.
4. With the tube still positioned in the magnetic separator, remove the supernatant. Take care not to disturb the microspheres.
5. Remove the tube from the magnetic separator and resuspend the microspheres in 100 μL dH2O by vortex and sonication for approximately 20 seconds.
6. Place the tube into a magnetic separator and allow separation to occur for 60 seconds.
7. With the tube still positioned in the magnetic separator, remove the supernatant. Take care not to disturb the microspheres.
8. Remove the tube from the magnetic separator and resuspend the washed microspheres in 80 μL 100 mM Monobasic Sodium Phosphate, pH 6.2 by vortex and sonication for approximately 20 seconds.
9. Add 10 μL of 50 mg/mL Sulfo-NHS (diluted in dH2O) to the microspheres and mix gently by vortex.
10. Add 10 μL of 50 mg/mL EDC (diluted in dH2O) to the microspheres and mix gently by vortex.
11. Incubate for 20 minutes at room temperature with gentle mixing by vortex at 10 minute intervals.
12. Place the tube into a magnetic separator and allow separation to occur for 60 seconds.
13. With the tube still positioned in the magnetic separator, remove the supernatant. Take care not to disturb the microspheres.
14. Remove the tube from the magnetic separator and resuspend the microspheres in 250 μL of 50 mM MES, pH 5.0 by vortex and sonication for approximately 20 seconds. See Technical Note 2 below.
15. Repeat steps 12 and 13. This is a total of two washes with 50 mM MES, pH 5.0.
16. Remove the tube from the magnetic separator and resuspend the activated and washed microspheres in 100 μL of 50 mM MES, pH 5.0 by vortex and sonication for approximately 20 seconds.
17. Add 20 μg protein or equivalent microvesicles to the resuspended microspheres.
18. Bring total volume to 500 μL with 50 mM IVIES, pH 5.0. Note: This volume can be scaled down in case of $10^6$ beads conjugation.
19. Mix coupling reaction by vortex.
20. Incubate for 2 hours with mixing (800 rpm on MixMate) at room temperature.
21. Place the tube into a magnetic separator and allow separation to occur 60 seconds.
22. With the tube still positioned in the magnetic separator, remove the supernatant. Take care not to disturb the microspheres.
23. Remove the tube from the magnetic separator and resuspend the coupled microspheres in 500 μL of PBS-T by vortex and sonication for approximately 20 seconds. See Technical Note 3 below.
24. Incubate for 30 minutes with mixing (by rotation) at room temperature. Performed this step as I used the microspheres same day.
25. Place the tube into a magnetic separator and allow separation to occur for 30 to 60 seconds.
26. With the tube still positioned in the magnetic separator, remove the supernatant. Take care not to disturb the microspheres.
27. Remove the tube from the magnetic separator and resuspend the microspheres in 1 mL of PBS-TBN by vortex and sonication for approximately 20 seconds. See Technical Note 4.
28. Repeat steps 25 and 26. This is a total of two washes with 1 mL PBS-TBN.
29. Remove the tube from the magnetic separator and resuspend the coupled and washed microspheres in 250 ul PBS-TBN (150 ul for 1 million beads in PBS-TBN).
30. Count the microsphere suspension by vicell Technical Note 1:

For a list of magnetic separators, see bead manufacturer recommendations. Optimal separation time may vary with the type of separator used.

Technical Note 2:

Coupling can be performed in 100 mM MES, pH 6.0 with similar results. In some cases, better solubility and better coupling may be achieved at a higher coupling pH or in a different buffer. If the target does not couple satisfactorily under these recommendations, try PBS, pH 7.4 as an alternate coupling buffer.

Technical Note 3:

Either PBS-TBN (PBS, 0.1% BSA, 0.02% Tween-20, 0.05% Azide, pH 7.4) or PBS-BN (PBS, 1% BSA, 0.05% Azide, pH 7.4) may be used as Blocking/Storage Buffer.

Technical Note 4:

Either PBS-TBN or PBS, 0.05% Tween-20 may be used as Wash Buffer.

Example 30: Microsphere Conjugated Microvesicles as a Platform for Identifying Cancer Specific Aptamers Strategies for partitioning of aptamer libraries include: (i) solid support fixed target (e.g., agarose, polymethyl methacrylate, or paramagnetic beads); (ii) gel mobility shift; (iii) nitrocellulose membrane which binds proteins but not DNA; and (iv) capillary electrophoresis. In order to develop an aptamer for a cancer specific protein, each of these approaches typically starts with recombinant protein already known to be associated (to at least some extent) with the cancer secured on solid support in a way which allows partitioning of aptamer pool into "binder" and "non-binder" populations. These approaches further assume that: (i) the recombinant protein folding will reflect the natural protein in situ (e.g., in a tissue or a bodily fluid such as blood), although chemical immobilization of protein may modify its structure and conformation; and (ii) there is no interaction with other components in the desired biological sample. Accordingly, identifying and developing aptamers to detect cancer using samples from patients with confirmed cancer as well as from healthy individuals remains a challenge. This Example describes one such approach that allows for selection of aptamers that differentiate cancer without prior knowledge of the aptamer target and wherein the targets are found in their native environment/conformation.

Intact microvesicles—instead of individual proteins—isolated from patient samples are conjugated directly to microspheres. Carboxylated beads are useful to immobilize microvesicles via primary amino groups of microvesicle surface proteins. Alternately, microvesicles can be immobilized via lipid anchoring. See Examples 28 above. Labeled microspheres allow conjugation and aptamer library enrichment to be confirmed directly in a single assay. Magnetic beads can provide additional convenience for handling Although microvesicles can be bound to microvesicles via non-covalent bonding (e.g., antibody or aptamer binding, adsorption), such binding typically has insufficient stability to allow efficient aptamer screening.

The aptamer development process is performed following these steps:

1) Isolate microvesicles from cancer and normal patient blood samples (plasma or serum). The samples are depleted of highly abundant proteins (e.g., IgG, human serum albumin (HSA)) prior to vesicle isolation.

2) Conjugate the isolated microvesicles to carboxylated beads using standard two-step carbodiimide chemistry as known in the art. Alternately, the microvesicles are conjugated via lipid anchoring.

3) Incubate the vesicle conjugated beads with an aptamer library in parallel for cancer and normal samples. The aptamer library is pre-incubated with assay components (e.g., beads and plasma coated beads) to remove any aptamers that bind such components.

4) Discard the supernatant containing unbound aptamers. Wash the vesicle conjugated beads ~10 times using phosphate buffered saline (PBS) with 0.1% Tween 20.

5) Disassociate aptamers bound to microvesicles by treatment with NaOH, neutralize the solution, precipitate aptamers and amplify the recovered aptamers using qPCR. The recovered qPCR products are used as the starting library for the next round of selection (i.e., to repeat the process starting at step 3).

6) Once the aptamer library complexity is decreased at least down to $10^6$ members (starting from, e.g., $10^{15}$), the aptamers are sequenced using high throughput next generation sequencing technology (Illumina MiSeq® System, Illumina, Inc., San Diego, Calif.). After sequencing cancer and normal specifically enriched aptamer pools in parallel, sequences overlapping in both the cancer and normal pools are discarded and those sequences specific for a majority of cancer samples are considered as aptamer candidates.

Example 31: Microvesicle Aptamer Selection Method

This Example presents a method of selecting aptamers that can be used to differentiate microvesicles from cancer patients and control samples without cancer (e.g., "normals"). The cancer can be chosen as a particular lineage of cancer. The controls can be divided into various pathology groups (e.g., positive for conditions other than the chosen cancer) to provide an additional layer of complexity. The method enriches an aptamer library for aptamer members that bind to cancer-derived microvesicles but not the control microvesicles.

In the scheme, "positive selection" refers to enrichment aptamers to cancer-derived microvesicles, whereas "negative selection" refers to depletion of aptamers that bind control microvesicles. Generally, the scheme alternates between positive and negative selection, such that negative selections is performed in between every positive selection. The selections are performed against bead-conjugated microvesicles as described above.

A cohort 250 plasma samples are obtained. Approximately one-third of the samples are from cancer patients and the rest are controls. The samples are pooled into pools of 5-6 samples, resulting in ~16 cancer pools. Microvesicles from the pooled samples are conjugated to microbeads using methods described above.

Positive selection is first performed for each pool. Next negative selection is performed. Seven positive/negative selections are performed in parallel. In each parallel selection, the pools are randomly ordered to avoid selection bias. See FIG. 13B for graphical depiction. After each round, the remaining aptamer pools are sequenced using Next-generation sequencing technology. The sequencing can identify any enrichment in the positive rounds and/or depletion in the negative rounds. Any consensus sequences (sequence and/or structure) are also identified after each round. If identified consensus sequences are lost after certain rounds in a minority of pools but not others, those pools can be analyzed to determine if any error has been introduced.

Example 32: ImmunoGold Labeling of Microvesicles Conjugated or Immunoprecipitated on Microspheres As described herein, standard methods for detection and characterization of microvesicles include Western blot, Dynamic Light Scattering, flow cytometry, and electron microscopy. As described above, microvesicles can be captured by antibody conjugated to microbeads and detected with another labeled antibody in a flow-based microbead assay. See Example 28. Electron microscopy can be used to confirm the presence of microvesicles captured on the beads in this immunoassay. This Example provides electron microscopy with ImmunoGold labeling to image microvesicles conjugated or immunoprecipitated on microspheres.

General Considerations: Microvesicles were isolated by ultracentrifugation from human plasma and conjugated to non-magnetic carboxylated microspheres (MicroPlex® Microspheres, Luminex Corporation, Austin Tex.). After conjugation, beads are labeled with murine anti-CD9 monoclonal antibody followed by anti-mouse-ImmunoGold (10 nm particles), mounted on poly-Lysine coated cover slip, dried, dehydrated, critical-point dried, carbon coated and imaged using Scanning Electron Microscopy with (a) Secondary Electrons (SE) mode—to visualize microvesicles and (b) Back Scattered Electrons (BSE) mode—to visualize the gold nanoparticles.

Steps involved include: (i) labeling microvesicles on beads with membrane protein specific antibody and corresponding anti-species Gold conjugate; (ii) regular sample preparation steps for scanning electron microscopy (SEM); (iii) carbon sputter coating (in place of Gold-Palladium); (iv) combination of SE and BSE imaging.

Conjugation of microvesicles to the beads can be replaced with immunoprecipitation of microvesicle to the beads, e.g., using beads conjugated to an antibody against a microvesicle surface antigen.

Protocol:

Starting material comprises microvesicle sample directly conjugated to MicroPlex beads. See Example 28 for general methodology.

1. Centrifuge 4 µl aliquot of starting material (in 1.5 ml microcentrifuge tube) for 1 min at 13,000 rpm to pellet beads. Remove supernatant without disturbing the pellet.
2. Add 20 µl of blocking buffer PBS-BSAT (phosphate buffered saline with bovine serum albumin and Tween®-20: (0.1M NaPO4 pH 7.2/150 mM NaCl/1% BSA/0.01% T20)) and resuspend the pellet. Incubate for 30 min at room temperature.
3. Centrifuge for 1 min at 13,000 rpm to pellet beads. Remove supernatant.
4. Add 20 µl of primary antibody solution (10 or 100 µg/ml, mouse monoclonal anti-CD9 antibody (BD Biosciences Catalog No. 555370, Lot 2097575) with PBS-BSAT) and resuspend the pellet. Incubate for 30 min at room temperature.
5. Wash 3 times with 50 µl PBS-BSAT (pellet by centrifuge 1 min at 13,000 rpm, remove supernatant) for 5 min at room temperature.
6. Add 20 µl of secondary antibody solution (at 1:100, 0.3 µg/ml, anti-mouse-gold (goat anti-mouse-Gold antibody, 10 nm, MP Biomedicals Catalog No. #67854) with PBS-BSAT) and resuspend the pellet. Incubate for 20 min at room temperature.
7. Wash 3 times with 50 µl PBS (1×, HyClone, pH 7.4) for 5 min at room temperature.
8. After removing supernatant, add 10 µl of PBS and resuspend the pellet.
9. Take 2 µl of labeled and resuspended beads to a poly-L-lysine precoated coverslip and smear gently to spread beads on surface
10. Incubate the cover slip in a humidified chamber for 10 min, covered at room temperature.
11. Primary fixing with 3 ml of 2% Glutaldehyde with 1×PBS, in individual disposal Petri dish, covered, for 30 min at room temperature. Work in safety hood.
12. Wash coverslip 3 times with 1×PBS. Dispose primary fixing solution and washes in designated hazardous waste container.
13. Secondary fixing with 0.5% Osmium tetraxide in 1×PBS, covered for 30 min at room temperature in safety hood.
14. Wash coverslip 3 times with nanopure water. Dispose secondary fixing solution and washes in designated hazardous waste container.
15. Dehydrate coverslip in series of ethanol, place coverslip in stainless steel mesh basket, 5 min each at room temperature: 1) 20% ethanol; 2) 50% ethanol; 3) 75% ethanol; 4) 100% ethanol; 5) repeat 100% ethanol twice more.
16. Critical-point dried (CPD) in liquid carbon dioxide.
17. Mount coverslip on aluminum stage with adhesive
18. Carbon sputter coating
19. Obtain images using SE (focusing) and BSE (detecting gold).

Results:

Imaging of bead-conjugated microvesicles according to the protocol above is shown in FIGS. 12A-12E.

REFERENCES

S. L. Erlandsen, P. T. Macechko and C. Frethem. High resolution backscatter electron (bse) imaging of immunogold with in-lens and below-the-lens field emission scanning electron microscopes. Scanning Microscopy 13:43-54 (1999).

Example 33: Competitive Isolation of Aptamers to Microvesicles

The method of Example 31 is performed to identify aptamers that bind microvesicle antigens of interest. Anti-tetraspanin antibodies are tethered to microbeads and incubated with cMVs from plasma samples from prostate cancer patient. The captured cMVs serve as the analyte in the method of Example 31. Aptamer candidates are disassociated from the microvesicle using the antibodies in Table 26.

TABLE 26

| Antibodies | | | |
|---|---|---|---|
| Target | Vendor | Catalog# | Lot# |
| 14-3-3 zeta/beta | Novus Biologicals | NB100-1964 | 2230612 |
| Aconitase 2 | Novus Biologicals | NBP2-02241 | A01 |
| ADAM 9 | Novus Biologicals | H00008754-M01 | D2041-3E6 |
| ADAM10 | R&D systems | MAB1427 | HZR0311111 |
| ADE2 | Novus Biologicals | NBP2-02817 | A01 |
| AFM | Creative Diagnostics | CAB-1089MH | PR78801Z |
| Ago2 | | | |
| AGR2 | Novus Biologicals | H00010551-M01 | 11042-1E5 |

TABLE 26-continued

| Antibodies | | | |
|---|---|---|---|
| Target | Vendor | Catalog# | Lot# |
| AKT1 | Neuromics | MO15107 | 401484 |
| ALDH1A3 | Origene | CF502841 | A003 |
| ALDH6A1 | LifeSpan Biosciences | LS-C156268 | 45269 |
| ALDOA | Novus Biologicals | H00000226-M03 | 08123-2E6, 11097-2E6 |
| ALIX | Thermo scientific | MA1-83977 | NL1643884, NL1640867 |
| ANGPTL4 | Novus Biologicals | H00051129-M01 | D3151-1F7 |
| ANXA1 | Millipore | MAB3773 | 2148887 |
| ANXA2 | Millipore | MAB3774 | 2148886, 2140018 |
| ANXA3 | Novus Biologicals | H00000306-M12 | 11258-4F1 |
| ANXA3 | Novus Biologicals | H00000306-M12 | D5231-4F1 |
| ANXA4 | LIFESPAN BIOSCIENCES | LS-B4279 | 32117 |
| AP1G1 | LIFESPAN BIOSCIENCES | LS-C171339 | 45239 |
| APAF1 | Lifespan Biosciences Inc. | LS-C3755 | 44521 |
| APE1 | Novus | NB100-116PUR | 32813 |
| APLP2 | Novus Biologicals | H00000334-M04 | 11326-4B5 |
| APLP2 | Novus Biologicals | H00000334-M04 | 06363-4B5, 11326-4B5 |
| ARF6 | LIFESPAN BIOSCIENCES | LS-C87646 | 44235, 44199 |
| Aspartyl Amino-peptidase/Dnpep | Novus Biologicals | H00023549-M01 | 08263-s3 |
| Ataxin 1 | Novus Biologicals | H00006310-M02 | D4291-4C5, D5071-4C5 |
| ATP5A1 | Proteintech | 66037-1-Ig | 10000914-barcode number |
| ATPase Na+/K+ alpha 3/ATP1A3 | Novus Biologicals | NB300-540 | NJ175778 |
| ATPase Na+/K+ beta 3/ATP1B3 | Novus Biologicals | H00000483-M03 | 6125-1E9-011b4by6 |
| ATPase Na+/K+ beta 3/ATP1B3 | Novus Biologicals | H00000483-M03 | D5311-1E9 |
| ATPB | Novus Biologicals | NB600-1171 | MJ163306 |
| AZGP1 | BD | 612354 | 80749, 3086574, 3121936 |
| B4GALT1 | Sino Biological | 11220-MM01 | HB06JL0607 |
| B7H3 | R&D systems | MAB1027 | HPA0411031 |
| BCHE | Lifespan biosciences | LS-C35215-100 | 42885 |
| BclG | Novus Biologicals | H00079370-M01 | 12108-1F2 |
| BDKRB2 | Novus Biologicals | H00000624-M01 | 11209-3F6 |
| BDNF | R&D systems | MAB848 | BBL1512091 |
| BDNF | R&D systems | MAB848 | BBL1211091 |
| beta 2 Microglobulin | Novus Biologicals | NB500-317 | 515273 |
| beta catenin | Novus Biologicals | H00001499-M02 | D2011-1C9 |
| BRG1 | Millipore | MABE60 | NRG1782322, 2207807 |
| CALM2 | Novus Biologicals | H00000805-M01 | D5311-S2 |
| Calmodulin 2/CALM2 | Novus Biologicals | H00000805-M01 | 10337-S2 |
| Calnexin | Novus Biologicals | H00000821-M08 | 11132-1D4, 08179-1D4 |
| Calpain | LIFESPAN BIOSCIENCES | LS-B4768 | 45956 |
| Catenin Alpha 1 | Novus Biologicals | NB100-74356 | OB183849 |
| CAV1 | Novus Biologicals | NBP1-74036 | A1120901 |
| CCR2/CD192 | Novus Biologicals | NB120-10396 | 061M1621 |
| CCR5 | Novus Biologicals | NBP1-43335 | E022691 |
| CCT2 (TCP1-beta) | Novus Biologicals | H00010576-M01 | 12108-2G6 |
| CD10 | BD Pharmingen | 555373 | 32631 |
| CD151 | R&D systems | MAB1884 | JFU0210121 |
| CD166/ALCAM | R&D Systems | MAB6561 | DXM0312051 |
| CD24 | BD Pharmingen | 555426 | 25844 |
| CD276 | Novus Biologicals | NBP2-12048 | 2013032102 |
| CD41 | Mybiosource | MBS210248 | 1003 |
| CD46 | Novus Biologicals | NB500-301 | 512525 |
| CD49d | Novus Biologicals | H00003676-M01 | 11039-2C11 |
| CD63 | BD pharmingen | 556019 | 2244712 |
| CD71/TRFR | Novus Biologicals | NB100-73092 | 709/08-TR26-E4 |
| CD81 | BD pharmingen | 555675 | 25099 |
| CD9 | Novus Biologicals | NB500-327 | 517304 |
| CD9 | Novus Biologicals | NB500-327 | 517304 |
| CD90/THY1 | Novus Biologicals | NBP1-43379 | E03908-1630 |
| CDH1 | NOVUS BIOLOGICALS | H00051343-M09 | 11139-3E12 |
| CDH2 | NOVUS BIOLOGICALS | H00001000-M06 | 1137-5E6 |
| CDKN1A | Thermo scientific | MA1-19271 | OB1661535 |
| CGA | Novus Biologicals | NB100-62251 | 030311 |
| CgA | Novus Biologicals | NBP1-23022 | A1113601 |
| CHRDL2 | R&D Systems | MAB24481 | WJU015101 |
| CIB1 | Novus Biologicals | NBP1-04279 | A088401 |
| CIB1 | Novus Biologicals | NBP1-04279 | D5301-51 |

TABLE 26-continued

| Antibodies | | | |
|---|---|---|---|
| Target | Vendor | Catalog# | Lot# |
| Claudin 4/CLDN4 | Novus Biologicals | H00001364-M02 | 08092-4A11 |
| Claudin 5 | Novus Biologicals | H00007122-M01 | 11291-3d8, 10334-3d8, 7149-3d8-00bcy6 |
| CLDN3 | NOVUS BIOLOGICALS | H00001365-M09 | D5311-2F2 |
| CLDN3- Claudin3 | NOVUS BIOLOGICALS | H00001365-M09 | D1281-2F2, 11256-2F2 |
| CLDN4 | Novus Biologicals | H00001364-M02 | D5311-4A11 |
| CLDN7 | Lifespan Biosciences Inc. | LS-B2918 | 44272 |
| CNDP2 | Novus Biologicals | NBP2-01281 | A01 |
| Coatomer Subunit Delta | Novus Biologicals | NBP2-01790 | A01 |
| Cofilin 2/cfL2 | Novus Biologicals | H00001073-M03 | 11238-6G9, 10106-6G9 |
| CORO1B | Novus Biologicals | H00057175-M01 | 07345-1E7, 10236-1E7 |
| Cortactin/CTTN | Novus Biologicals | H00002017-M01 | 08312-2B5 |
| COX2/PTGS2 | Life Technologies | 358200 | 1251212A |
| COX5b | Novus Biologicals | H00001329-M03 | 12241-1E, 11088-1E8 |
| CSE1L | Lifespan biosciences | LS-C104925 | 41780 |
| CTH | Novus Biologicals | H00001491-M03 | 10292-S51, 12167-S51 |
| CTNND1/delta 1-catenin/p120-catenin | Origene | CF800968 | W001 |
| CTNND2 | Novus Biologicals | H00001501-M01 | D5071-6E11 |
| CXCR3 | R&D systems | MAB160 | AOU101121 |
| CYCS | Novus Biologicals | NB100-78345 | B152009 |
| Cystatin C | Novus Biologicals | NBP1-05763 | 10/09-cc1-13 |
| Cytochrome C | Novus Biologicals | NB100-78345 | B152009 |
| Cytokeratin 18 | Novus Biologicals | NB500-353 | L41K |
| Cytokeratin 8 | Novus Biologicals | NB500-350 | 515894 |
| Cytokeratin basic | ACRIS | AM10030PU-L | 2620 |
| DBF4B/DRF1 | Novus Biologicals | H00080174-M01 | 08361-1a7 |
| DBI* | Abcam | ab16775-100 | 374264, GR122424-1 |
| DCTN-50/DCTN2 | Novus Biologicals | H00010540-M01 | 12143-2G7, 11312-2G7 |
| DDAH1 | Novus Biologicals | H00023576-M01 | D3151-3F7 |
| DDAH1 | Novus Biologicals | H00023576-M01 | D3151-3f7 |
| DDX1 | Novus Biologicals | H00001653-M02 | 09226-4F6 |
| Destrin | Novus Biologicals | NBP2-00560 | A01 |
| DIP13B/appl2 | Novus Biologicals | H00055198-M06 | 08183-1C10 |
| DIP13B/appl2 | Novus Biologicals | H00055198-M06 | D5311-1C10 |
| DLG1 | Novus Biologicals | NBP1-48054 | 1007 |
| Dnpep | Novus Biologicals | H00023549-M01 | D5311-S3 |
| E-Cadherin | Novus | NB110-61005 | 2013022601 |
| ECH1 | Novus Biologicals | H00001891-M01 | 09198-5G8, 09020-5G8 |
| ECHS1 | Novus Biologicals | H00001892-M05 | 07355-3C6 |
| ECHS1 | Novus Biologicals | H00001892-M05 | D5311-3C6 |
| EDIL3 (del-1) | Novus Biologicals | H00010085-M01 | 11074-4C9 |
| EDN-3 | Millipore | ST1513-100UG | 11287-S1 |
| EDNRB/EDN3 | Novus Biologicals | H00001908-M01 | 11287-S1, 11053-S1 |
| EGFR | Novus Biologicals | H00001956-M02 | CA091-4H2 |
| EIF4A3 | Creative Biomart | CAB-3210MH | ML7809Z |
| ENTPD4 | Novus Biologicals | H00009583-M01 | 08141-4H7 |
| EpoR | NOVUS BIOLOGICALS | H00002057-M02 | 08088-3F6 |
| EpoR | NOVUS BIOLOGICALS | H00002057-M02 | D5311-3F6 |
| ERAB | Novus Biologicals | NBP2-02118 | A01 |
| ESD | Novus Biologicals | H00002098-M01 | 12080-1E1 |
| ESD | Novus Biologicals | H00002098-M01 | 12080-1E1 |
| ETS1 | Novus Biologicals | H00002113-M02 | 09174-2G10 |
| ETS1 | Novus Biologicals | H00002113-M02 | 09174-2G10 |
| ETS-2 | Origene | CF505365 | ? |
| EZH2 | Novus Biologicals | H00002146-M07 | D5031-1D11 |
| EZH2/KMT6 | Novus Biologicals | H00002146-M07 | 11263-1D11 |
| EZR | LIFESPAN BIOSCIENCES | LS-C88343 | 44198, 44201 |
| FABP5 | Novus Biologicals | NBP1-50810 | 10/12-F29-31 |
| FARSLA | Novus Biologicals | H00002193-M01 | D3151-2D8 |
| FASN | MYBIOSOURCE | MBS850333 | NA |
| FKBP5/FKBP51 | Novus Biologicals | NB110-96873 | 802 |
| FLNB | MyBioSource | MBS531705 | 5534 |
| FTL (light and heavy) | Novus biologicals | H00002512-M16 | 10061-X1 |
| FUS | Millipore | MABE465 | QVP1212055, VP1309301 |
| GAL3 | R&D systems | MAB11541 | CAVJ0210011 |
| gamma-catenin | Novus Biologicals | H00003728-M01 | D5271-2G9 |
| GDF15 | R&D SYSTEMS | MAB957 | UDC0512091 |
| GDI2 | Prolab Marketing PVT LTD Proteintech | 60078-1-lg | lot1 |
| GGPS1 | Abcam | ab56579 | GR939546-1 |
| GGPS1 | Abgent | AT2196a | D5211 |
| GITRL | Novus Biologicals | H00008995-M01 | 11340-6F7, 08143-6F7 |
| GloI | NOVUS BIOLOGICALS | NBP1-19015 | A-2 |
| GLUD2 | Novus Biologicals | H00002747-M01 | CB231-3C2, 12124-3C2 |

TABLE 26-continued

Antibodies

| Target | Vendor | Catalog# | Lot# |
|---|---|---|---|
| GM2A | Novus Biologicals | H00002760-M02 | 08246-2c8 |
| GM-CSF | Invitrogen | AHC2012 | 1188352A |
| GOLM1/GOLPH2 Mab; clone 3B10 | Novus Biologicals | H00051280-M04 | D5301-3B10 |
| GOLPH2 | Abgent | AT2239a | 12227 |
| GOLPH2 | Abgent | AT2239a | 12227 |
| GPC6 | MyBioSource | MBS601169 | no lot No. |
| GRP94 | Novus Biologicals | NB110-61640 | 811 |
| GSTP1 | NOVUS BIOLOGICALS | H00002950-M01 | 12174-S2 |
| GSTP1 | NOVUS BIOLOGICALS | H00002950-M01 | D5092-S2 |
| H3F3A | Novus Biologicals | NB120-12179 | 079K4862, 083K4870 |
| HADH/HADHSC | Novus Biologicals | H00003033-M01 | 11039-4b5 |
| HGF | R&D Systems | MAB694 | AWW0411061 |
| HIST1H3A | Creative Diagnostics | DMABT-H12861 | AB04011Z |
| Histone H4 | Novus Biologicals | NBP1-78445-50ul | 1040711 |
| hK2/Kif2a | NOVUS BIOLOGICALS | H00003796-M01 | D2041-2D4 |
| hnRNP A1 | Novus Biologicals | NB100-672 | 101M4762 |
| hnRNP A2B1 | Novus Biologicals | NB120-6102 | 044K4766 |
| hnRNP C1 + C2 | Novus Biologicals | NB600-585 | 064K4808, 6414808 |
| hnRNP K (F45)* | Novus Biologicals | NB100-74524 | u151623 |
| hnRNP L | Novus Biologicals | NB120-6106 | 1051108 |
| hnRNP M1-M4 | Novus | NB200-314PUR | 32813 |
| HOXB13 | Novus Biologicals | H00010481-M07 | 08109-1E9 |
| Hsp10/HSPE1 | Novus Biologicals | H00003336-M01 | D3151-S1 |
| Hsp40/DNAJB1 | Novus Biologicals | NBP1-04302 | A077301 |
| Hsp60 | Novus Biologicals | NB120-5479 | 048-106, 0C186263 |
| HSP90AA1 | Lifespan biosciences | LS-C36617-50 | 21937 |
| Hsp90B | Novus Biologicals | NB110-96871 | 803 |
| HSPA1A | LIFESPAN BIOSCIENCES | LS-C59523 | 44127 |
| HSPB1 | Sigma-Aldrich | WH0003315-M4 | 08115-3G3 |
| IDH2 | Novus Biologicals | H00003418-M01 | ca0515f11, D30815f11, D2061-5f11 |
| IDH3B | Novus Biologicals | H00003420-M01 | 082003a10 |
| IDH3B | Novus Biologicals | H00003420-M01 | D5311-3A10 |
| IGFBP-2 | R&D systems | MAB6741 | EYP0211041 |
| IGFBP-3 | Lifespan biosciences | LS-C45037 | 45268 |
| IgG1 | R&D Systems | MAB002 | IX2612061 |
| IgG2A | R&D Systems | MAB003 | MV0912111 |
| IgG2B | R&D Systems | MAB004 | NZ1012041 |
| IgM | Thermo Scientific Pierce | 31778 | |
| IL1alpha | NOVUS BIOLOGICALS | H00003552-M03 | 09209-4C6 |
| IL1alpha | NOVUS BIOLOGICALS | H00003552-M03 | D5031-4C6 |
| Integrin beta 7 | Novus Biologicals | NB100-78036 | B165318 |
| IQGAP1 | NOVUS BIOLOGICALS | H00008826-M01 | 12181-2C5 |
| ITGAL | LIFESPAN BIOSCIENCES | LS-C140412-100 | 41655 |
| KLHL12/C3IP1 | Novus Biologicals | NBP2-22359 | 100803 |
| KLK1 | NOVUS BIOLOGICALS | H00003816-M01 | 11074-3G2 |
| KLK10 | NOVUS BIOLOGICALS | H00005655-M01 | D3011-1G8, 08344-1G8, 09233-1G8 |
| KLK11 | R&D Systems | MAB1595 | ITM0310091 |
| KLK12 | R&D SYSTEMS | MAB4034 | YHJ016101 |
| KLK13 | NOVUS BIOLOGICALS | H00026085-M01 | 08186-1G9 |
| KLK14 | NOVUS BIOLOGICALS | H00043847-M05 | 08284-2A7 |
| KLK15 | R&D Systems | MAB2540 | KTL025041 |
| KLK4 | NOVUS BIOLOGICALS | H00009622-M09 | 08172-2A4 |
| KLK5 | NOVUS BIOLOGICALS | H00025818-M01 | 08270-3H3 |
| KLK6 | NOVUS BIOLOGICALS | H00005653-M01 | 11067-4A10 |
| KLK7 | NOVUS BIOLOGICALS | NBP2-11753 | 20130110801 |
| KLK8 | NOVUS BIOLOGICALS | H00011202-M01 | 11109-2F11 |
| KLK9 | Lifespan biosciences | LS-C37111 | 42449 |
| Ku70 (XRCC6) | Novus Biologicals | H00002547-M01 | D4291-S1 |
| Lamin B1 | LIFESPAN BIOSCIENCES | LS-C25124 | 45298 |
| LAMP1 | Novus Biologicals | NB100-1952-100ug | 711 |
| Lamp-2 | Novus Biologicals | H00003920-M01 | 11062-2G10 |
| LDH-A | NOVUS BIOLOGICALS | NBP1-74023-100ul | A119401 |
| LGALS3BP | proteintech | 60066-2-Ig | 1 |
| LGALS8 | Abgent | AT2702a | 11125 |
| Lipoamide Dehydrogenase | Novus Biologicals | NBP2-01109 | A01 |
| LLGL2 | Novus Biologicals | H00003993-M06 | cc211-4g2 |
| LSP1 | NOVUS BIOLOGICALS | H00004046-M07 | 08179-1C4 |
| LSP1 | NOVUS BIOLOGICALS | H00004046-M07 | D5311-1C4 |
| LTBP2 | Novus Biologicals | H00004053-M01 | D4011-5D7 |
| MATR3 | Lifespan Biosciences Inc. | LC-C137527 | 44577 |
| MBD5 | Novus Biologicals | H00055777-M01 | 08179-S1 |
| MDH2 | Novus Biologicals | H00004191-M06 | D4081-2A7, 07283-2a7 |
| MDM4 | Origene | TA505712 | A001 |

TABLE 26-continued

Antibodies

| Target | Vendor | Catalog# | Lot# |
|---|---|---|---|
| ME1 | Novus Biologicals | H00004199-M03 | 12171-3H5, 11182-3H5 |
| MKI67/Ki67 | Novus Biologicals | H00004288-M01 | 11195-7B8 |
| MMP 1 | Novus Biologicals | NBP1-28604 | H0205-R931 |
| MMP 2 | Thermo scientific | MA1-12892 | OB1661361 |
| MMP 25 | R&D SYSTEMS | MAB11421 | GTT013111 |
| MMP10 | R&D systems | MAB9103 | EWC0310041 |
| MMP-14/MT1-MMP | Novus | NB110-60993 | 2013052204 |
| MMP3 | Novus Biologicals | NB100-78555 | B114136 |
| MMP7* | milipore | MAB3315 | 1957964 |
| Mortalin | Novus Biologicals | NBP1-47800 | A01 |
| MTA1 | Novus Biologicals | H00009112-M10 | 08057-1C3, 07317-1C3 |
| nAnS | Novus Biologicals | H00054187-M01 | 09015-3G6 |
| nAnS | Novus Biologicals | H00054187-M01 | D5311-3G6 |
| Nav1.7/SCN9A | NOVUS BIOLOGICALS | H00006335-M01 | 12157-5A11 |
| NCL | Lifespan Biosciences Inc. | LC-C85348 | 35642 |
| NDRG1 | Novus Biologicals | H00010397-M03 | 12094-2D7 |
| NKX3-1 | Novus Biologicals | H00004824-M02 | 10328-1C7, 12215-1C7 |
| NONO | Novus Biologicals | NBP2-02060 | A001 |
| Notch1 | R&D systems | MAB5317 | CCGK0110031 |
| NOTCH4 | Biolegend | 349002 | B165966 |
| NRP1/CD304 | Novus Biologicals | H00008829-M05 | D2041-1B3 |
| Nucleobindin-1 | Novus Biologicals | NBP2-01446 | A01 |
| Nucleophosmin | Novus Biologicals | NBP1-04323 | A065101 |
| p130/RBL2 | Novus Biologicals | H00005934-M03 | D3151-1E2 |
| p97/VCP | Novus Biologicals | H00007415-M03 | 12178-4A8 |
| PAP - same as ACPP | US biological | P9054-67H | L11092257C13020764 |
| PHGDH | Novus Biologicals | H00026227-M01 | D2191-S2 |
| PhIP | Novus Biologicals | H00055023-M01 | D1281-4D7, 12178-4D7 |
| PIP3/BPNT1 | Novus Biologicals | H00010380-M01 | 08297-2E1 |
| PKA R2 | Novus Biologicals | NBP2-02520 | A01 |
| PKM2 | My Biosource | MBS200150 | |
| PKM2 | My Biosource | MBS200150 | A1018601 |
| PKP1 | Novus Biologicals | NB110-13474 | 130202618 |
| PKP3 | Novus Biologicals | NBP1-97675 | 1123 |
| PLEKHC1/Kindlin-2 | Novus Biologicals | H00010979-M09 | D4161-2G11 |
| PRDX2 | Novus Biologicals | H00007001-M01 | CA081-S1 |
| PRKCSH | Novus Biologicals | H00005589-M01 | 08297-3H7, 09114-3H7 |
| Prohibitin | Novus Biologicals | H00005245-M01 | D3191-S3 |
| Proteasome 19S 10B | Novus Biologicals | NBP2-01028 | A01 |
| Proteasome 20S beta 7 | Novus Biologicals | NBP2-01832 | A01 |
| PSAP | Novus Biologicals | H00005660-M01 | 12265-S1 |
| PSMA | Novus Biologicals | NBP1-45057 | 516937 |
| PSMA1 | Novus Biologicals | H00005682-M01 | 11280-S3 |
| PSMA1 | Novus Biologicals | H00005682-M01 | D5031-S3, D5311-S3 |
| PSMD7 | Novus Biologicals | H00005713-M01 | 08130-2G5 |
| PSMD7 | Novus Biologicals | H00005713-M01 | D5311-2G5 |
| PSME3 | My Biosource | MBS850788 | no lot No. |
| PSP94/MSP/IGBF | Novus Biologicals | H00004477-M08 | 12118-3B11 |
| PTBP1 | Novus Biologicals | H00005725-M01 | D3151-3H8 |
| PTEN | Novus Biologicals | H00005728-M01 | 12055-2G9 |
| PTPN13/PTPL1 | R&D SYSTEMS | MAB3577 | XXI0109051 |
| Rab1A | Novus Biologicals | H00005861-M07A | 08231-3f10, 11258-3f10 |
| RAB3B | Novus Biologicals | H00005865-M01 | D3191-3F12 |
| Rab5a | Novus Biologicals | NBP1-04340 | A088001 |
| Rad51b | Genetex | GTX11050 | 12257 |
| RPL10 | Novus Biologicals | H00006134-M01 | 07295-3H7 |
| RPL10 | Novus Biologicals | H00006134-M01 | D5311-3H7 |
| RPL14 | Novus Biologicals | H00009045-M01 | 09244-1B4 |
| RPL14 | Novus Biologicals | H00009045-M01 | 09233-1B4, 09244-1B4 |
| RPL19 | Novus Biologicals | H00006143-M01 | 12115-3H4 |
| RUVBL2 | Novus Biologicals | NBP2-01764 | A01 |
| SCARB2 | Novus biologicals | H00000950-M01 | 08312-1c8 |
| seprase/FAP | R&D systems | MAB3715 | CCHZ0212041 |
| SerpinB6 | Novus Biologicals | NBP2-01650 | A01, A001 (same conc.) |
| SET | Novus Biologicals | H00006418-M01 | D2041-S1 |
| SH3PX1 | z | NBP2-02609 | A01, A001 (same conc.) |
| SLC20A2 | Novus Biologicals | H00006575-M04 | 08153-4b1 |
| SLC3A2/CD98 | Novus Biologicals | NB600-772 | 0610 |
| SLC9A3R2 | abcam | ab151443 | GR121588-1 |
| SMARCA4 | life technologies | 730011 | 1139083A1 |
| Sorbitol Dehydrogenase | Novus Biologicals | NBP2-02126 | A01 |
| SPEN/RBM15 | Novus Biologicals | H00064783-M19 | 08295-2C1 |
| SPOCK1 | R&D | MAB2327 | XCX0108121 |

TABLE 26-continued

Antibodies

| Target | Vendor | Catalog# | Lot# |
|---|---|---|---|
| SPR | Novus Biologicals | NBP2-03257 | A01 |
| SRVN | Novus Biologicals | H00000332-M01 | 12101-5B10 |
| Stanniocalcin 2/STC2 | Novus Biologicals | H00008614-M08 | 11252-2B11 |
| STEAP1 | Novus Biologicals | NBP1-07094 | A0912501 |
| Synaptogyrin 2/SYNGR2 | Novus Biologicals | H00009144-M01 | 08312-5C3, 08318-5C3, 6286-5C3-00LcY5 |
| Syndecan | NOVUS BIOLOGICALS | NBP1-43351 | E04056-1632 |
| SYNGR2 | Novus Biologicals | H00009144-M01 | D5311-5C3 |
| SYT9 | NeuroMab | 75-306 | 449-3AK-64 |
| TAF1B/GRHL1 | MYBIOSOURCE | MBS120474 | no lot given |
| TBX5 | Novus Biologicals | H00006910-M01 | 12250-1G10 |
| TGFB | Novus Biologicals | NBP2-00426 | E05980-1630 |
| TGM2 | Sigma Aldrich | WH0007052M10 | 11294-2F4 |
| TGN46/TGOLN2 | Novus Biologicals | H00010618-M02 | 11350-2f11 |
| TIMP-1 | Sigma-Aldrich | WH0007076M1 | 11025-4D12, 11097-4D12 |
| TLR3 | Abcam | ab13915 | GR123770-1, GR117728-1 |
| TLR4 (CD284) | Novus Biologicals | H00007099-M02 | 12250-3B6 |
| TLR9/CD289 | Novus Biologicals | H00054106-M03 | D1111-1E8 |
| TM9SF2 | Novus Biologicals | H00009375-M12 | 09247-1C2 |
| TMBIM6 | ACRIS | AM20308PU-N | AB090612A-01 |
| TMPRSS1 | NOVUS BIOLOGICALS | H00003249-M02 | 10341-2D5 |
| TMPRSS2 | Millipore/Calbiochem | ST1676-100UG | 08162-2F4, 11027-2F4 |
| TNFR1 | US biological | T9162-51 | L13020614C13020614 |
| TNFRI | R&D systems | MAB225 | IP0912041 |
| TNFRII | R&D Systems | MAB2261 | BQH0310061 |
| TNFSF18/GITRL | Novus Biologicals | H00008995-M01 | D5311-6F7 |
| TNFα | Novus Biologicals | H00007124-M04 | 07254-S1 |
| TNFα | Novus Biologicals | H00007124-M04 | D5311-S1 |
| Tollip | Novus Biologicals | NBP1-28621 | L5505-T719C, L5505-T719D |
| TOM1 | Novus Biologicals | H00010043-M01 | D3131-5A3 |
| TOMM22 | Novus Biologicals | H00056993-M01 | D2251-4g4, D3011-4g4 |
| Trop2/TACSTD2 | eBioscience | 14-6024-82 | E13280-103 |
| TSNAXIP1 | Novus Biologicals | H00055815-M02 | 07205-1D6 |
| TWEAK | R&D systems | MAB1090 | VIV0110091 |
| U2AF2 | Novus Biologicals | H00011338-M03 | 11305-5G8 |
| uPA | Novus Biologicals | NBP1-05160 | U 16-0109-001 |
| uPAR/CD87 | BD pharmingen | 555767 | 2104802 |
| USP14 | Novus Biologicals | H00009097-M04 | 12195-6D6 |
| USP14 | Novus Biologicals | H00009097-M04 | 12195-6D6 |
| VAMP8 | Novus Biologicals | NBP1-40484 | YJ032819CS |
| VASP | Novus Biologicals | NBP2-00555 | A01 |
| VDAC2 | Novus Biologicals | H00007417-M01 | 12194-3D2 |
| VEGFA | Novus Biologicals | NB110-60975 | 2012081301 |
| VEGFR1/FLT1 | US biological | V2110-16N | L13053059 C13053059 |
| VEGFR2 | Novus Biologicals | NBP1-18646 | 0511R07-3 |
| VPS28 | Origene | CF505691 | |
| XRCC5/Ku80 | Novus Biologicals | H00007520-M02 | 11350-3D8, 10096-3D8 |
| XRCC5/Ku80 | Novus Biologicals | H00007520-M02 | D5311-3D8 |

The method is used to develop aptamer to substitute for the antibodies in Table 26. The aptamers are used for capture and/or detection of microvesicles of interest. The method is used to develop aptamers to EGFR, TOMM22, NDRG1, VDAC2, KLK6, MMP7, EDIL3 (del-1), CCR5, BDNF, Hsp10, GOLPH2, Hsp4O/DNAJB1, KLK4, LGALS3BP, p130/RBL2, SCARB2, Stanniocalcin 2/STC2, TGN46/TGOLN2, ANXA2, TMPRSS1, KLK14, SPEN/RBM15, ME1, PhIP, ALDOA, MMP25, NCL, EDNRB/EDN3, MTA1, CDH1, KLK15, CHRDL2, CXCR3. The method is used to develop aptamers to CD81, EDN-3, Cytochrome C, CD10, CD151, seprase/FAP, HGF, PAP, CD41, IGFBP-2, TWEAK, MMP 2, H3F3A, DDX1, 99-14-3-3 zeta/beta, IDH2, CD49d, KLK12, DCTN2-50, Histone H4, EDIL3 (del-1), CD9, COX2, hnRNP M1-M4, CDH2, SPEN/RBM15, 81-Prohibitin, SYT9. These aptamers are used with an anti-E Cadherin (CDH1) antibody or aptamer to for a capture/detector pair to detect microvesicles of interest. The microvesicles are identified to distinguish prostate cancer samples from non-prostate cancer samples.

Although preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US10942184B2). An electronic copy of the "Sequence Listing" will also be available from the USPTO upon request and payment of the fee set forth in 37 CFR 1.19(b)(3).

What is claimed is:

1. A method comprising;
   (a) contacting a biological sample comprising microvesicles with a pool of different aptamers enriched to target one or more microvesicles;
   (b) removing unbound aptamers;
   (c) eluting bound aptamers;
   (d) identifying the aptamers that are eluted by sequencing, and
   (e) determining the presence and copy number of the identified aptamers; wherein it is not necessary to know the precise targets of the different aptamers.

2. The method of claim 1, wherein the pool of different aptamers are pre-selected through at least one step of positive and/or negative selection, wherein positive selection comprises selection of aptamers against a sample having substantially similar characteristics compared to the biological sample, and wherein negative selection comprises selection of aptamers against a sample having substantially different characteristics compared to the biological sample.

3. The method of claim 1, wherein the sequencing comprises performing high-throughput sequencing.

4. The method of claim 1, wherein the biological sample is from a subject suspected of having or being predisposed to having a cancer.

5. The method of claim 4, wherein the cancer comprises an acute lymphoblastic leukemia; acute myeloid leukemia; adrenocortical carcinoma; AIDS-related cancers; AIDS-related lymphoma; anal cancer; appendix cancer; astrocytomas; atypical teratoid/rhabdoid tumor; basal cell carcinoma; bladder cancer; brain stem glioma; brain tumor (including brain stem glioma, central nervous system atypical teratoid/rhabdoid tumor, central nervous system embryonal tumors, astrocytomas, craniopharyngioma, ependymoblastoma, ependymoma, medulloblastoma, medulloepithelioma, pineal parenchymal tumors of intermediate differentiation, supratentorial primitive neuroectodermal tumors and pineoblastoma); breast cancer; bronchial tumors; Burkitt lymphoma; cancer of unknown primary site; carcinoid tumor; carcinoma of unknown primary site; central nervous system atypical teratoid/rhabdoid tumor; central nervous system embryonal tumors; cervical cancer; childhood cancers; chordoma; chronic lymphocytic leukemia; chronic myelogenous leukemia; chronic myeloproliferative disorders; colon cancer; colorectal cancer; craniopharyngioma; cutaneous T-cell lymphoma; endocrine pancreas islet cell tumors; endometrial cancer; ependymoblastoma; ependymoma; esophageal cancer; esthesioneuroblastoma; Ewing sarcoma; extracranial germ cell tumor; extragonadal germ cell tumor; extrahepatic bile duct cancer; gallbladder cancer; gastric (stomach) cancer; gastrointestinal carcinoid tumor; gastrointestinal stromal cell tumor; gastrointestinal stromal tumor (GIST); gestational trophoblastic tumor; glioma; hairy cell leukemia; head and neck cancer; heart cancer; Hodgkin lymphoma; hypopharyngeal cancer; intraocular melanoma; islet cell tumors; Kaposi sarcoma; kidney cancer; Langerhans cell histiocytosis; laryngeal cancer; lip cancer; liver cancer; lung cancer; malignant fibrous histiocytoma bone cancer; medulloblastoma; medulloepithelioma; melanoma; Merkel cell carcinoma; Merkel cell skin carcinoma; mesothelioma; metastatic squamous neck cancer with occult primary; mouth cancer; multiple endocrine neoplasia syndromes; multiple myeloma; multiple myeloma/plasma cell neoplasm; mycosis fungoides; myelodysplastic syndromes; myeloproliferative neoplasms; nasal cavity cancer; nasopharyngeal cancer; neuroblastoma; Non-Hodgkin lymphoma; nonmelanoma skin cancer; non-small cell lung cancer; oral cancer; oral cavity cancer; oropharyngeal cancer; osteosarcoma; other brain and spinal cord tumors; ovarian cancer; ovarian epithelial cancer; ovarian germ cell tumor; ovarian low malignant potential tumor; pancreatic cancer; papillomatosis; paranasal sinus cancer; parathyroid cancer; pelvic cancer; penile cancer; pharyngeal cancer; pineal parenchymal tumors of intermediate differentiation; pineoblastoma; pituitary tumor; plasma cell neoplasm/multiple myeloma; pleuropulmonary blastoma; primary central nervous system (CNS) lymphoma; primary hepatocellular liver cancer; prostate cancer; rectal cancer; renal cancer; renal cell (kidney) cancer; renal cell cancer; respiratory tract cancer; retinoblastoma; rhabdomyosarcoma; salivary gland cancer; Sezary syndrome; small cell lung cancer; small intestine cancer; soft tissue sarcoma; squamous cell carcinoma; squamous neck cancer; stomach (gastric) cancer; supratentorial primitive neuroectodermal tumors; T-cell lymphoma; testicular cancer; throat cancer; thymic carcinoma; thymoma; thyroid cancer; transitional cell cancer; transitional cell cancer of the renal pelvis and ureter; trophoblastic tumor; ureter cancer; urethral cancer; uterine cancer; uterine sarcoma; vaginal cancer; vulvar cancer; Waldenstrm macroglobulinemia; or Wilm's tumor.

6. The method of claim 1, wherein the biological sample comprises a cell culture or a biological fluid.

7. The method of claim 6, wherein the biological fluid comprises a bodily fluid.

8. The method of claim 6, wherein the biological fluid comprises peripheral blood, sera, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, female ejaculate, sweat, fecal matter, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, or umbilical cord blood.

9. The method of claim 1, wherein the biological sample comprises isolated microvesicles.

10. The method of claim 9, wherein the biological sample is contacted with the plurality of aptamers before isolating microvesicles.

11. The method of claim 10, wherein the microvesicles are isolated using chromatography, filtration, ultrafiltration, centrifugation, ultracentrifugation, flow cytometry, affinity capture, and/or microfluidics.

12. The method of claim 1, wherein at least one member of the pool of aptamers binds a polypeptide or fragment thereof.

13. The method of claim 1, wherein at least one member of the pool of aptamers binds a polypeptide or fragment thereof and the polypeptide or fragment thereof is soluble or membrane bound.

14. The method of claim 1, wherein at least one member of the pool of aptamers binds a microvesicle surface antigen.

15. The method of claim 1, wherein the pool of aptamers comprises at least 20 different aptamer members.

16. The method of claim 1, wherein the pool of aptamers comprises at least 50 different aptamer members.

17. The method of claim 1, wherein an altered presence or copy number of the pool of aptamers that formed a complex with the microvesicles as compared to a reference sample indicates that the sample is cancerous or predisposed to be cancerous.

18. The method of claim 1, wherein each of the pool of aptamers binds to a different target.

* * * * *

UNITED STATES PATENT AND TRADEMARK OFFICE
CERTIFICATE OF CORRECTION

PATENT NO. : 10,942,184 B2  
APPLICATION NO. : 15/913772  
DATED : March 9, 2021  
INVENTOR(S) : Halbert et al.

Page 1 of 1

It is certified that error appears in the above-identified patent and that said Letters Patent is hereby corrected as shown below:

On the Title Page

Column 1, Line 5, under item (60) "Related U.S. Application Data", delete "2012." and insert -- 2012, provisional application No. 61/731,419, filed on Nov. 29, 2012, provisional application No. 61/735,915, filed on Dec. 11, 2012, provisional application No. 61/748,437, filed on Jan. 2, 2013, provisional application No. 61/749,773, filed on Jan. 7, 2013, provisional application No. 61/750,331, filed on Jan. 8, 2013, provisional application No. 61/754,471, filed on Jan. 18, 2013, provisional application No. 61/767,131, filed on Feb. 20, 2013, provisional application No. 61/769,064, filed on Feb. 25, 2013, provisional application No. 61/805,365, filed on Mar. 26, 2013, provisional application No. 61/808,144, filed on Apr. 3, 2013, provisional application No. 61/820,419, filed on May 7, 2013, provisional application No. 61/826,957, filed on May 23, 2013, provisional application No. 61/838,762, filed on Jun. 24, 2013, provisional application No. 61/843,256, filed on Jul. 5, 2013, provisional application No. 61/862,809, filed on Aug. 6, 2013, provisional application No. 61/863,828, filed on Aug. 8, 2013, provisional application No. 61/866,014, filed on Aug. 14, 2013, provisional application No. 61/867,978, filed on Aug. 20, 2013, provisional application No. 61/871,107, filed on Aug. 28, 2013, provisional application No. 61/874,621, filed on Sep. 6, 2013. --

In the Claims

Column 254, Line 51, Claim 5, delete "Waldenstrm" and insert -- Waldenström --

Column 254, Line 51, Claim 5, delete "Wilm's" and insert -- Wilms' --

Column 254, Line 60, Claim 8, delete "broncheoalveolar" and insert -- bronchoalveolar --

Column 254, Line 67, Claim 8, delete "blastocyl" and insert -- blastocoel --

Column 255, Line 6, Claim 11, delete "claim 10" and insert -- claim 9, --

Signed and Sealed this  
Eighth Day of February, 2022

Drew Hirshfeld  
*Performing the Functions and Duties of the  
Under Secretary of Commerce for Intellectual Property and  
Director of the United States Patent and Trademark Office*